(12) United States Patent
LaRocque et al.

(10) Patent No.: US 11,002,699 B2
(45) Date of Patent: May 11, 2021

(54) WATER VAPOR DISTILLATION APPARATUS, METHOD AND SYSTEM

(71) Applicant: DEKA Products Limited Partnership, Manchester, NH (US)

(72) Inventors: Ryan Keith LaRocque, Manchester, NH (US); Russell H. Beavis, Merrimack, NH (US); Christopher C. Langenfeld, Nashua, NH (US); Andrew A. Schnellinger, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/457,291

(22) Filed: Mar. 13, 2017

(65) Prior Publication Data
US 2017/0184529 A1 Jun. 29, 2017

Related U.S. Application Data

(62) Division of application No. 13/952,195, filed on Jul. 26, 2013, now Pat. No. 9,593,809.

(60) Provisional application No. 61/819,919, filed on May 6, 2013, provisional application No. 61/676,597, filed on Jul. 27, 2012.

(51) Int. Cl.
| | | |
|---|---|---|
| *B01D 3/42* | (2006.01) | |
| *F17D 3/01* | (2006.01) | |
| *G01N 27/10* | (2006.01) | |
| *B01D 1/00* | (2006.01) | |
| *C02F 1/00* | (2006.01) | |
| *C02F 1/04* | (2006.01) | |
| *G01N 33/18* | (2006.01) | |

(52) U.S. Cl.
CPC ............ *G01N 27/10* (2013.01); *B01D 1/0082* (2013.01); *B01D 3/42* (2013.01); *C02F 1/008* (2013.01); *C02F 1/04* (2013.01); *F17D 3/01* (2013.01); *G01N 33/1893* (2013.01); *C02F 2209/005* (2013.01); *C02F 2209/05* (2013.01); *C02F 2209/40* (2013.01); *Y02W 10/37* (2015.05); *Y10T 137/0318* (2015.04); *Y10T 137/87917* (2015.04)

(58) Field of Classification Search
CPC ................ B01D 3/43; B01D 3/42; F17D 3/01
USPC ........................... 33/152.4; 137/5; 366/152.4
See application file for complete search history.

(56) References Cited

U.S. PATENT DOCUMENTS

| | | | |
|---|---|---|---|
| 2006/0138031 A1* | 6/2006 | Kloos ................ | B01D 61/022 210/96.2 |
| 2007/0012625 A1* | 1/2007 | Sieth .................. | B01D 61/025 210/652 |

(Continued)

*Primary Examiner* — David L Sorkin
(74) *Attorney, Agent, or Firm* — Michael George Norris

(57) ABSTRACT

A system for product water output. The system includes a controller, a first conductivity sensor in communication with the controller, a first product valve downstream from the first conductivity sensor and in communication with the controller, a second product valve downstream from the first product valve and in communication with the controller, a second conductivity sensor downstream from the second product valve and in communication with the controller, and a divert valve downstream from the first conductivity sensor and upstream from the first product valve and in communication with the controller.

16 Claims, 332 Drawing Sheets

(56) References Cited

U.S. PATENT DOCUMENTS

| | | | | |
|---|---|---|---|---|
| 2008/0030204 A1* | 2/2008 | Rossi | ............... | A61M 1/1605 |
| | | | | 324/630 |
| 2009/0025399 A1* | 1/2009 | Kamen | ............... | B01D 1/02 |
| | | | | 62/6 |
| 2010/0292944 A1* | 11/2010 | Howell | ............... | G01N 27/07 |
| | | | | 702/65 |
| 2015/0005699 A1* | 1/2015 | Burbank | ............... | A61M 1/285 |
| | | | | 604/29 |

* cited by examiner

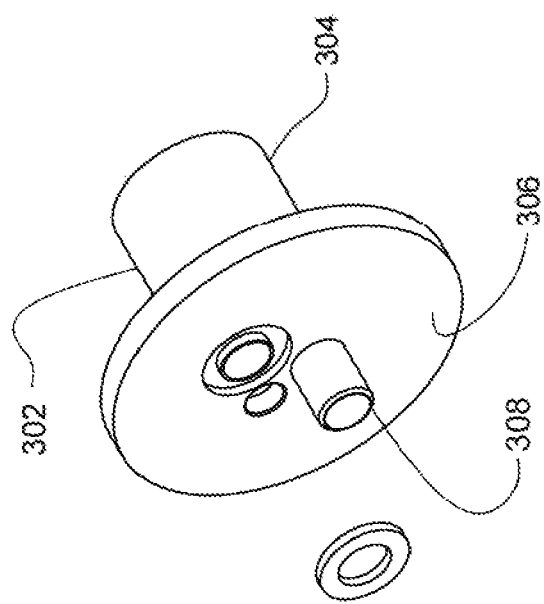
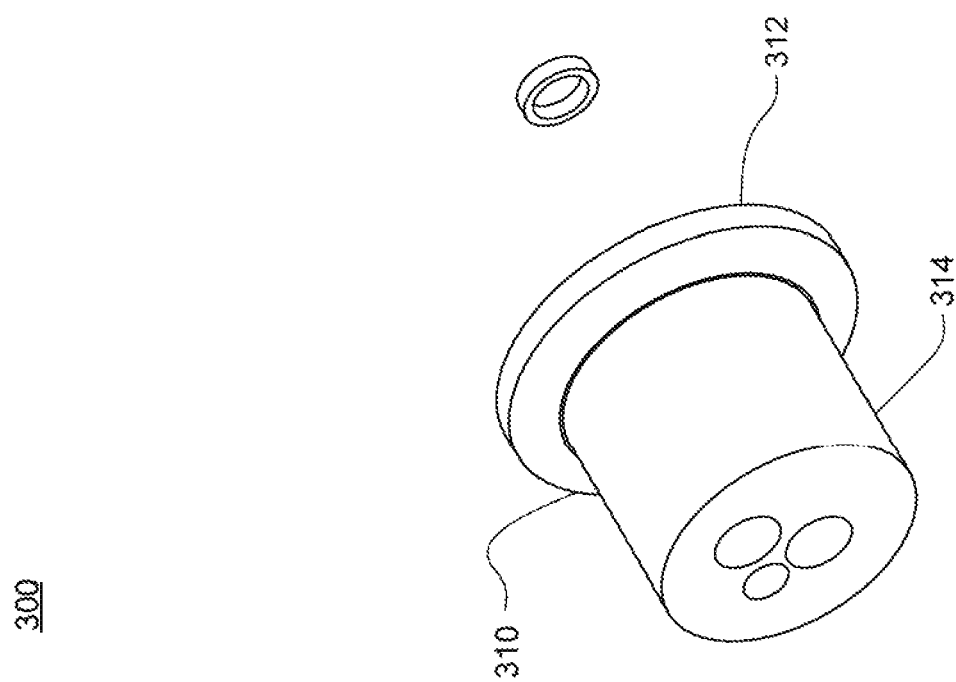
FIG. 3
PRIOR ART

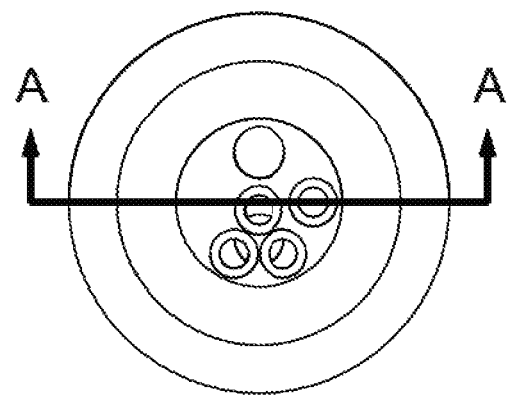
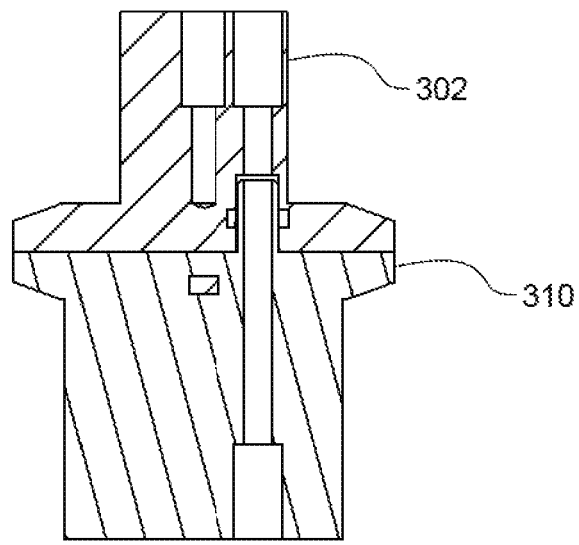
FIG.3A
PRIOR ART

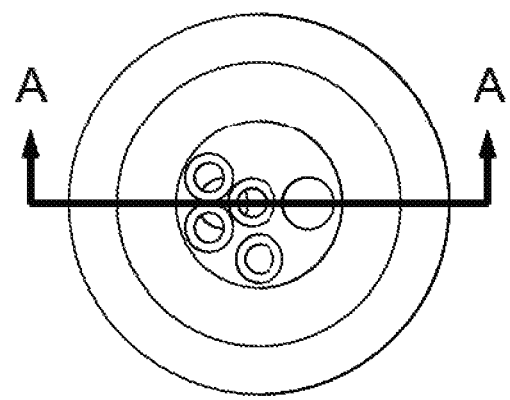
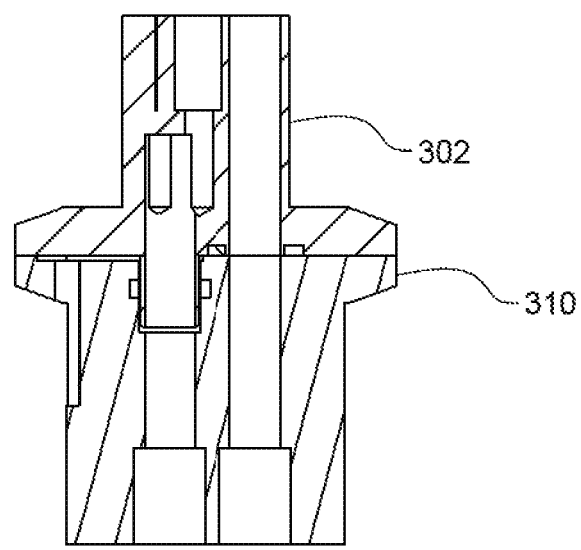
FIG.3B
PRIOR ART

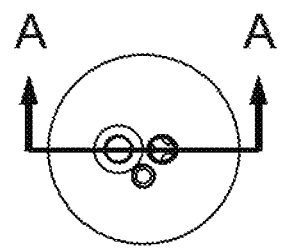
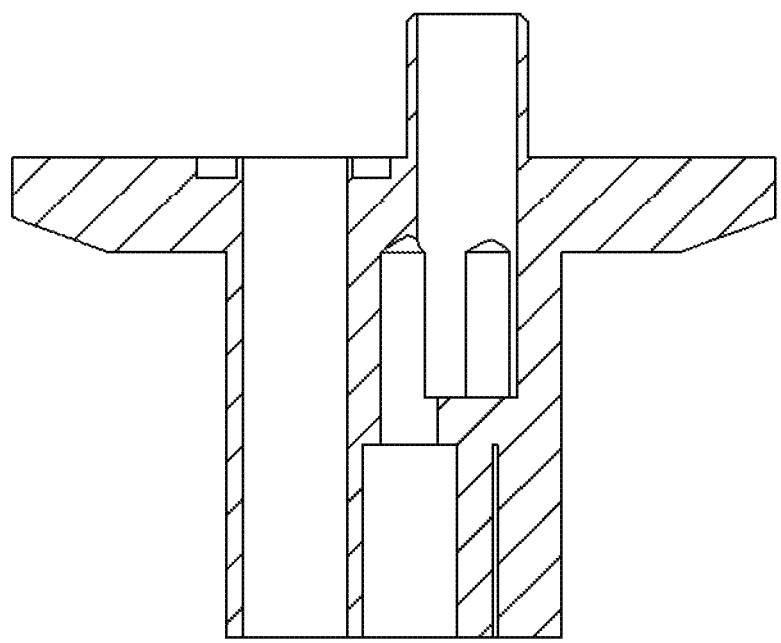
FIG.3E
PRIOR ART

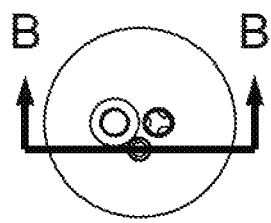
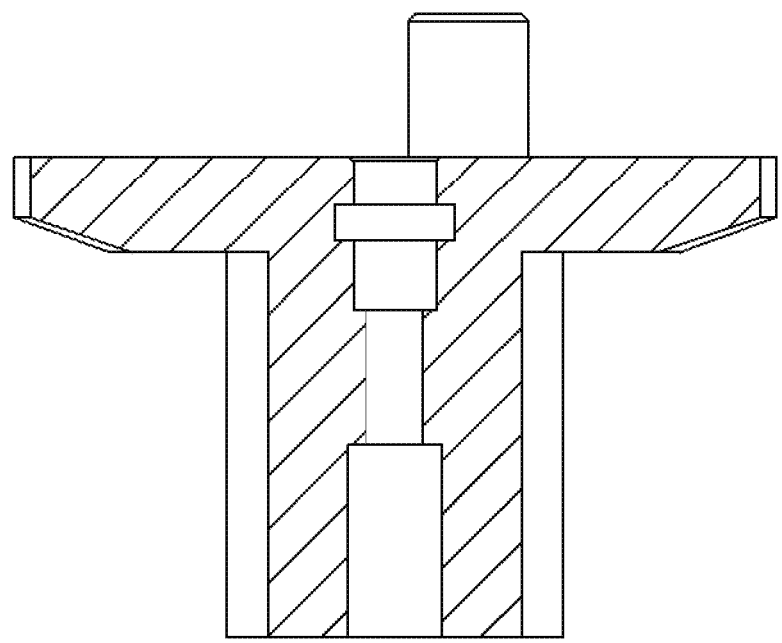
FIG.3F
PRIOR ART

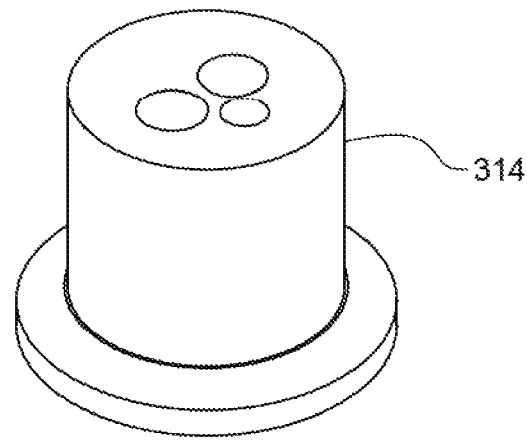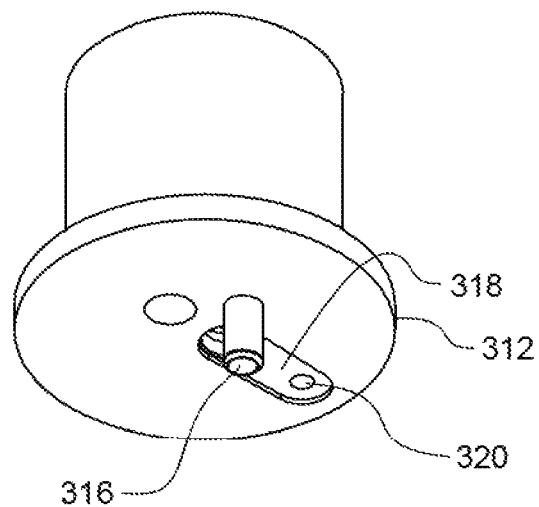
FIG.3G
PRIOR ART

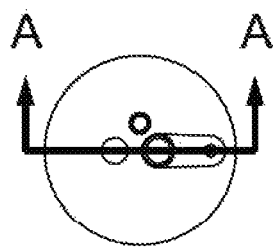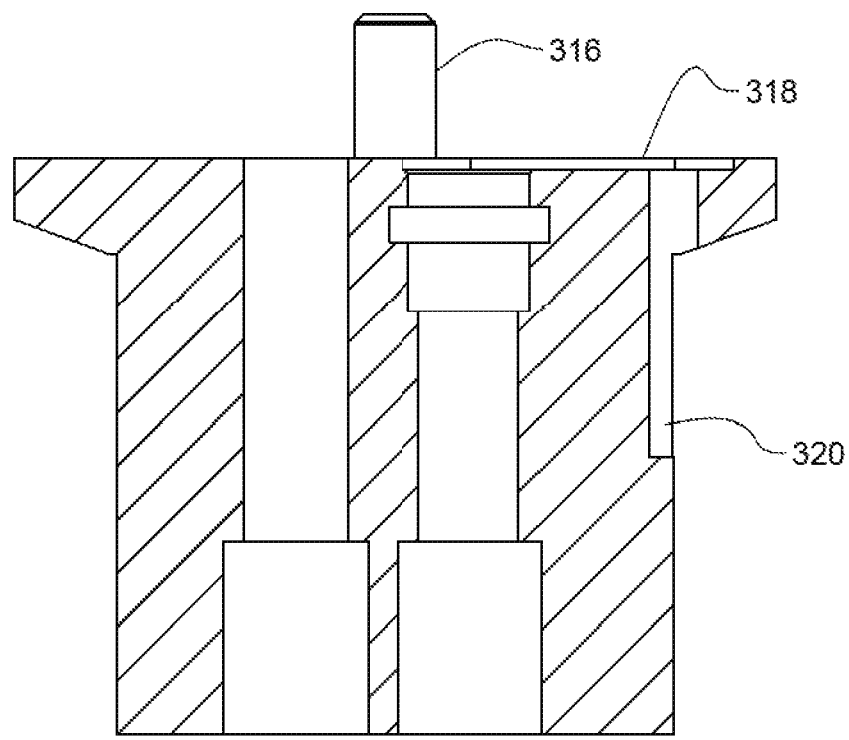
FIG.3I
PRIOR ART

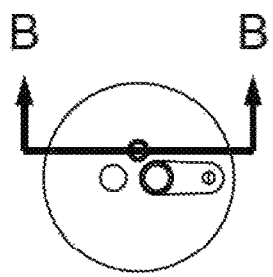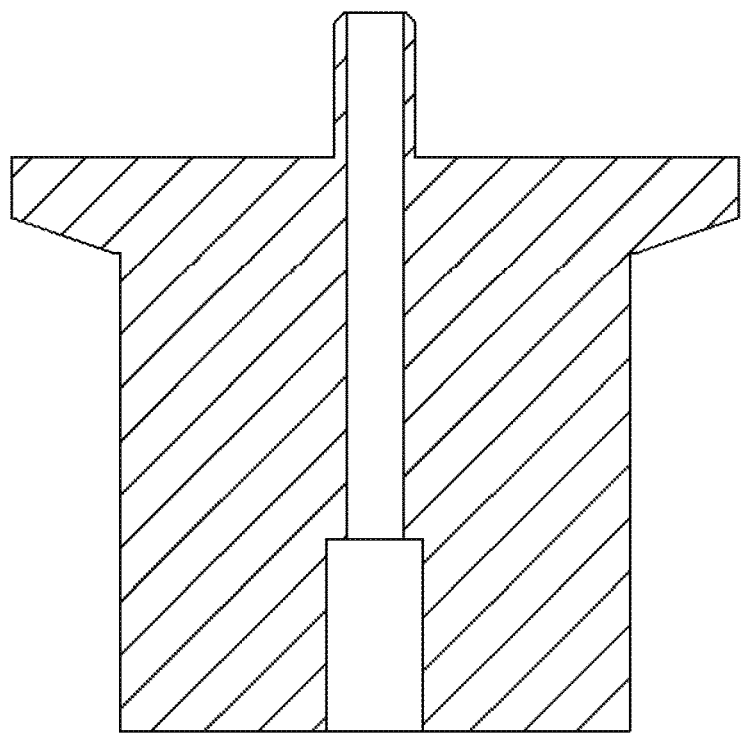
FIG.3J
PRIOR ART

420

600

800

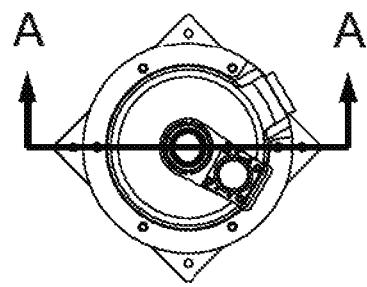
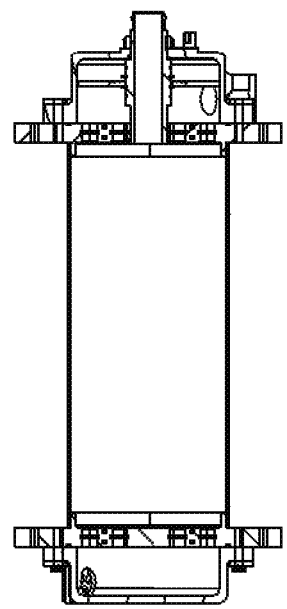
FIG. 13A
PRIOR ART

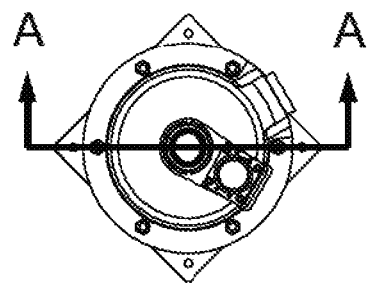
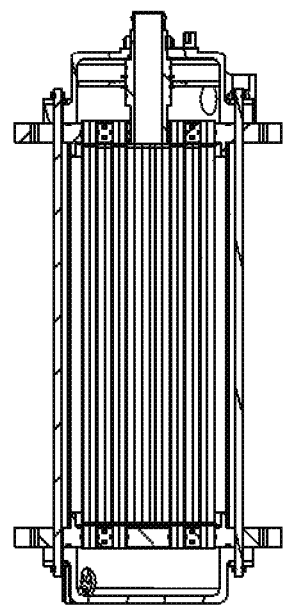
FIG.13C
PRIOR ART

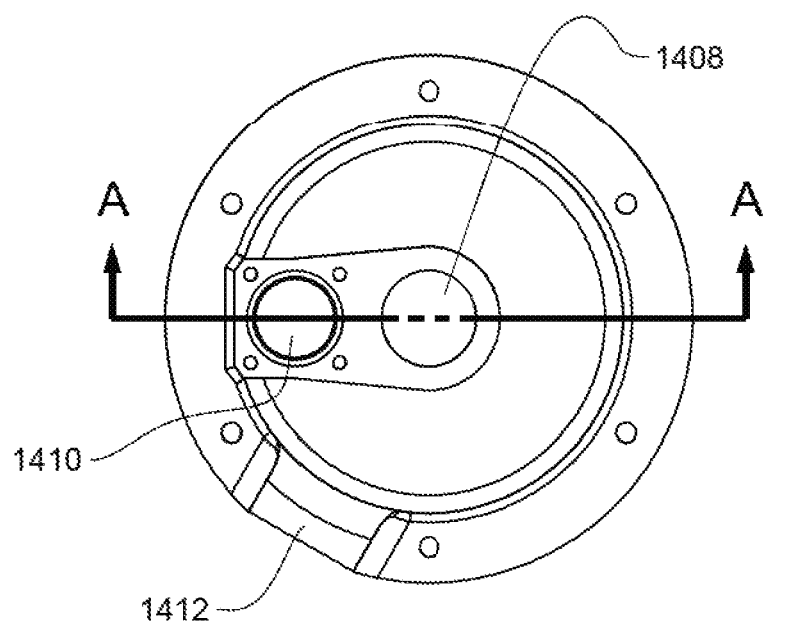
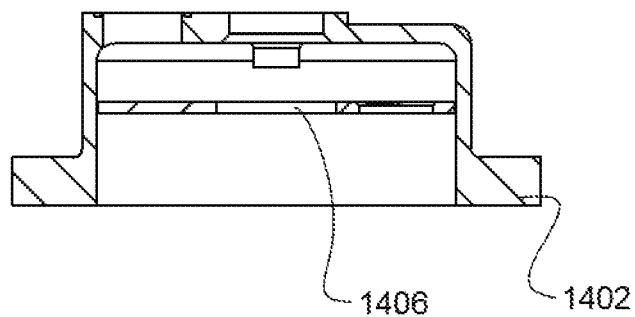
FIG.14C
PRIOR ART

1500

1502

1504

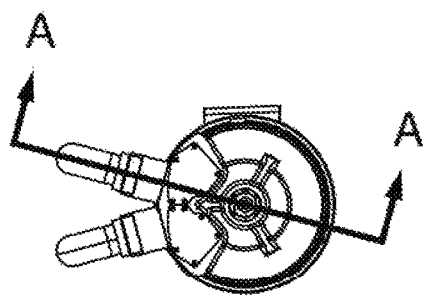
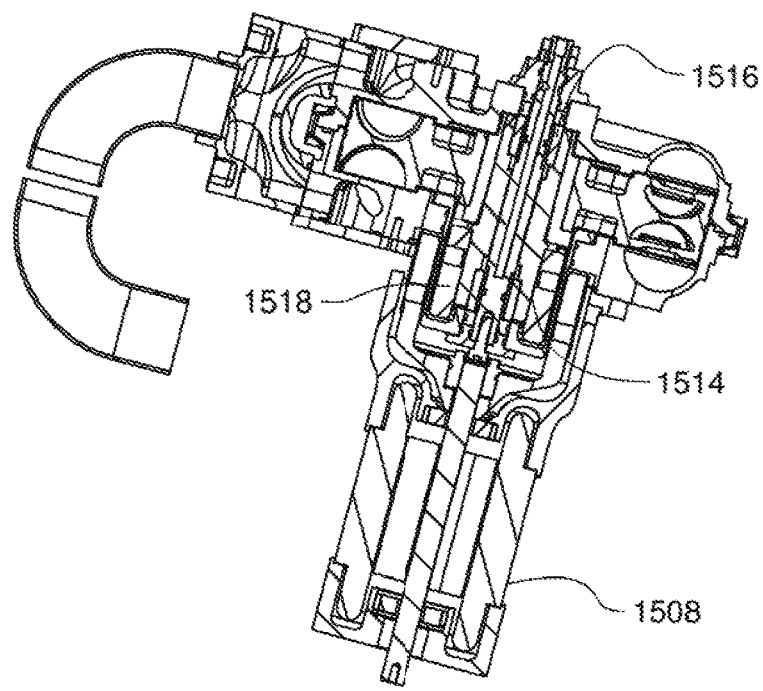
FIG.15J
PRIOR ART

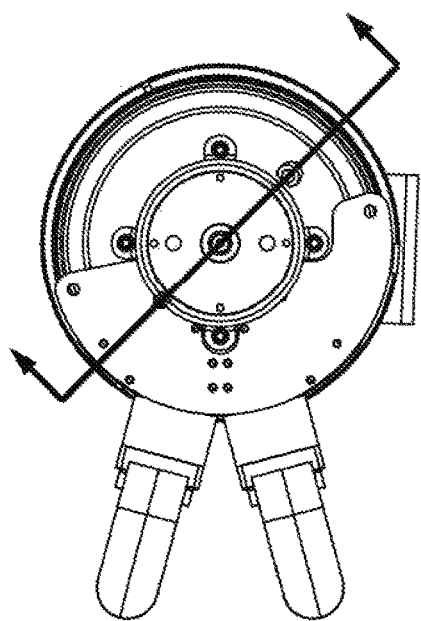
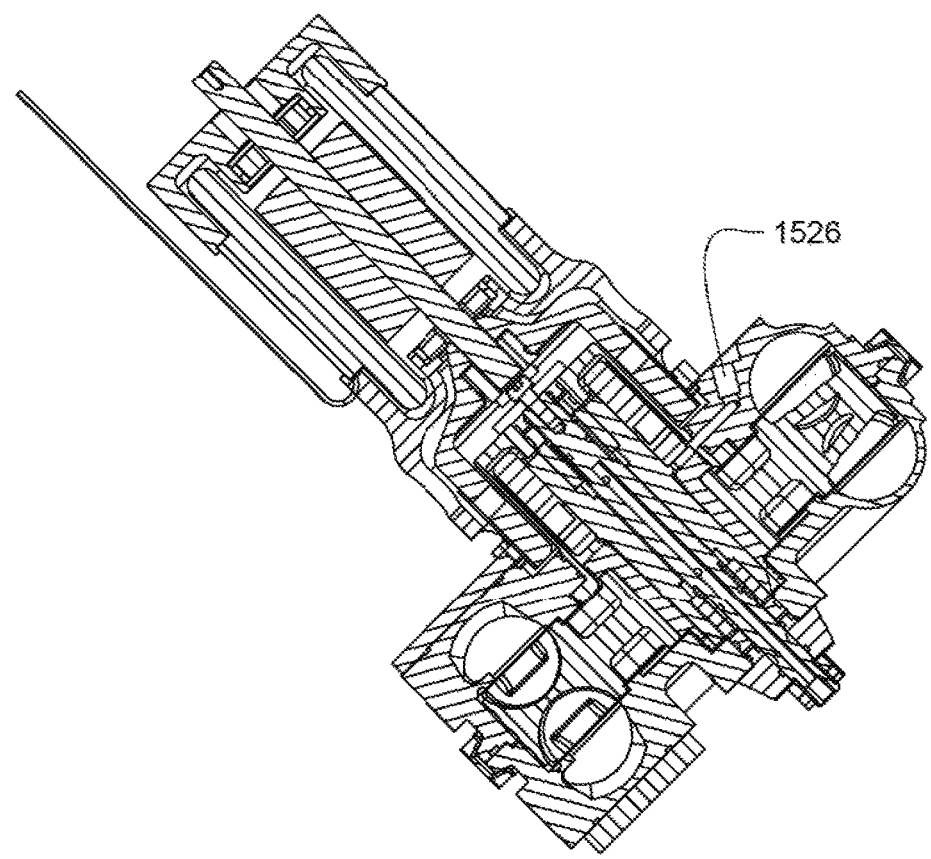
FIG.15L
PRIOR ART

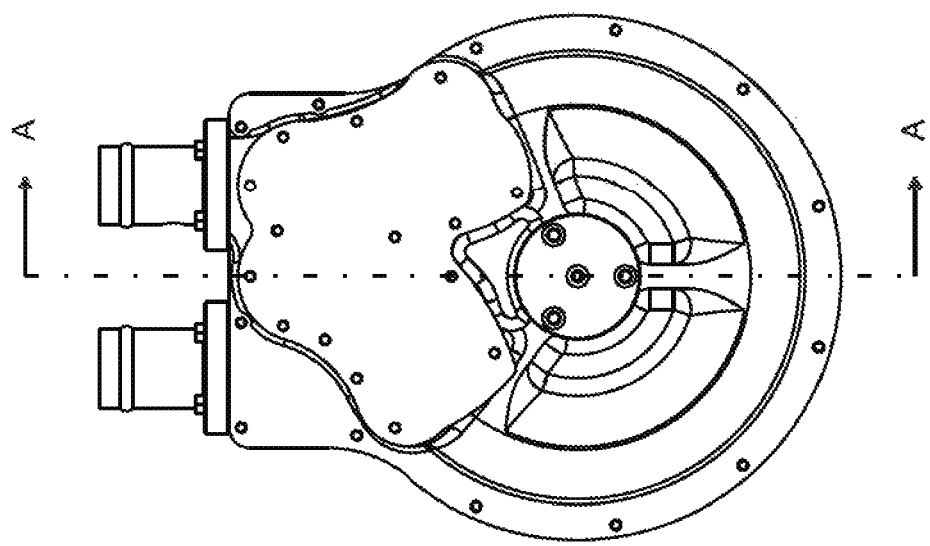
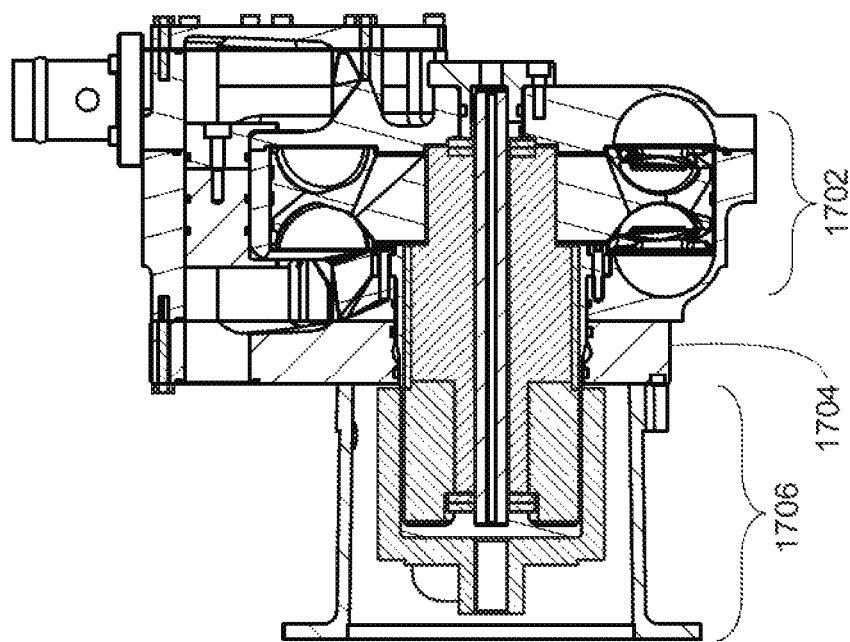
FIG. 17B
PRIOR ART

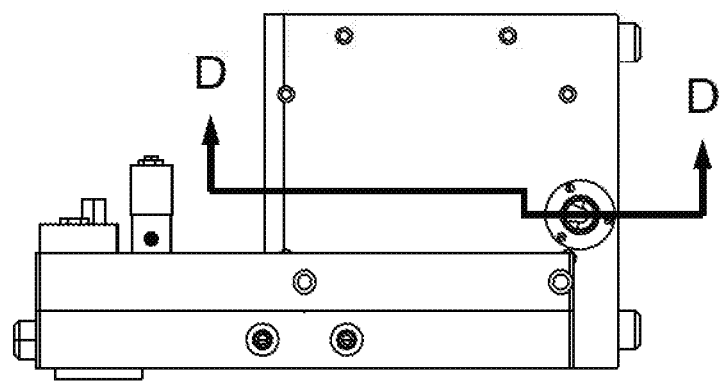
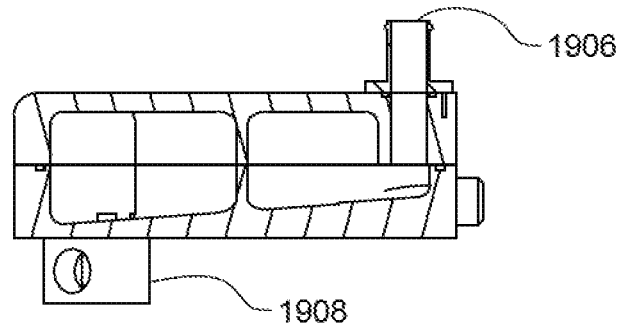
FIG.19B
PRIOR ART

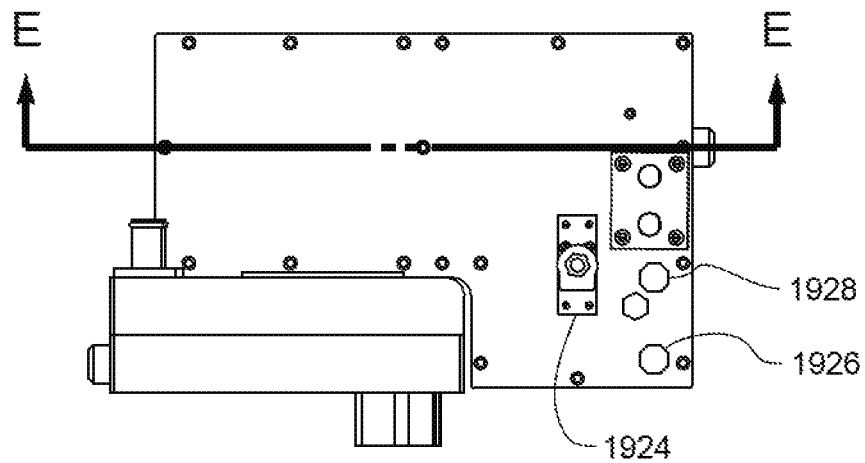
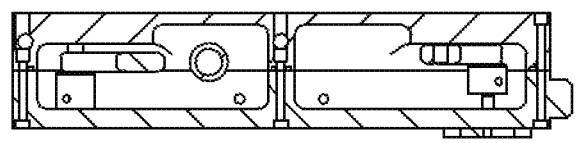
FIG.19C
PRIOR ART

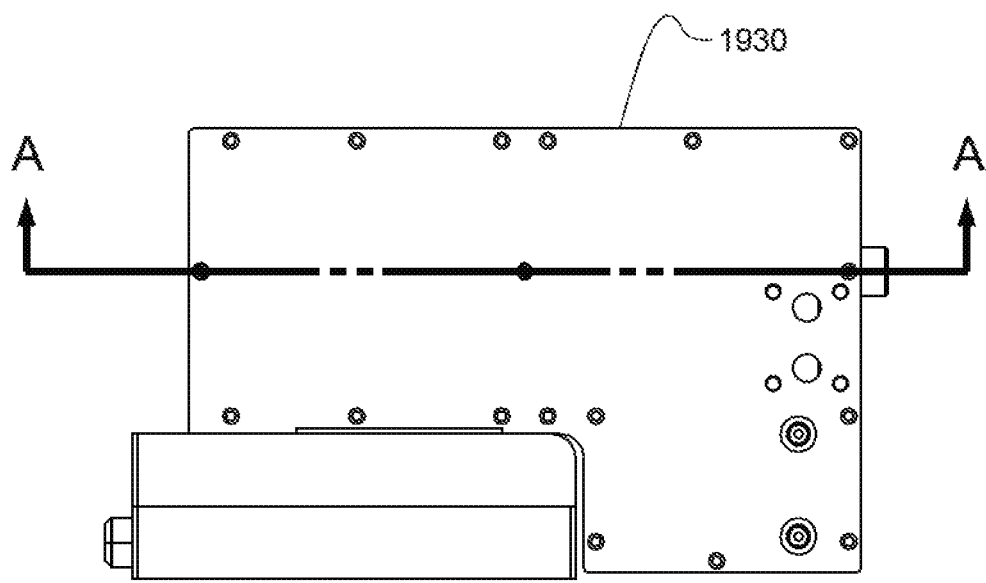
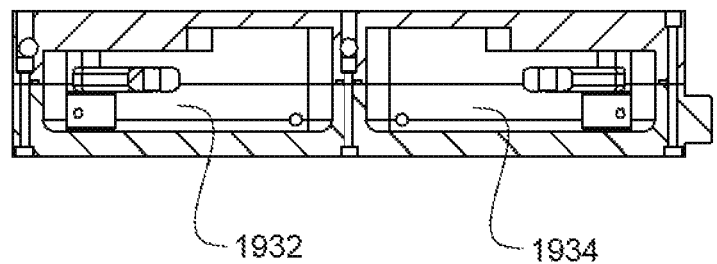
FIG.19F
PRIOR ART

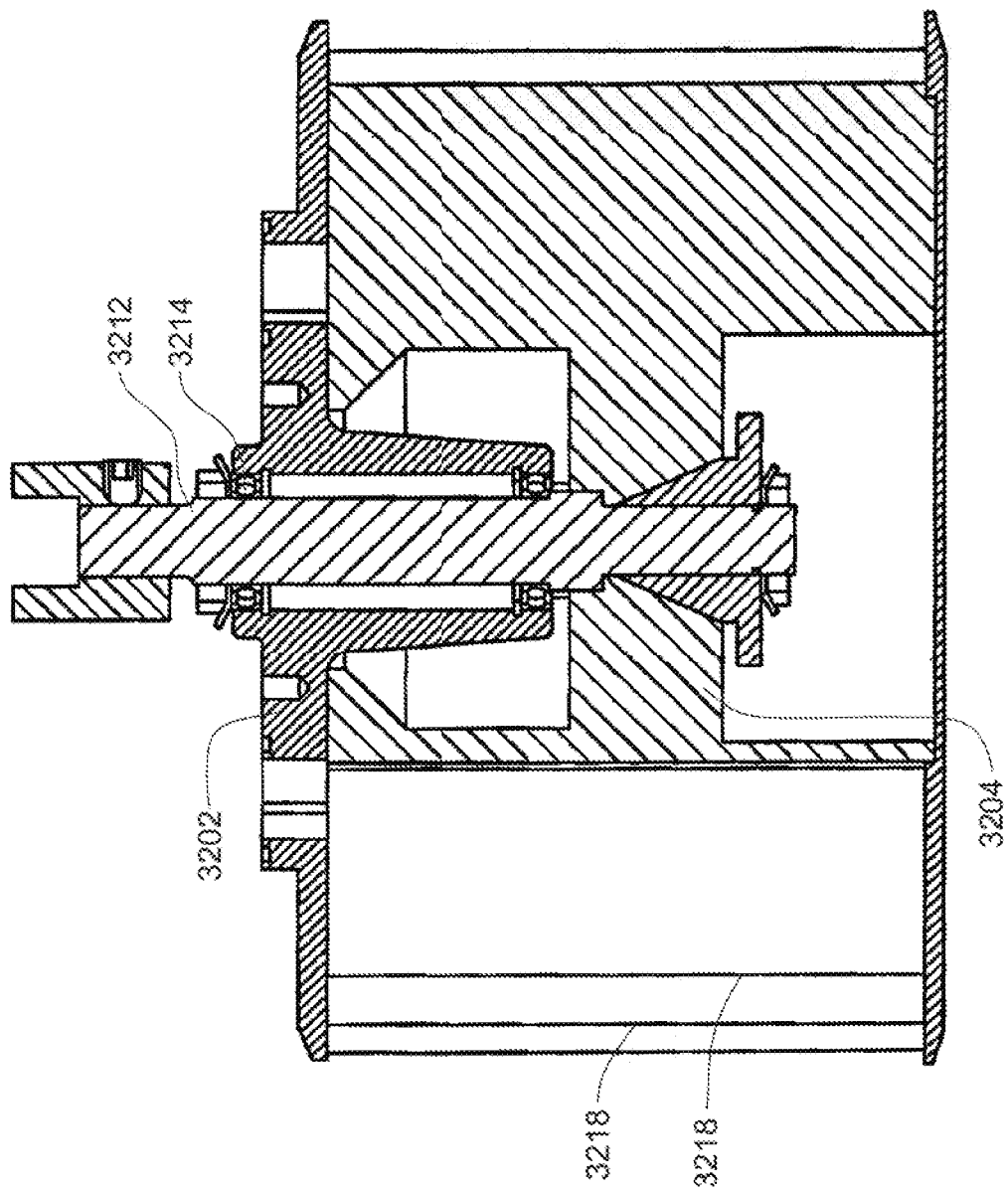
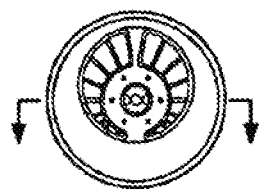
FIG.32C
PRIOR ART

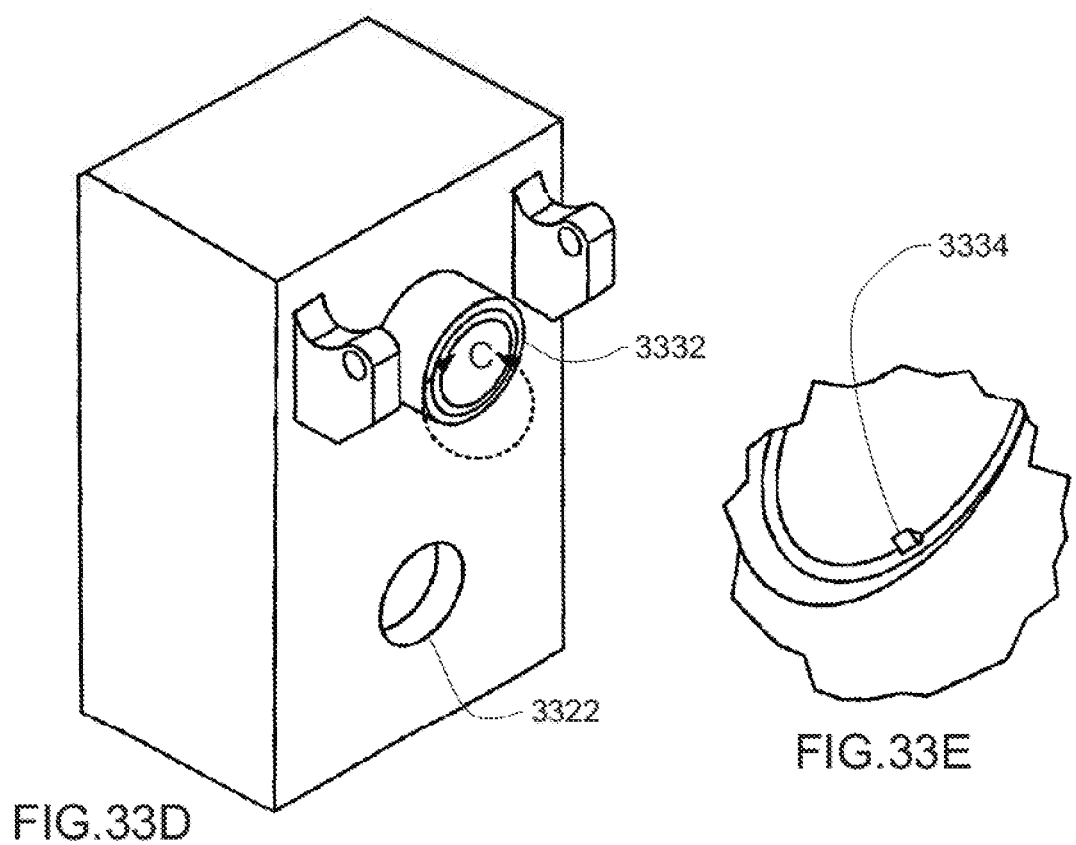
FIG.33D
FIG.33E
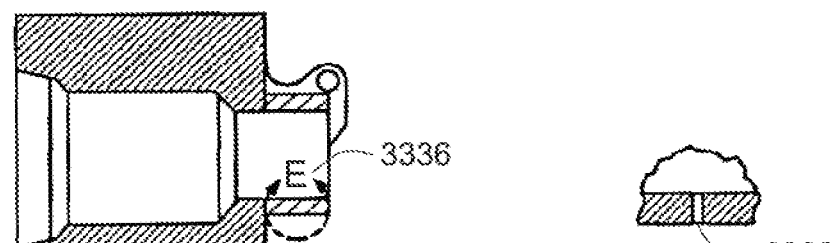
FIG.33F
FIG.33G
PRIOR ART

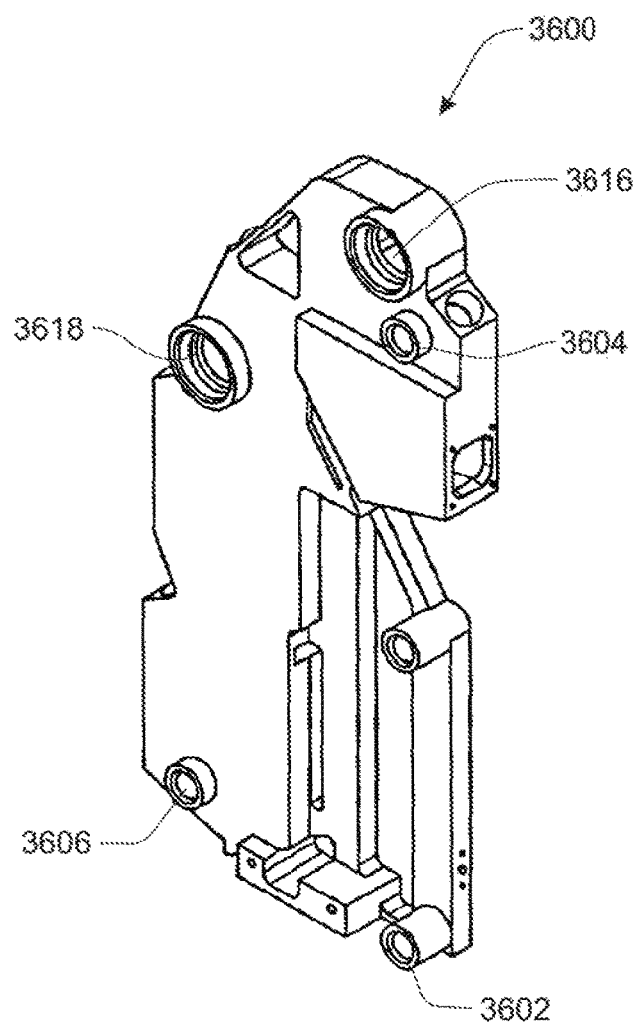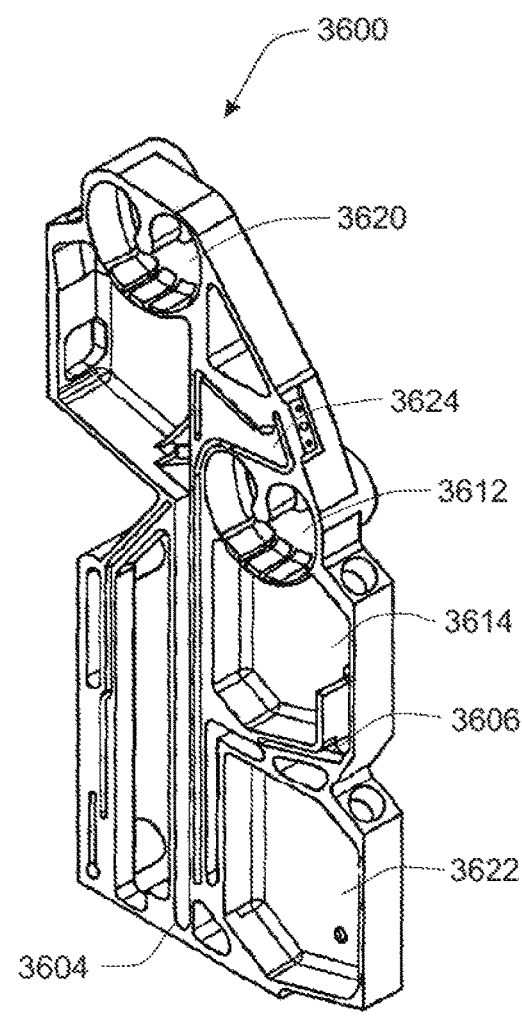
FIG.36B
FIG.36C
PRIOR ART

READY FOR START OF
COMPRESSION STROKE

END OF COMPRESSION STROKE

READY FOR START OF
EXPANSION STROKE

END OF EXPANSION STROKE

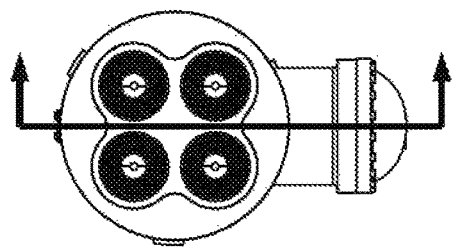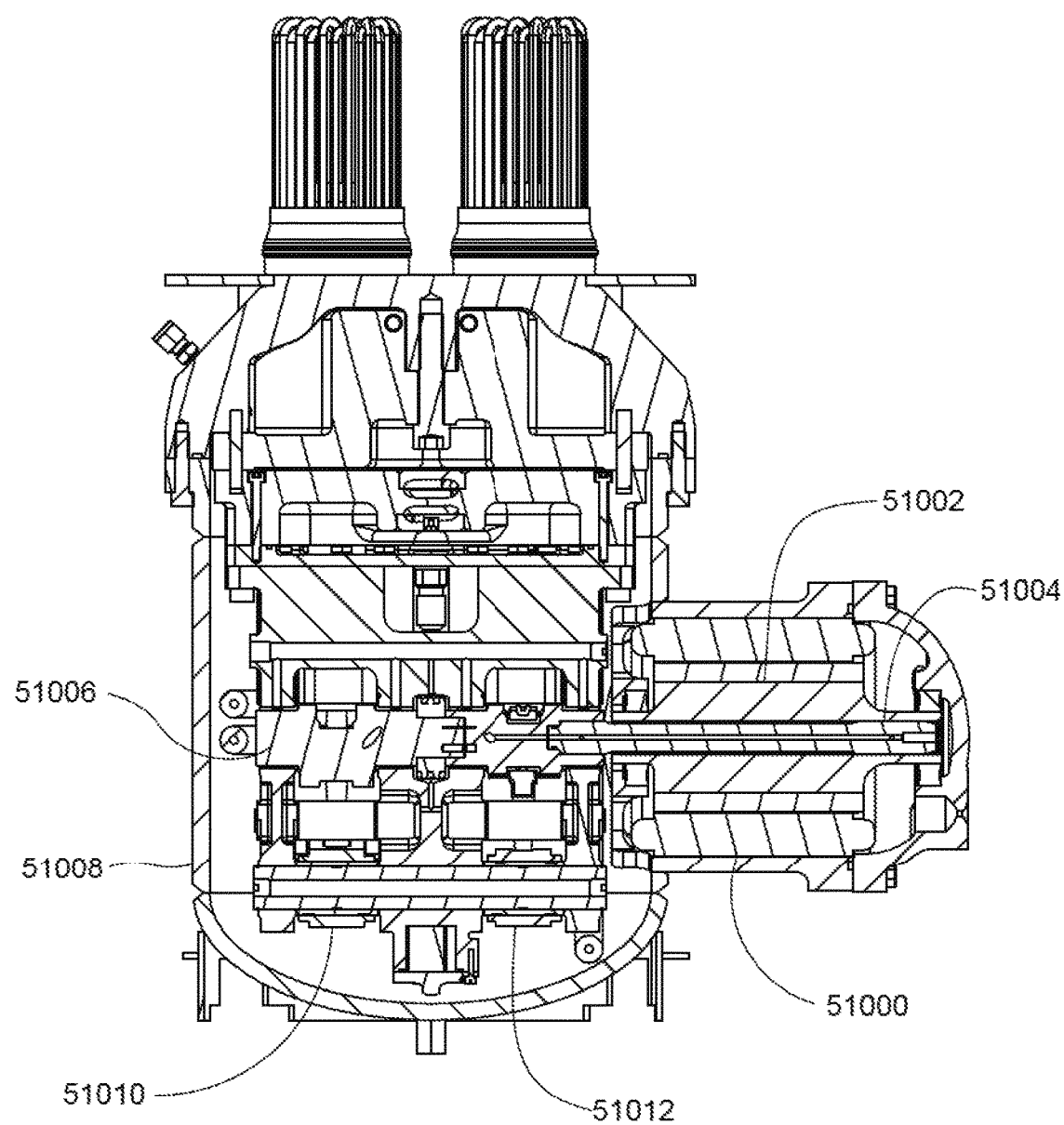
FIG. 54A
PRIOR ART

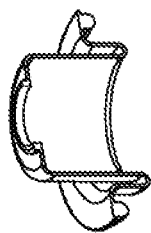
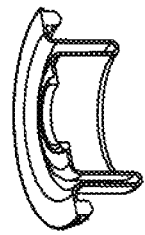
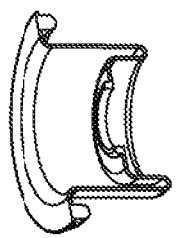
51300
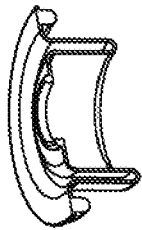
FIG. 57D
PRIOR ART

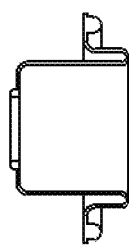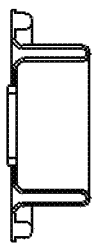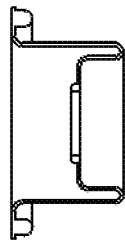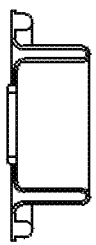
51300
FIG. 57E
PRIOR ART

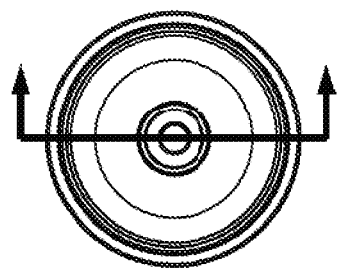
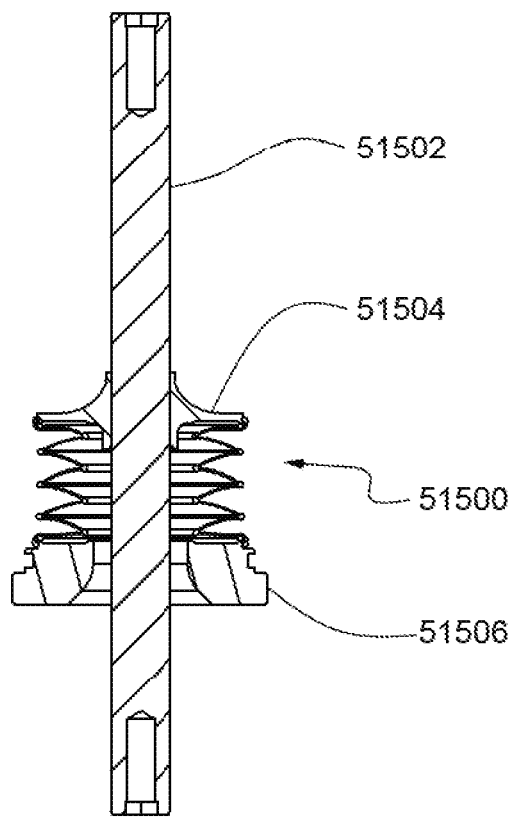
FIG. 59A
PRIOR ART

7400

WATER VAPOR DISTILLATION APPARATUS, METHOD AND SYSTEM

CROSS REFERENCE TO RELATED APPLICATIONS

The present application is a Divisional of U.S. application Ser. No. 13/952,195, filed Jul. 26, 2013, entitled Water Vapor Distillation Apparatus, Method and System, now U.S. Publication No. 2014-0202542-A1, published Jul. 24, 2014, which is a Non-Provisional application which claims priority from U.S. Provisional Patent Application Ser. No. 61/819,919, filed May 6, 2013 and entitled Water Vapor Distillation Apparatus, Method and System, and U.S. Provisional Patent Application Ser. No. 61/676,597, filed Jul. 27, 2012 and entitled Water Vapor Distillation Apparatus, Method and System, both of which are hereby incorporated herein by reference in their entireties.

TECHNICAL FIELD

The present invention relates to water distillation and more particularly, to a water vapor distillation apparatus, method, and system.

BACKGROUND INFORMATION

A dependable source of clean water eludes vast segments of humanity. For example, the Canadian International Development Agency reports that about 1.2 billion people lack access to safe drinking water. Published reports attribute millions and millions of deaths per year, mostly children, to water related diseases. Many water purification techniques are well known, including carbon filters, chlorination, pasteurization, and reverse osmosis. Many of these techniques are significantly affected by variations in the water quality and do not address a wide variety of common contaminants, such as bacteria, viruses, organics, arsenic, lead, mercury, and pesticides that may be found in water supplies in the developing world and elsewhere. Some of these systems require access to a supply of consumables, such as filters or chemicals. Moreover, some of these techniques are only well suited to centralized, large-scale water systems that require both a significant infrastructure and highly trained operators. The ability to produce reliable clean water without regard to the water source, on a smaller, decentralized scale, without the need for consumables and constant maintenance is very desirable, particularly in the developing world.

The use of vapor compression distillation to purify water is well known and may address many of these concerns. However, the poor financial resources, limited technical assets, and low population density that does not make it feasible to build centralized, large-scale water systems in much of the developing world, also limits the availability of adequate, affordable, and reliable power to operate vapor compression distillation systems, as well as hindering the ability to properly maintain such systems. In such circumstances, an improved vapor compression distillation system and associated components that increases efficiency and production capability, while decreasing the necessary power budget for system operation and the amount of system maintenance required may provide a solution.

SUMMARY

In accordance with one aspect of the present invention, a system for product water output is disclosed. The system includes a controller, a first conductivity sensor in communication with the controller, a first product valve downstream from the first conductivity sensor and in communication with the controller, a second product valve downstream from the first product valve and in communication with the controller, a second conductivity sensor downstream from the second product valve and in communication with the controller, and a divert valve downstream from the first conductivity sensor and upstream from the first product valve and in communication with the controller.

Some embodiments of this aspect of the present invention include one or more of the following: wherein the controller opens the divert valve and maintains the first product valve and second product valve in a closed position when the first conductivity sensor determines that the conductivity of product water is not within a first acceptable range; wherein the controller opens the first product valve and the second product valve when the first conductivity sensor determines that the conductivity of product water is within an acceptable range; wherein the second conductivity sensor determines the conductivity of the product water and the controller indicates a fault condition when the second conductivity sensor determines that the conductivity of product water is not within a second acceptable range; wherein the first acceptable range is lower than the second acceptable range; wherein the controller compares the conductivity from the first conductivity sensor and the second conductivity sensor and if the conductivity from the first conductivity sensor differs more than a threshold amount from the conductivity of the second conductivity sensor, a fault condition is indicated; wherein if it is determined that either the first conductivity sensor reading or the second conductivity sensor reading is not within the acceptable range, or threshold range for acceptability, then a fault condition is indicated; wherein the first conductivity sensor and the second conductivity sensor comprising: three probes connected by a cable, at least one of the three probes comprising a temperature sensor and wherein the resistance between each of the three probes is 500 k Ohms; wherein when the divert valve is open, if the controller receives a reading from the second conductivity sensor, a fault condition is indicated; wherein the system further includes a flow meter downstream from the first product valve and upstream from the second product valve.

In accordance with one aspect of the present invention, a method for determining the quality of product water output is disclosed. The method includes providing a controller, providing a first conductivity sensor in communication with the controller, providing a first product valve downstream from the first conductivity sensor and in communication with the controller, providing a second product valve downstream from the first product valve and in communication with the controller, providing a second conductivity sensor downstream from the second product valve and in communication with the controller, and providing a divert valve downstream from the first conductivity sensor and upstream from the first product valve and in communication with the controller.

Some embodiments of this aspect of the present invention include one or more of the following: wherein the method further includes the first conductivity sensor determining that the conductivity of product water is not within a first acceptable range and opening the divert valve and maintaining the first product valve and second product valve in a closed position; wherein the method further includes the first conductivity sensor determining that the conductivity of product water is within an acceptable range and opening the first product valve and the second product valve; wherein the method further includes the second conductivity sensor determining the conductivity of the product water and the controller indicating a fault condition when the second conductivity sensor determining that the conductivity of product water is not within a second acceptable range; wherein the method further includes wherein the first acceptable range is lower than the second acceptable range; wherein the method further includes comparing the conductivity from the first conductivity sensor and the second conductivity sensor, and if the conductivity from the first conductivity sensor differs more than a threshold amount from the conductivity of the second conductivity sensor, indicating a fault condition; wherein the method further includes determining that either the first conductivity sensor reading or the second conductivity sensor reading is not within the acceptable range, or threshold range for acceptability, and indicating a fault condition; wherein the method further includes wherein the first conductivity sensor and the second conductivity sensor including three probes connected by a cable, at least one of the three probes comprising a temperature sensor and wherein the resistance between each of the three probes is 500 k Ohms; wherein the method further includes opening a divert valve, receiving a reading from the second conductivity sensor, and indicating a fault condition; wherein the method further includes providing a flow meter downstream from the first product valve and upstream from the second product valve.

In accordance with one aspect of the present invention, a fluid vapor distillation system is disclosed. The system includes a control system for controlling a fluid vapor distillation apparatus including a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input.

Some embodiments of this aspect of the present invention include one or more of the following: wherein the control system further includes at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water. Also, wherein the system further includes a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporator condenser whereby compressed steam is transformed into product fluid. Wherein the heat exchanger is disposed about the housing of the evaporator condenser. Wherein the heat exchanger further includes wherein the outer tube is a source fluid flow path and the at least one inner tube is a product fluid flow path. Wherein the heat exchanger further includes at least three inner tubes. Wherein the at least three inner tubes are twined to form a substantially helical shape. Wherein the heat exchanger further includes two ends, and at each end a connector is attached, whereby the connectors form a connection to the evaporator condenser. Wherein the evaporator condenser tubes further includes packing inside the tubes. Wherein the packing is a rod. Wherein the evaporator condenser further including a steam chest fluidly connected to the plurality of tubes. Wherein the regenerative blower further includes an impeller assembly driven by a magnetic drive coupling. Wherein the control system includes at least two processors, a motor control engine processor and an ARM processor. Wherein the fluid vapor distillation apparatus further includes a conductivity meter and a conductivity cell to determine the conductivity of the product fluid.

In accordance with another aspect of the present invention, a fluid vapor distillation apparatus is disclosed. The apparatus includes a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporative condenser whereby compressed steam is transformed into product fluid, also, a control system for controlling the fluid vapor distillation apparatus including a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input.

Some embodiments of this aspect of the present invention include one or more of the following: at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water. Wherein the heat exchanger is disposed about the housing of the evaporator condenser. Wherein the heat exchanger further includes wherein the outer tube is a source fluid flow path and the at least one inner tube is a product fluid flow path. Wherein the heat exchanger further includes at least three inner tubes. Wherein the at least three inner tubes are twined to form a substantially helical shape. Wherein the heat exchanger further includes two ends, and at each end a connector is attached, whereby the connectors form a connection to the evaporator condenser. Wherein the evaporator condenser tubes further includes packing inside the tubes. Wherein the packing is a rod. Wherein the evaporator condenser further including a steam chest fluidly connected to the plurality of tubes. Wherein the regenerative blower further includes an impeller assembly driven by a magnetic drive coupling. Wherein the control system includes at least two processors, a motor control engine processor and an ARM processor. Wherein the fluid vapor distillation apparatus further includes a conductivity meter and a conductivity cell to determine the conductivity of the product fluid.

In accordance with one aspect of the present invention, a fluid vapor distillation apparatus is disclosed. The apparatus includes a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporative condenser whereby compressed steam is transformed into product fluid, also, a control system for controlling the fluid vapor distillation apparatus.

Some embodiments of this aspect of the present invention include one or more of the following: Wherein, the control system includes a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input. Wherein the control system includes at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water. Wherein the heat exchanger is disposed about the housing of the evaporator condenser. Wherein the heat exchanger further includes wherein the outer tube is a source fluid flow path and the at least one inner tube is a product fluid flow path. Wherein the heat exchanger further includes at least three inner tubes. Wherein the at least three inner tubes are twined to form a substantially helical shape. Wherein the heat exchanger further includes two ends, and at each end a connector is attached, whereby the connectors form a connection to the evaporator condenser. Wherein the evaporator condenser tubes further includes packing inside the tubes. Wherein the packing is a rod. Wherein the evaporator condenser further including a steam chest fluidly connected to the plurality of tubes. Wherein the regenerative blower further includes an impeller assembly driven by a magnetic drive coupling. Wherein the control system includes at least two processors, a motor control engine processor and an ARM processor. Wherein the fluid vapor distillation apparatus further includes a conductivity meter and a conductivity cell to determine the conductivity of the product fluid.

In accordance with one aspect of the present invention, a water vapor distillation system is disclosed. The system includes a water vapor distillation apparatus including a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporative condenser whereby compressed steam is transformed into product fluid, also, a control system for controlling the water vapor distillation apparatus, and, a Stirling engine electrically connected to the water vapor distillation apparatus, wherein the Stirling engine at least partially powers the water vapor distillation apparatus.

Some embodiments of this aspect of the present invention include one or more of the following: wherein the control system includes a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input. Wherein the system for controlling the apparatus further includes at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water. Wherein the Stirling engine includes at least one rocking drive mechanism including a rocking beam having a rocker pivot, at least one cylinder, at least one piston, the piston housed within a respective cylinder whereby the piston is capable of substantially linearly reciprocating within the respective cylinder, and at least one coupling assembly having a proximal end and a distal end, the proximal end being connected to the piston and the distal end being connected to the rocking beam by an end pivot, whereby linear motion of the piston is converted to rotary motion of the rocking beam, a crankcase housing the rocking beam and housing a first portion of the coupling assembly, a crankshaft coupled to the rocking beam by way of a connecting rod, whereby the rotary motion of the rocking beam is transferred to the crankshaft, a working space housing the at least one cylinder, the at least one piston and a second portion of the coupling assembly, and a seal for sealing the workspace from the crankcase. Some embodiments of this embodiment of the system may include one or more of the following: Wherein the seal is a rolling diaphragm. Wherein the coupling assembly further includes a piston rod, and a link rod, the piston rod and link rod coupled together by a coupling means. Wherein the system further including a lubricating fluid pump in the crankcase. Various embodiments of the system may include one or more of the following: Wherein the heat exchanger is disposed about the housing of the evaporator condenser. Wherein the heat exchanger further includes where the outer tube is a source fluid flow path and the at least one inner tube is a product fluid flow path. Wherein the heat exchanger further comprising at least three inner tubes.

In accordance with another aspect of the present invention, a water vapor distillation apparatus is disclosed. The apparatus includes a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input.

Some embodiments of this aspect of the present invention include one or more of the following: wherein the apparatus further includes at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water. Wherein the apparatus further includes including a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporative condenser whereby compressed steam is transformed into product fluid. Wherein the heat exchanger is disposed about the housing of the evaporator condenser. Wherein the heat exchanger further includes wherein the outer tube is a source fluid flow path and the at least one inner tube is a product fluid flow path. Wherein the heat exchanger further includes at least three inner tubes. Wherein the at least three inner tubes are twined to form a substantially helical shape. Wherein the heat exchanger further includes two ends, and at each end a connector is attached, whereby the connectors form a connection to the evaporator condenser. Wherein the evaporator condenser tubes further includes packing inside the tubes. Wherein the packing is a rod. Wherein the evaporator condenser further including a steam chest fluidly connected to the plurality of tubes. Wherein the regenerative blower further includes an impeller assembly driven by a magnetic drive coupling. Wherein the control system includes at least two processors, a motor control engine processor and an ARM processor. Wherein the fluid vapor distillation apparatus further includes a conductivity meter and a conductivity cell to determine the conductivity of the product fluid.

In accordance with another aspect of the present invention, a water vapor distillation apparatus is disclosed. The apparatus includes a control system for controlling the water vapor distillation apparatus, the control system including at least one controller, an idle state wherein the at least one controllers are off, a fill state wherein the source valve is opened and source fluid enters a sump in the fluid vapor distillation apparatus, a heat state wherein a heater in the sump is maximized until fluid in the sump reaches a predetermined temperature, a heat exchanger prime state wherein the source valve is opened to a predetermined duty cycle, a start pump state wherein a bearing feed pump is run at a predetermined speed, and a blow motor is started, and a run state wherein the fluid vapor distillation apparatus produces product water.

Some embodiments of this aspect of the present invention include one or more of the following: Wherein the control system further includes a blow down controller for controlling a blow down valve, a source flow controller for controlling a source flow valve, and a blow down level sensor in communication with a blow down controller and a source flow controller, the blow down level sensor sends signals related to the blow down level to the blow down controller and the source flow controller indicative of the blow down level, wherein the source flow controller actuates the source flow valve based at least on the blow down level sensor signals, and wherein the blow down controller actuates the blow down valve based at least on the blow down level sensor signals, whereby the blow down level and the source flow level are maintained using the blow down level sensor signals as input. Wherein the apparatus further includes a source fluid input, an evaporator condenser apparatus including a substantially cylindrical housing, and a plurality of tubes in the housing, whereby the source fluid input is fluidly connected to the evaporator condenser and the evaporator condenser transforms source fluid into steam and transforms compressed steam into product fluid, a heat exchanger fluidly connected to the source fluid input and a product fluid output, the heat exchanger including an outer tube, and at least one inner tube, and a regenerative blower fluidly connected to the evaporator condenser, whereby the regenerative blower compresses steam, and whereby compressed steam flows to the evaporative condenser whereby compressed steam is transformed into product fluid. Wherein the heat exchanger is disposed about the housing of the evaporator condenser. Wherein the heat exchanger further includes wherein the outer tube is a source fluid flow path and the at least one inner tube is a product fluid flow path. Wherein the heat exchanger further includes at least three inner tubes. Wherein the at least three inner tubes are twined to form a substantially helical shape. Wherein the heat exchanger further includes two ends, and at each end a connector is attached, whereby the connectors form a connection to the evaporator condenser. Wherein the evaporator condenser tubes further includes packing inside the tubes. Wherein the packing is a rod. Wherein the evaporator condenser further including a steam chest fluidly connected to the plurality of tubes. Wherein the regenerative blower further includes an impeller assembly driven by a magnetic drive coupling. Wherein the control system includes at least two processors, a motor control engine processor and an ARM processor. Wherein the fluid vapor distillation apparatus further includes a conductivity meter and a conductivity cell to determine the conductivity of the product fluid.

In accordance with one aspect of the present invention, a fluid vapor distillation apparatus is disclosed. The apparatus includes a source fluid input, and an evaporator condenser apparatus. The evaporator condenser apparatus includes a substantially cylindrical housing and a plurality of tubes in the housing. The source fluid input is fluidly connected to the evaporator condenser and the evaporator condenser transforms source fluid into steam and transforms compressed steam into product fluid. Also included in the fluid vapor distillation apparatus is a heat exchanger fluidly connected to the source fluid input and a product fluid output. The heat exchanger includes an outer tube and at least one inner tube. Also included in the fluid vapor distillation apparatus is a regenerative blower fluidly connected to the evaporator condenser. The regenerative blower compresses steam, and the compressed steam flows to the evaporative condenser where compressed steam is transformed into product fluid. The fluid vapor distillation apparatus also includes a control system.

Some embodiments of this aspect of the present invention include one or more of the following: where the heat exchanger is disposed about the housing of the evaporator condenser; where the heat exchanger further includes wherein the outer tube is a source fluid flow path and the at least one inner tube is a product fluid flow path; where the heat exchanger further includes at least three inner tubes; where the at least three inner tubes are twined to form a substantially helical shape; where the heat exchanger further includes two ends, and at each end a connector is attached, whereby the connectors form a connection to the evaporator condenser; where the evaporator condenser tubes further include packing inside the tubes; where the packing is a rod; where the evaporator condenser further includes a steam chest fluidly connected to the plurality of tubes; and where the regenerative blower further comprising an impeller assembly driven by a magnetic drive coupling.

In accordance with another aspect of the present invention, a water vapor distillation system is disclosed. The water vapor distillation system includes a source fluid input, and an evaporator condenser apparatus. The evaporator condenser apparatus includes a substantially cylindrical housing and a plurality of tubes in the housing. The source fluid input is fluidly connected to the evaporator condenser and the evaporator condenser transforms source fluid into steam and transforms compressed steam into product fluid. Also included in the fluid vapor distillation apparatus is a heat exchanger fluidly connected to the source fluid input and a product fluid output. The heat exchanger includes an outer tube and at least one inner tube. Also included in the fluid vapor distillation apparatus is a regenerative blower fluidly connected to the evaporator condenser. The regenerative blower compresses steam, and the compressed steam flows to the evaporative condenser where compressed steam is transformed into product fluid.

The water vapor distillation system also includes a Stirling engine electrically connected to the water vapor distillation apparatus. The Stirling engine at least partially powers the water vapor distillation apparatus.

Some embodiments of this aspect of the present invention include where the Stirling engine includes at least one rocking drive mechanism where the rocking drive mechanism includes: a rocking beam having a rocker pivot, at least one cylinder and at least one piston. The piston is housed within a respective cylinder. The piston is capable of substantially linearly reciprocating within the respective cylinder. Also, the drive mechanism includes at least one coupling assembly having a proximal end and a distal end. The proximal end is connected to the piston and the distal end is connected to the rocking beam by an end pivot. The linear motion of the piston is converted to rotary motion of the rocking beam. Also, a crankcase housing the rocking beam and housing a first portion of the coupling assembly is included. A crankshaft coupled to the rocking beam by way of a connecting rod is also included. The rotary motion of the rocking beam is transferred to the crankshaft. The machine also includes a working space housing the at least one cylinder, the at least one piston and a second portion of the coupling assembly. A seal is included for sealing the workspace from the crankcase.

Additionally, some embodiments of this aspect of the present invention include any one or more of the following: where the seal is a rolling diaphragm; also, where the coupling assembly further includes a piston rod and a link rod; where the piston rod and link rod are coupled together by a coupling means; where the heat exchanger is disposed about the housing of the evaporator condenser; where the heat exchanger further comprising wherein the outer tube is a source fluid flow path and the at least one inner tube is a product fluid flow path; where the heat exchanger further comprising at least three inner tubes; where the evaporator condenser further includes a steam chest fluidly connected to the plurality of tubes; and where the regenerative blower further includes an impeller assembly driven by a magnetic drive coupling.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 2O is a schematic of an alternate embodiment of the tube-in-tube heat exchanger configuration;

FIG. 3 is an exploded view of the connectors for the fitting assembly that attaches to the tube-in-tube heat exchanger;

FIG. 3A is a cross-section view of fitting assembly for the tube-in-tube heat exchanger;

FIG. 3B is a cross-section view of fitting assembly for the tube-in-tube heat exchanger;

FIG. 3E is a cross-section view of the exemplary embodiment for the first connector;

FIG. 3F is a cross-section view of the exemplary embodiment for the first connector;

FIG. 3G is an isometric view of the exemplary embodiment for the second connector;

FIG. 3I is a cross-section view of the exemplary embodiment for the second connector;

FIG. 3J is a cross-section view of the exemplary embodiment for the second connector;

FIG. 13A is a cross-section view of the alternate embodiment of the evaporator/condenser;

FIG. 13C is a cross-section view of the alternate embodiment of the evaporator/condenser illustrating the arrangement of the tubes;

FIG. 14C is a cross-section view of the mist eliminator assembly;

FIG. 15J is a cross-section view of the exemplary embodiment of the regenerative blower;

FIG. 15L is a cross-section view of the exemplary embodiment of the regenerative blower;

FIG. 17B is a cross-section view of the alternate embodiment of the regenerative blower assembly;

FIG. 19B is cross-section view of the settling tank within the level sensor housing;

FIG. 19C is cross-section view of the blowdown sensor and product level sensor reservoirs within the level sensor housing;

FIG. 19F is a cross-section view of an alternate embodiment of the level sensor assembly;

FIG. 22 is a schematic of the flow path of the source water for the exemplary embodiment of the water vapor distillation apparatus;

FIG. 22A is a schematic of the source water entering the heat exchanger;

FIG. 22B is a schematic of the source water passing through the heat exchanger;

FIG. 22C is a schematic of the source water exiting the heat exchanger;

FIG. 22D is a schematic of the source water passing through the regenerative blower;

FIG. 22E is a schematic of the source water exiting the regenerative blower and entering FIG. 23 is a schematic of the flow paths of the blowdown water for the exemplary embodiment of the water vapor distillation apparatus;

FIG. 23A is a schematic of the blowdown water exiting evaporator/condenser assembly and entering the level sensor housing;

FIG. 23B is a schematic of the blowdown water filling the settling tank within the level sensor housing;

FIG. 23C is a schematic of the blowdown water filling the blowdown level sensor reservoir within the level sensor housing;

FIG. 23D is a schematic of the blowdown water exiting the level sensor housing and entering the strainer;

FIG. 23E is a schematic of the blowdown water exiting the strainer and entering the heat exchanger;

FIG. 23F is a schematic of the blowdown water passing through the heat exchanger;

Figure 23:
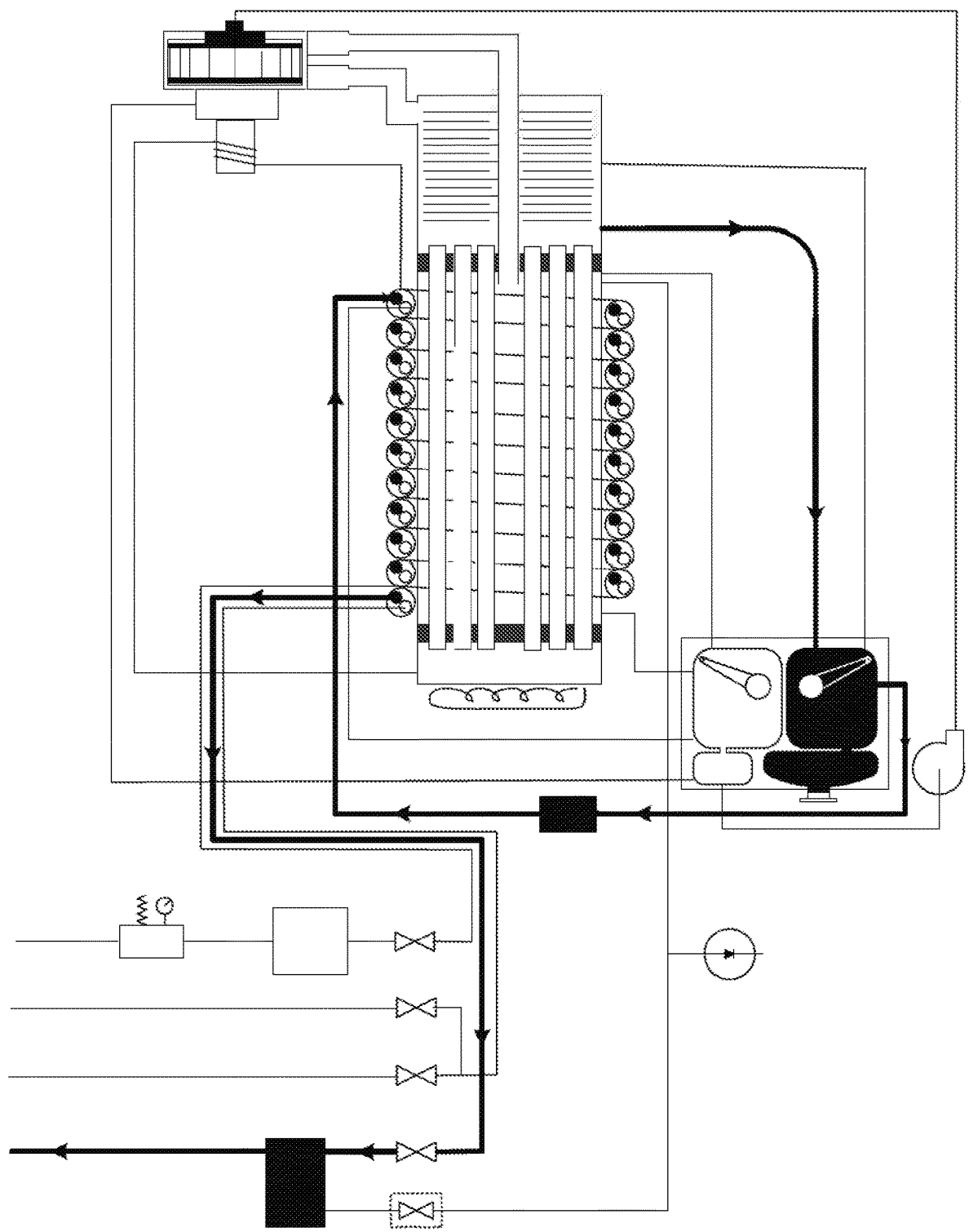
Figure 23A:
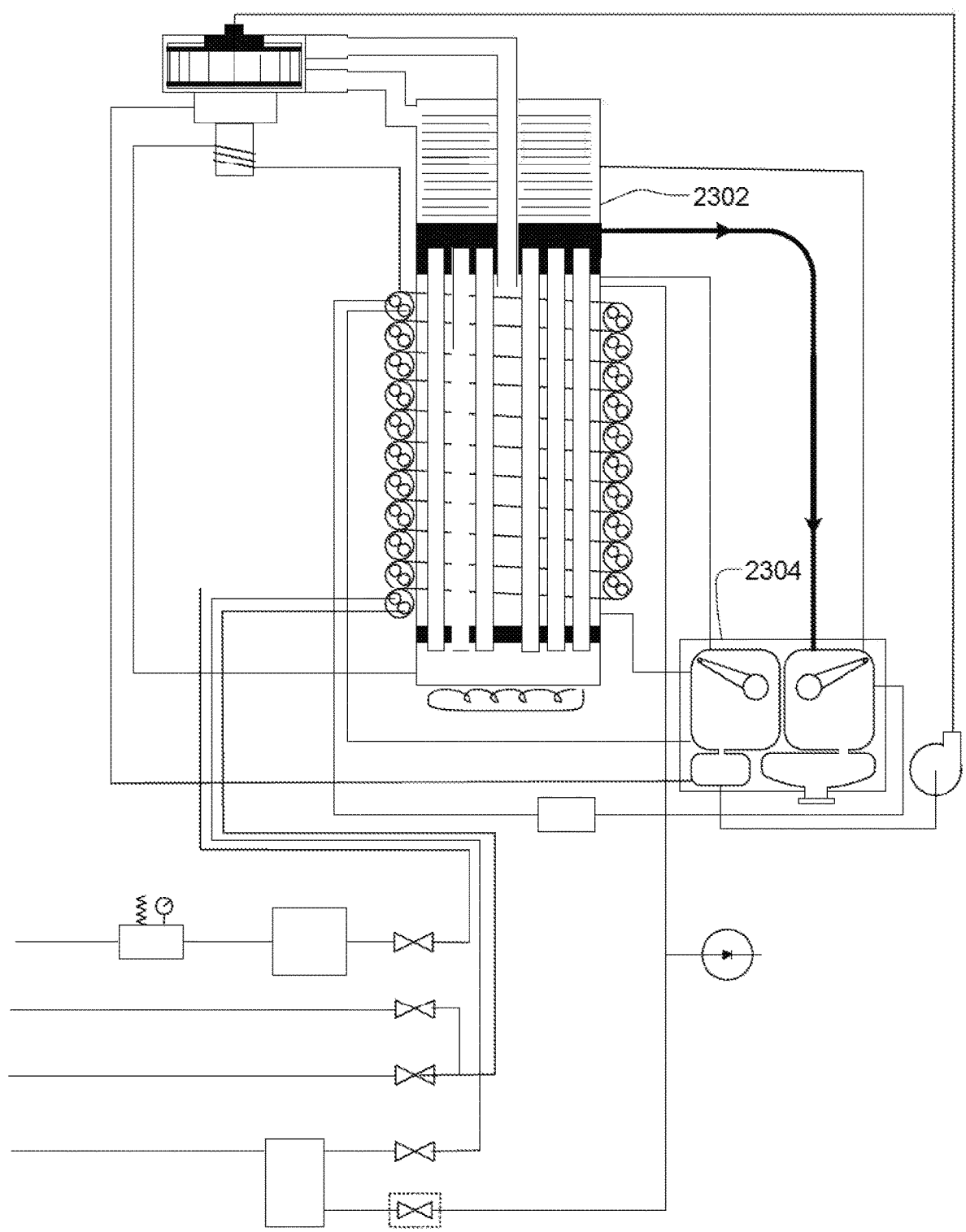
Figure 23B:
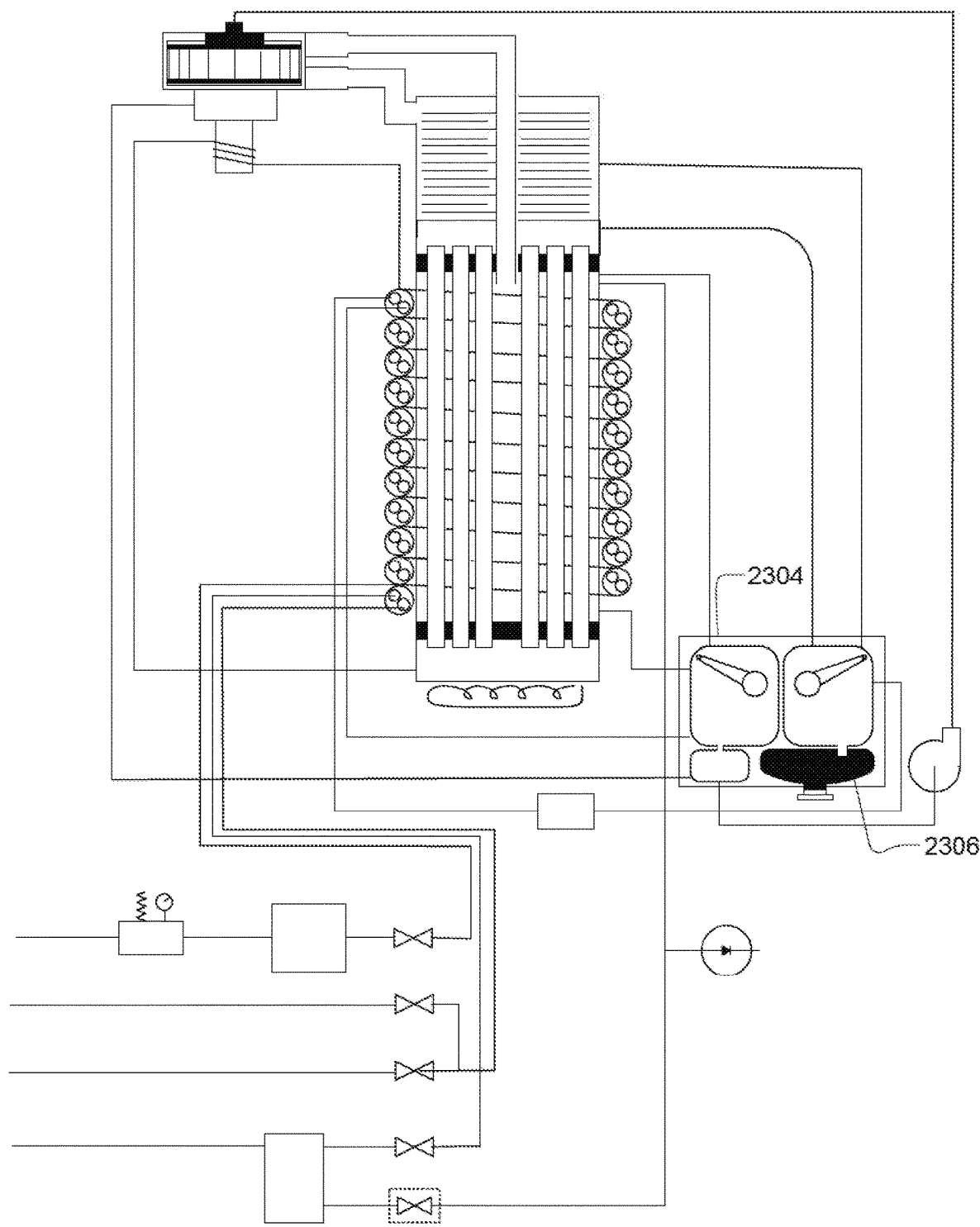
Figure 23C:
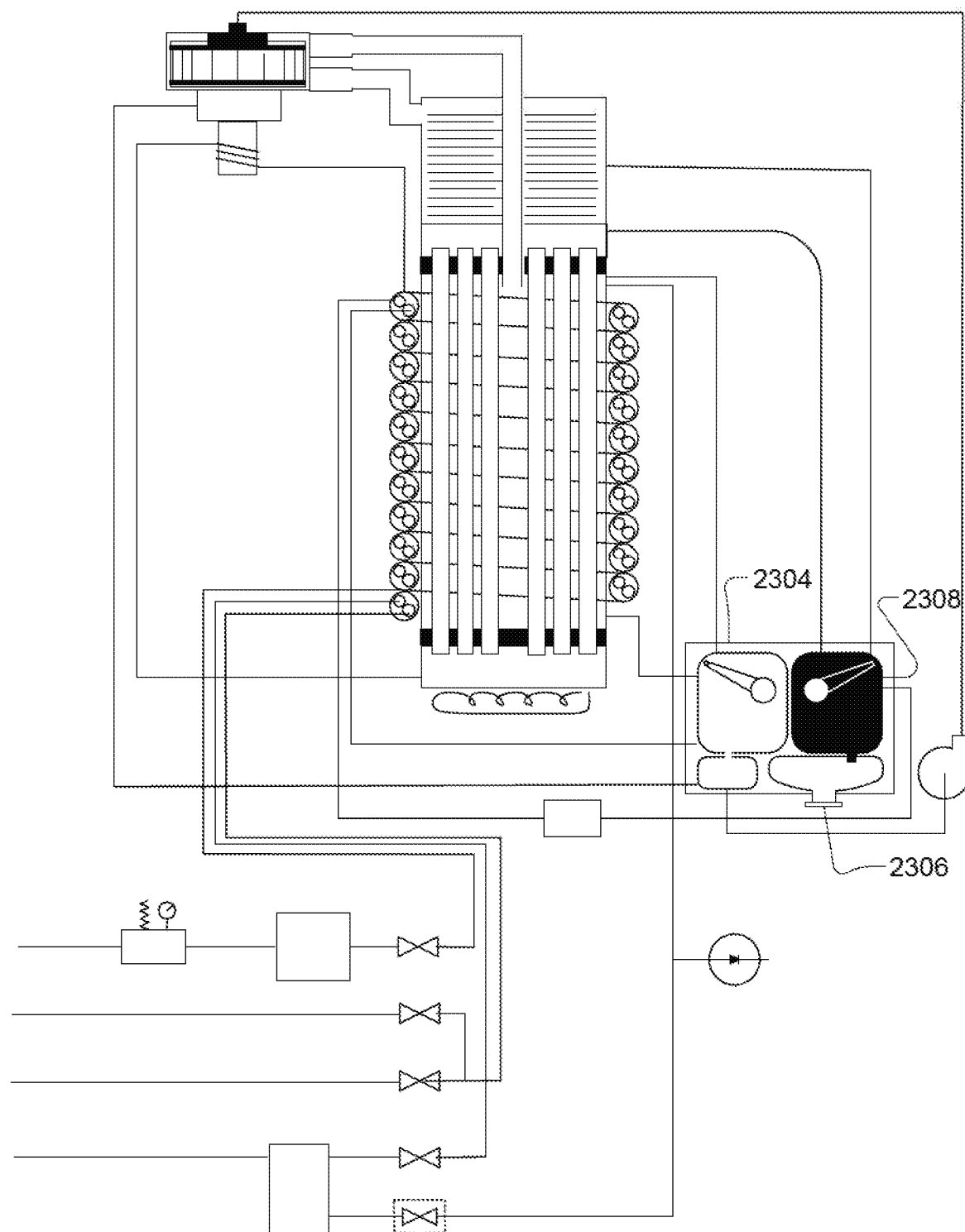
Figure 23D:
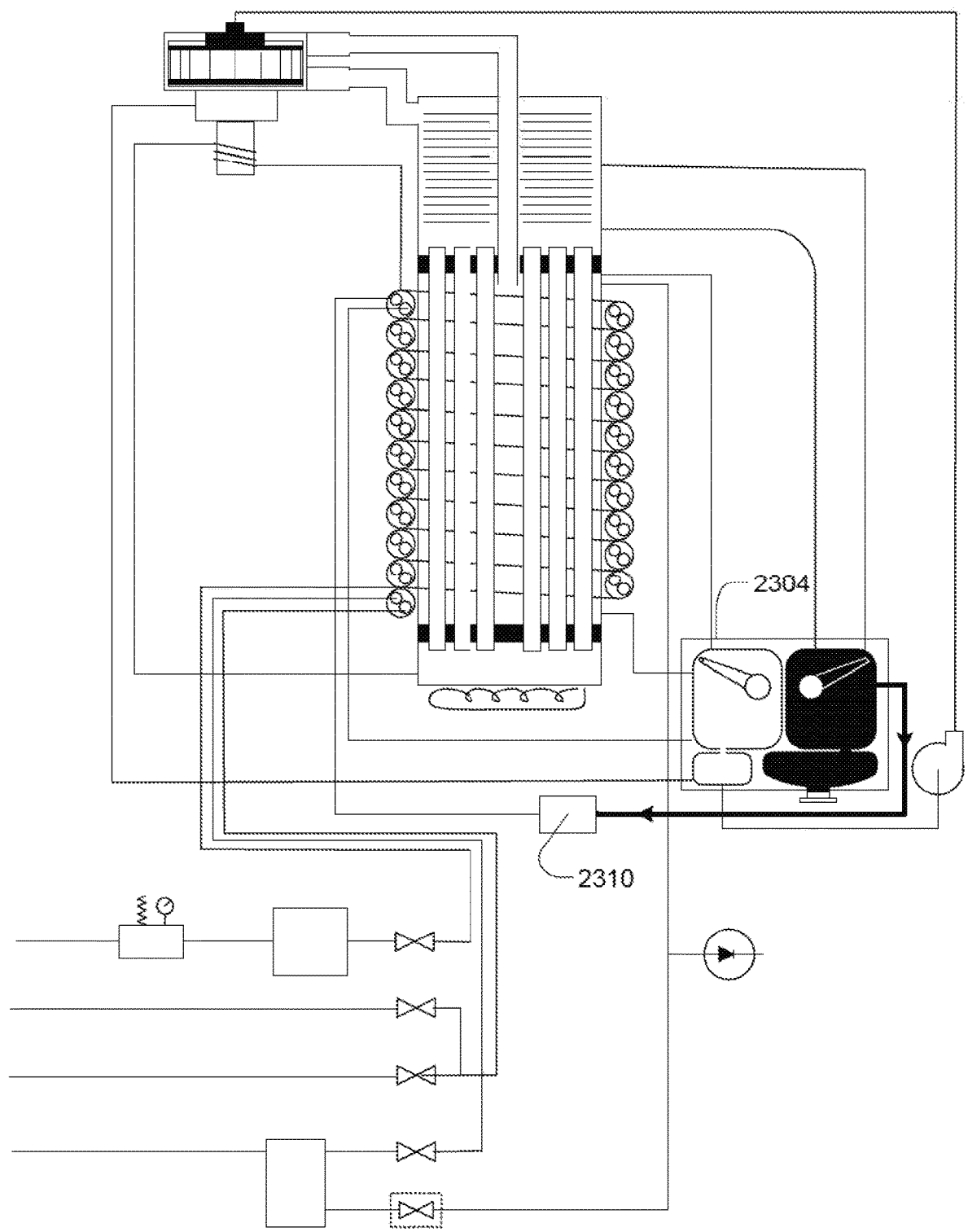
Figure 23E:
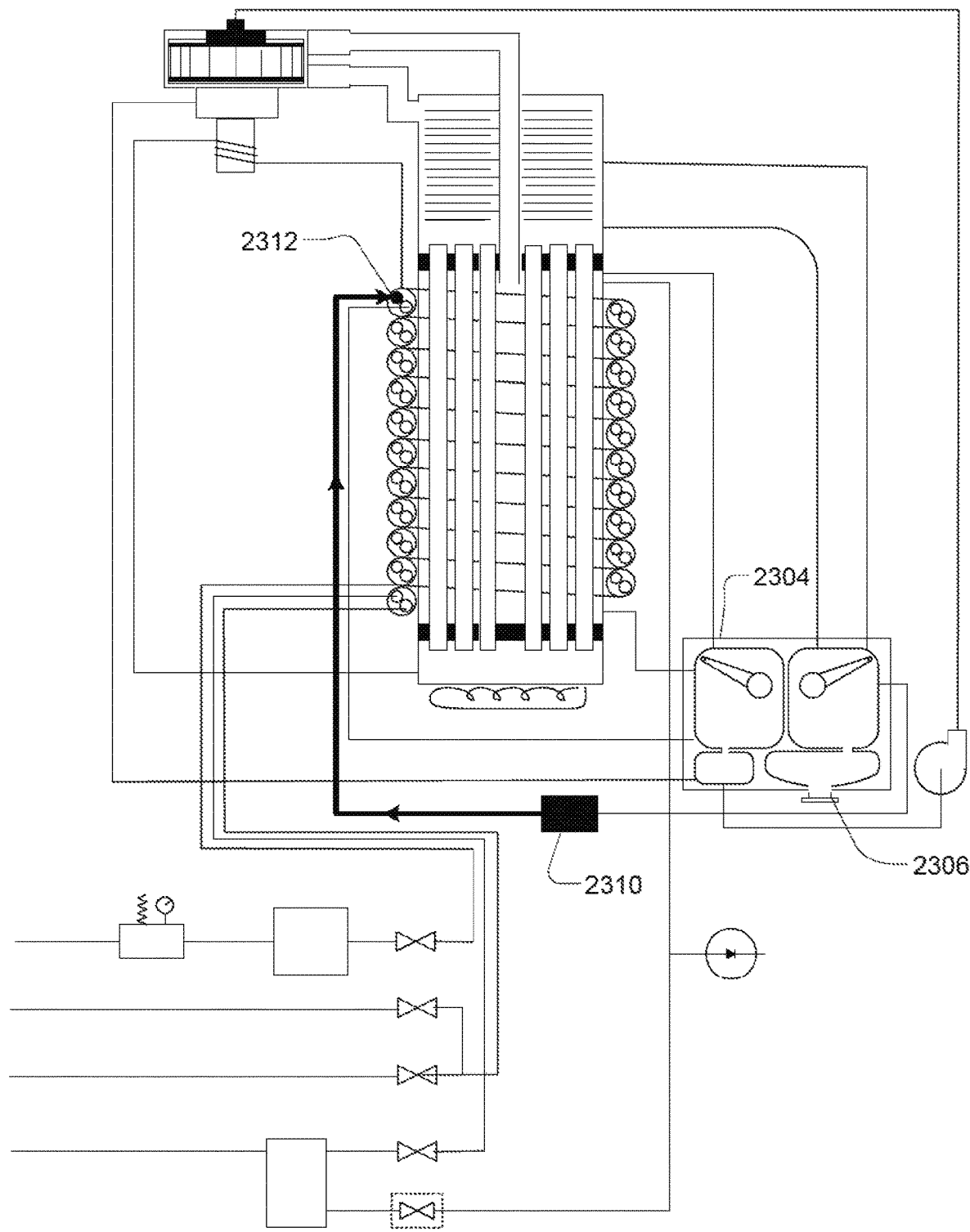
Figure 23F:
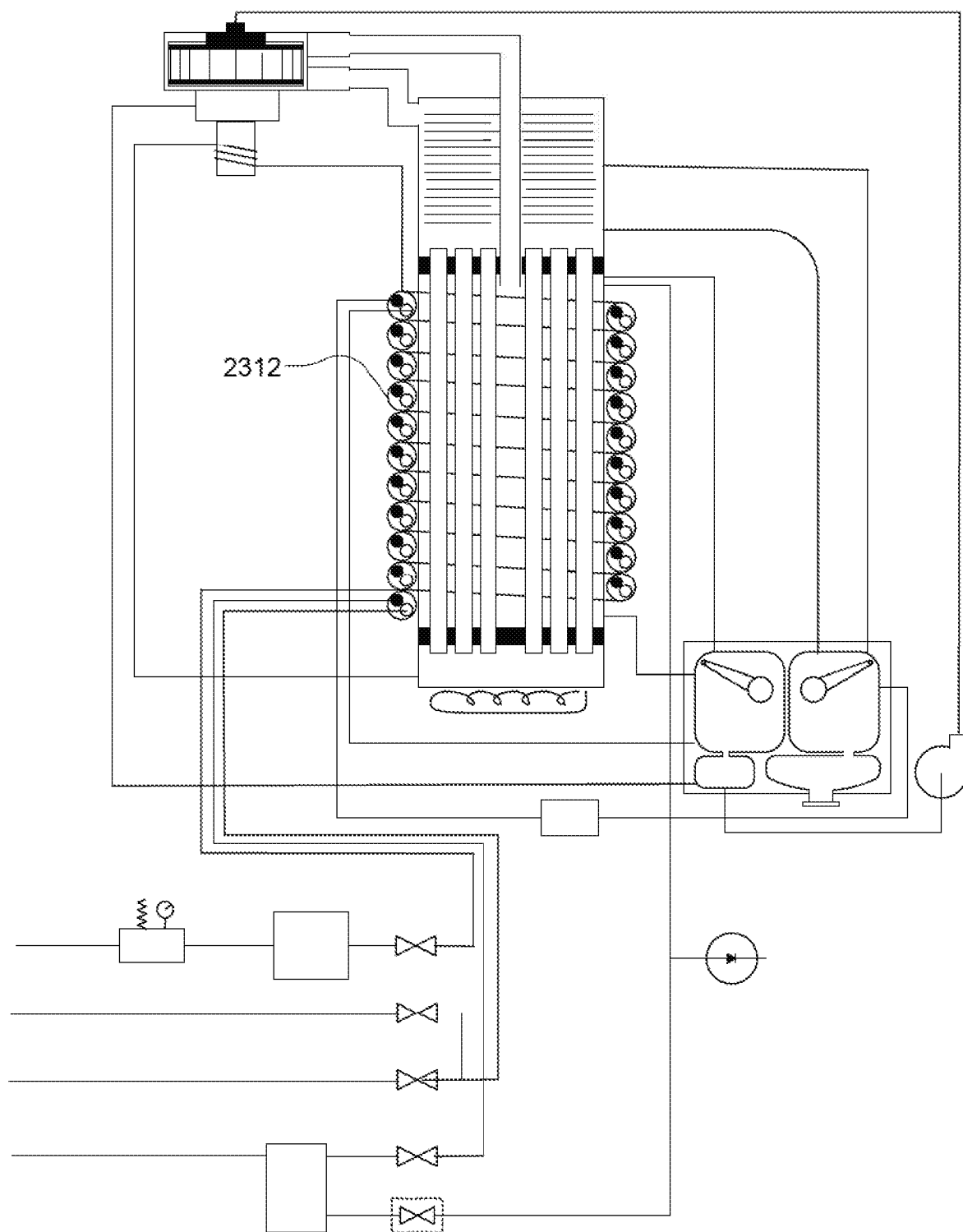
Figure 23G:
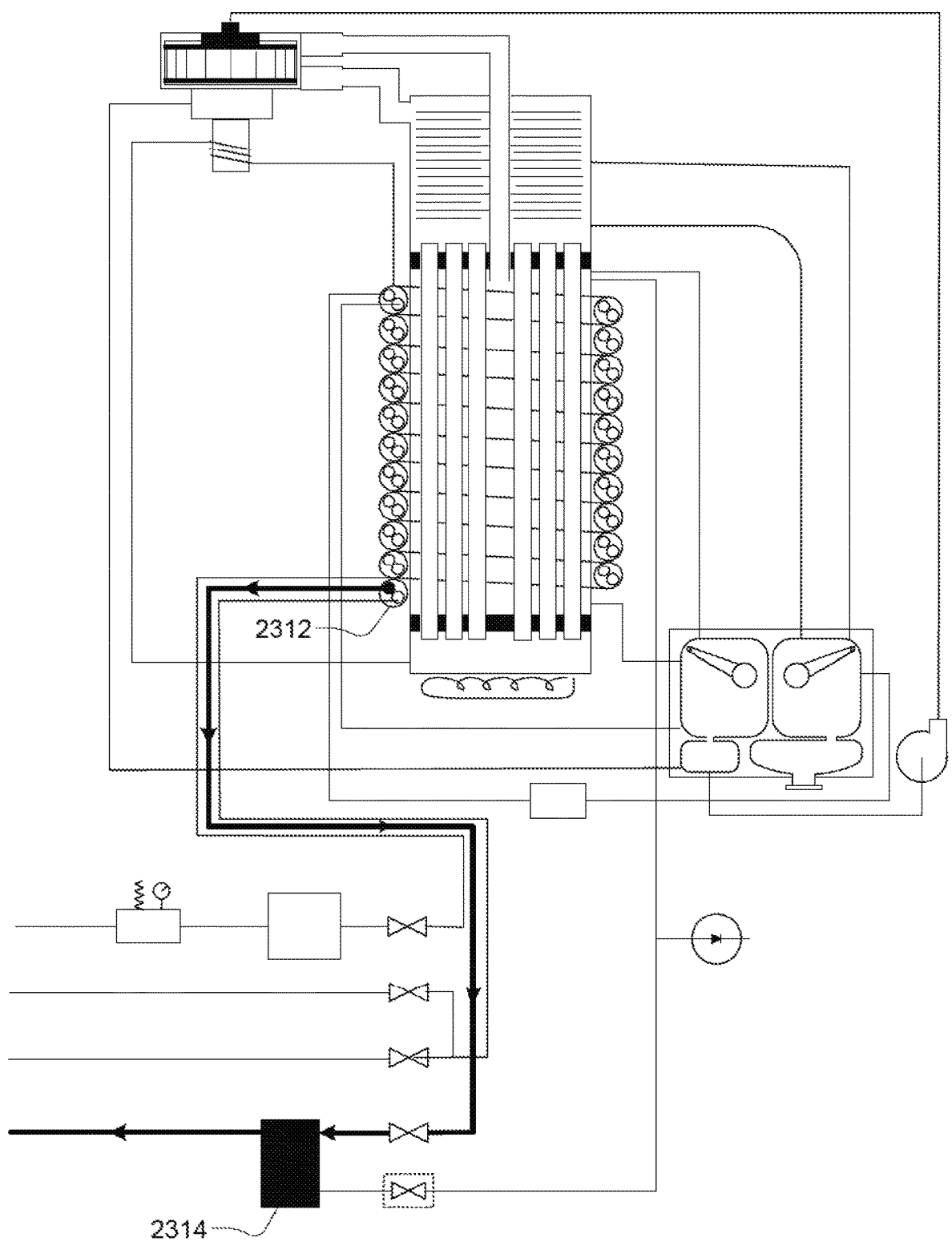
Figure 24:
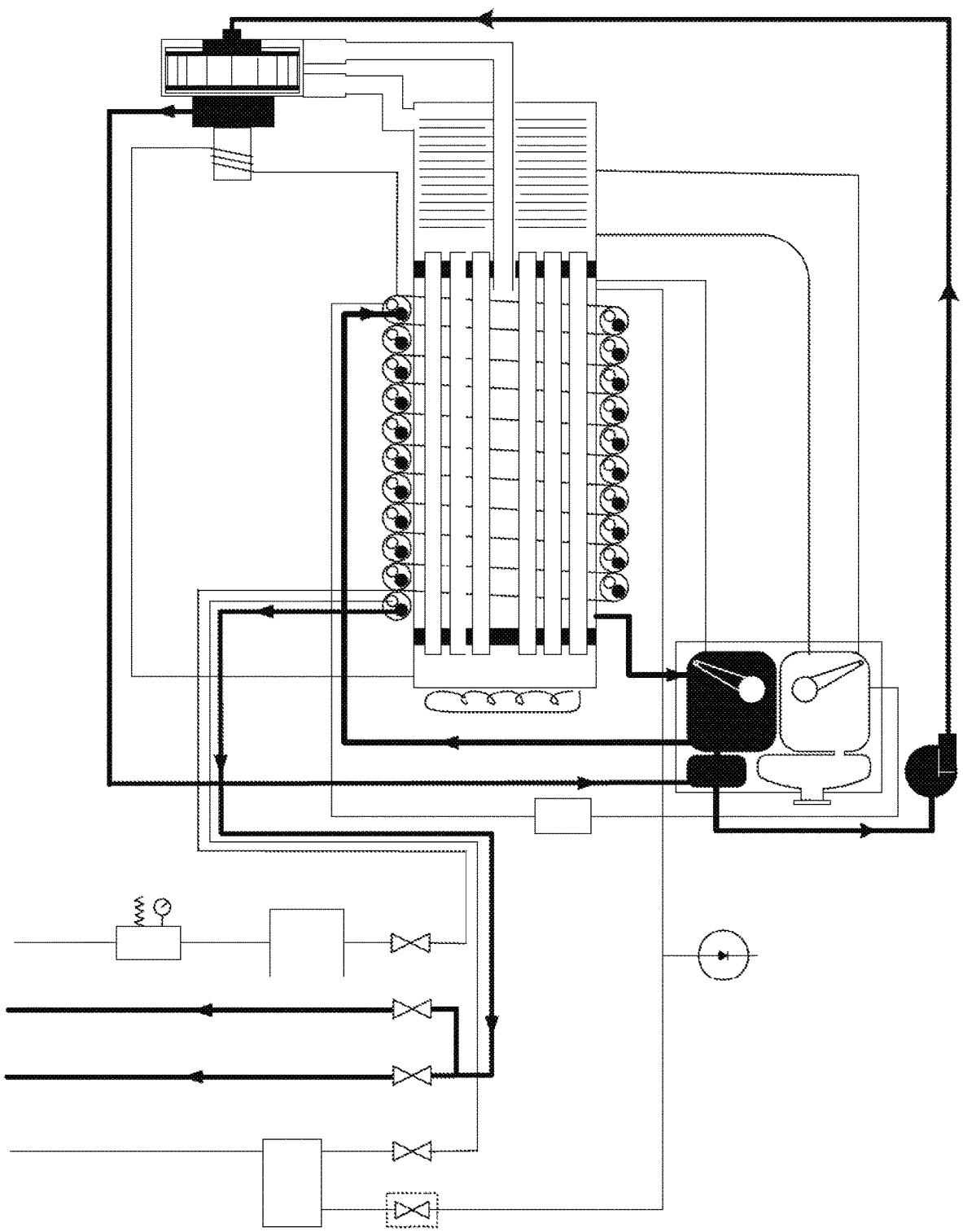
Figure 24A:
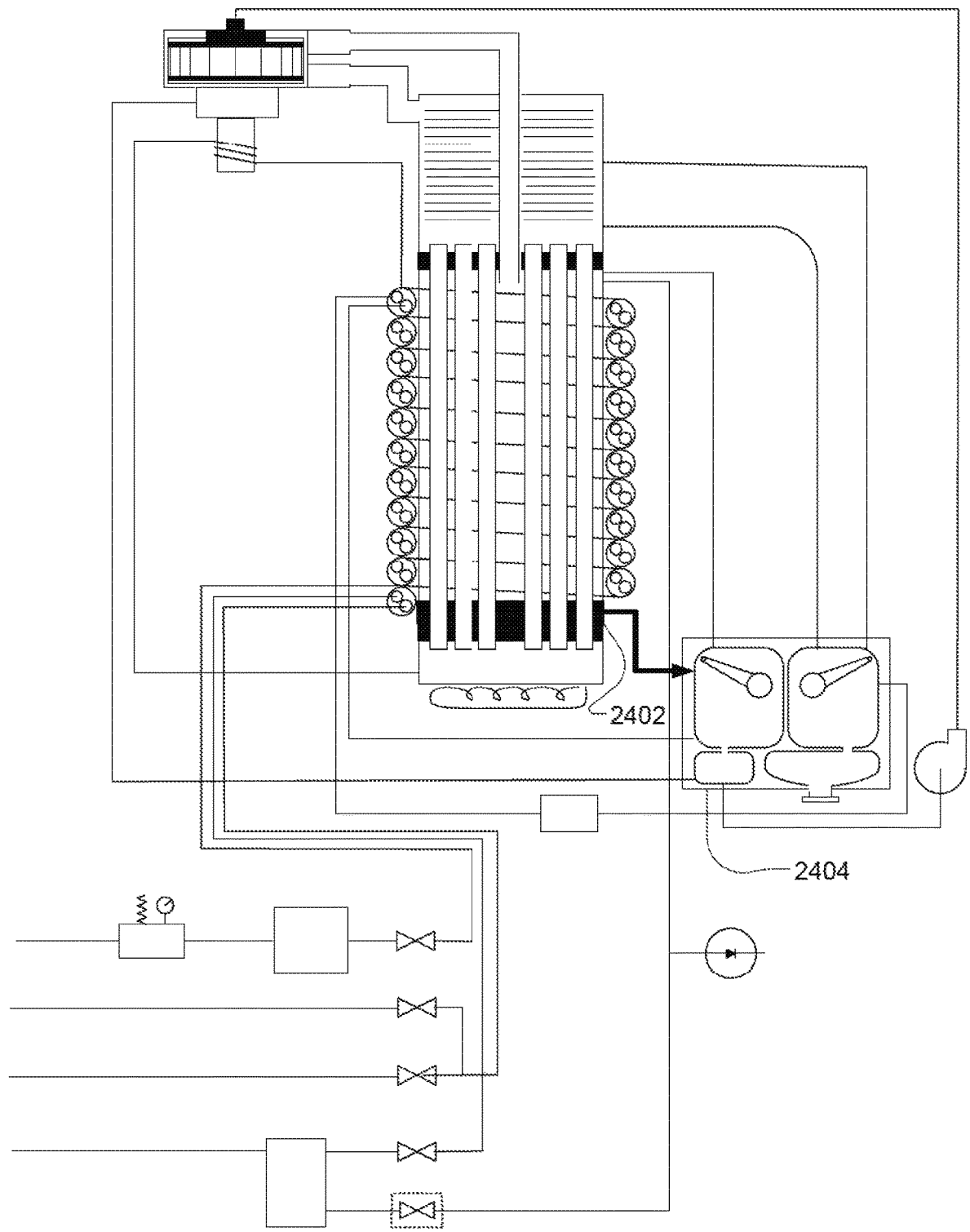
Figure 24B:
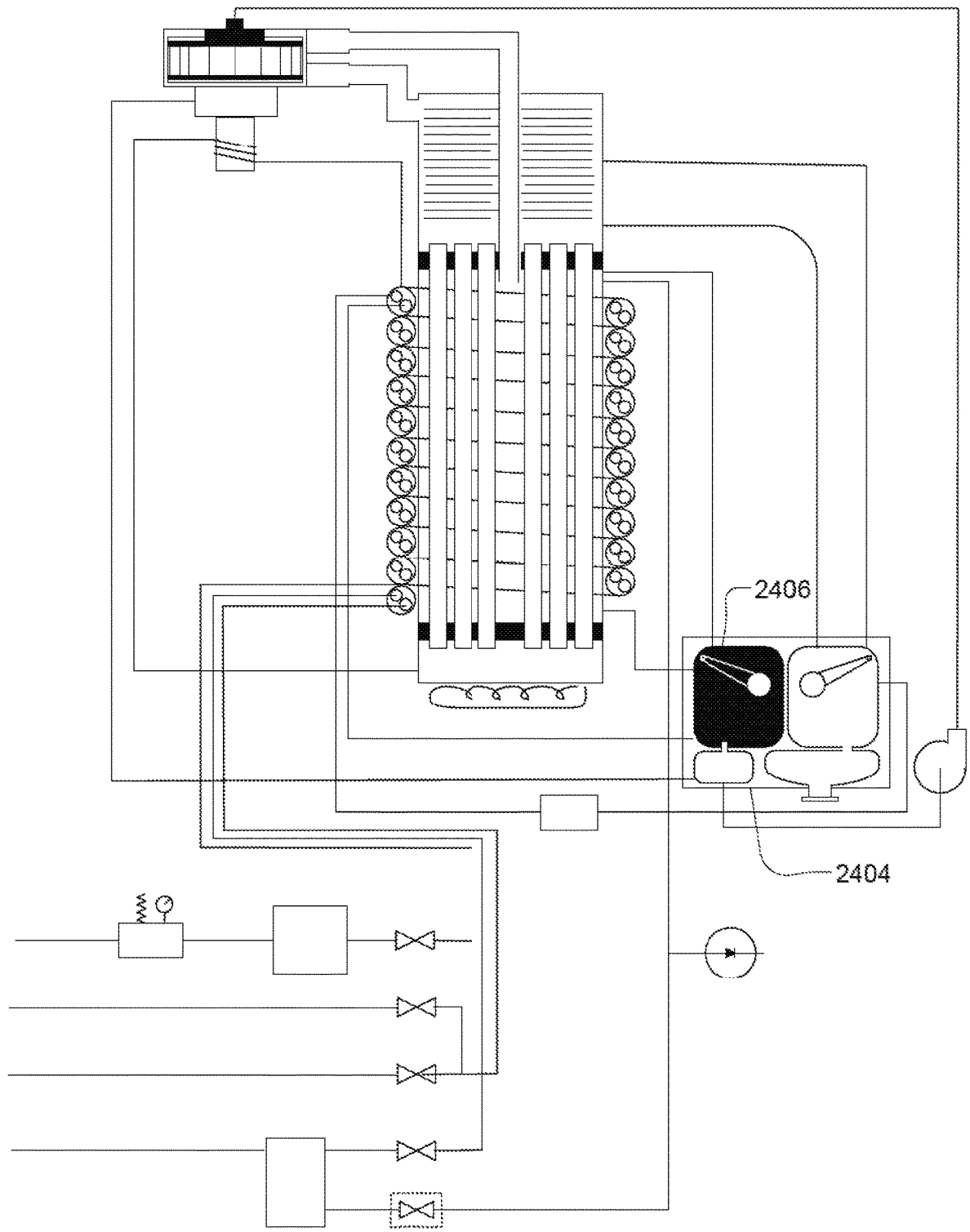
Figure 24C:
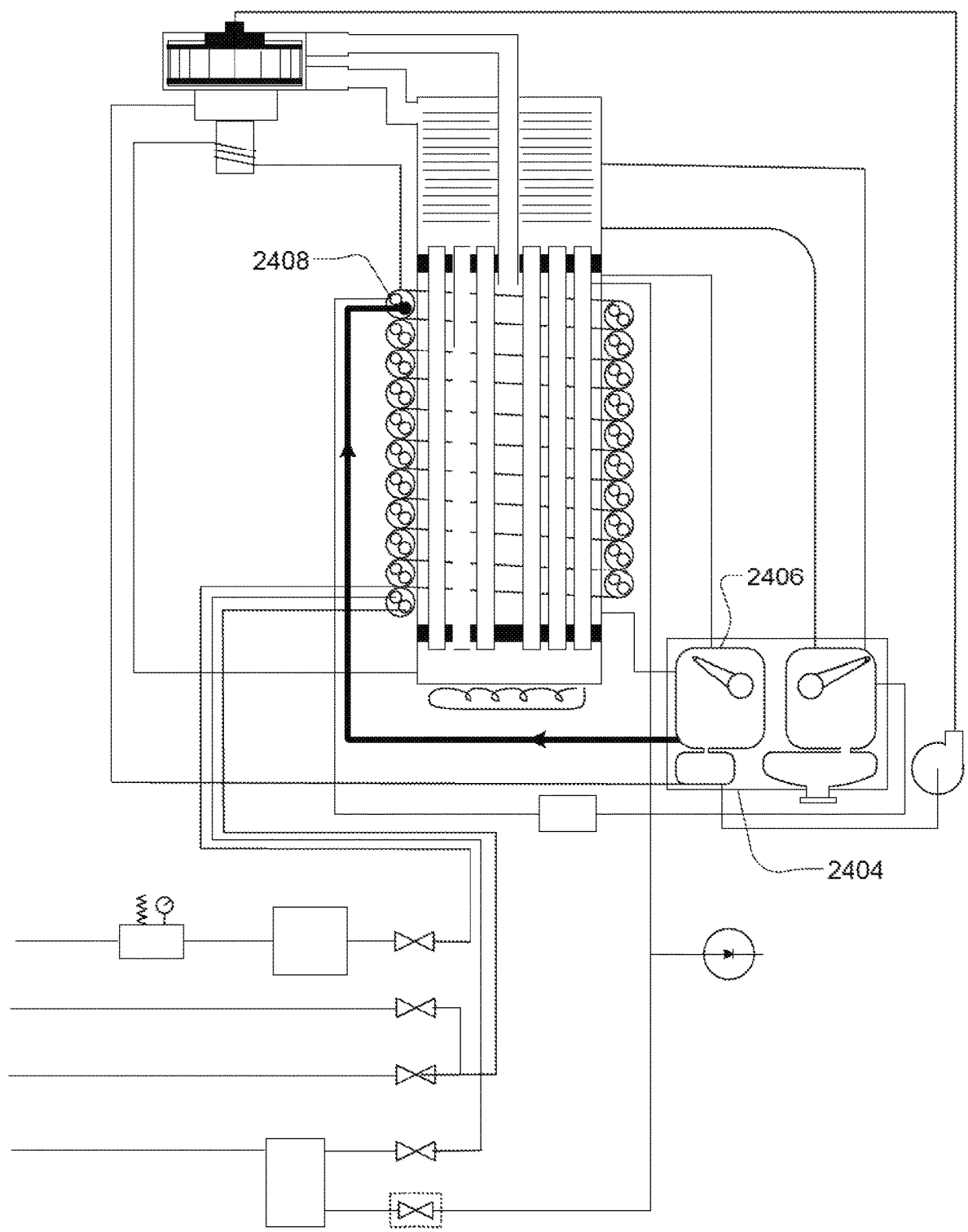
Figure 24D:
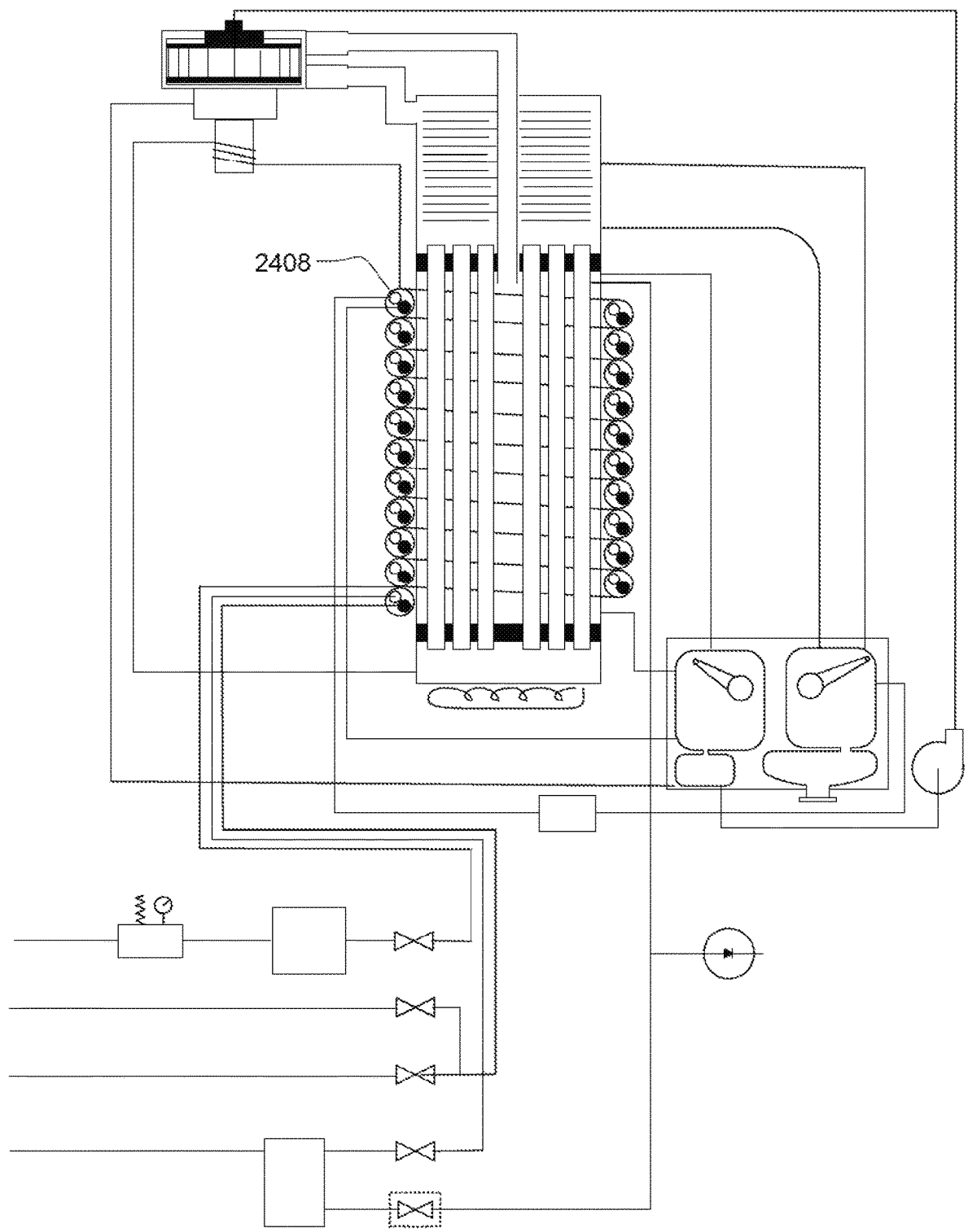
Figure 24E:
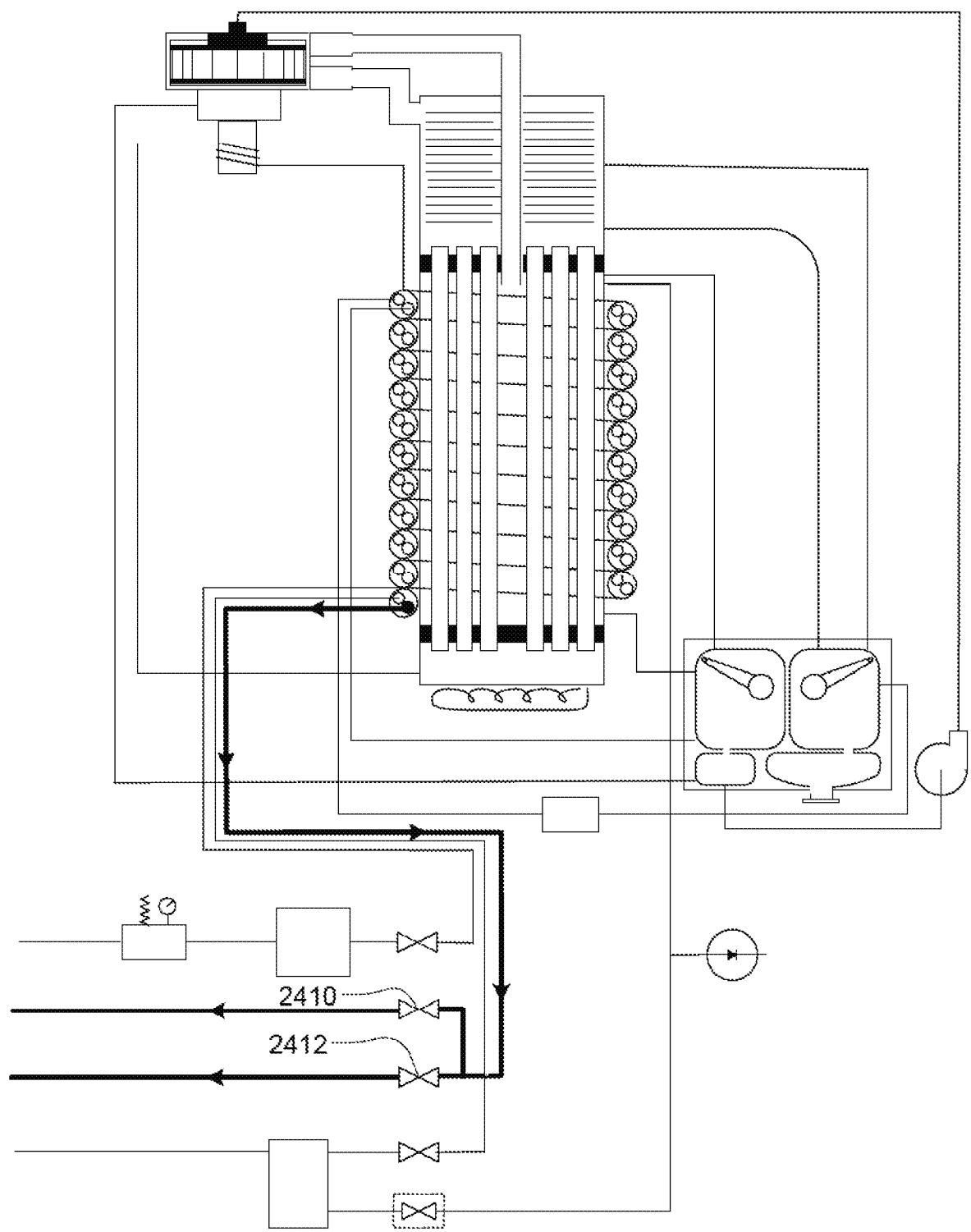
Figure 24F:
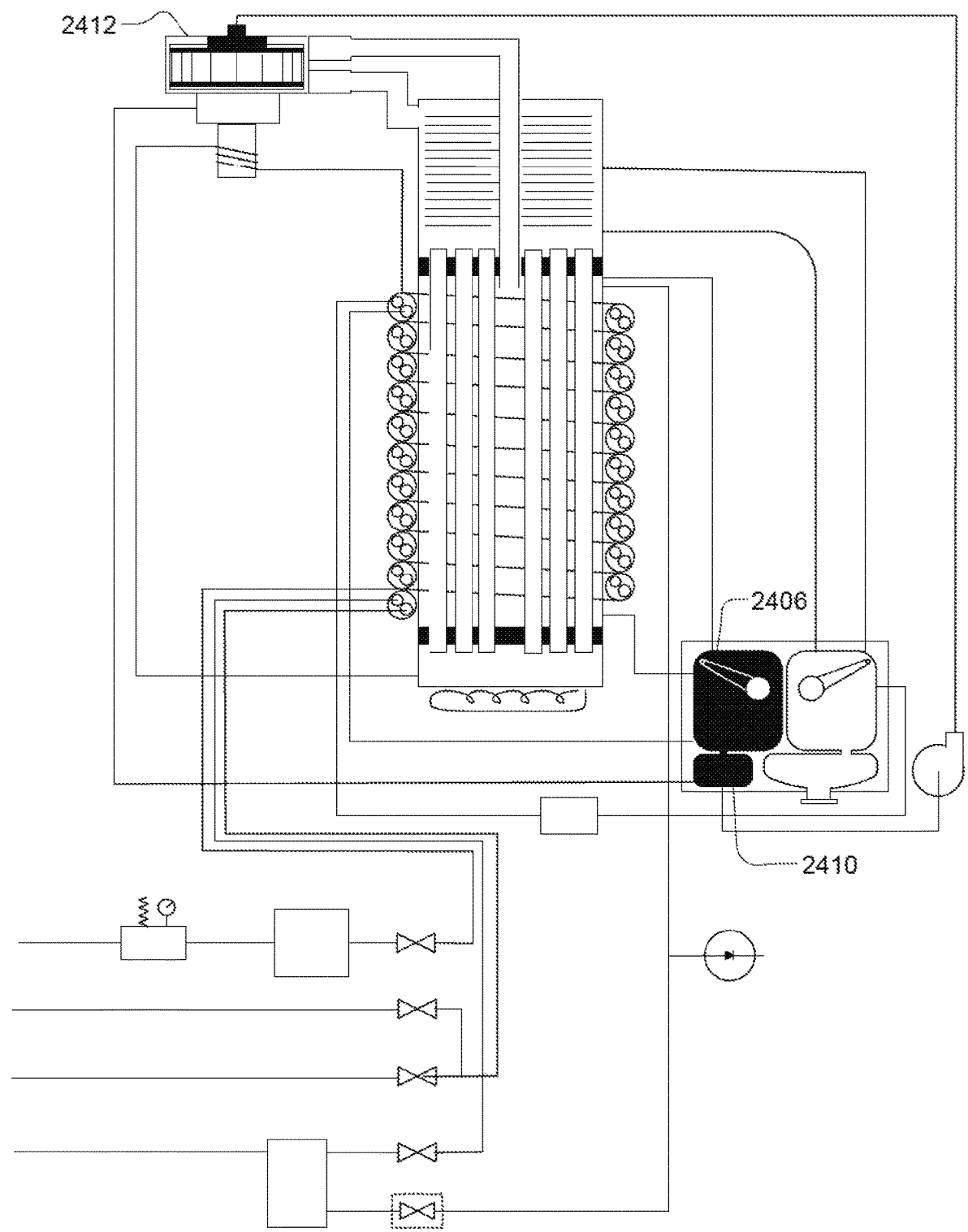
Figure 24G:
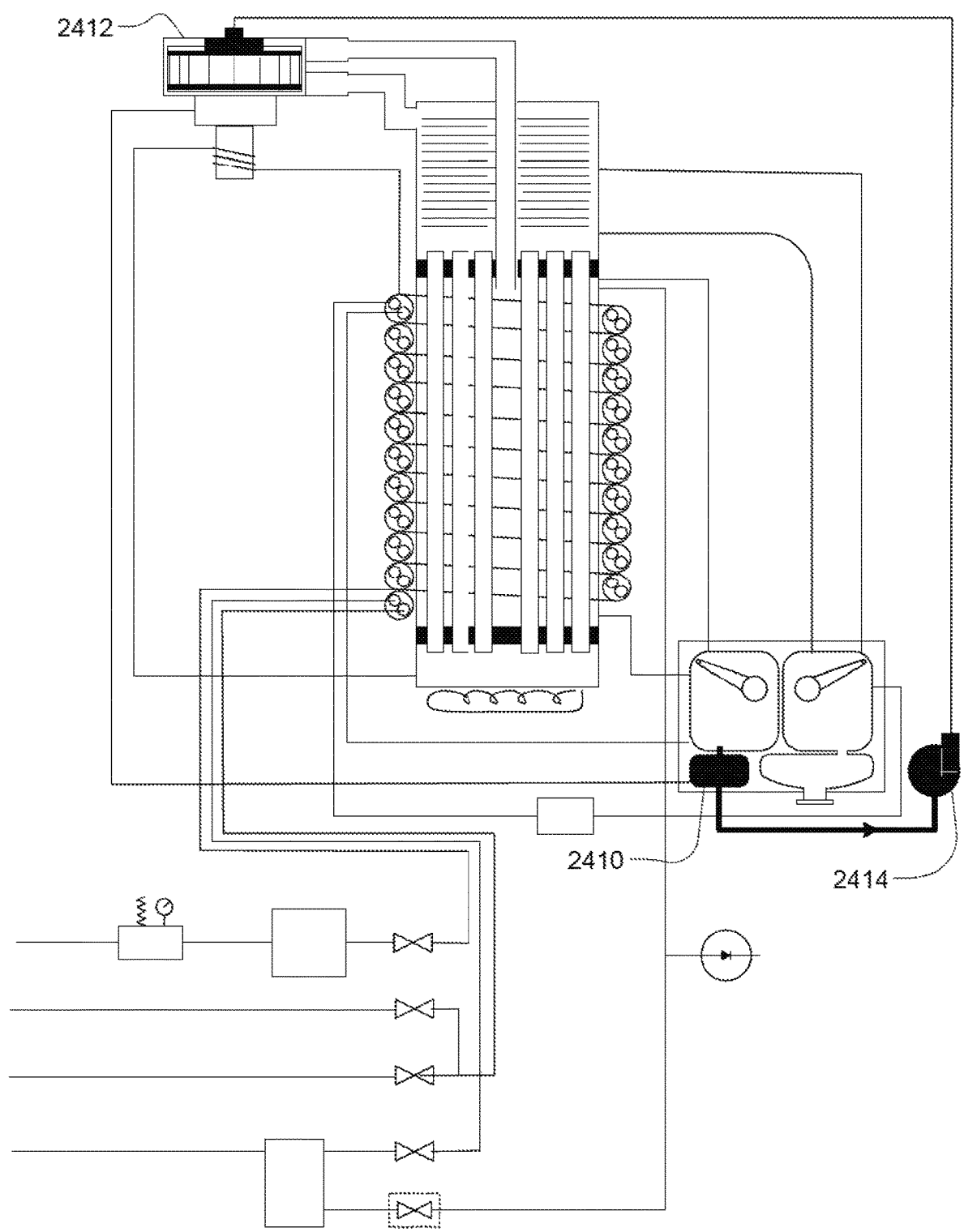
Figure 24H:
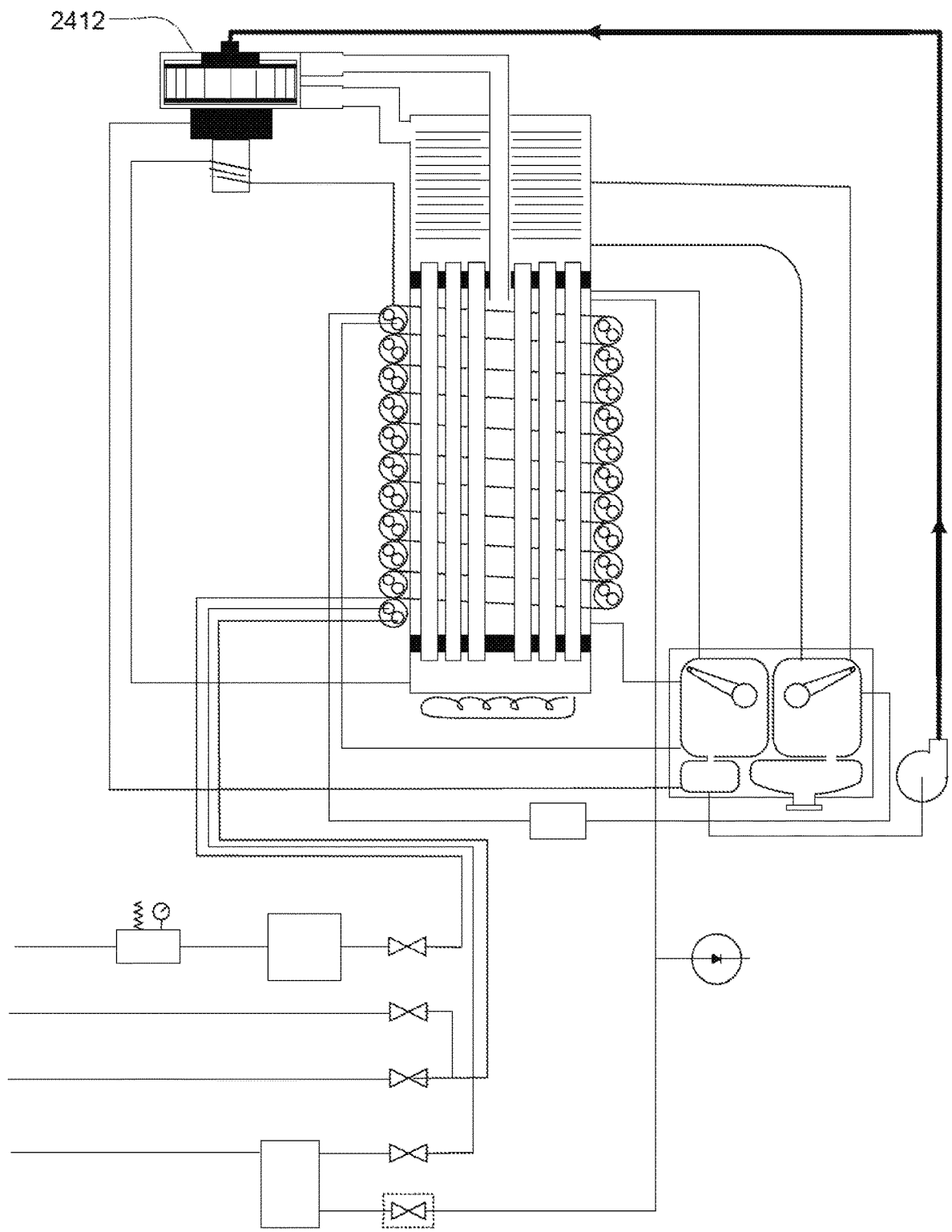
Figure 24I:
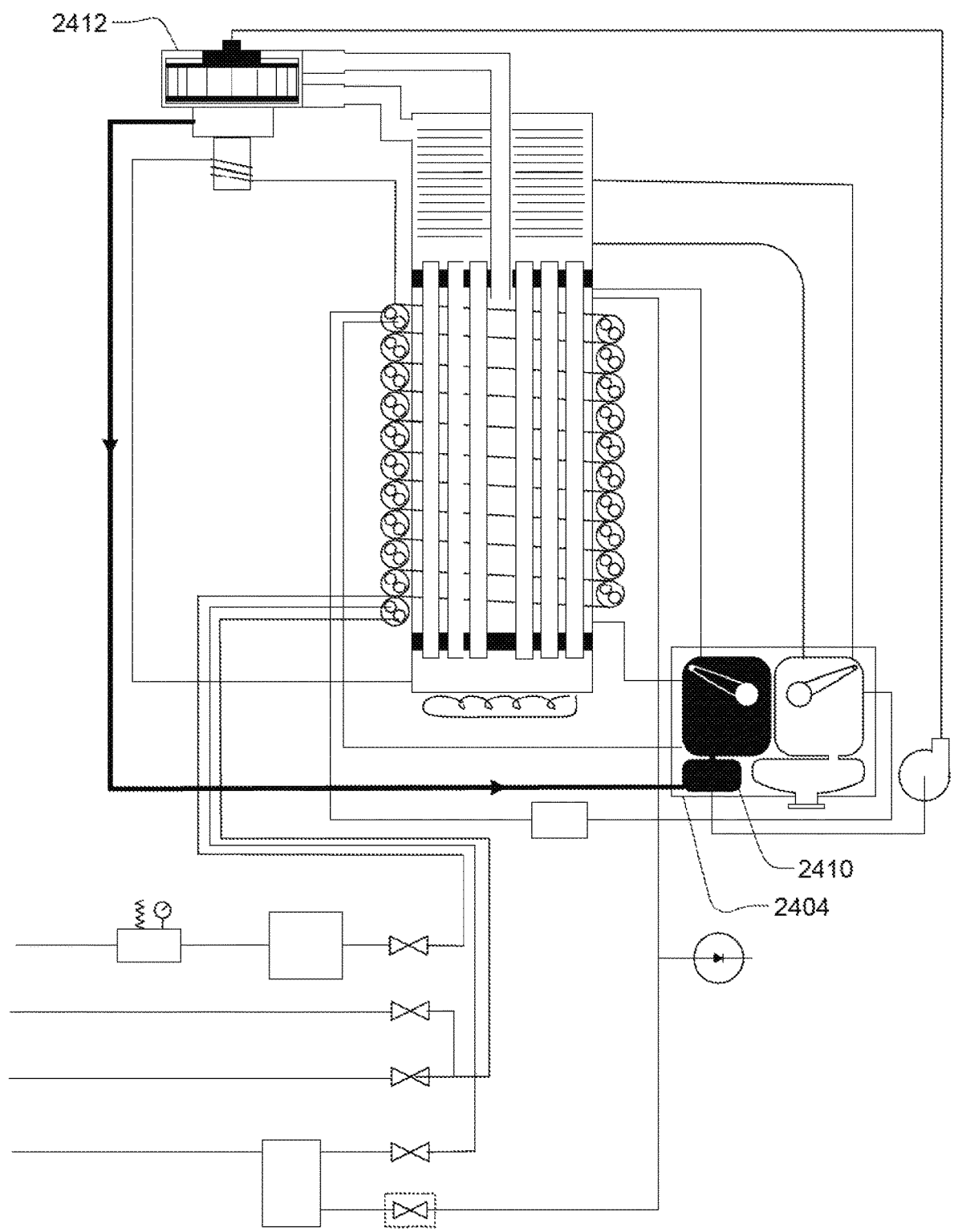
Figure 25:
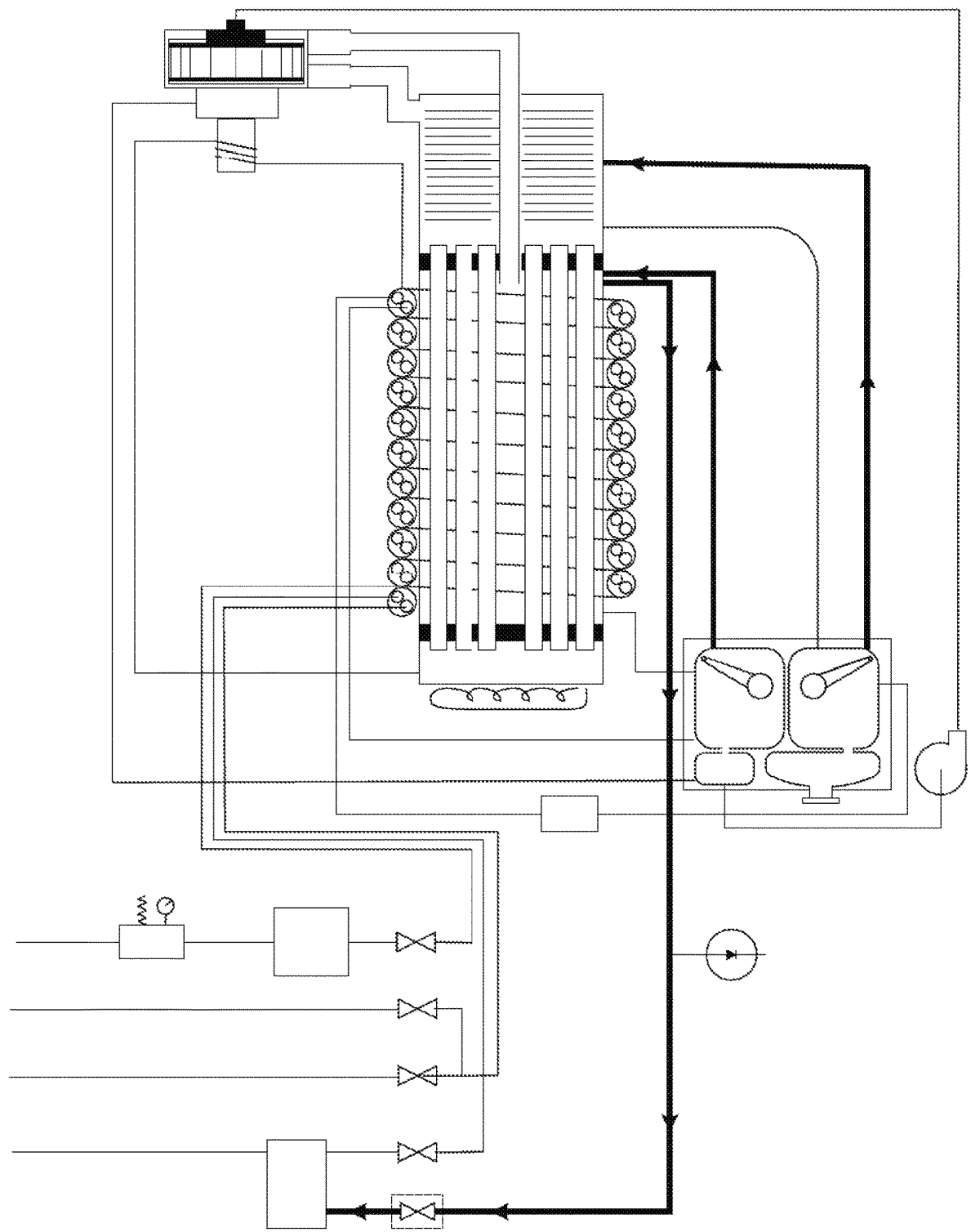
Figure 25A:
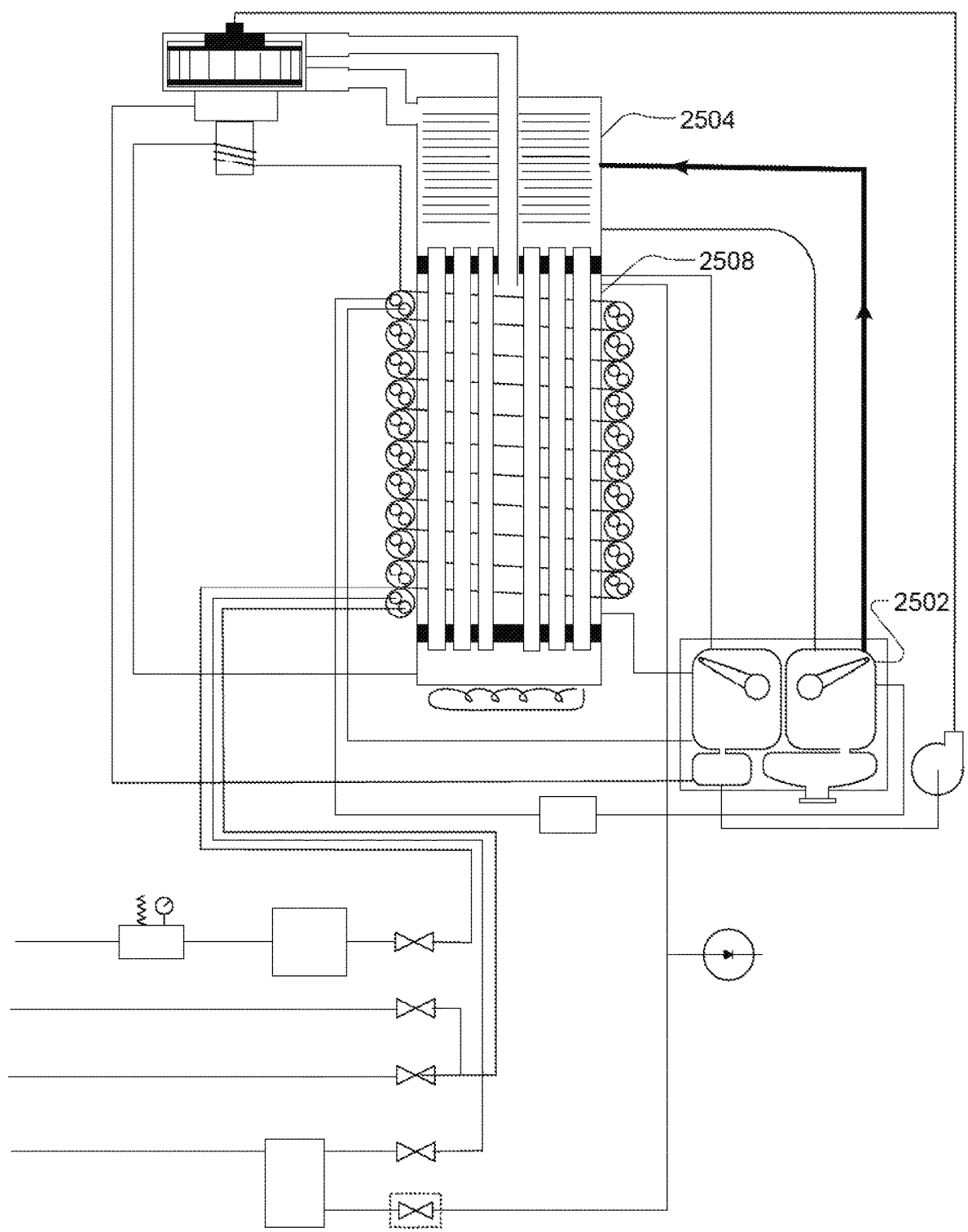
Figure 25B:
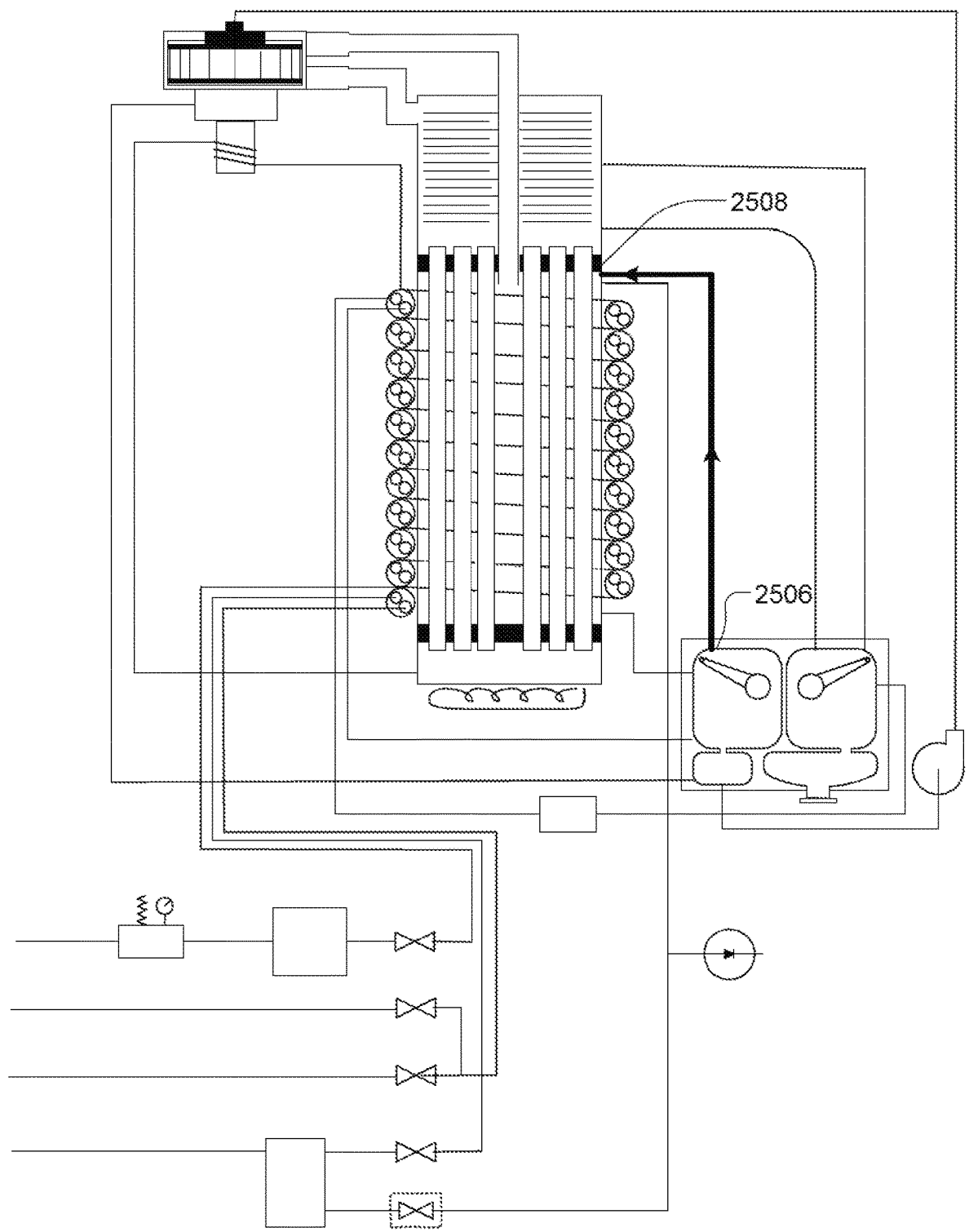
Figure 25C:
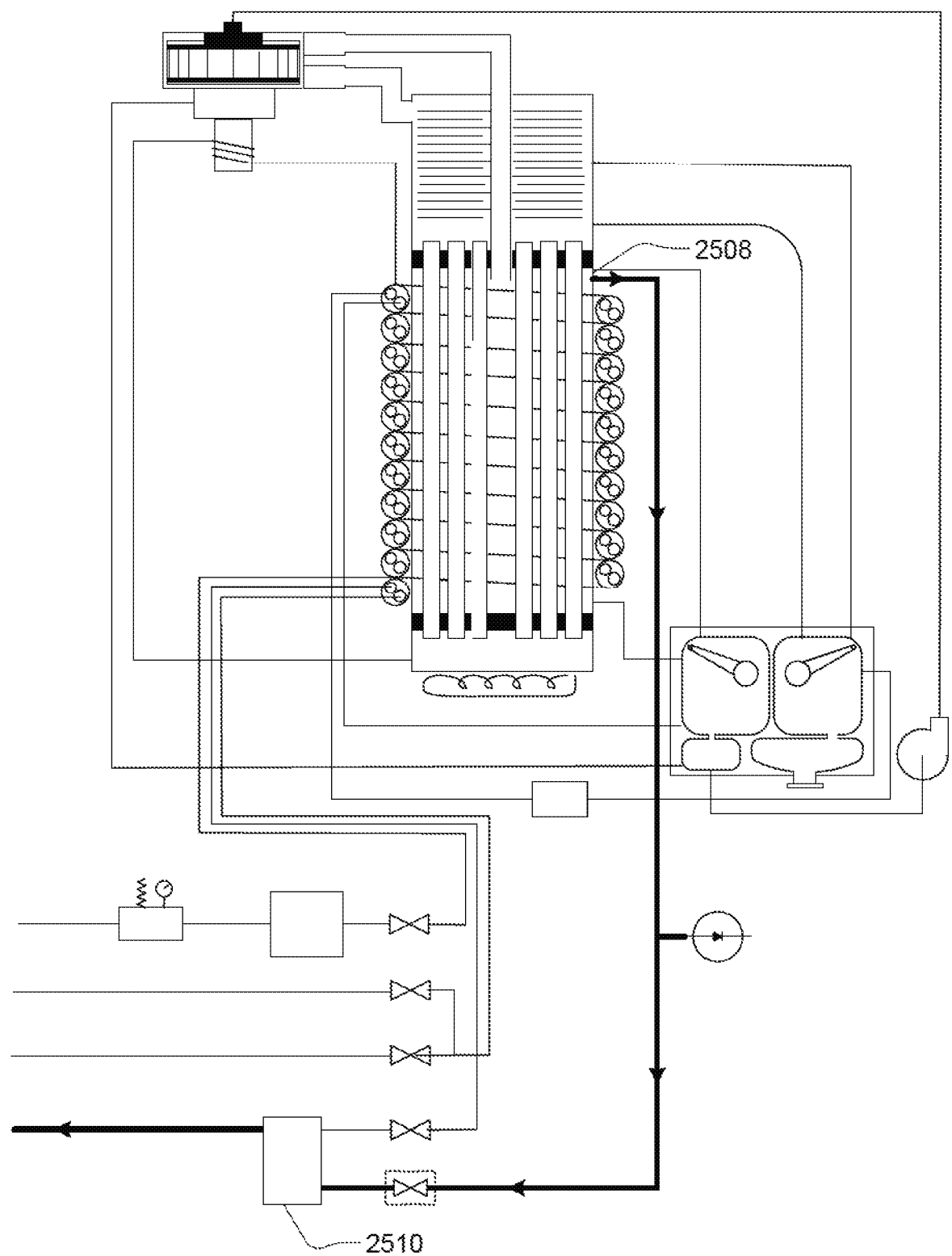
Figure 26:
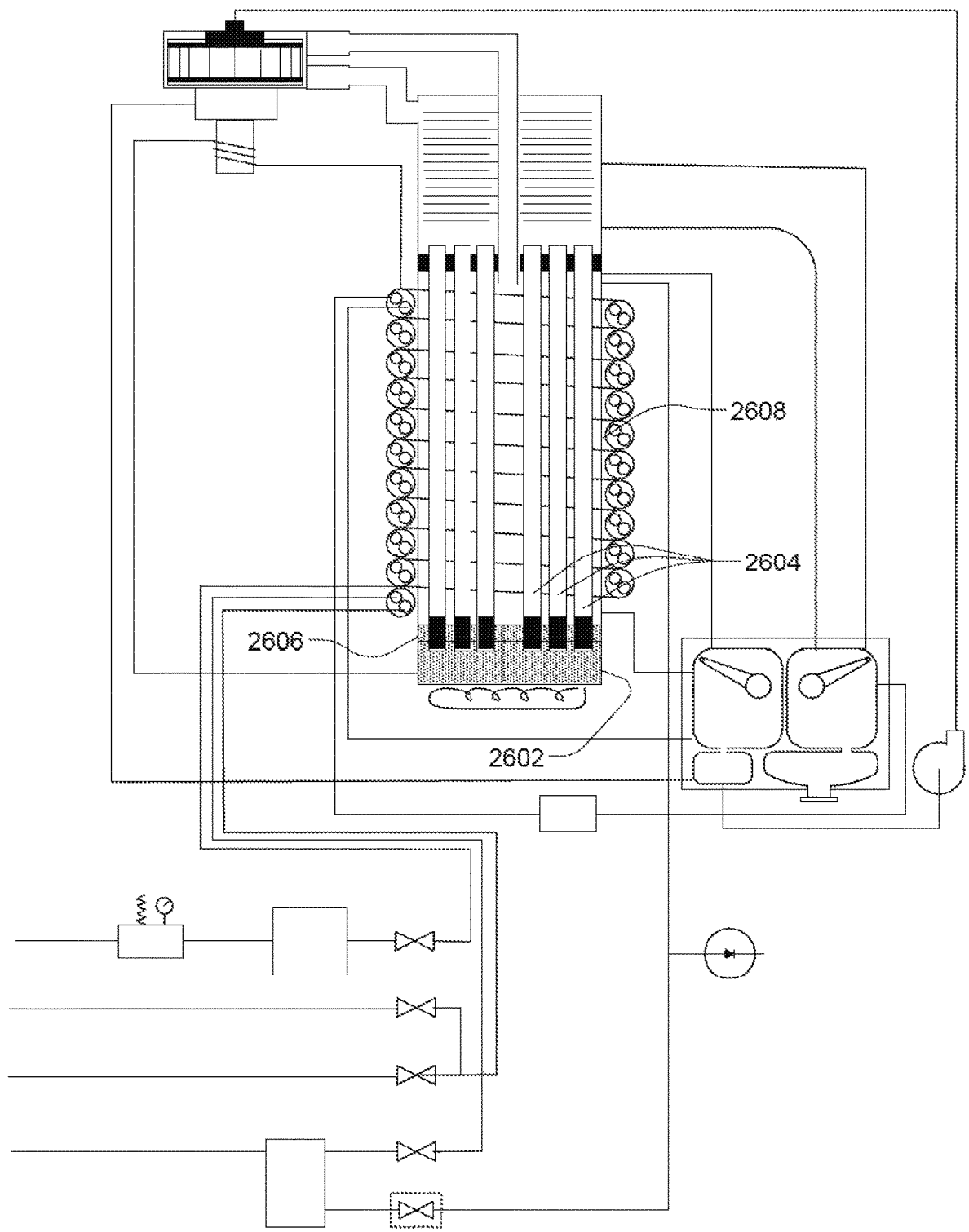
Figure 26A:
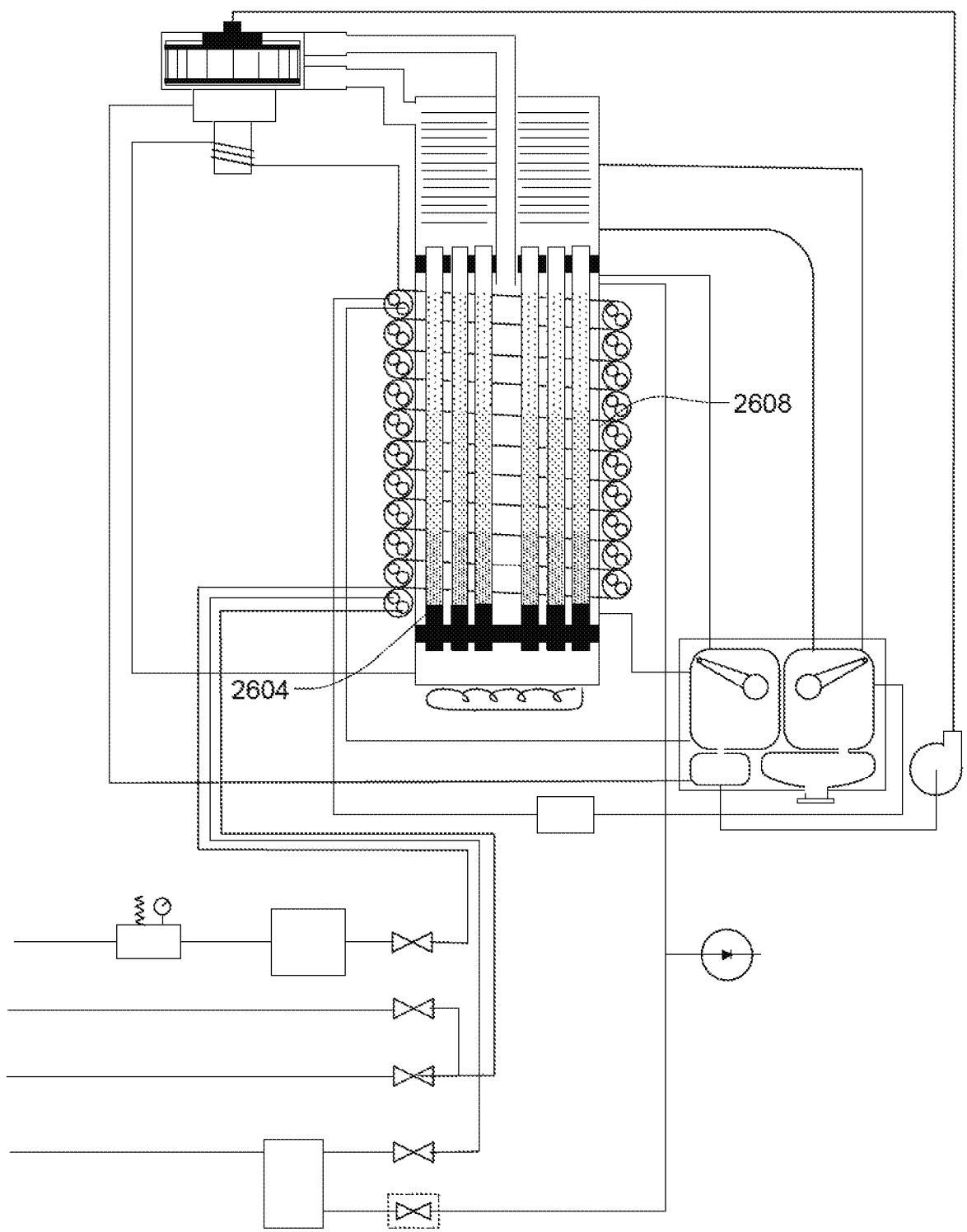
Figure 26B:
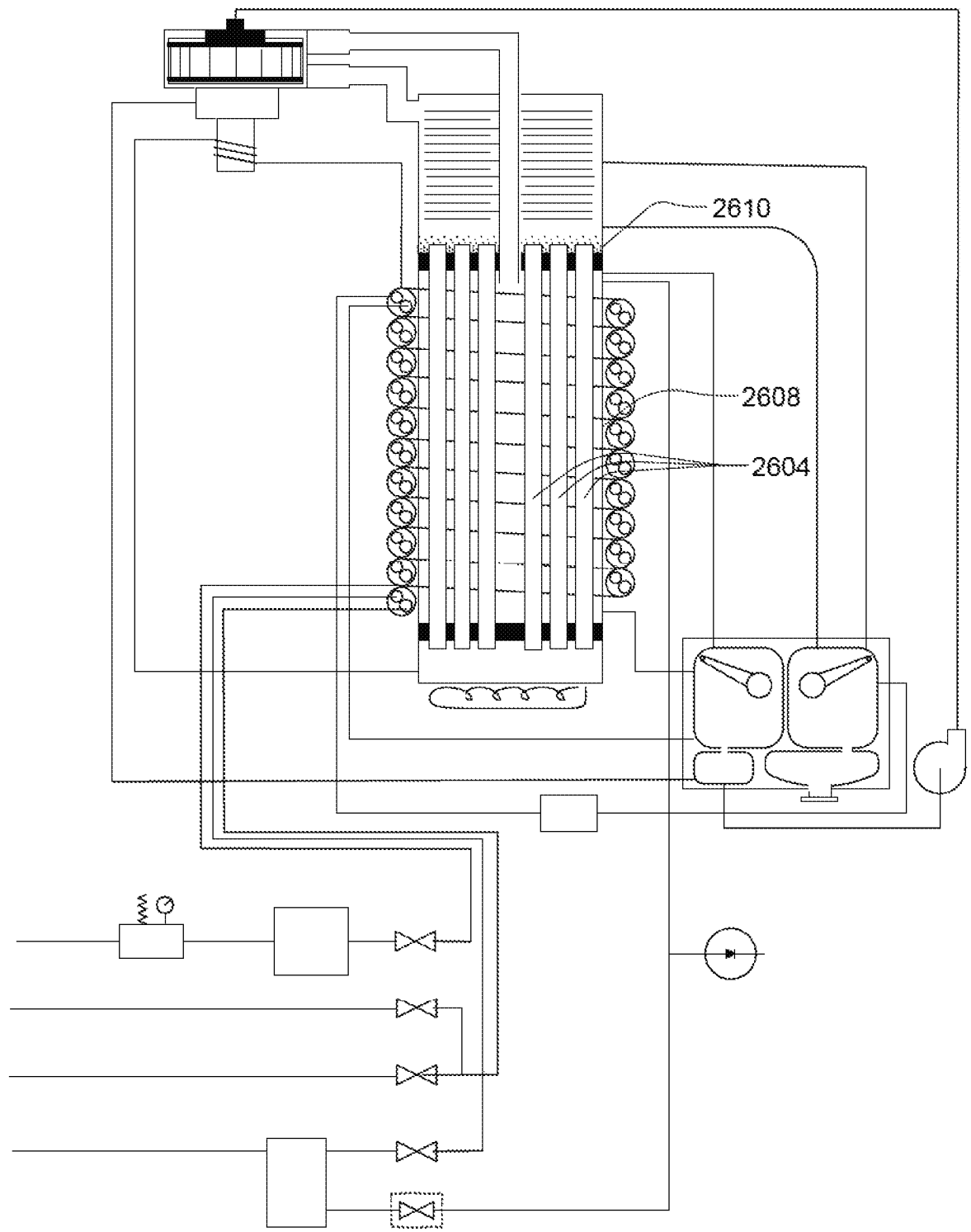
Figure 26C:
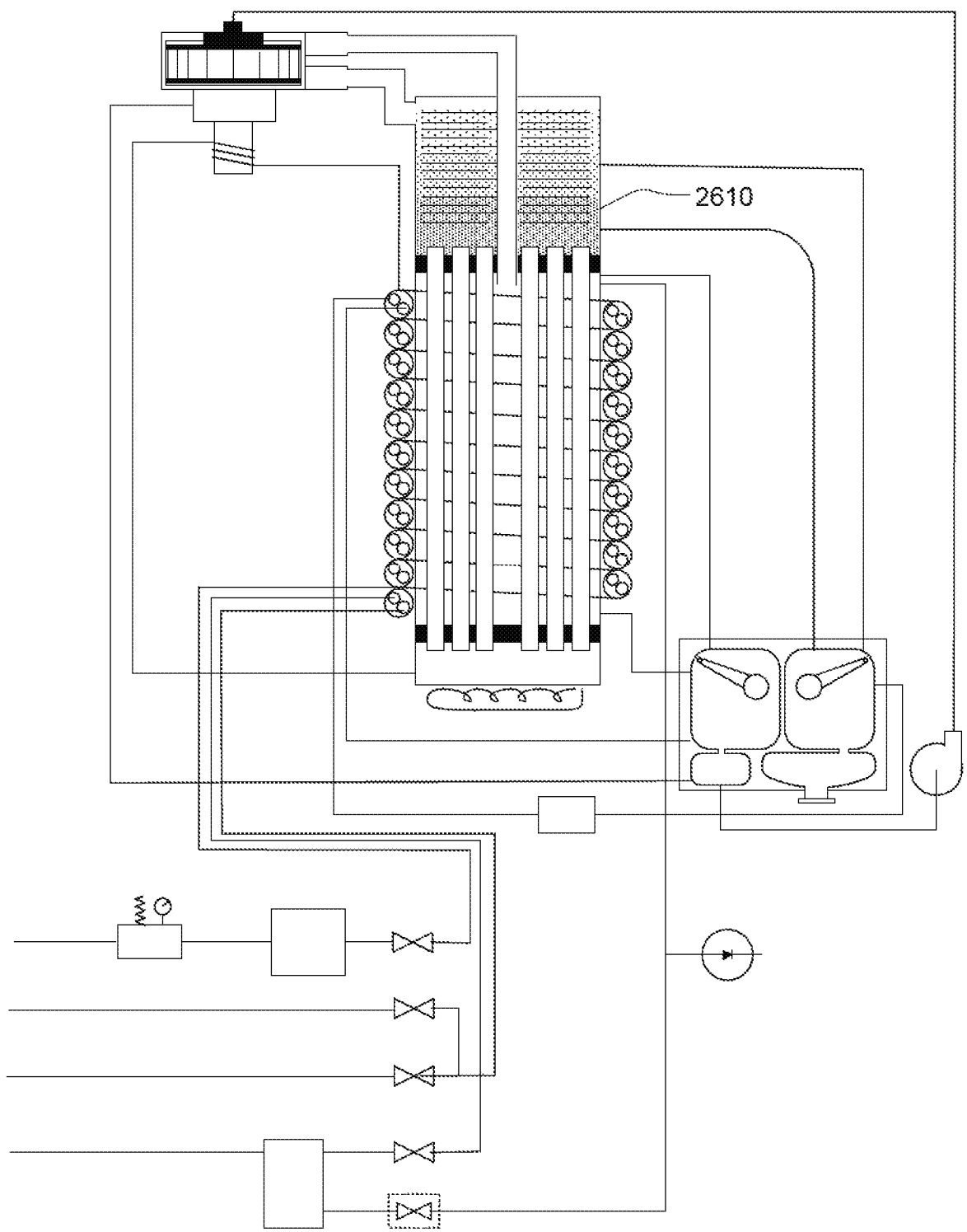
Figure 26D:
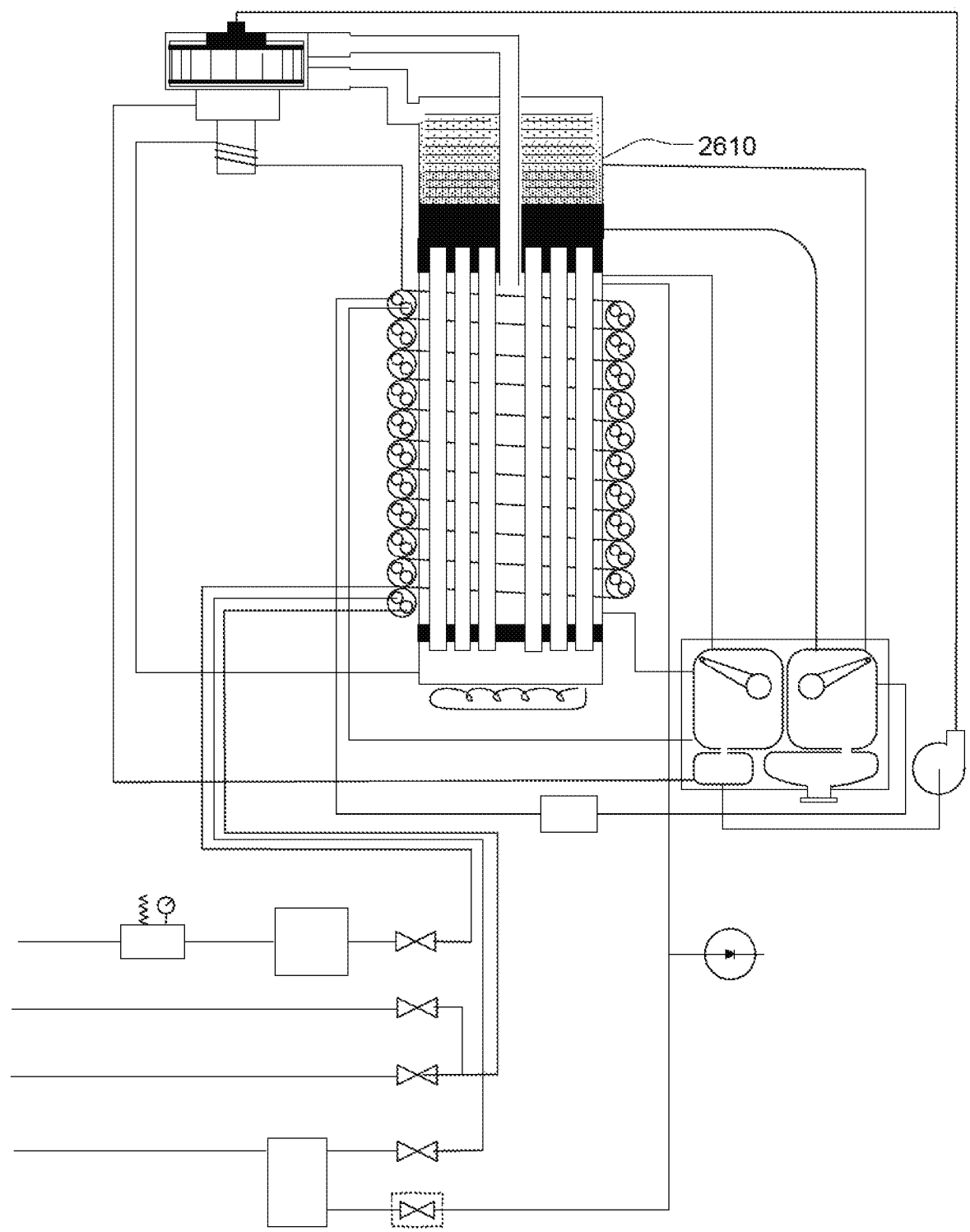
Figure 26E:
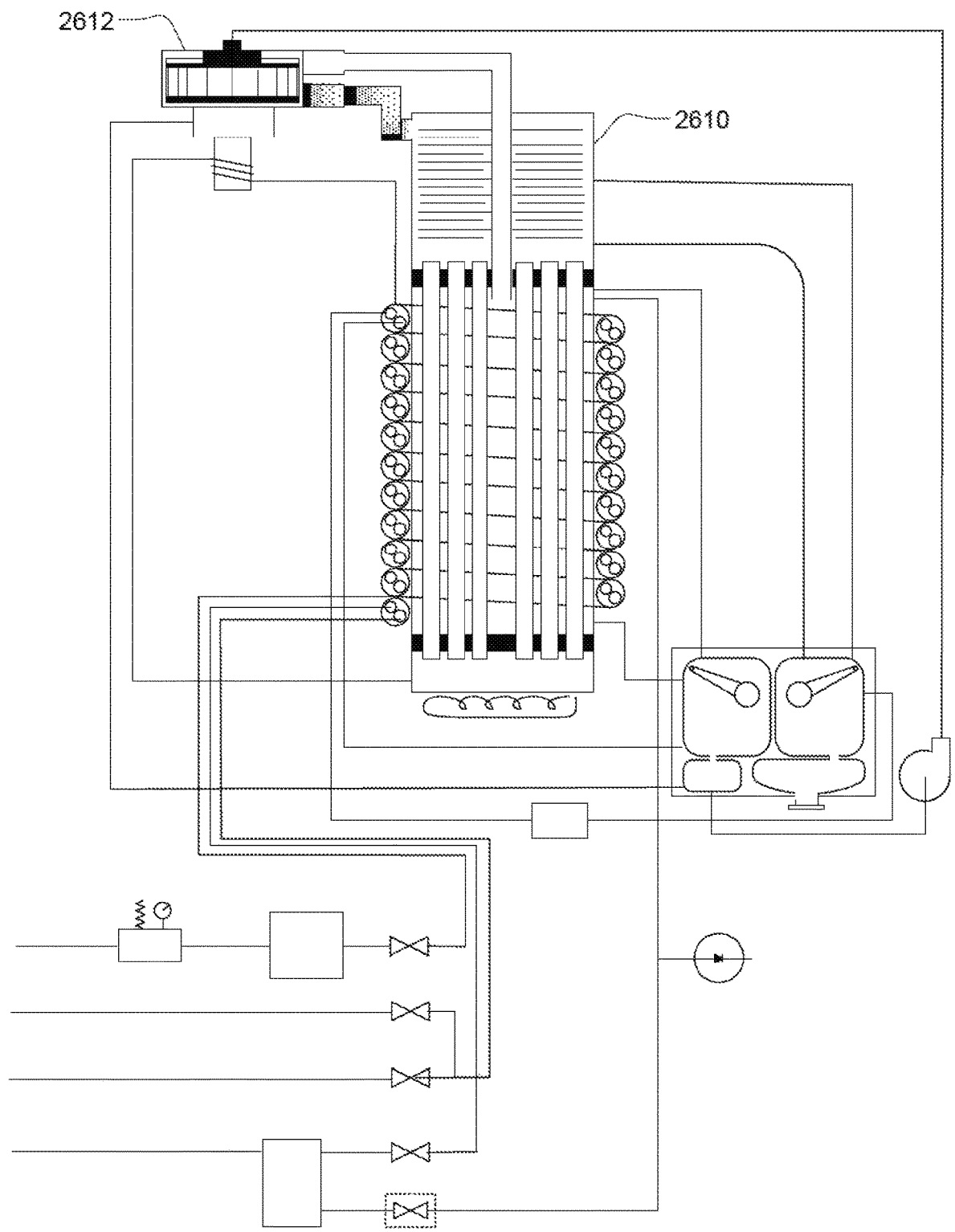
Figure 26F:
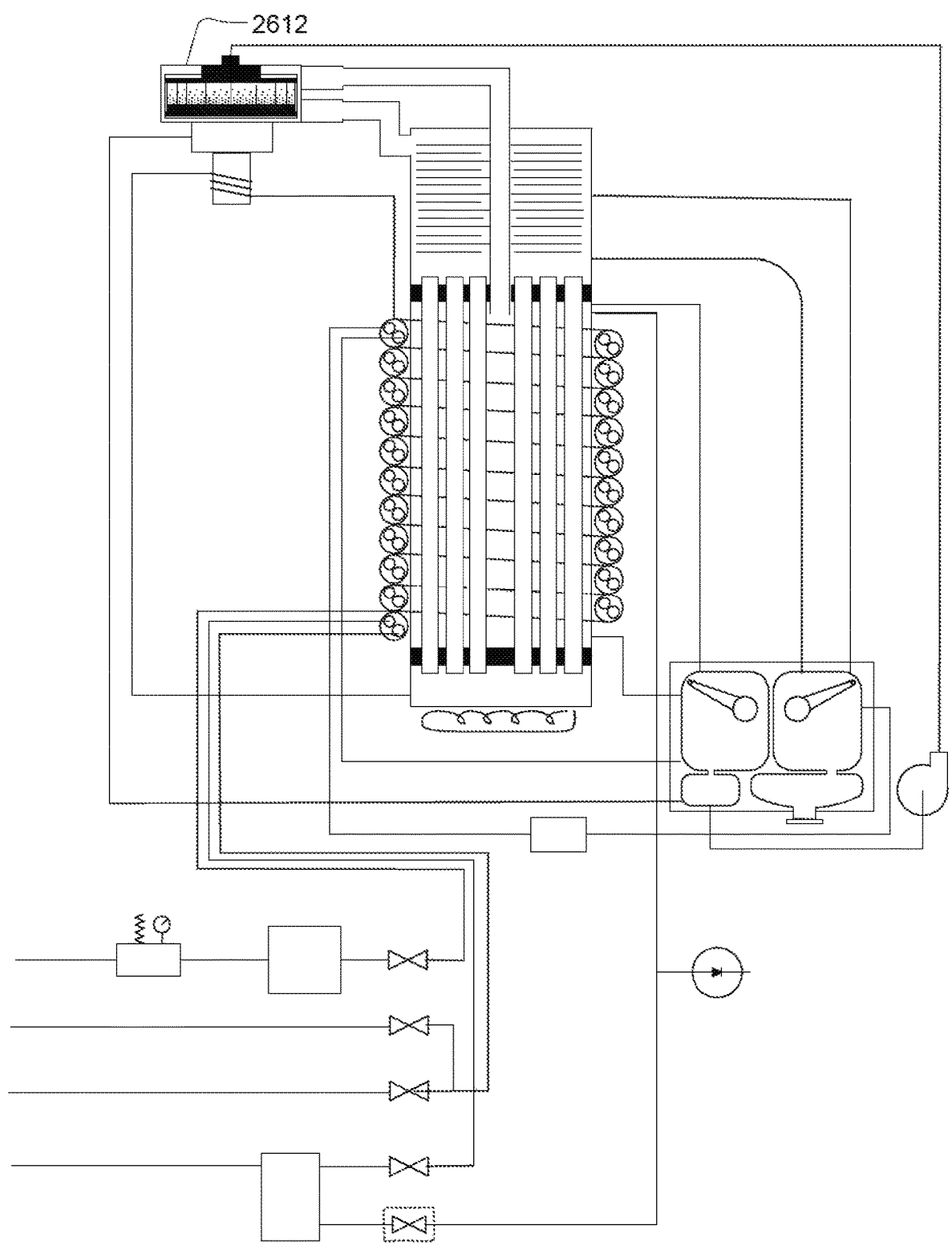
Figure 26G:
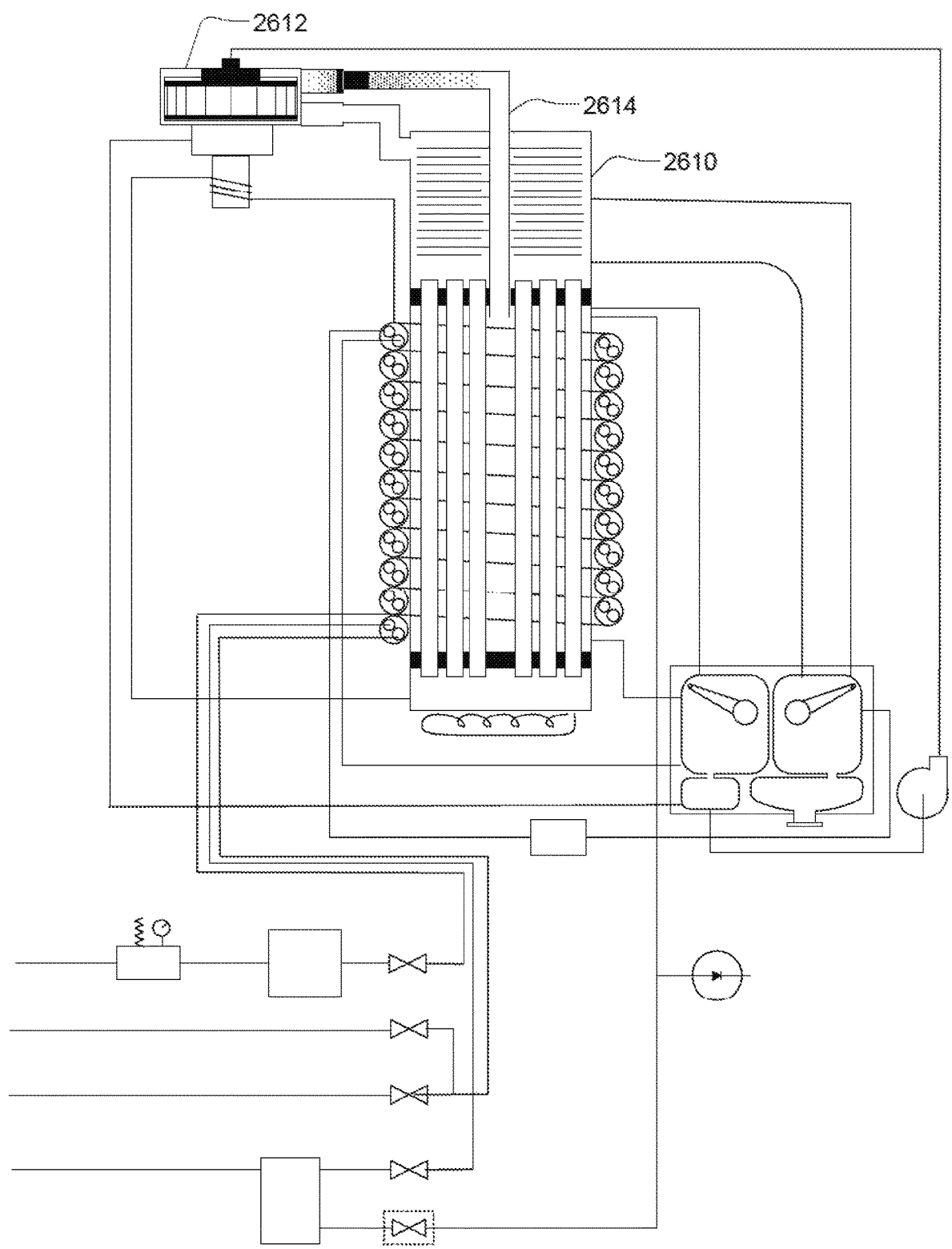
Figure 26H:
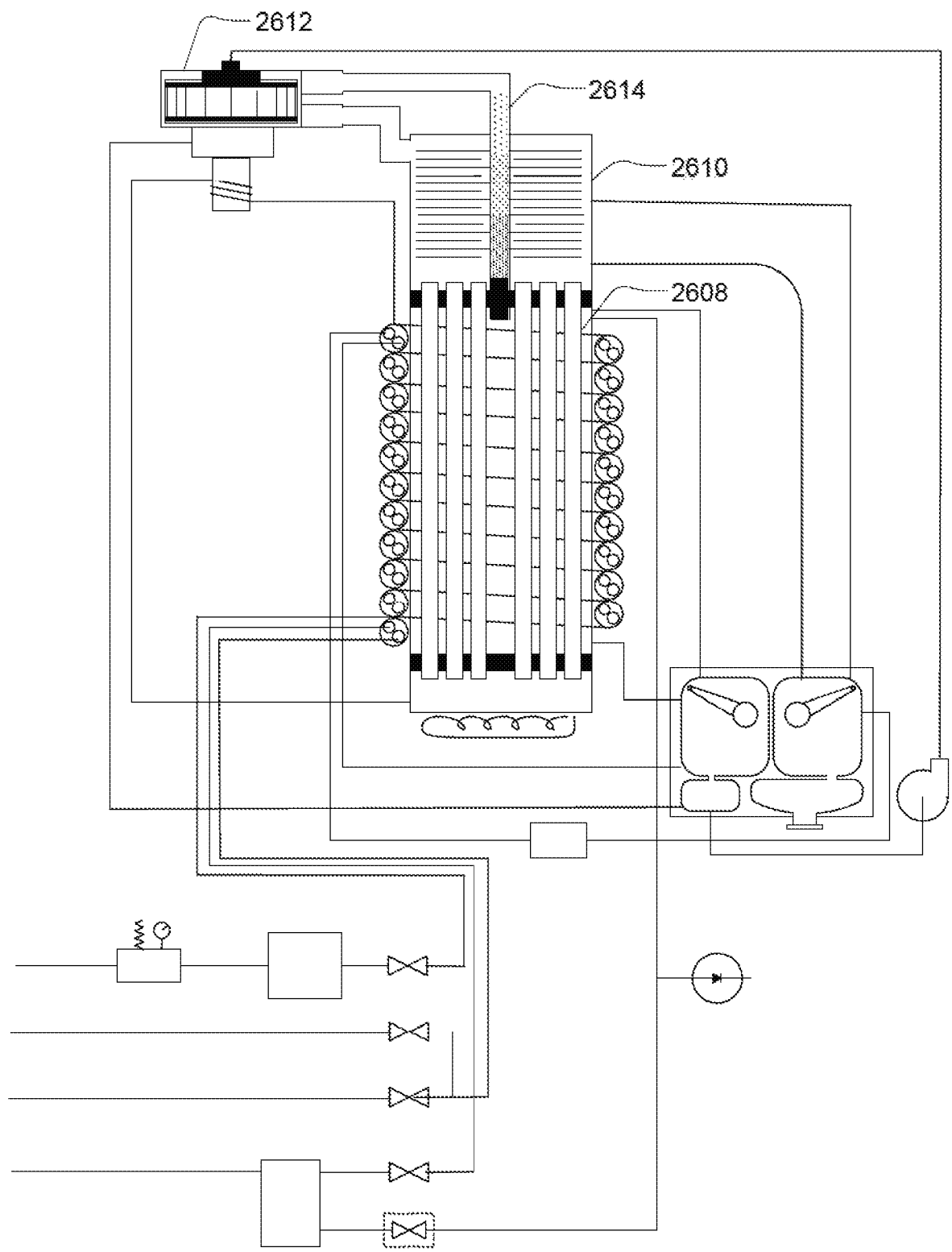
Figure 26I:
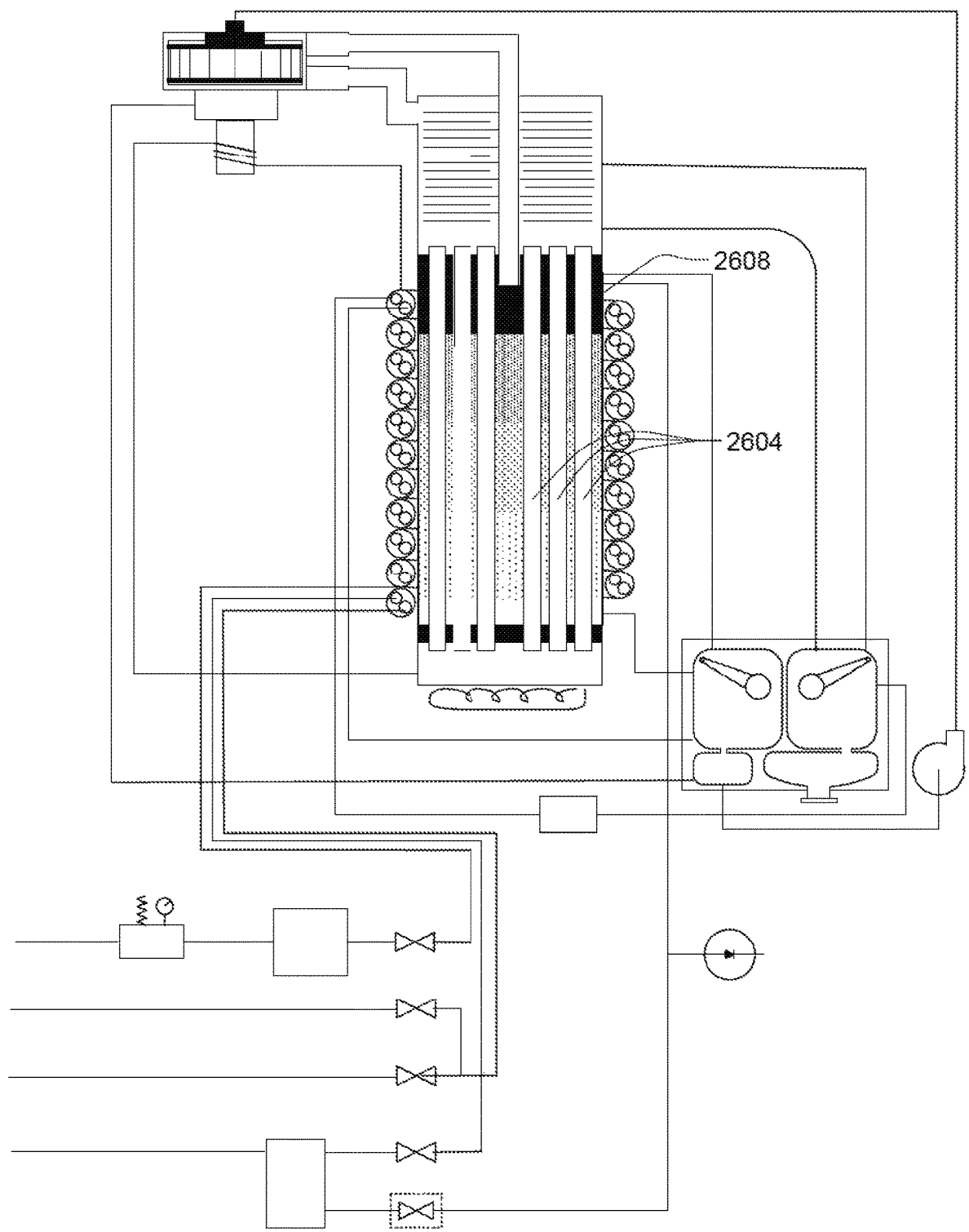
Figure 26J:
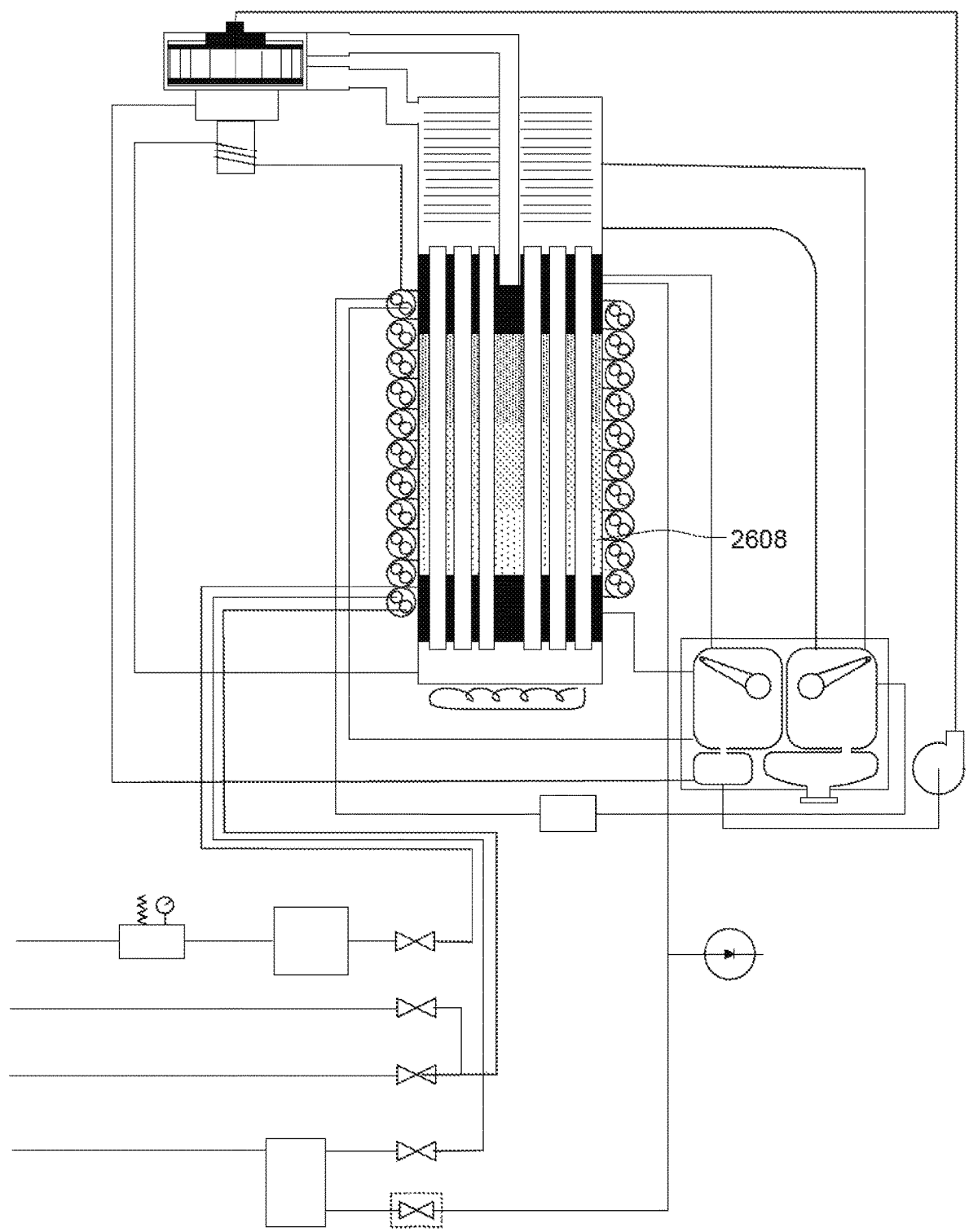
Figure 27:
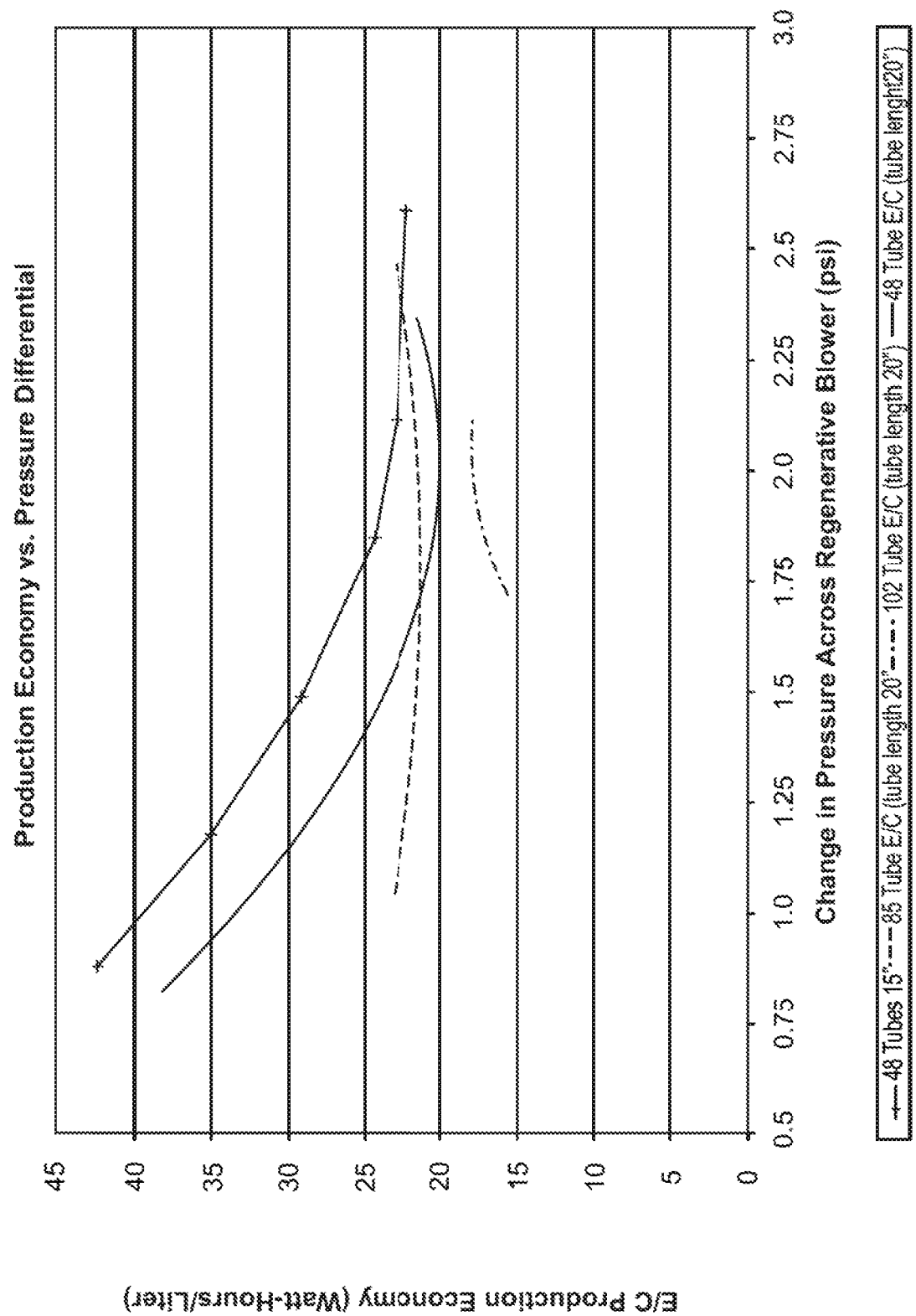
Figure 28:
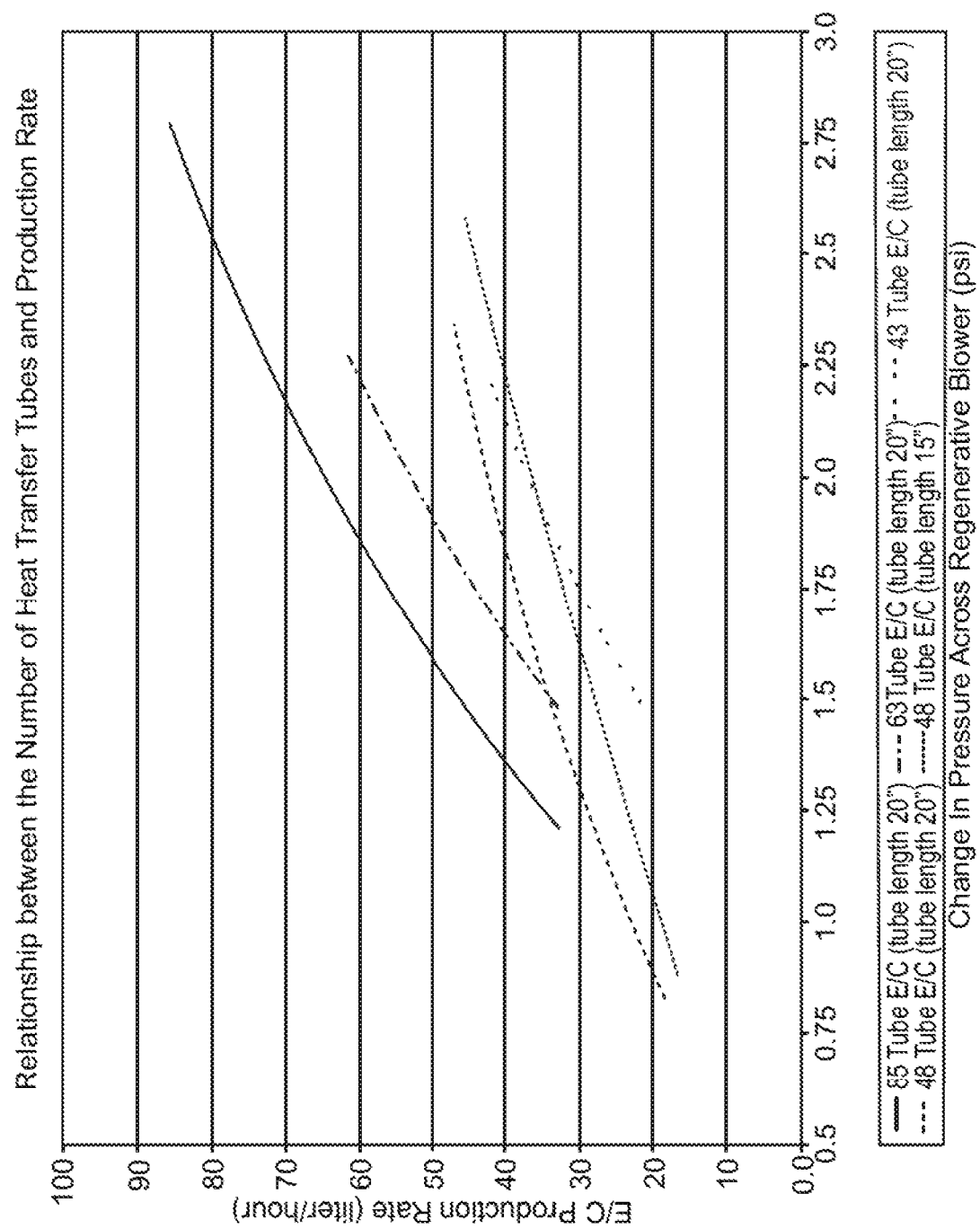
Figure 29:
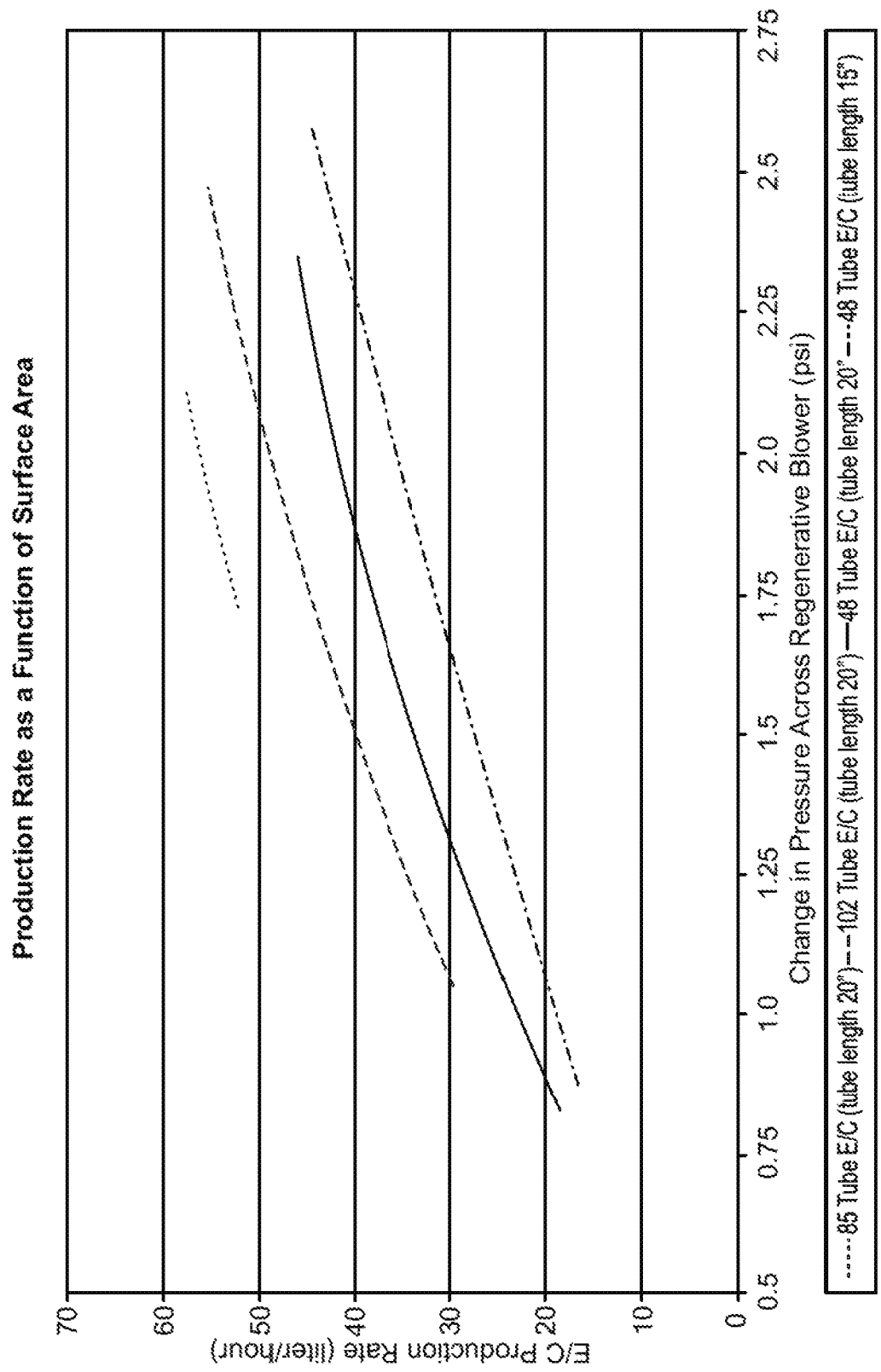
Figure 30:
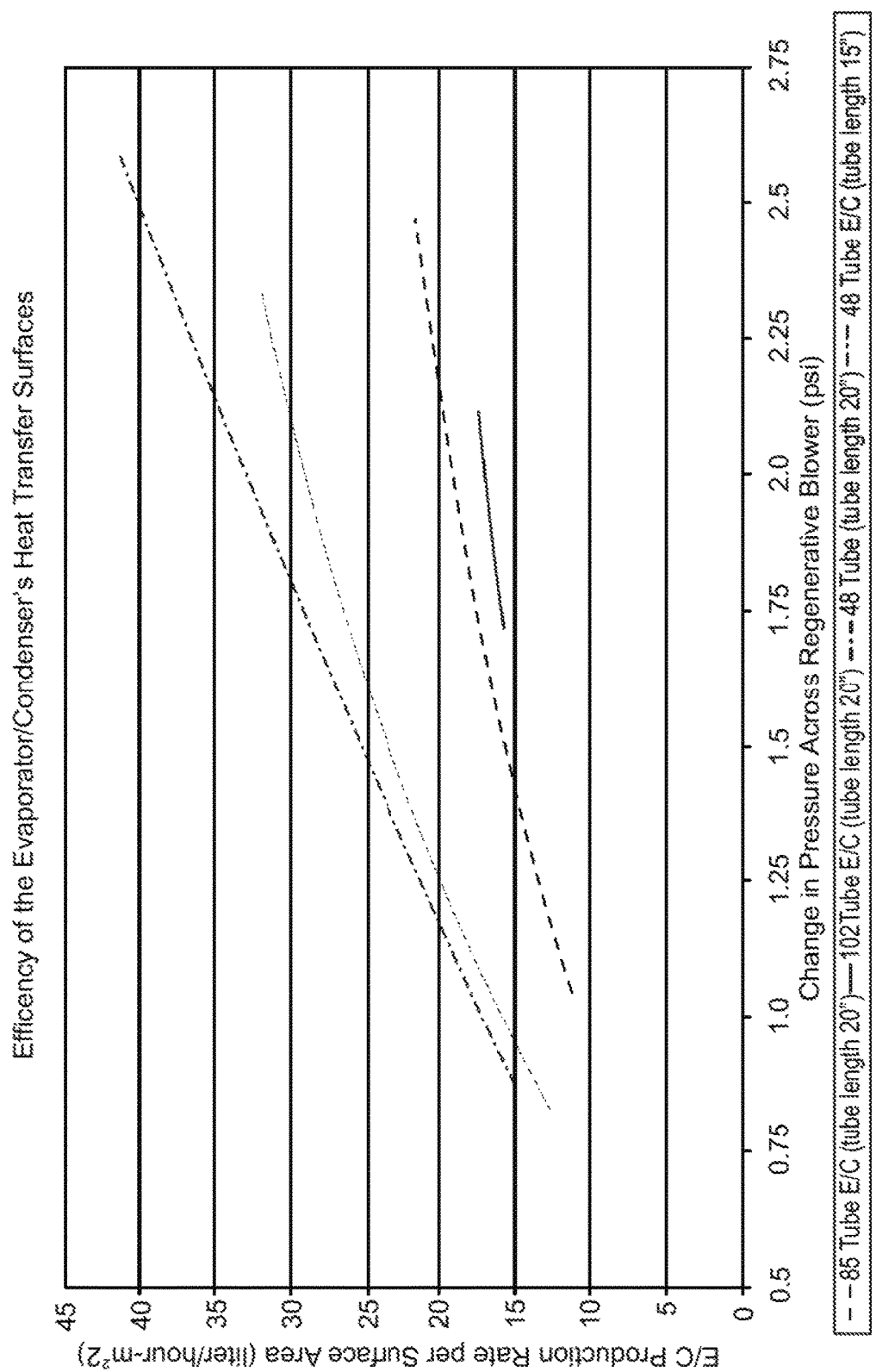
Figure 31:
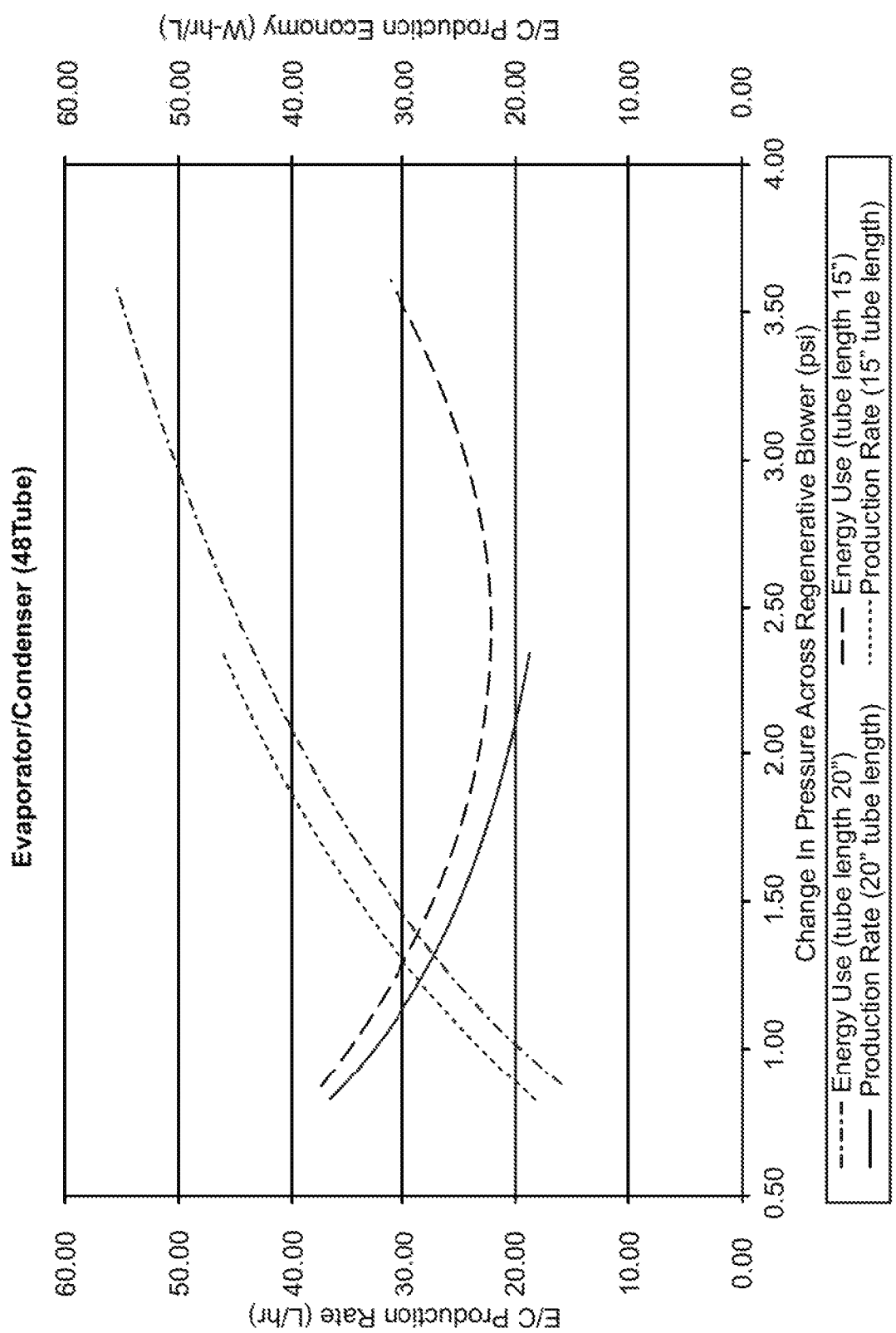
Figure 32:
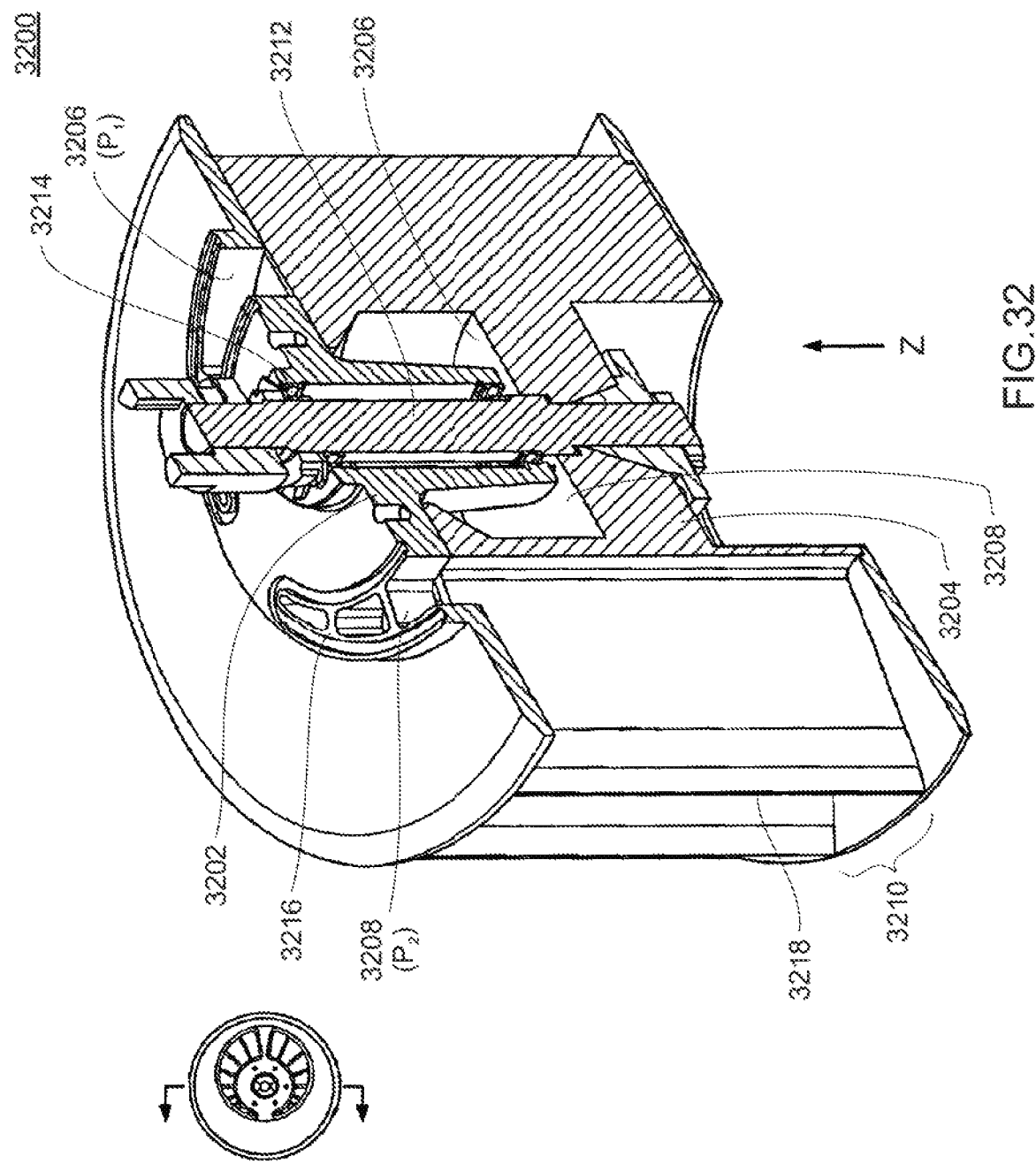
Figure 32A:
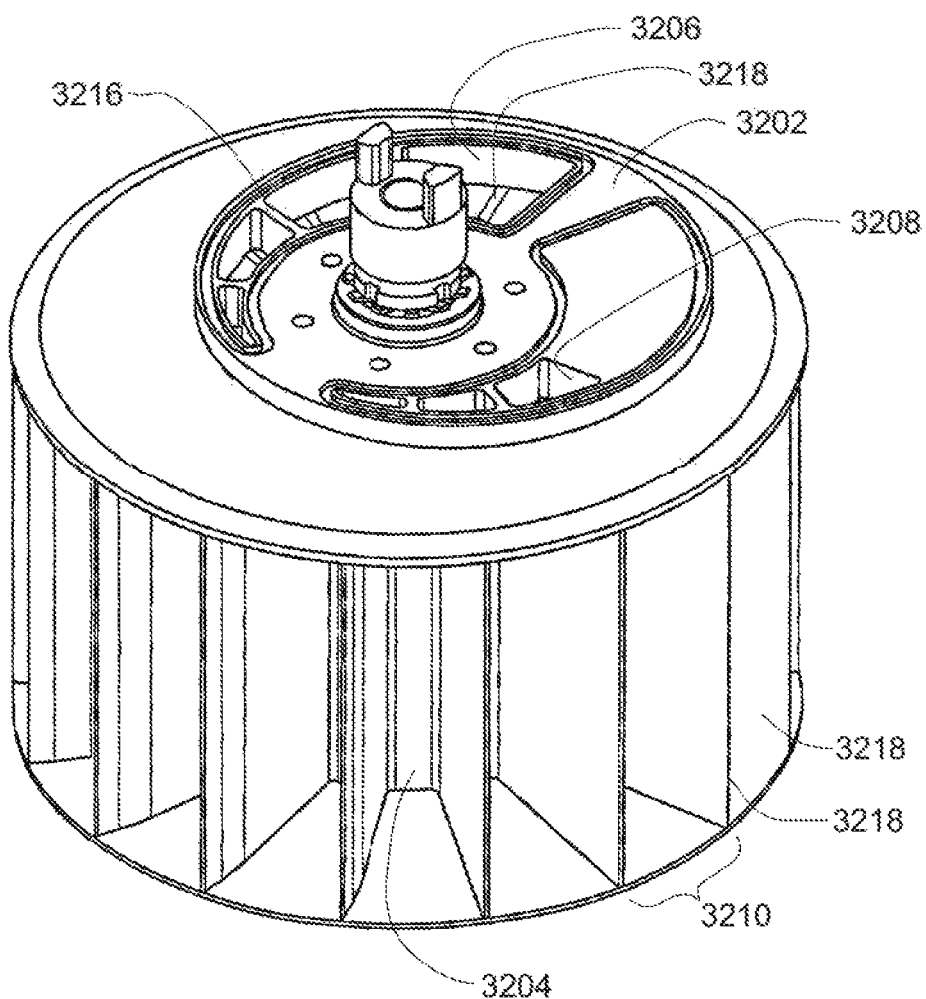
Figure 32B:
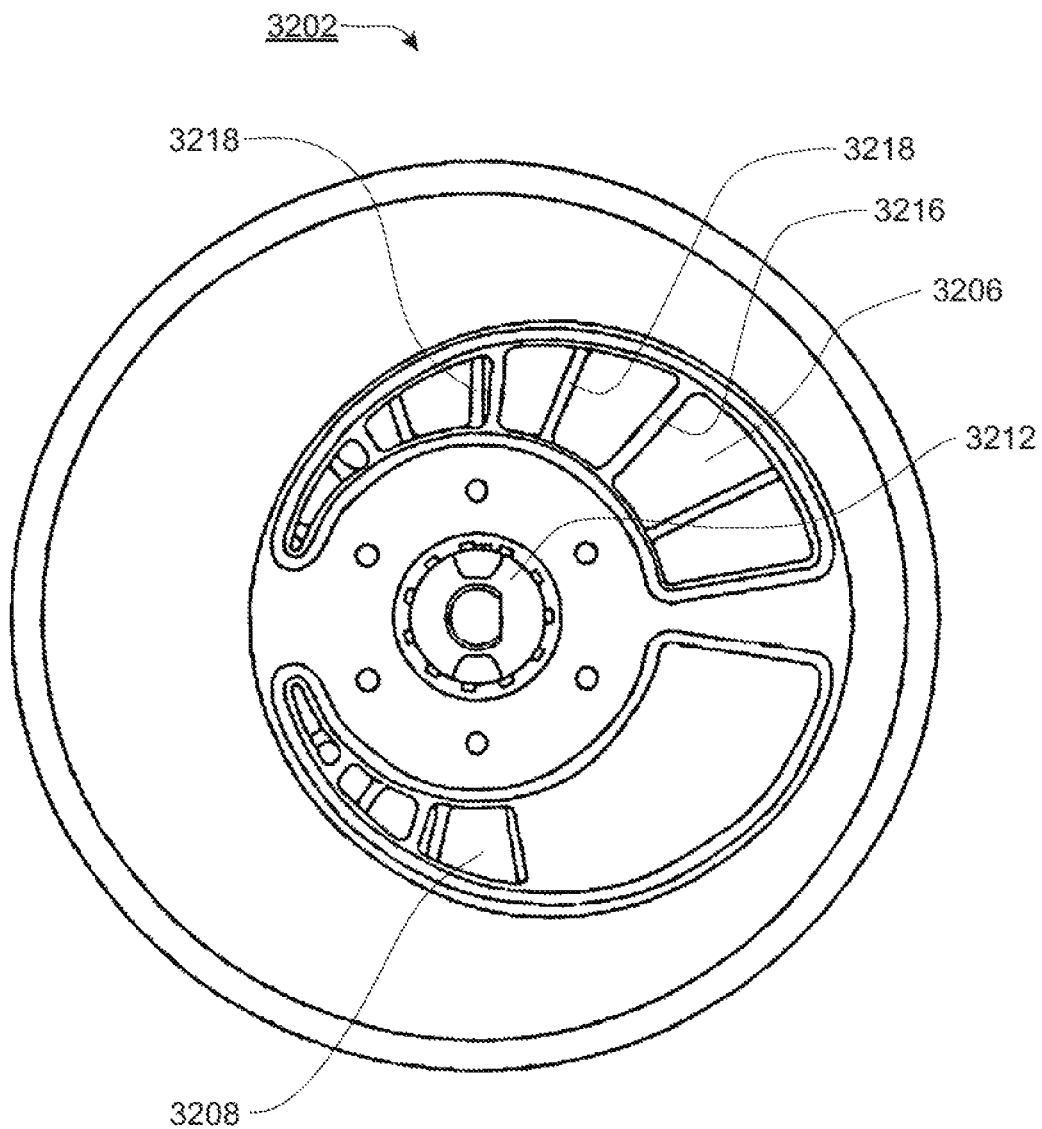
Figure 32D:
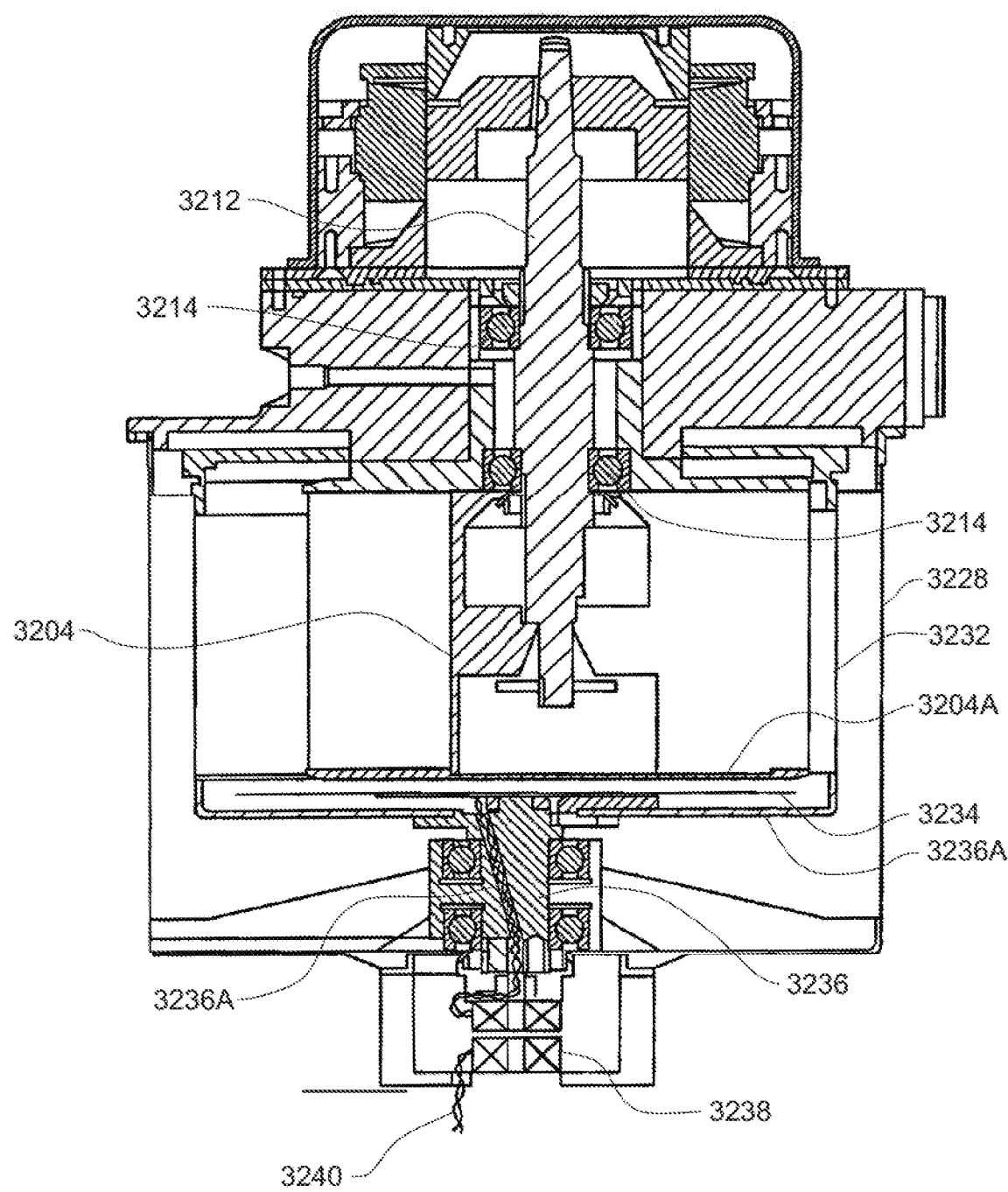
Figure 32E:
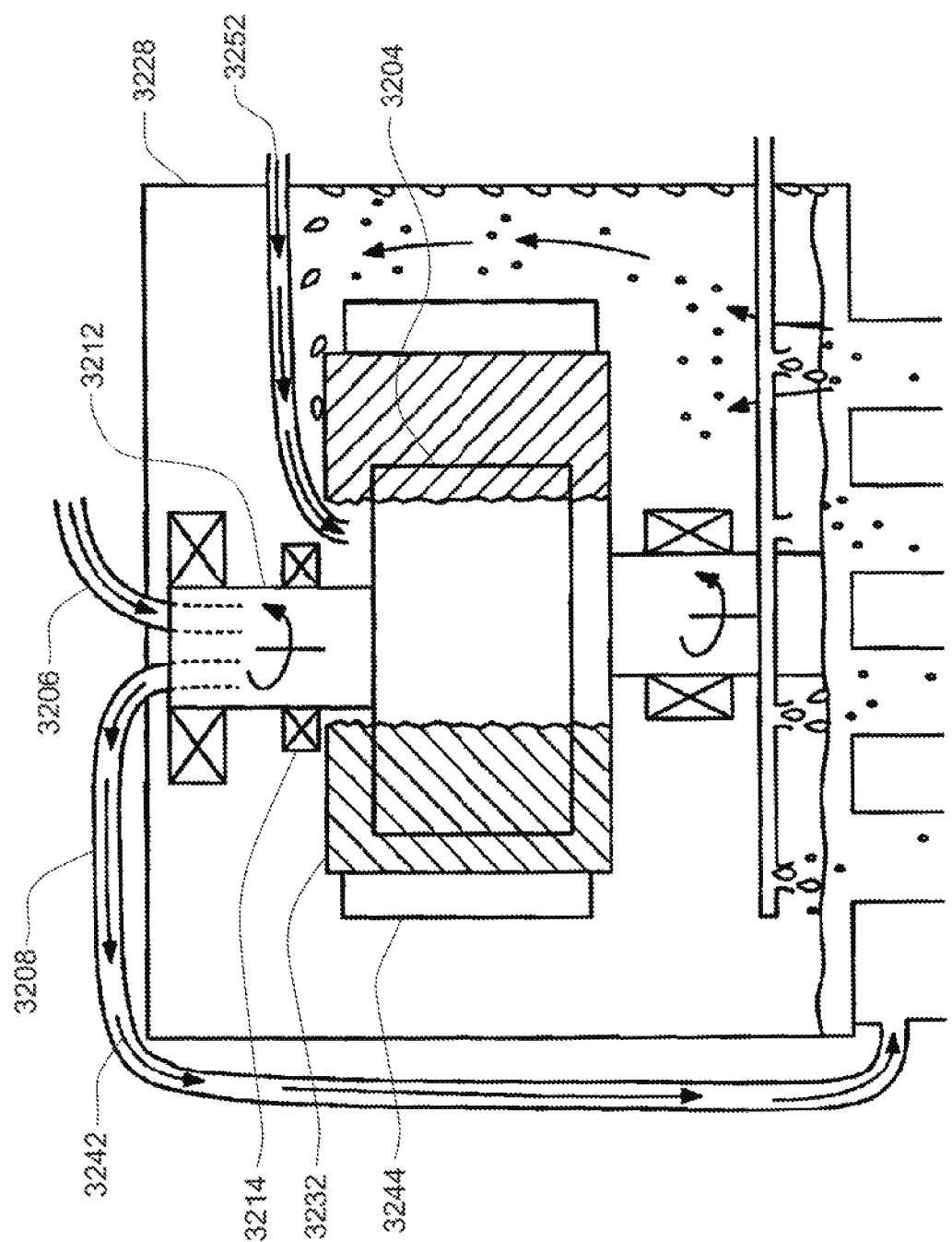
Figure 32F:
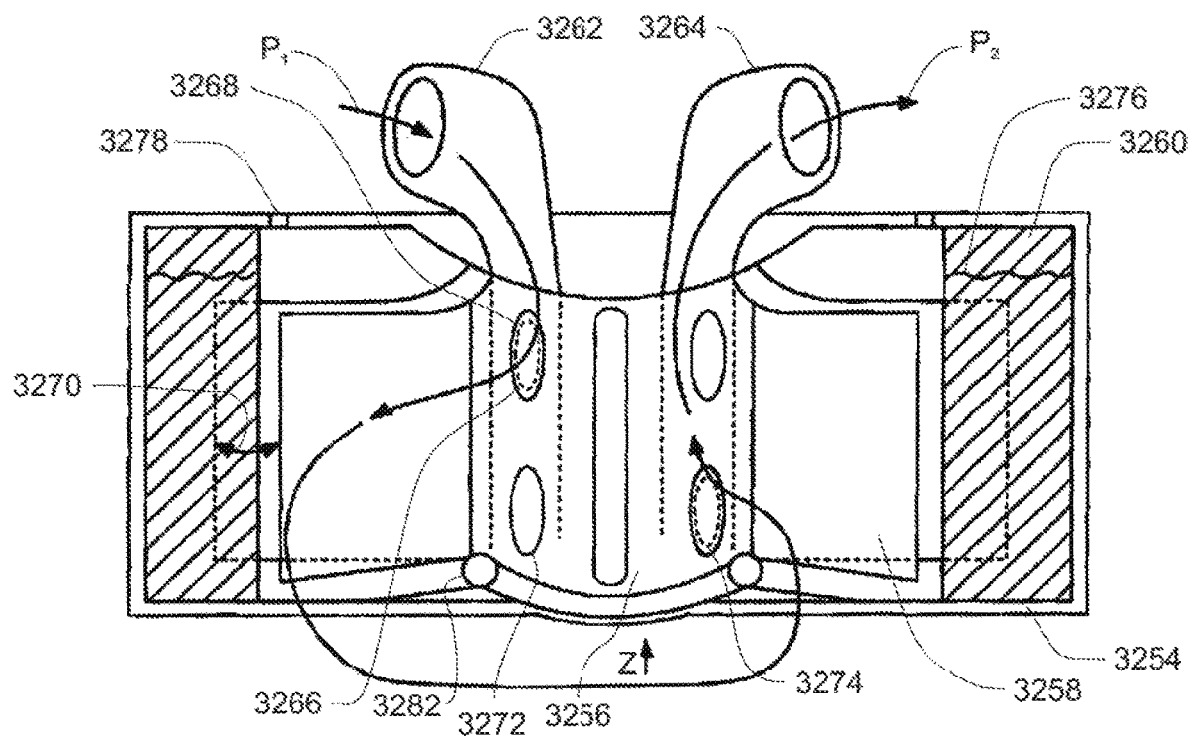
Figure 32G:
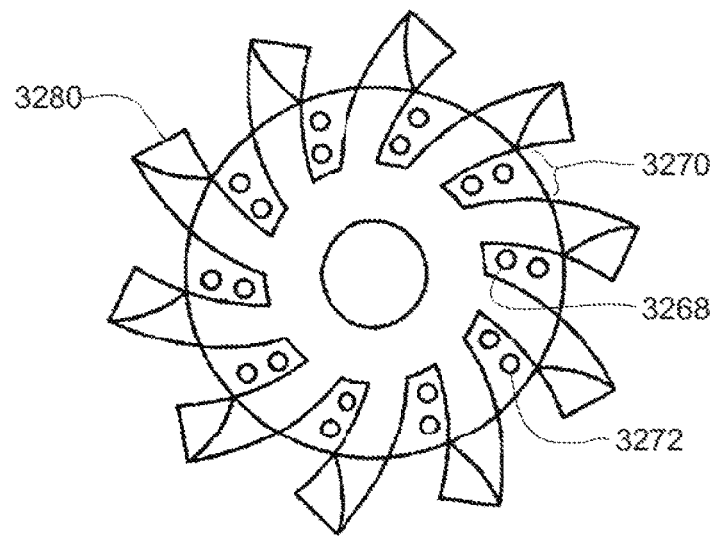
Figure 32H:
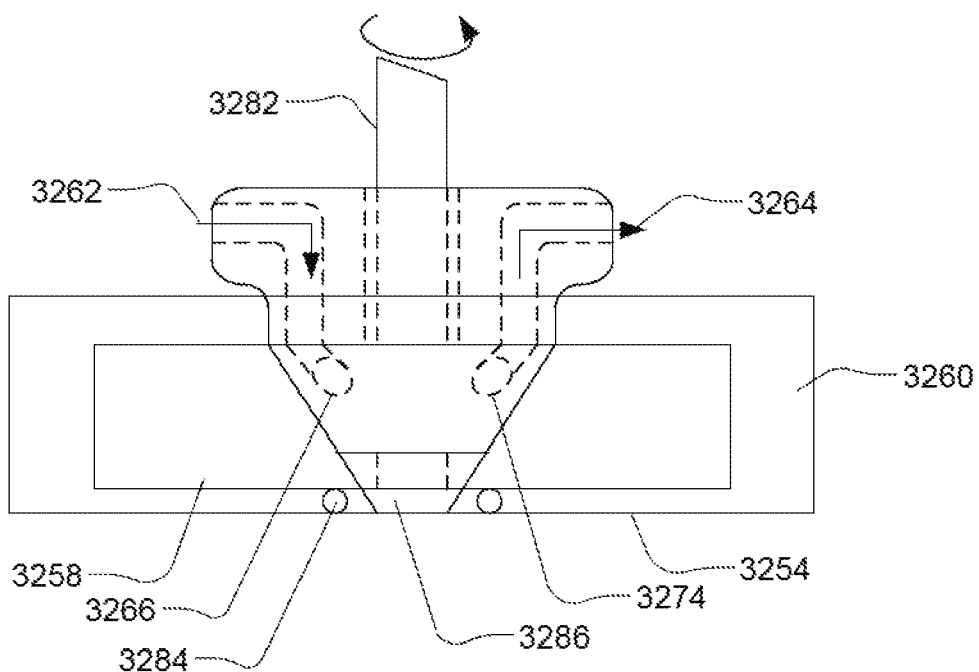
Figure 32I:
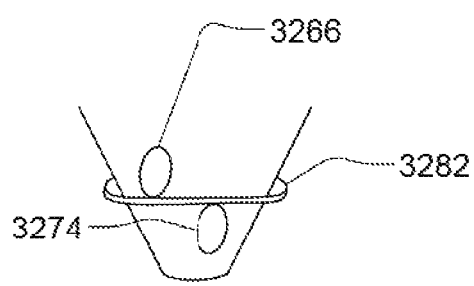
Figure 33:
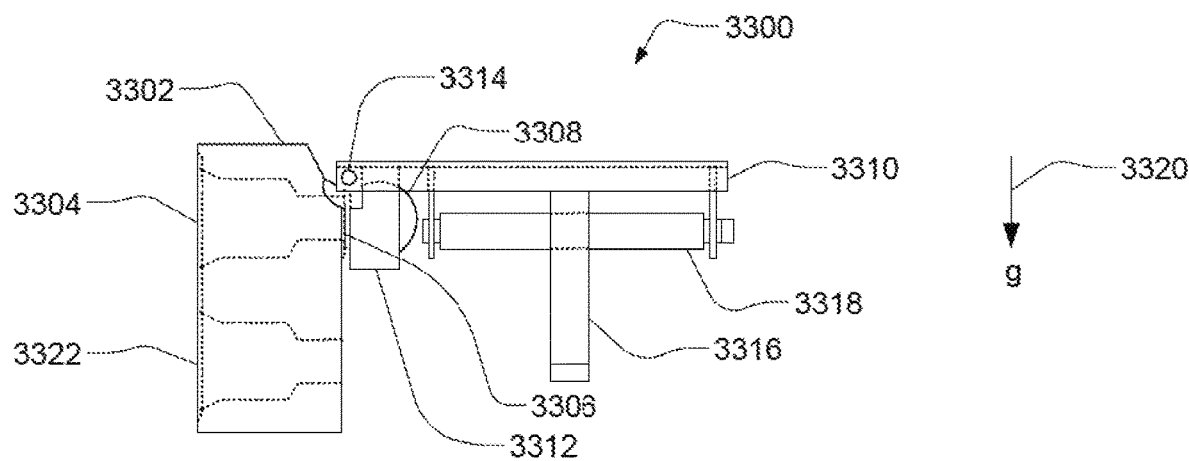
Figure 33A:
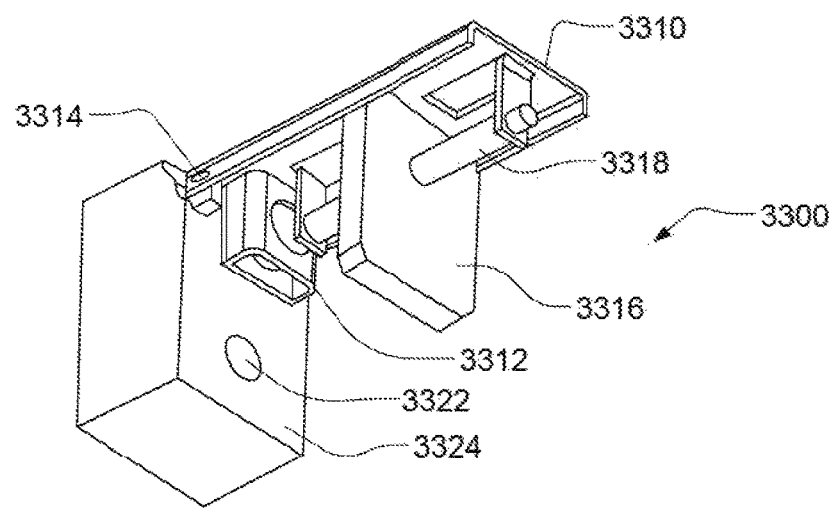
Figure 33B:
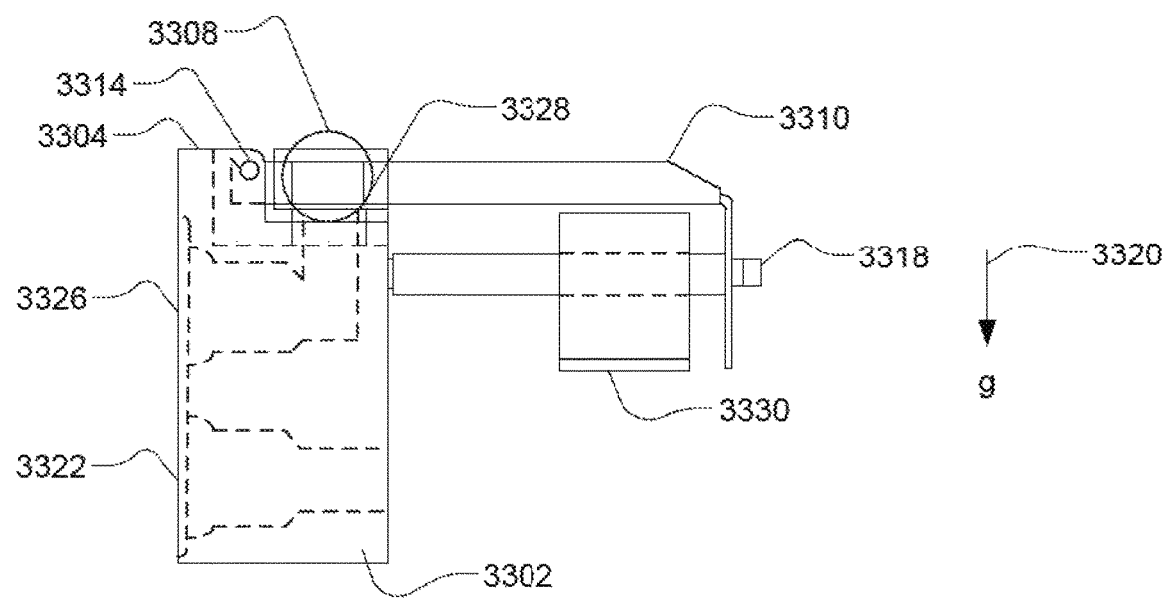
Figure 33C:
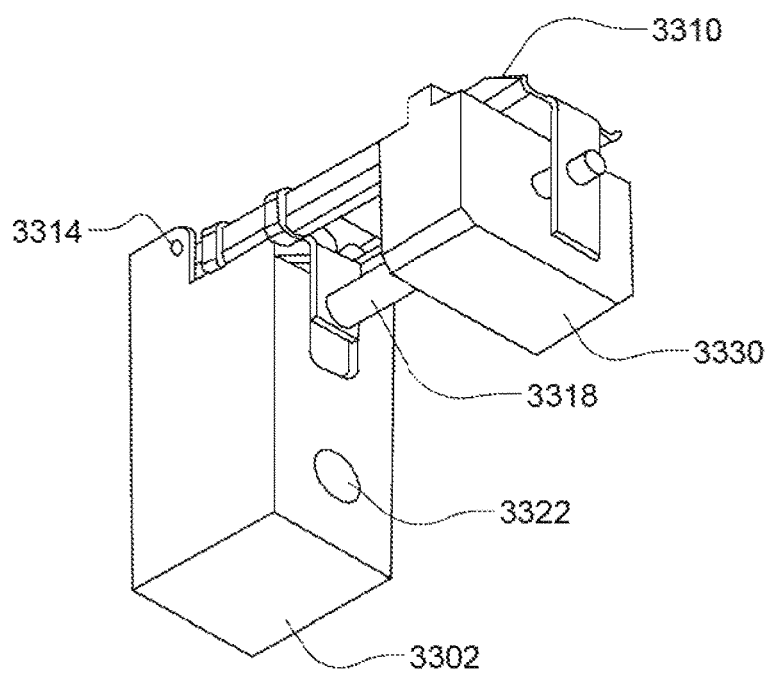
Figure 34:
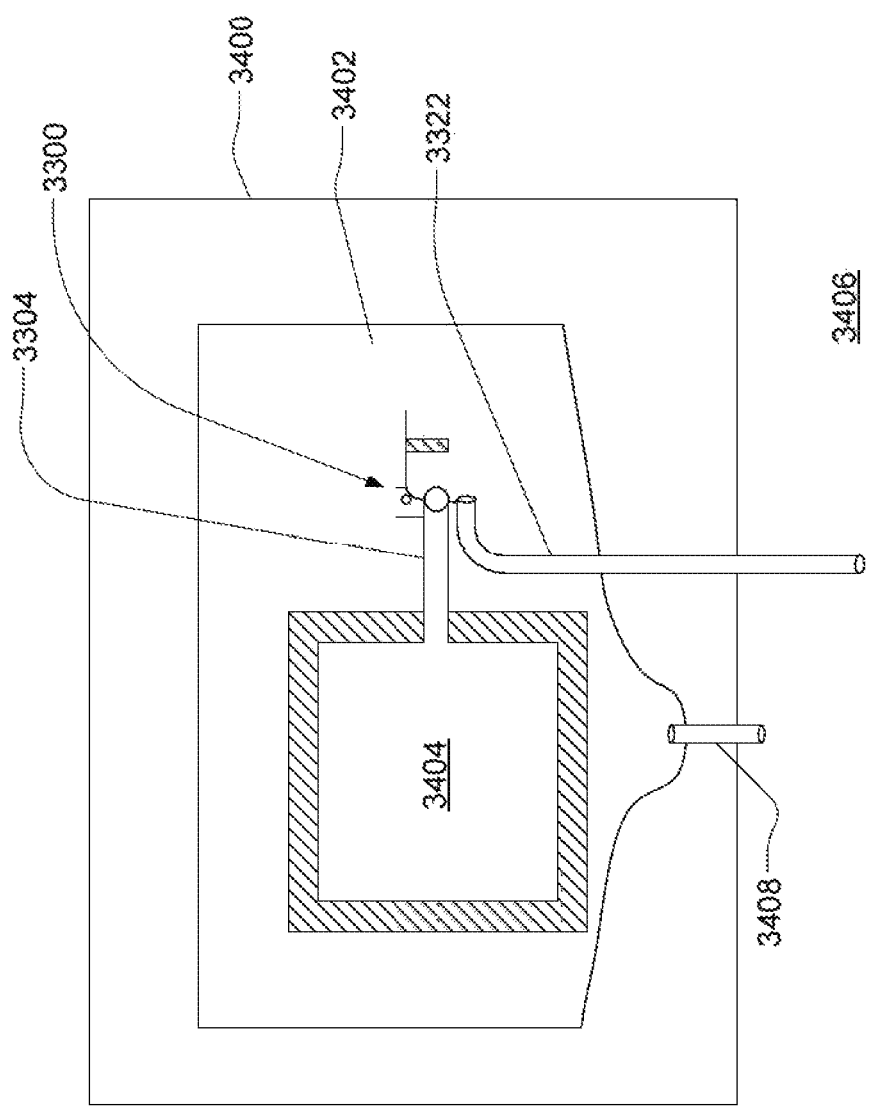
Figure 35:
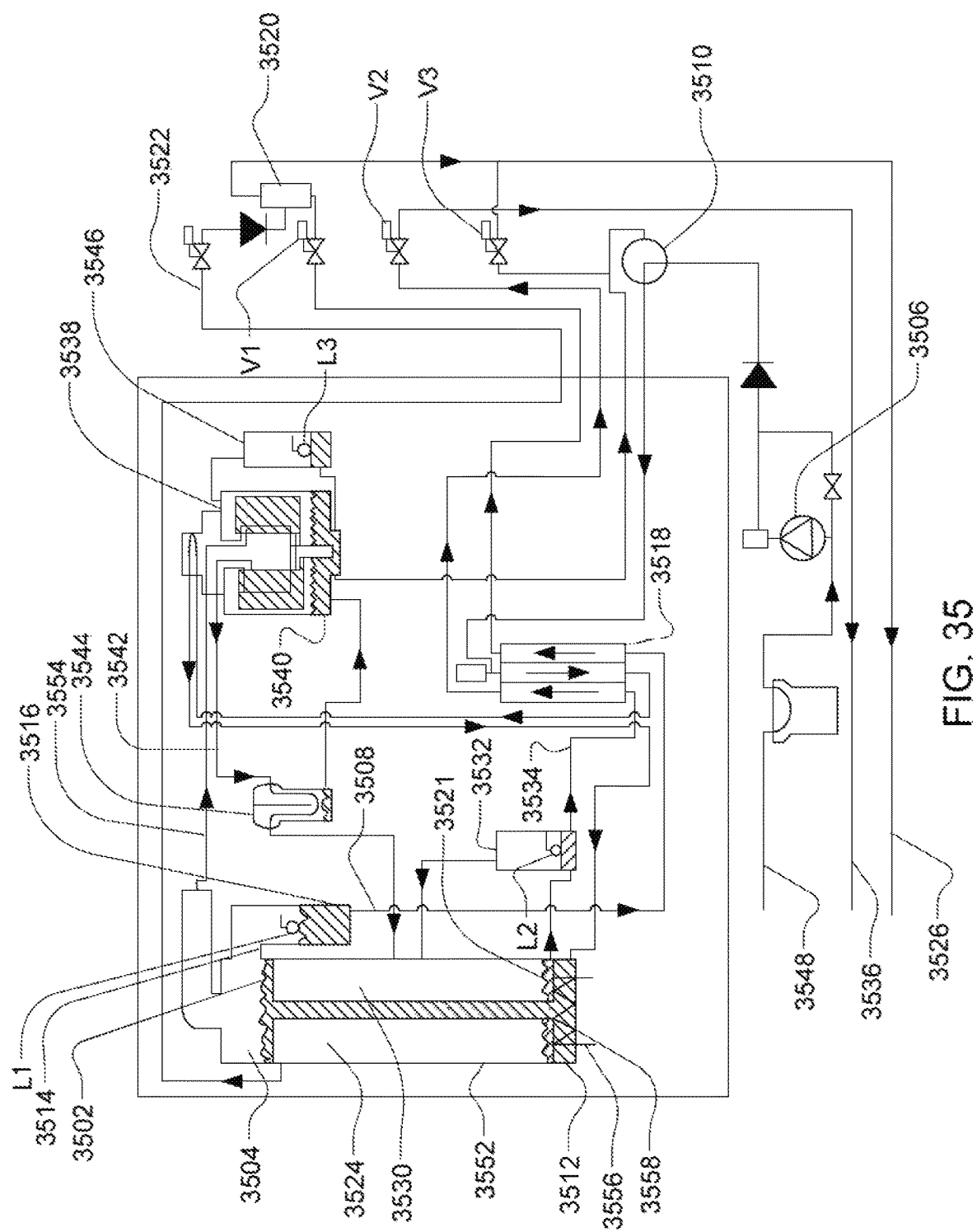
Figure 35A:
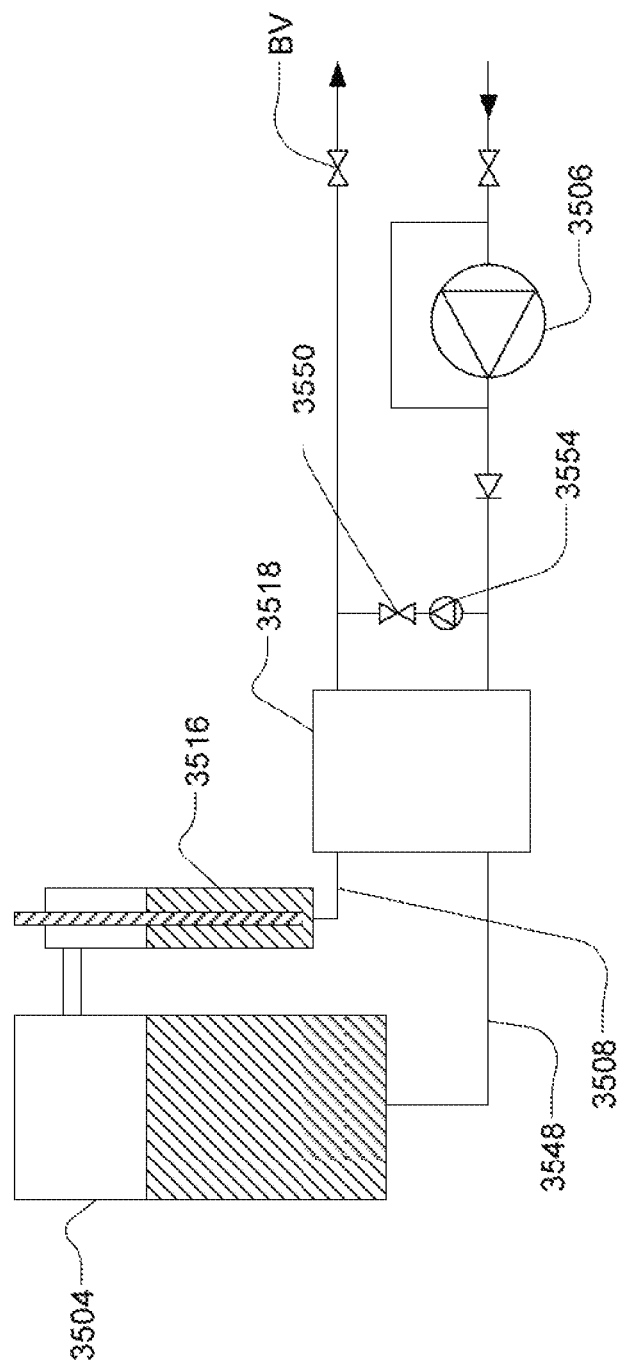
Figure 36:
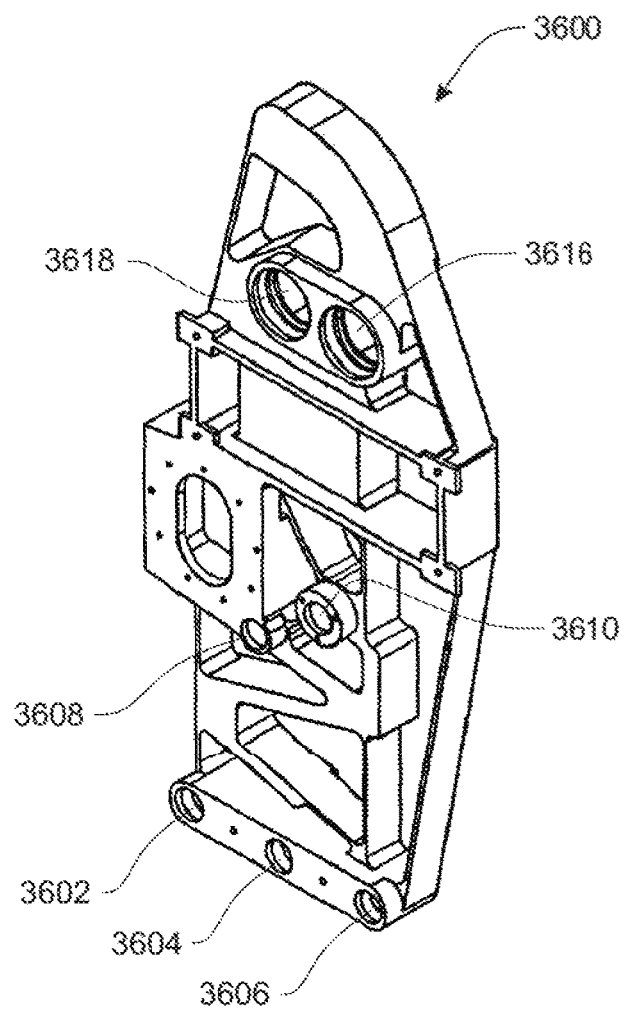
Figure 36A:
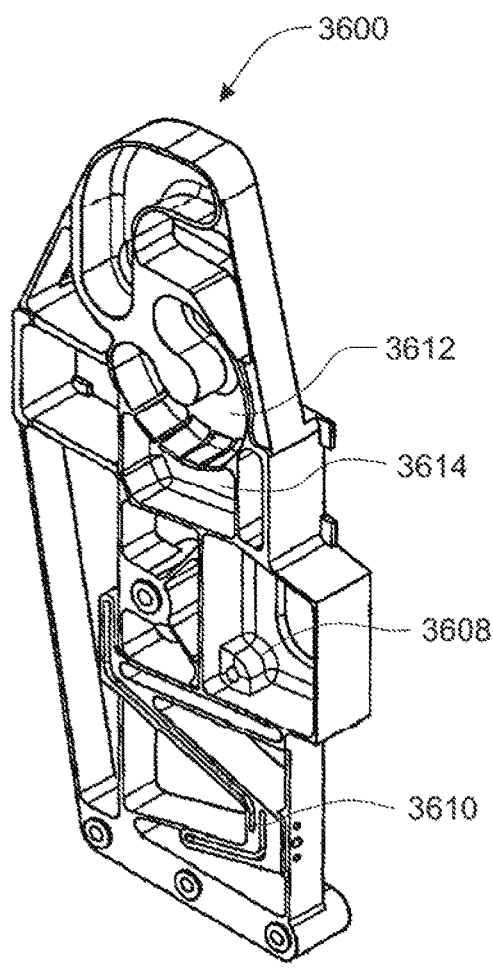
Figure 37:
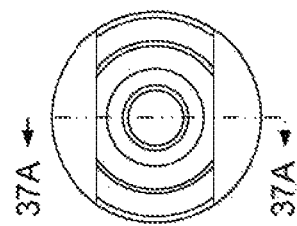
Figure 37A:
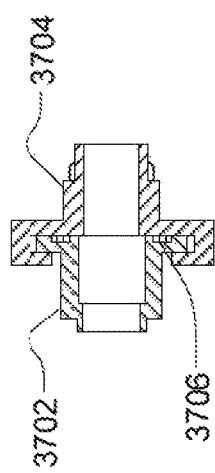
Figure 38:
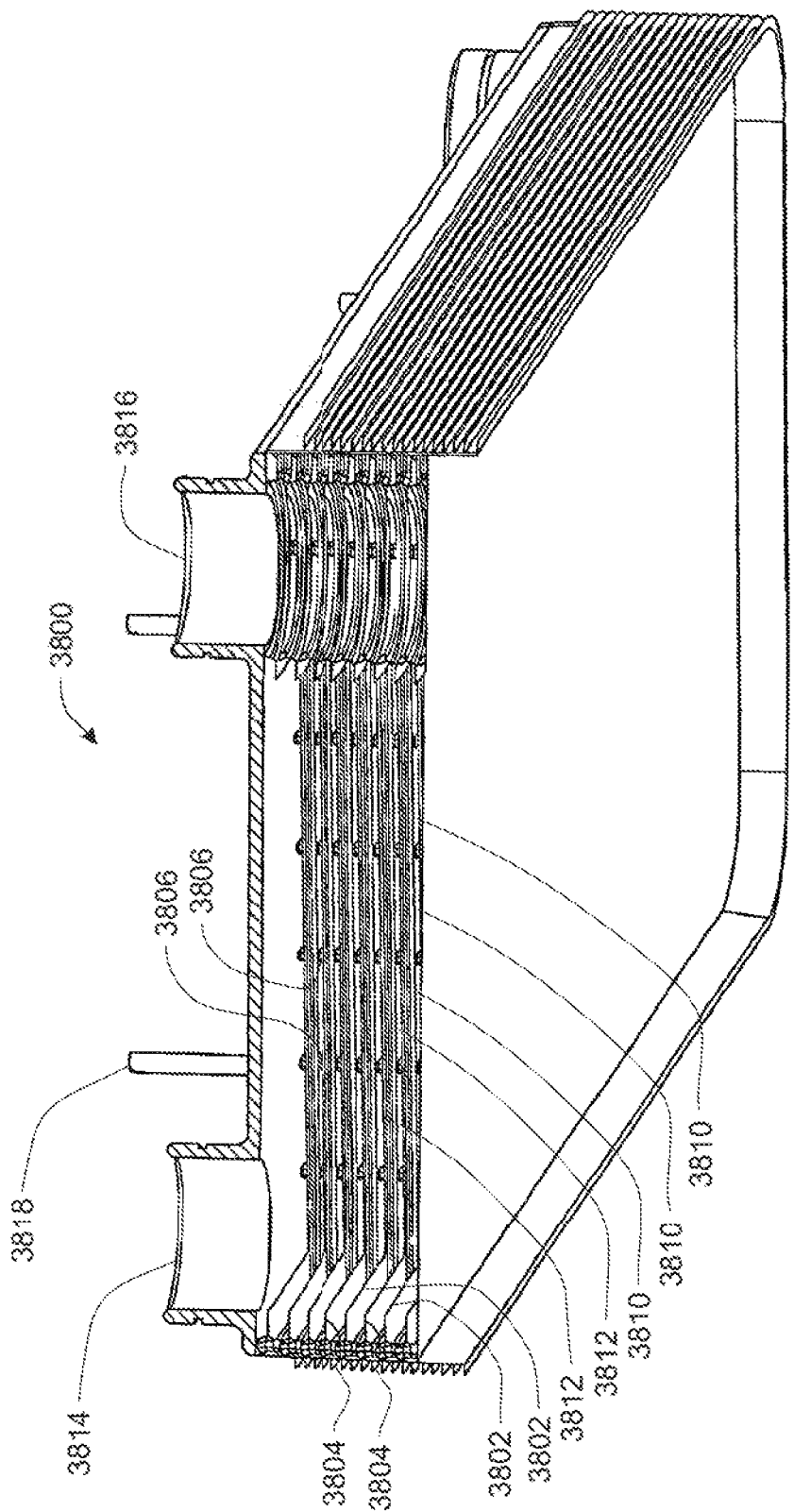
Figure 38A:
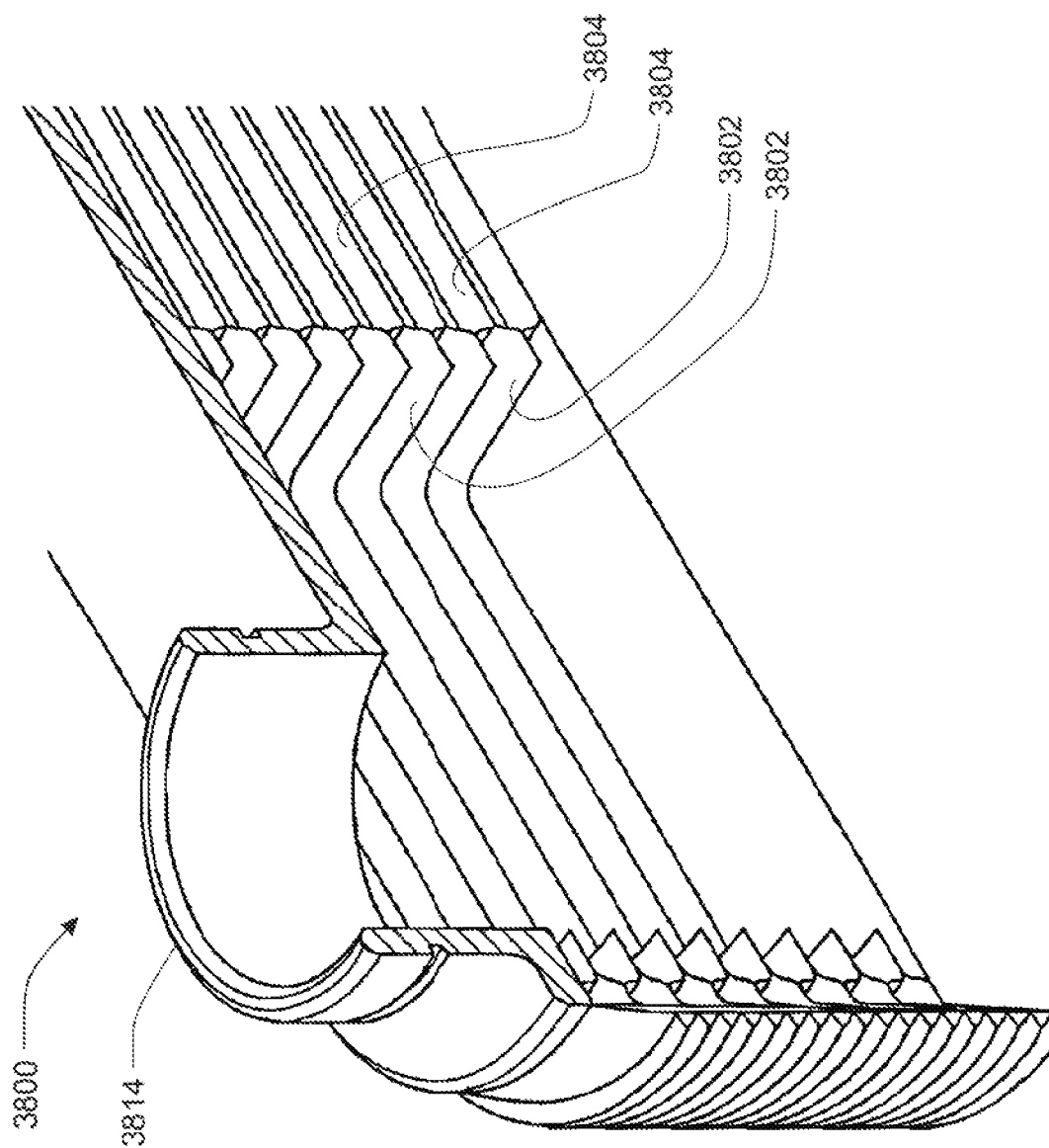
Figure 39:
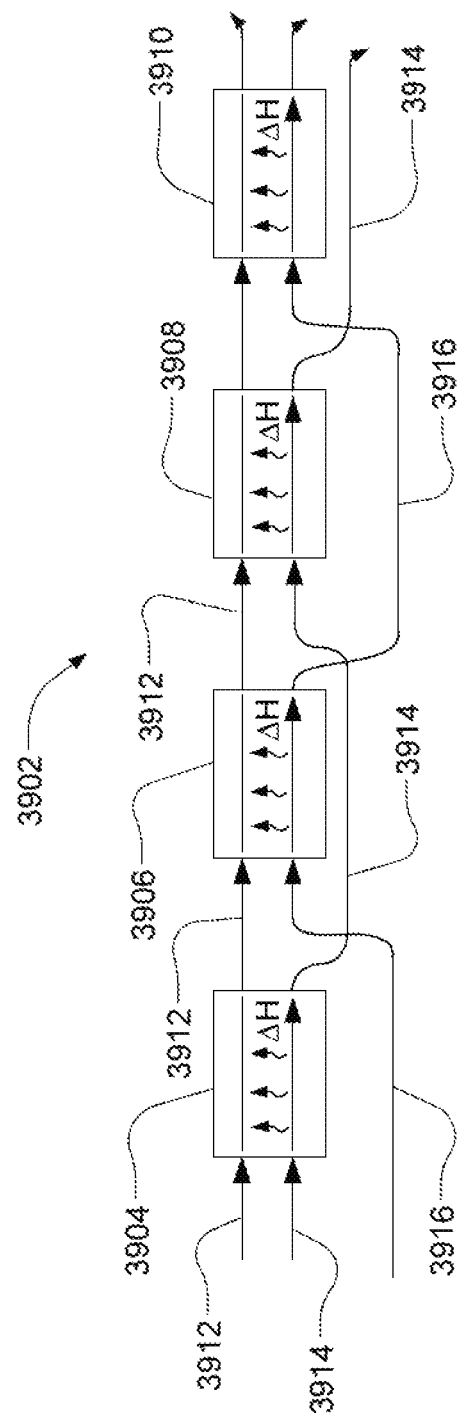
Figure 39A:
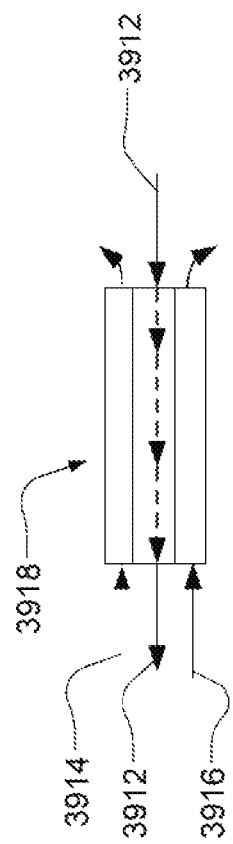
Figure 40:
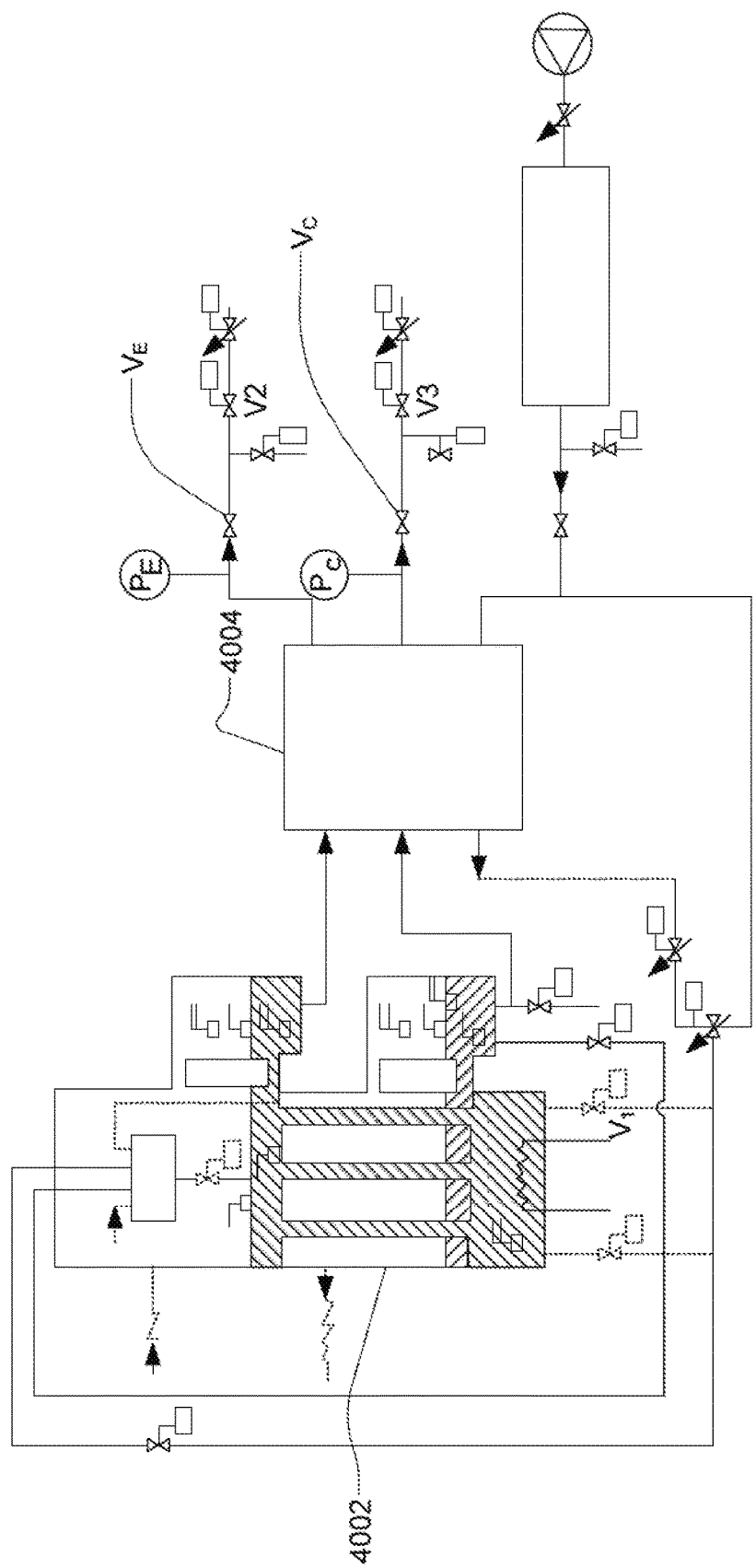
Figure 41:
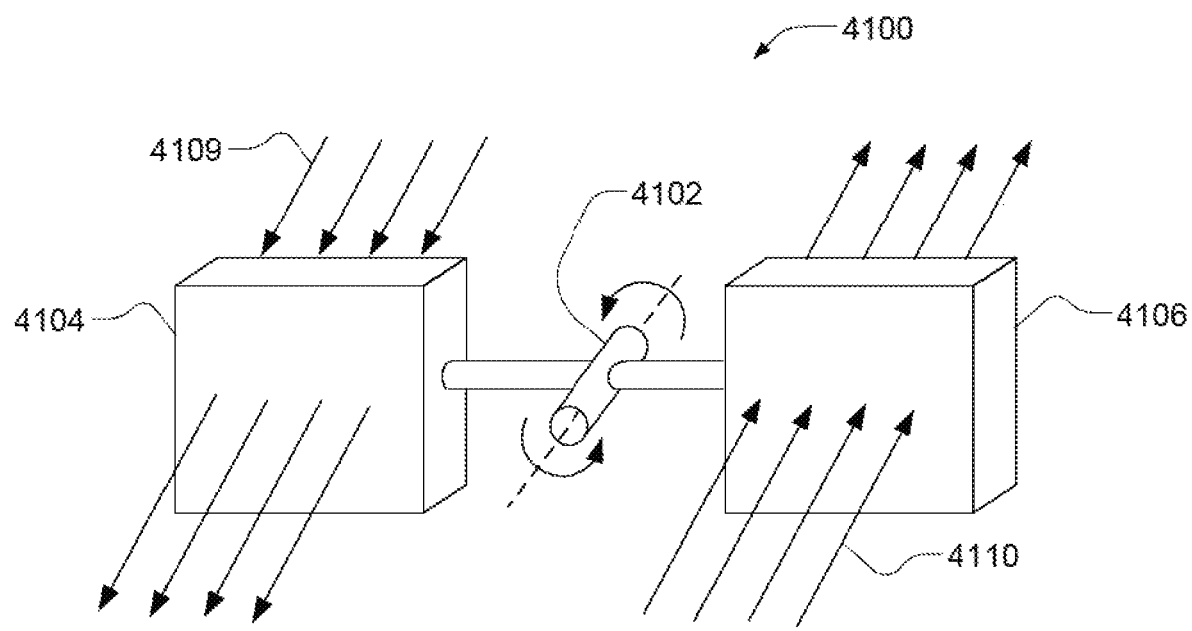
Figure 41A:
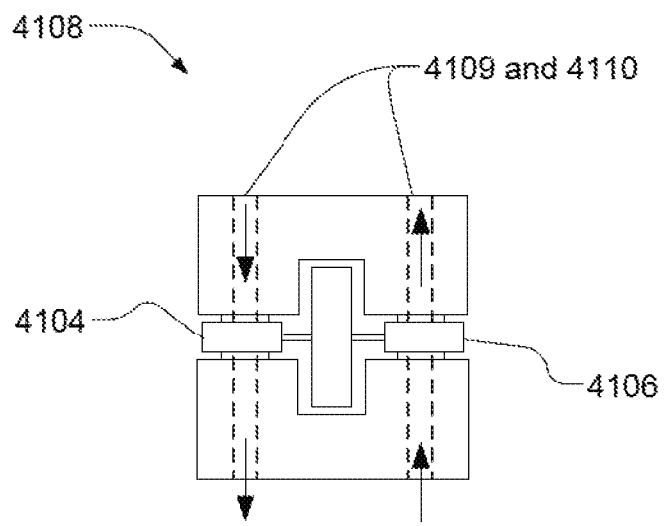
Figure 41B:
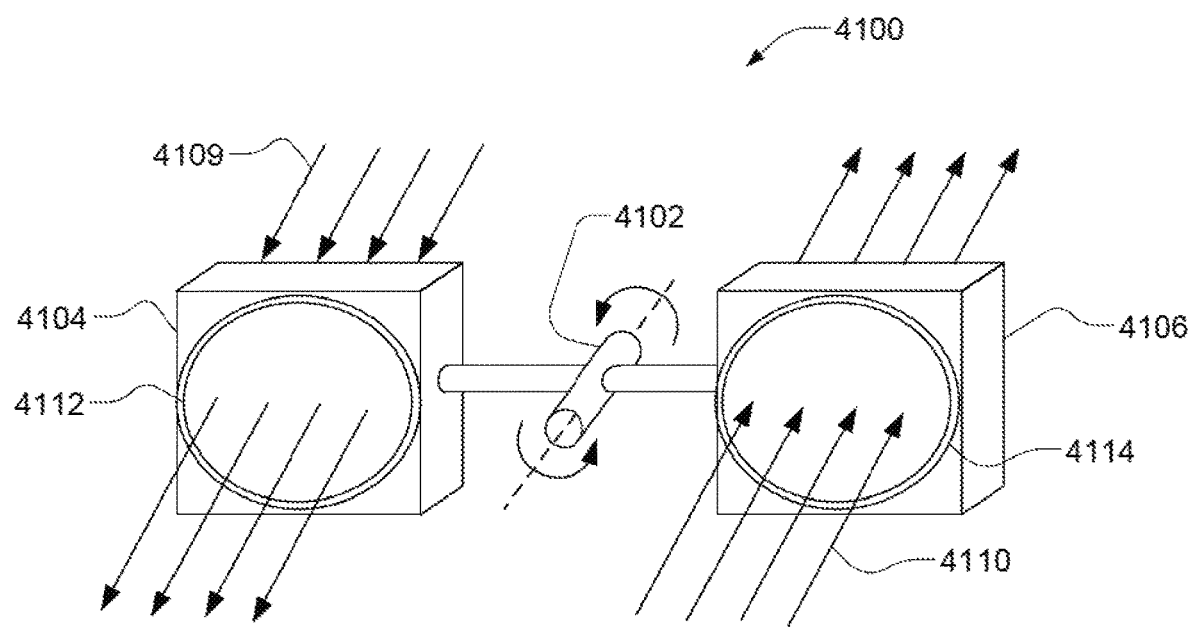
Figure 41C:
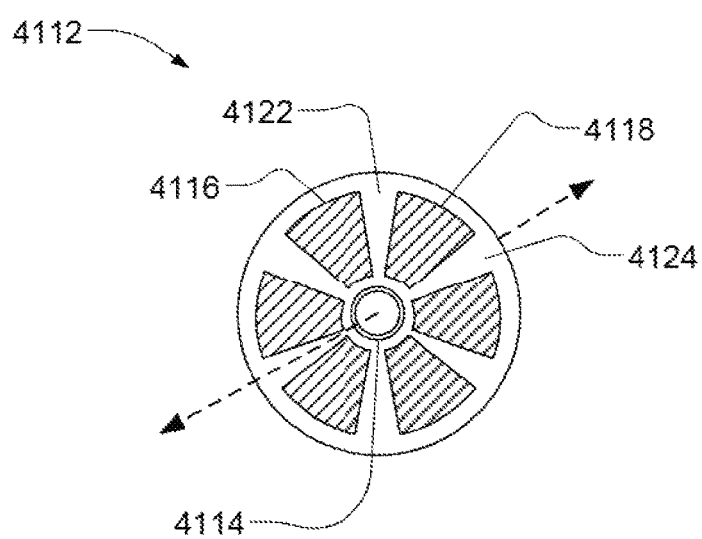
Figure 41D:
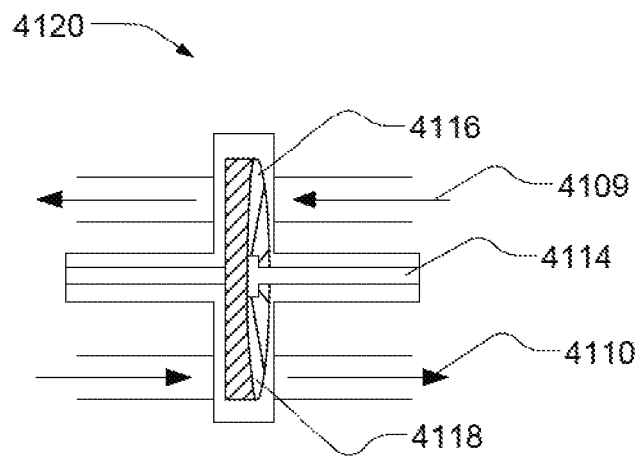
Figure 41E:
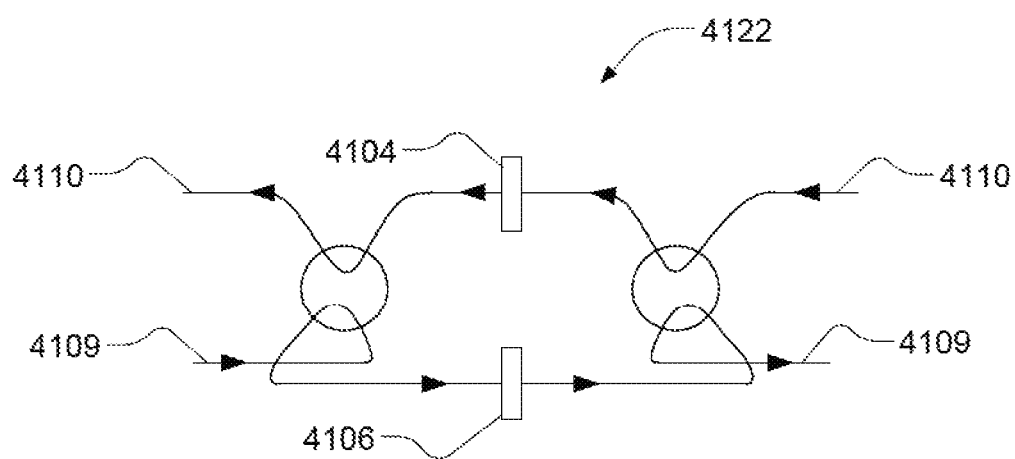
Figure 41F:
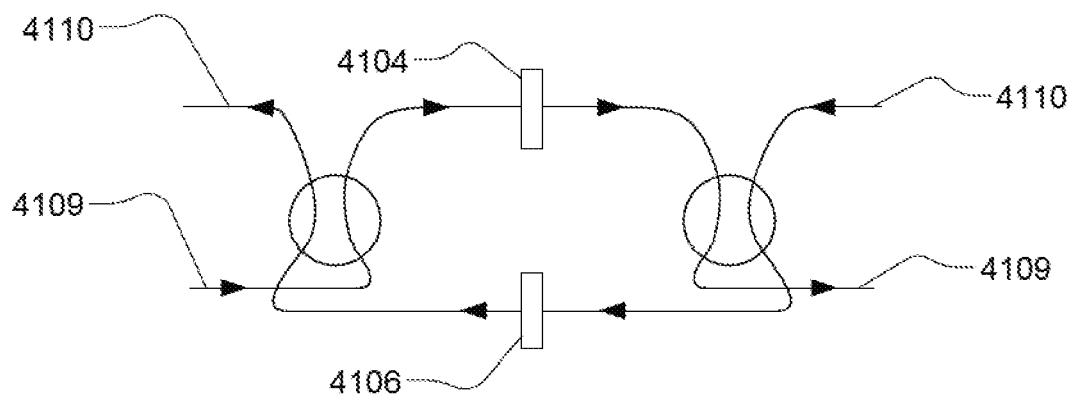
Figure 42:
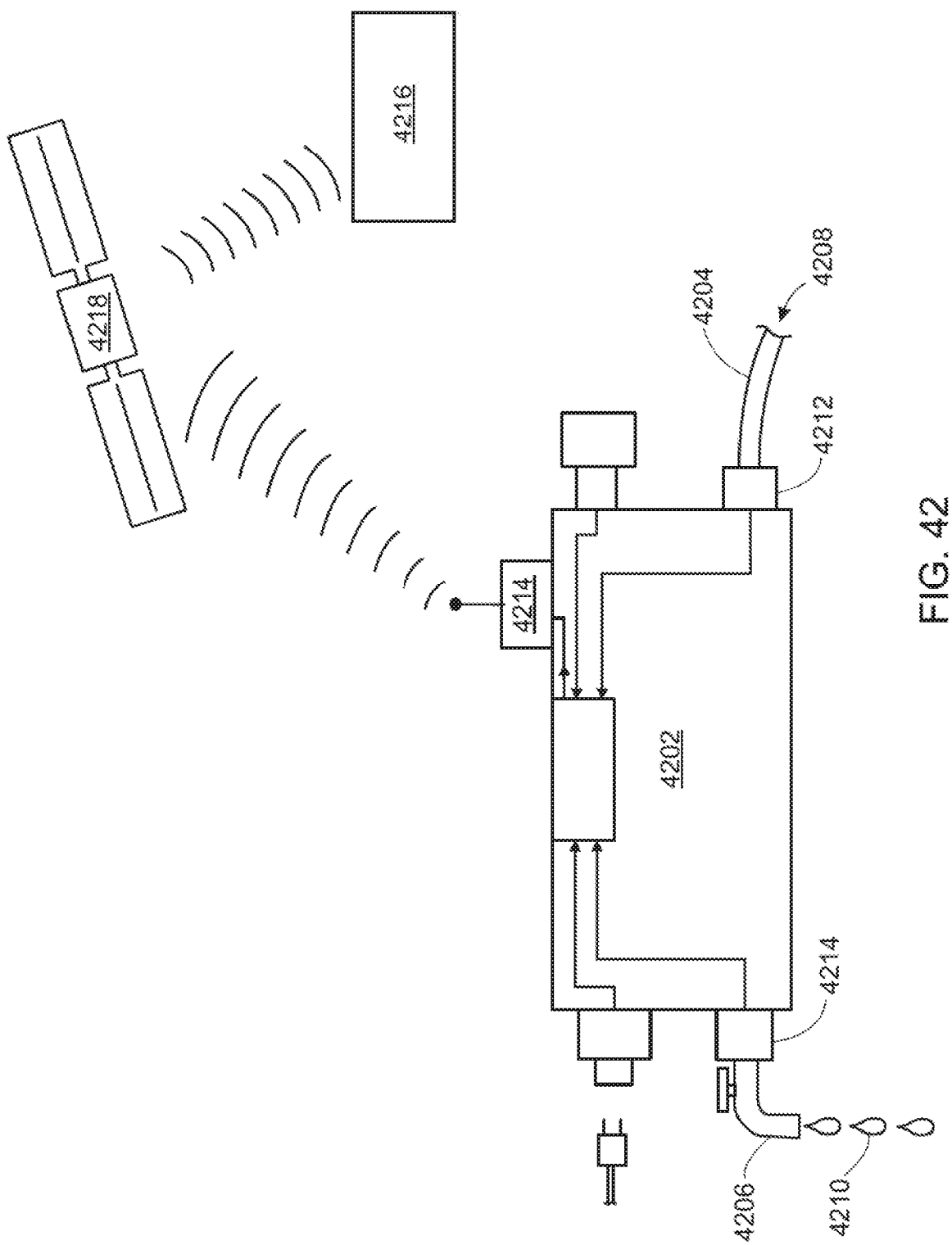
Figure 43:
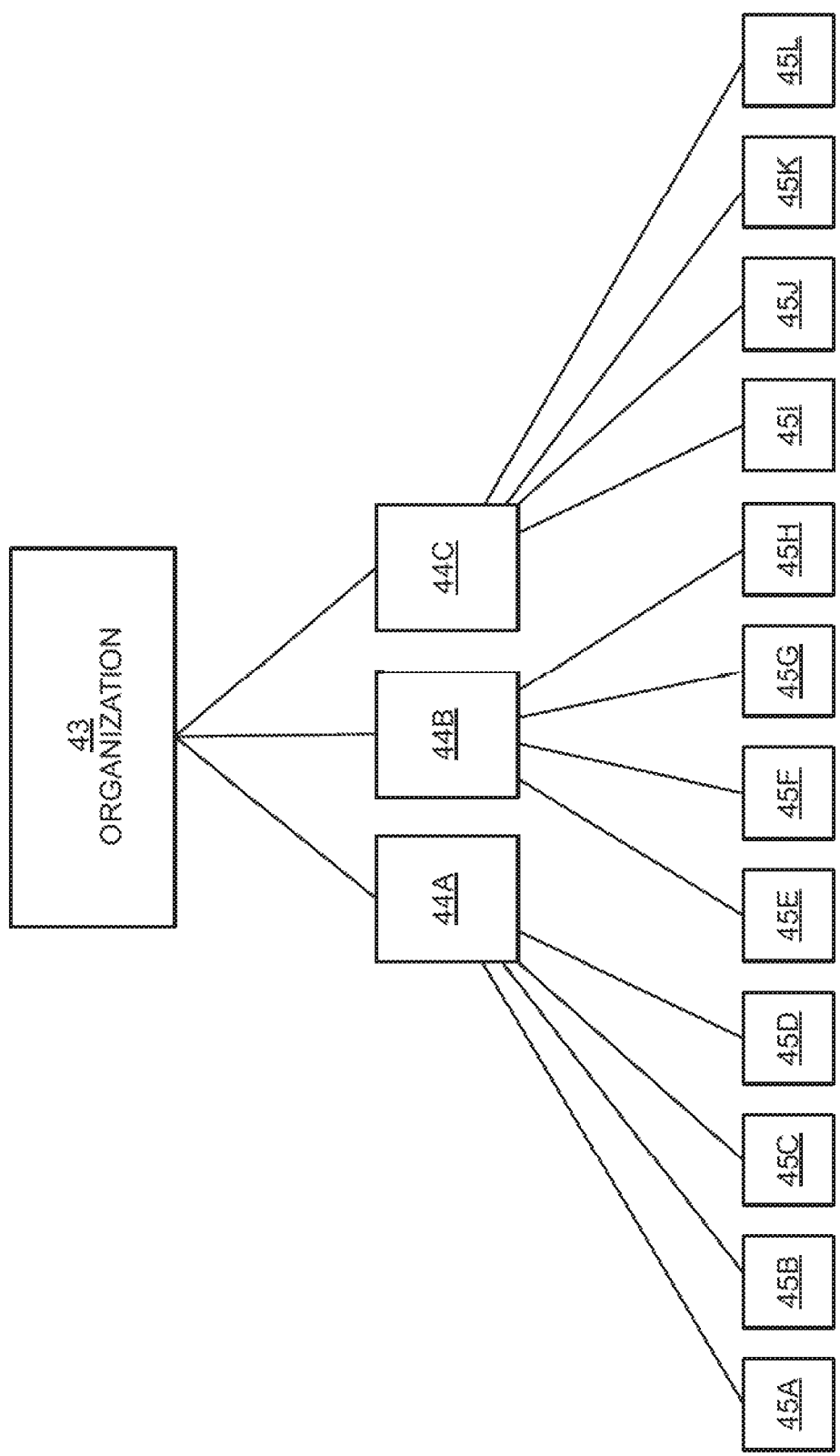
Figure 44:
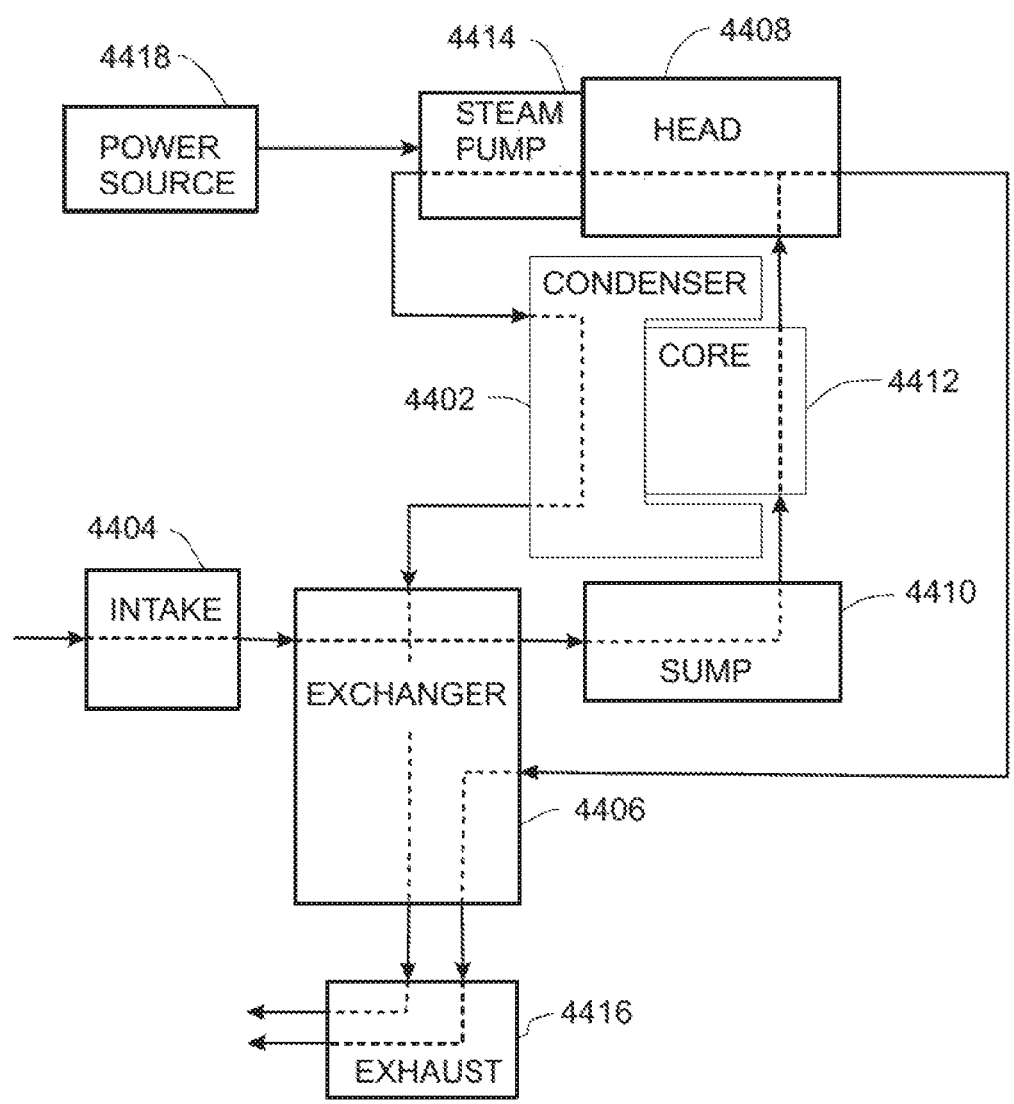
Figure 44A:
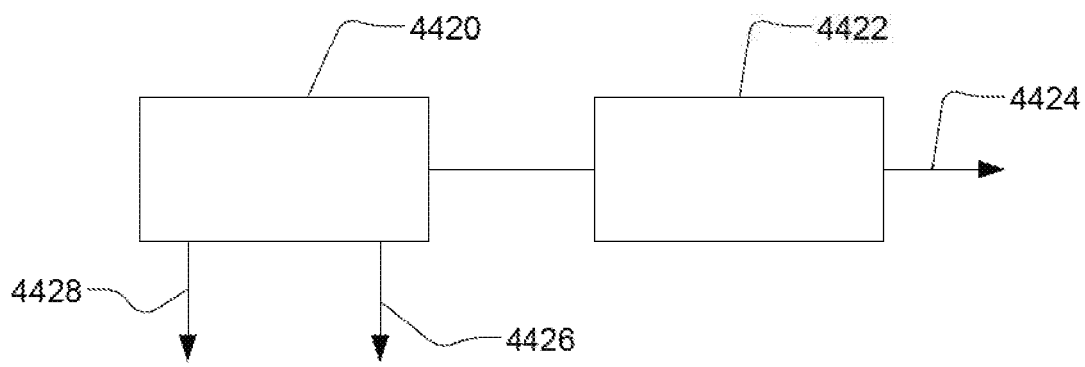
Figure 46:
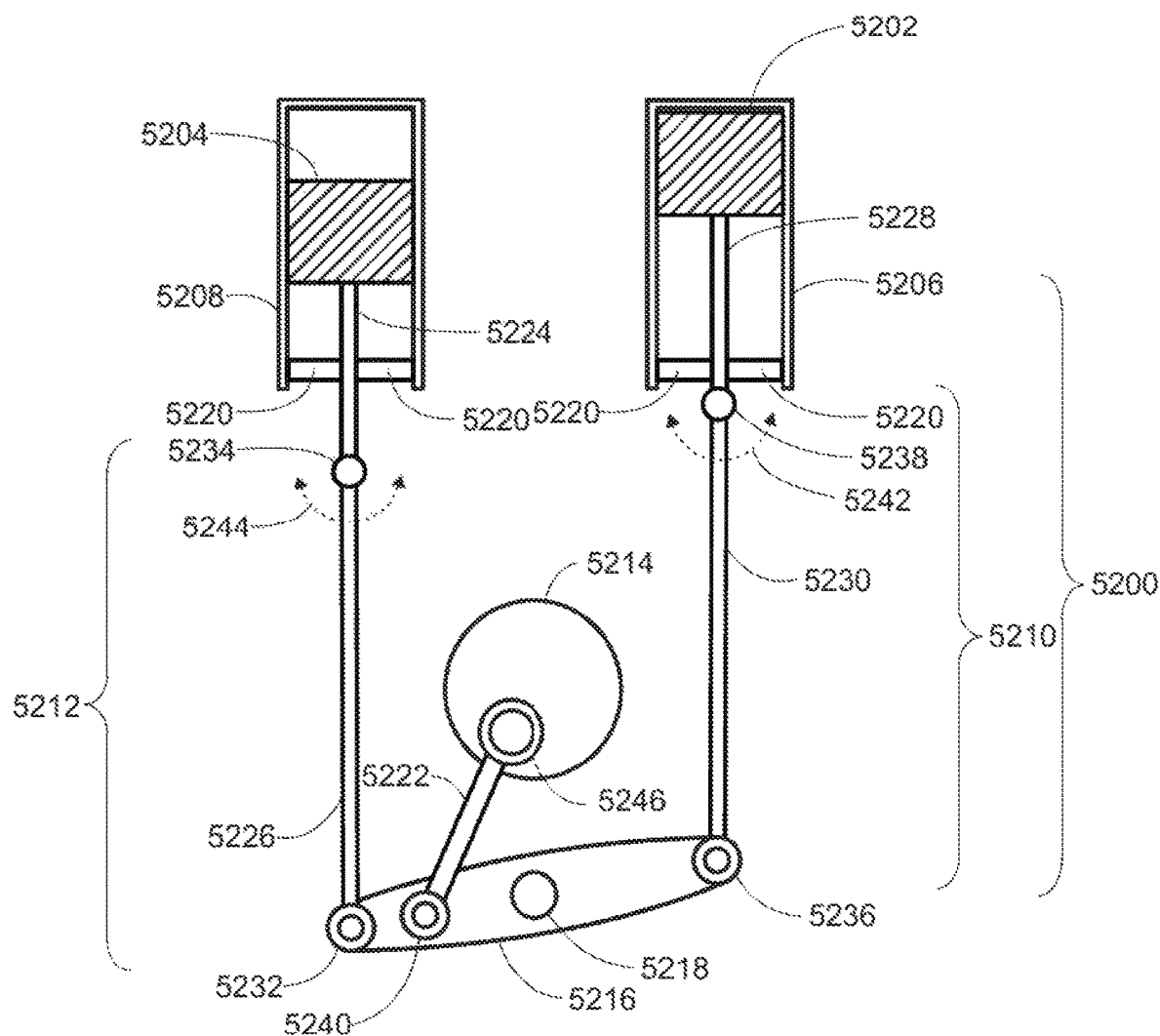
Figure 47:
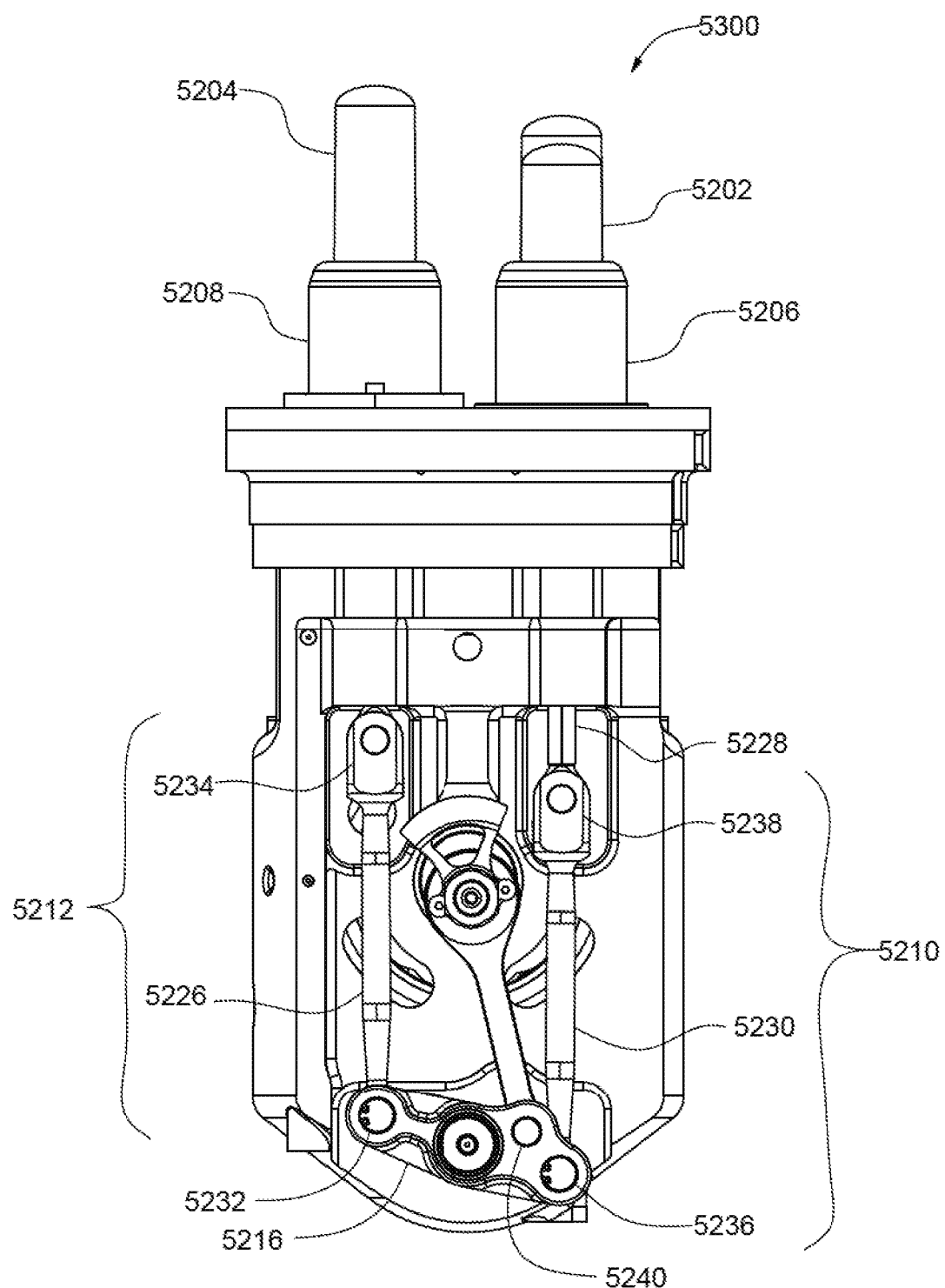
Figure 48:
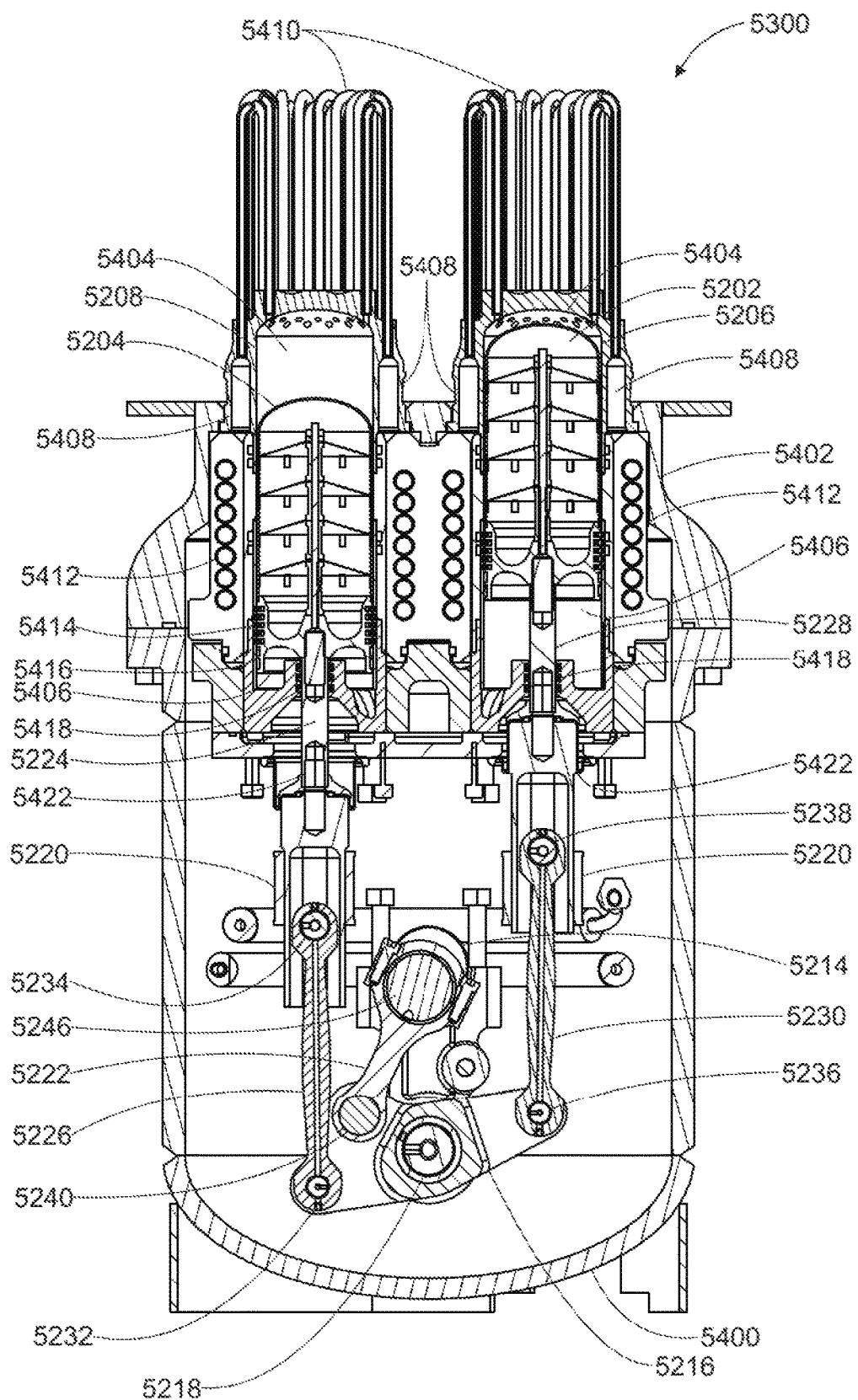
Figure 50:
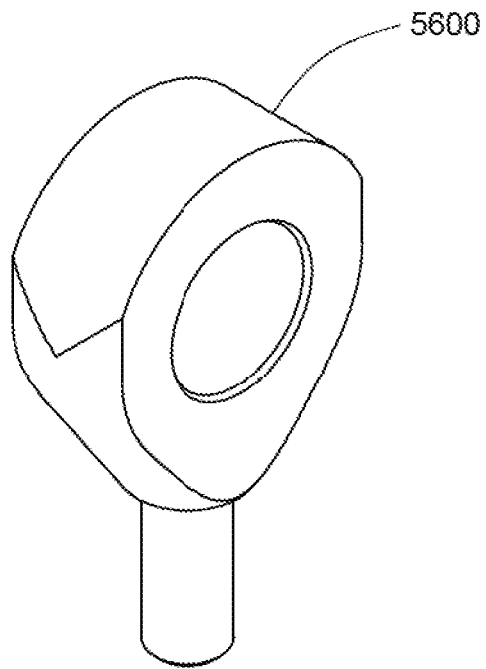
Figure 51A:
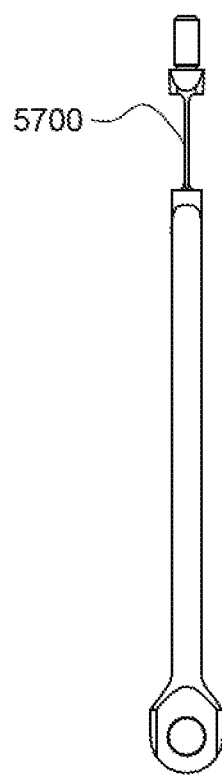
Figure 51B:
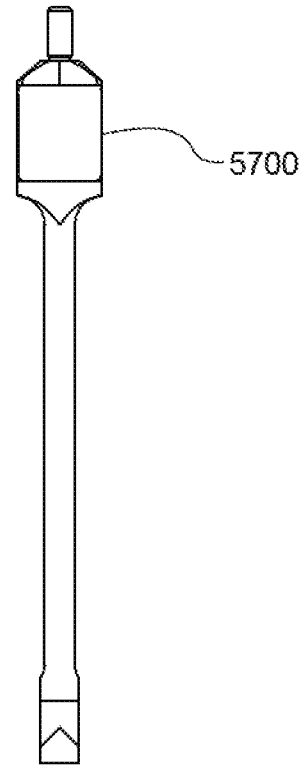
Figure 52:
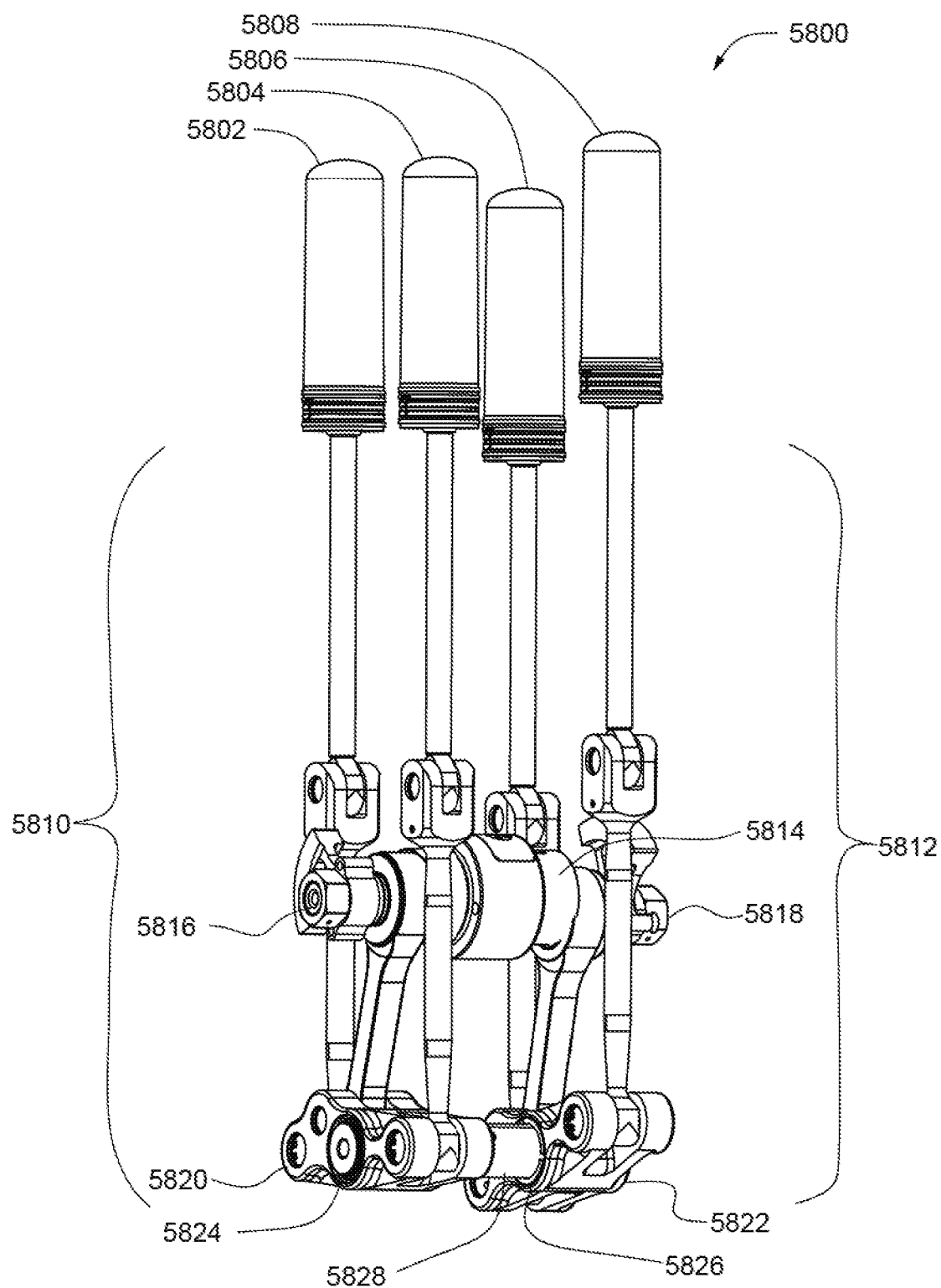
Figure 53:
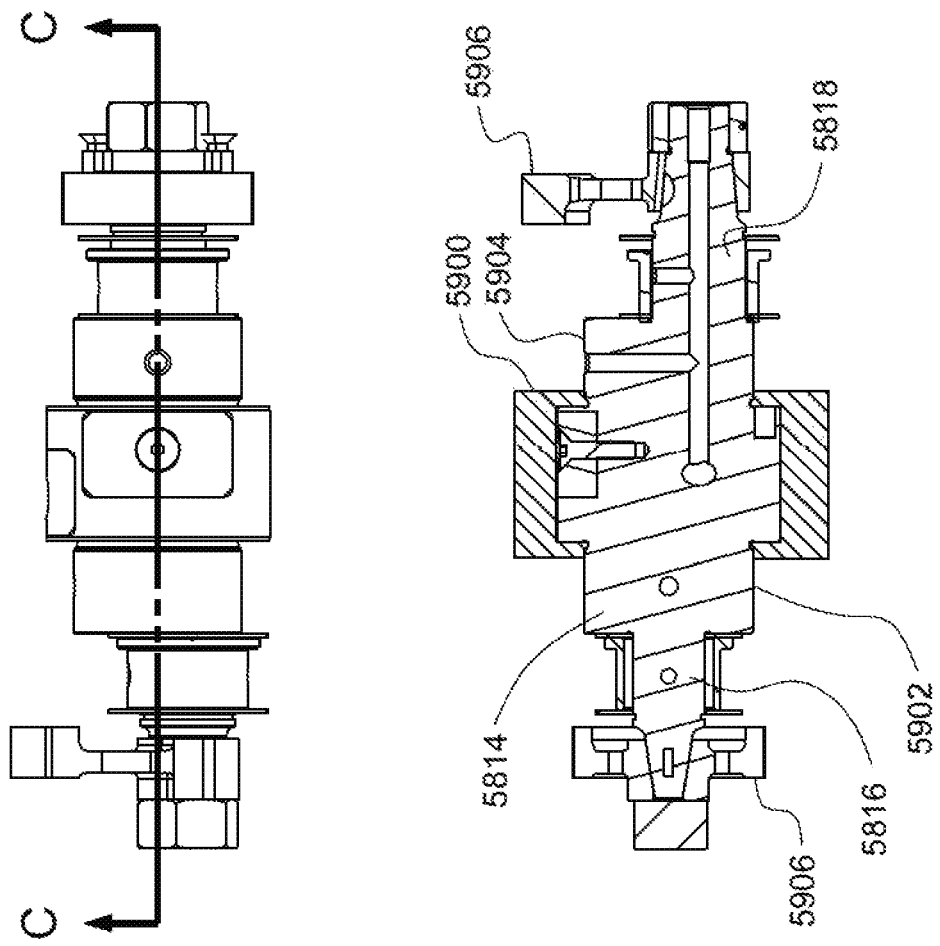
Figure 54B:
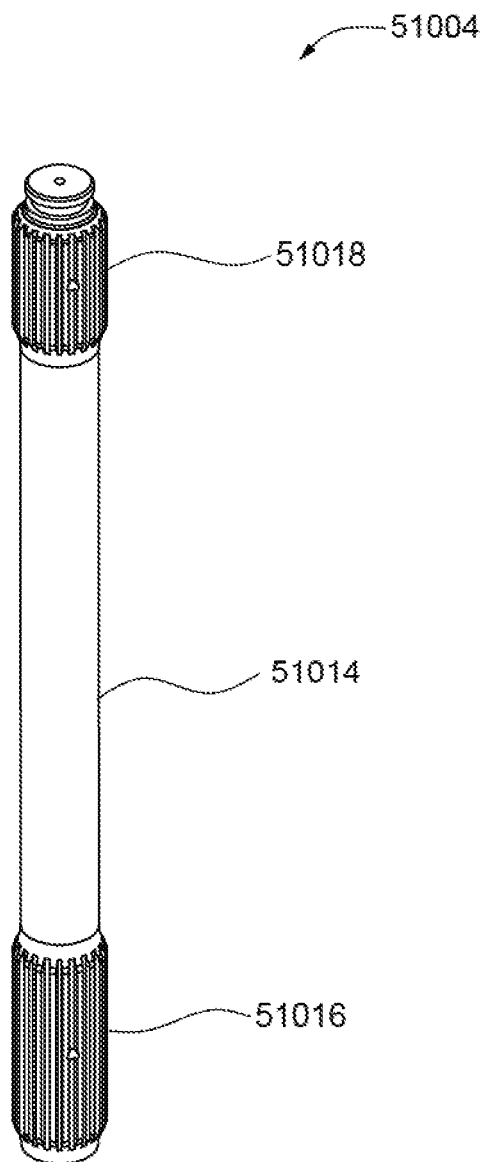
Figure 54C:
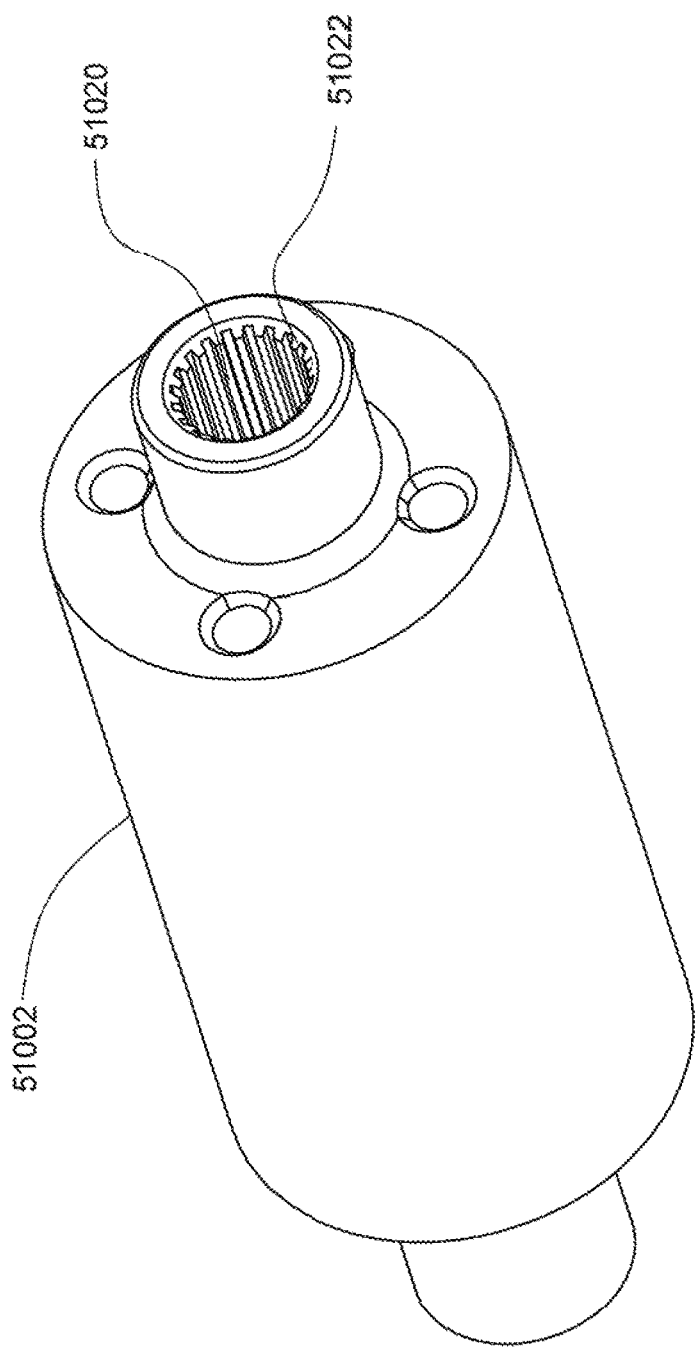
Figure 54D:
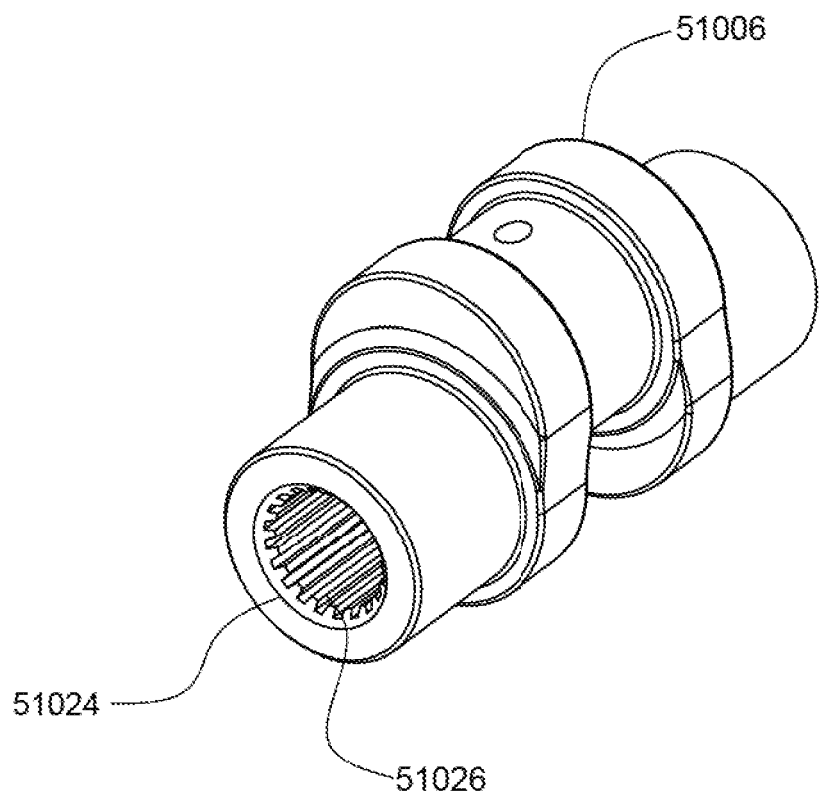
Figures 54E, 54F:
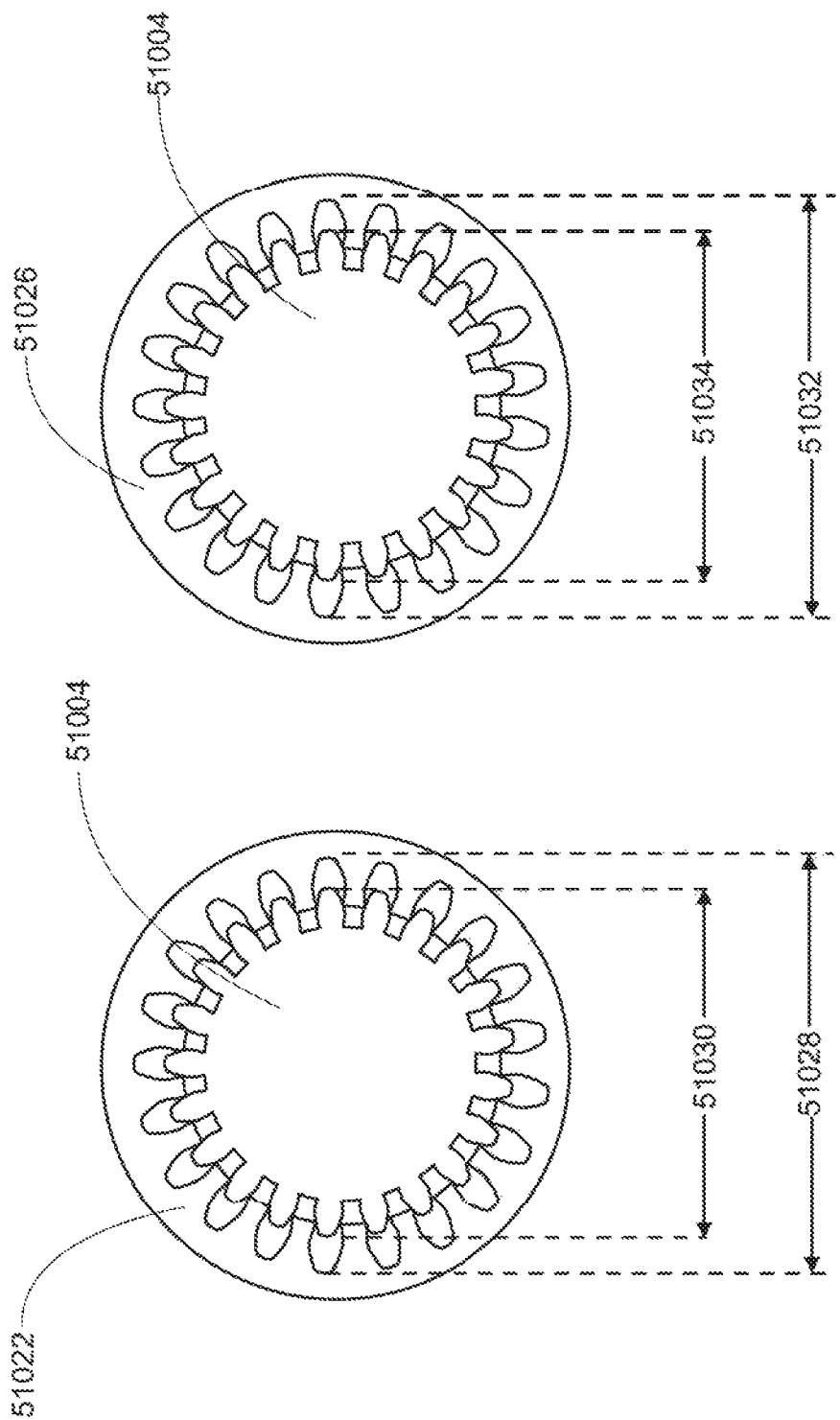
Figure 54G:
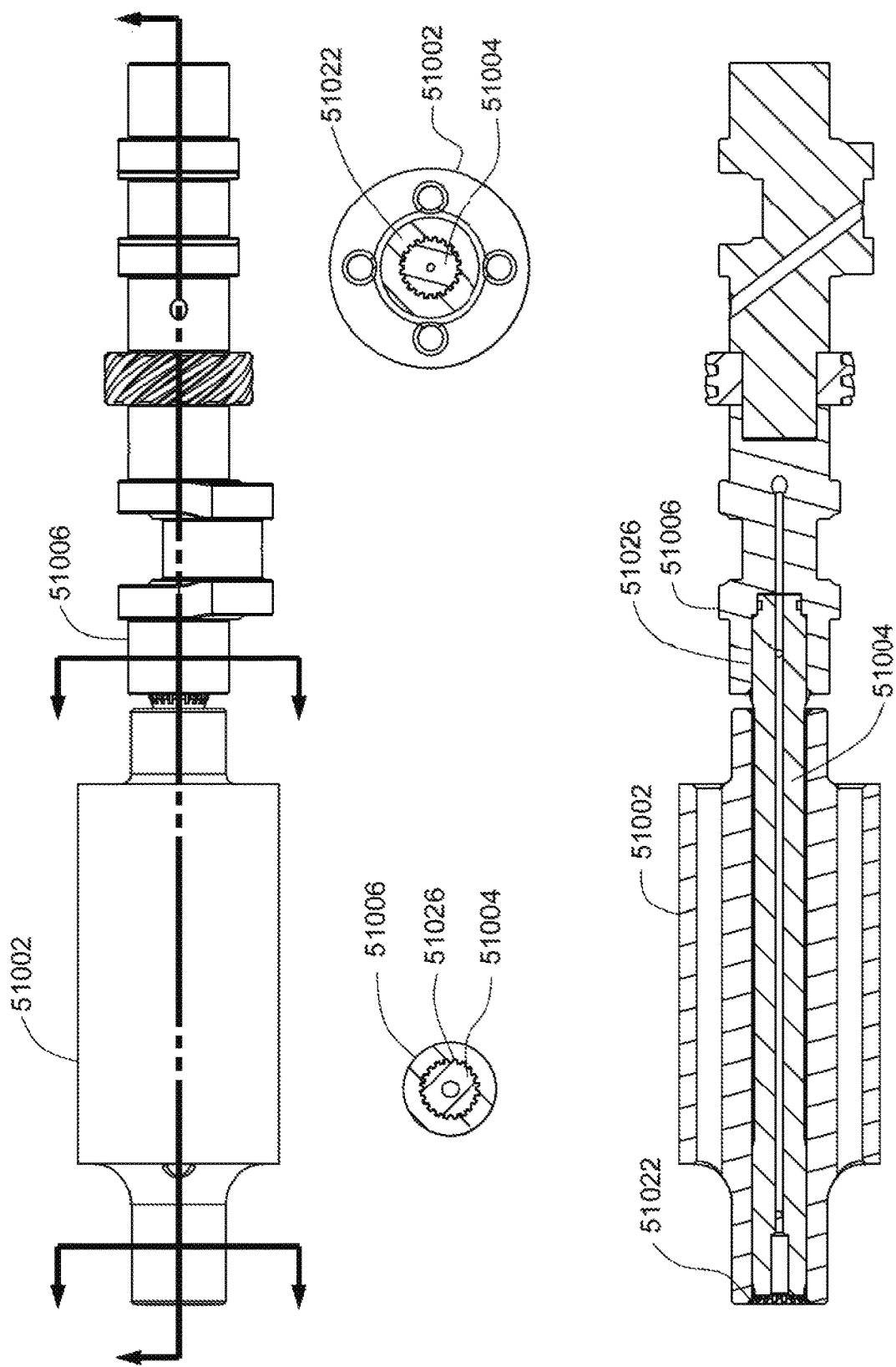
Figure 55:
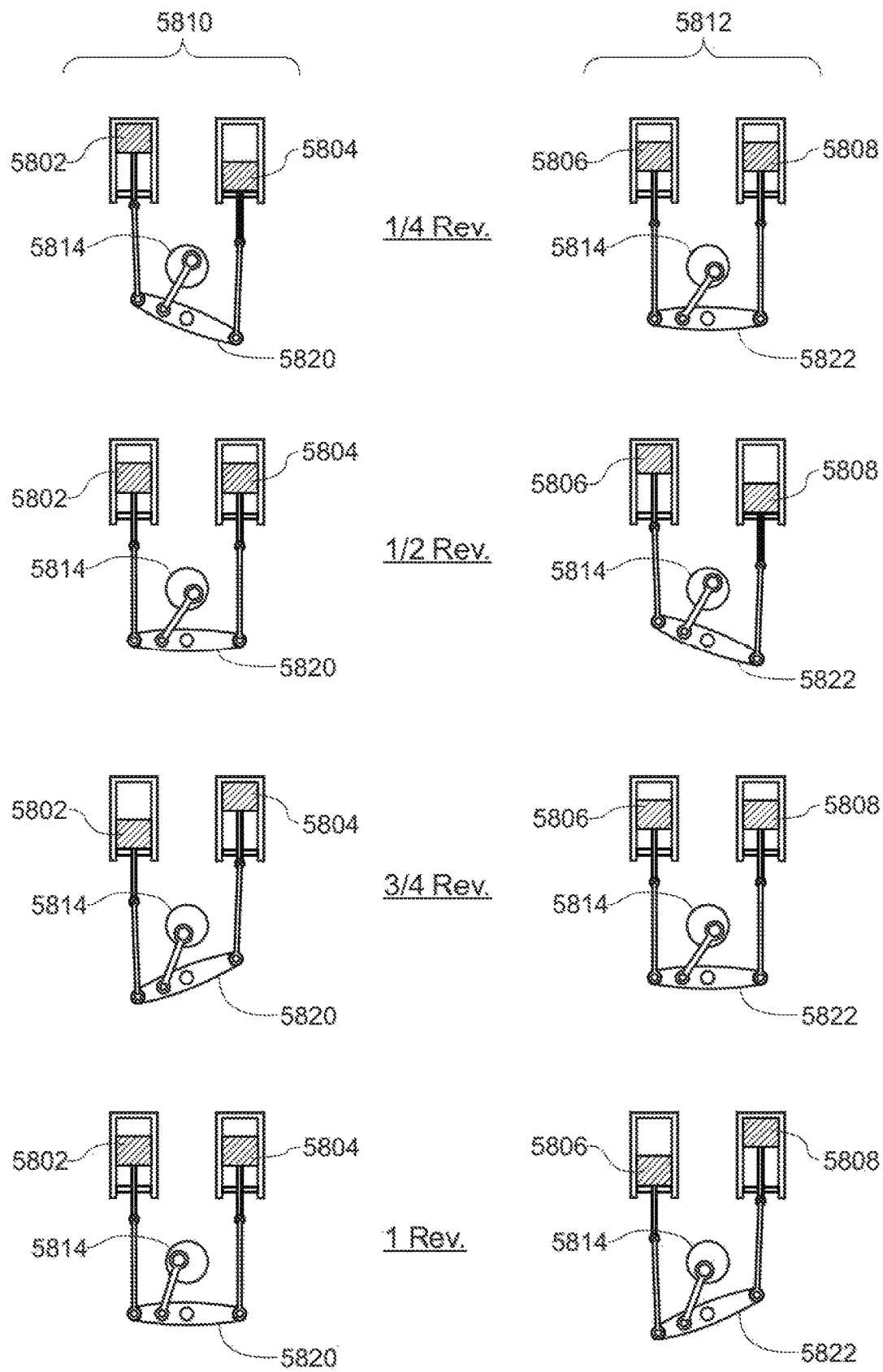
Figure 56A:
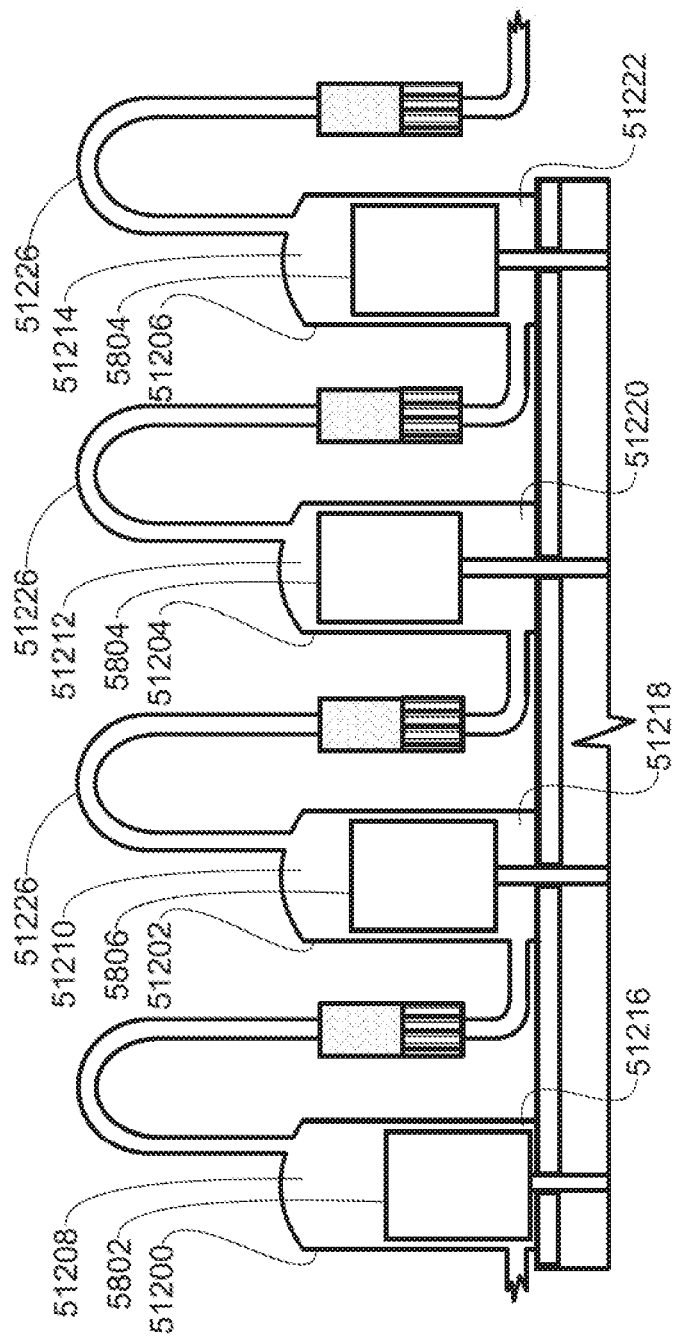
Figure 56B:
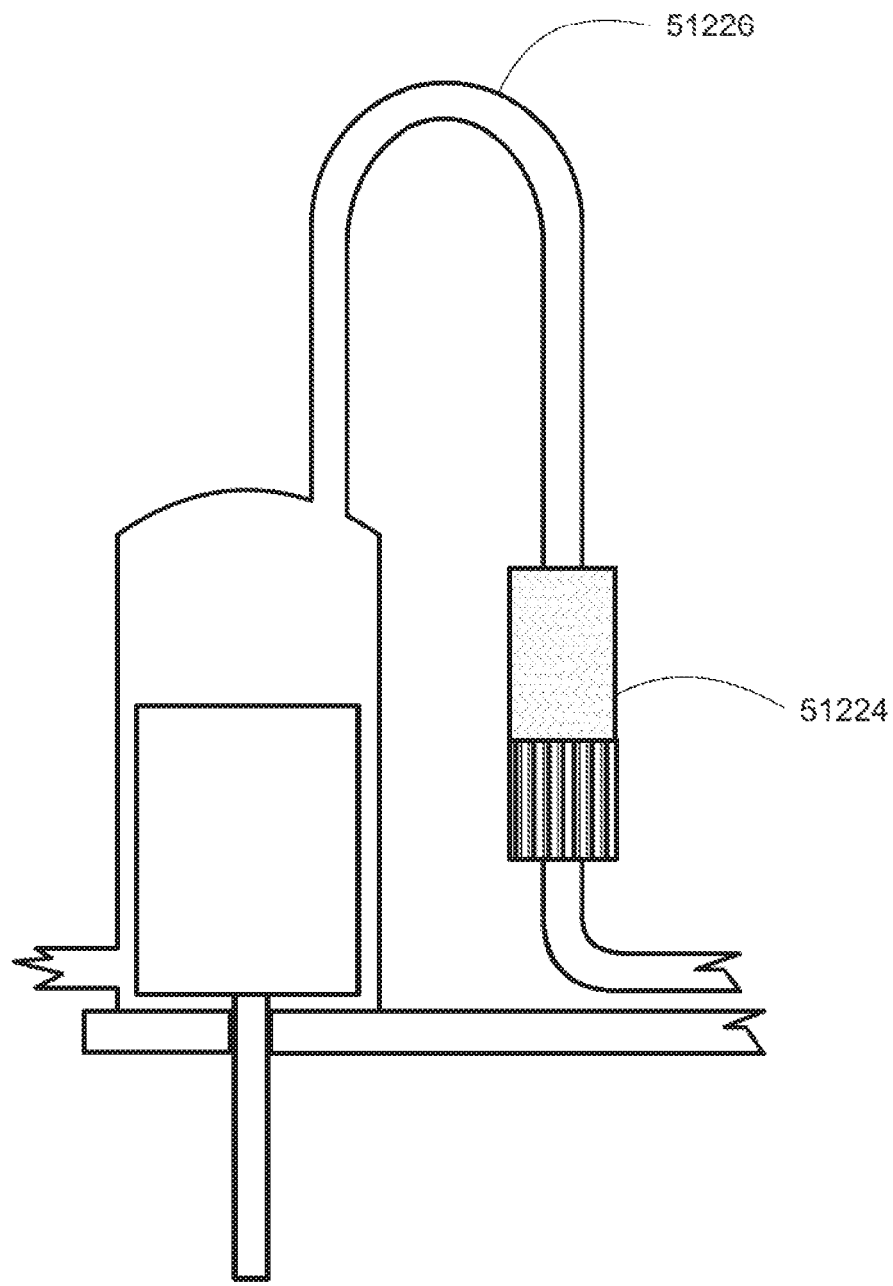
Figure 56C:
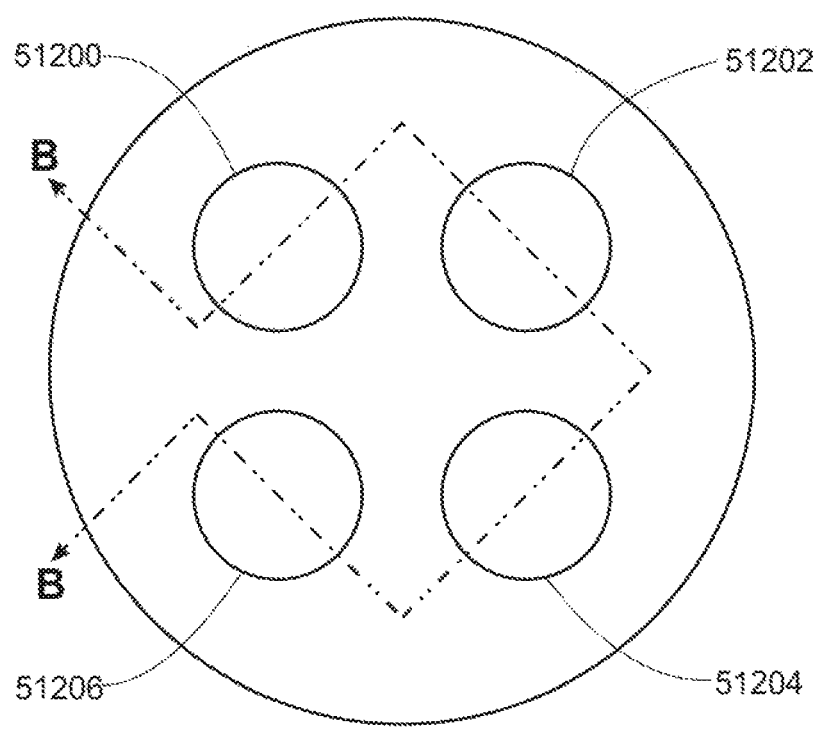
Figure 57A:
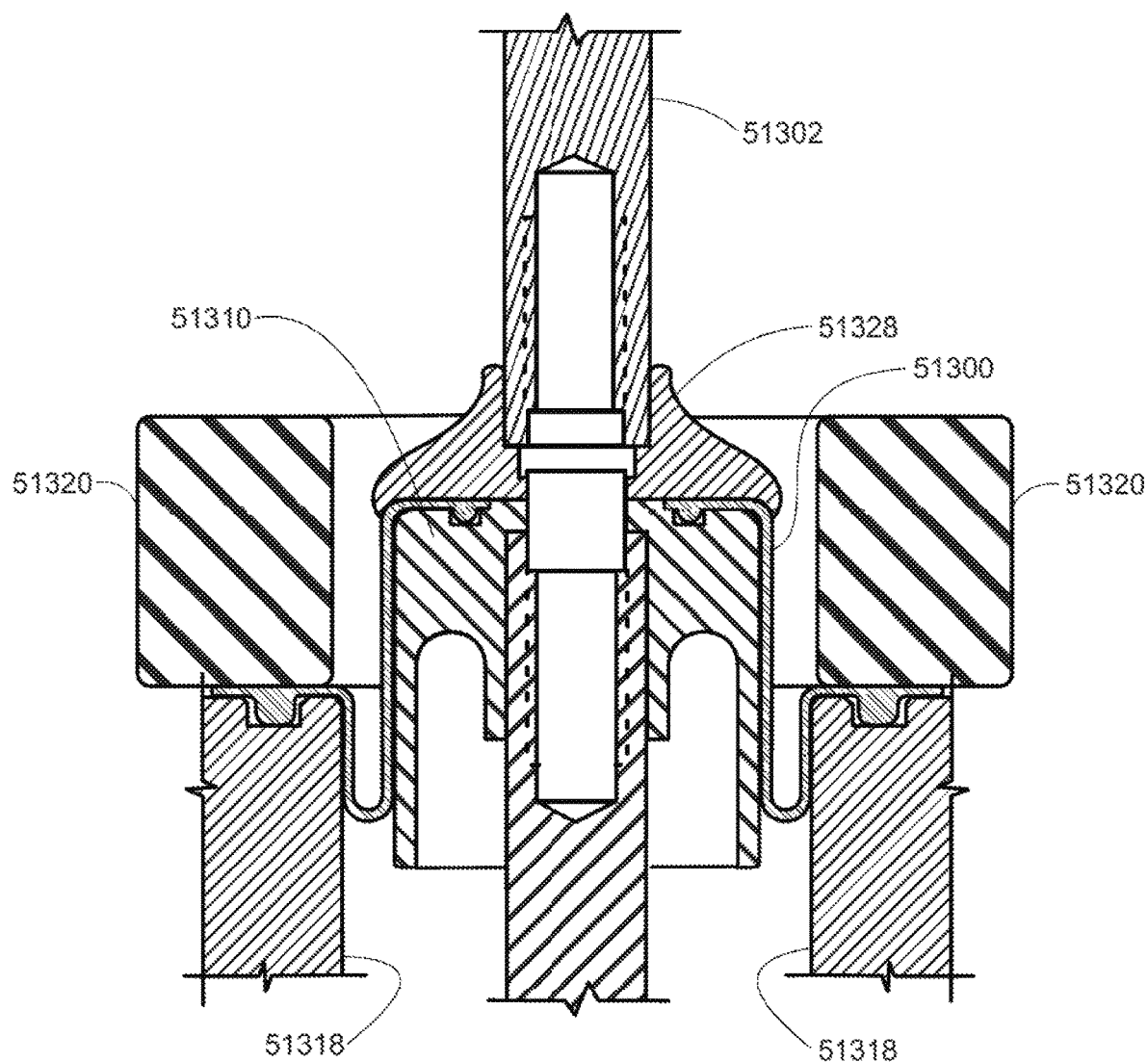
Figure 57B:
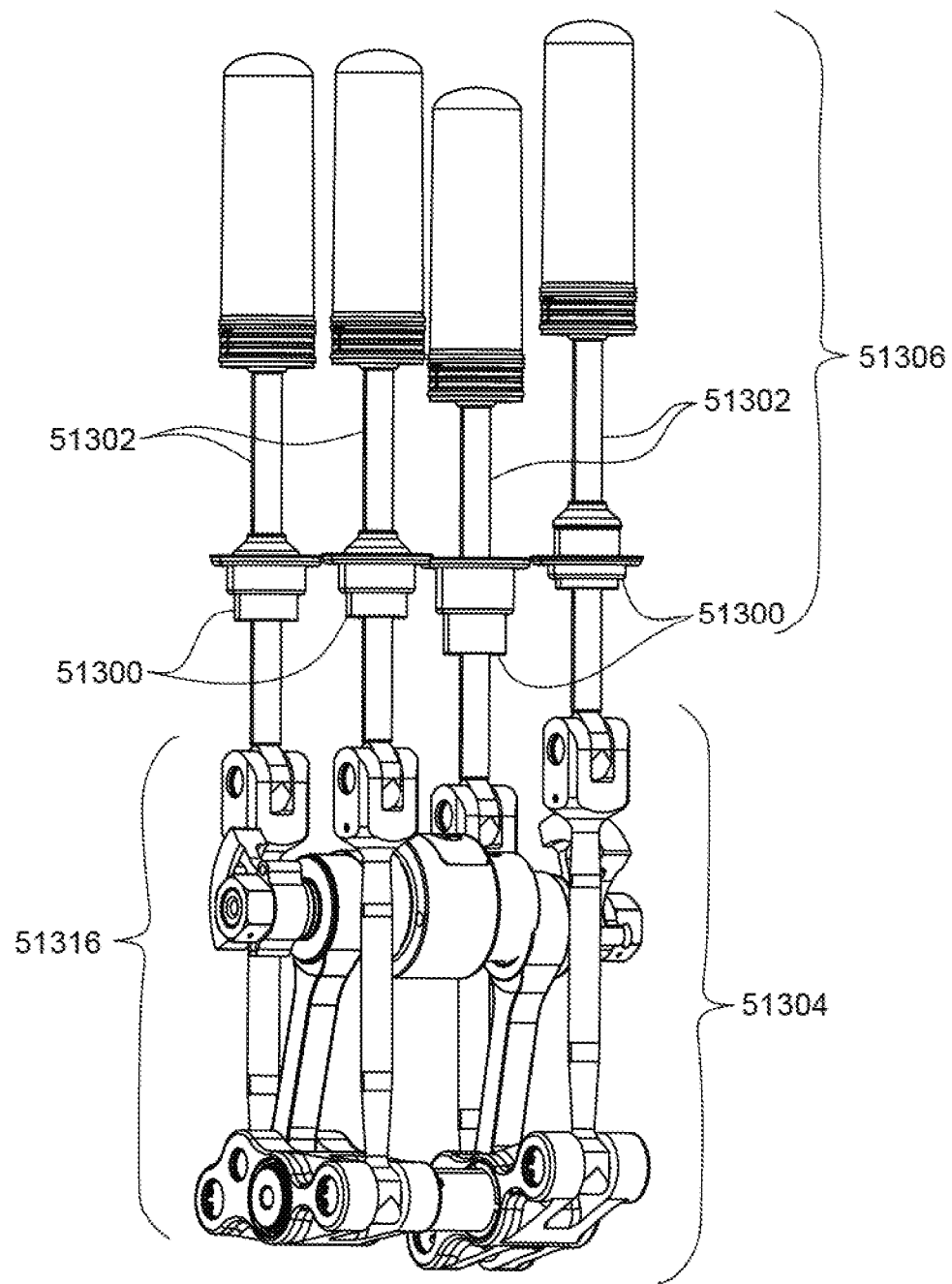
Figure 57C:
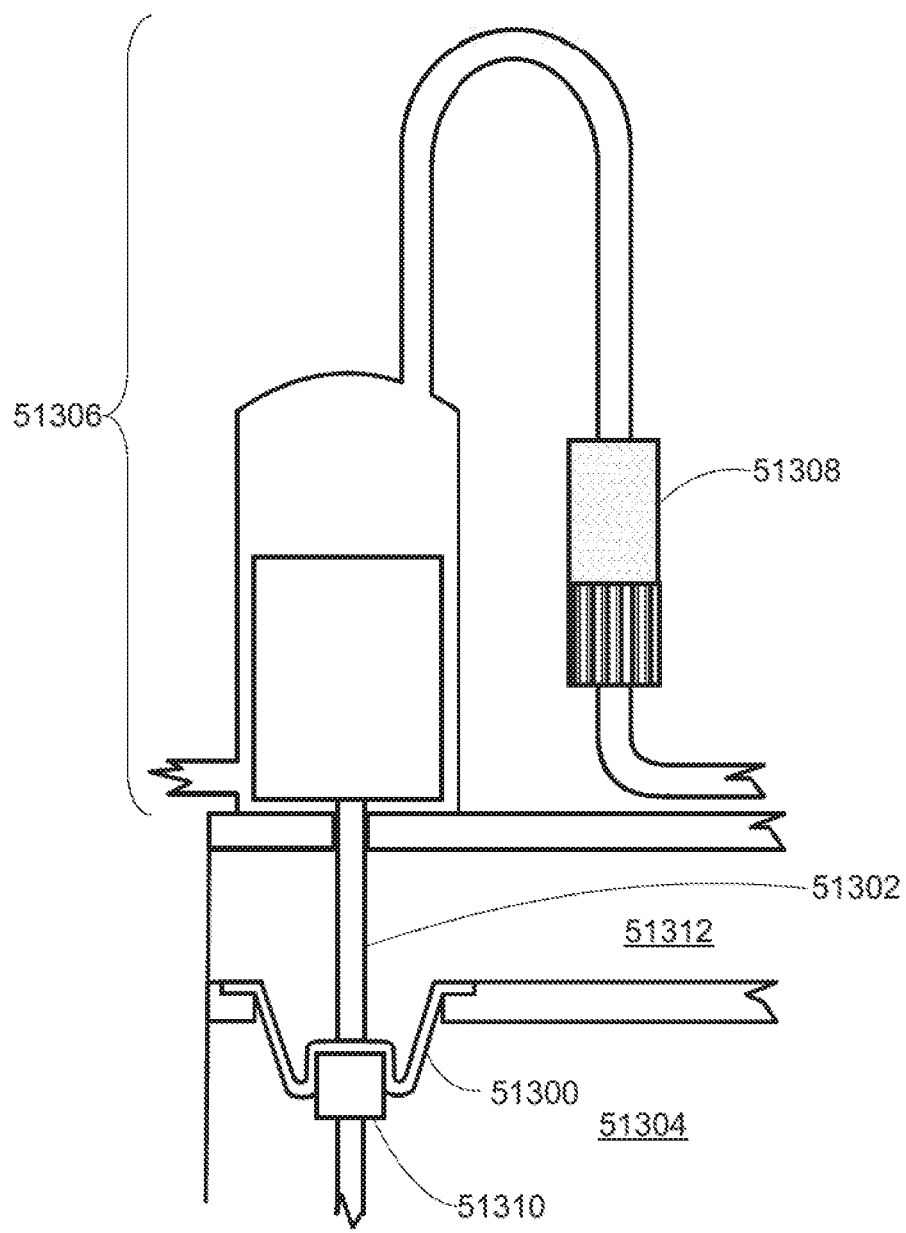
Figure 57F:
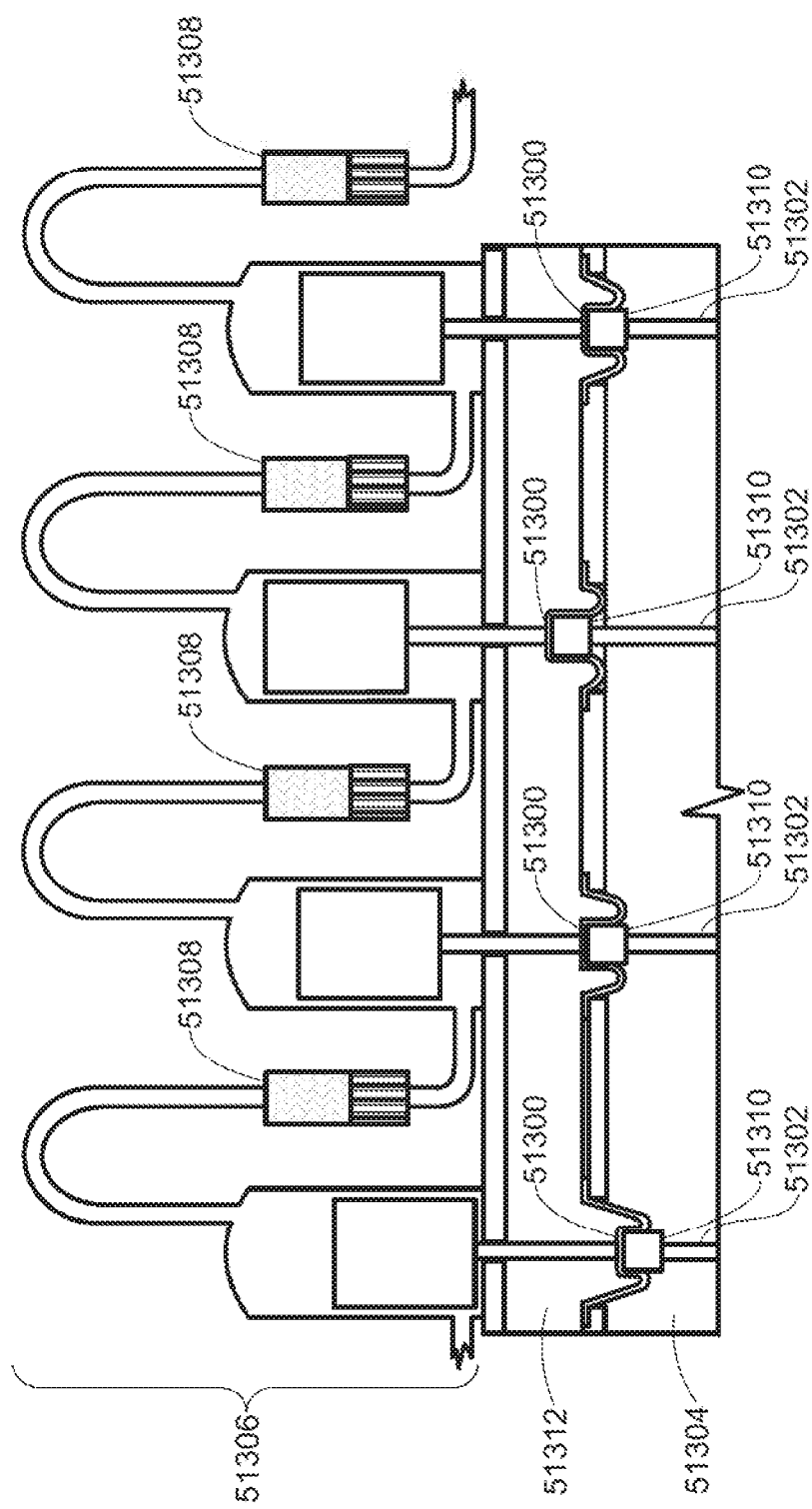
Figure 57G:
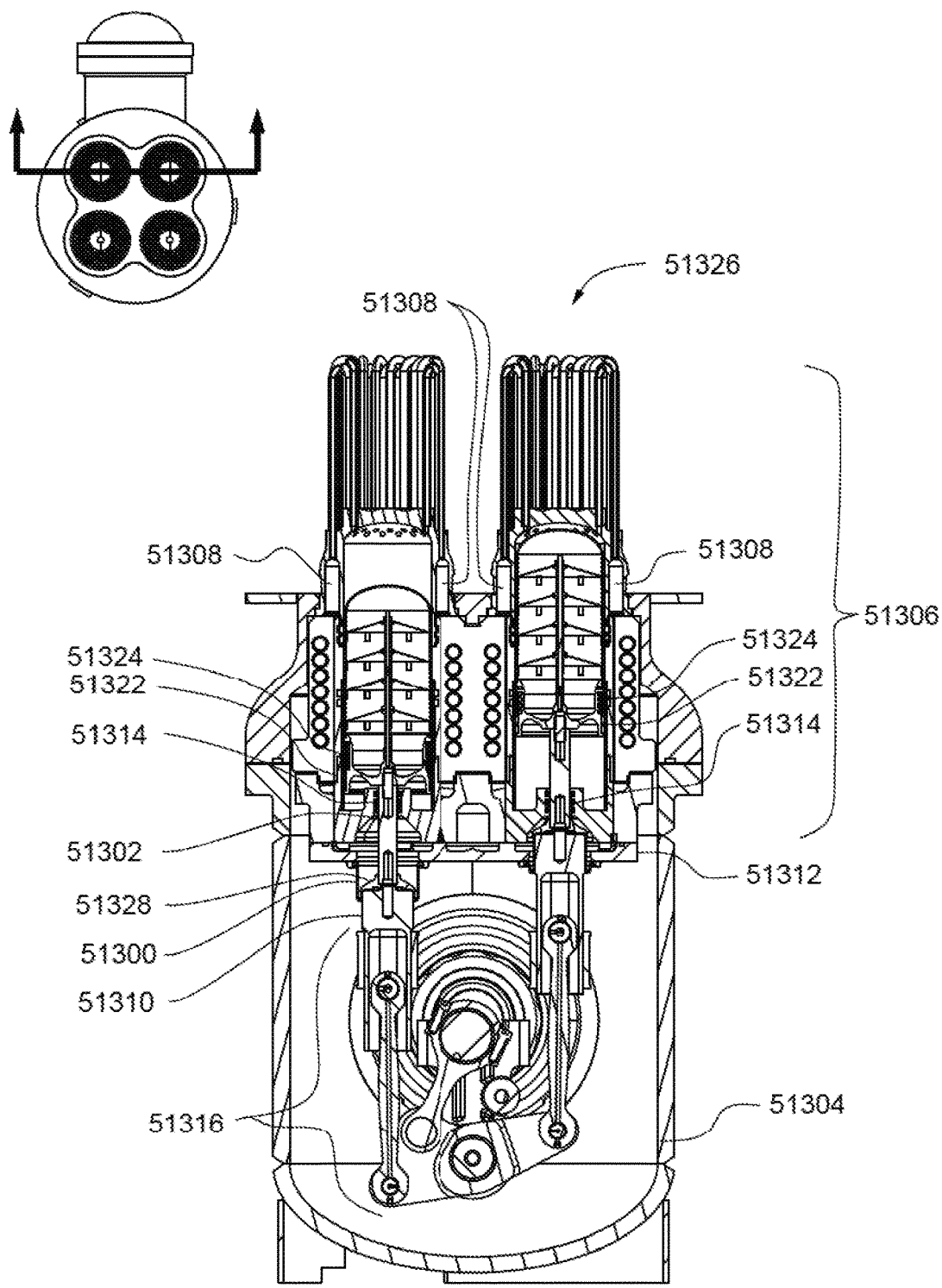
Figure 59E:
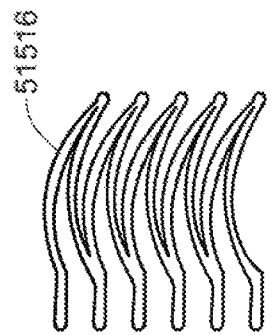
Figure 59F:
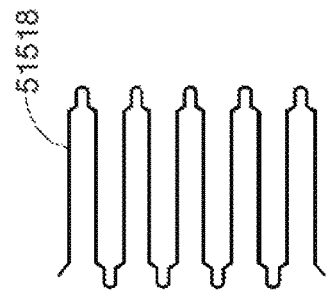
Figure 59G:
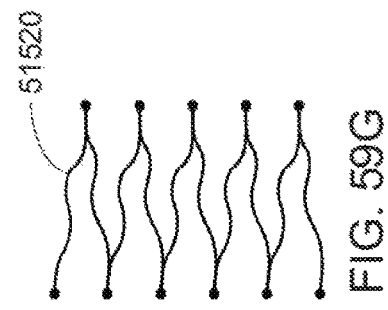
Figure 59B:
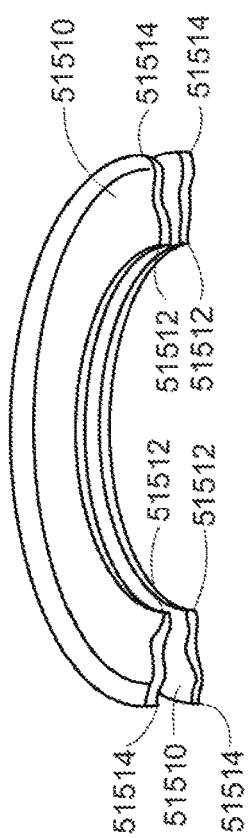
Figure 59C:
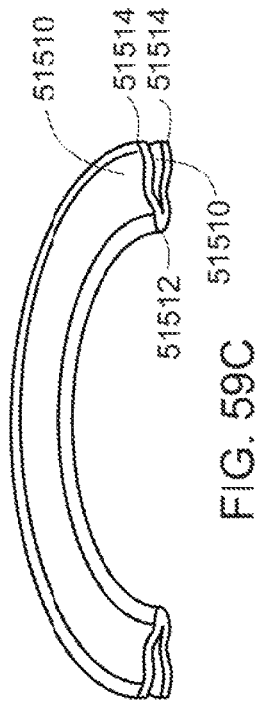
Figure 59D:
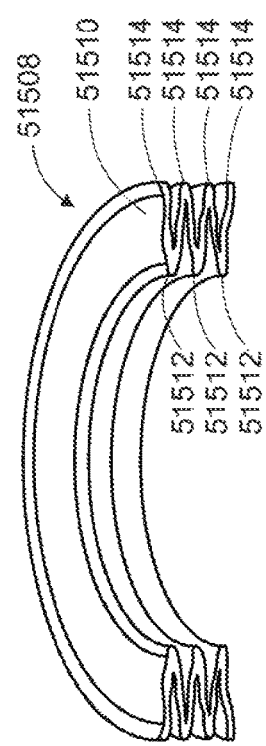
Figure 59H:
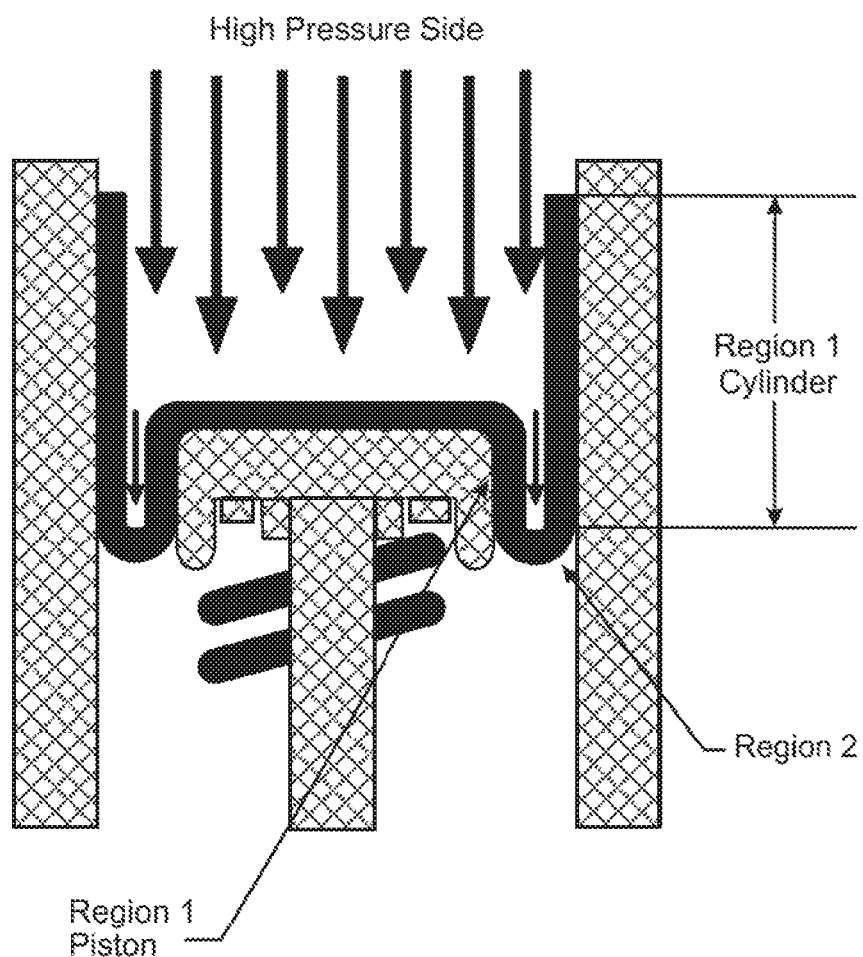
Figure 59I:
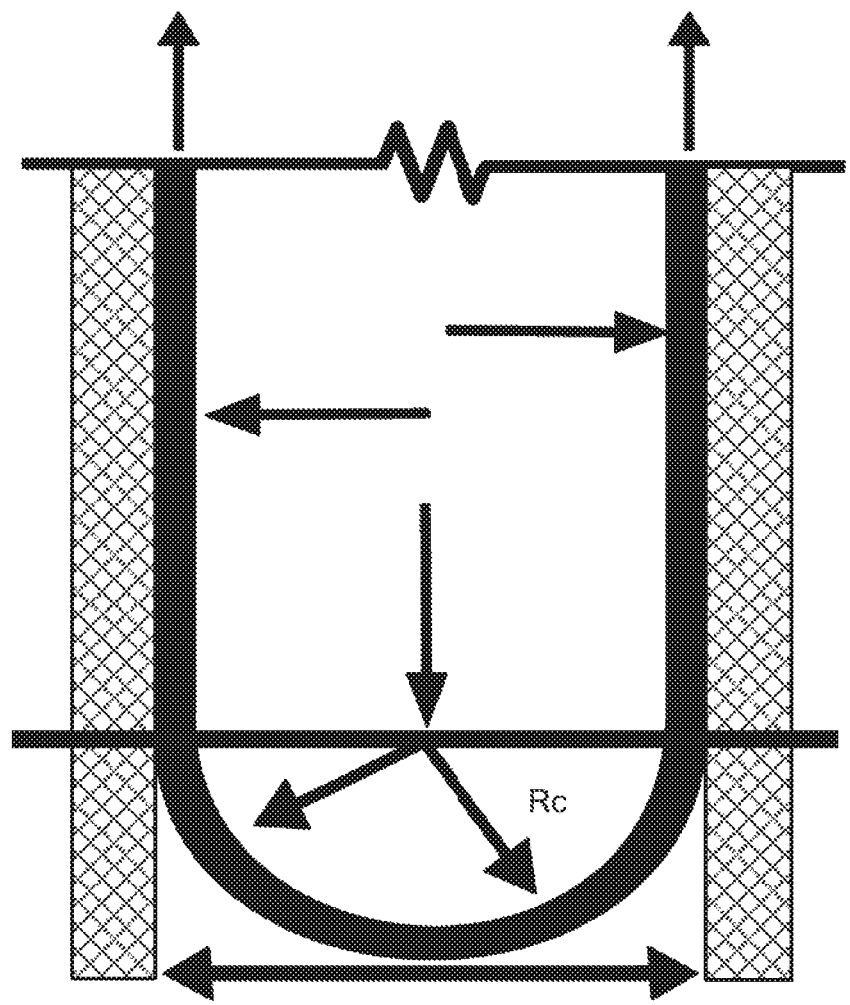
Figure 60:
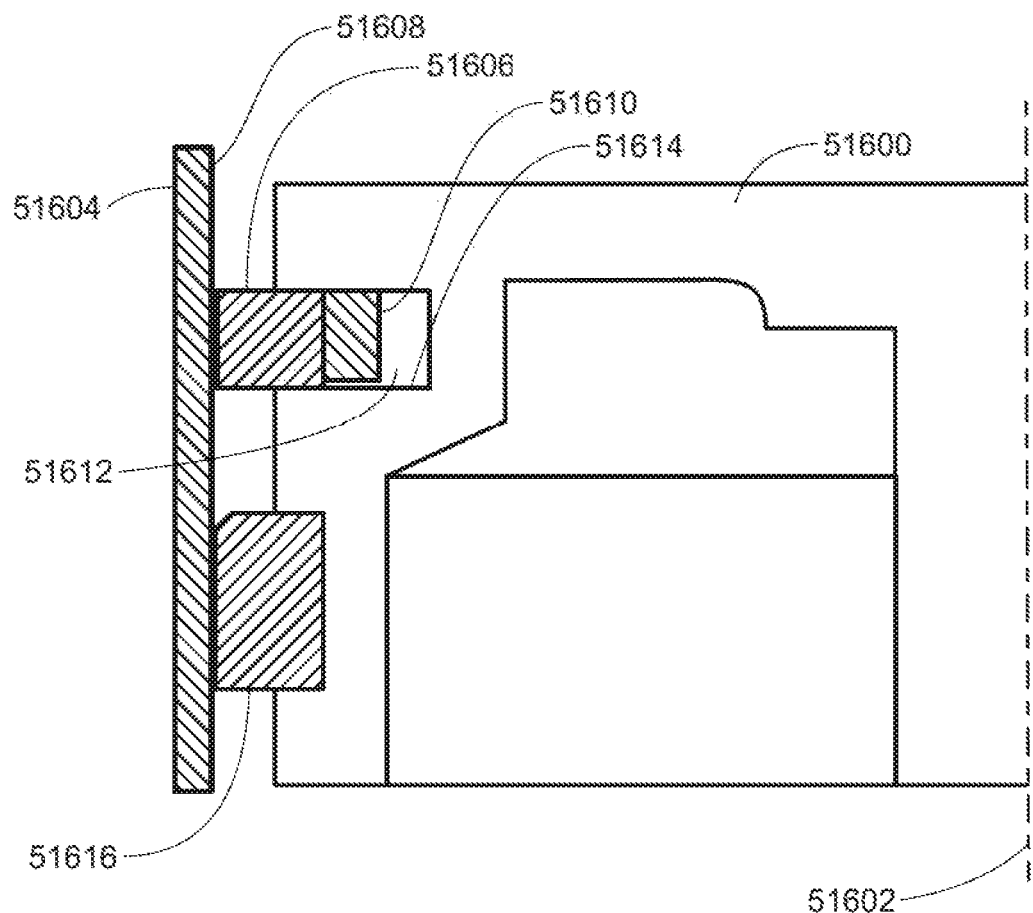
Figure 61:
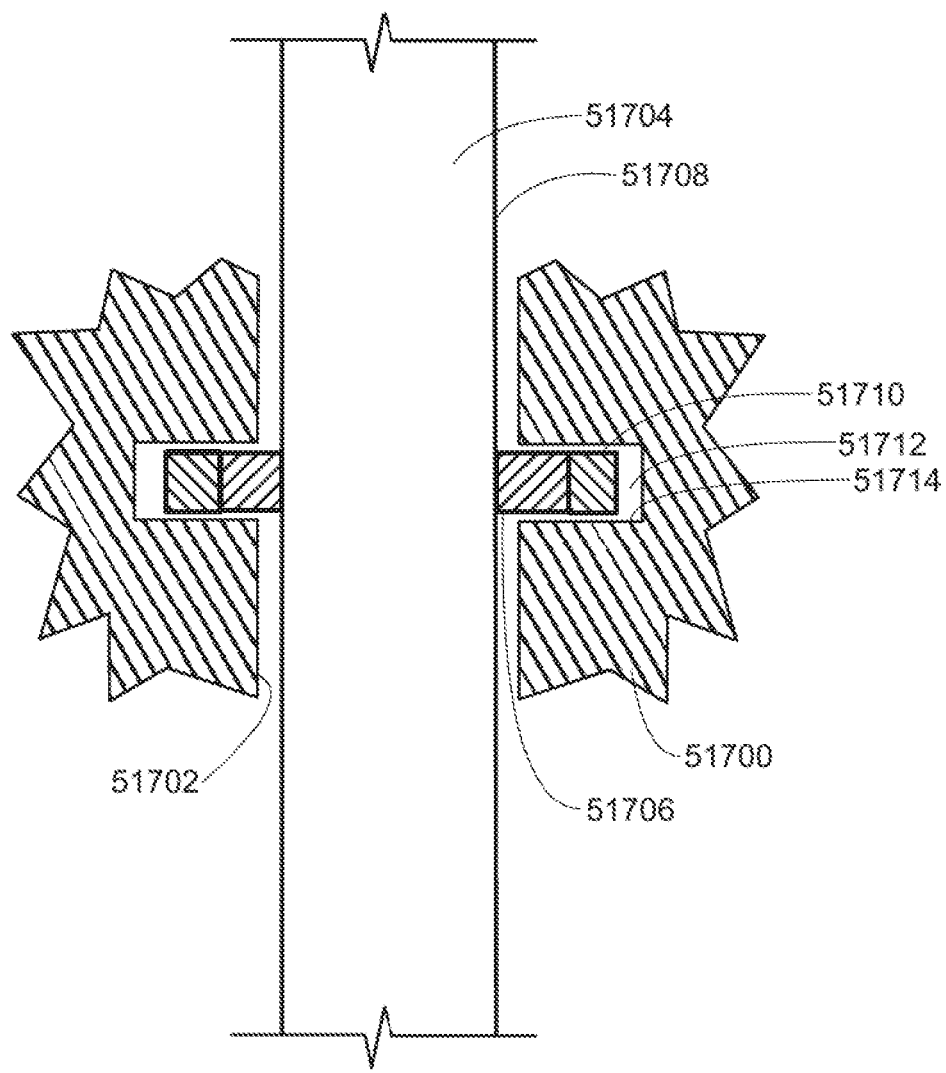
Figure 62A:
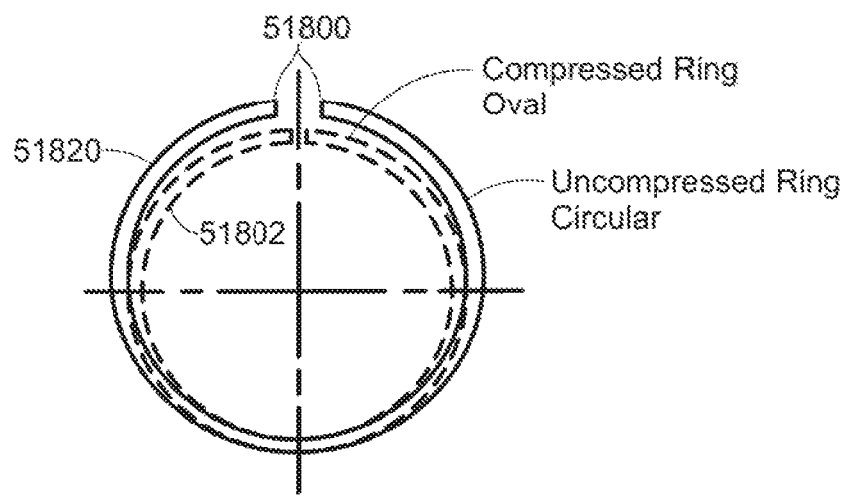
Figure 62B:
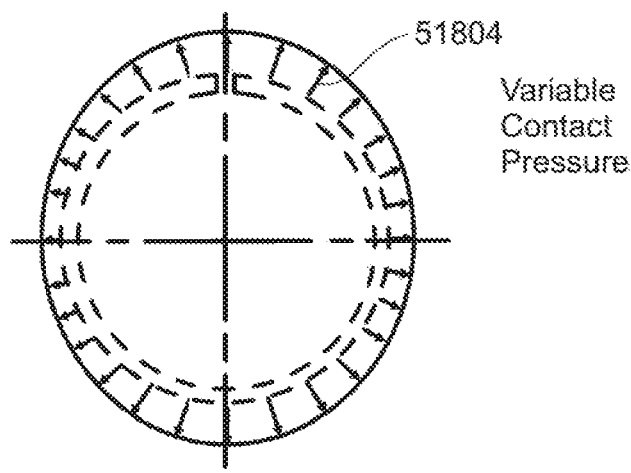
Figure 62C:
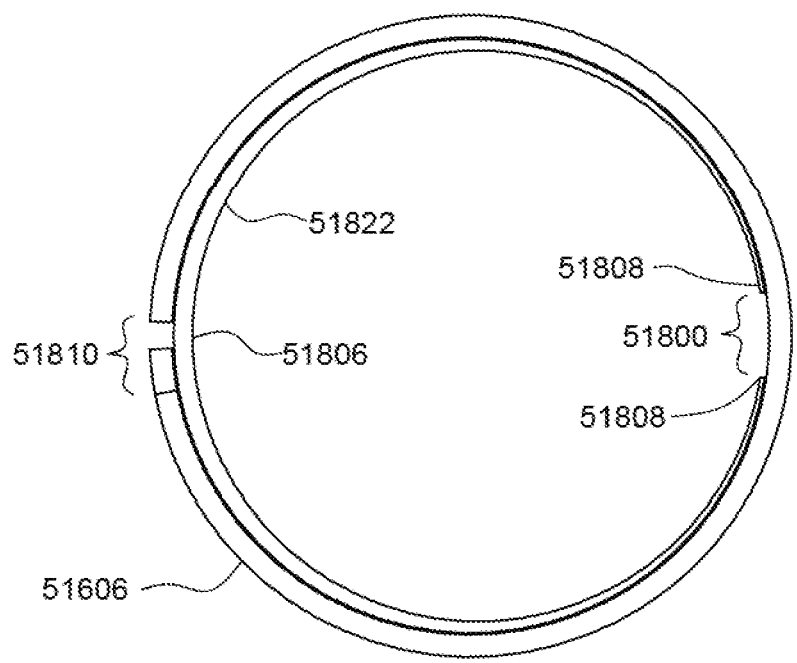
Figure 62D:
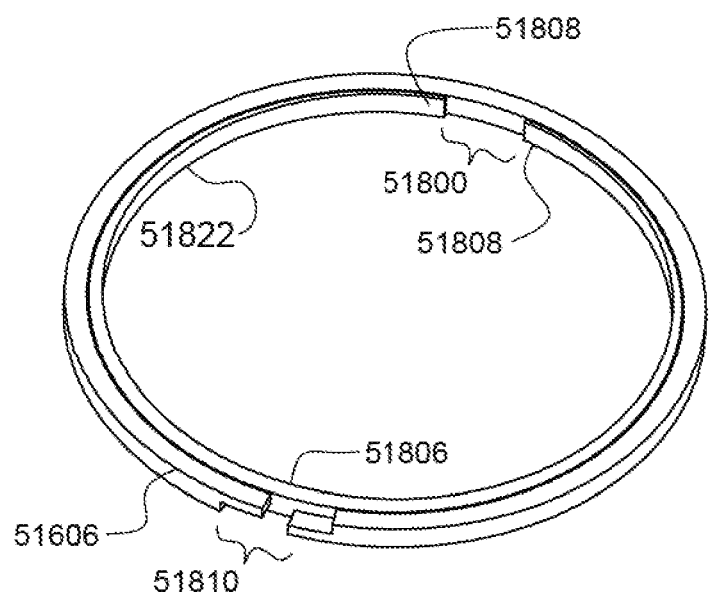
Figure 62E:
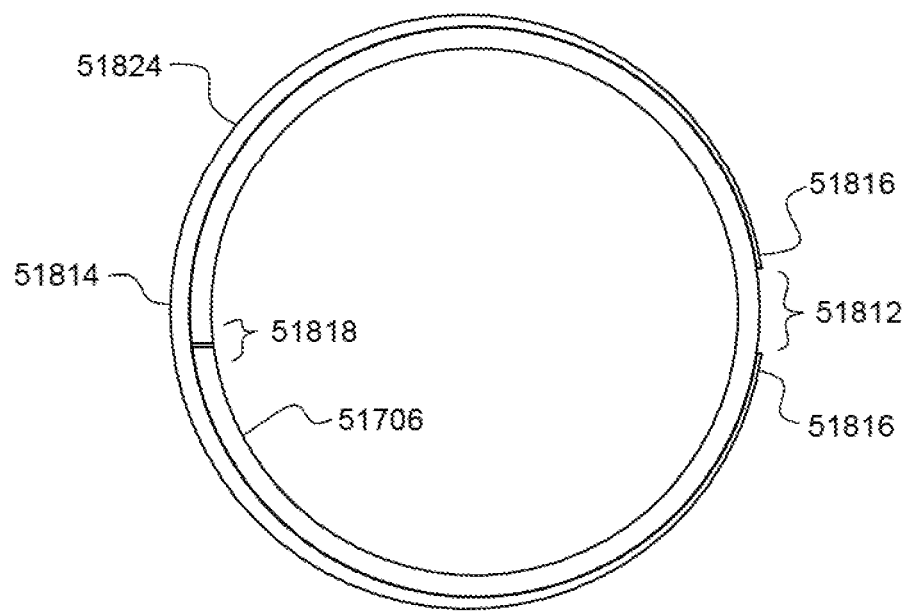
Figure 62F:
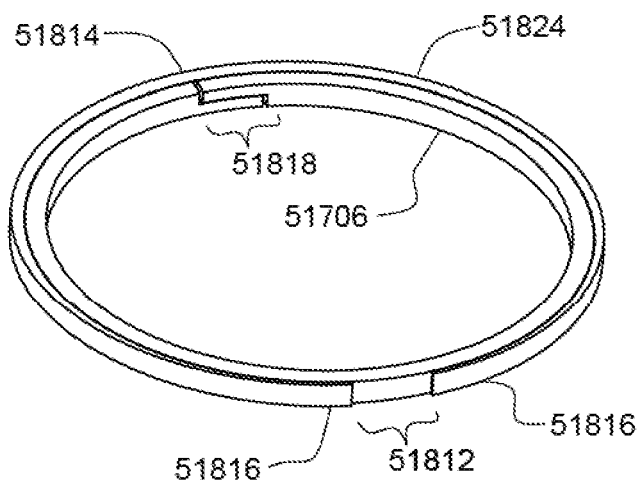
Figure 63A:
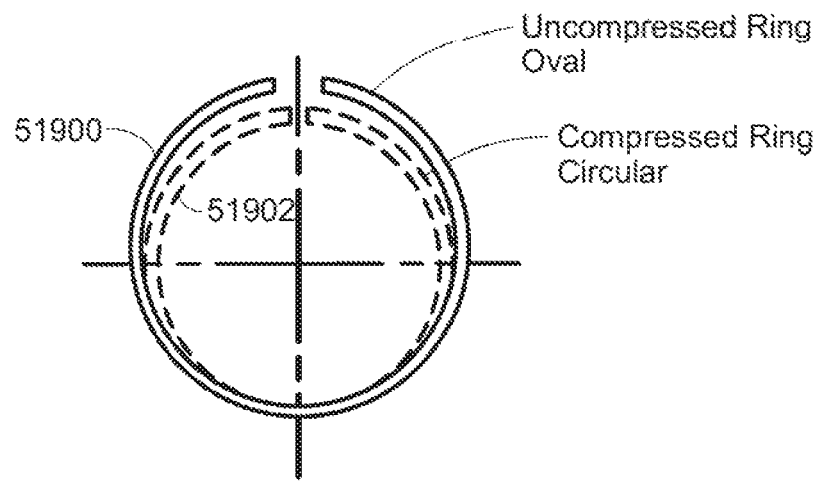
Figure 63B:
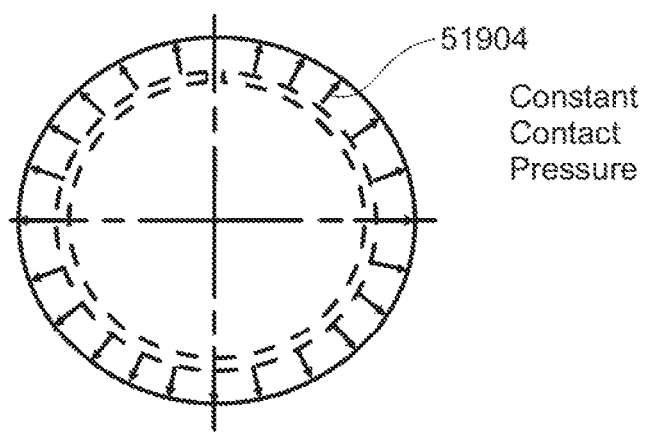
Figure 64A:
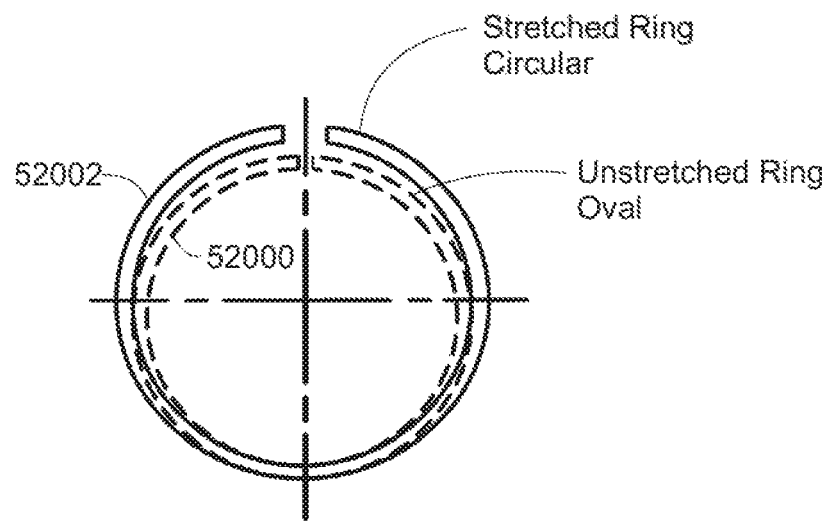
Figure 64B:
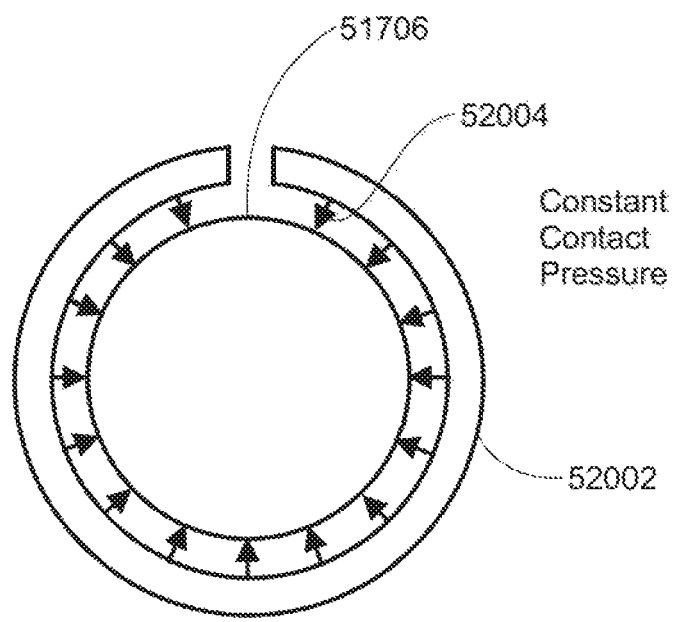
Figure 65:
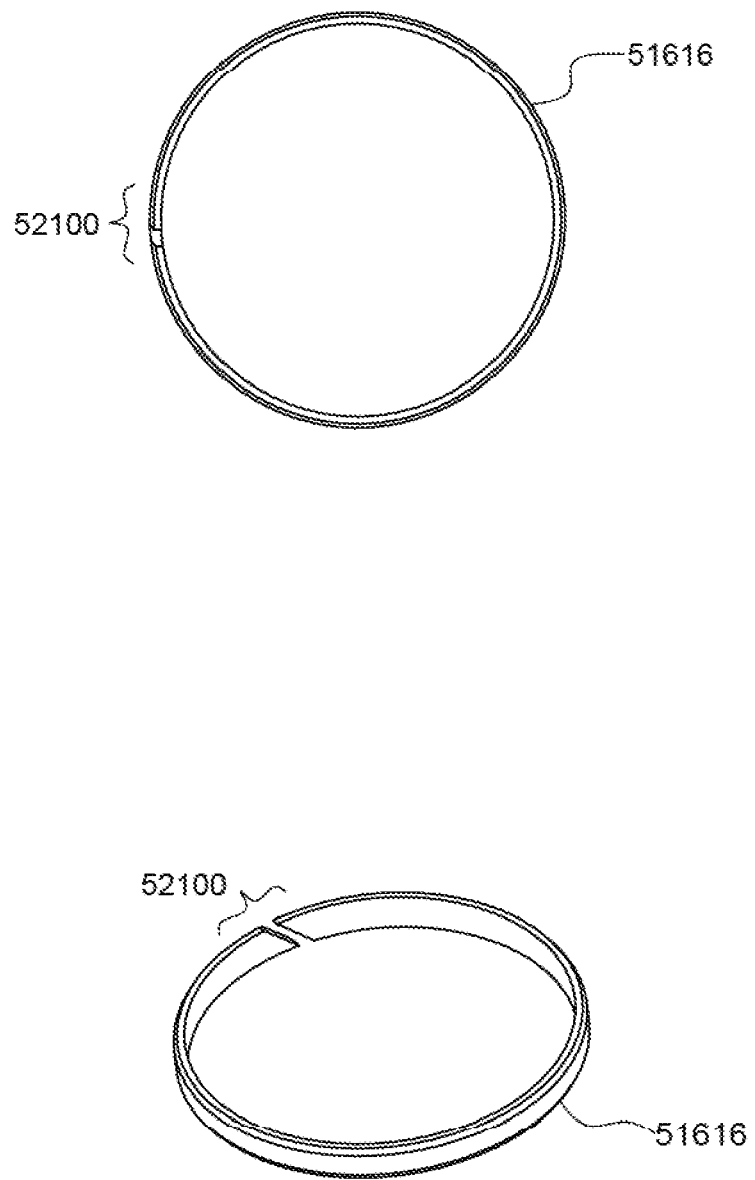
Figure 66:
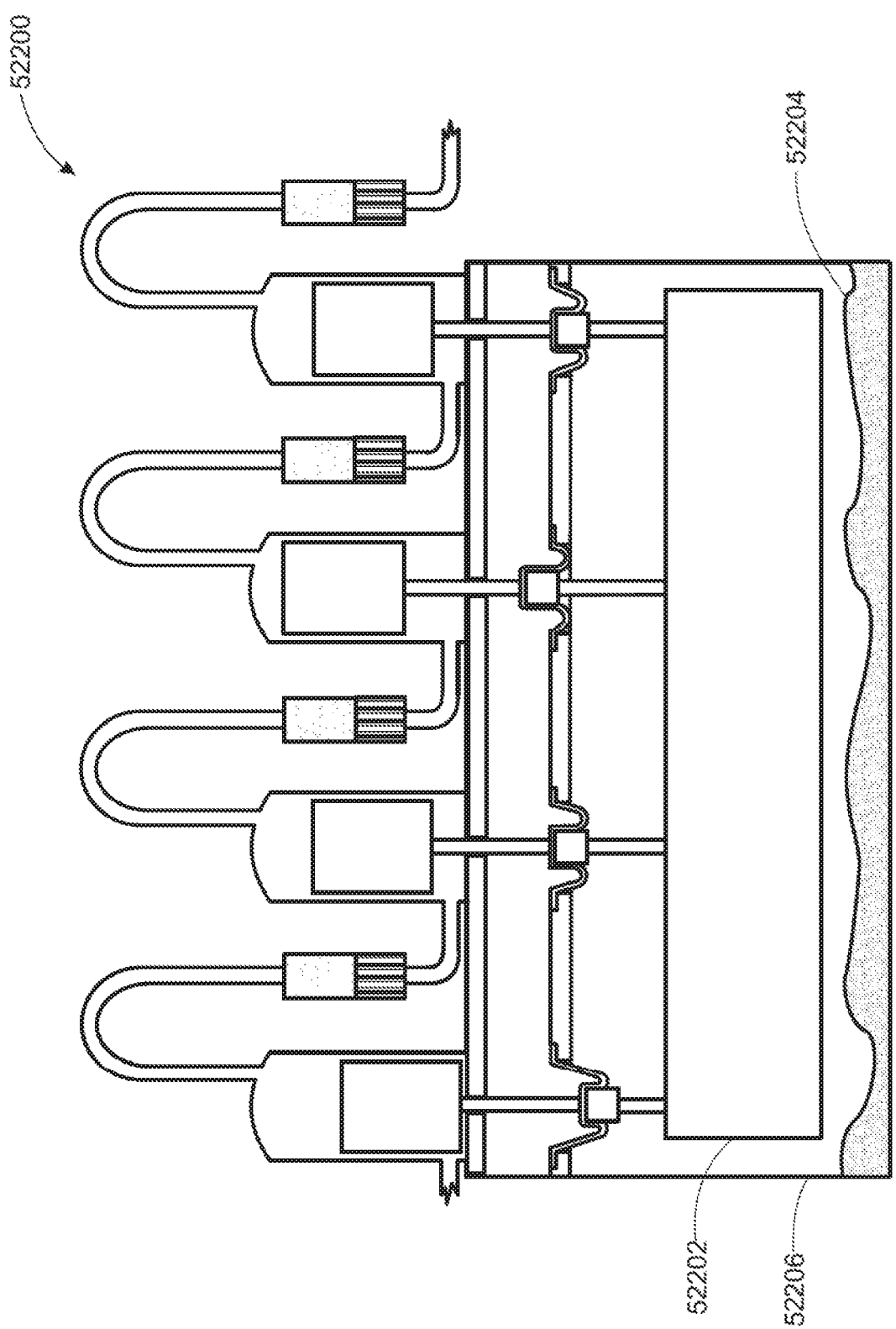
Figure 67A:
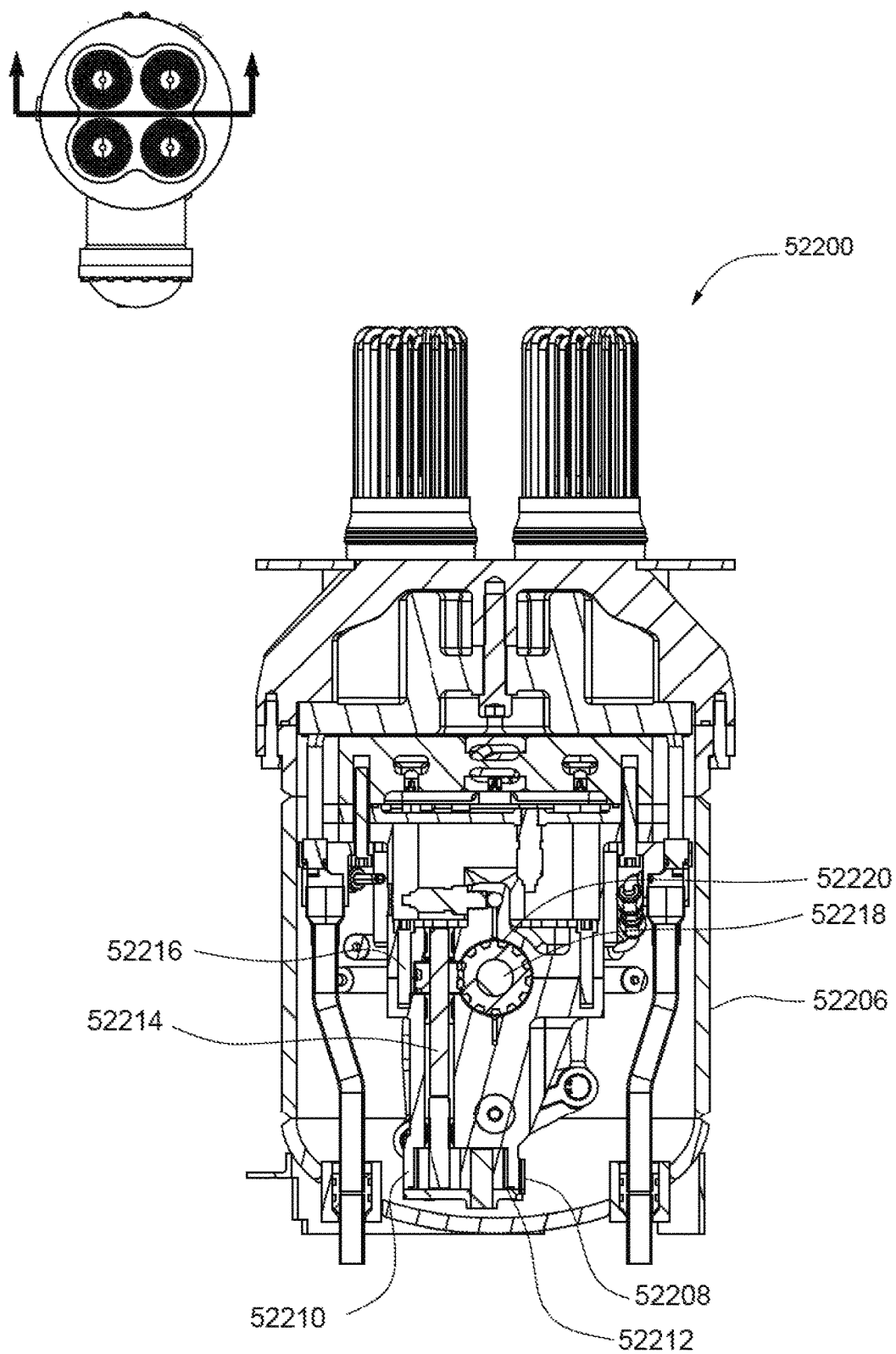
Figure 67B:
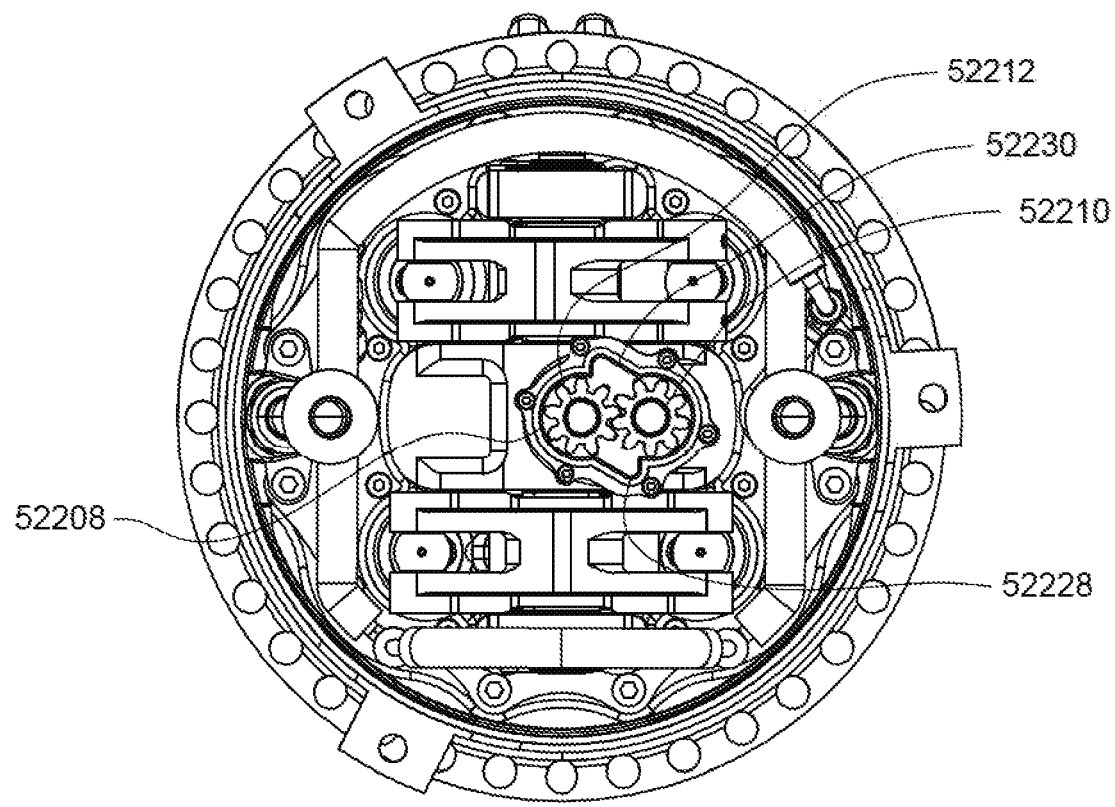
Figure 68:
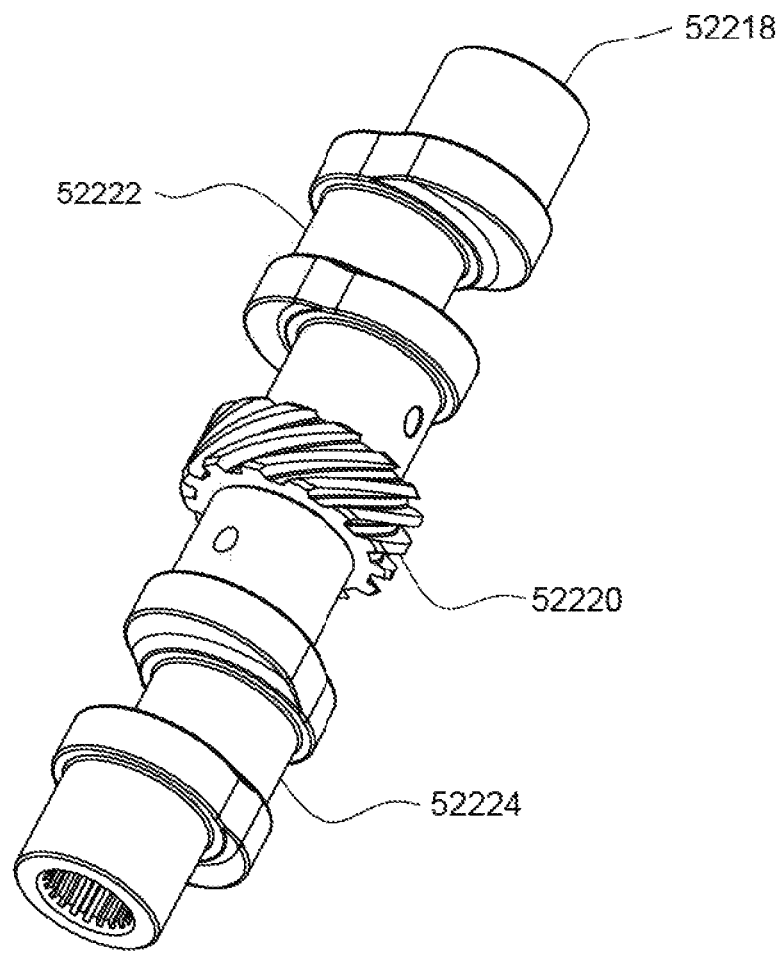
Figure 69A:
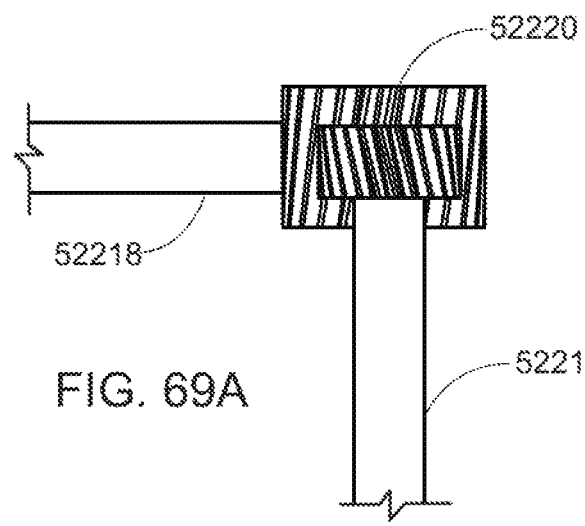
Figure 69B:
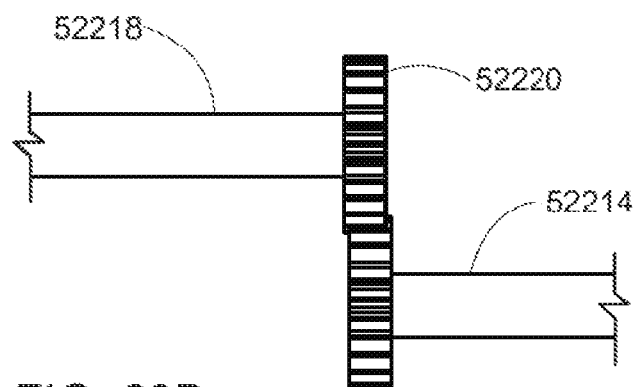
Figure 69C:
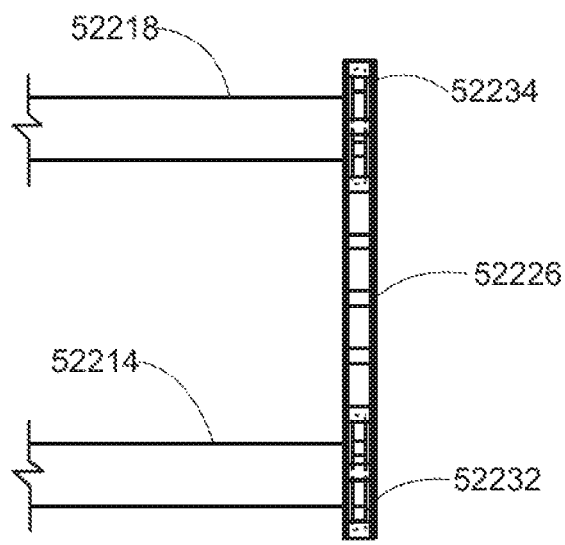
Figure 70A:
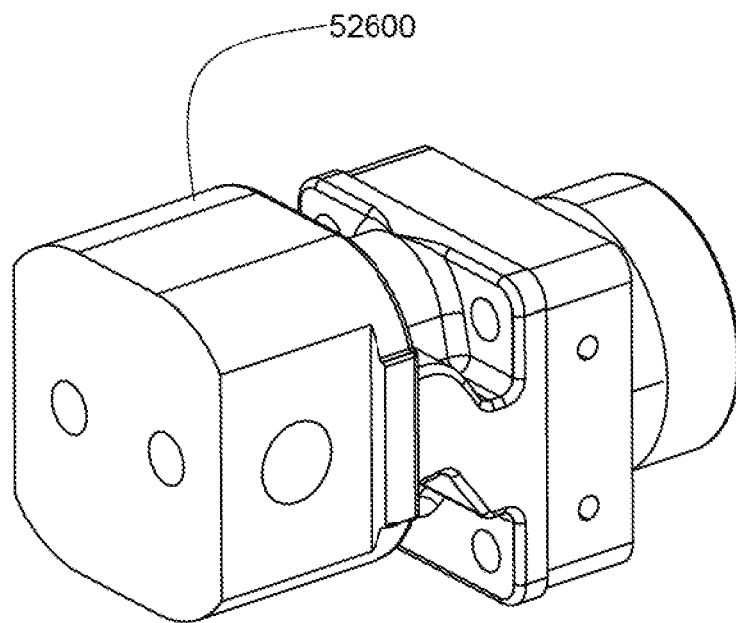
Figure 70B:
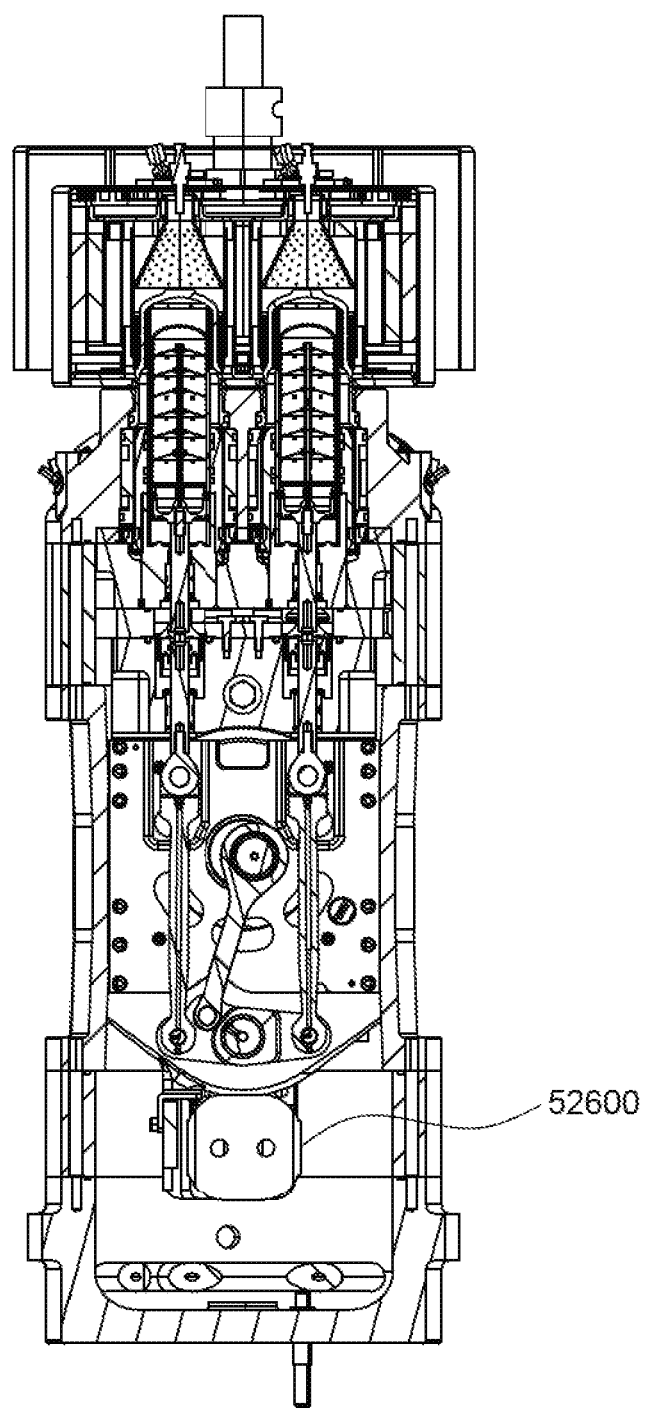
Figure 70C:
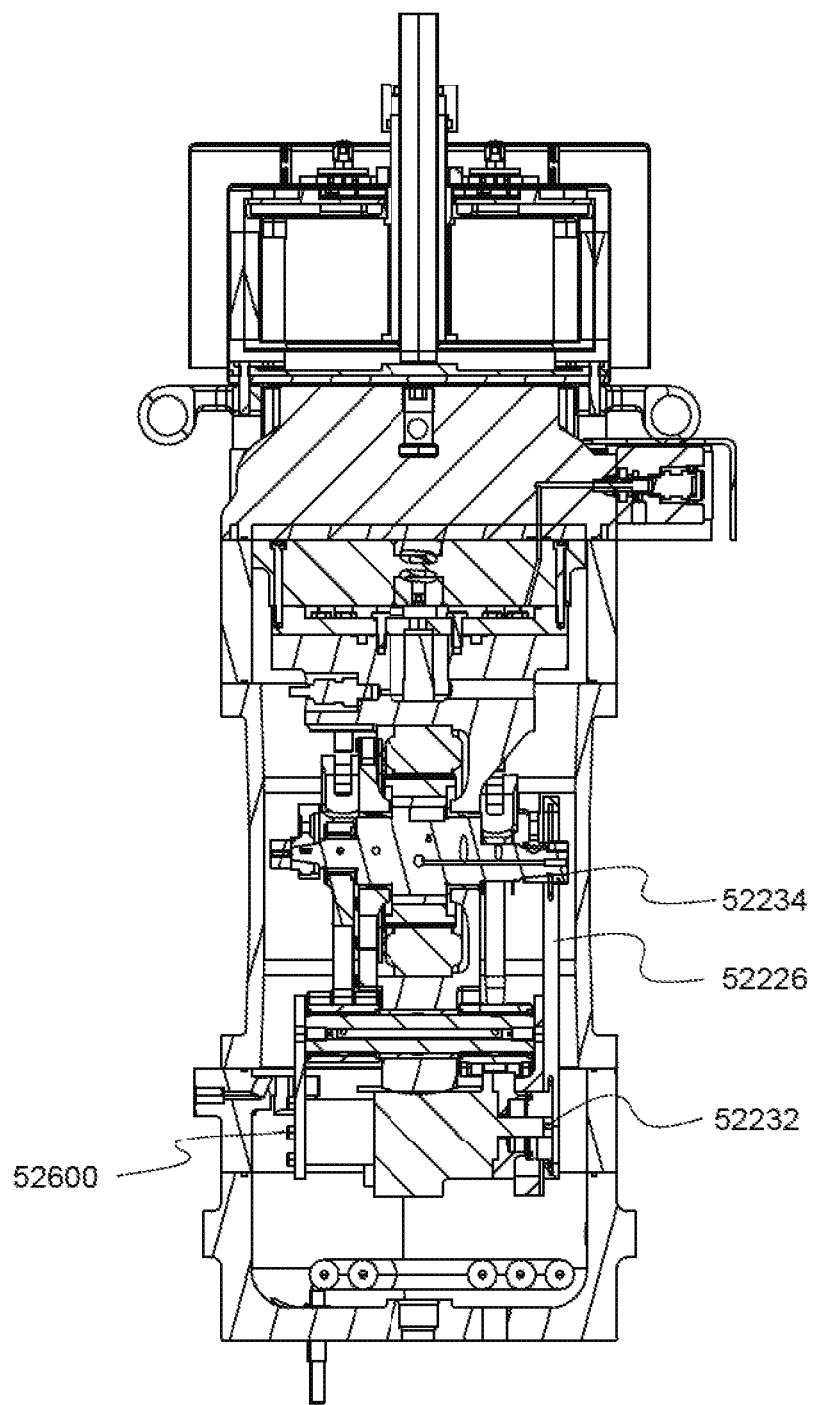
Figure 71A:
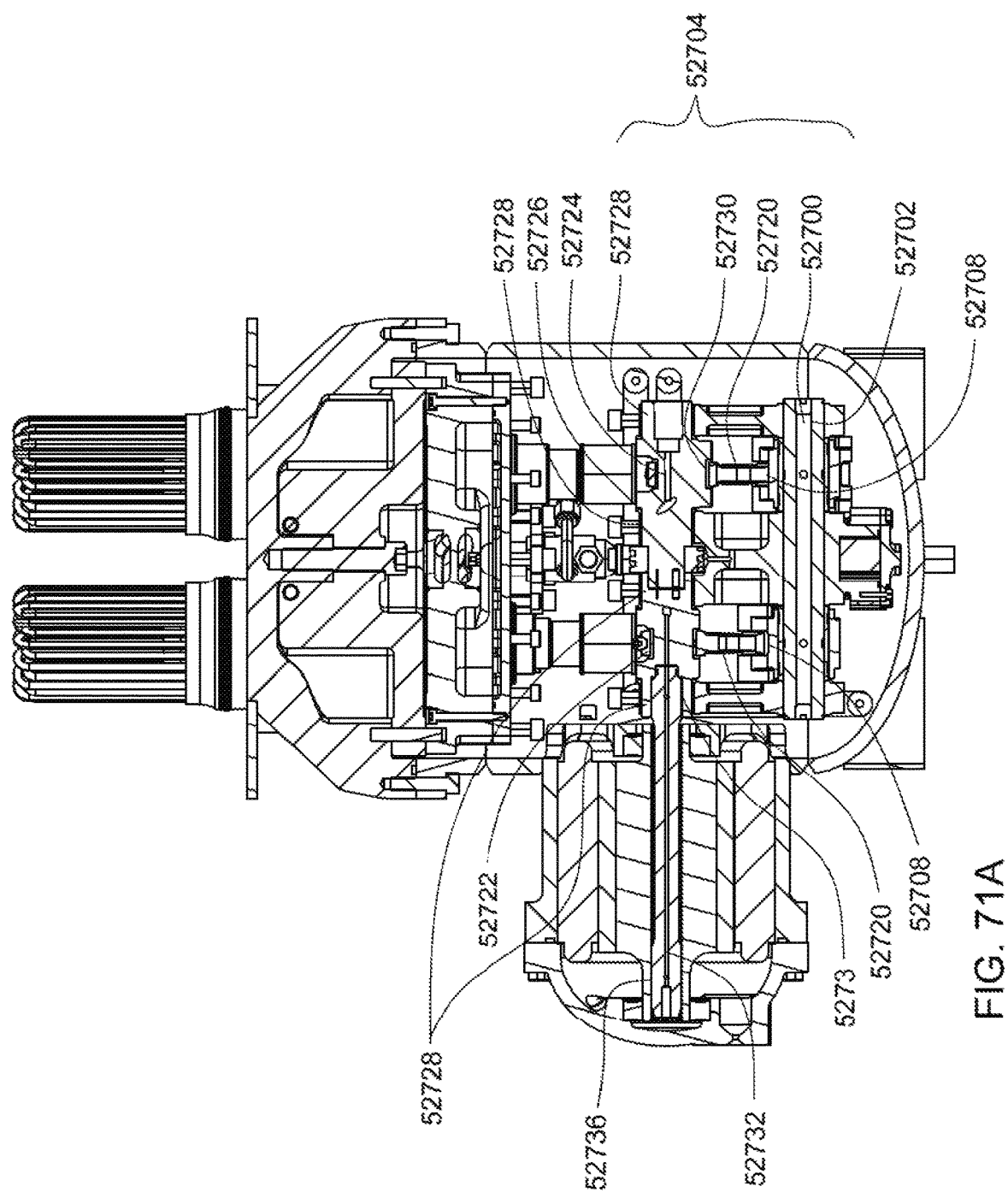
Figure 71B:
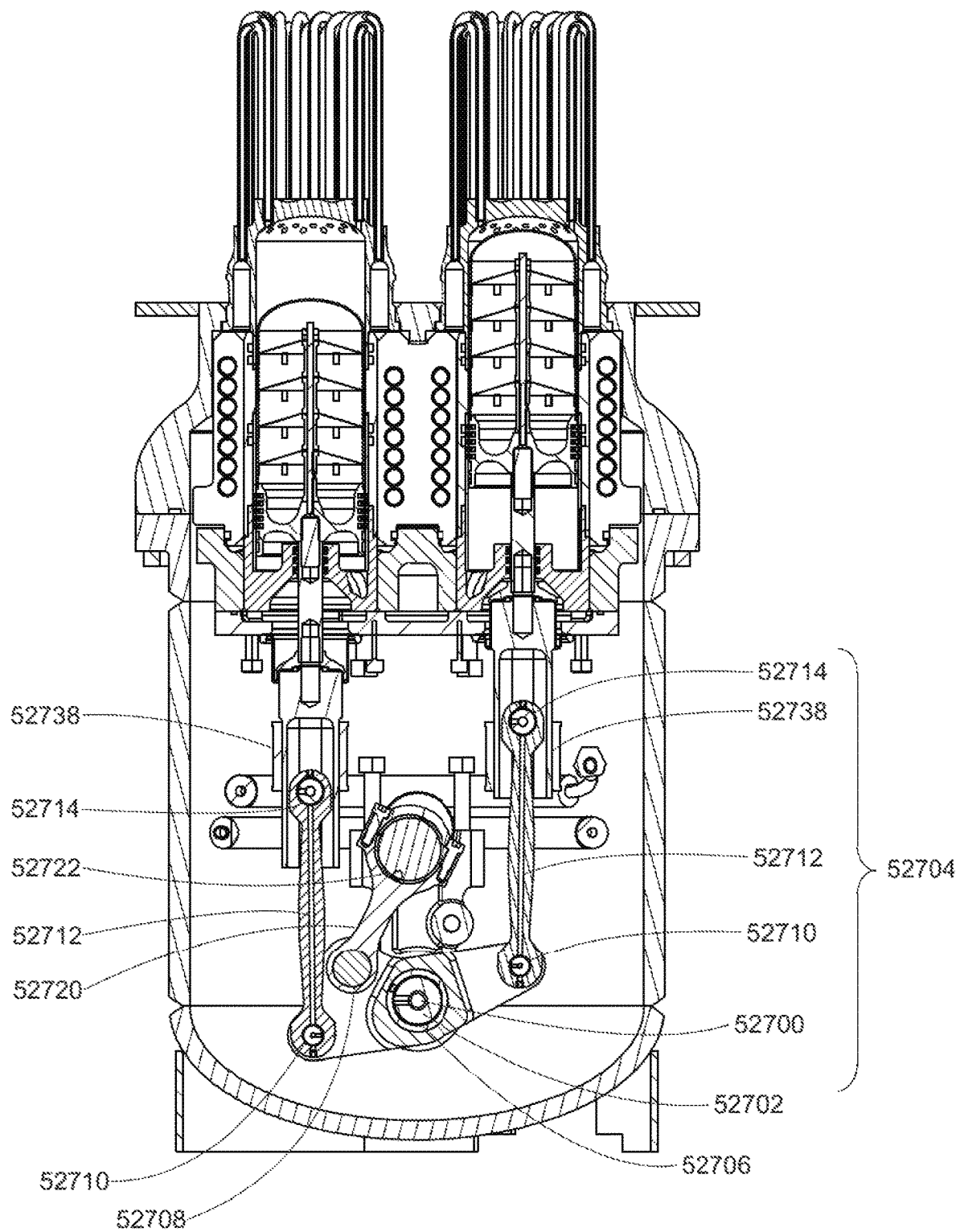
Figure 71C:
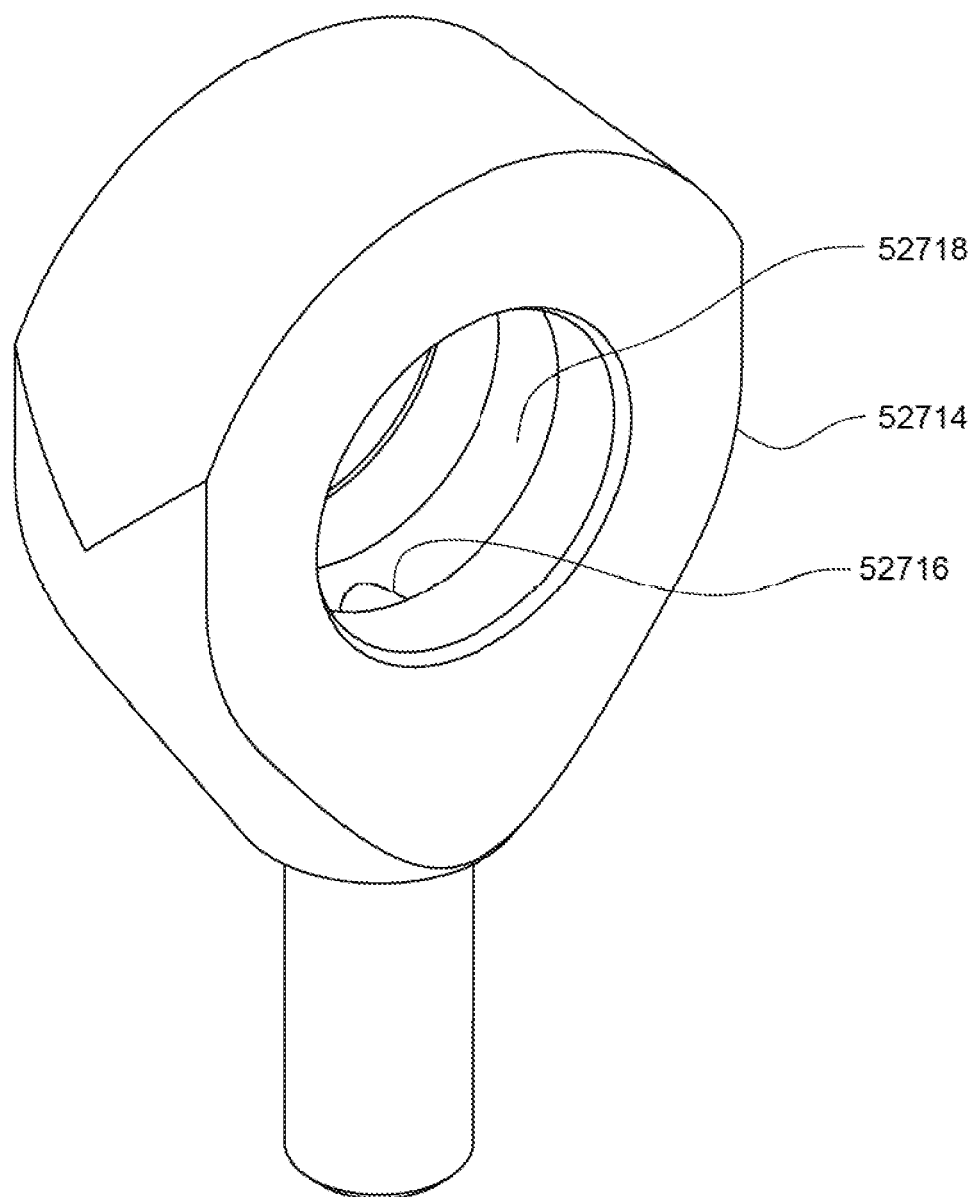
Figure 71D:
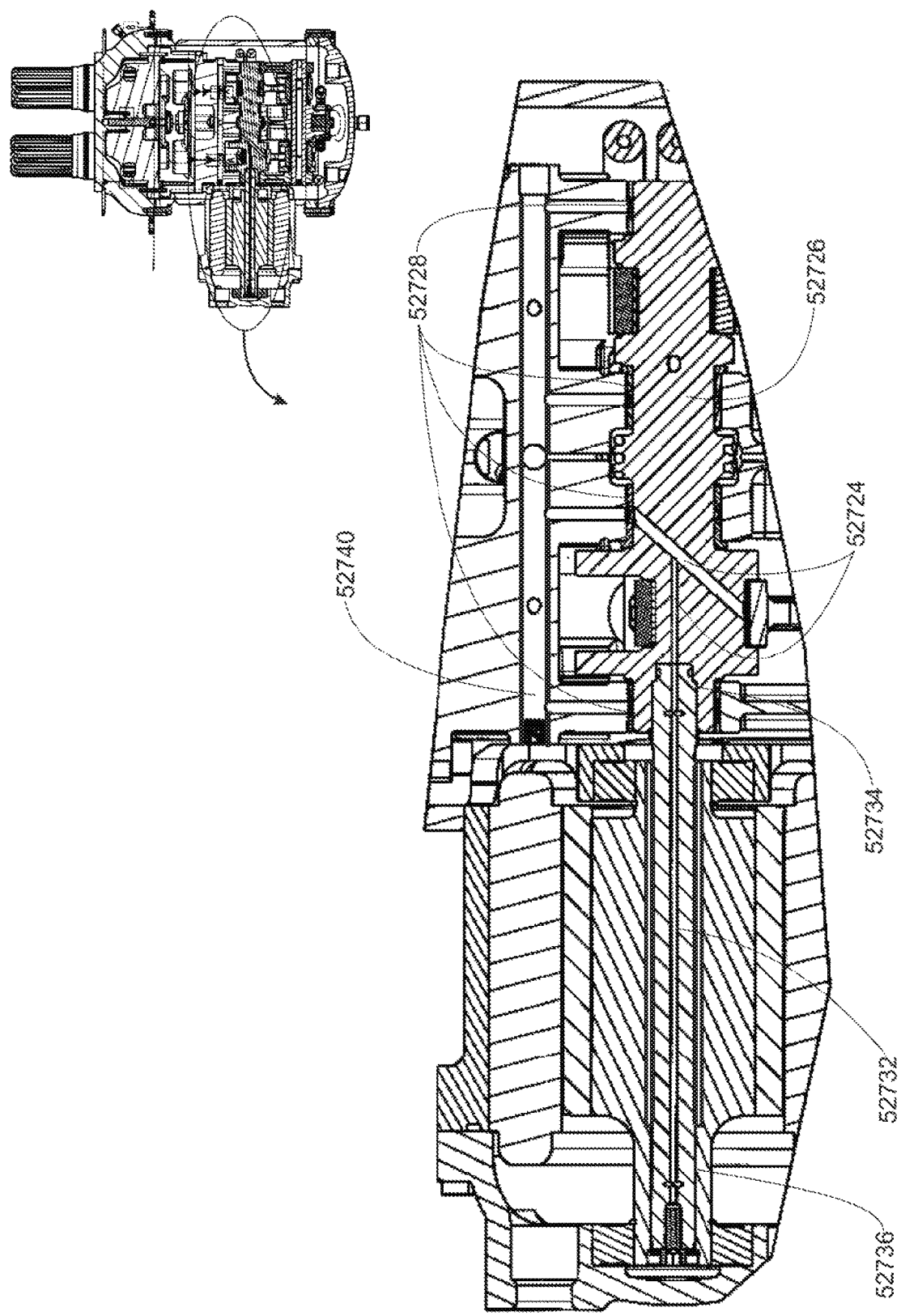
Figure 72A:
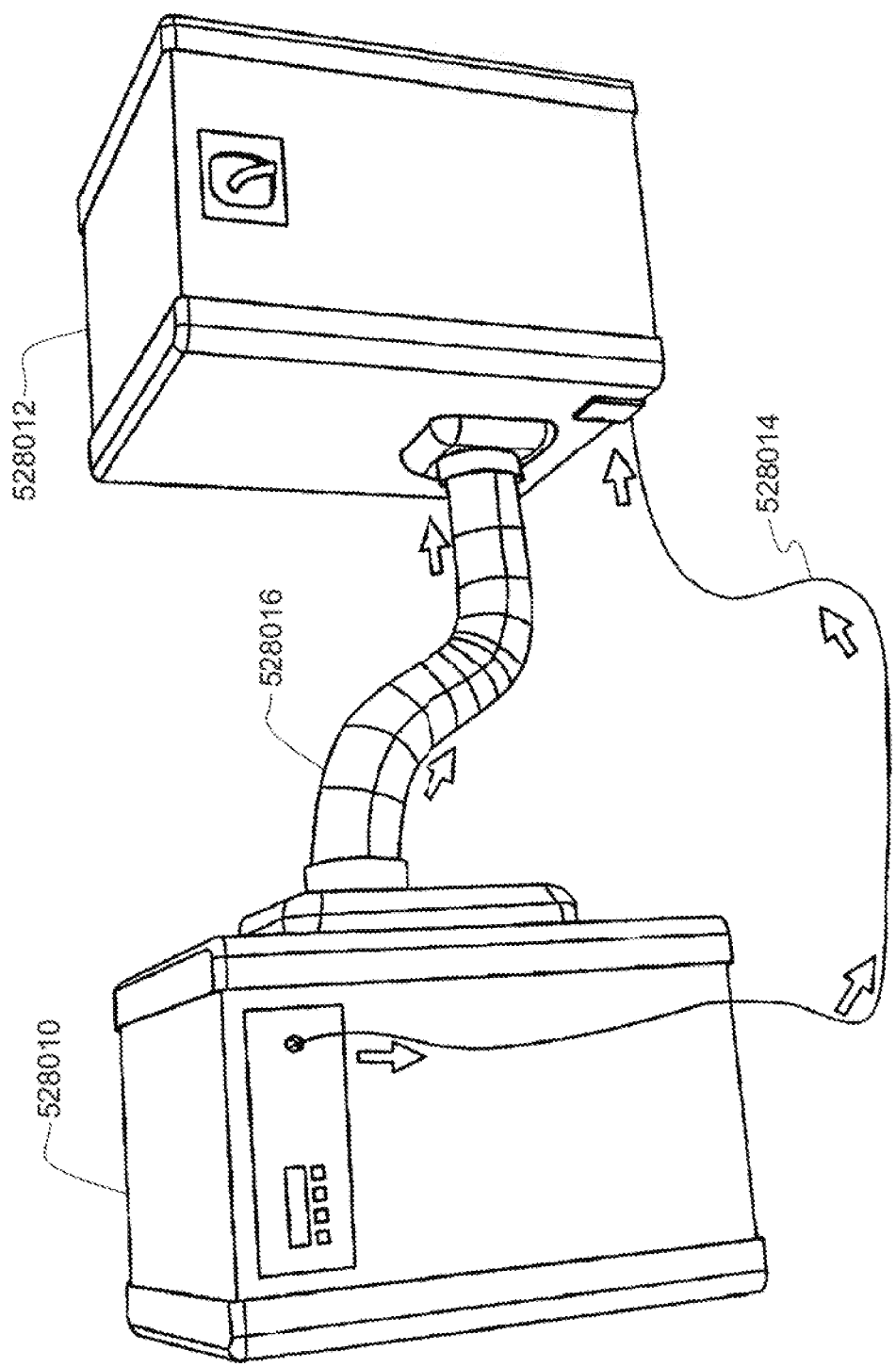
Figure 72B:
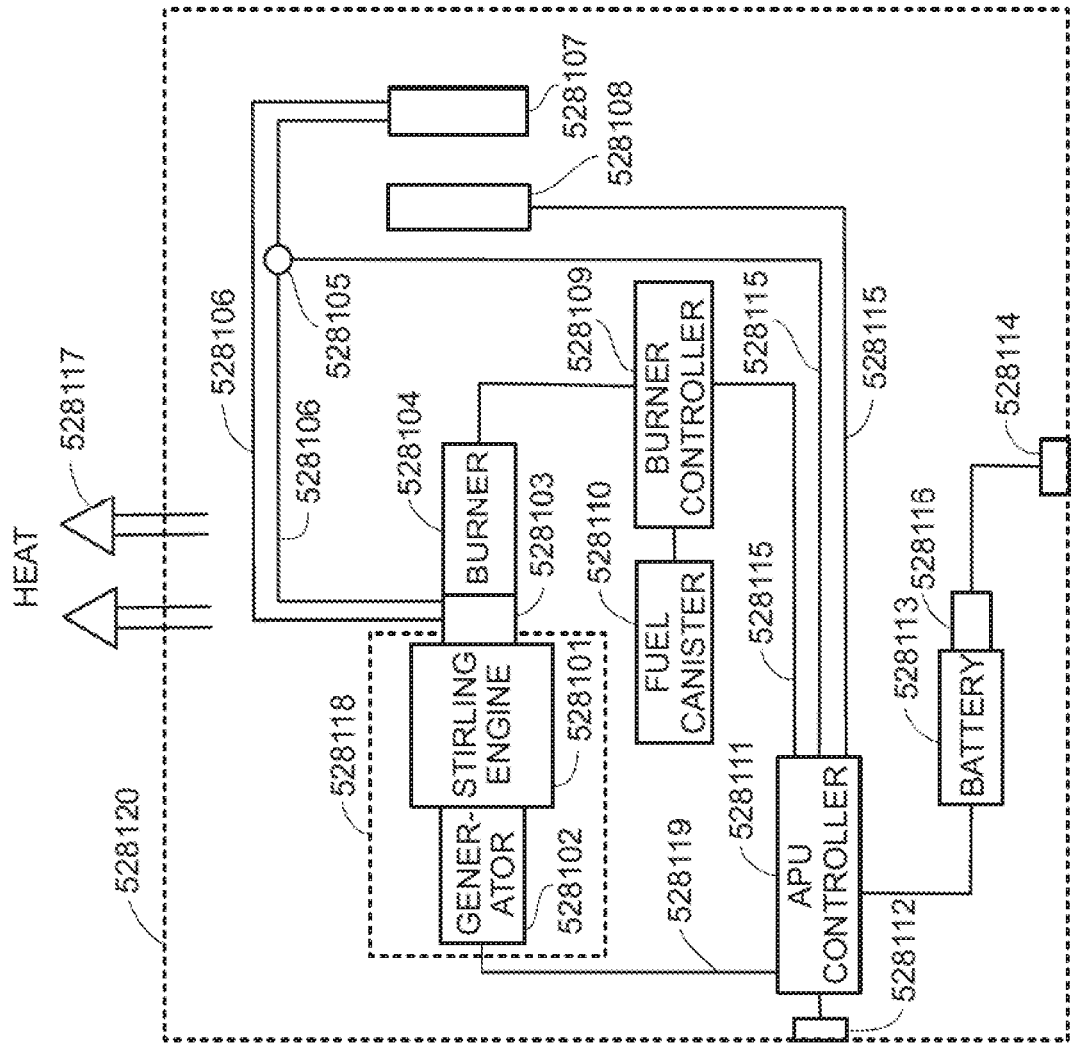
Figure 72C:
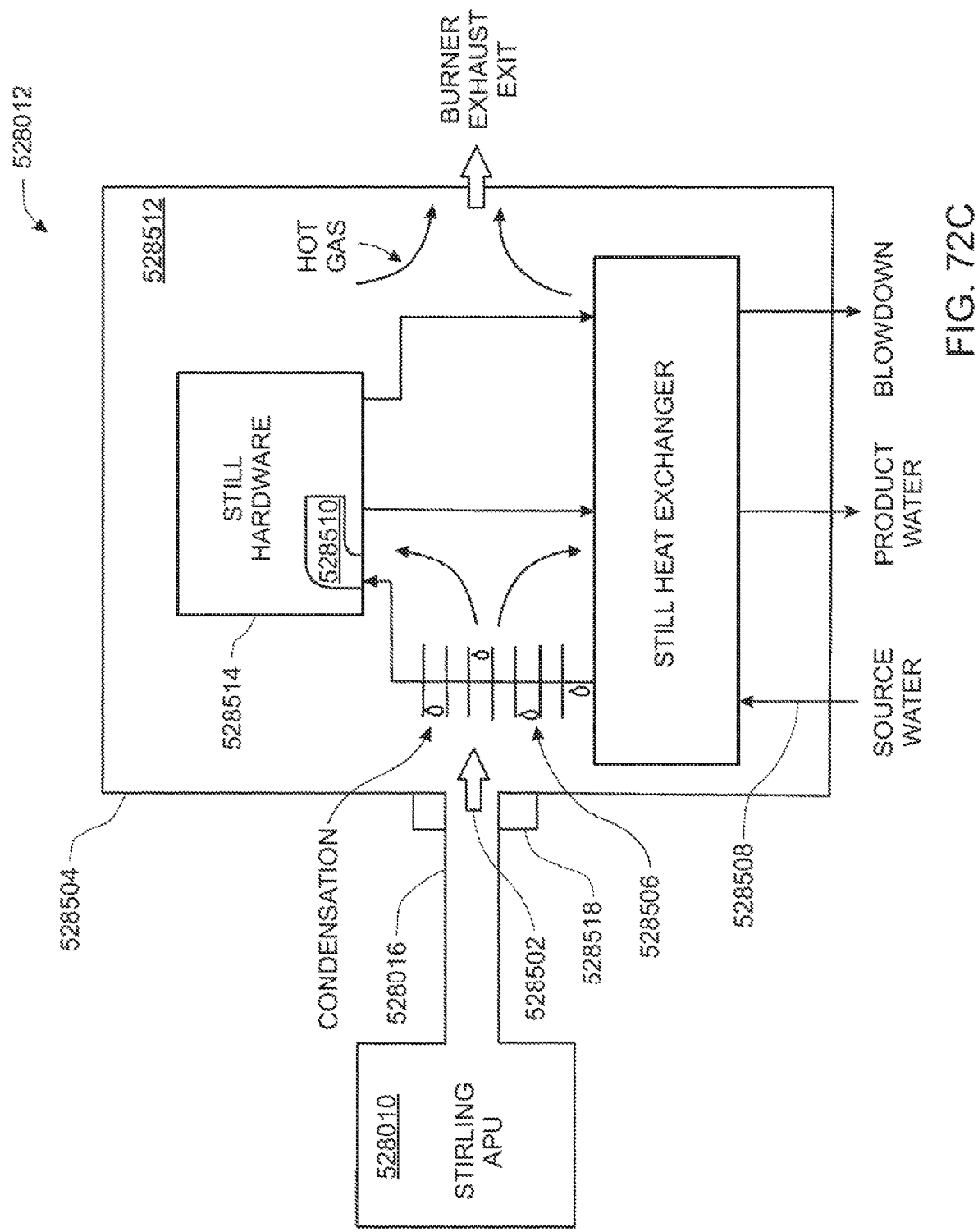
Figure 73:
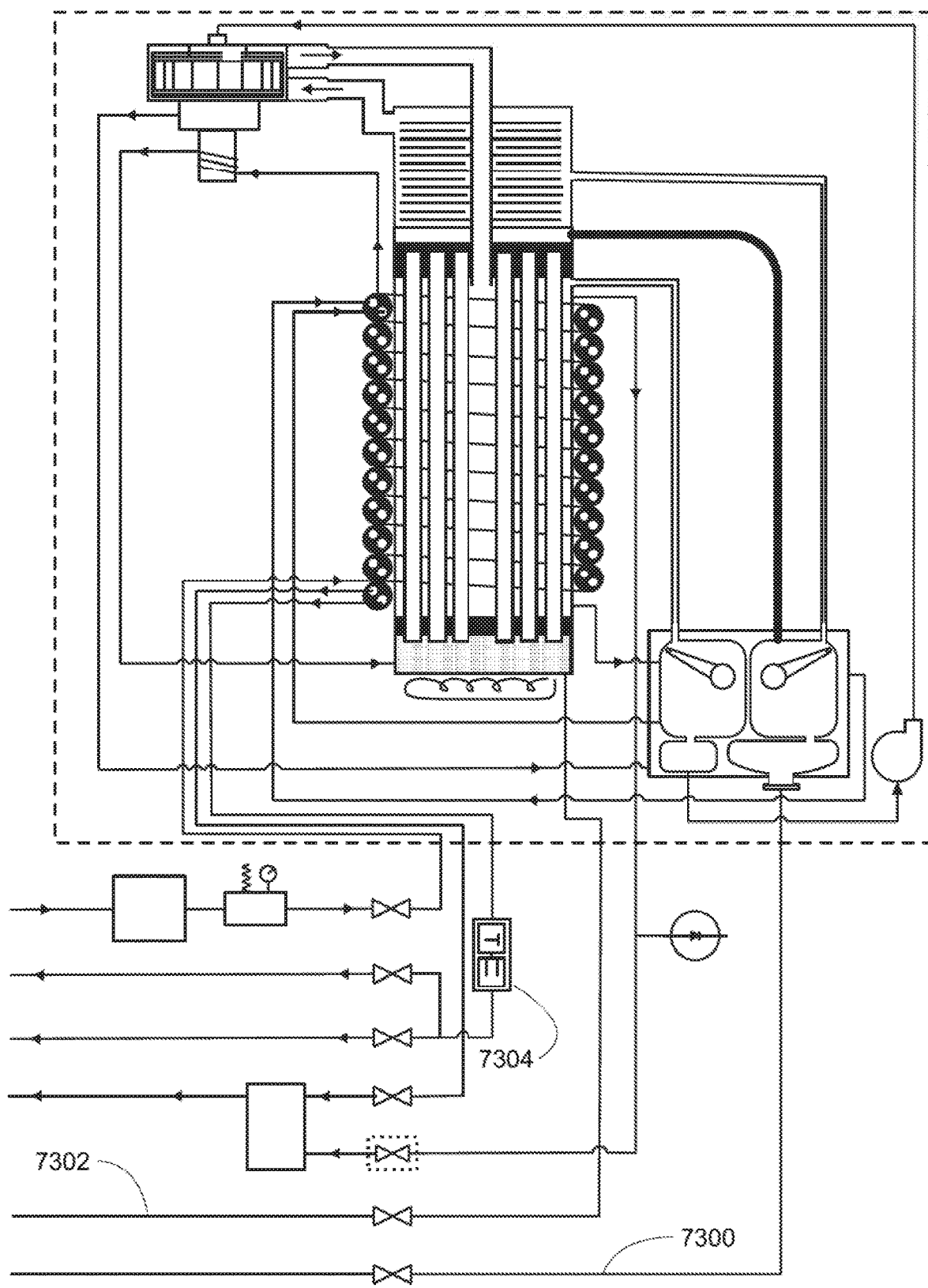
Figure 74:
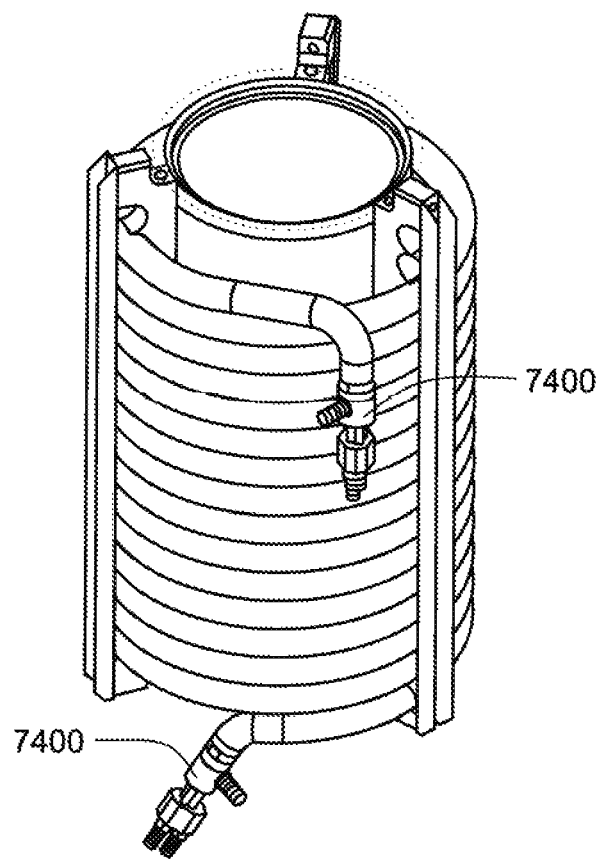
Figure 74A:
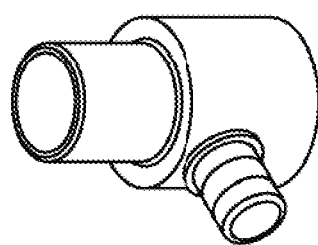
Figure 74B:
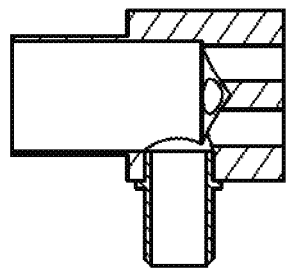
Figure 74C:
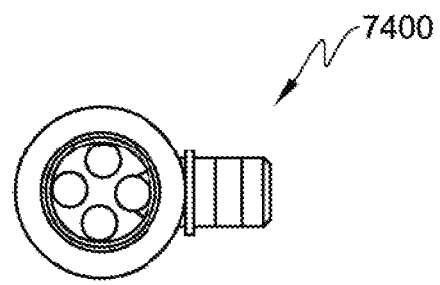
Figure 75:
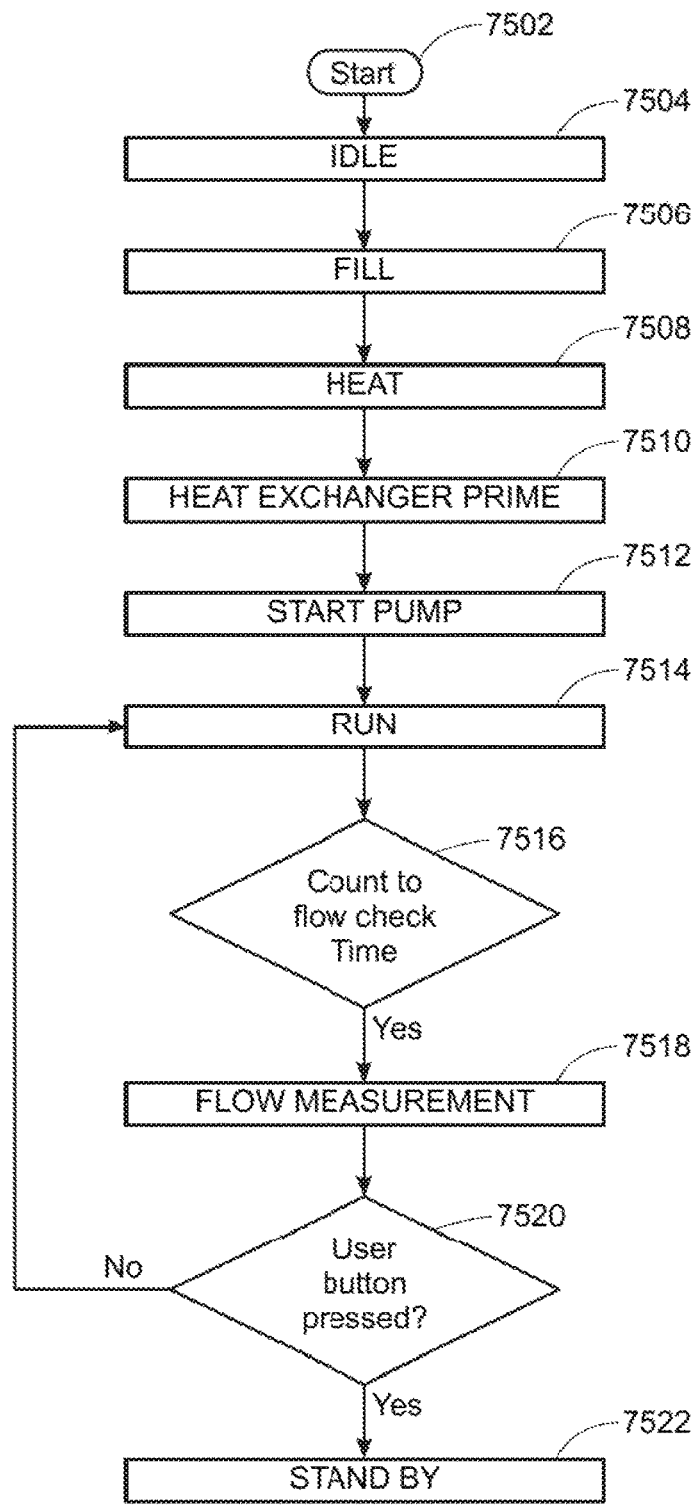
Figure 76:
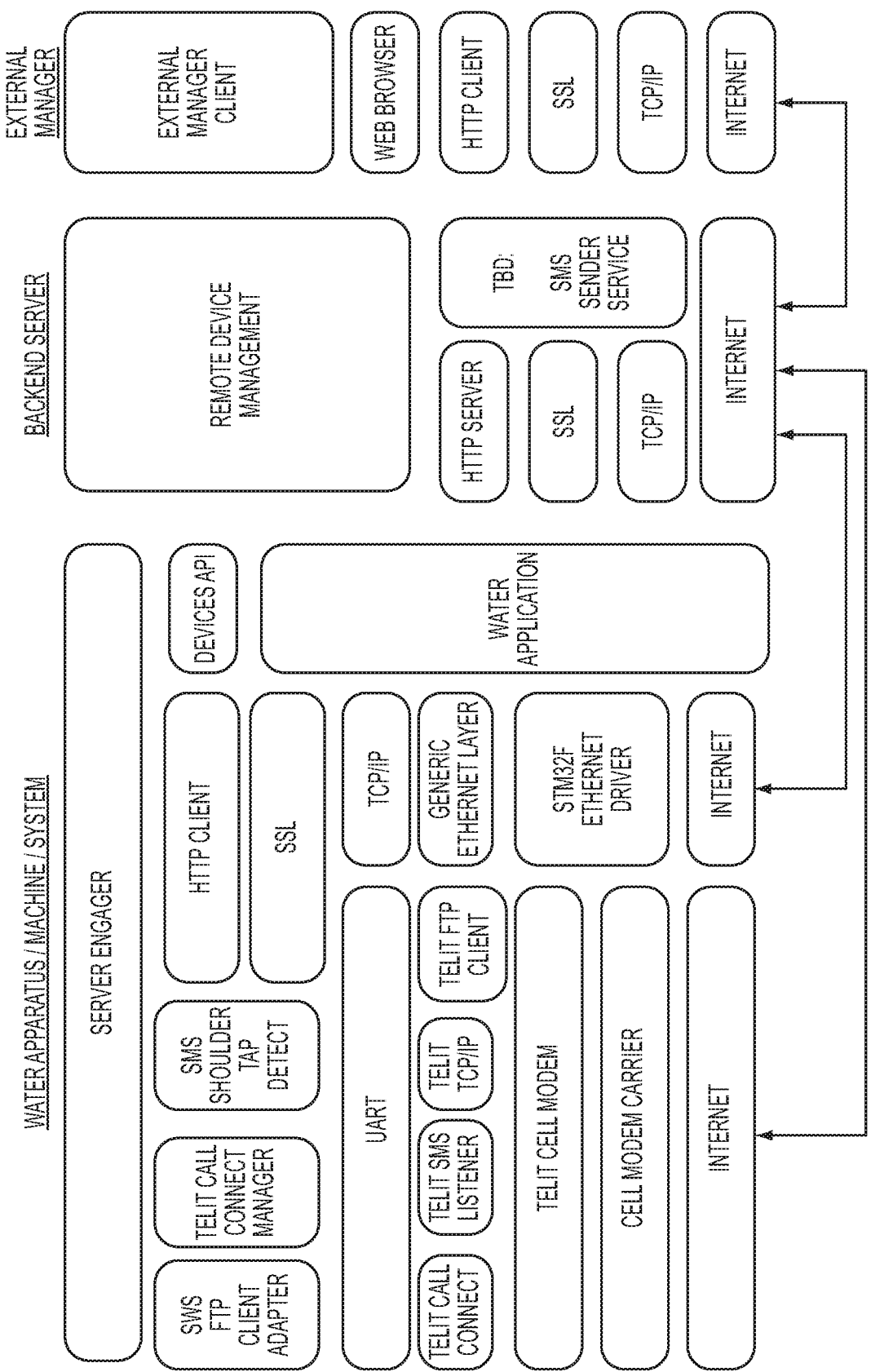
Figure 77:
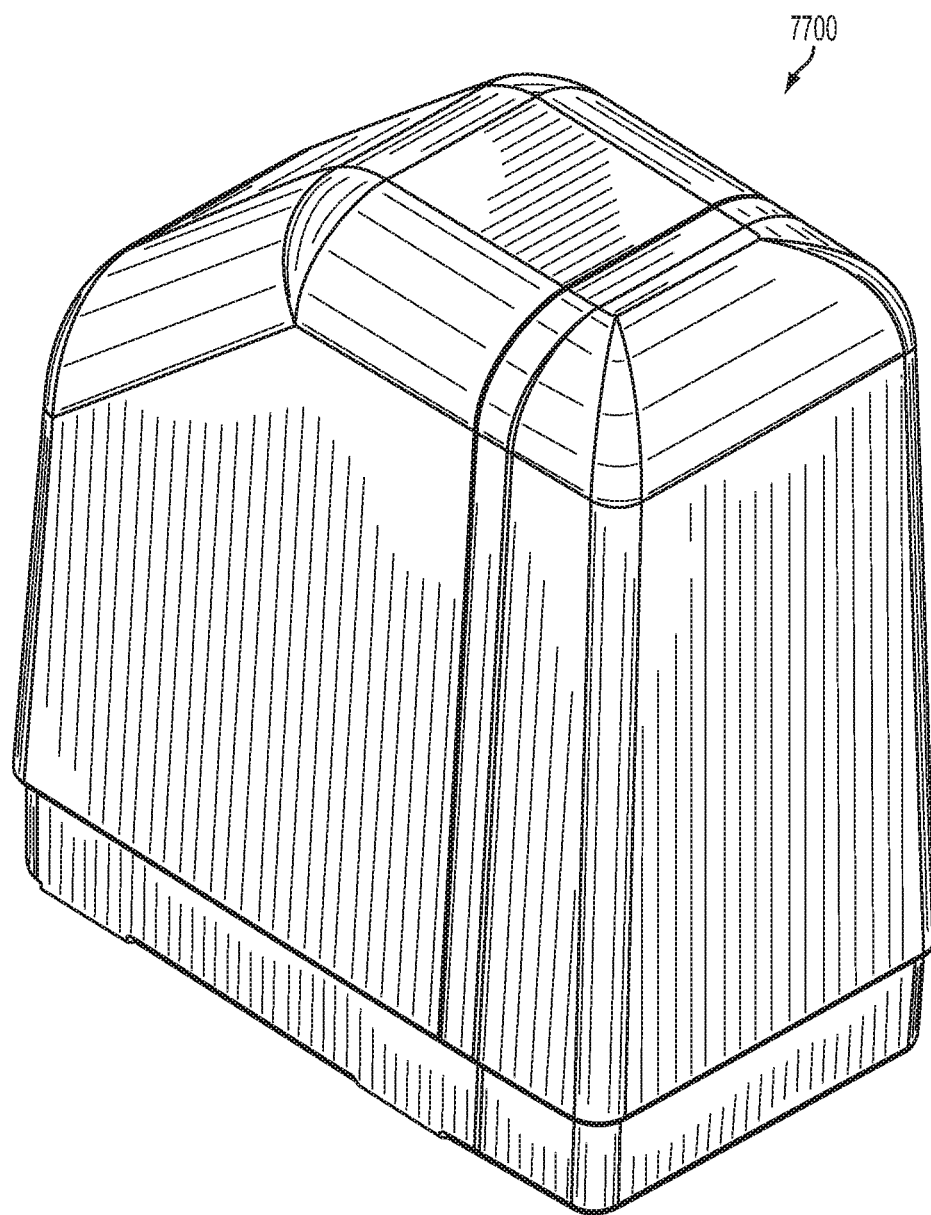
Figure 78:
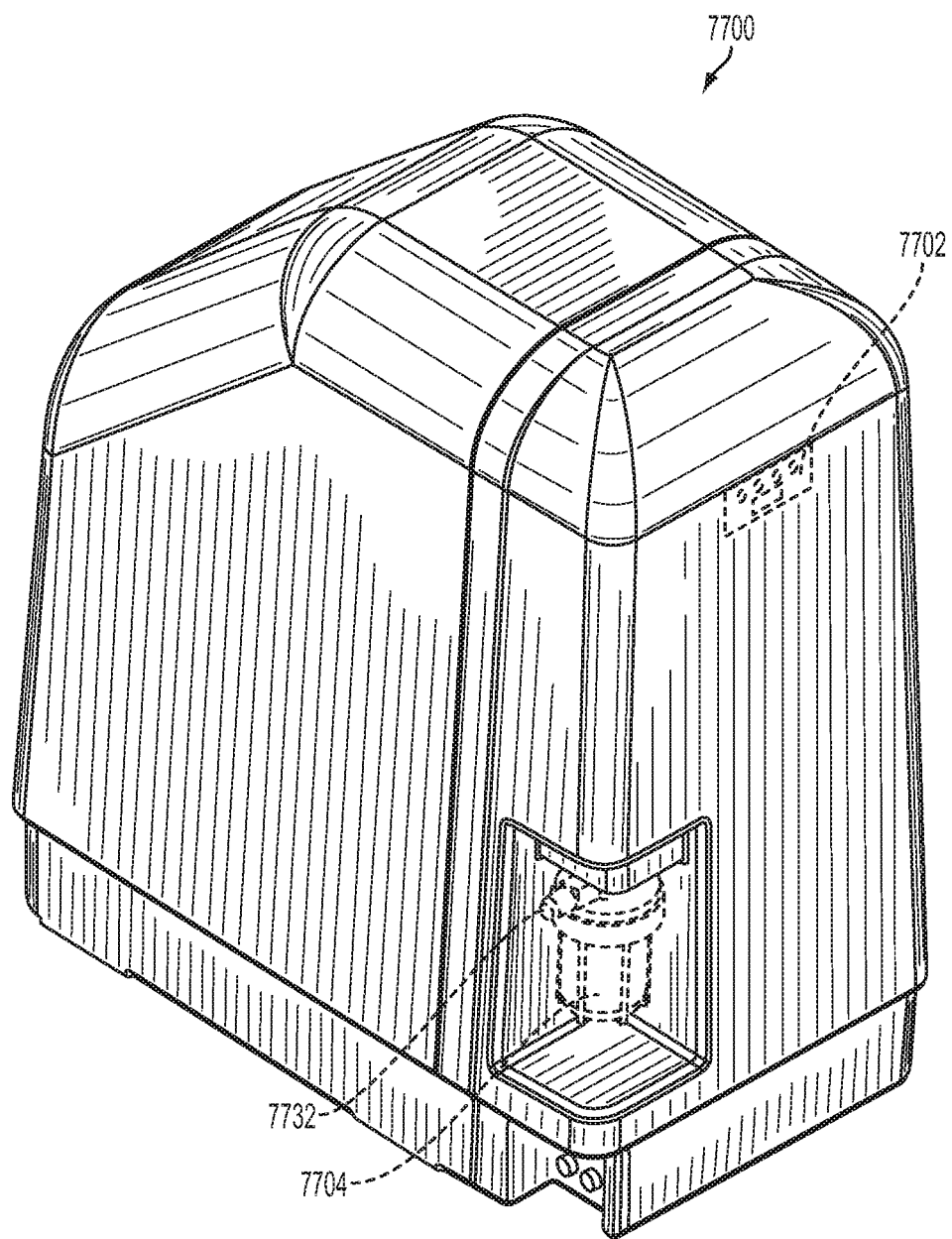
Figure 79A:
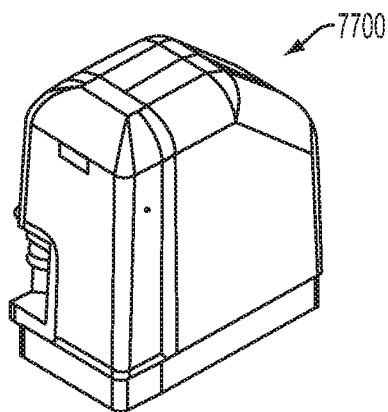
Figure 79B:
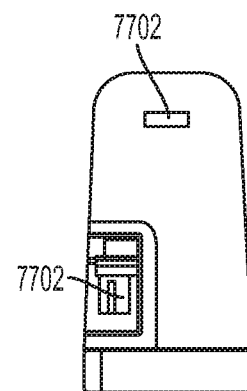
Figure 79C:
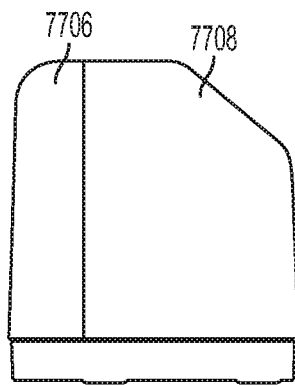
Figure 79D:
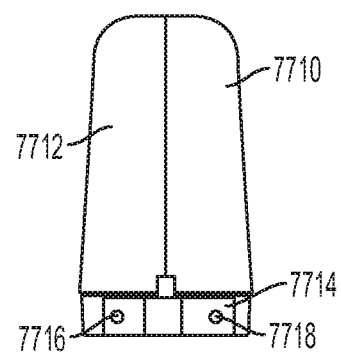
Figure 79E:
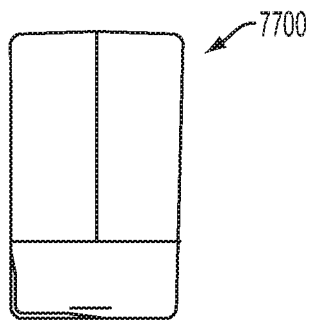
Figure 80:
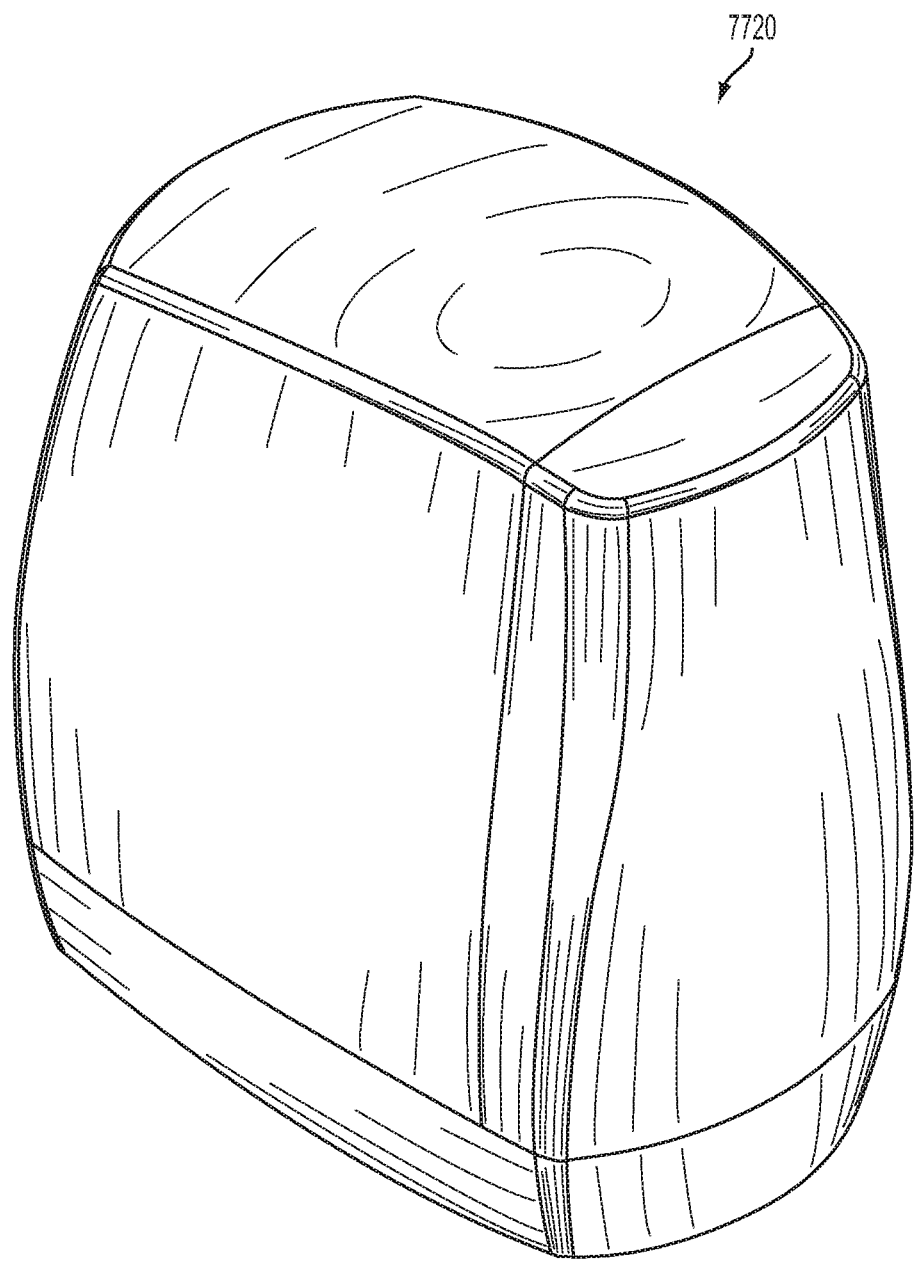
Figure 81:
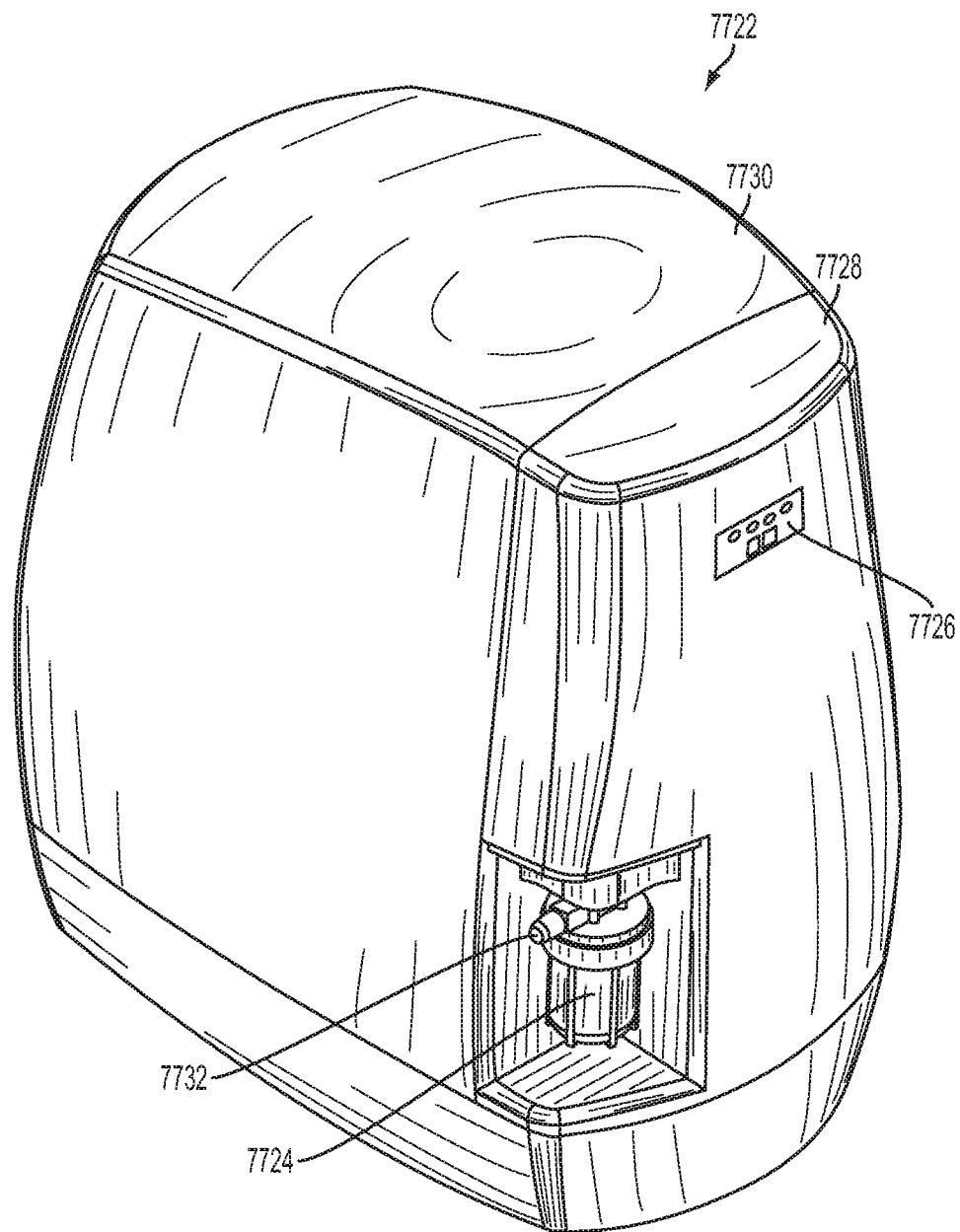
Figure 82:
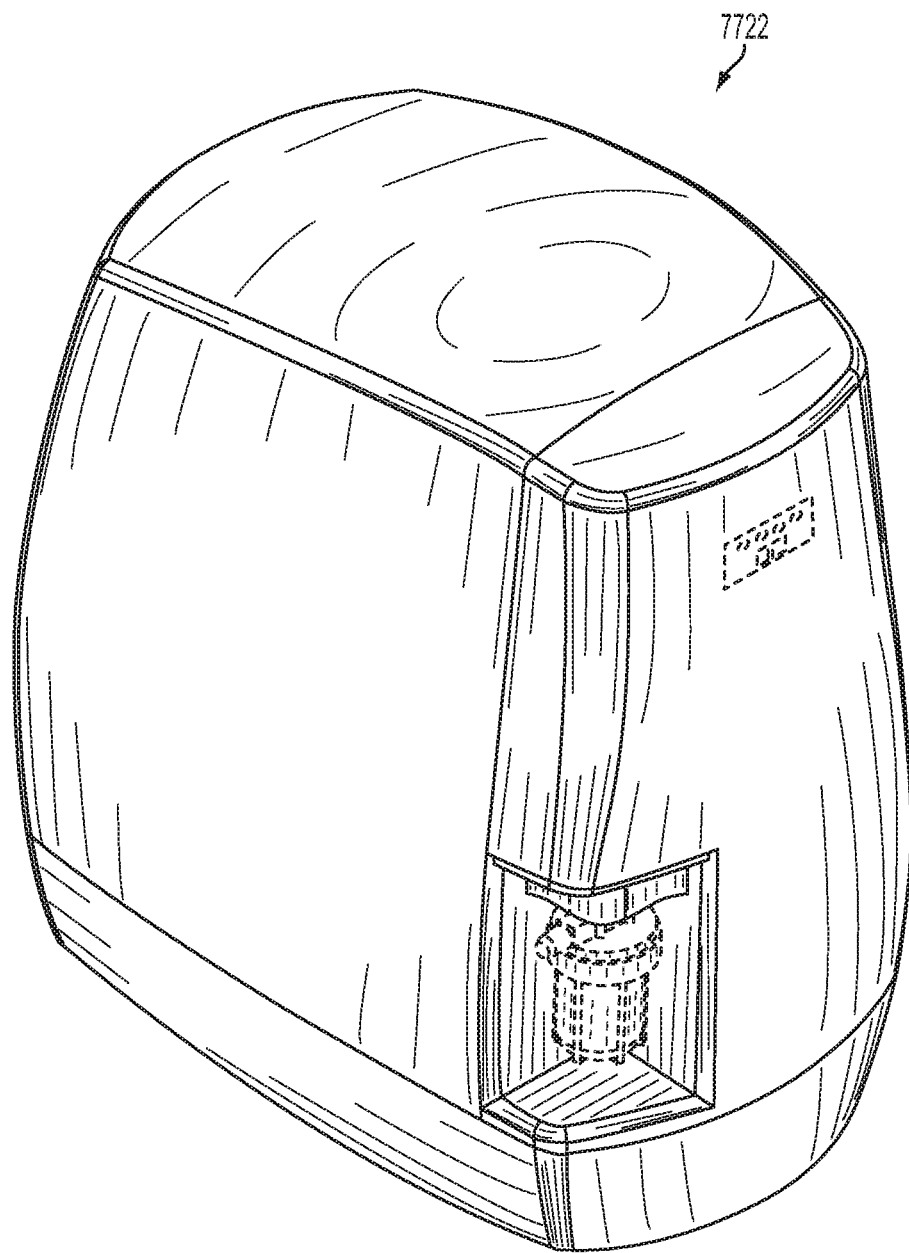
Figure 83:
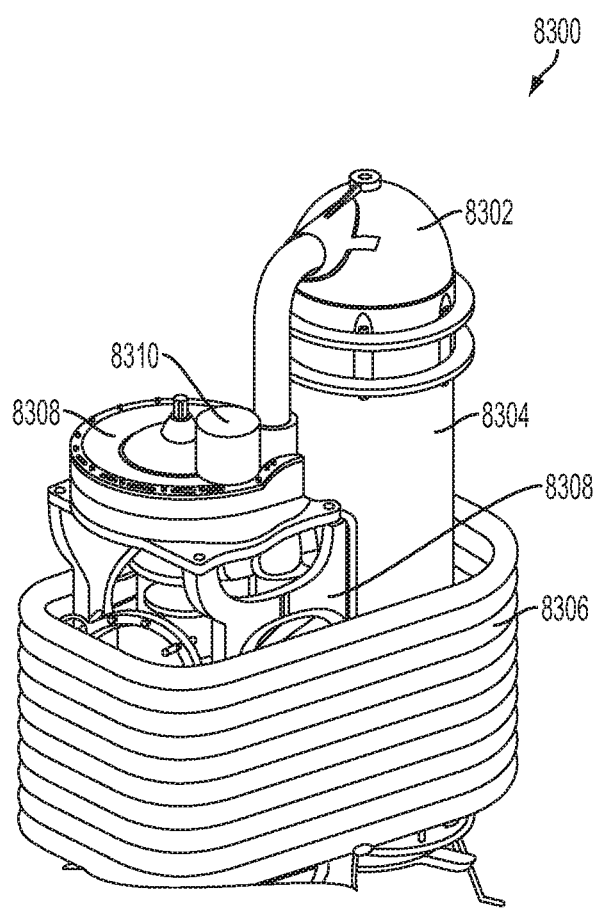
Figure 84A:
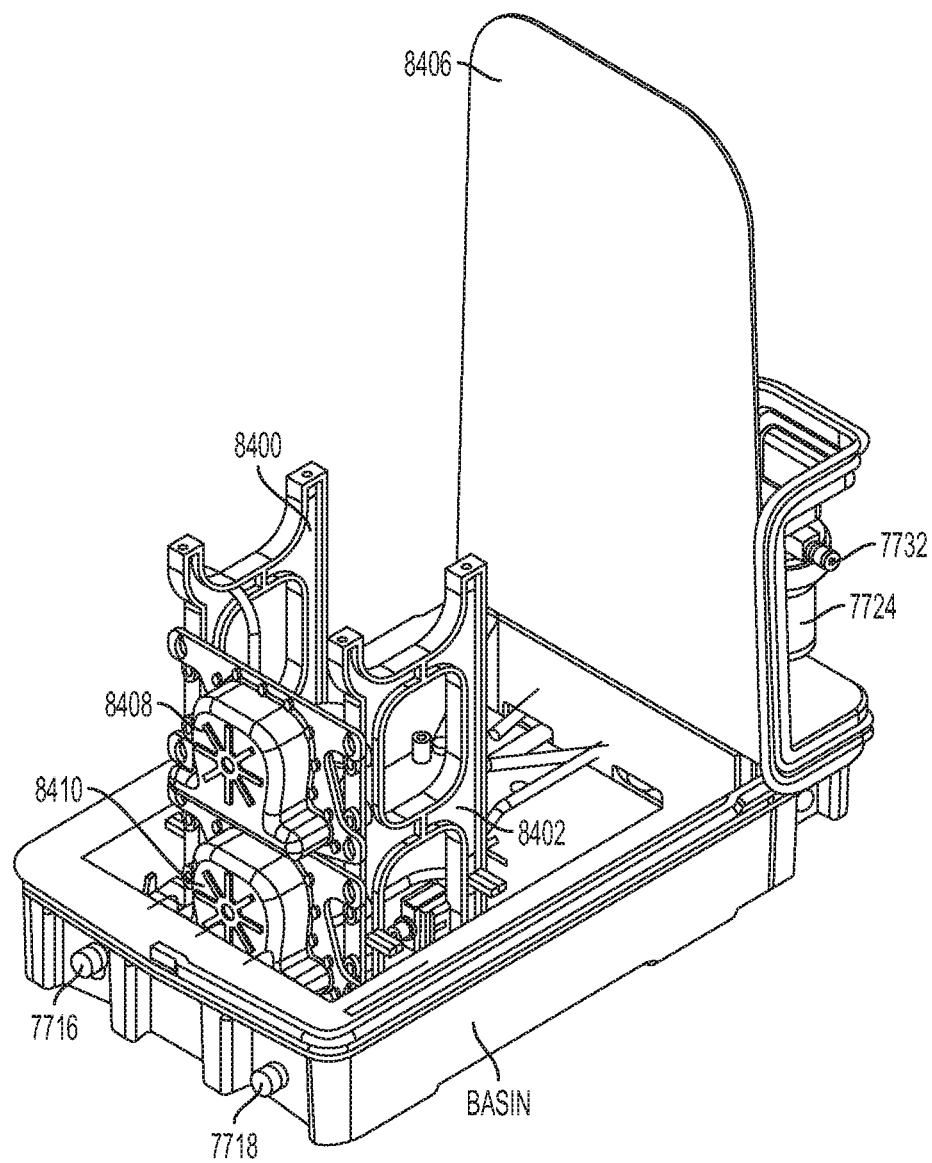
Figure 84B:
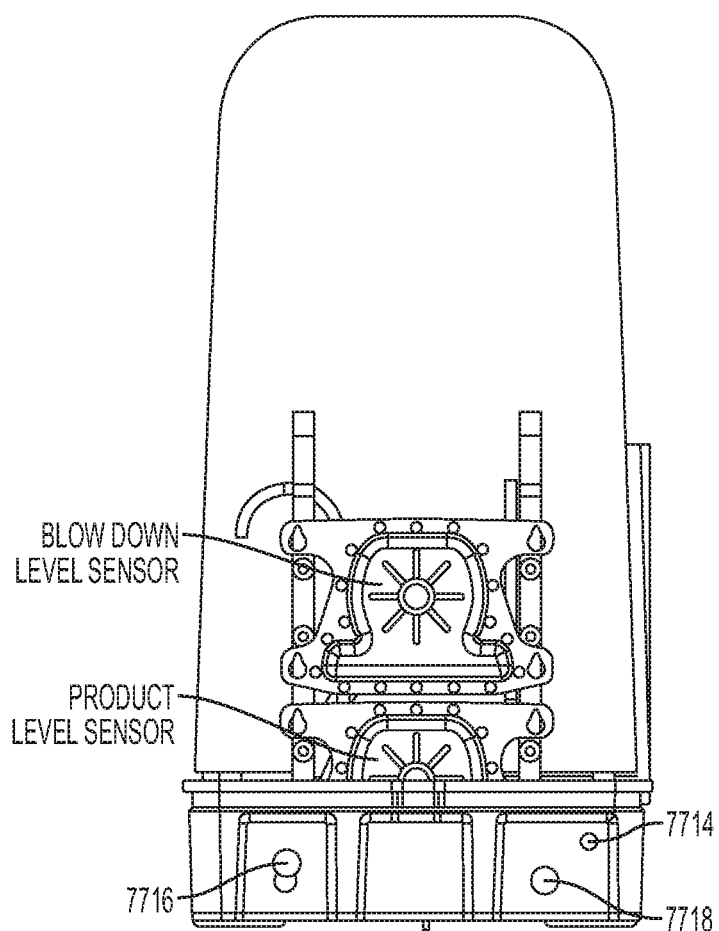
Figure 84C:
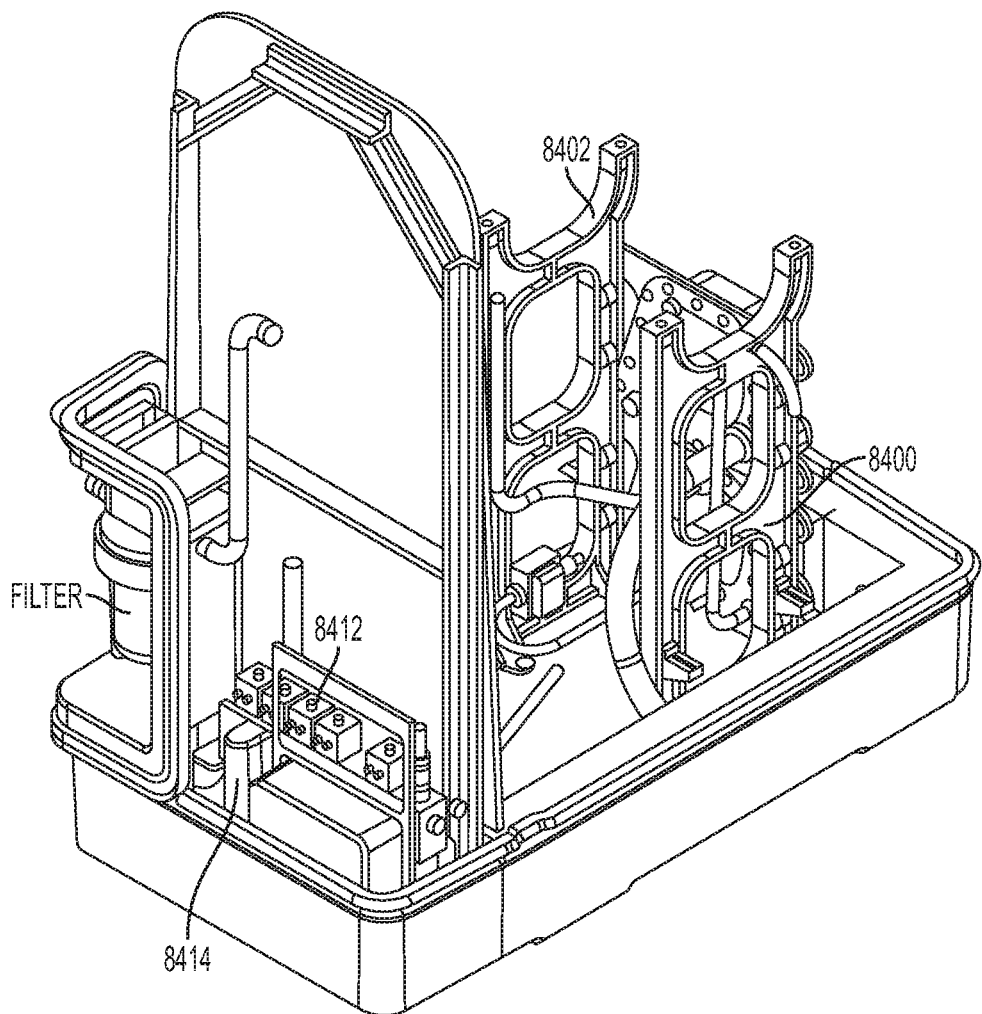
Figure 84D:
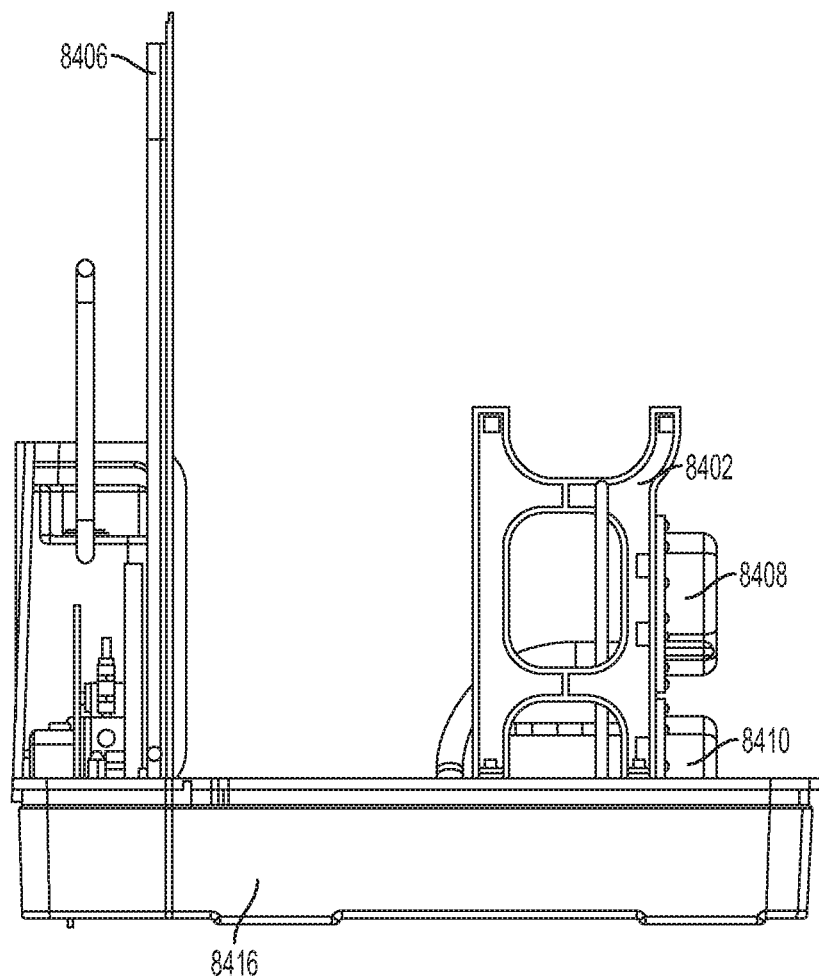
Figure 84E:
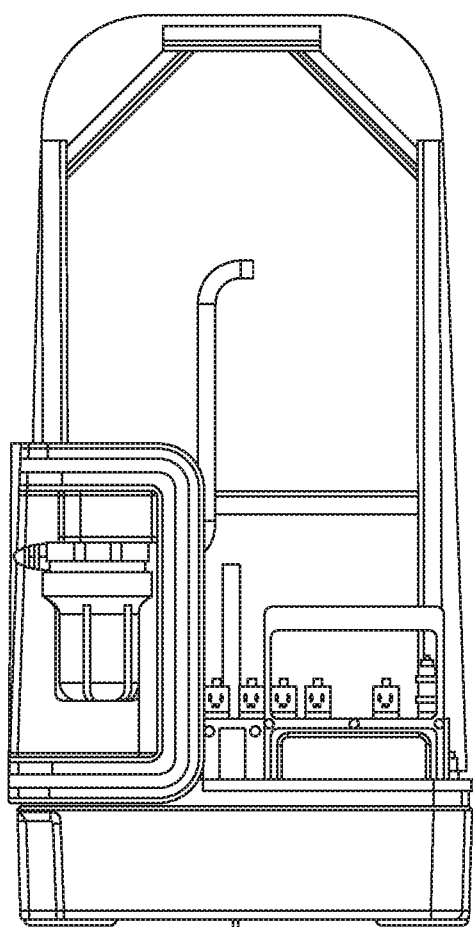
Figure 84F:
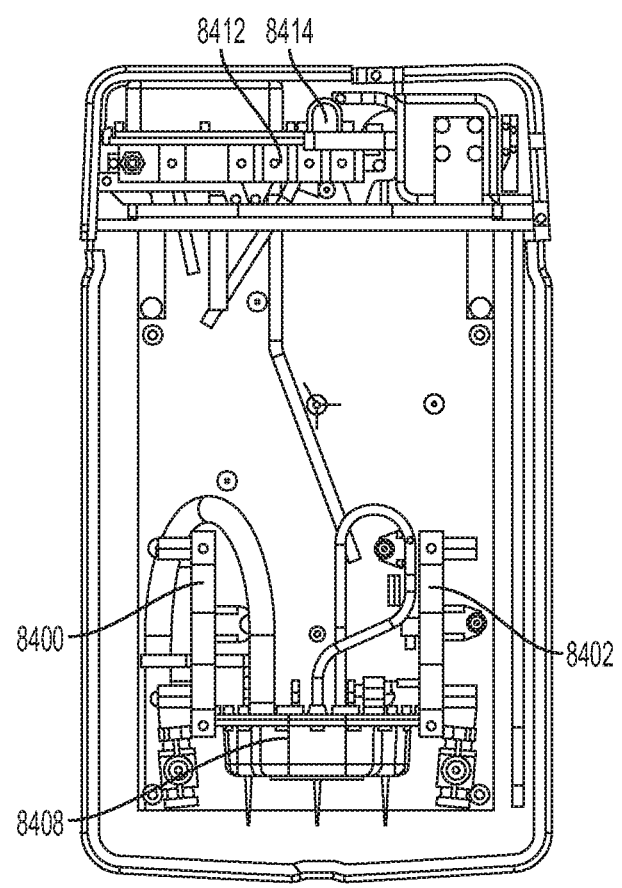
Figure 85A:
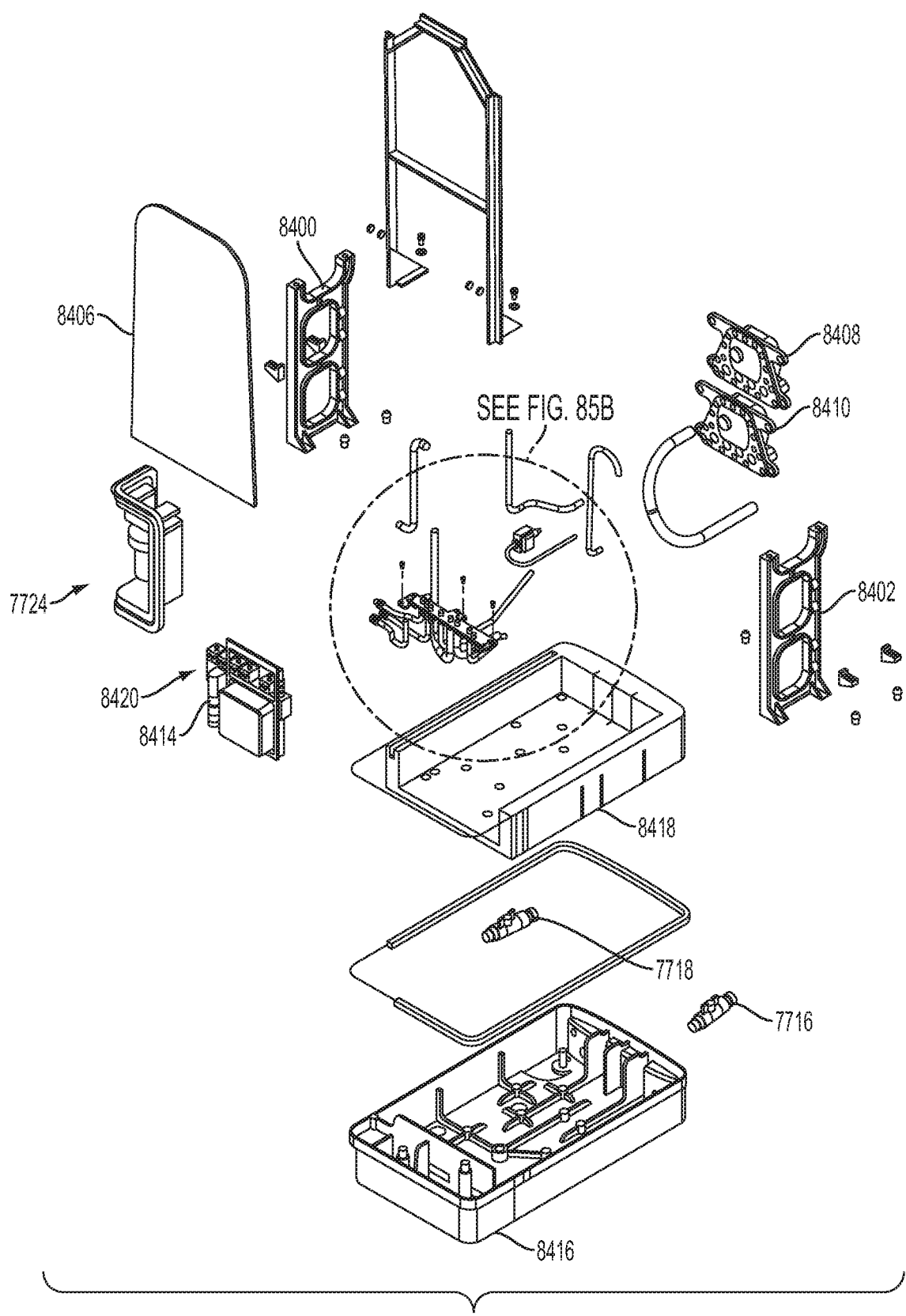
Figure 85B:
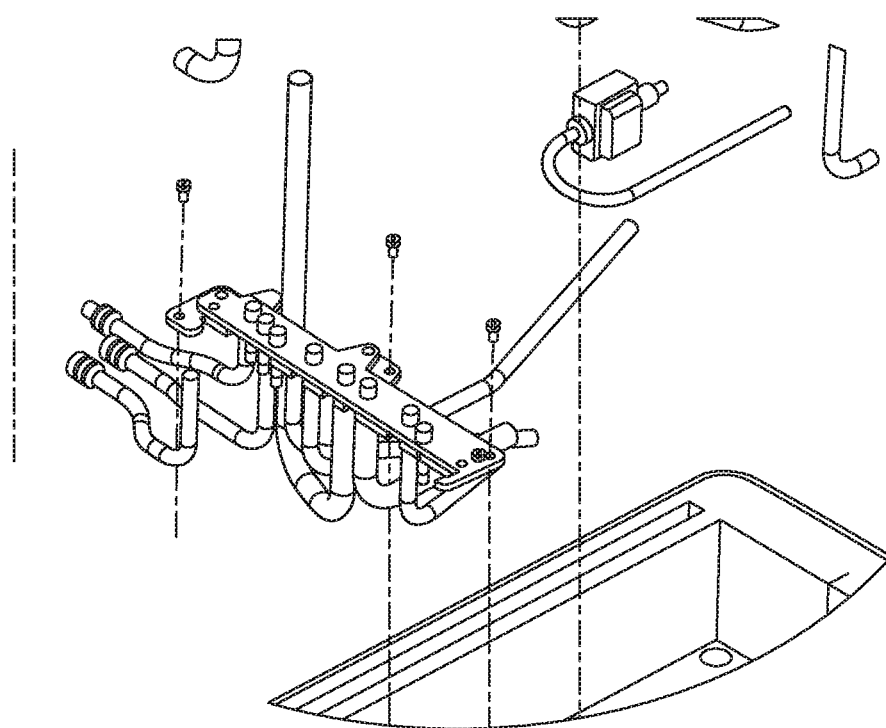
Figure 86:
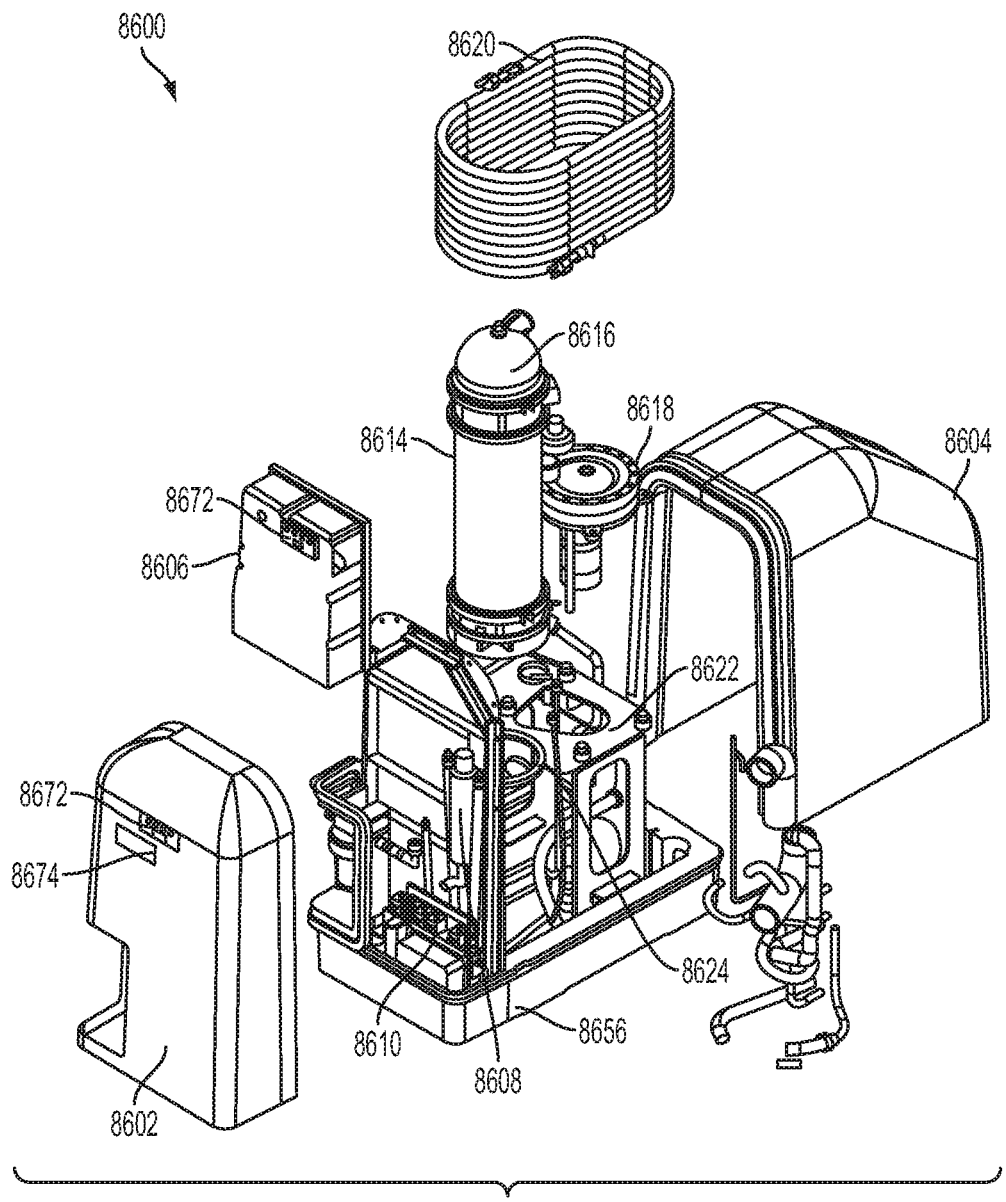
Figure 87A:
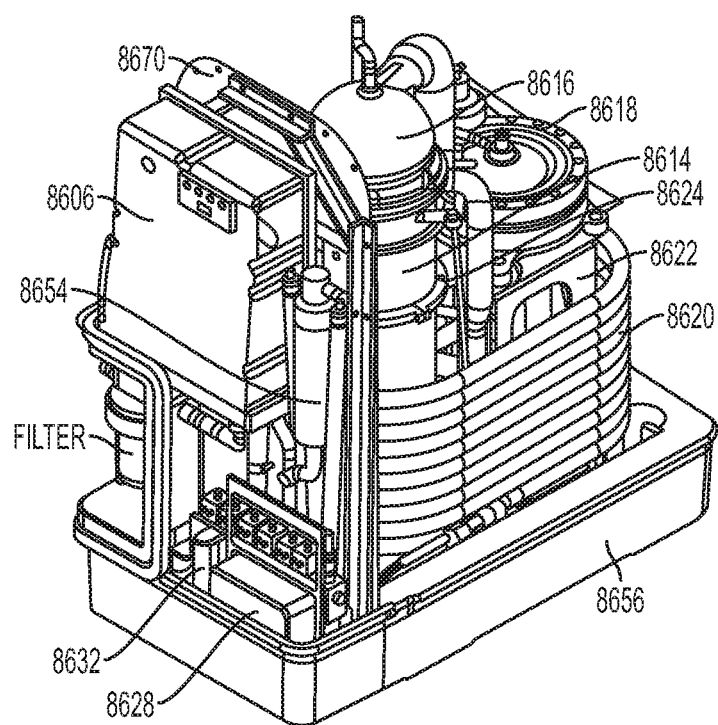
Figure 87B:
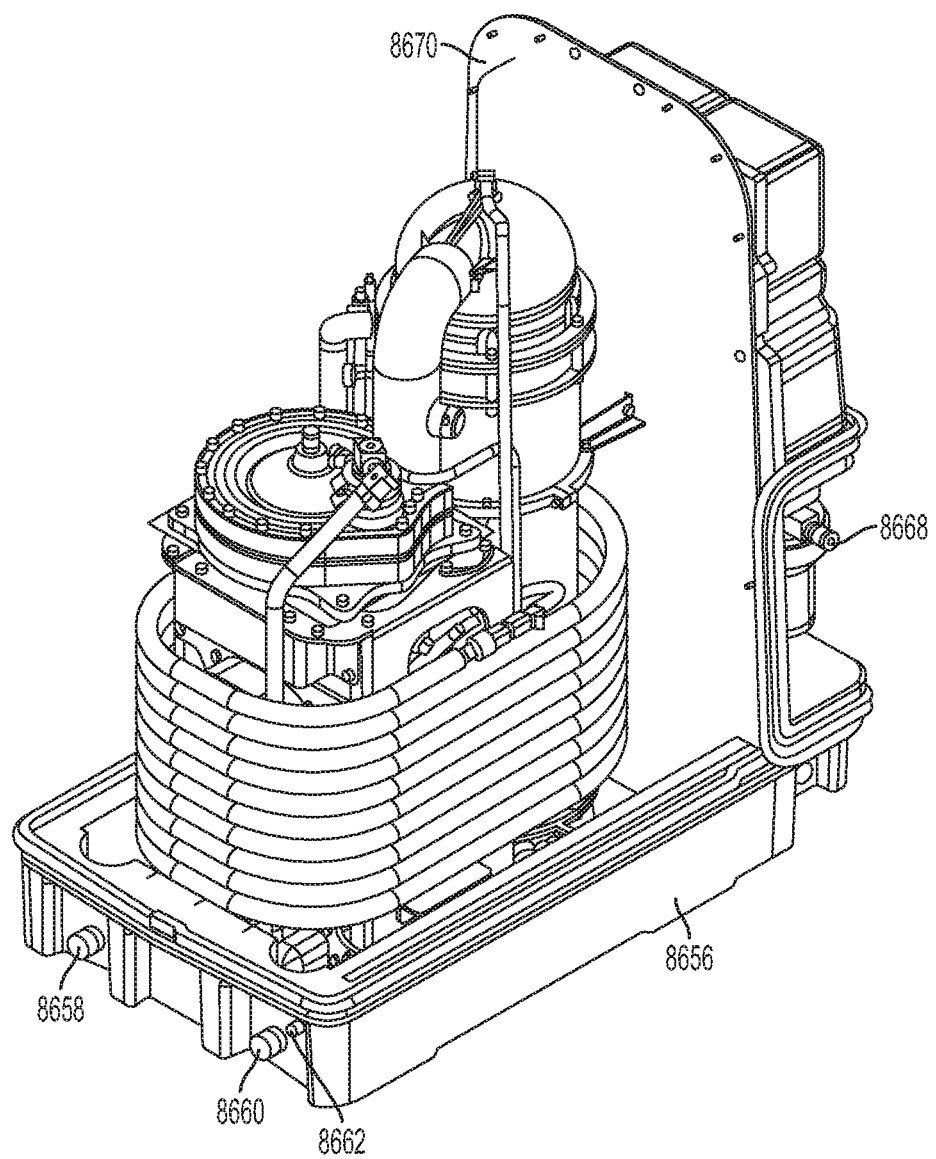
Figure 87C:
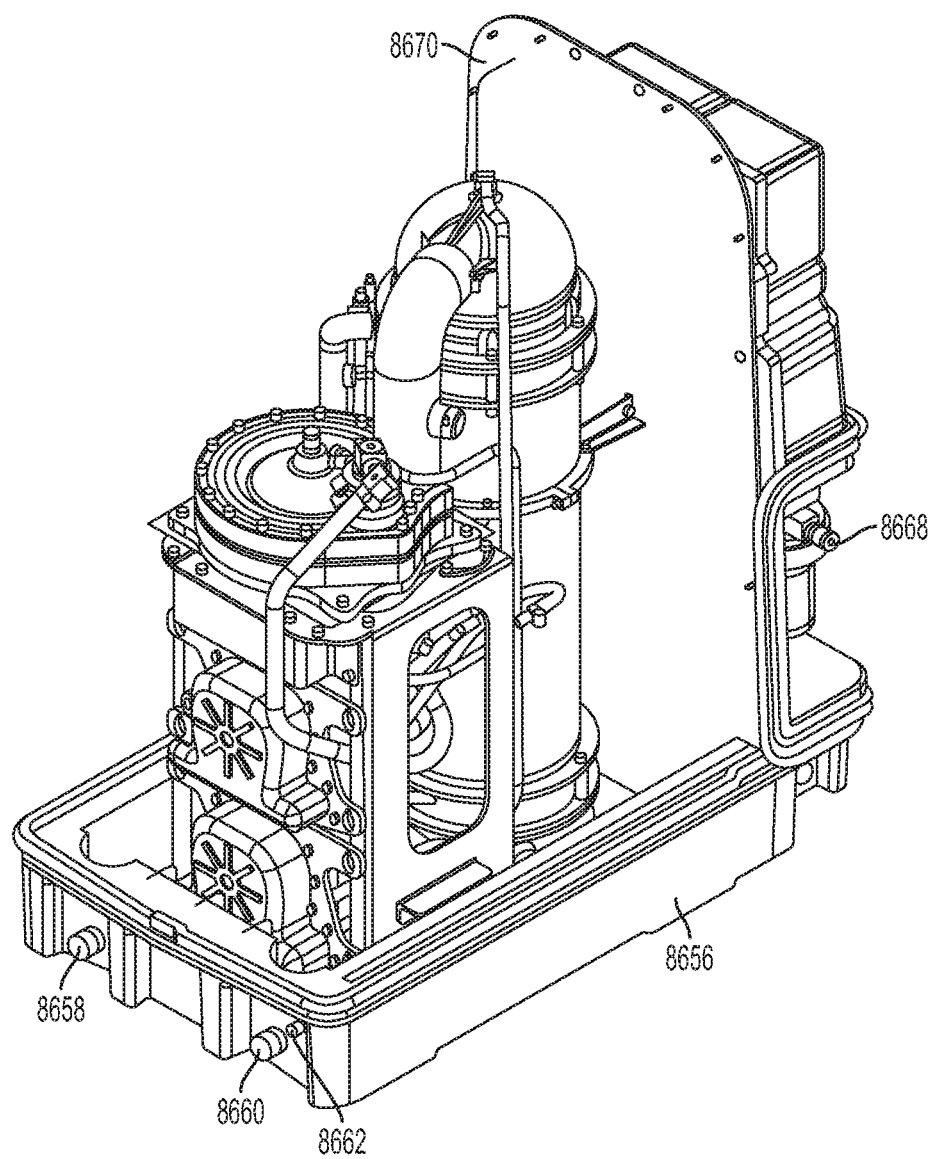
Figure 87D:
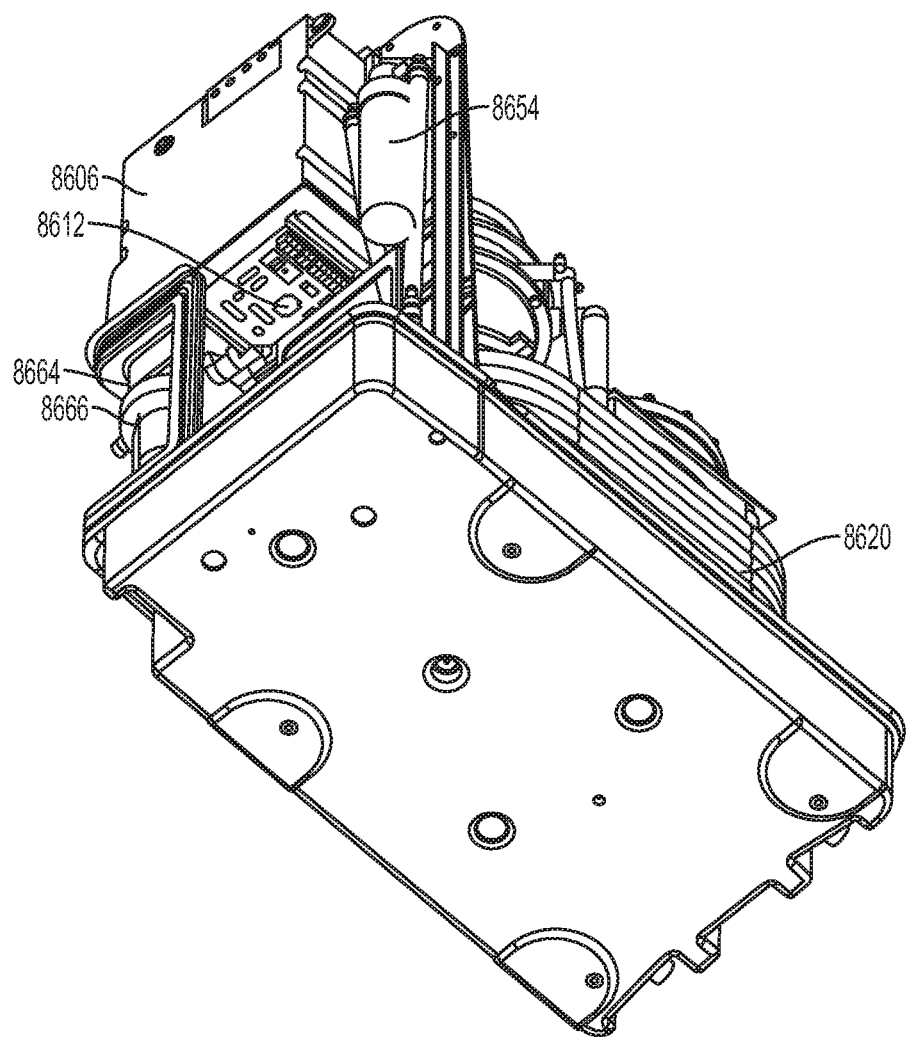
Figure 88:
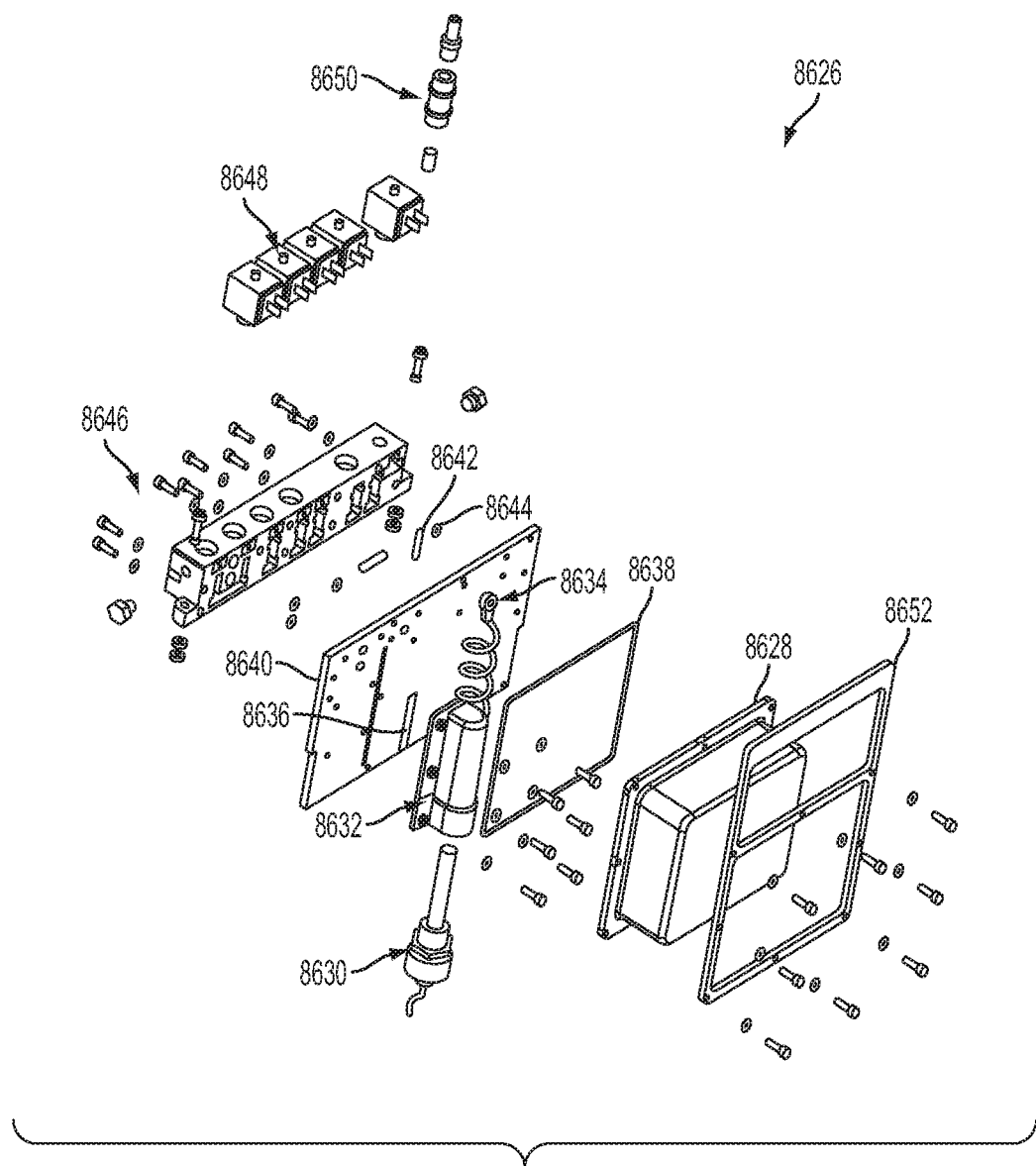
Figure 90A:
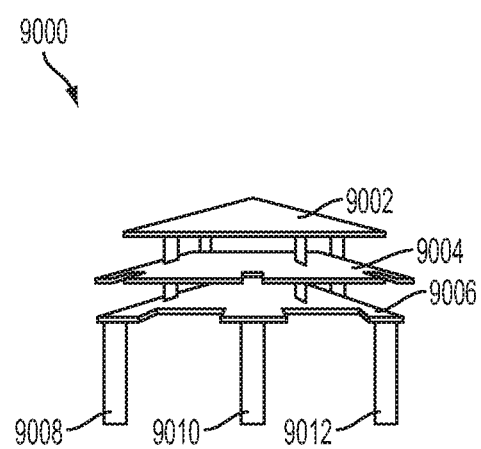
Figure 90B:
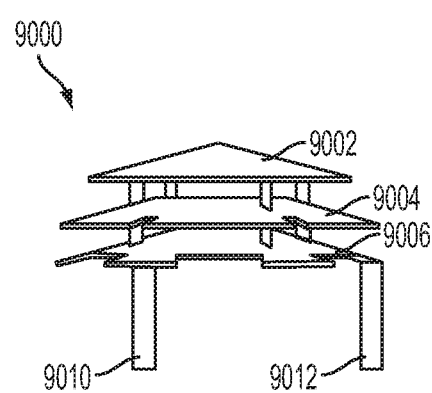
Figure 90C:
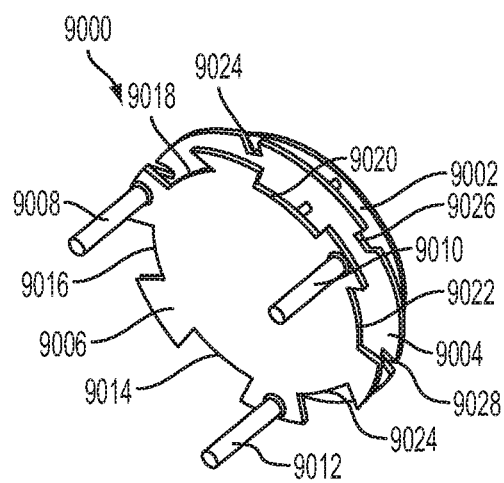
Figure 90D:
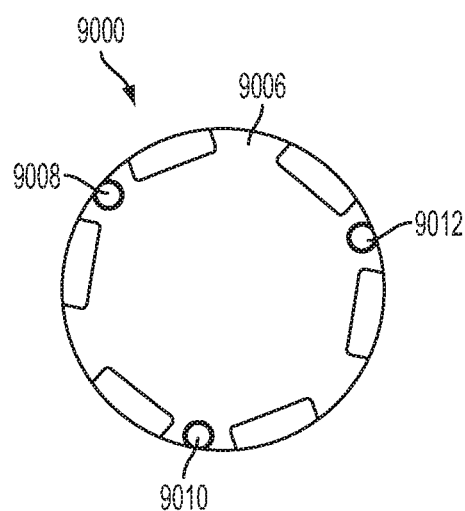
Figure 90E:
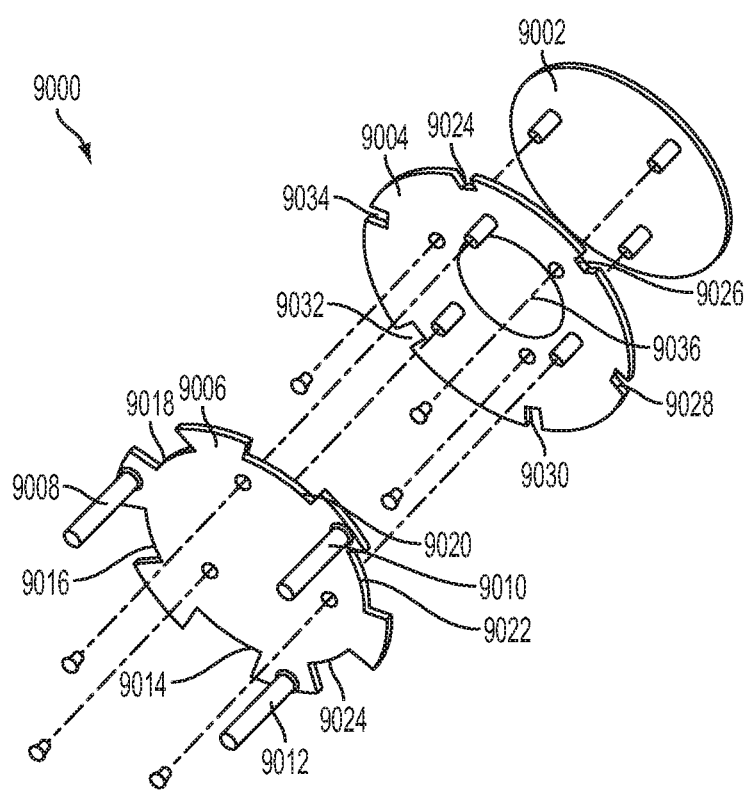
Figure 91A:
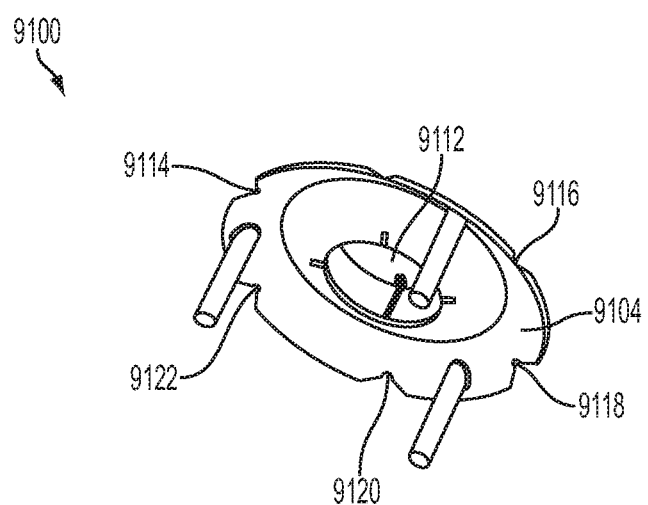
Figure 91B:
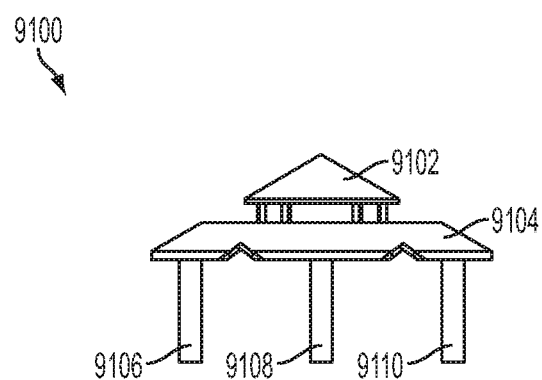
Figure 92A:
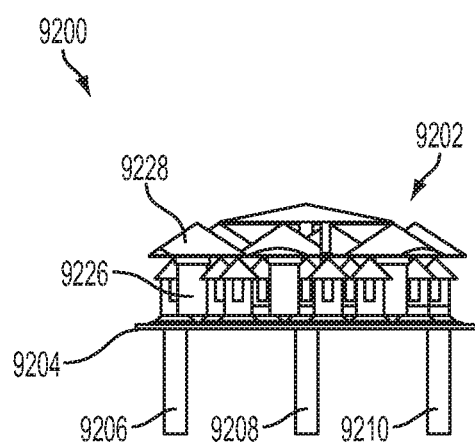
Figure 92B:
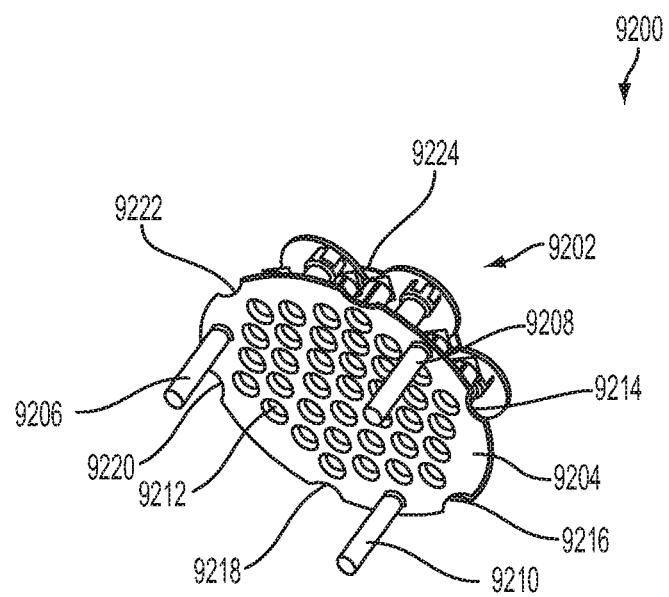
Figure 93A:
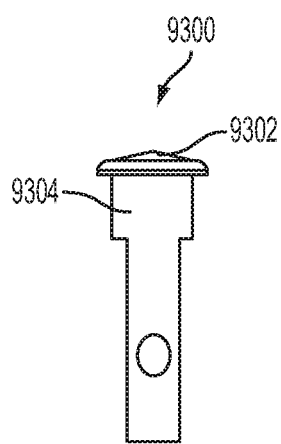
Figure 93B:
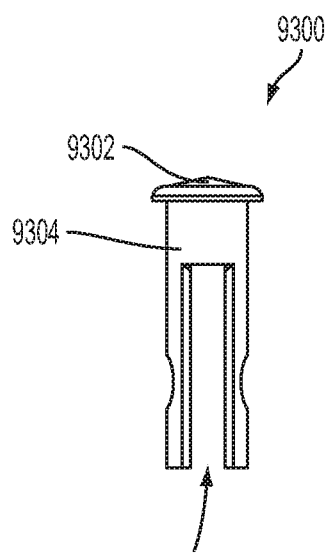
Figure 94:
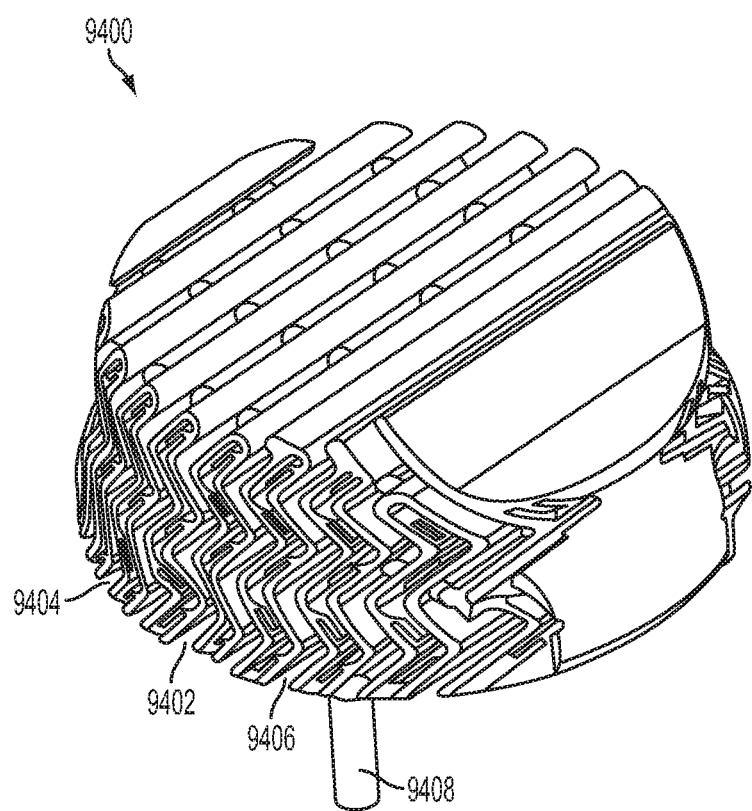
Figure 95A:
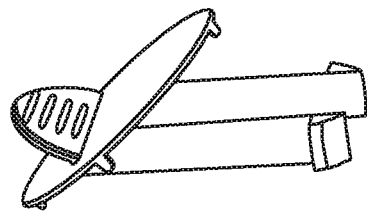
Figure 95B:
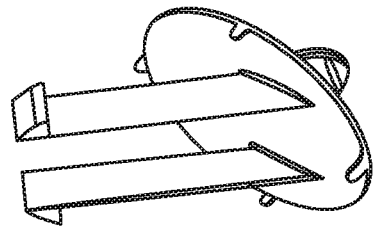
Figure 96:
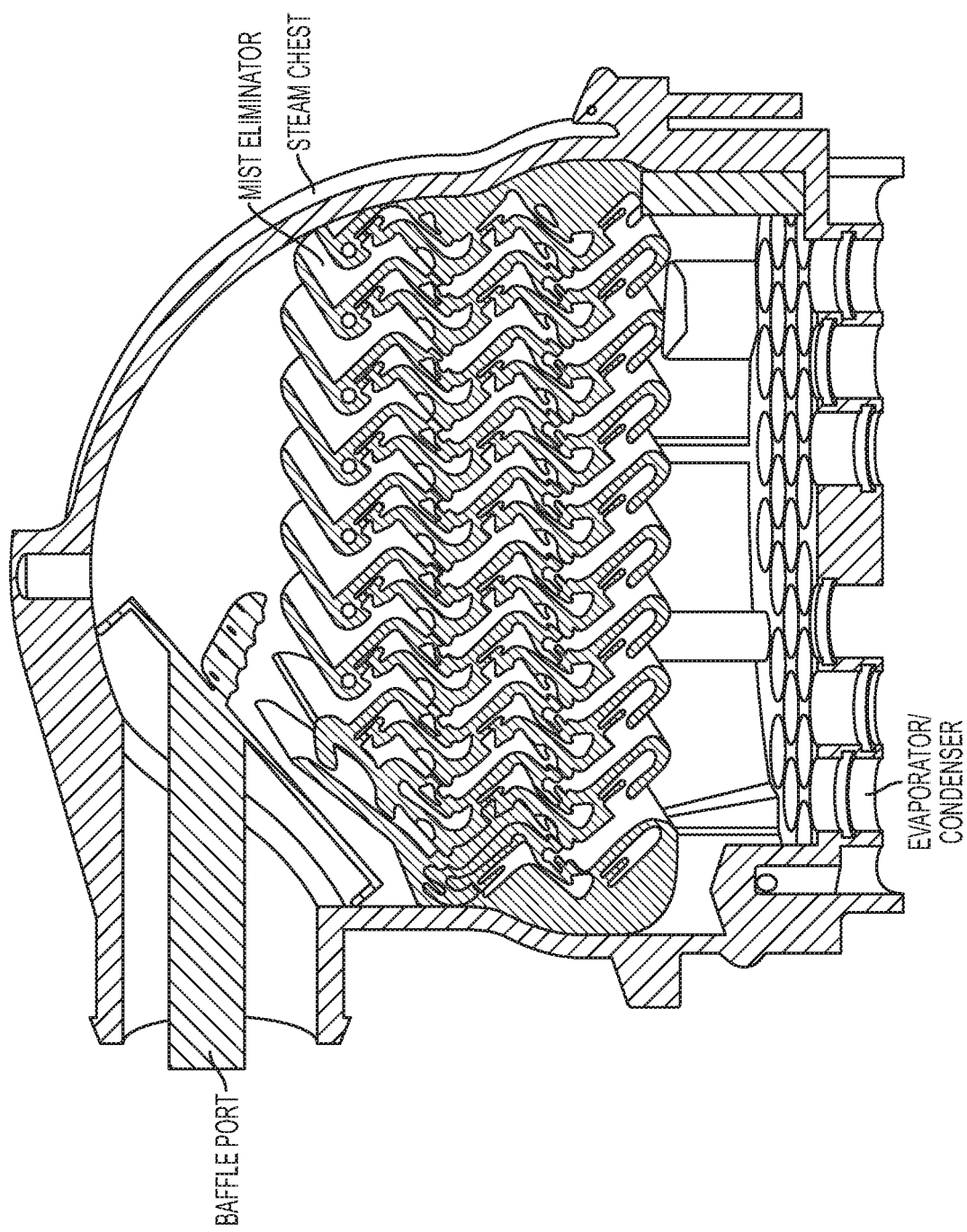
Figure 97:
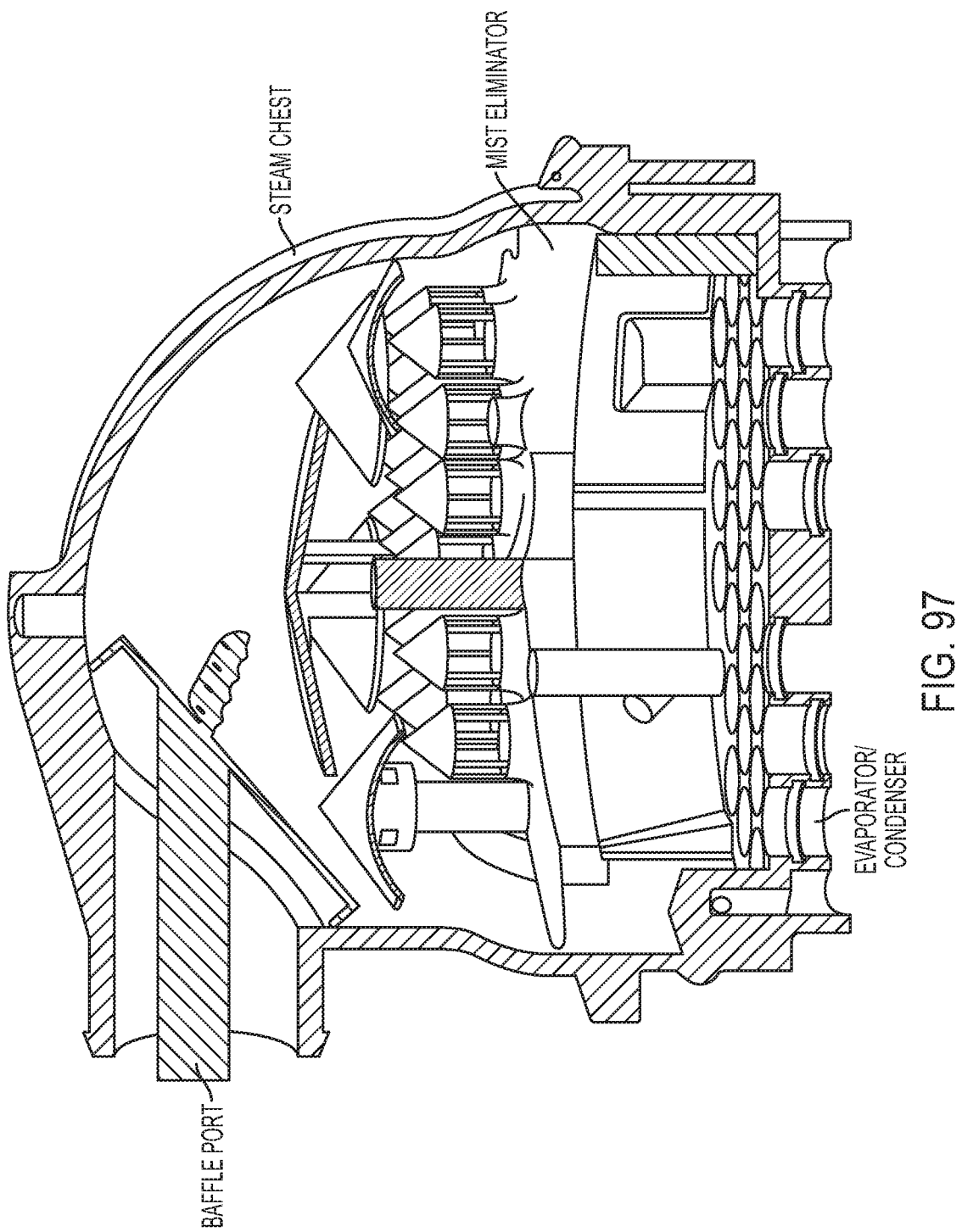
Figures 98A, 98B:
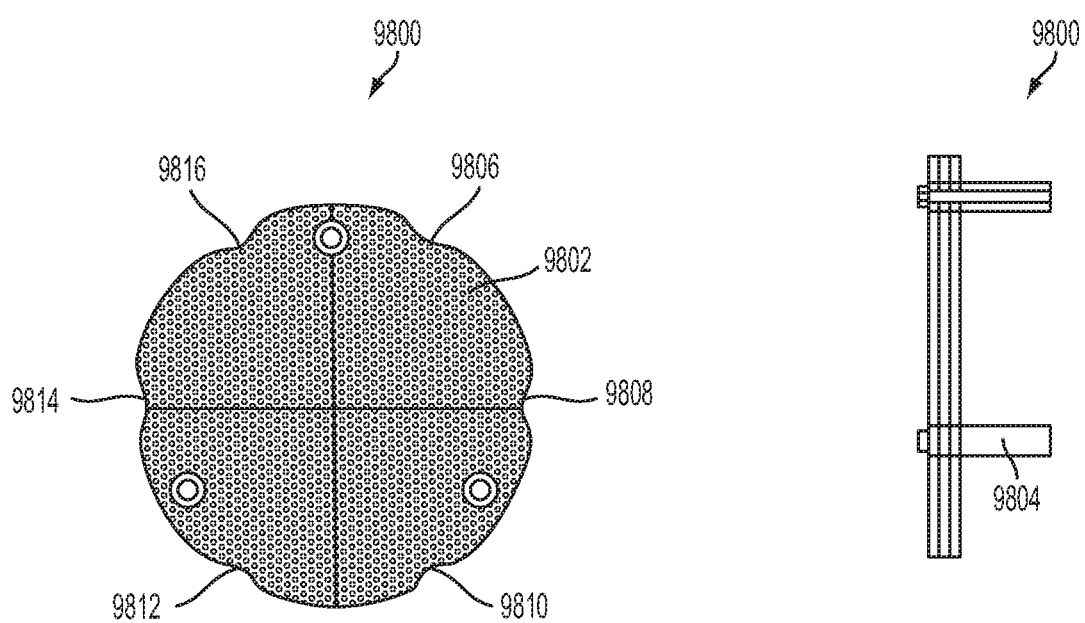
Figure 99A:
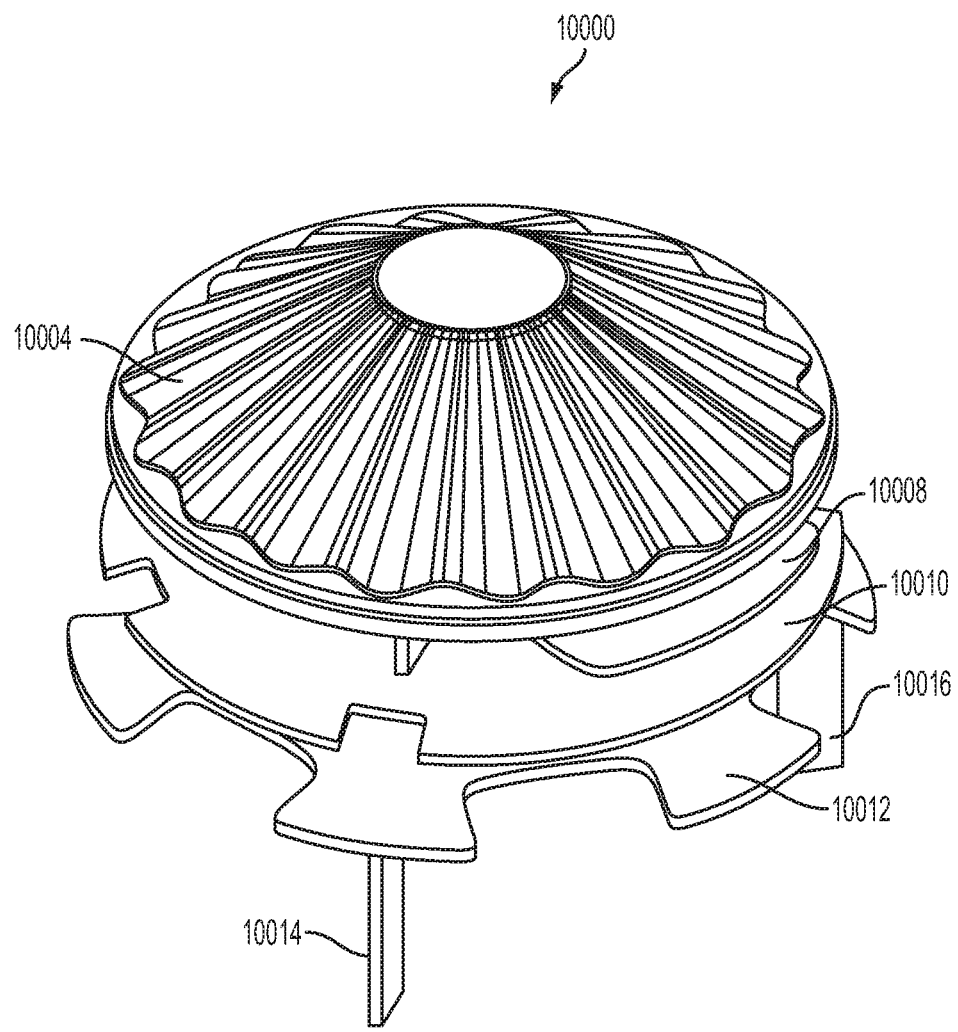
Figure 99B:
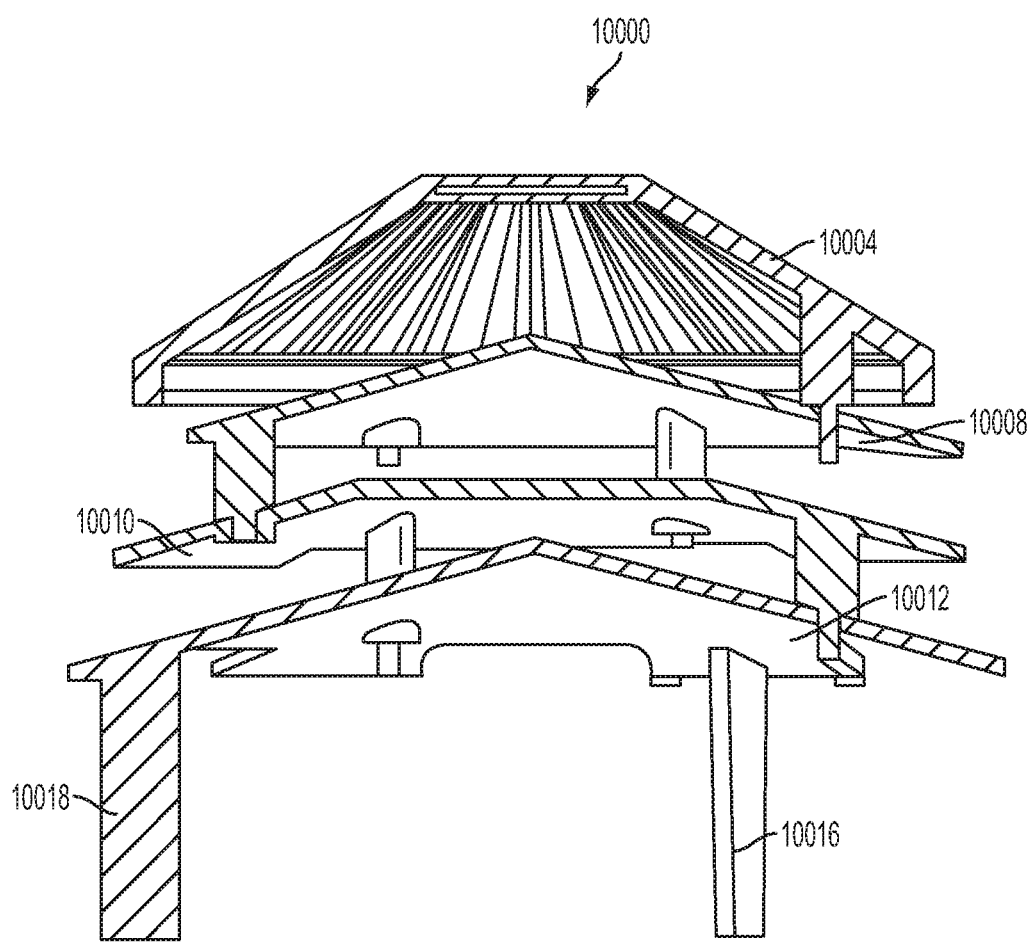
Figure 99C:
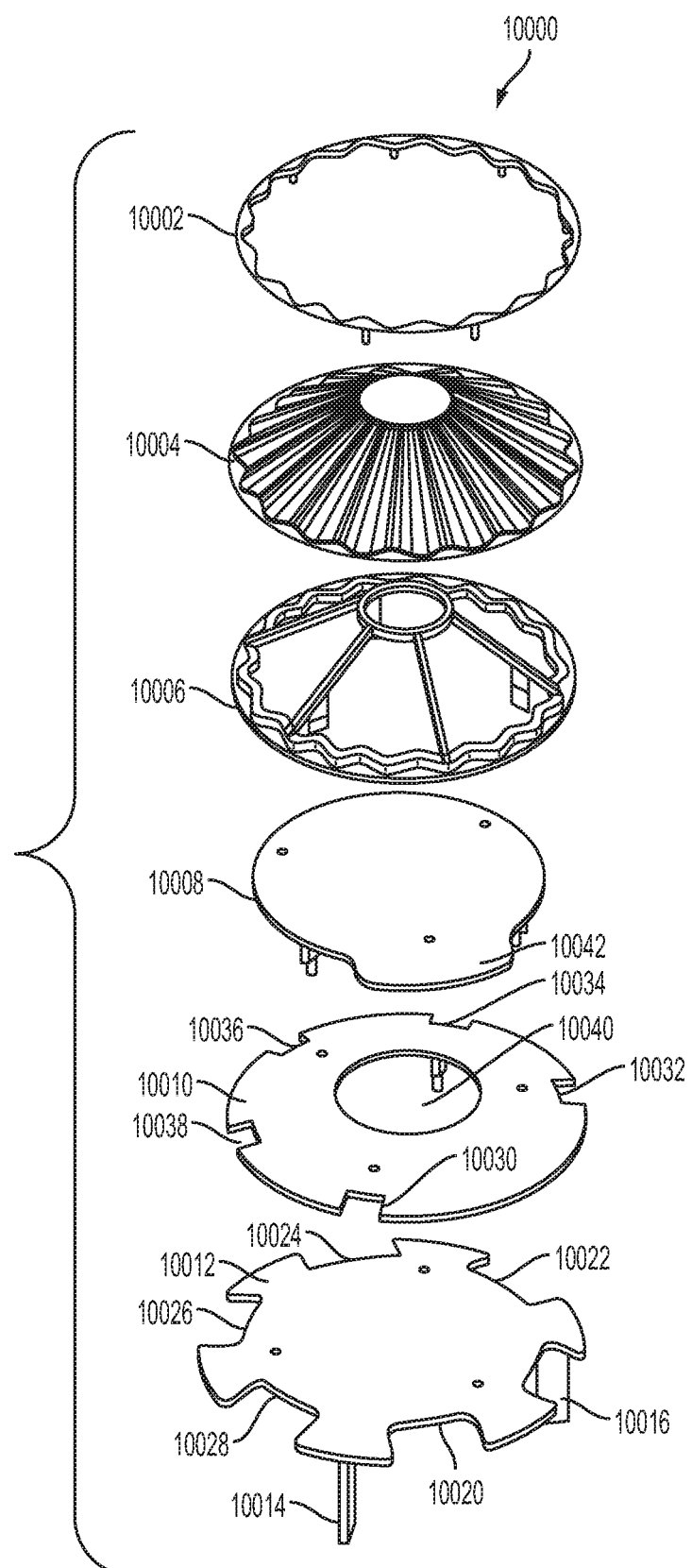
Figure 100A:
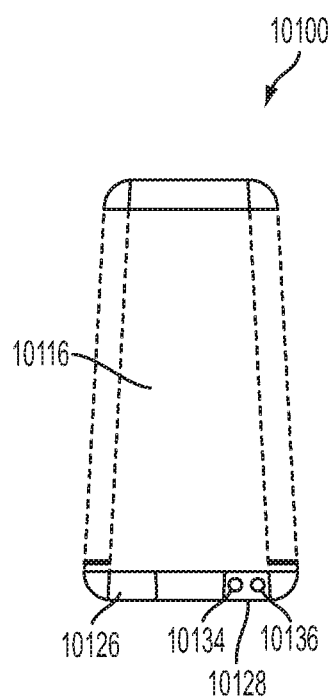
Figure 100B:
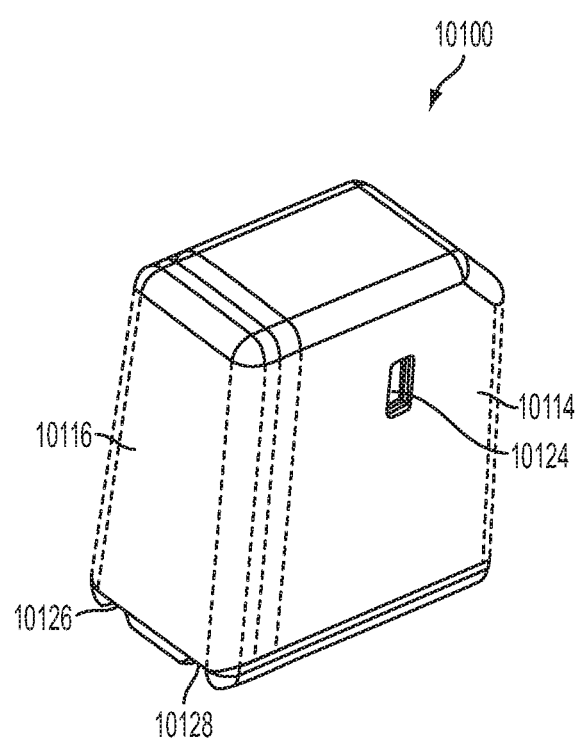
Figure 100C:
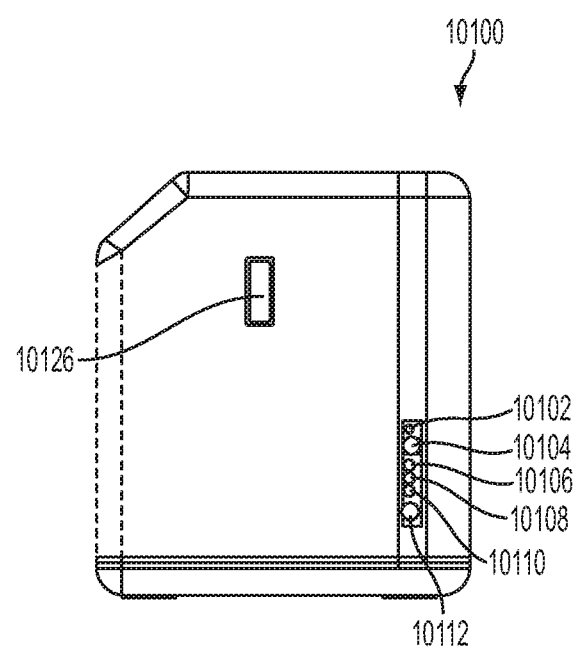
Figure 101:
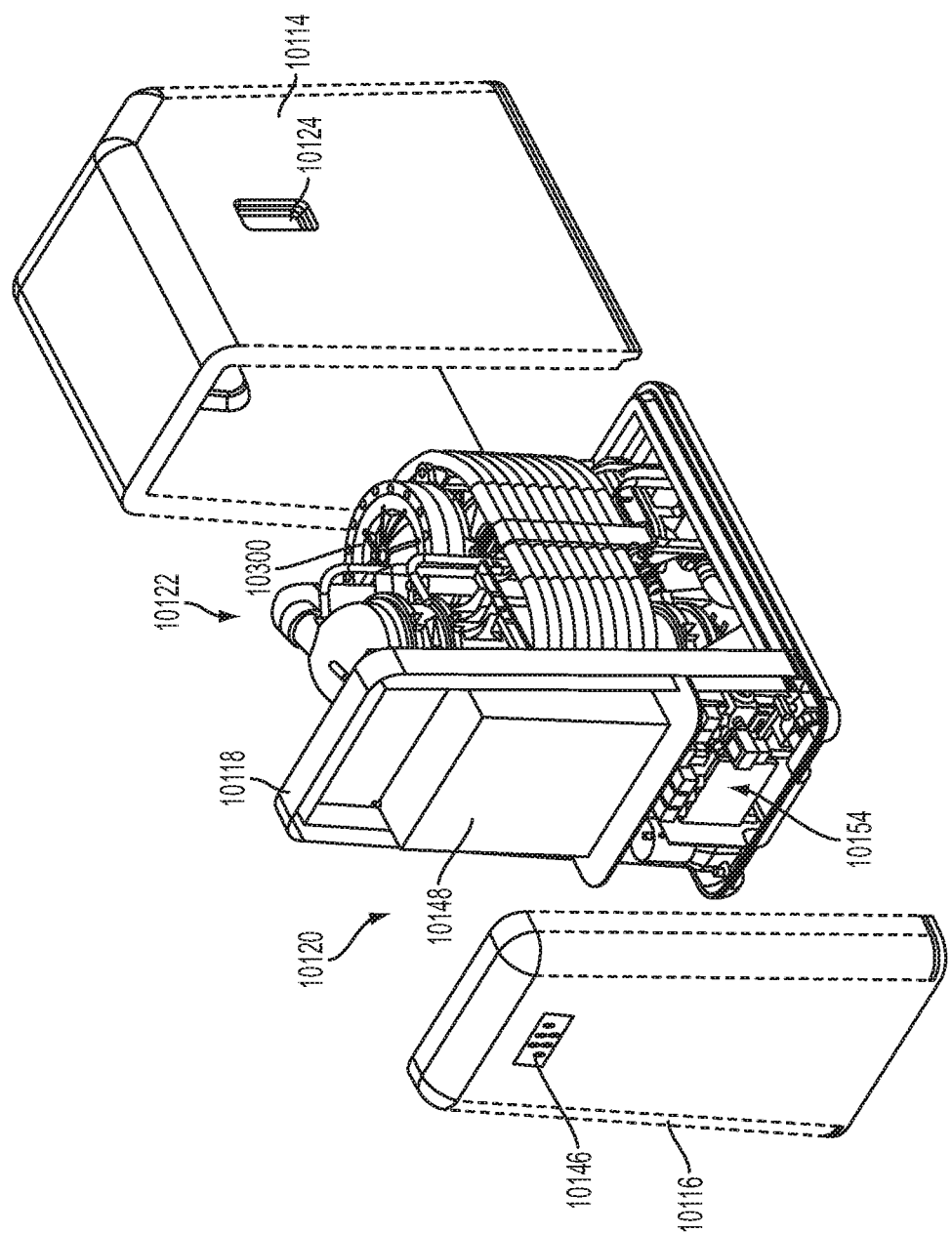
Figure 102:
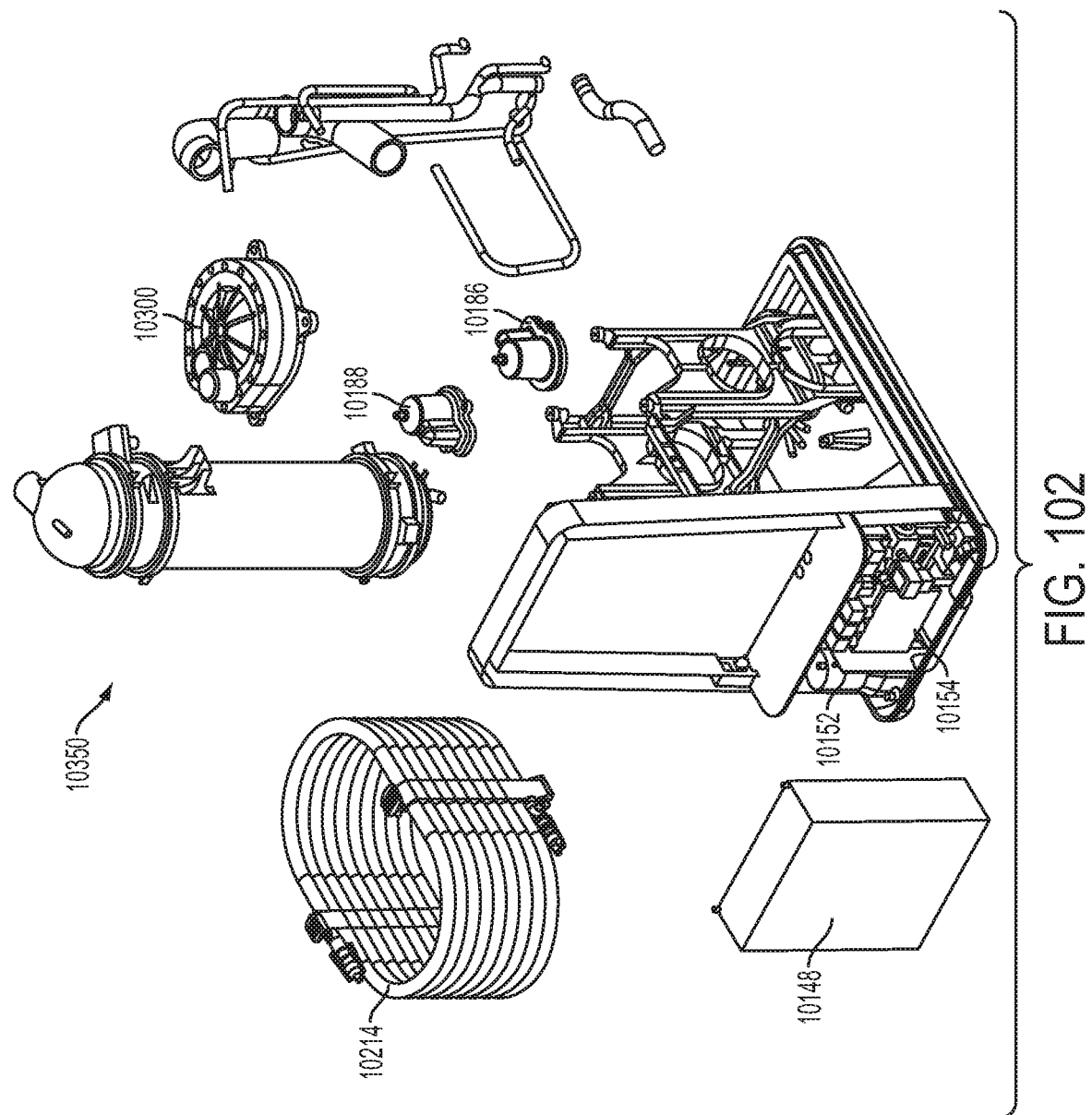
Figure 103:
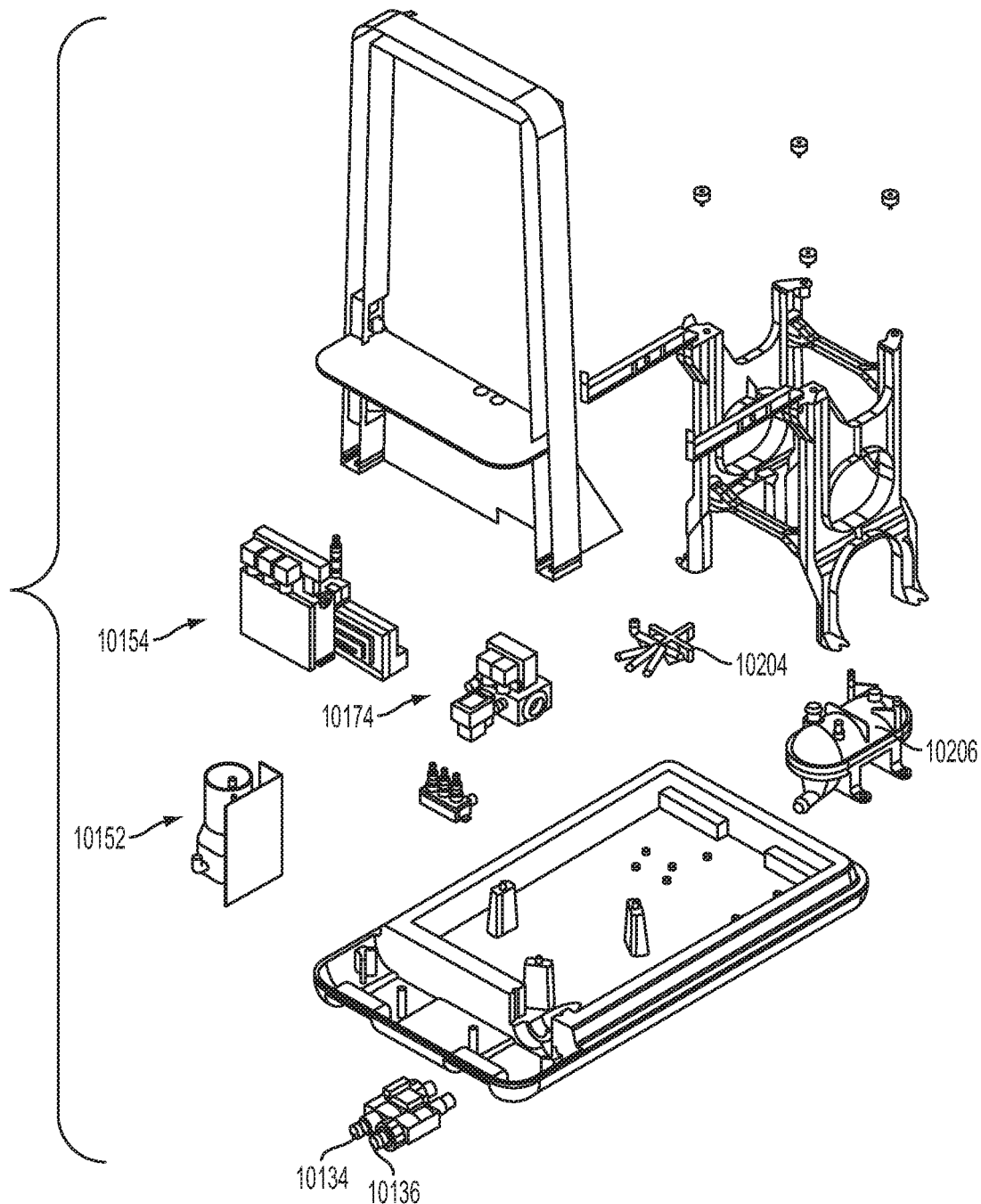
Figure 104:
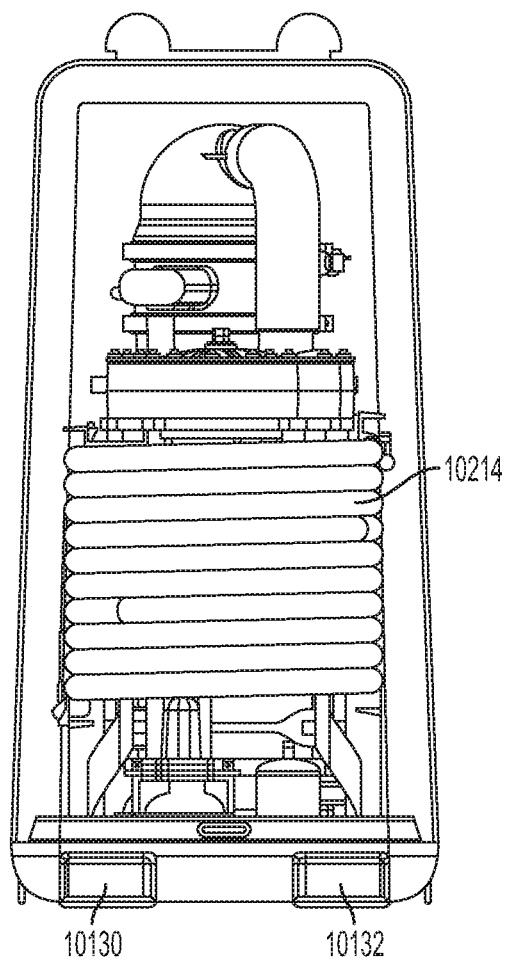
Figure 105:
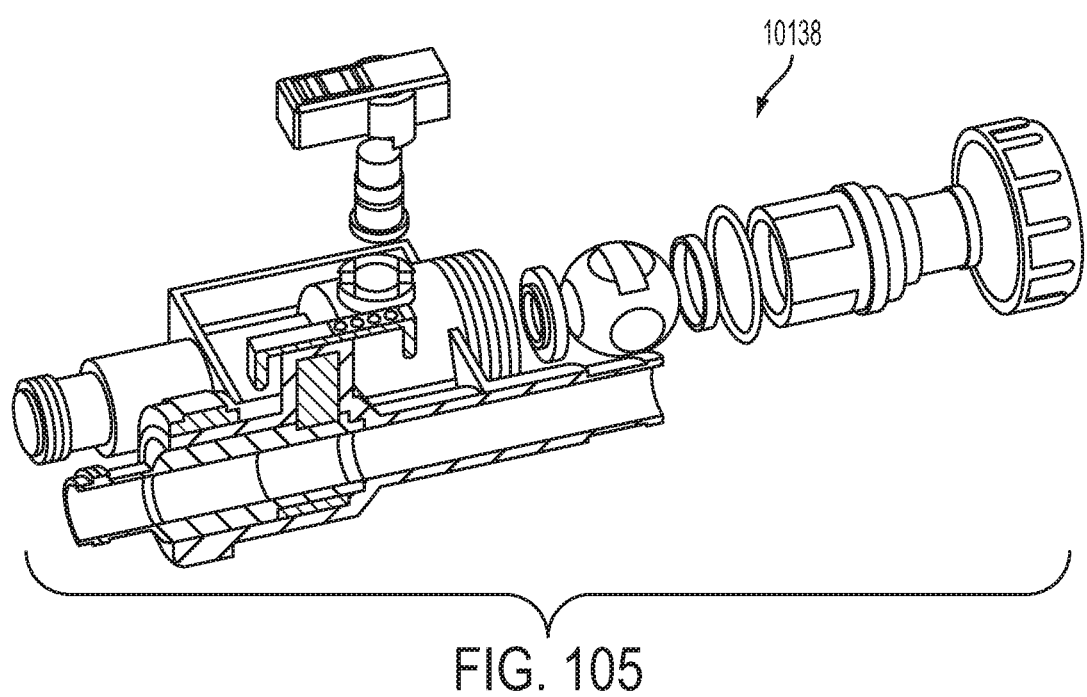
Figure 106:
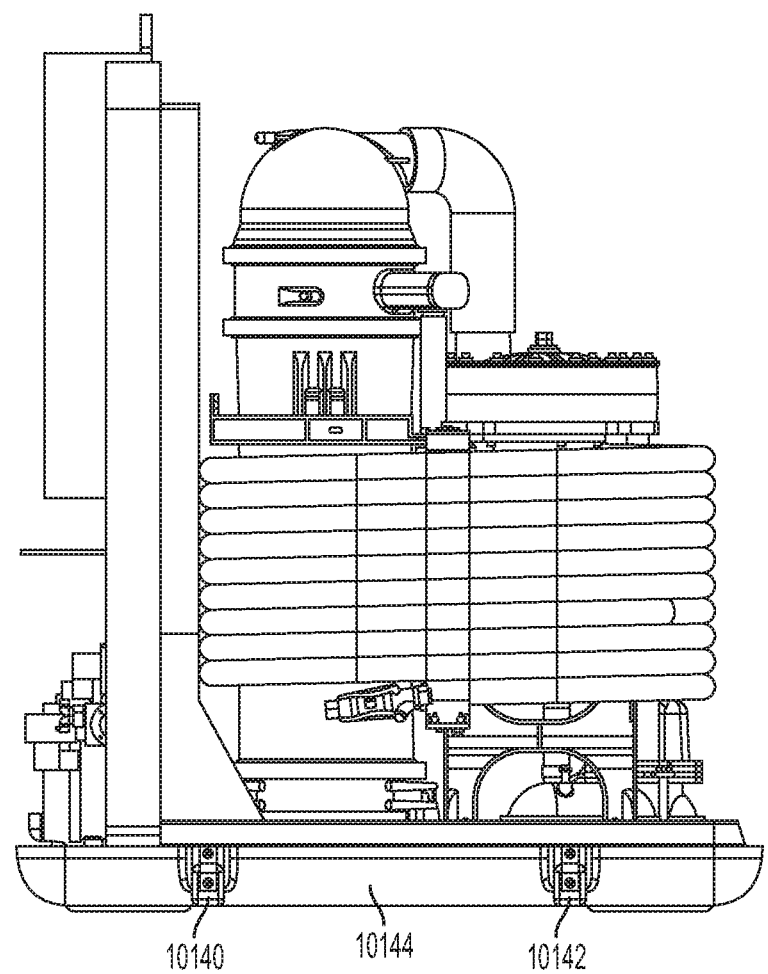
Figure 107:
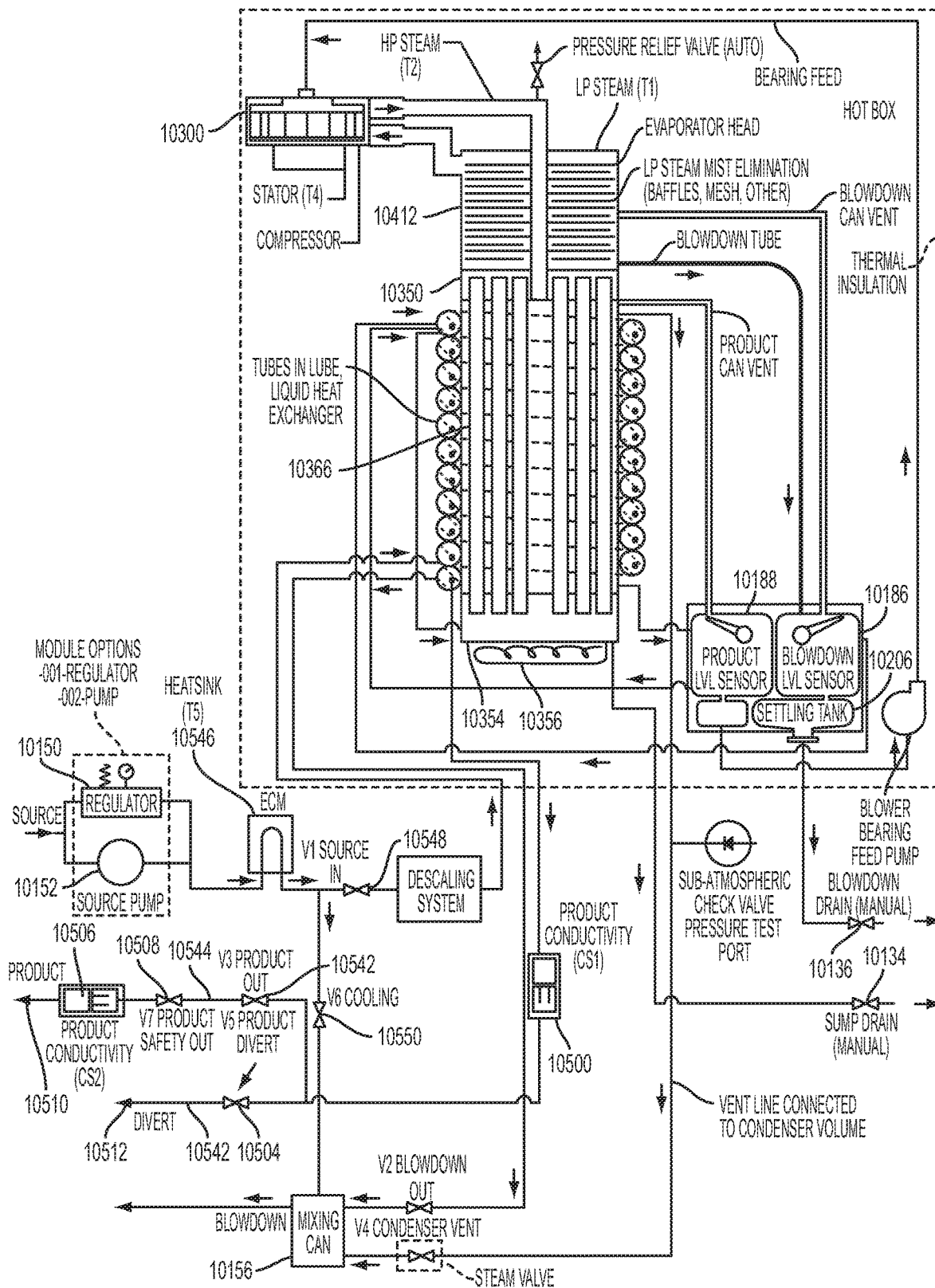
Figure 108:
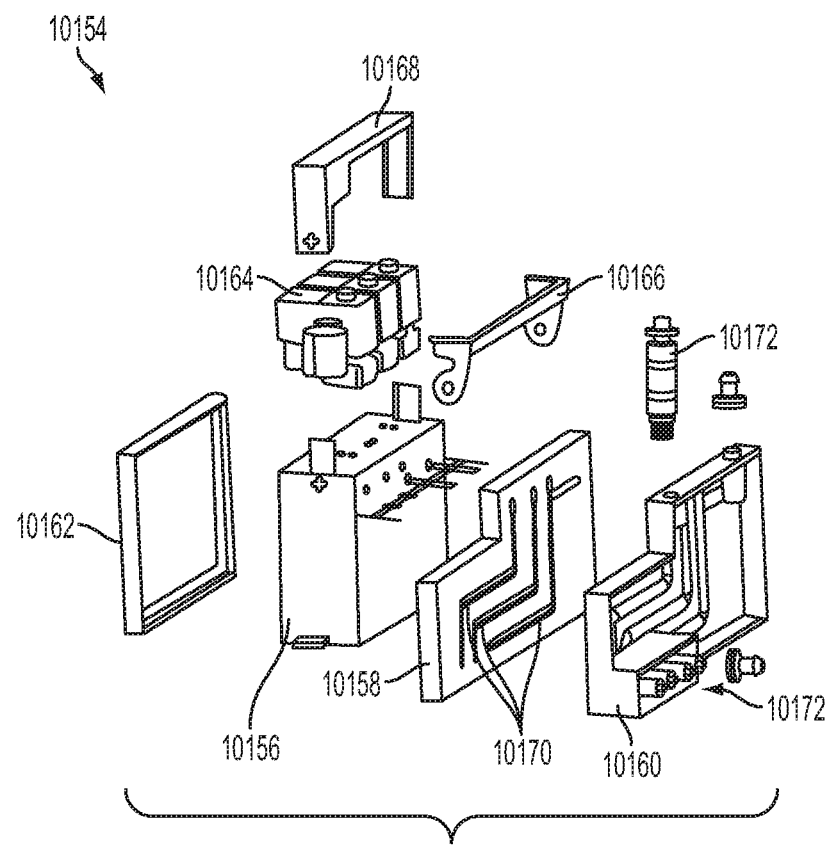
Figure 109:
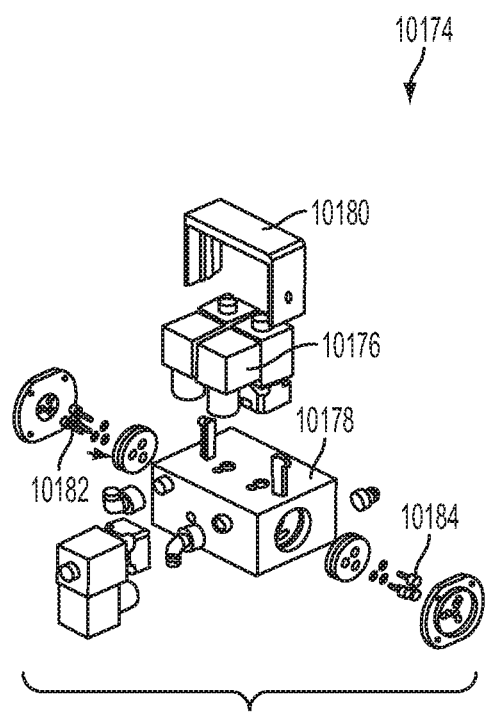
Figure 110:
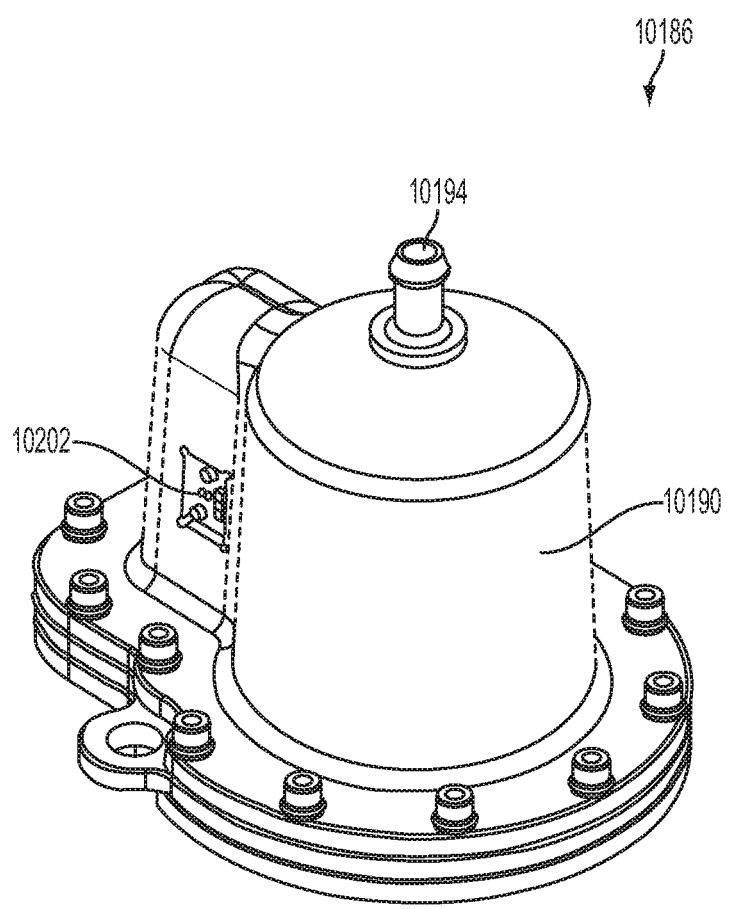
Figure 111:
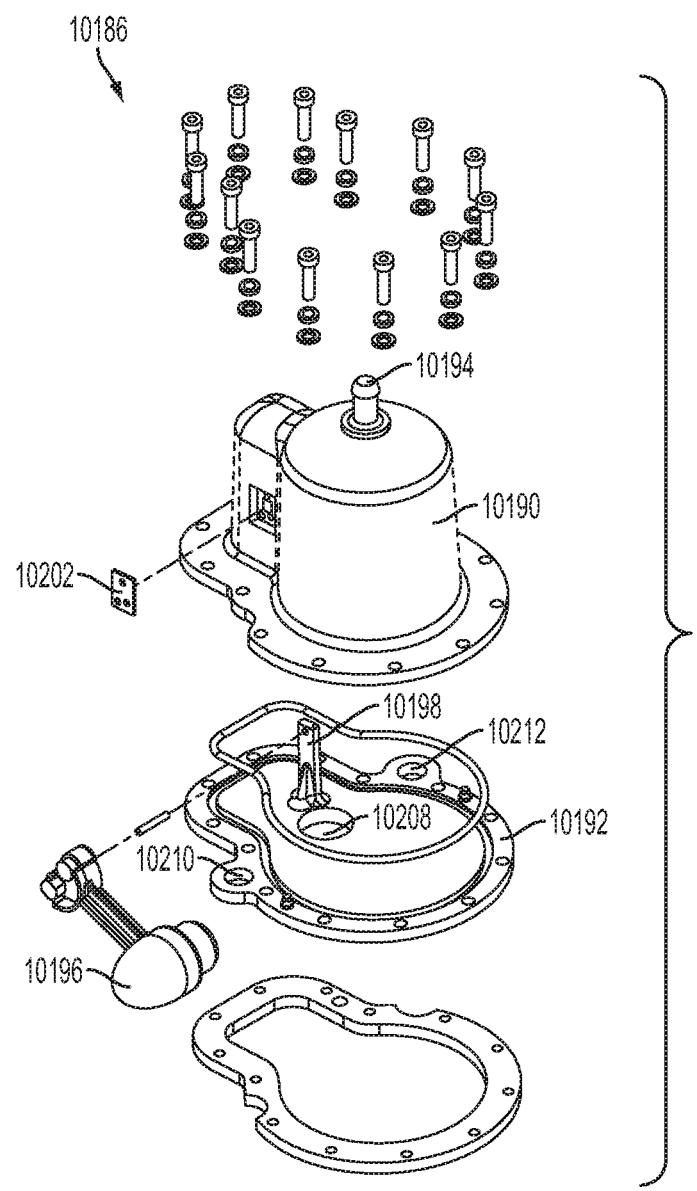
Figure 112:
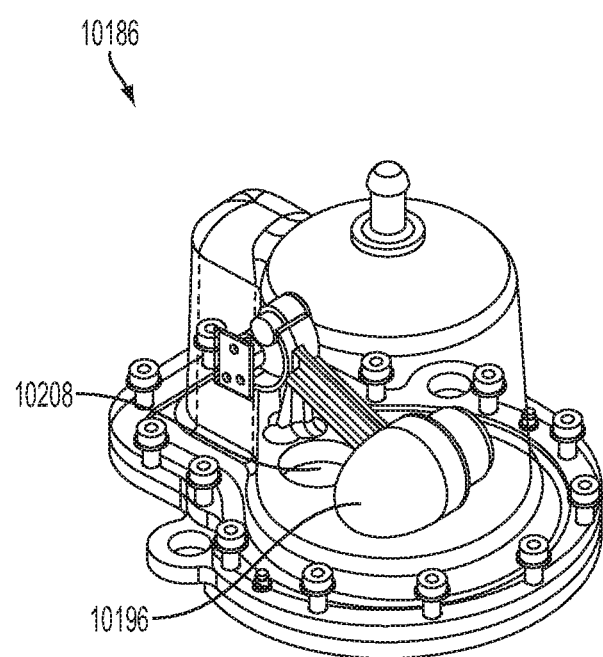
Figure 113:
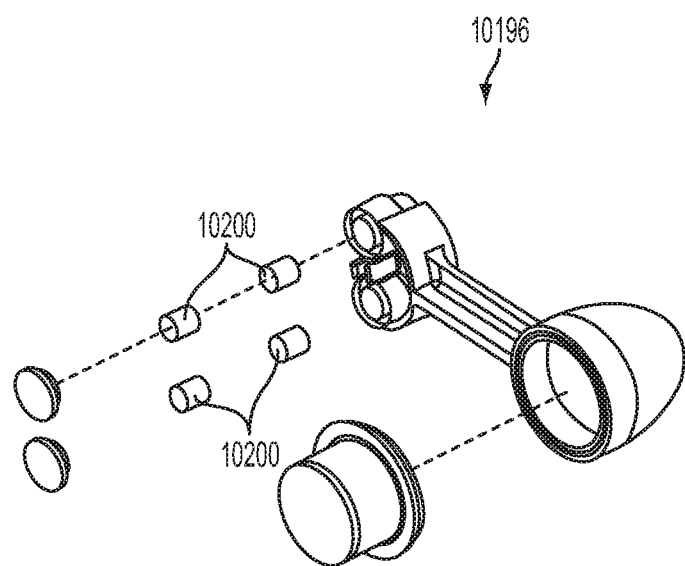
Figure 114:
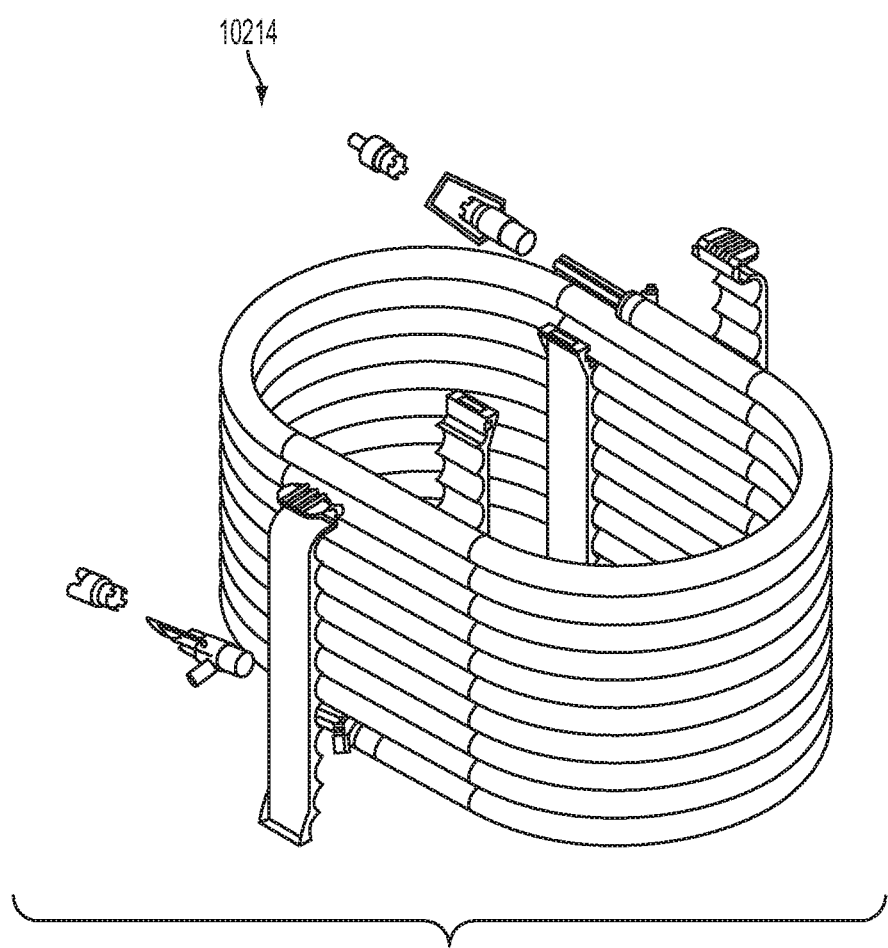
Figure 115A:
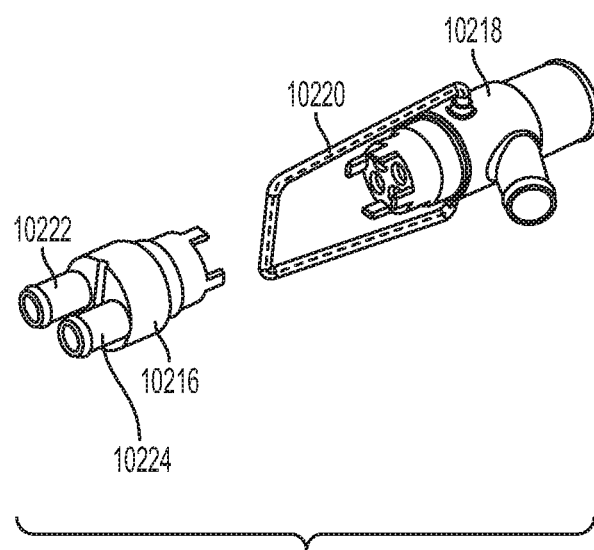
Figure 115B:
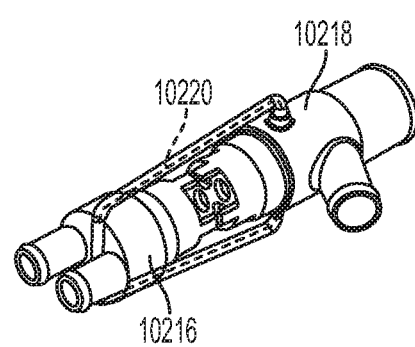
Figure 116:
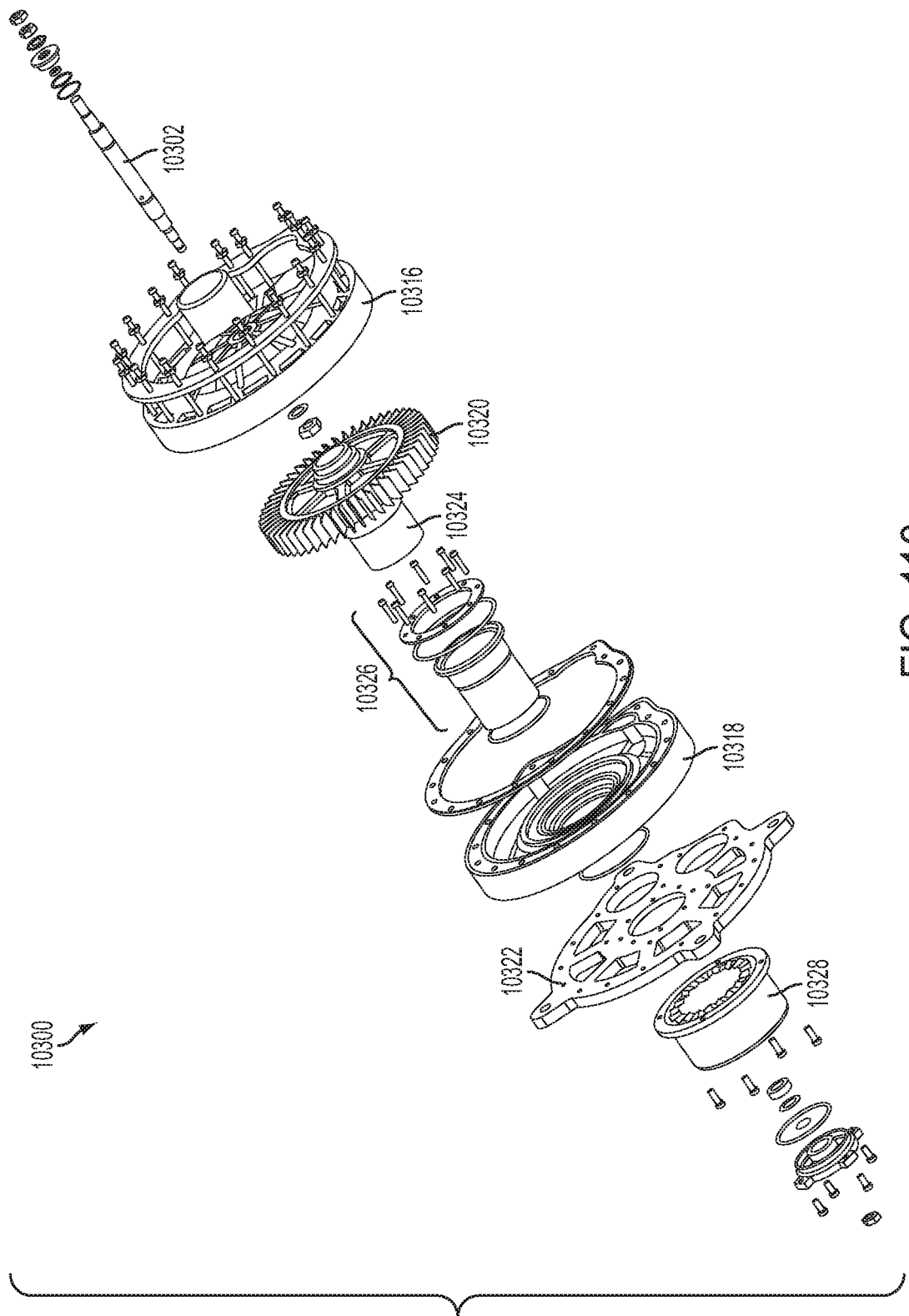
Figure 117:
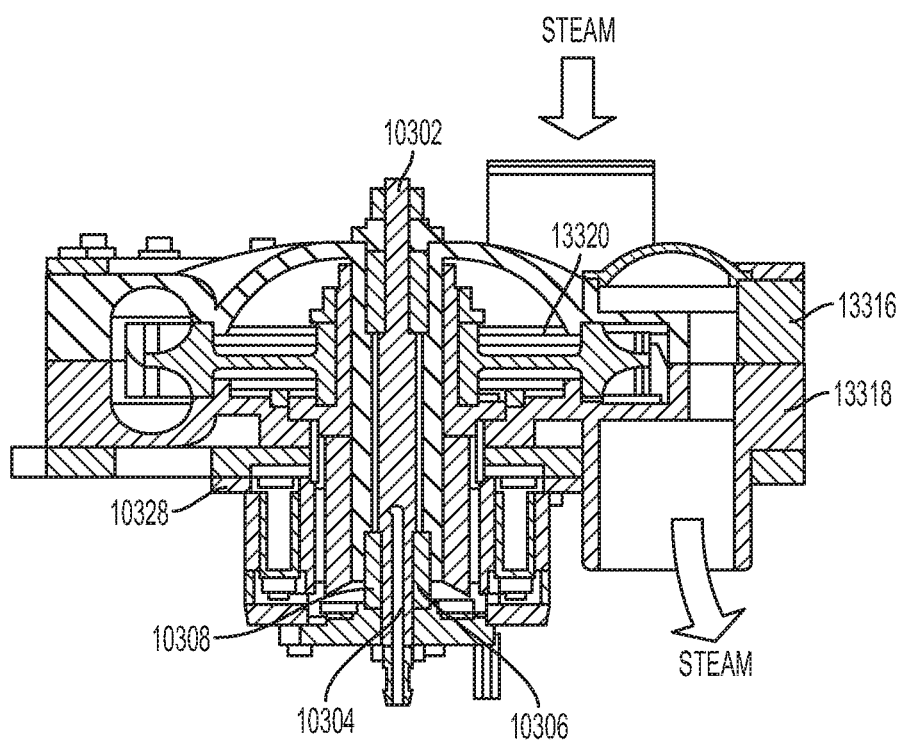
Figure 118A:
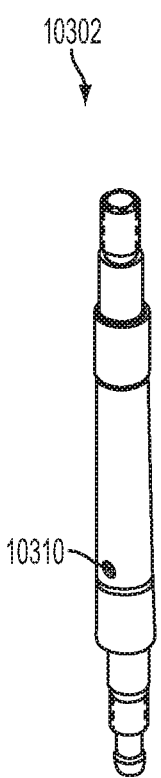
Figure 118B:
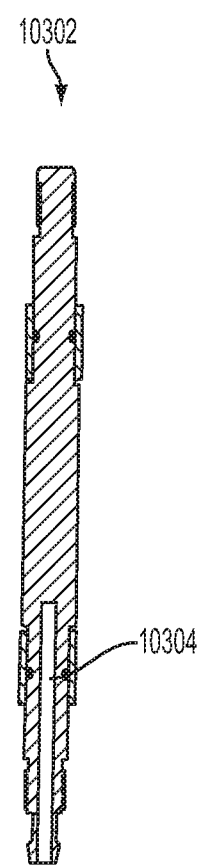
Figure 119:
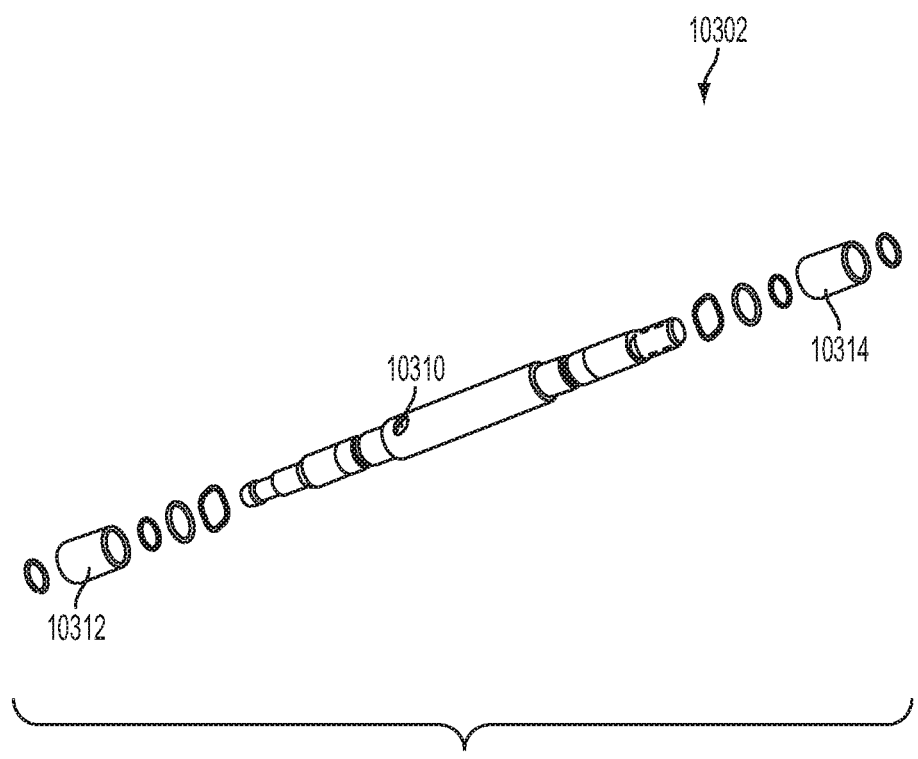
Figure 120:
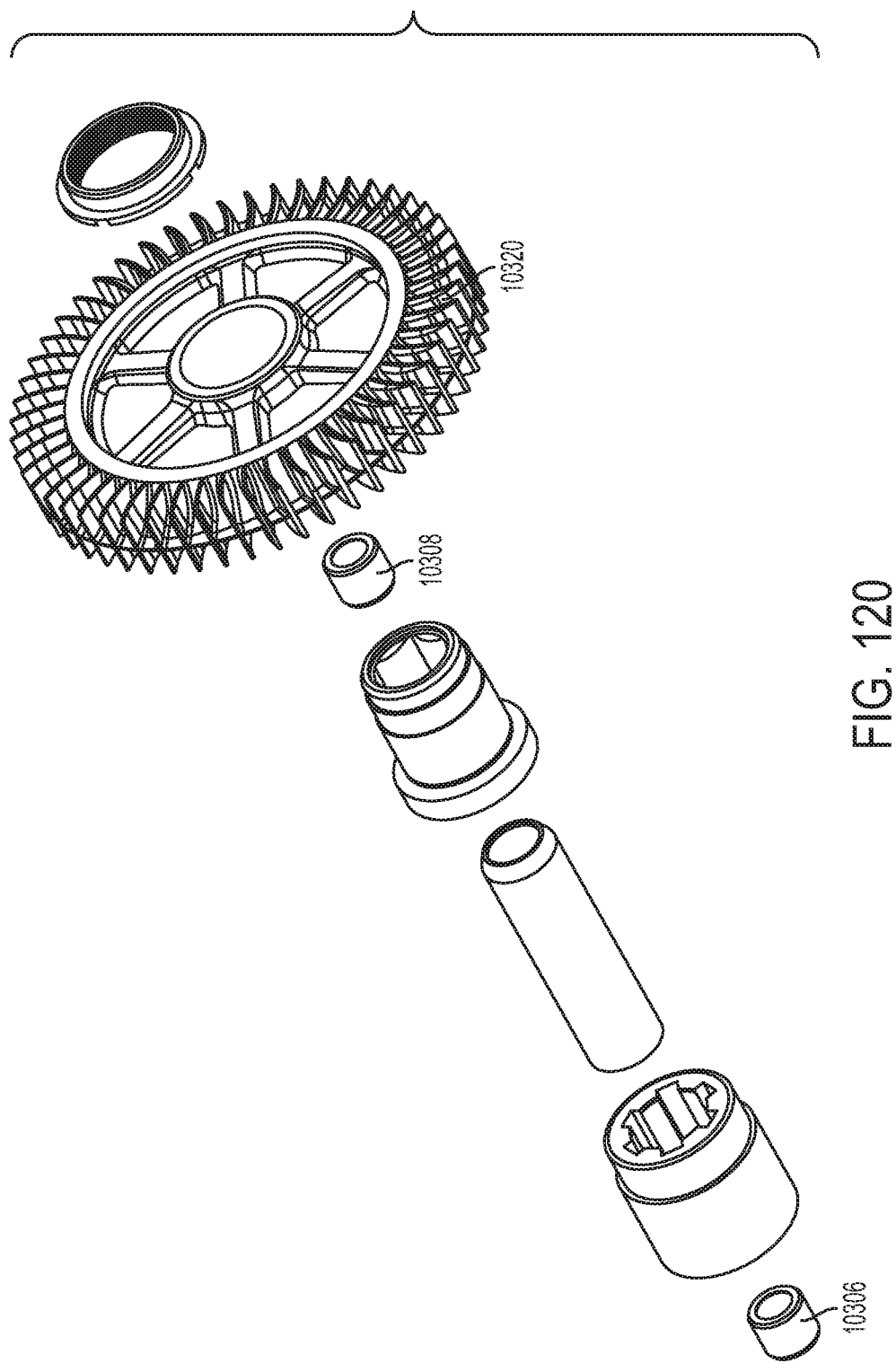
Figure 121:
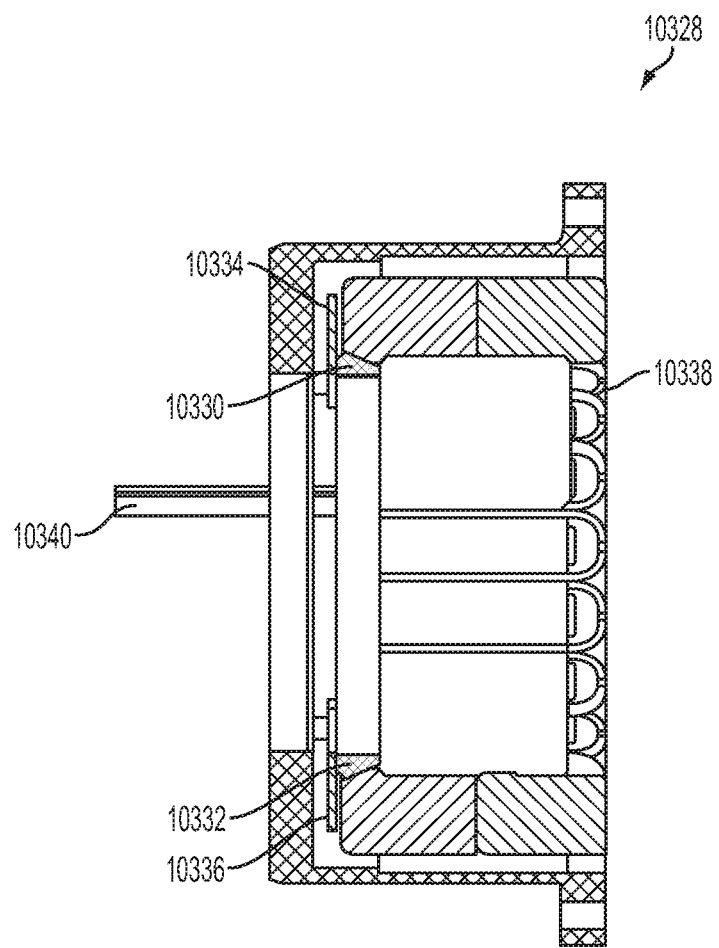
Figure 122:
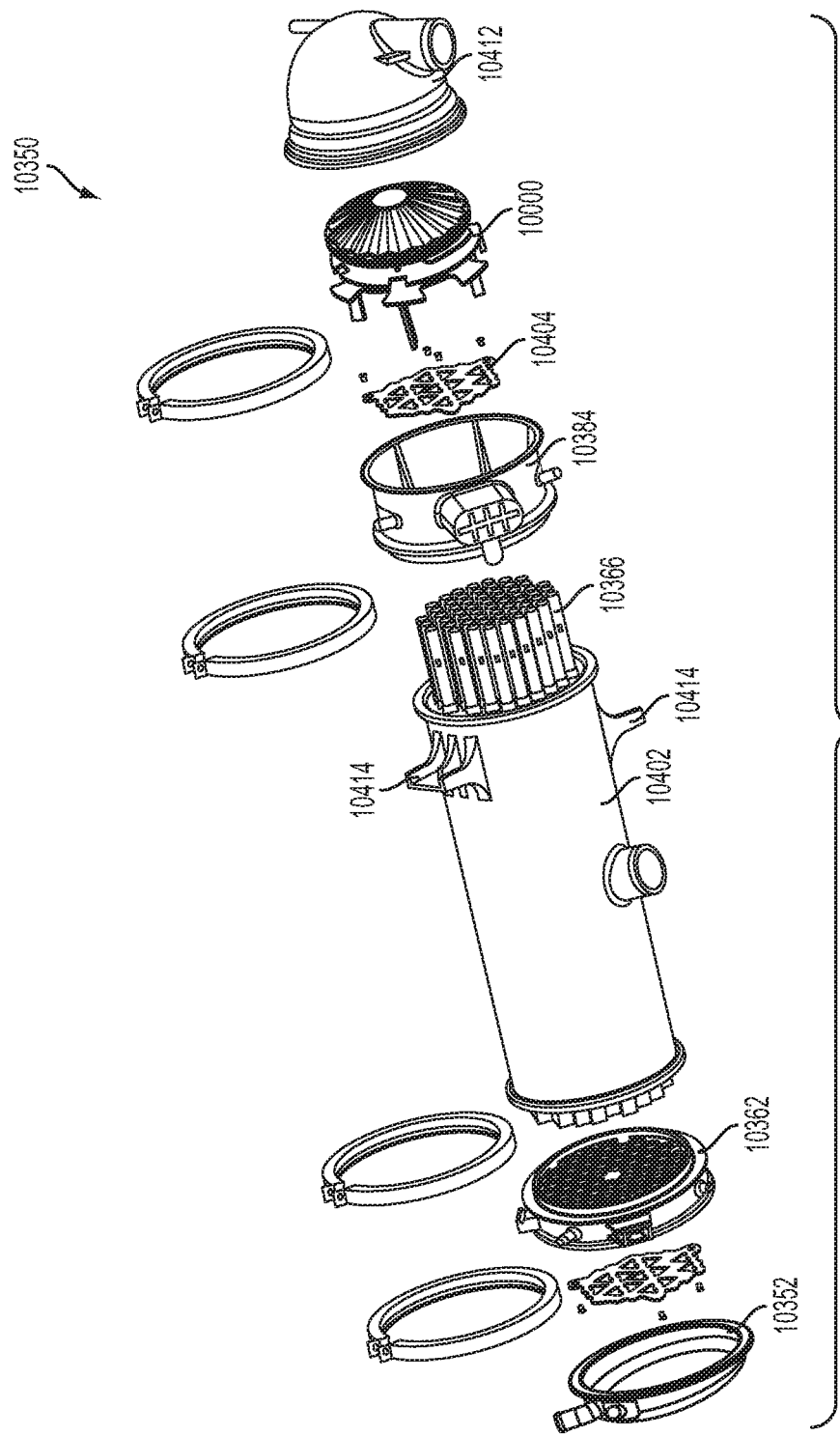
Figure 123:
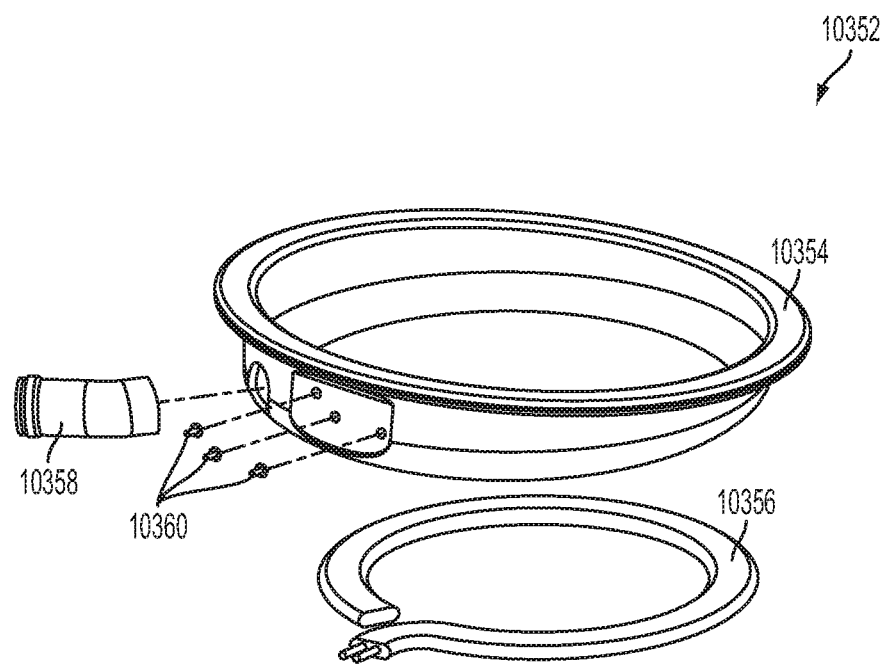
Figure 124:
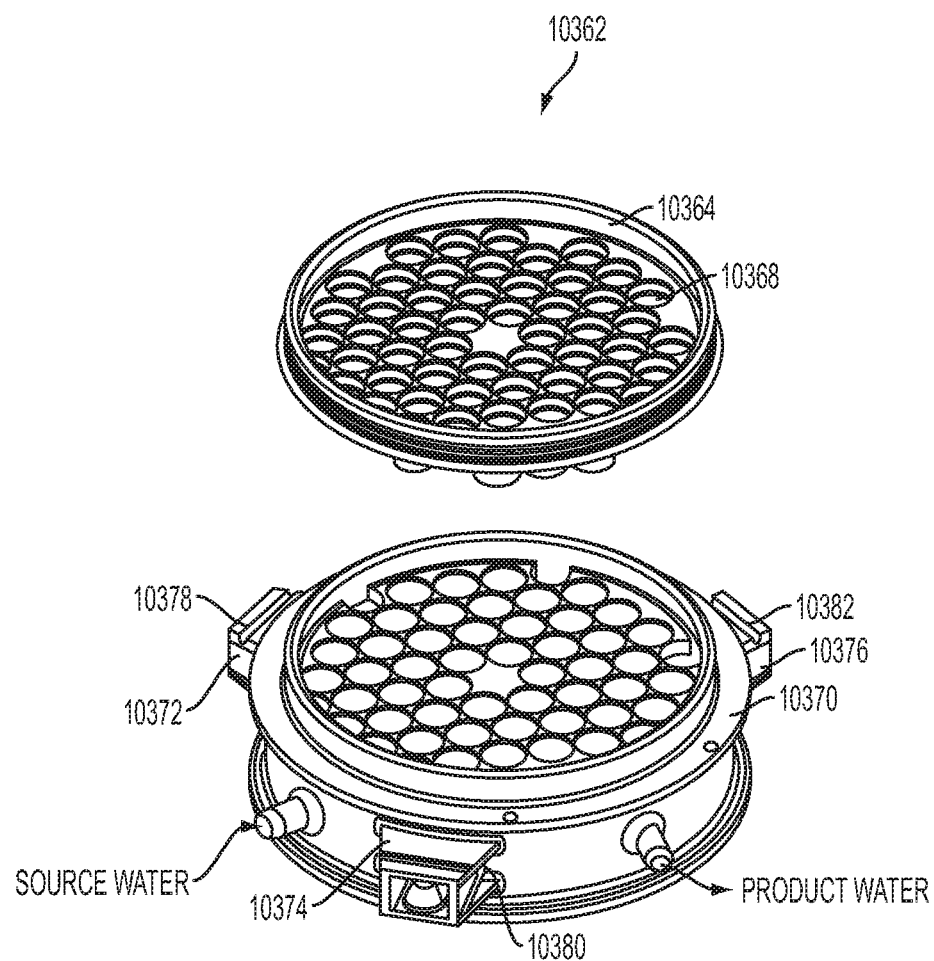
Figure 125A:
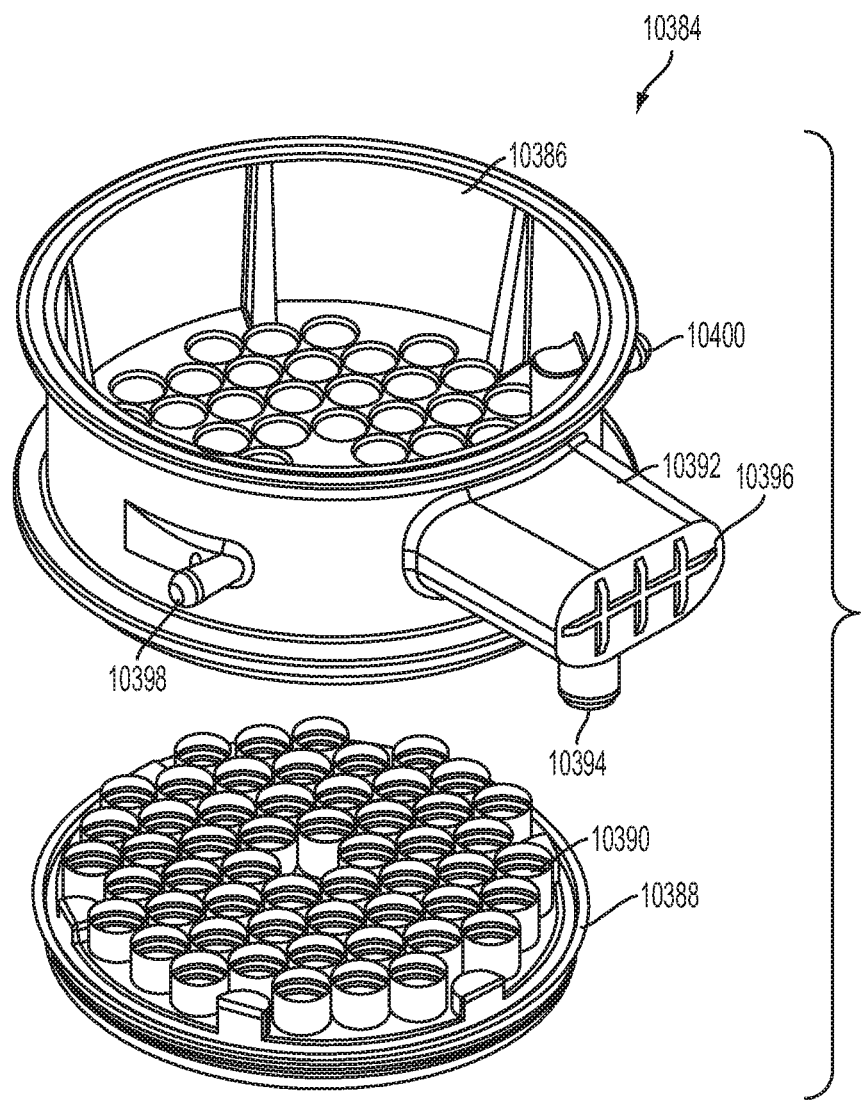
Figure 125B:
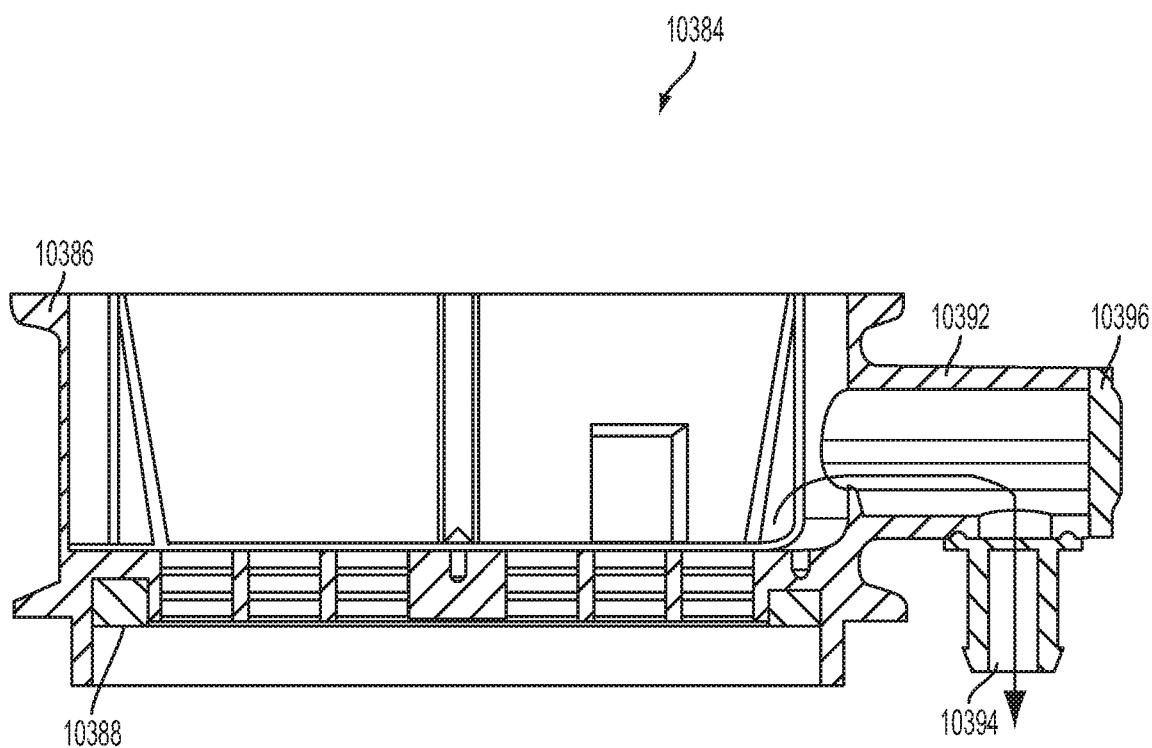
Figure 126:
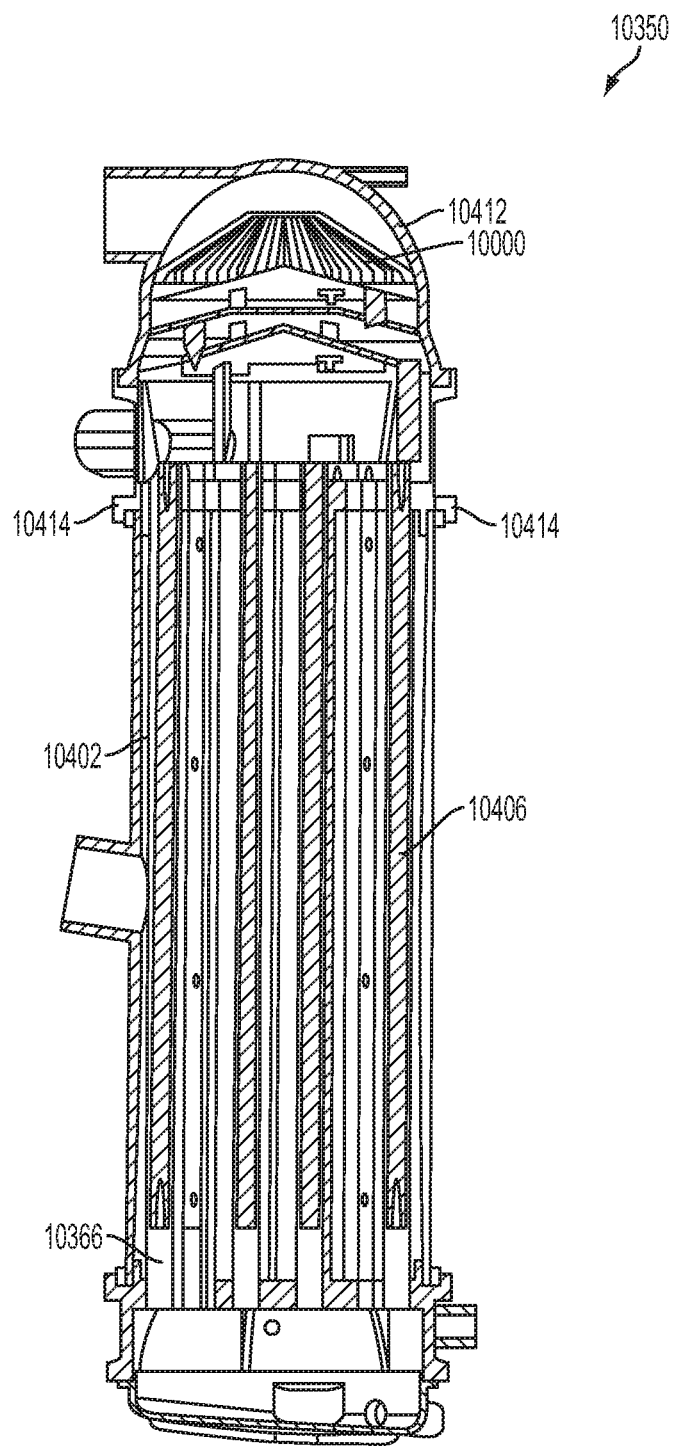
Figure 127A:
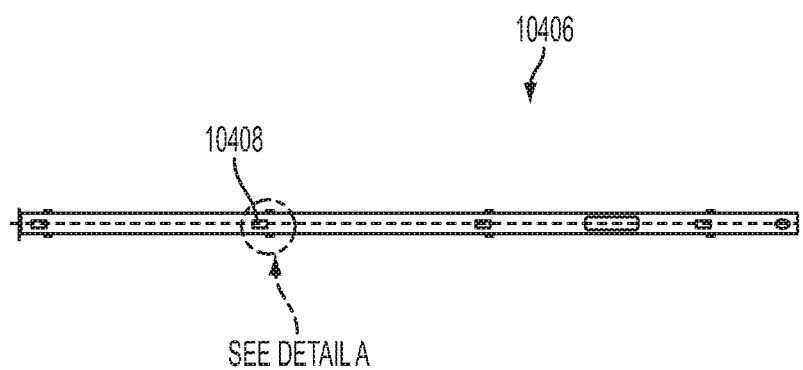
Figure 127B:
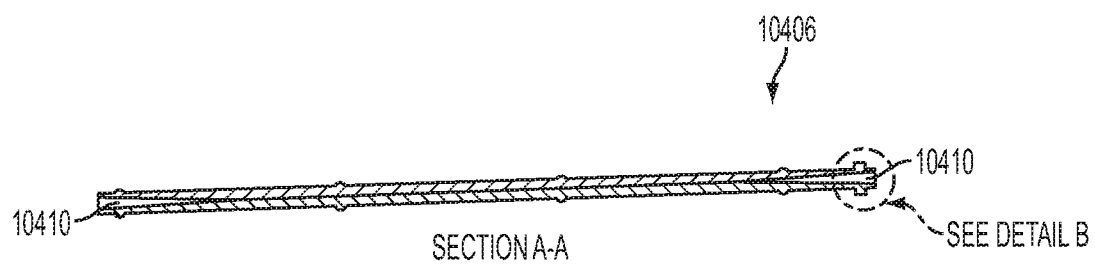
Figure 128A:
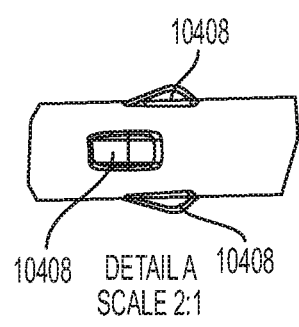
Figure 128B:
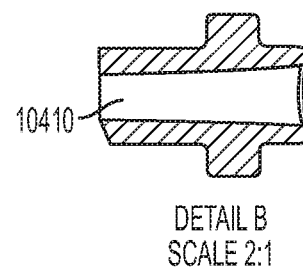
Figure 129:
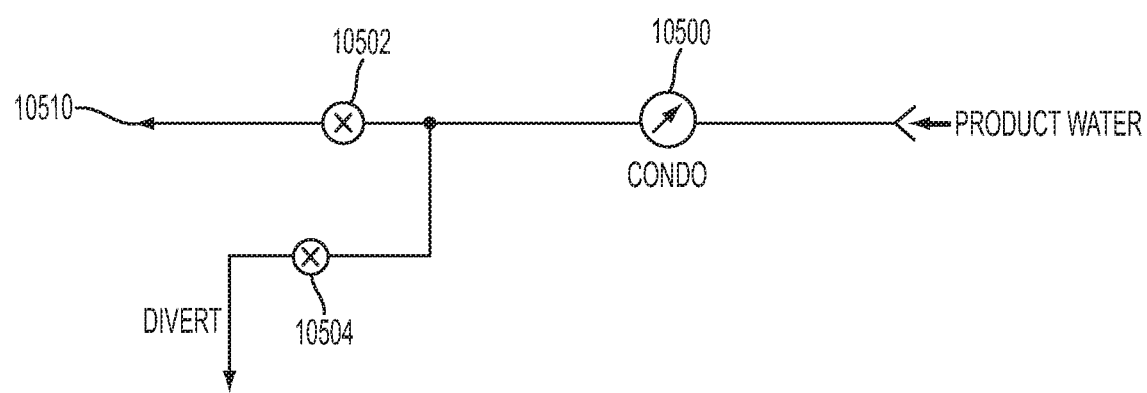
Figure 130:
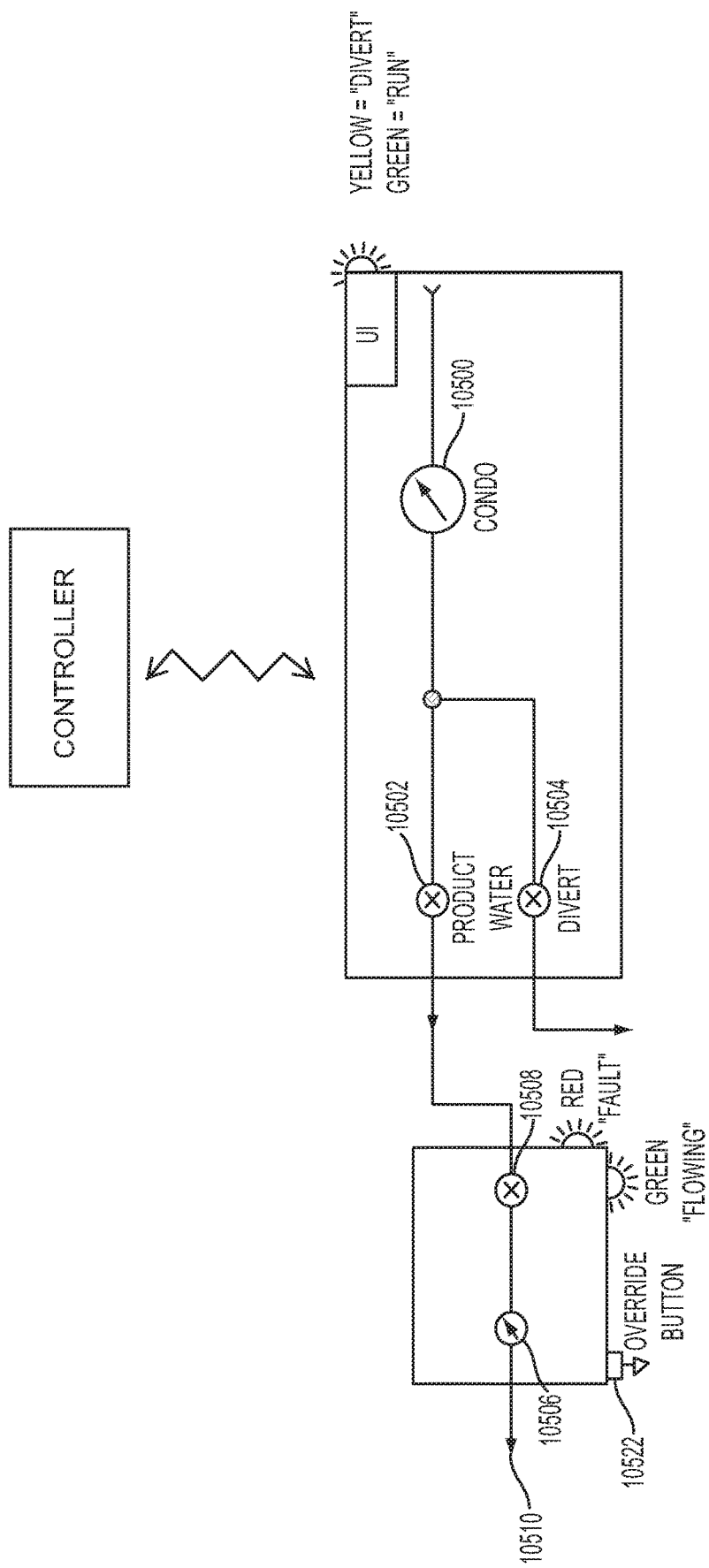
Figure 131:
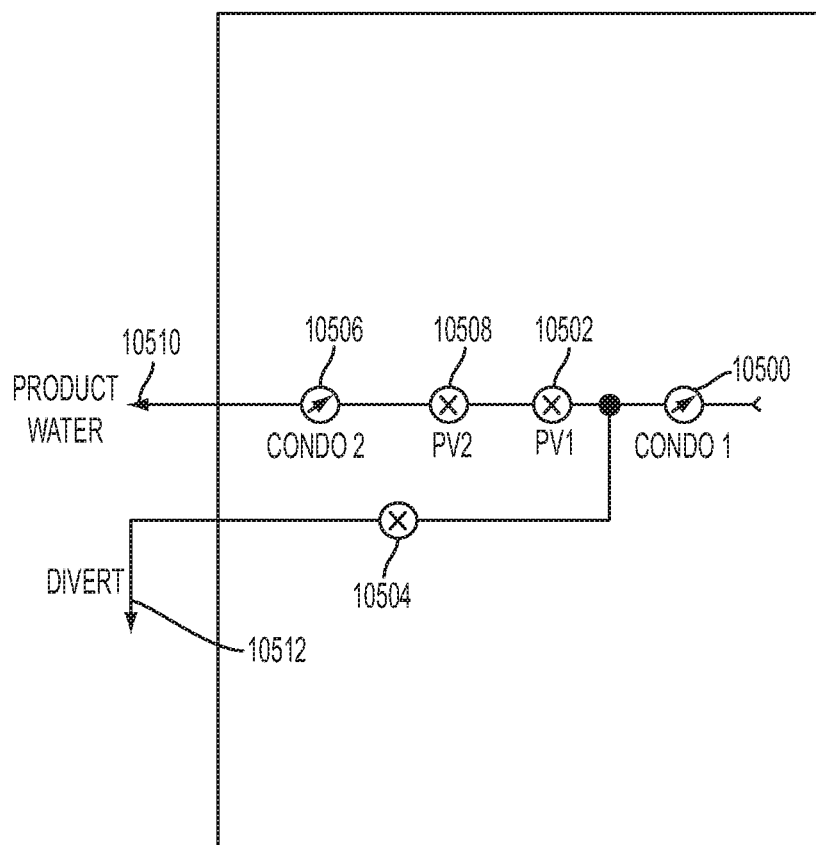
Figure 132:
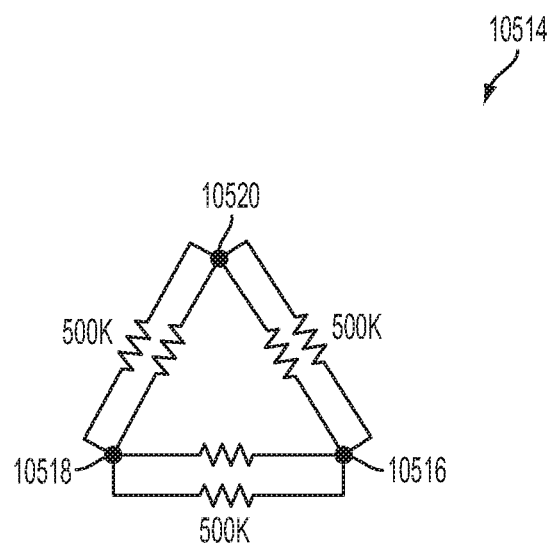
Figure 133:
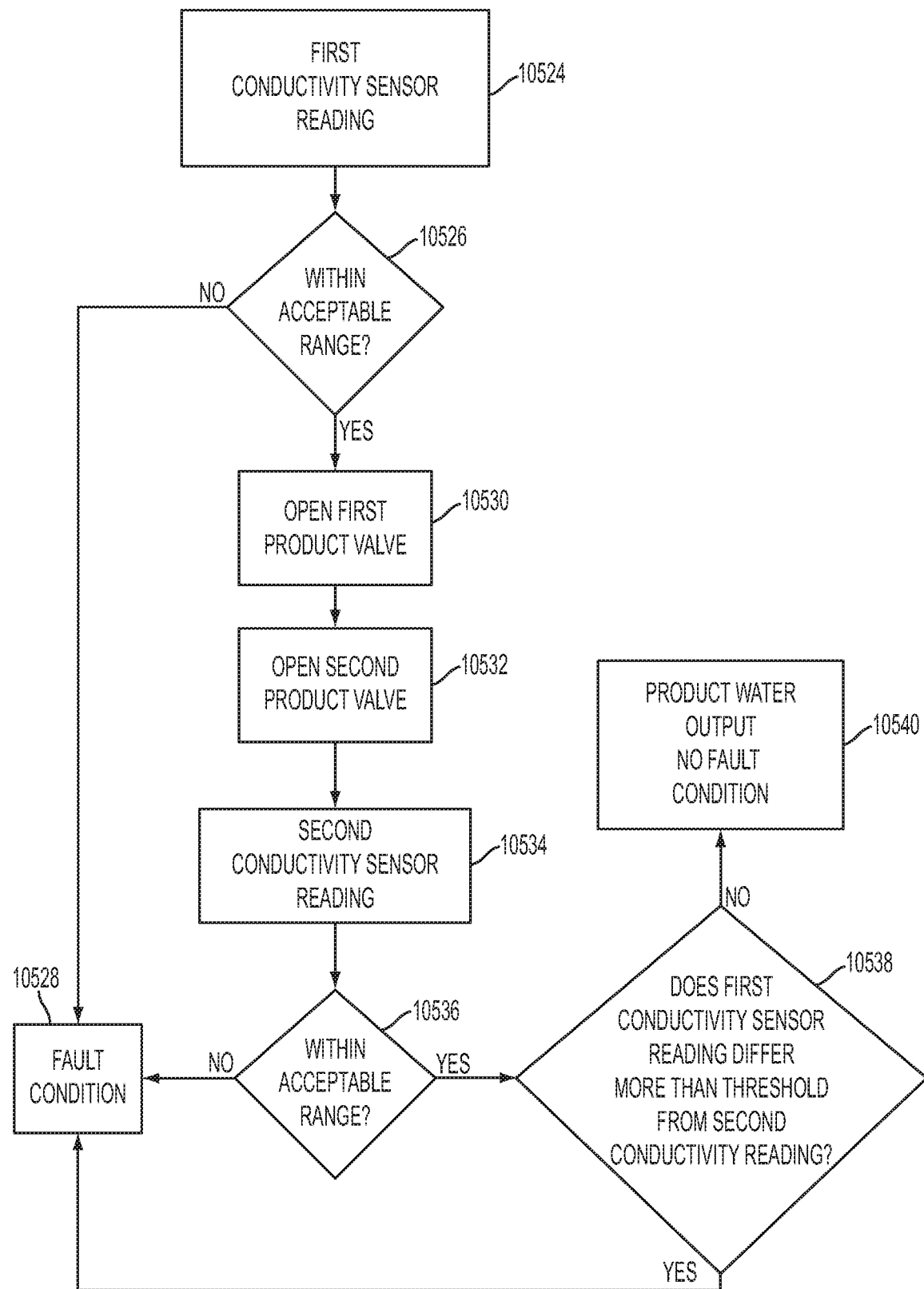
Figure 134:
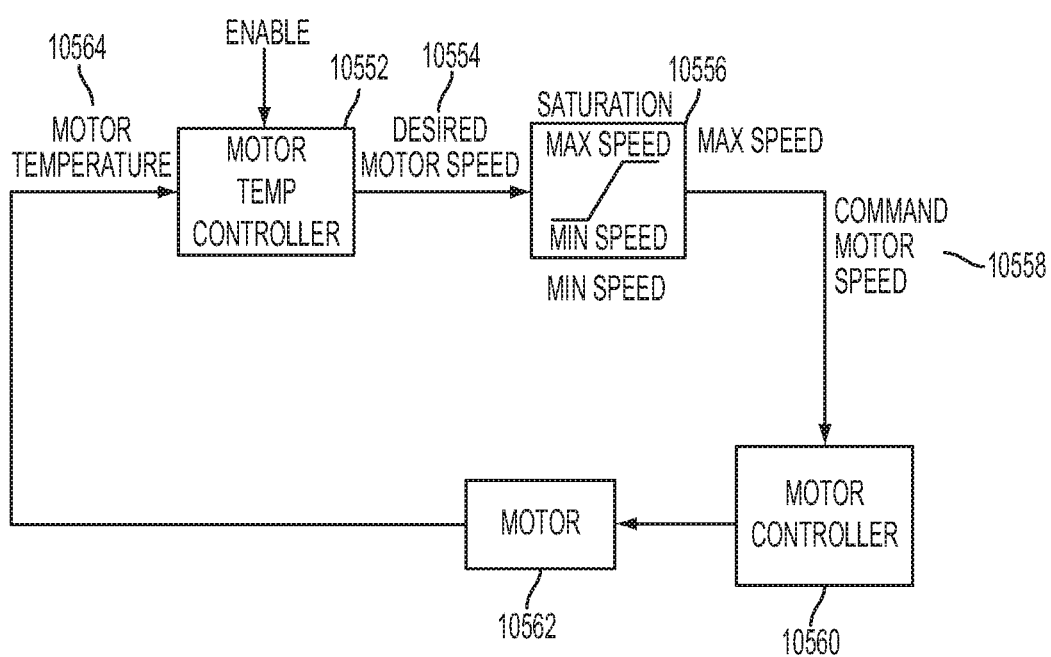
Figure 135:
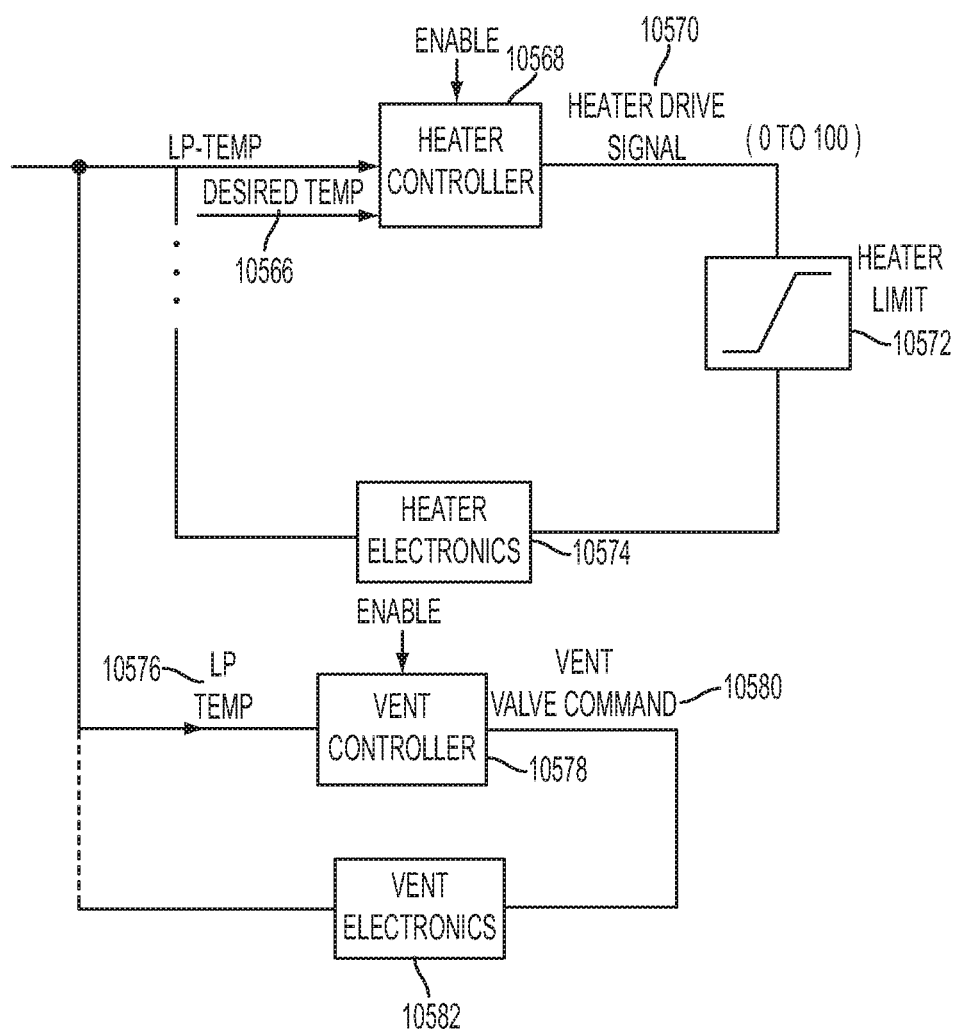
Figure 136:
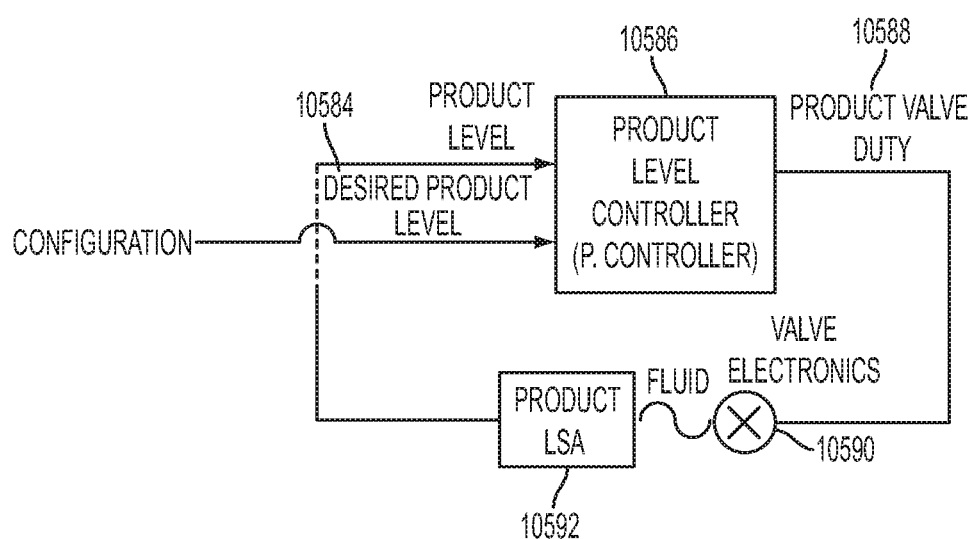
Figure 137:
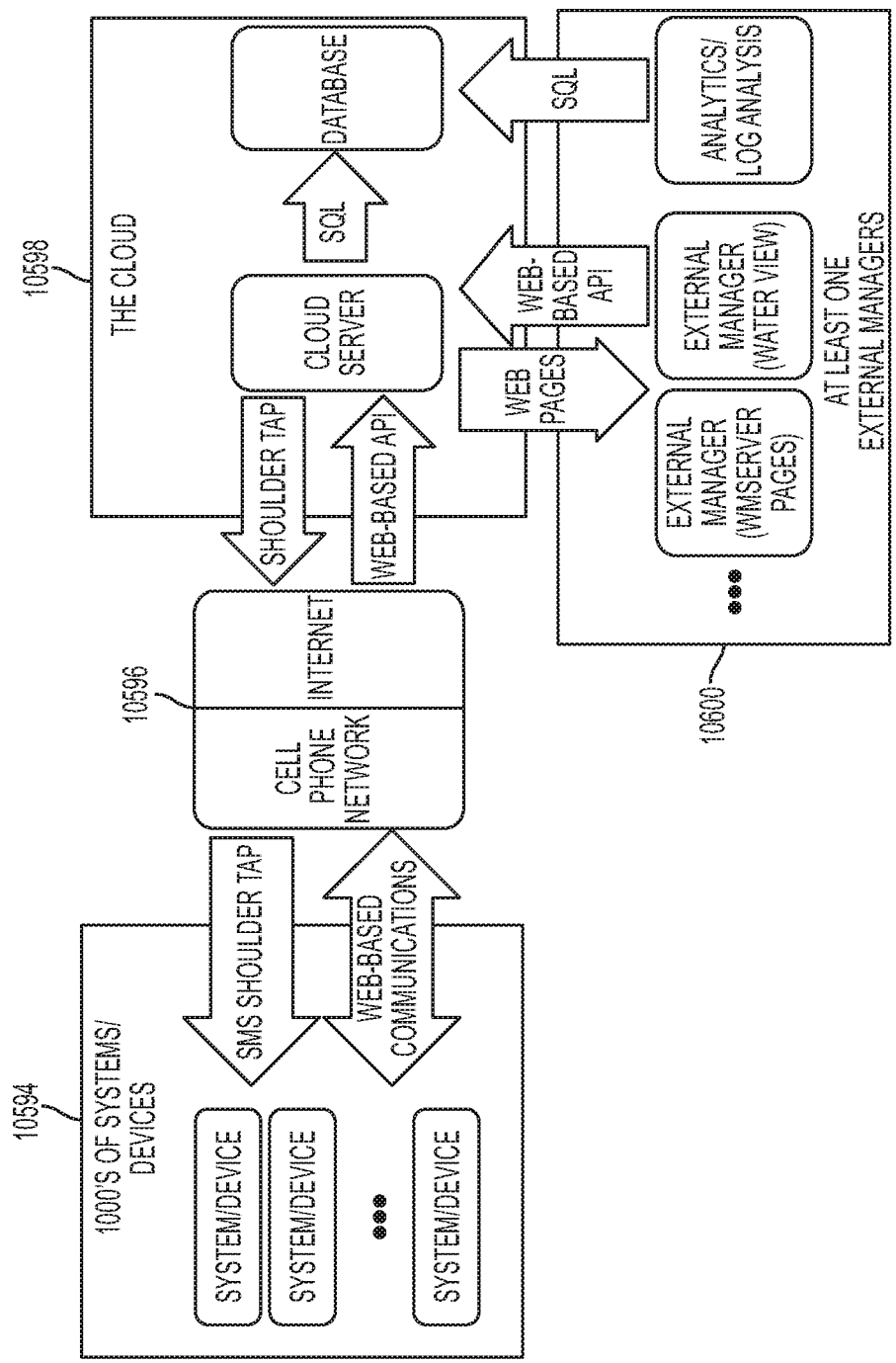
Figure 138:
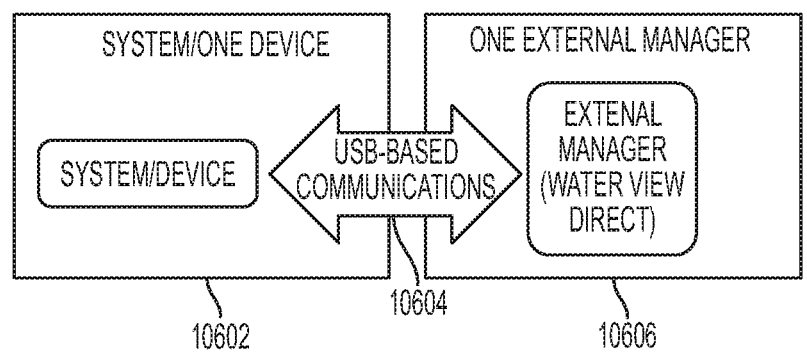
Figure 139:
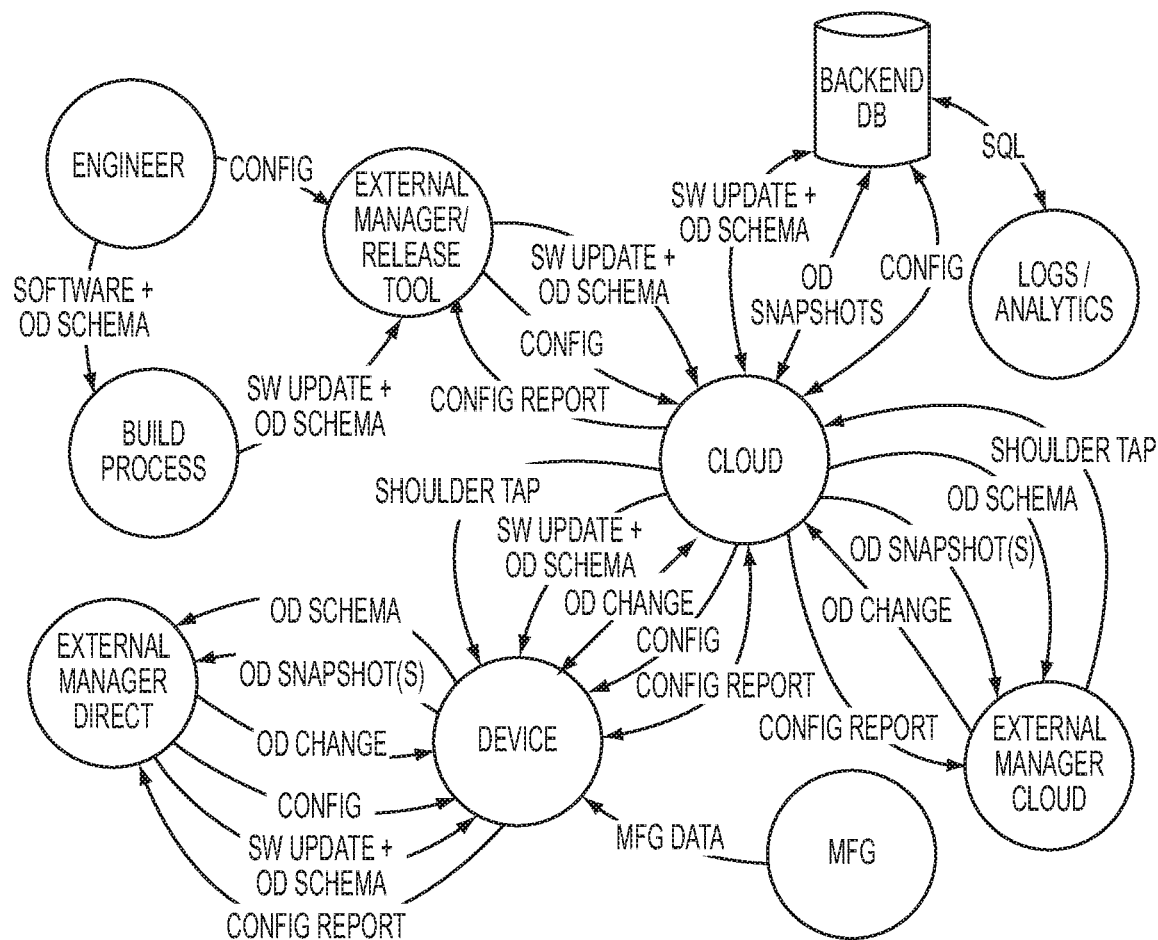

FIG. 23G is a schematic of the blowdown water exiting the heat exchanger;

FIG. 24 is a schematic of the flow paths of the product water for the exemplary embodiment the water vapor distillation apparatus;

FIG. 24A is a schematic of the product water exiting the evaporator/condenser assembly and entering the level sensor housing;

FIG. 24B is a schematic of the product water entering the product level sensor reservoir within the level sensor housing;

FIG. 24C is a schematic of the product water exiting the product level sensor reservoir and entering the heat exchanger;

FIG. 24D is a schematic of the product water passing through the heat exchanger;

FIG. 24E is a schematic of the product water exiting the heat exchanger;

FIG. 24F is a schematic of the product water entering the bearing-feed water reservoir within the level sensor housing;

FIG. 24G is a schematic of the product water exiting the level sensor housing and entering the bearing feed-water pump;

FIG. 24H is a schematic of the product water exiting the bearing feed-water pump and entering the regenerative blower;

FIG. 24I is a schematic of the product water exiting the regenerative blower and entering the level sensor housing;

FIG. 25 is a schematic of the vent paths for the exemplary embodiment the water vapor distillation apparatus;

FIG. 25A is a schematic of the vent path allowing air to exit the blowdown sensor reservoir and enter the evaporative/condenser;

FIG. 25B is a schematic of the vent path allowing air to exit the product sensor reservoir and enter the evaporative/condenser;

FIG. 25C is a schematic of the vent path allowing air to exit the evaporator/condenser assembly;

FIG. 26 is a schematic of the low-pressure steam entering the tubes of the evaporator/condenser assembly from the sump;

FIG. 26A is a schematic of the low-pressure steam passing through the tubes of the evaporator/condenser assembly;

FIG. 26B is a schematic of the wet-low-pressure steam exiting the tubes of the evaporator/condenser assembly and entering the steam chest;

FIG. 26C is a schematic of the wet-low-pressure steam flowing through the steam chest of the evaporator/condenser assembly;

FIG. 26D is a schematic of the creation of blowdown water as the low-pressure steam passing through the steam chest;

FIG. 26E is a schematic of the dry-low-pressure steam exiting the steam chest and entering the regenerative blower;

FIG. 26F is a schematic of the dry-low-pressure steam passing through the regenerative blower;

FIG. 26G is a schematic of the high-pressure steam exiting the regenerative blower;

FIG. 26H is a schematic of the high-pressure steam entering the steam tube;

FIG. 26I is a schematic of the high-pressure steam exiting the steam tube and entering the evaporator/condenser chamber;

FIG. 26J is a schematic of the creation of product water from the high-pressure steam condensing within the evaporator/condenser chamber;

FIG. 27 is a chart illustrating the relationship between the differential pressure across the regenerative blower and the amount of energy required to produce one liter of product;

FIG. 28 is a chart illustrating the relationship between the production rate of product and the number of heat transfer tubes within the evaporator/condenser assembly;

FIG. 29 is a chart illustrating the production rate of product water of the evaporator/condenser assembly as a function of the amount of heat transfer surface area with the evaporator/condenser chamber;

FIG. 30 is a chart illustrating the efficiency of heat transfer surfaces for a varying amount of heat transfer tubes within the evaporator/condenser chamber as related to the change in pressure across the regenerative blower;

FIG. 31 is a chart illustrating the production rate and the amount of energy consumed by the evaporator/condenser assembly at different pressure differentials across the regenerative blower;

FIG. 32 is a cross-sectional and top view of a rotor and stator in accordance with a particular embodiment showing the support structure for the input, the vanes and chambers between the vanes, and the rotating drive shaft;

FIG. 32A is a side top view of a rotor and stator corresponding to the embodiment shown in FIG. 32, showing the support structures for the input and output, the vanes, the eccentric configuration within the housing unit, and the drive shaft;

FIG. 32B is a top view of a rotor and stator corresponding to the embodiment shown in FIGS. 32 and 32A, showing support structures for input and output, the vanes, the eccentric configuration within the housing unit, and the drive shaft;

FIG. 32C is a cross-sectional view of a rotor and stator corresponding to the embodiment shown in FIGS. 32, 32A, and 32B showing vanes, drive shaft, and bearings;

FIG. 32D is a cross-sectional view of a liquid ring pump according to one embodiment showing a capacitive sensor;

FIG. 32E is a cross-sectional view of a liquid ring pump according to one embodiment showing the eccentric rotor, rotor vanes, drive shaft with bearings, the rotating housing unit for the liquid ring pump, the still housing, and the cyclone effect and resulting mist and water droplet elimination from the steam;

FIG. 32F is a schematic diagram of An alternate embodiment for the liquid ring pump;

FIG. 32G is a top view of an alternate embodiment for a rotor showing multiple vanes and chambers between the vanes, and intake and exit holes in each individual chamber;

FIG. 32H is further detail of a liquid ring pump showing the stationary intake port and the rotating drive shaft, rotor and housing unit;

FIG. 32I is a view of a seal which may be present between the stationary and rotor sections of a liquid ring pump separating the intake orifice from the exit orifice;

FIG. 33 is side view of a backpressure regulator in accordance with one embodiment;

FIG. 33A is a diagonal view of the backpressure regulator shown in FIG. 33;

FIG. 33B is a side view of an alternate embodiment of the backpressure regulator having a vertically positioned port;

FIG. 33C is a diagonal view of the backpressure regulator shown in FIG. 33B;

FIG. 33D is a diagonal view of an alternate embodiment of the backpressure regulator;

FIG. 33E is a close-up view of section C of FIG. 33D, depicting a notch in the port of the backpressure regulator;

FIG. 33F is a cutaway side view of one embodiment of the backpressure regulator;

FIG. 33G is a close up view of section E of FIG. 33F, depicting a small opening in an orifice of the backpressure regulator;

FIG. 34 is a schematic of a backpressure regulator implemented within a apparatus;

FIG. 35 is a schematic of an alternate embodiment for a water vapor distillation apparatus;

FIG. 35A is a detailed schematic of an alternate embodiment for the level sensor housing illustrating an external connecting valve between source and blowdown fluid lines;

FIG. 36 is a view of one face of the pump side of a fluid distribution manifold;

FIG. 36A is a view of a second face of the pump side of a fluid distribution manifold;

FIG. 36B is a view of one face of the evaporator/condenser side of a fluid distribution manifold;

FIG. 36C is a view of a second face of the evaporator/condenser side of a fluid distribution manifold;

FIG. 37 is a top view of a coupler of an alternate embodiment of a fitting assembly;

FIG. 37A is a side view of an alternate embodiment of a fitting assembly in FIG. 37;

FIG. 38 is a cross-sectional view of alternate embodiment of the evaporator/condenser having individual heating layers and ribs;

FIG. 38A is a detail of a cross-section of an alternate embodiment of the evaporator/condenser showing how the ribs effectively partition the steam/evaporation from the liquid/condensation layers;

FIG. 39 is a schematic diagram of an alternate embodiment for the heat exchanger;

FIG. 39A is schematic diagram of an alternative embodiment for the heat exchanger;

FIG. 40 is a schematic overview of the an alternate embodiment of the water vapor distillation apparatus including a pressure measurement of the system using a cold sensor;

FIG. 41 is shows a view of a flip-filter with the intake stream and blowdown stream flowing through filter units, each filter unit rotating around a pivot joint about a center axis;

FIG. 41A shows flip filter housing;

FIG. 41B is detail view of the flip-filter in FIG. 41;

FIG. 41C is an alternative embodiment of a multi-unit flip filter;

FIG. 41D is a schematic of an alternate embodiment of a flip-filter;

FIG. 41E is a schematic of the flow path of one embodiment of the flip-filter;

FIG. 41F is a schematic illustrating a manual switch for changing water flow through individual units of a flip-filter in FIG. 41E;

FIG. 42 is a depiction of a monitoring system for distributed utilities;

FIG. 43 is a depiction of a distribution system for utilities;

FIG. 44 is a conceptual flow diagram of a possible embodiment of a system incorporating an alternate embodiment of the water vapor distillation apparatus;

FIG. 44A is a schematic block diagram of a power source for use with the system shown in FIG. 44;

FIGS. 45A-45E depict the principle of operation of a Stirling cycle machine;

FIG. 46 shows a view of a rocking beam drive in accordance with one embodiment;

FIG. 47 shows a view of a rocking beam drive in accordance with one embodiment;

FIG. 48 shows a view of an engine in accordance with one embodiment;

FIGS. 49A-49D depicts various views of a rocking beam drive in accordance with one embodiment;

FIG. 50 shows a bearing style rod connector in accordance with one embodiment;

FIGS. 51A-51B show a flexure in accordance with one embodiment;

FIG. 52 shows a four cylinder double rocking beam drive arrangement in accordance with one embodiment;

FIG. 53 shows a cross section of a crankshaft in accordance with one embodiment;

FIG. 54A shows a view of an engine in accordance with one embodiment;

FIG. 54B shows a crankshaft coupling in accordance with one embodiment;

FIG. 54C shows a view of a sleeve rotor in accordance with one embodiment;

FIG. 54D shows a view of a crankshaft in accordance with one embodiment;

FIG. 54E is a cross section of the sleeve rotor and spline shaft in accordance with one embodiment;

FIG. 54F is a cross section of the crankshaft and the spline shaft in accordance with one embodiment;

FIG. 54G are various views a sleeve rotor, crankshaft and spline shaft in accordance with one embodiment;

FIG. 55 shows the operation of pistons of an engine in accordance with one embodiment;

FIG. 56A shows an unwrapped schematic view of a working space and cylinders in accordance with one embodiment;

FIG. 56B shows a schematic view of a cylinder, heater head, and regenerator in accordance with one embodiment;

FIG. 56C shows a view of a cylinder head in accordance with one embodiment;

FIG. 57A shows a view of a rolling diaphragm, along with supporting top seal piston and bottom seal piston, in accordance with one embodiment;

FIG. 57B shows an exploded view of a rocking beam driven engine in accordance with one embodiment;

FIG. 57C shows a view of a cylinder, heater head, regenerator, and rolling diaphragm, in accordance with one embodiment;

FIGS. 57D-57E show various views of a rolling diaphragm during operation, in accordance with one embodiment;

FIG. 57F shows an unwrapped schematic view of a working space and cylinders in accordance with one embodiment;

FIG. 57G shows a view of an external combustion engine in accordance with one;

FIGS. 58A-58E show views of various embodiments of a rolling diaphragm;

FIG. 59A shows a view of a metal bellows and accompanying piston rod and pistons in accordance with one embodiment;

FIGS. 59B-59D show views of metal bellows diaphragms, in accordance with one embodiment;

FIGS. 59E-59G show a view of metal bellows in accordance with various embodiments;

FIG. 59H shows a schematic of a rolling diaphragm identifying various load regions;

FIG. 59I shows a schematic of the rolling diaphragm identifying the convolution region;

FIG. 60 shows a view of a piston and piston seal in accordance with one embodiment;

FIG. 61 shows a view of a piston rod and piston rod seal in accordance with one embodiment;

FIG. 62A shows a view of a piston seal backing ring in accordance with one embodiment;

FIG. 62B shows a pressure diagram for a backing ring in accordance with one embodiment;

FIGS. 62C and 62D show a piston seal in accordance with one embodiment;

FIGS. 62E and 62F show a piston rod seal in accordance with one embodiment;

FIG. 63A shows a view of a piston seal backing ring in accordance with one embodiment;

FIG. 63B shows a pressure diagram for a piston seal backing ring in accordance with one embodiment;

FIG. 64A shows a view of a piston rod seal backing ring in accordance with one embodiment;

FIG. 64B shows a pressure diagram for a piston rod seal backing ring in accordance with one embodiment;

FIG. 65 shows views of a piston guide ring in accordance with one embodiment;

FIG. 66 shows an unwrapped schematic illustration of a working space and cylinders in accordance with one embodiment;

FIG. 67A shows a view of an engine in accordance with one embodiment;

FIG. 67B shows a view of an engine in accordance with one embodiment;

FIG. 68 shows a view of a crankshaft in accordance with one embodiment;

FIGS. 69A-69C show various configurations of pump drives in accordance with various embodiments;

FIG. 70A shows a view of an oil pump in accordance with one embodiment;

FIG. 70B shows a view of an engine in accordance with one embodiment;

FIG. 70C shows another view of the engine depicted in FIG. 70B;

FIGS. 71A and 71B show views of an engine in accordance with one embodiment;

FIG. 71C shows a view of a coupling joint in accordance with one embodiment;

FIG. 71D shows a view of a crankshaft and spline shaft of an engine in accordance with one embodiment;

FIG. 72A shows an illustrative view of a generator connected to one embodiment of the apparatus;

FIG. 72B shows a schematic representation of an auxiliary power unit for providing electrical power and heat to a water vapor distillation apparatus;

FIG. 72C shows a schematic view of a system according to one embodiment;

FIG. 73 is a schematic of the flow paths for an embodiment of the water vapor distillation apparatus;

FIG. 74 is an isometric view of the of an embodiment of the tube-in-tube heat exchanger from the front with one embodiment of a connector;

FIGS. 74A-74C are isometric, cross sectional and end views, respectively, of one embodiment of the connector shown in FIG. 74;

FIG. 75 is a flow chart of the water task states;

FIG. 76 is a schematic of a communications system for the at least one water vapor distillation apparatus, according to one embodiment;

FIG. 77 is an isometric view of one embodiment of a case/shell for various embodiments of a water vapor distillation apparatus;

FIG. 78 is an isometric view of one embodiment of a case/shell for various embodiments of a water vapor distillation apparatus;

FIGS. 79A-79E are various views of one embodiment of a case/shell for various embodiments of a water vapor distillation apparatus;

FIG. 80 is an isometric view of one embodiment of a case/shell for various embodiments of a water vapor distillation apparatus;

FIG. 81 is an isometric view of one embodiment of a case/shell for various embodiments of a water vapor distillation apparatus;

FIG. 82 is an isometric view of one embodiment of a case/shell for various embodiments of a water vapor distillation apparatus;

FIG. 83 is a partial view of a water vapor distillation apparatus according to one embodiment;

FIG. 84A-84F are various views of a partial water vapor distillation apparatus and system according to one embodiment;

FIG. 85A is an exploded view of a partial water vapor distillation apparatus and system according to one embodiment;

FIG. 85B is a detailed view of "A" shown in FIG. 85B;

FIG. 86 is an exploded view of one embodiment of the water vapor distillation apparatus and system;

FIG. 87A is an isometric view of one embodiment of the water vapor distillation apparatus;

FIG. 87B is an isometric view of one embodiment of the water vapor distillation apparatus;

FIG. 87C is a partial isometric view of one embodiment of the water vapor distillation apparatus;

FIG. 87D is a bottom isometric view of one embodiment of the water vapor distillation apparatus and system;

FIG. 88 is an exploded view of one embodiment of the hydraulic manifold;

FIG. 90A is a front view of one embodiment of a mist eliminator;

FIG. 90B is a sectional view of the mist eliminator shown in FIG. 90A;

FIG. 90C is bottom isometric view of the mist eliminator shown in FIG. 90A;

FIG. 90D is a bottom view of the mist eliminator shown in FIG. 90A;

FIG. 90E is an exploded view of the mist eliminator shown in FIG. 90A;

FIG. 91A is a bottom isometric view of one embodiment of a mist eliminator;

FIG. 91B is a front view of the embodiment of the mist eliminator shown in FIG. 91A;

FIG. 92A is a front view of one embodiment of a mist eliminator;

FIG. 92B is a bottom view of the embodiment of the mist eliminator shown in FIG. 92A;

FIG. 93A is a front view of an embodiment of a mist eliminator;

FIG. 93B is a side view of the embodiment of the mist eliminator shown in FIG. 93A;

FIG. 94 is an isometric view of one embodiment of a mist eliminator;

FIGS. 95A-95B are view of a baffle port;

FIG. 96 is a cross sectional view of the embodiment of a mist eliminator shown in FIG. 94 and a baffle port inside a steam chest with a partial view of the evaporator condenser;

FIG. 97 is a cross sectional view of an embodiment of a mist eliminator shown in FIG. 92A and a baffle port inside a steam chest with a partial view of the evaporator condenser;

FIG. 98A is a top view of one embodiment of a mist eliminator;

FIG. 98B is a side view of the embodiment of the mist eliminator shown in FIG. 98A;

FIG. 99A is an isometric view of one embodiment of the mist eliminator;

FIG. 99B is a cross sectional view of the embodiment of the mist eliminator shown in FIG. 99A;

FIG. 99C is an exploded view of the embodiment of the mist eliminator shown in FIG. 99A;

FIGS. 100A-100C are various view of the one embodiment of the case/shell of the system;

FIG. 101 is a partially exploded view of one embodiment of the system;

FIG. 102 is an exploded view of some components of the system, according to one embodiment;

FIG. 103 is an exploded view of some components of the system, according to one embodiment;

FIG. 104 is a back view of one embodiment of portions of the system;

FIG. 105 is an isometric, exploded and partial cross sectional view of one embodiment of the drain valves;

FIG. 106 is a side view of one embodiment of portions of the system;

FIG. 107 is one embodiment of a fluid schematic of the water vapor distillation apparatus;

FIG. 108 is an exploded view of one embodiment of the valve manifold;

FIG. 109 is an exploded view of one embodiment of the conductivity manifold;

FIG. 110 is an isometric view of one embodiment of a level sensor assembly;

FIG. 111 is an exploded view of one embodiment of a level sensor assembly;

FIG. 112 is a view of one embodiment of a level sensor assembly with portions in ghost lines;

FIG. 113 is an exploded view of one embodiment of a level sensor;

FIG. 114 is an isometric partially exploded view of one embodiment of the heat exchanger;

FIG. 115A is an exploded view of one embodiment of the source water termination and a tube termination;

FIG. 115B is an isometric view of one embodiment of the source water termination and a tube termination;

FIG. 116 is an exploded view of the compressor assembly according to one embodiment;

FIG. 117 is a cross sectional view of one embodiment of the compressor assembly;

FIG. 118A is a view of one embodiment of the shaft;

FIG. 118B is a sectional view of one embodiment of the shaft;

FIG. 119 is an exploded view one embodiment of the shaft;

FIG. 120 is an exploded view of portions of the compressor assembly according to one embodiment;

FIG. 121 is a cross sectional view of the stator assembly according to one embodiment;

FIG. 122 is an exploded view of the evaporator/condenser assembly according to one embodiment;

FIG. 123 is an exploded view of the sump assembly;

FIG. 124 is an exploded view of the bottom tubesheet assembly according to one embodiment;

FIG. 125A is an exploded view of the top tubesheet assembly according to one embodiment;

FIG. 125B is a cross sectional view of the top tubesheet assembly according to one embodiment;

FIG. 126 is a cross sectional view of the evaporator/compressor according to one embodiment;

FIG. 127A is a top view of one embodiment of a filler rod;

FIG. 127B is a cross sectional view of the embodiment of the filler rod shown in FIG. 127A;

FIG. 128A is a detail view of "Detail A" from FIG. 127A;

FIG. 128B is a detail view of "Detail B" from FIG. 127B;

FIG. 129 is one embodiment of a conductivity fluid schematic;

FIG. 130 is one embodiment of a conductivity fluid schematic;

FIG. 131 is one embodiment of a conductivity fluid schematic;

FIG. 132 is one embodiment of a conductivity sensor;

FIG. 133 is a flow diagram of one method of determining the quality of product water output, according to one embodiment;

FIG. 134 is one embodiment of a motor temperature controller;

FIG. 135 is one embodiment of a heater and vent controller;

FIG. 136 is one embodiment of a product level controller;

FIG. 137 is a diagrammatic representation of one embodiment of a network;

FIG. 138 is a diagrammatic representation of one embodiment of communication between one system/device and one external manager;

FIG. 139 is a diagrammatic representation of one embodiment of a network; and

Figure 140:
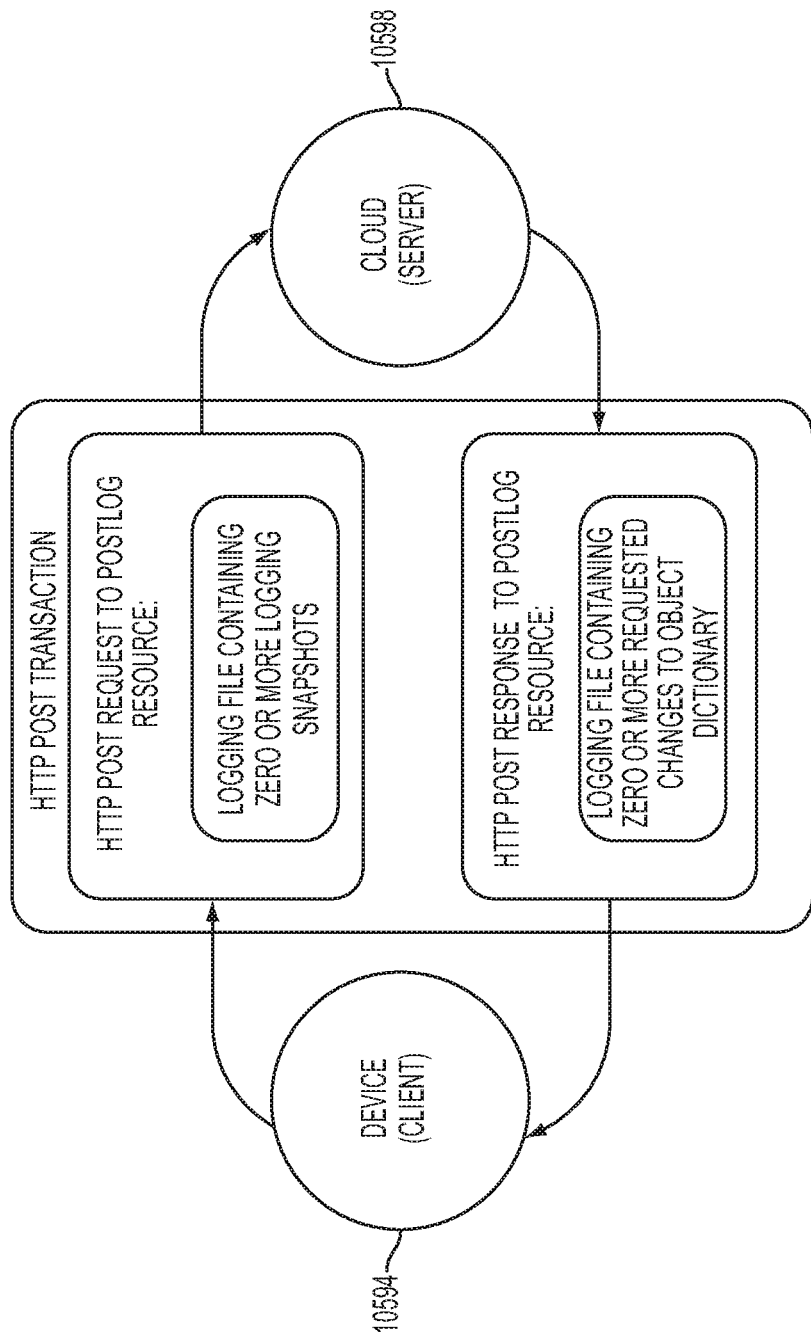

FIG. 140 is a diagrammatic representation of one embodiment of logging data in one embodiment of a network.

DETAILED DESCRIPTION OF THE PREFERRED EMBODIMENTS

Definitions. As used in this description and the accompanying claims, the following terms shall have the meanings indicated, unless the context otherwise requires.

The term "fluid" is used herein to include any type of fluid including water. Thus, although the exemplary embodiment and various other embodiments are described herein with reference to water, the scope of the apparatus, system and methods includes any type of fluid. Also, herein, the term "liquid" may be used to indicate the exemplary embodiment, where the fluid is a liquid.

The term "evaporator condenser" is used herein to refer to an apparatus that is a combination evaporator and condenser. Thus, a structure is referred to as an evaporator condenser where the structure itself serves as both. The evaporator condenser structure is referred to herein as an evaporator/condenser, evaporator condenser or evaporator and condenser. Further, in some instances, where either the evaporator or the condenser is being referred to individually, it should be understood that the term is not limiting and refers to the evaporator condenser structure.

The term "unclean water" is used herein to refer to any water wherein it is desired to make cleaner prior to consuming the water.

The term "cleaner water" is used herein to refer to water that is cleaner as product water than as source water.

The term "source water" refers to any water that enters the apparatus.

The term "product water" refers to the cleaner water that exits the apparatus.

The term "purifying" as used herein, and in any appended claims, refers to reducing the concentration of one or more contaminants or otherwise altering the concentration of one or more contaminants.

The term "specified levels" as used herein refers to some desired level of concentration, as established by a user for a particular application. One instance of a specified level may be limiting a contaminant level in a fluid to carry out an industrial or commercial process. An example is eliminating contaminant levels in solvents or reactants to a level acceptable to enable an industrially significant yield in a chemical reaction (e.g., polymerization). Another instance of a specified level may be a certain contaminant level in a fluid as set forth by a governmental or intergovernmental agency for safety or health reasons. Examples might include the concentration of one or more contaminants in water to be used for drinking or particular health or medical applications, the concentration levels being set forth by organizations such as the World Health Organization or the U.S. Environmental Protection Agency.

The term "system" as used herein may refer to any combination of elements, including but not limited to, a water vapor distillation apparatus (which may be referred to as a water system or a water vapor distillation system) and a water vapor distillation apparatus together with a power source, such as a Stirling engine.

Herein is disclosed an apparatus for distilling unclean water known as source water into cleaner water known as product water. The apparatus cleanses the source water by evaporating the water to separate the particulate from the source water. The term "purifying" as used herein, and in any appended claims, refers to substantially reducing the concentration of one or more contaminants to less than or equal to specified levels or otherwise substantially altering the concentration of one or more contaminants to within a specified range.

The source water may first pass through a counter flow tube-in-tube heat exchanger to increase the temperature of the water. Increasing the temperature of the source water reduces the amount of thermal energy required to evaporate the water within the evaporator/condenser. The source water may receive thermal energy from the other fluid streams present in the heat exchanger. Typically, these other streams have a higher temperature than the source water motivating thermal energy to flow from the higher temperature streams to the lower temperature source water.

Receiving the heated source water is the evaporator area of the evaporator/condenser assembly. This assembly evaporates the source water to separate the contaminants from the water. Thermal energy may be supplied using a heating element and high-pressure steam. Typically, the heating element will be used during initial start-up, thus under normal operating conditions the thermal energy will be provided by the high-pressure steam. The source water fills the inner tubes of the evaporator area of the evaporator/condenser. When the high-pressure steam condenses on the outer surfaces of these tubes thermal energy is conducted to the source water. This thermal energy causes some of the source water to evaporate into low-pressure steam. After the source water transforms into a low-pressure steam, the steam may exit the outlet of the tubes and pass through a separator. The separator removes any remaining water droplets within the steam ensuring that the low-pressure steam is dry before entering the compressor.

Upon exiting the evaporator area of the evaporator/condenser the low-pressure steam enters a compressor. The compressor creates high-pressure steam by compressing the low-pressure steam. As the steam is compressed the temperature of the steam increases. With the steam at an elevated temperature and pressure the steam exits the compressor.

The high-pressure steam enters the condenser area of the evaporator/condenser. As the steam fills the internal cavity the steam condenses on the tubes contained within the cavity. The high-pressure steam transfers thermal energy to the source water within the tubes. This heat transfer causes the steam to condense upon the outer surface of the tubes creating product water. The product water is collected in the base of the condenser area of the evaporator/condenser. The product water leaves the evaporator area of the evaporator/condenser and enters the level sensor housing.

The level sensor housing contains level sensors for determining the amount of product and blowdown water within the apparatus. These sensors allow an operator to adjust the amount of product water being produced or the amount of incoming source water depending on the water levels within the apparatus.

The water vapor distillation apparatus as described herein with respect to various embodiments may further be used in conjunction with a Stirling engine to form a water vapor distillation system. The power needed by the water vapor distillation apparatus may be provided by a Stirling engine electrically connected to the water vapor distillation apparatus.

Figure 1:
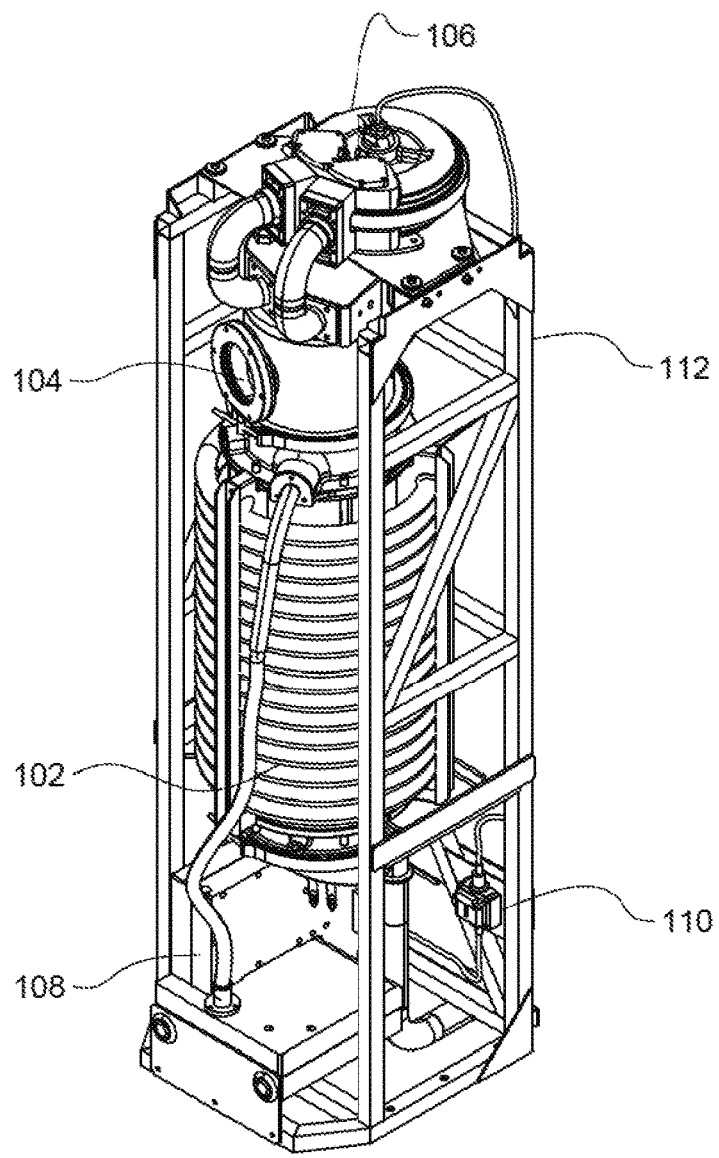
FIG. 1 is an isometric view of the water vapor distillation apparatus.

Referring to FIG. 1, one embodiment of the water vapor distillation apparatus 100 is shown. For the purposes of this description, the embodiment shown in FIG. 1 will be referred to as the exemplary embodiment. Other embodiments are contemplated some of which will be discussed herein. The apparatus 100 may include a heat exchanger 102, evaporator/condenser assembly 104, regenerative blower 106, level sensor assembly 108, a bearing feed-water pump 110, and a frame 112. See also FIGS. 1A-E for additional views and cross sections of the water vapor distillation apparatus 100.

Figure 1A:
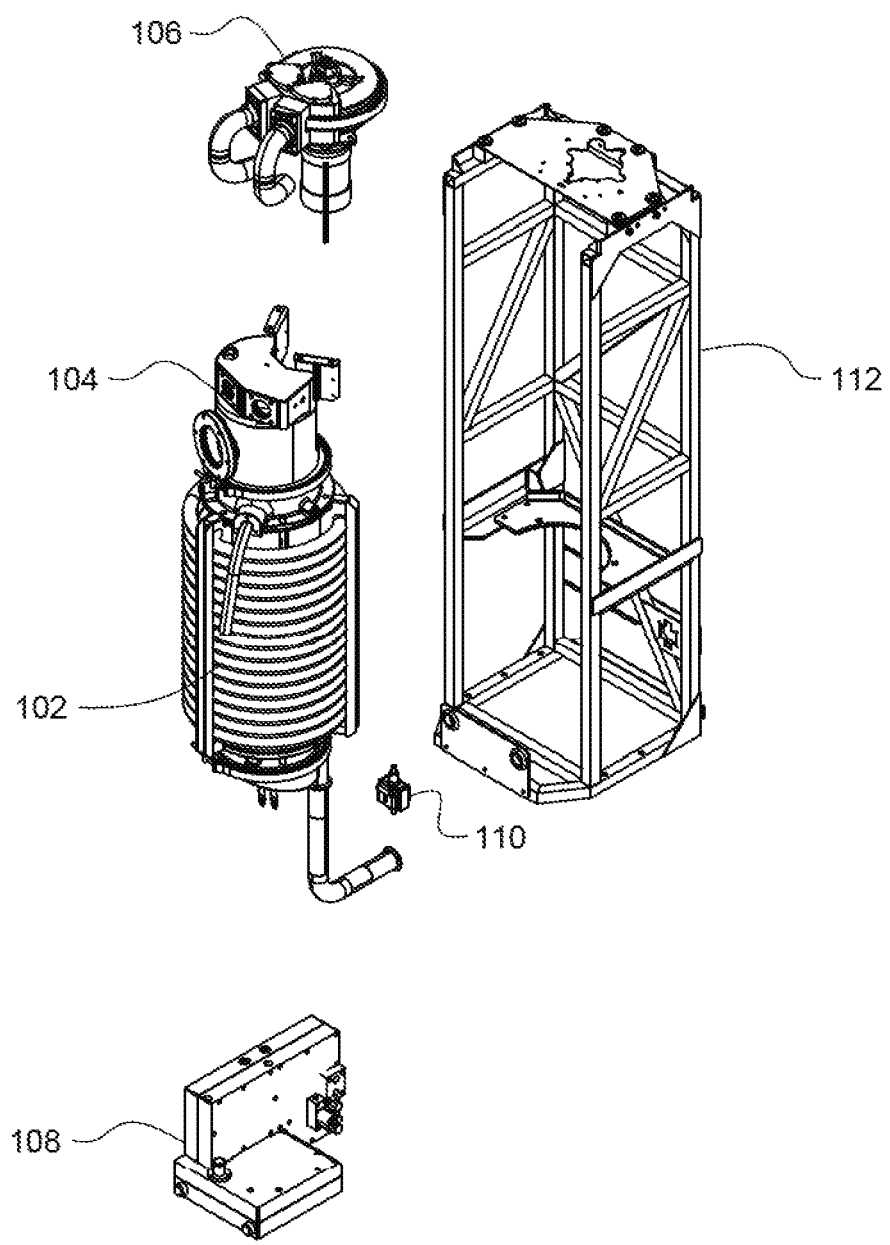
FIG. 1A is an exploded view of the exemplary embodiment of the disclosure.
Figure 1B:
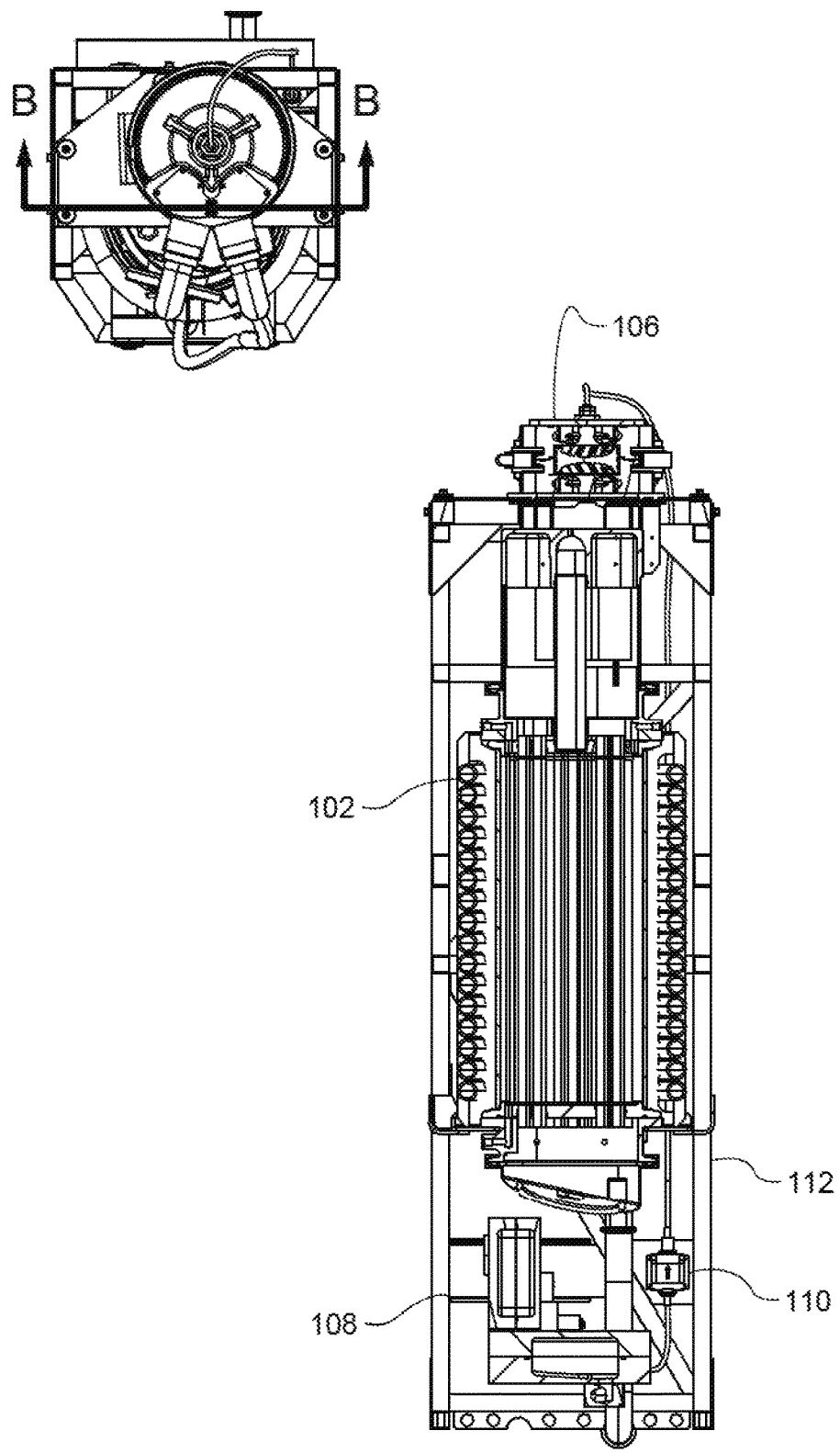
FIG. 1B is a cross-section view of the exemplary embodiment.
Figure 1C:
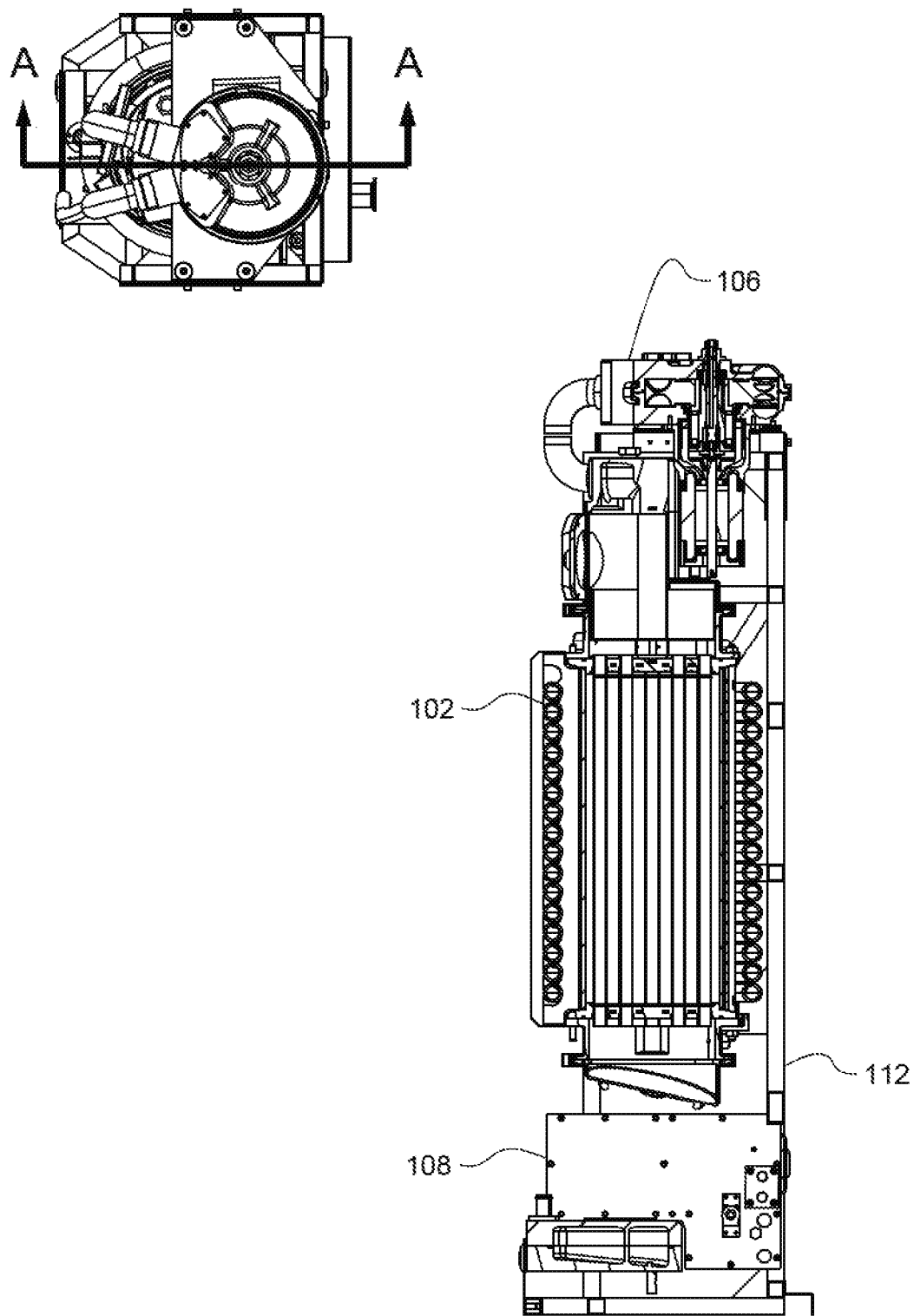
FIG. 1C is a cross-section view of the exemplary embodiment.
Figure 1D:
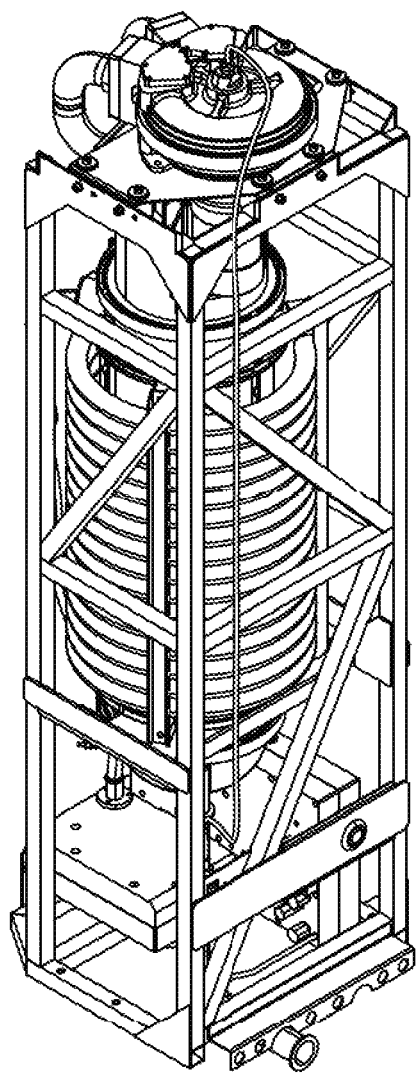
FIG. 1D is an assembly view of the exemplary embodiment.
Figure 1E:
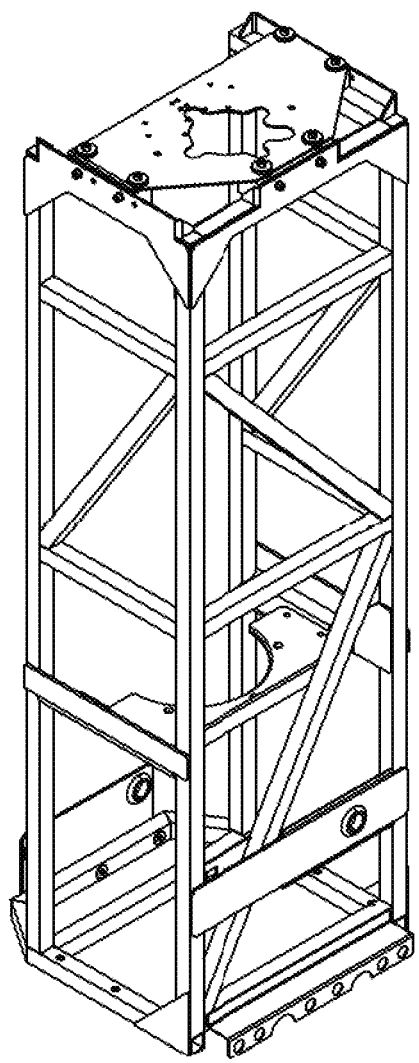
FIG. 1E is a detail view of the exemplary embodiment of the frame.
Figure 1F:
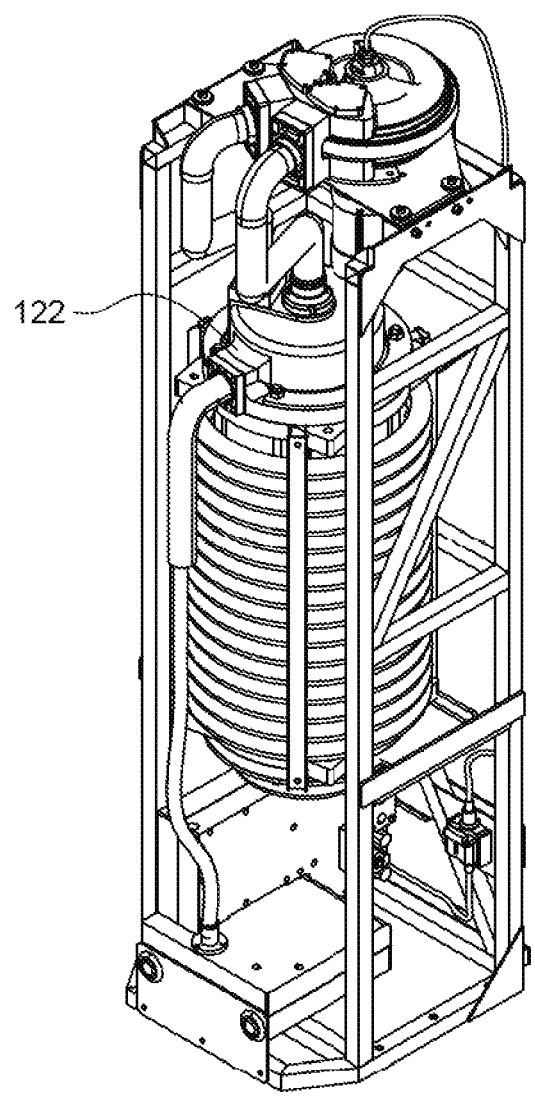
FIG. 1F is an assembly view of an alternate embodiment.
Figure 1G:
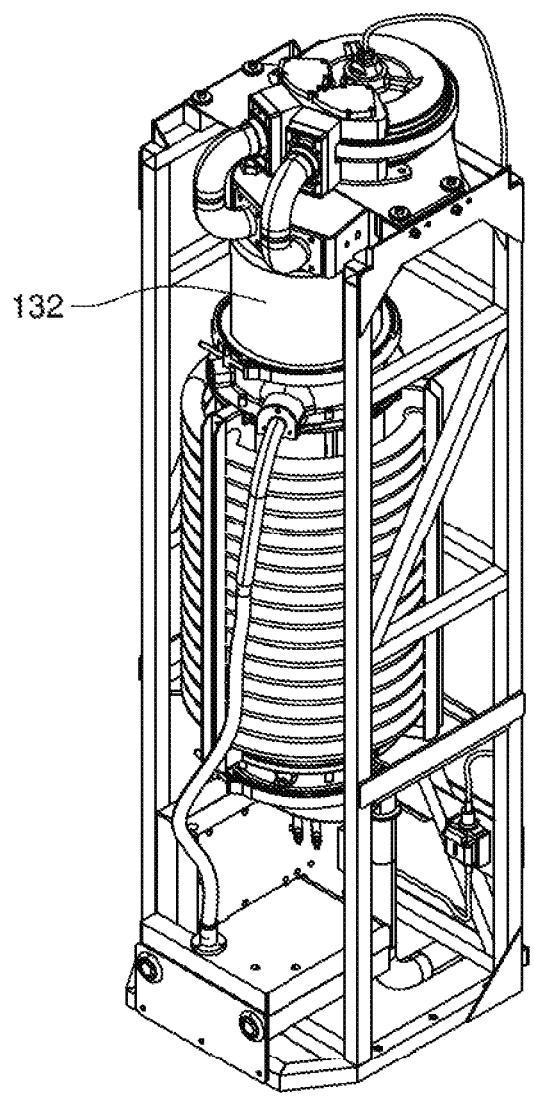
FIG. 1G is an assembly view of an alternate embodiment.
Figure 1H:
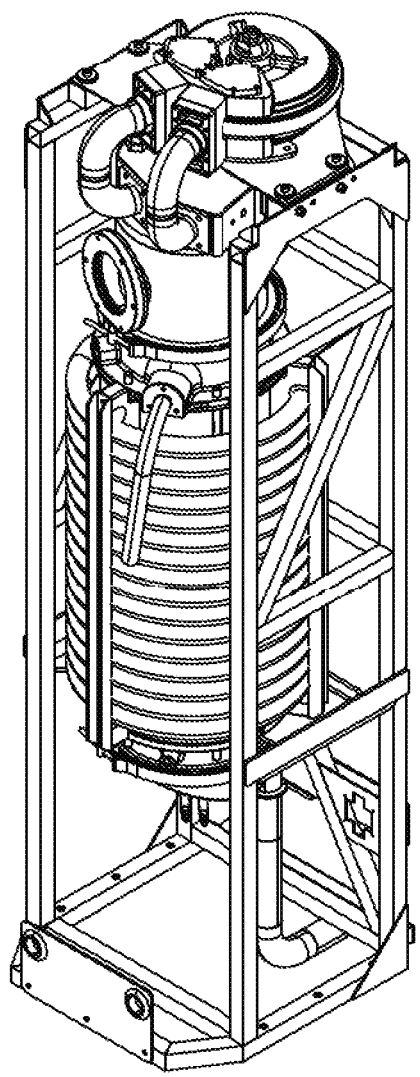
FIG. 1H is an assembly view of an alternate embodiment.

Referring to FIGS. 1F-H, these figures illustrate alternate embodiments of the water vapor distillation apparatus 100. FIG. 1F depicts an apparatus 120 having an alternate configuration of the evaporator/condenser assembly 122. Similarly, FIG. 1G discloses an apparatus having another configuration of the evaporator/condenser assembly 132. Similarly, FIG. 1H illustrates another embodiment of the apparatus not including the level sensor assembly 108 and bearing feed-water pump 110 from FIGS. 1-1E.

Heat Exchanger

Figure 2:
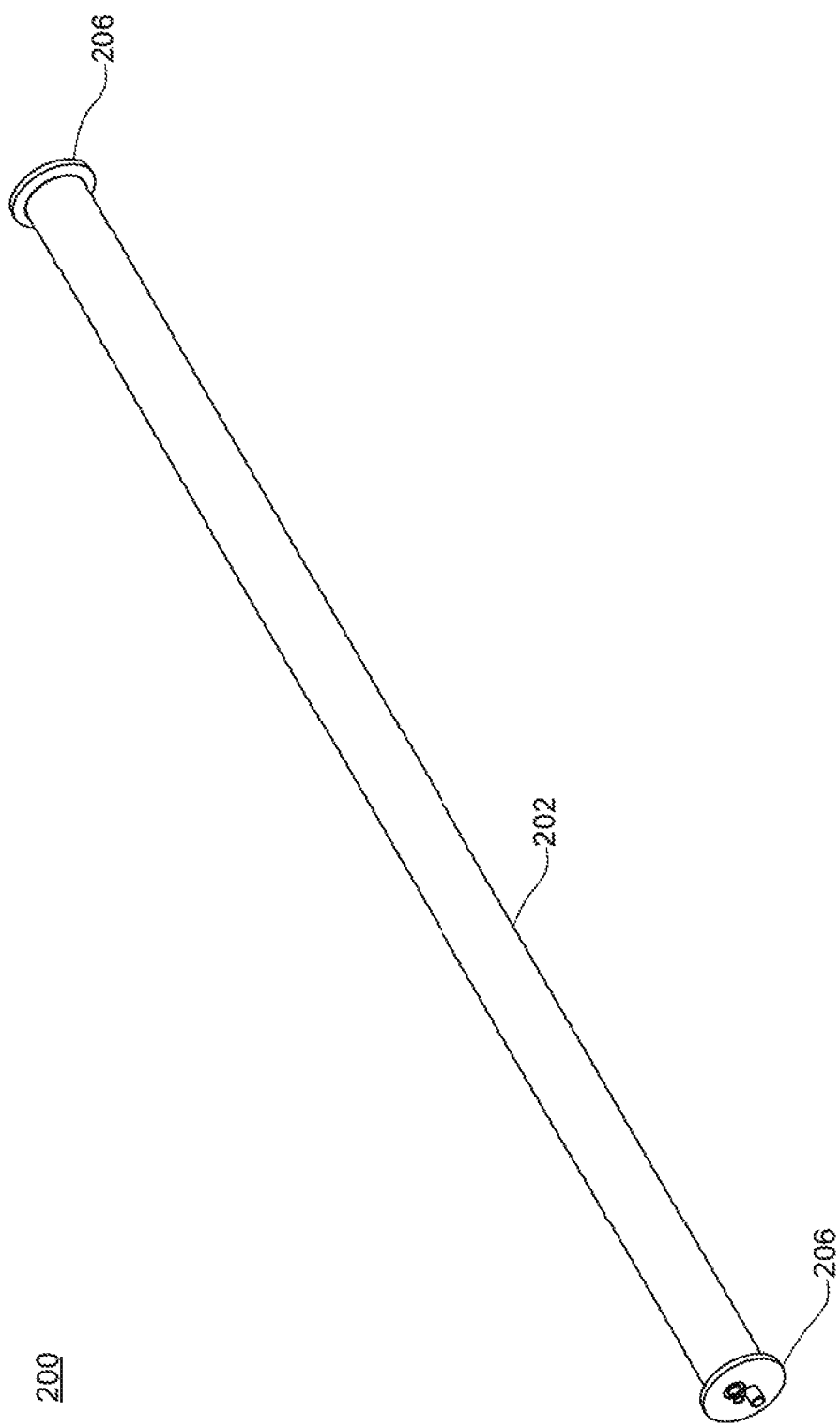
FIG. 2 is an assembly view of the exemplary embodiment of the tube-in-tube heat exchanger assembly.
Figure 2A:
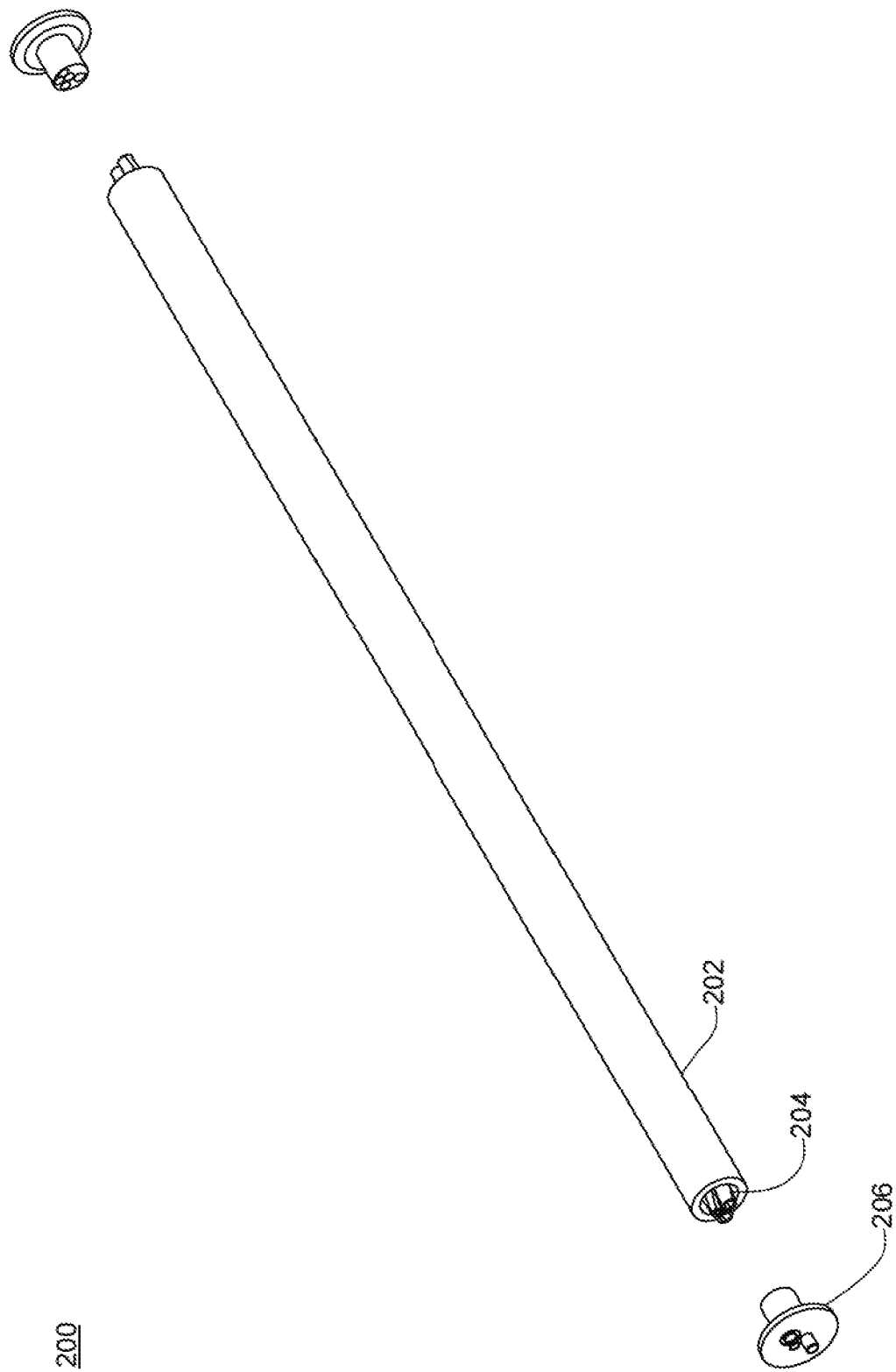
FIG. 2A is an exploded view one embodiment of the tube-in-tube heat exchanger.

Referring now to FIGS. 2-2A, in the exemplary embodiment of the water vapor distillation apparatus, the heat exchanger may be a counter flow tube-in-tube heat exchanger assembly 200. In this embodiment, heat exchanger assembly 200 may include an outer tube 202, a plurality of inner tubes 204 and a pair of connectors 206 illustrated in FIG. 2A. Alternate embodiments of the heat exchanger assembly 200 may not include connectors 206.

Still referring to FIGS. 2-2A, the heat exchanger assembly 200 may contain several independent fluid paths. In the exemplary embodiment, the outer tube 202 contains source water and four inner tubes 204. Three of these inner tubes 204 may contain product water created by the apparatus. The fourth inner tube may contain blowdown water.

Still referring to FIGS. 2-2A, the heat exchanger assembly 200 increases the temperature of the incoming source water and reduces the temperature of the outgoing product water. As the source water contacts the outer surface of the inner tubes 204, thermal energy is conducted from the higher temperature blowdown and product water to the lower temperature source water through the wall of the inner tubes 204. Increasing the temperature of the source water improves the efficiency of the water vapor distillation apparatus 100 because source water having a higher temperature requires less energy to evaporate the water. Moreover, reducing the temperature of the product water prepares the water for use by the consumer.

Still referring to FIGS. 2-2A, in the exemplary embodiment the heat exchanger 200 is a tube-in-tube heat exchanger having an outer tube 202 having several functions. First, the outer tube 202 protects and contains the inner tubes 204. The outer tube 202 protects the inner tubes 204 from corrosion by acting as a barrier between the inner tubes 204 and the surrounding environment. In addition, the outer tube 202 also improves the efficiency of the heat exchanger 200 by preventing the exchange of thermal energy to the surrounding environment. The outer tube 202 insulates the inner tubes 204 reducing any heat transfer to or from the surrounding environment. Similarly, the outer tube 202 may resist heat transfer from the inner tubes 204 focusing the heat transfer towards the source water and improving the efficiency of the heat exchanger 200.

Still referring to FIGS. 2-2A, the outer tube 202 may be manufactured from any material, but low thermal conductivity is desirable. The low thermal conductivity is important, because the outer tube 202 insulates the inner tubes 204 from the surrounding environment. The low thermal conductivity of the outer tube improves the efficiency of the heat exchanger, because a low thermal conductive material reduces thermal energy losses or gains to the surrounding environment. In addition, low thermal conductive material lowers the amount of thermal energy that may be transferred from the inner tubes 204 to the outer tube 202. This resistance to heat transfer allows more thermal energy to be transferred to the source water rather than escaping from the apparatus through the outer tube 202. Thus an outer tube 202 manufactured from a material having a low thermal conductivity allows more thermal energy to be transferred to the source water rather than lost or gained to the surrounding environment.

Still referring to FIGS. 2-2A, in the exemplary embodiment the outer tube 202 is manufactured from a clear silicone. In addition to having a low thermal conductivity, silicone material is also corrosion resistant. This is an important characteristic to prevent corrosion of the heat exchanger 200. The source water within the outer tube 202 may contain chemicals and/or other highly reactive materials. These materials may cause outer tubing 202 made from other materials to breakdown reducing the service life of the heat exchanger 200. In alternate embodiments, the outer tube 202 may be manufactured from other materials, such as plastic or rubber having high temperatures resistance. Also, in one embodiment the outer tube 202 is made from convoluted tubing to enhance mixing, which increases heat transfer efficiency.

Figure 2B:
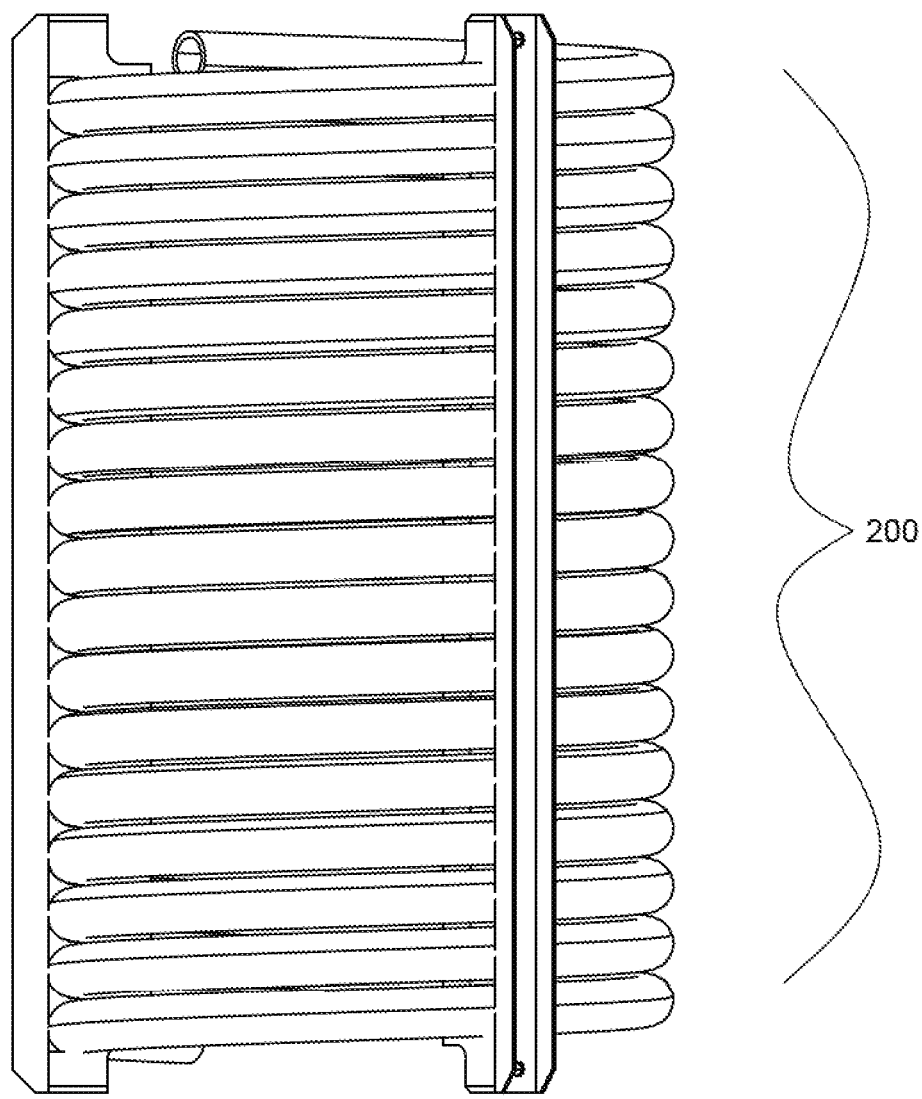
FIG. 2B is an isometric view of the exemplary embodiment of the tube-in-tube heat exchanger from the back.
Figure 2C:
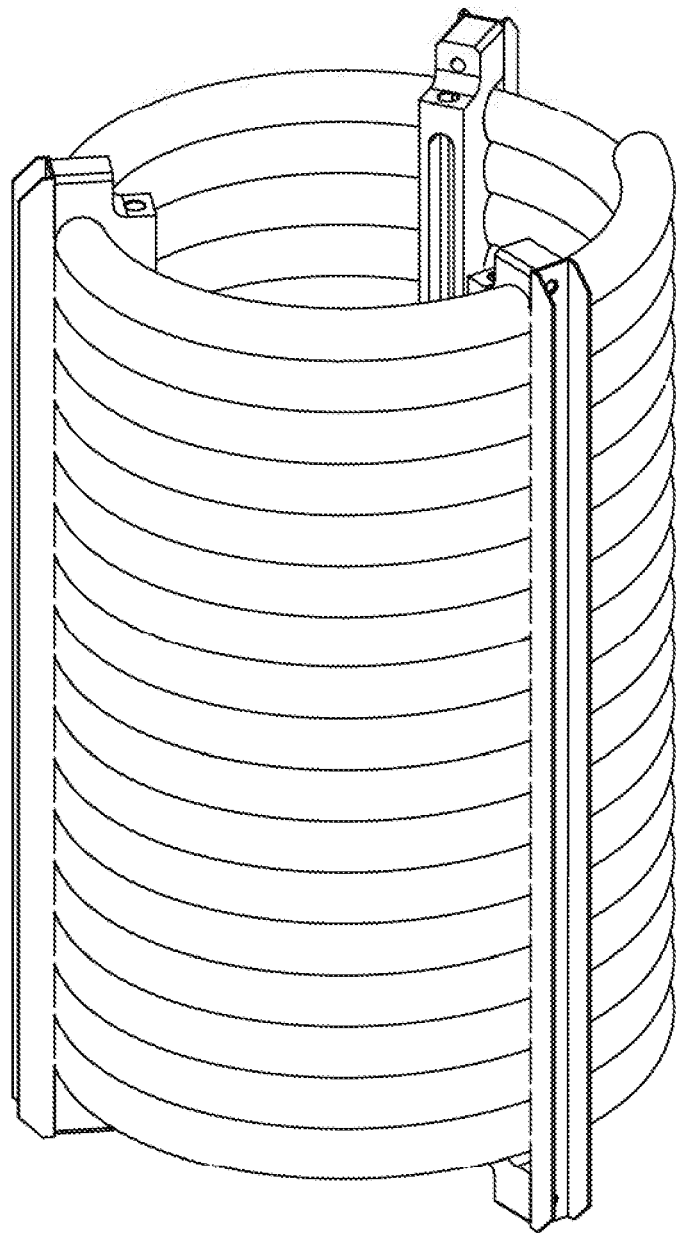
FIG. 2C is an isometric view of the exemplary embodiment of the tube-in-tube heat exchanger from the front.

Referring now to FIGS. 2B-C, another desirable characteristic is for the outer tubing 202 to be sufficiently elastic to support installation of the heat exchanger 200 within the water vapor distillation apparatus 100. In some applications space for the distillation apparatus may be limited by other environmental or situational constraints. For example, in the exemplary embodiment the heat exchanger 200 is wrapped around the evaporator/condenser. In other embodiments, the heat exchanger may also be integrated into the insulated cover of the water vapor distillation apparatus to minimize heat lost or gained from the environment. In the exemplary embodiment the heat exchanger 200 is configured in a coil as shown in FIGS. 2B-C. To achieve this configuration the inner tubes 204 are slid into the outer tube 202 and then wound around a mandrel. An elastic outer tube 202 assists with positioning the ends of the heat exchanger 200 at particular locations within the apparatus. Thus, having an elastic outer tube 202 may facilitate in the installation of the heat exchanger 200 within the water vapor distillation apparatus 100.

Still referring to FIGS. 2B-C, the elasticity of the outer tubing 202 material may also be affected by the wall thickness. Tubing having a thick wall thickness has less flexibility. The thicker wall thickness, however, may improve the thermal characteristics of the tubing, because the thicker wall has greater resistance heat transfer. In addition, the wall thickness of the tubing must be sufficient to withstand the internal pressures generated by the source water within the tubing. Tubing having an increased wall thickness, however, has decreased elasticity and increases the size of the heat exchanger assembly. Thicker walled tubing requires a larger bend radius affecting the installation the heat exchanger 200. Conversely, tubing having too little wall thickness tends to kink during installation. This distortion of the tubing may restrict the flow of source water through the outer tube 202 causing a reduction in the efficiency of the heat exchanger 200.

The diameter of the outer tube 202 may be any diameter capable of containing a plurality of inner tubes 204. The larger the diameter, however, lowers the flexibility of the tubing. Any reduction in flexibility may adversely affect the installation of the heat exchanger into the water vapor distillation apparatus 100. In the exemplary embodiment, the diameter of the outer tube 202 is one inch. This diameter allows the tube-in-tube heat exchanger 200 to be wrapped around the evaporator/condenser 104 upon final installation and contains four inner tubes 204 for transporting product and blowdown water. In alternate embodiments the heat exchanger may have as few as two inner tubes 204. Similarly, in other embodiments the heat exchanger may have more than four inner tubes 204.

Figure 2D:
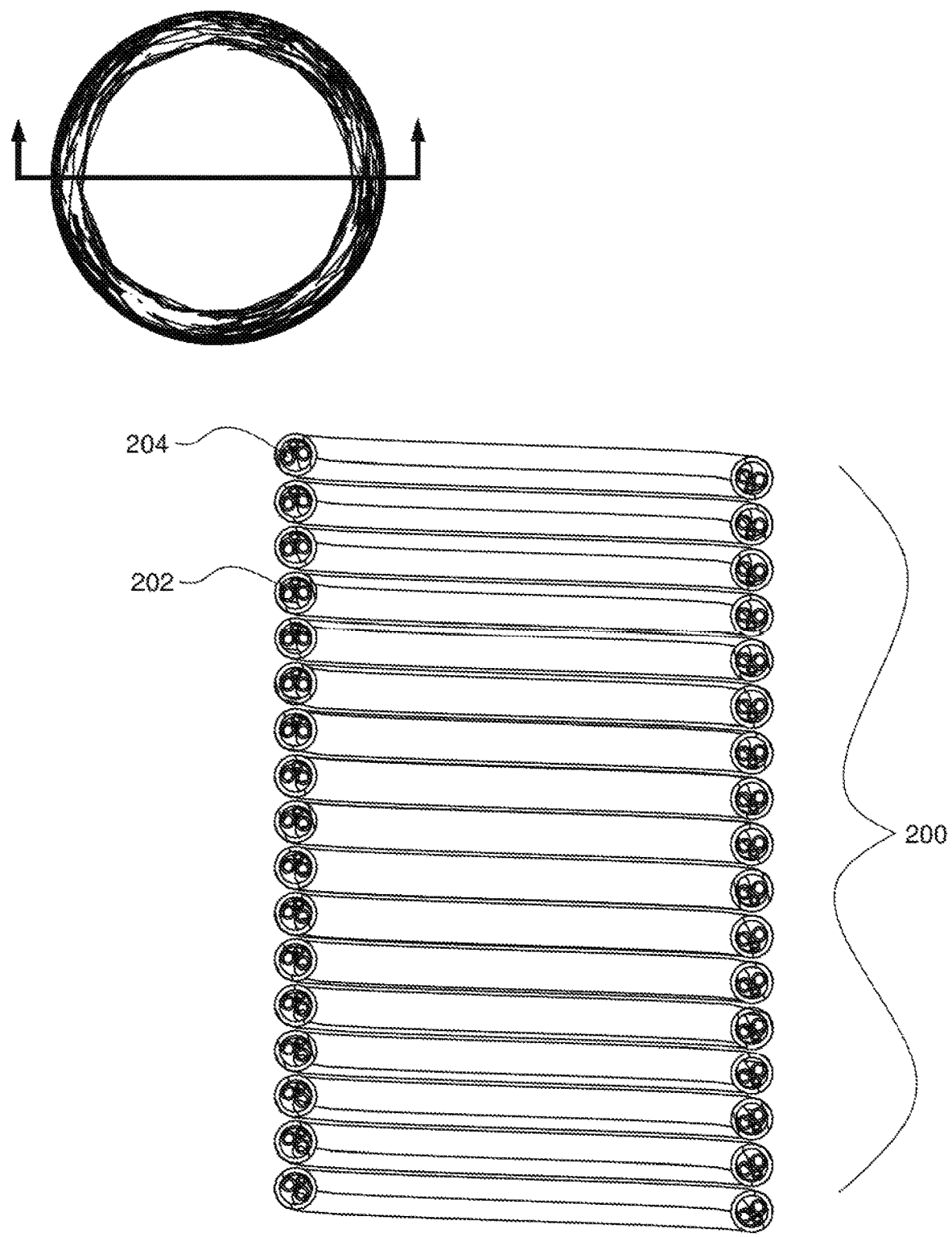
FIG. 2D is a cross-section view of one embodiment of the tube-in-tube heat exchanger.

Now referring to FIGS. 2A and 2D, the inner tubes 204 may provide separate flow paths for the source, product, and blowdown water. In the exemplary embodiment, these tubes contain product and blowdown water. However, in other embodiments, the inner tubes may contain additional fluid streams. The inner tubes 204 separate the clean and safe product water from the contaminated and unhealthy source and blowdown water. In the exemplary embodiment, there are three inner tubes 204 for product water and one inner tube 204 for blowdown. The source water travels within the outer tube 202 of the heat exchanger 200. In various other embodiments, the number of inner tubes may vary, i.e., greater number of inner tubes may be included or a lesser number of inner tubes may be included.

Still referring to FIGS. 2A and 2D, the inner tubes 204 conduct thermal energy through the tube walls. Thermal energy flows from the high temperature product and blowdown water within the inner tubes 204 through the tube walls to the low temperature source water. Thus, the inner tubes 204 are preferably made from a material having a high thermal conductivity, and additionally, preferably from a material that is corrosion resistant. In the exemplary embodiment, the inner tubes 204 are manufactured from copper. The inner tubes 204 may be manufactured from other materials such as brass or titanium with preference that these other materials have the properties of high thermal conductivity and corrosion resistance. For applications where the source and blowdown water may be highly concentrated, such as sea water, the inner tubes 204 may be manufactured from but not limited to copper-nickel, titanium or thermally conductive plastics.

In addition to the tubing material, the diameter and thickness of the tubing may also affect the rate of thermal energy transfer. Inner tubing 204 having a greater wall thickness may have less thermal efficiency because increasing the wall thickness of the tubing mat also increase the resistance to heat transfer. In the exemplary embodiment, the inner tubes 204 have 0.25 inch outside diameter. Although a thinner wall thickness increases the rate of heat transfer, the wall thickness must be sufficient to be shaped or formed without distorting. Thinner walled tubing is more likely to kink, pinch or collapse during formation. In addition, the wall thickness of the inner tubes 204 must be sufficient to withstand the internal pressure created by the water passing through the tubes.

Still referring to FIGS. 2A and 2D, additional methods for improving the rate of heat transfer of the inner tubes 204 may include unequal inner tube diameters and extended surfaces on the inner tubes to enhance heat transfer (fins, pins, ribs . . . ). In addition, the outer tube 202 may have a textured interior surface causing turbulence in the flow of the source water to enhance heat transfer. The rate of heat transfer is increased because the texture surface produces a turbulent flow within the tube 202. The turbulence increases the amount of water that contacts the outer surfaces of the inner tubes 204 where the heat transfer occurs. In contrast, without a texture surface the water may flow in a more laminar manner. This laminar flow will allow only a limited amount of water to contact the outer surfaces of the inner tubes 204. The remaining water not in contact with the inner tubes 204 receives less thermal energy because the convective thermal transfer between the water near the inner tubes and the remaining water is not as efficient as the heat transfer near the outer surface of the inner tubes 204. Some examples of textured surfaces may include but are not limited to dimples, fins, bumps or grooves. In another embodiment may shrink to fit outer tube to increase shell side flow velocity and therefore enhance heat transfer.

Figure 2E:
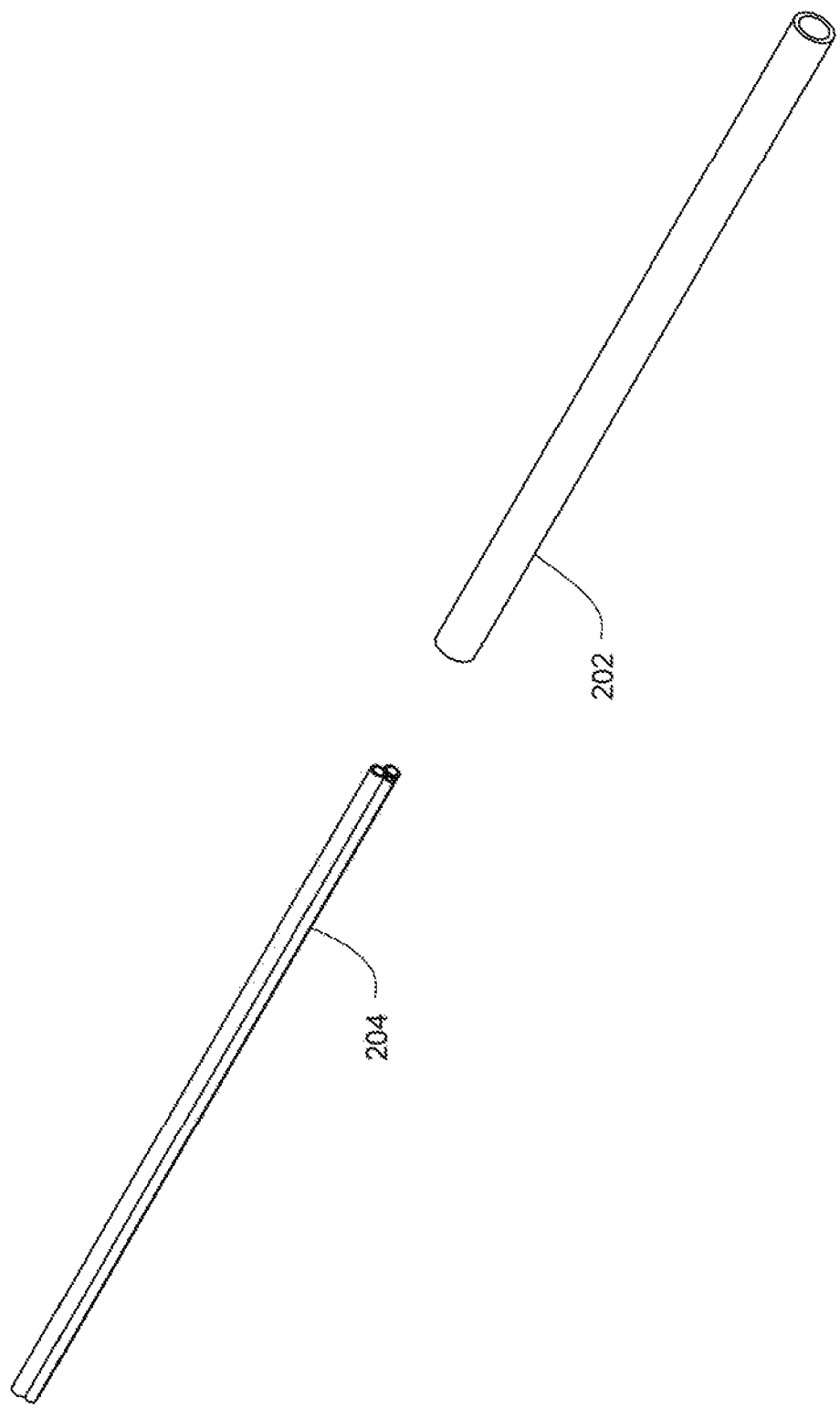
FIG. 2E is an exploded view of an alternate embodiment of a tube-in-tube heat exchanger.
Figure 2F:
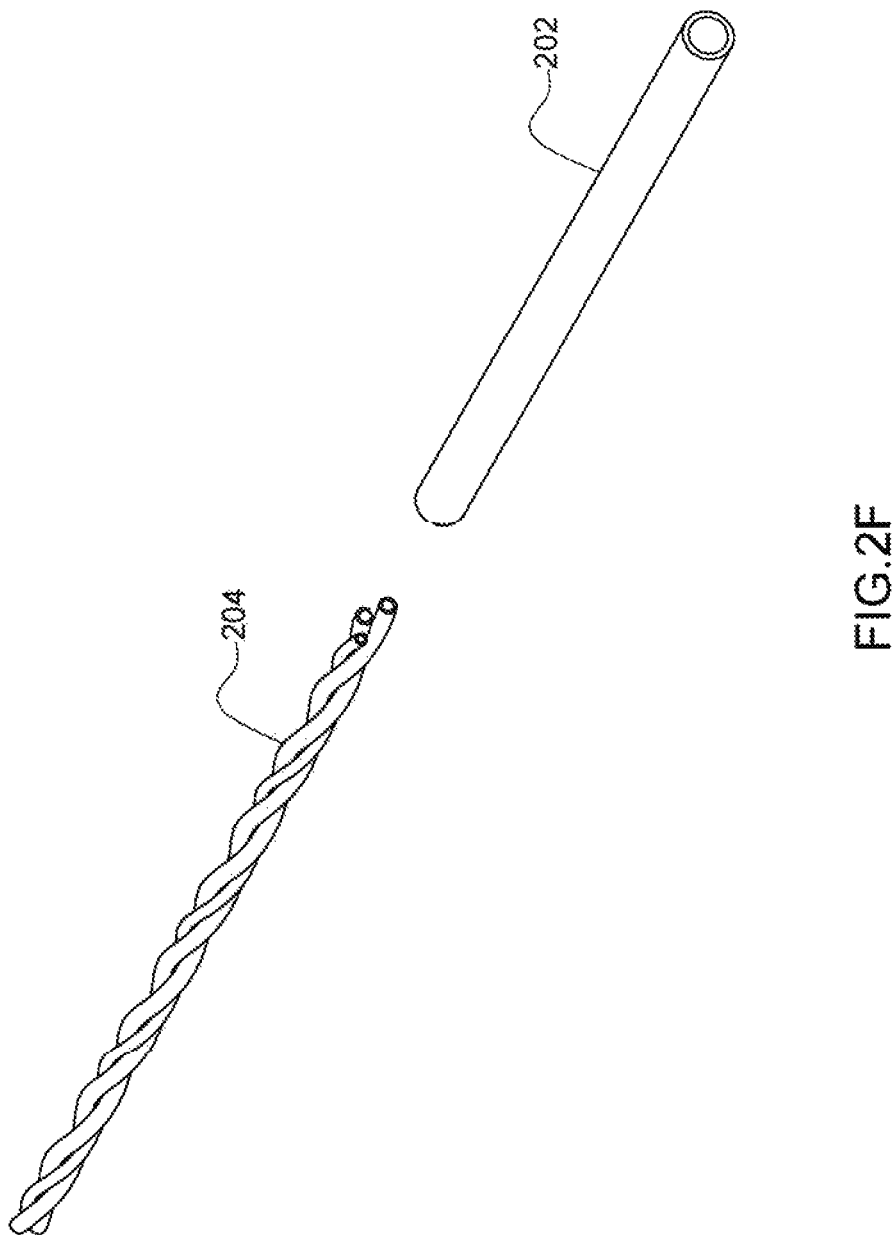
FIG. 2F is a cut away view of one embodiment of the tube-in-tube heat exchanger illustrating the helical arrangement of the inner tubes.
Figure 2G:
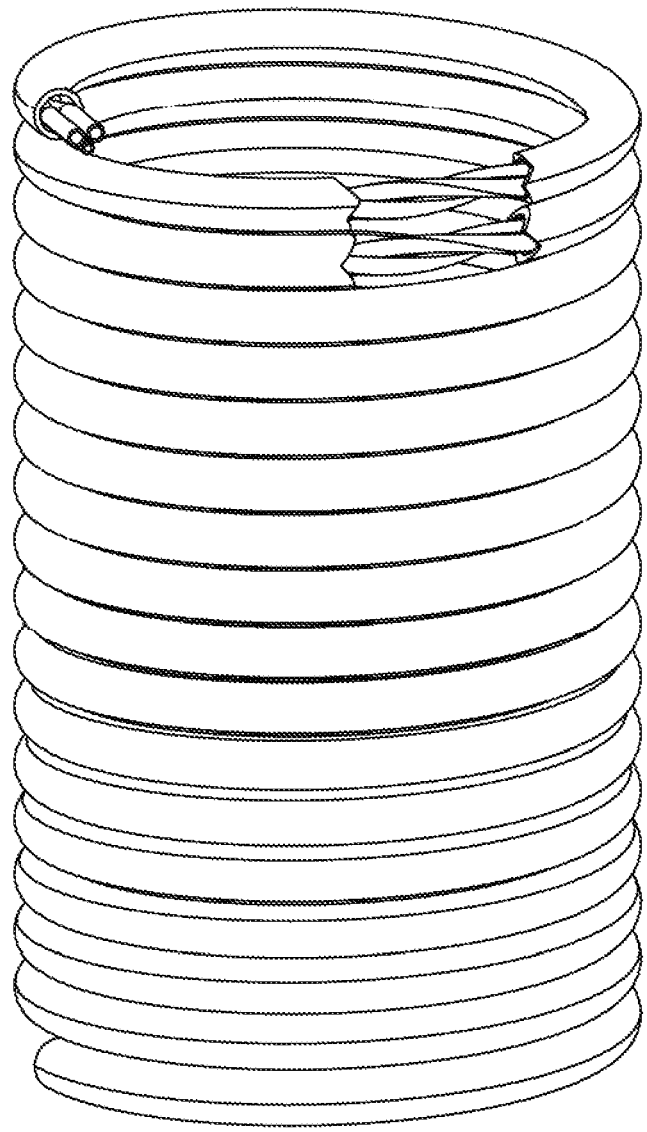
FIG. 2G is an exploded view of an alternate embodiment of a tube-in-tube heat exchanger.
Figure 2H:
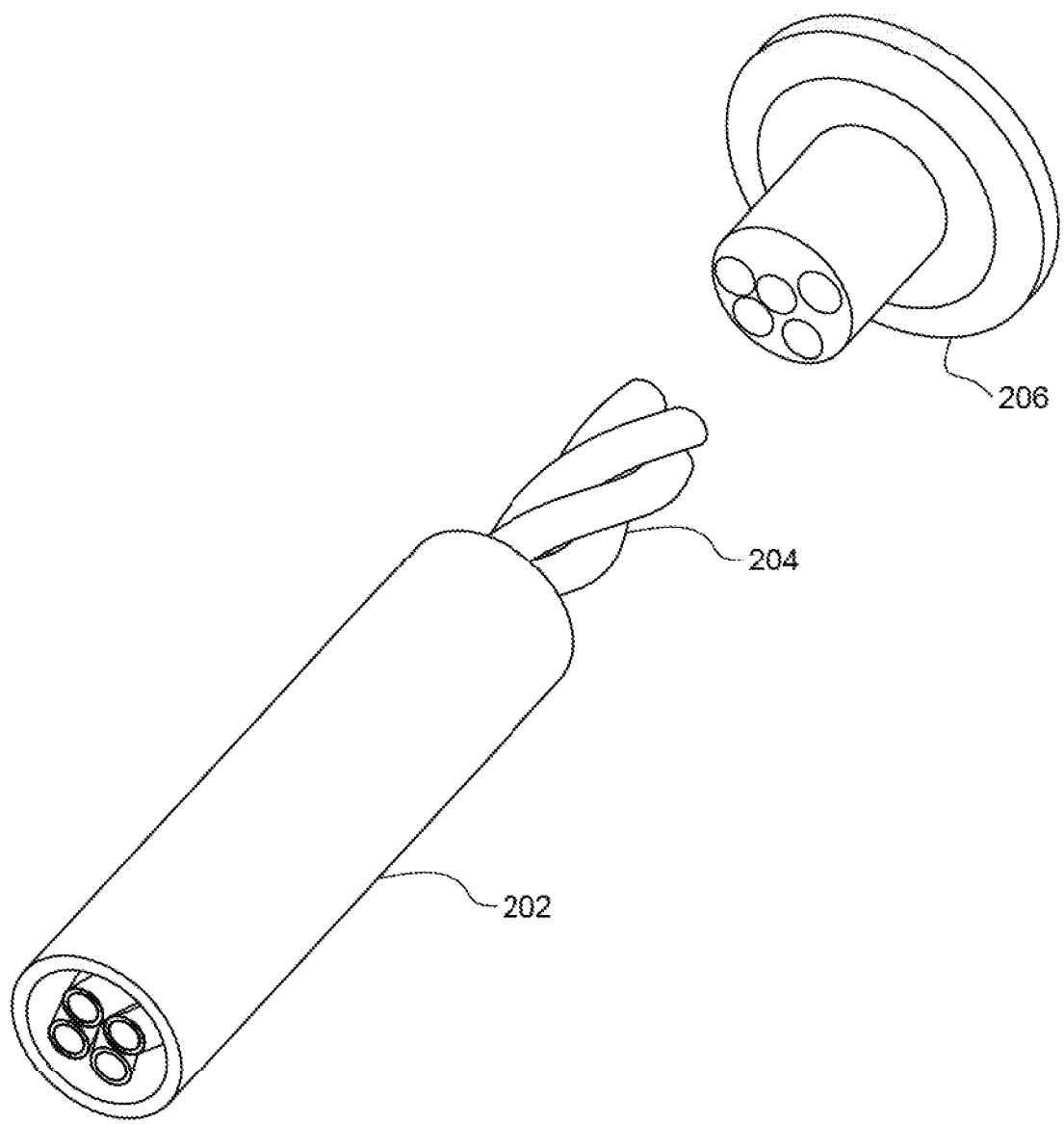
FIG. 2H is an isometric view of the exemplary embodiment of the tube-in-tube heat exchanger.
Figure 2I:
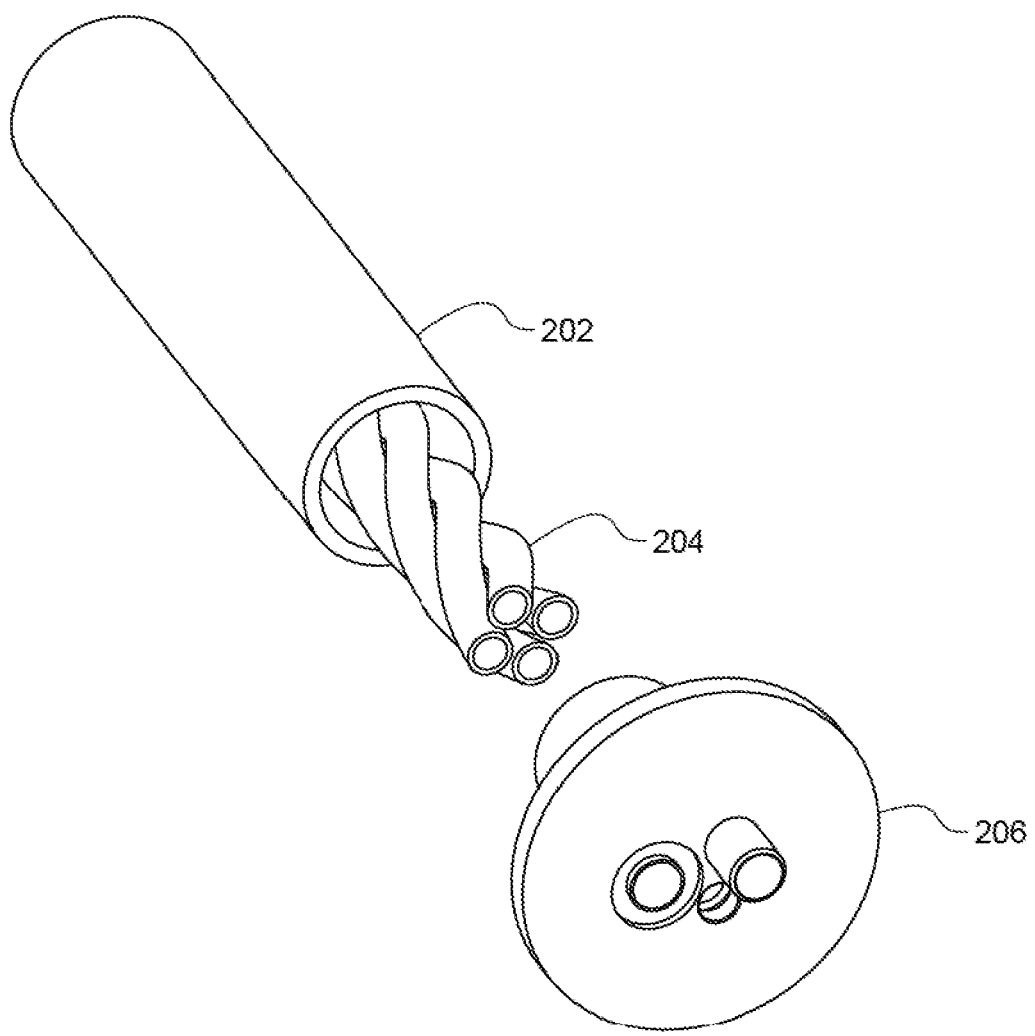
FIG. 2I is an isometric view of the exemplary embodiment of the tube-in-tube heat exchanger.

Referring now to FIG. 2E, typically, the inner tubes 204 are positioned parallel to one another. In some embodiments, however, the inner tubes 204 are braided or twined together to form a helix or a substantially helical shape as illustrated in FIGS. 2F-G. The helix shape increases the amount of surface area for heat transfer, because the length of the inner tubes 204 is longer than inner tubes 204 of the parallel arrangement. The increased surface area provides more area for heat transfer, thus increasing the efficiency of the heat exchanger 200. In addition, the helical shape may cause a turbulent flow of source water within the outer tubing 202 improving the heat transfer efficiency as previously described. In the exemplary embodiment, the heat exchanger 200 has four inner tubes 204 arranged in a helical shape illustrated on FIGS. 2H-I.

The total length of the tubes-in-tube heat exchanger 200 is governed by the desired efficiency of the apparatus. A heat exchanger 200 having a longer length yields better efficiency. In the exemplary embodiment, the heat exchanger 200 is approximately 50 feet long. This yields approximately 90% efficiency. Alternatively, a length of 25 feet yields an efficiency of approximately 84%.

Figure 2J:
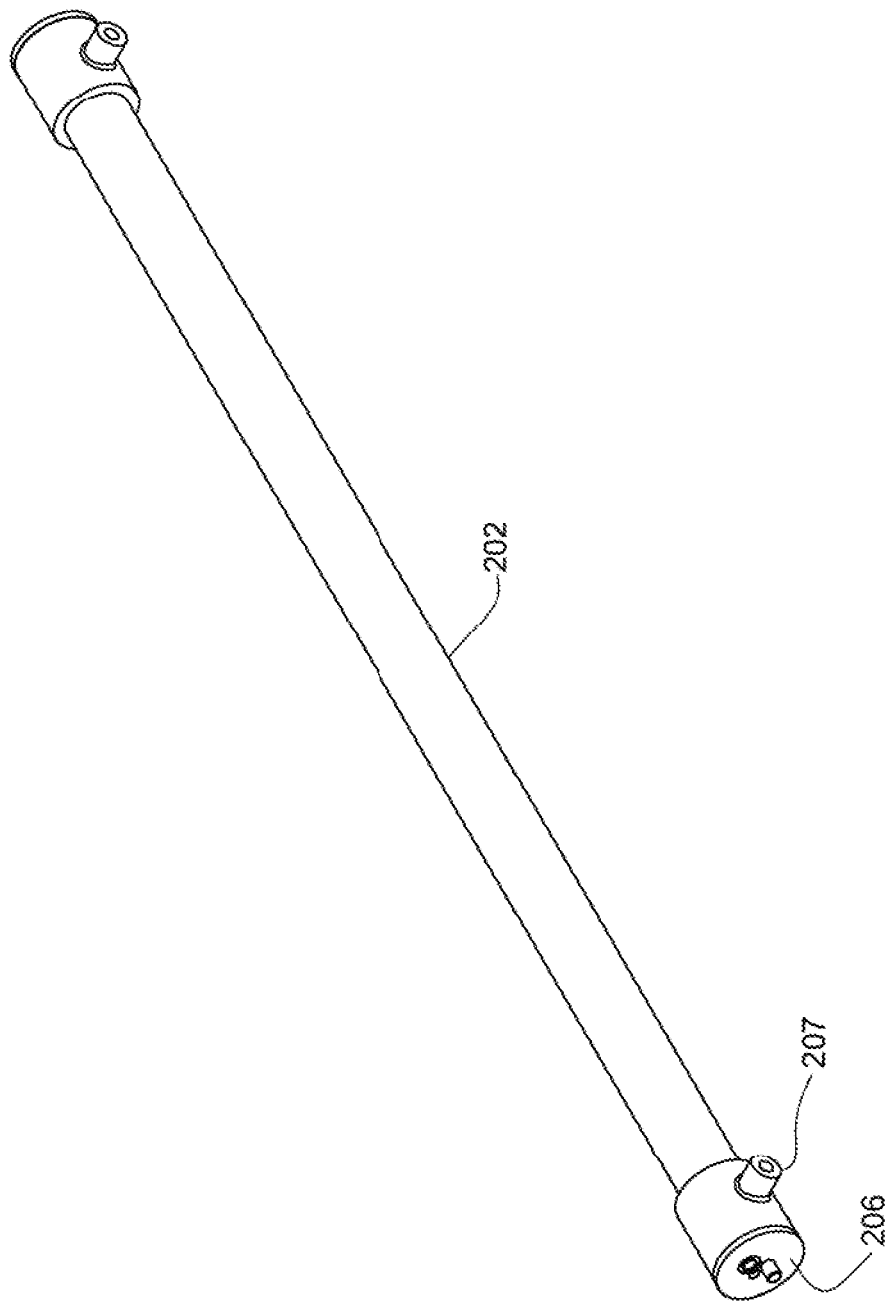
FIG. 2J is an exploded view of an alternate embodiment of the tube-in-tube heat exchanger configuration.
Figure 2K:
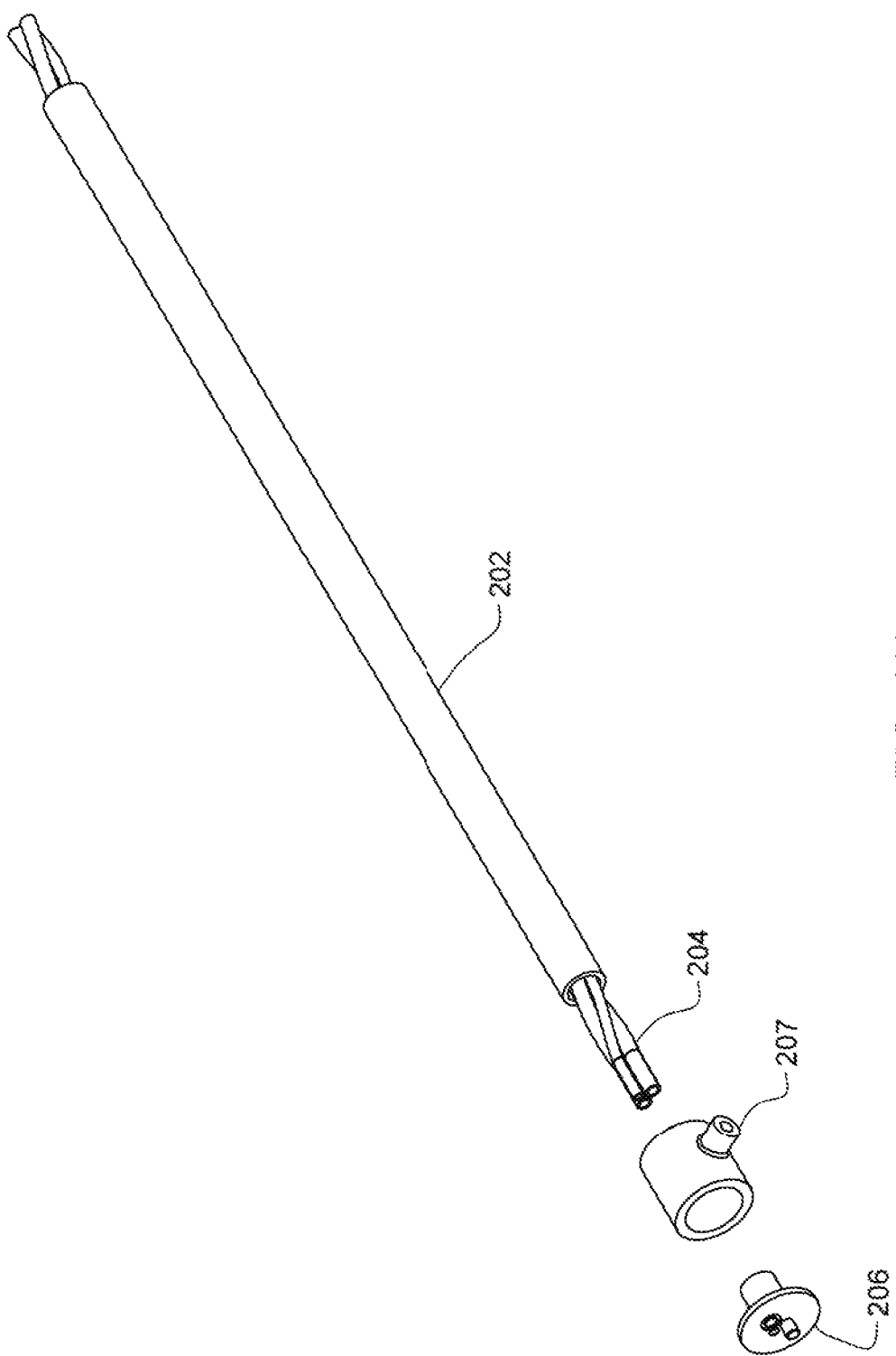
FIG. 2K is an assembly view of an alternate embodiment of the tube-in-tube heat exchanger configuration.
Figure 2L:
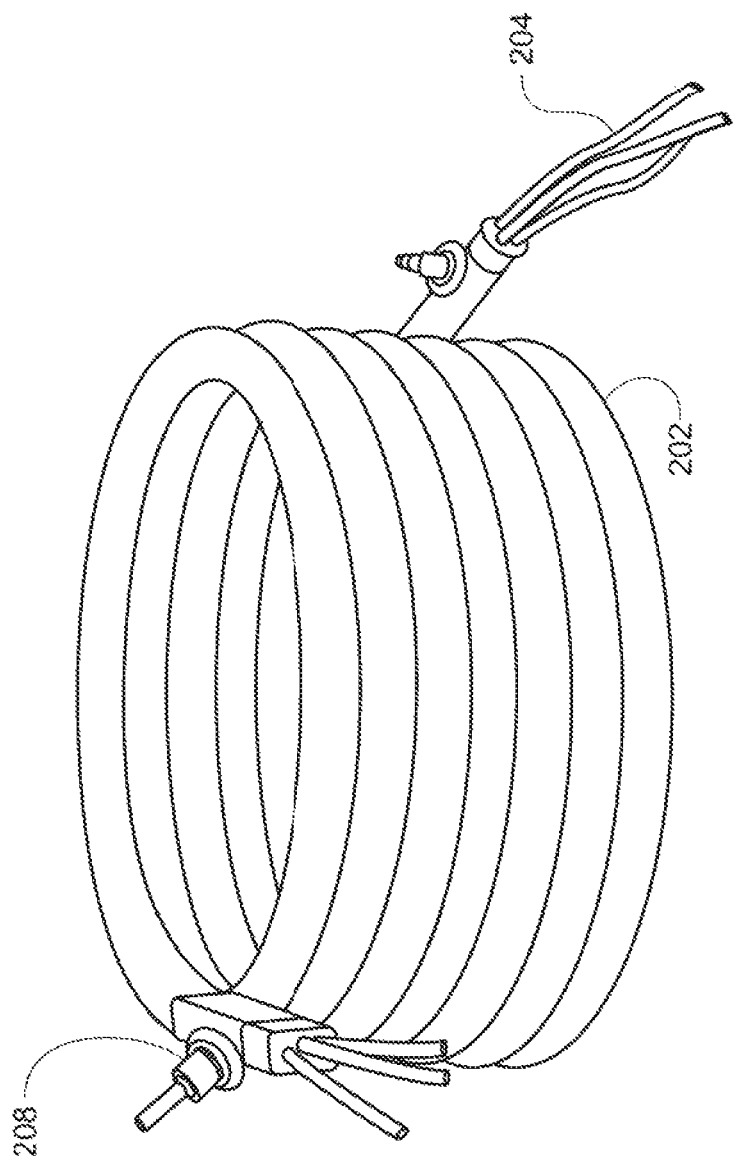
FIG. 2L is an assembly view of an alternate embodiment of the tube-in-tube heat exchanger configuration.
Figure 2M:
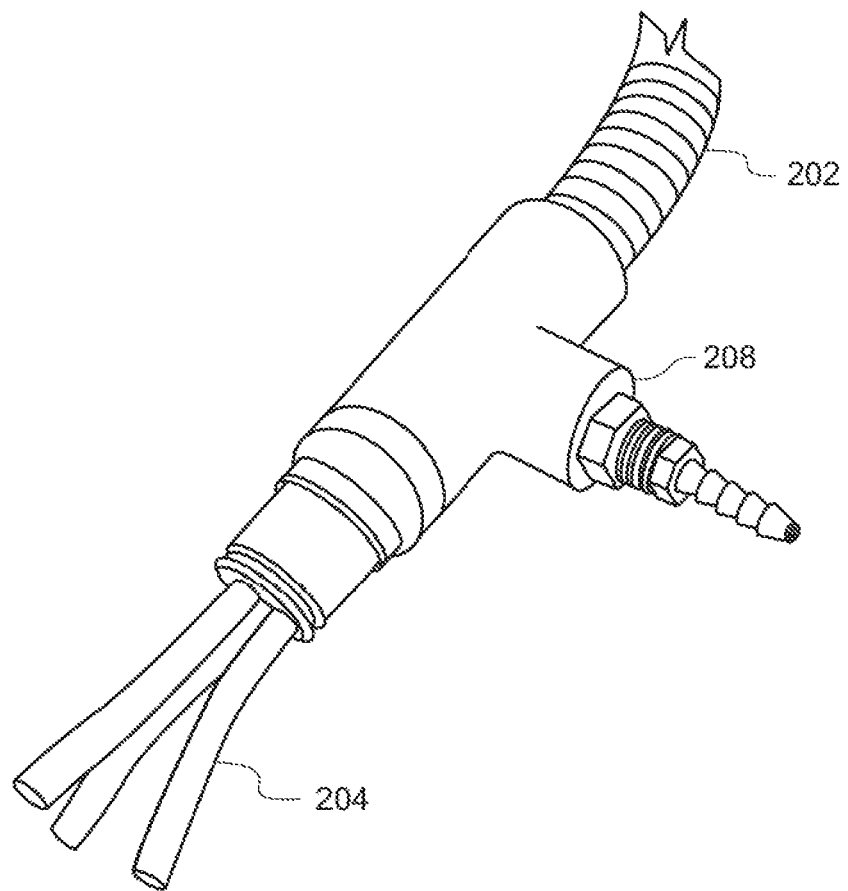
FIG. 2M is a detail view of an alternate embodiment of the tube-in-tube heat exchanger configuration.

Referring now to FIGS. 2, 2J, and 2K the heat exchanger assembly 200 may also include a connector 206 at either end of the heat exchanger 200. In the exemplary embodiment, the heat exchanger 200 has two connectors located at either end of the assembly. These connectors 206 along with the outer tube 202 define an inner cavity for containing the source water. In addition, the connectors attach to the ends of the inner tubes 204 and provide separate fluid paths for the product and blowdown water to enter and/or exit the heat exchanger 200. The connectors 206 allow the heat exchanger assembly to be mechanically connected to the evaporator/condenser and other apparatus components. In some embodiments an extension 207 may be included within the heat exchanger 200 to provide an additional port to remove or supply water to the heat exchanger 200.

Figure 2N:
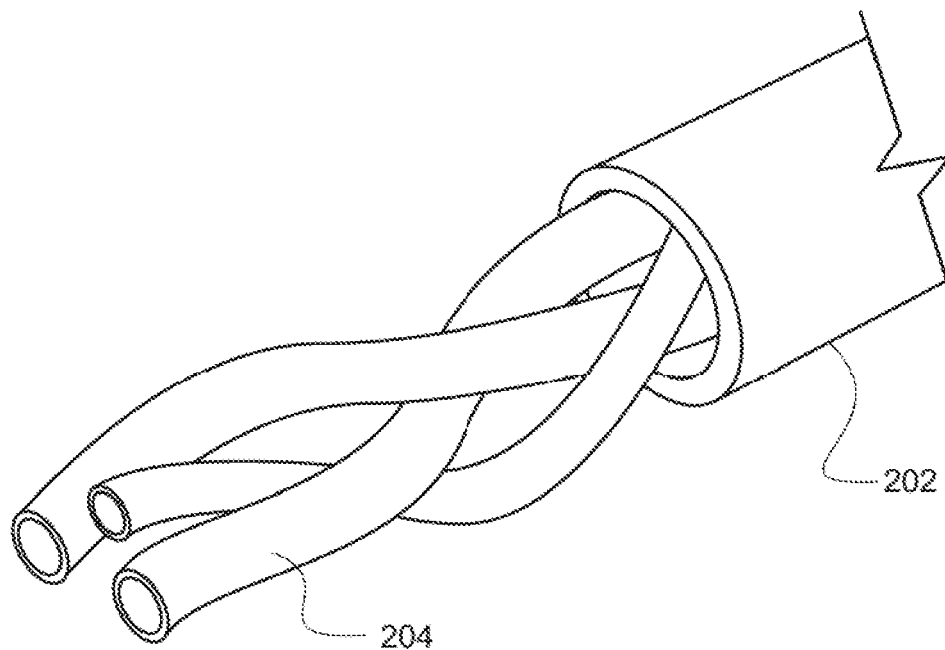
FIG. 2N is a detail view of an alternate embodiment of the tube-in-tube heat exchanger configuration.

Referring now to FIGS. 2L-O, these figures illustrate an alternate embodiment of the heat exchanger 200 having three inner tubes 204 passing through connectors 208. The connectors 208 are sealed and attached to the inner tubes 204 and the outer tube 202 at either end of the heat exchanger 200 to contain the source water inside the outer tube 202. An o-ring may be installed within the connectors 208 to seal the interface between the connector 208 and the inner tubes 204. This type seal may allow the inner tubes 204 to move freely and independently of the connector 208. Furthermore, the inner tubes 204 may be arranged in a helical shape as shown in FIG. 2N. Referring also to FIGS. 74-74C, another embodiment of the connector 7400 is shown, which may be used in any of the embodiments described herein.

Figure 2P:
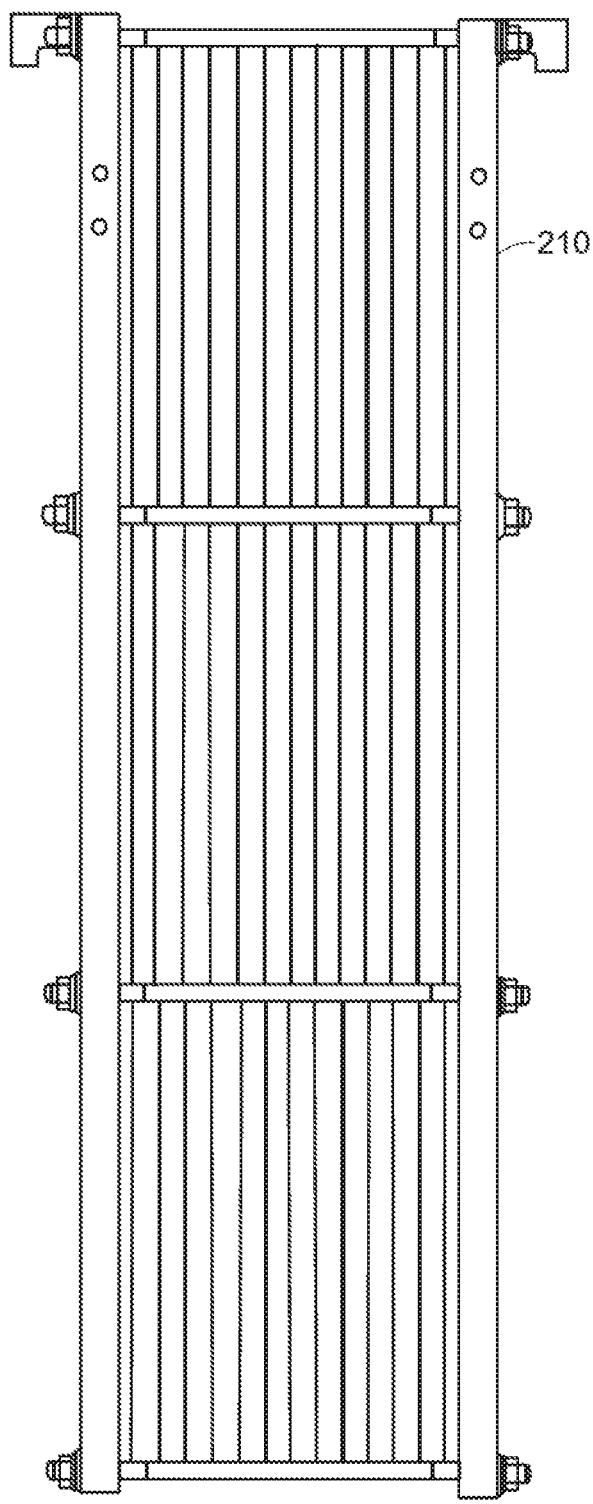
FIG. 2P is an assembly view of an alternate embodiment of the heat exchanger.
Figure 2Q:
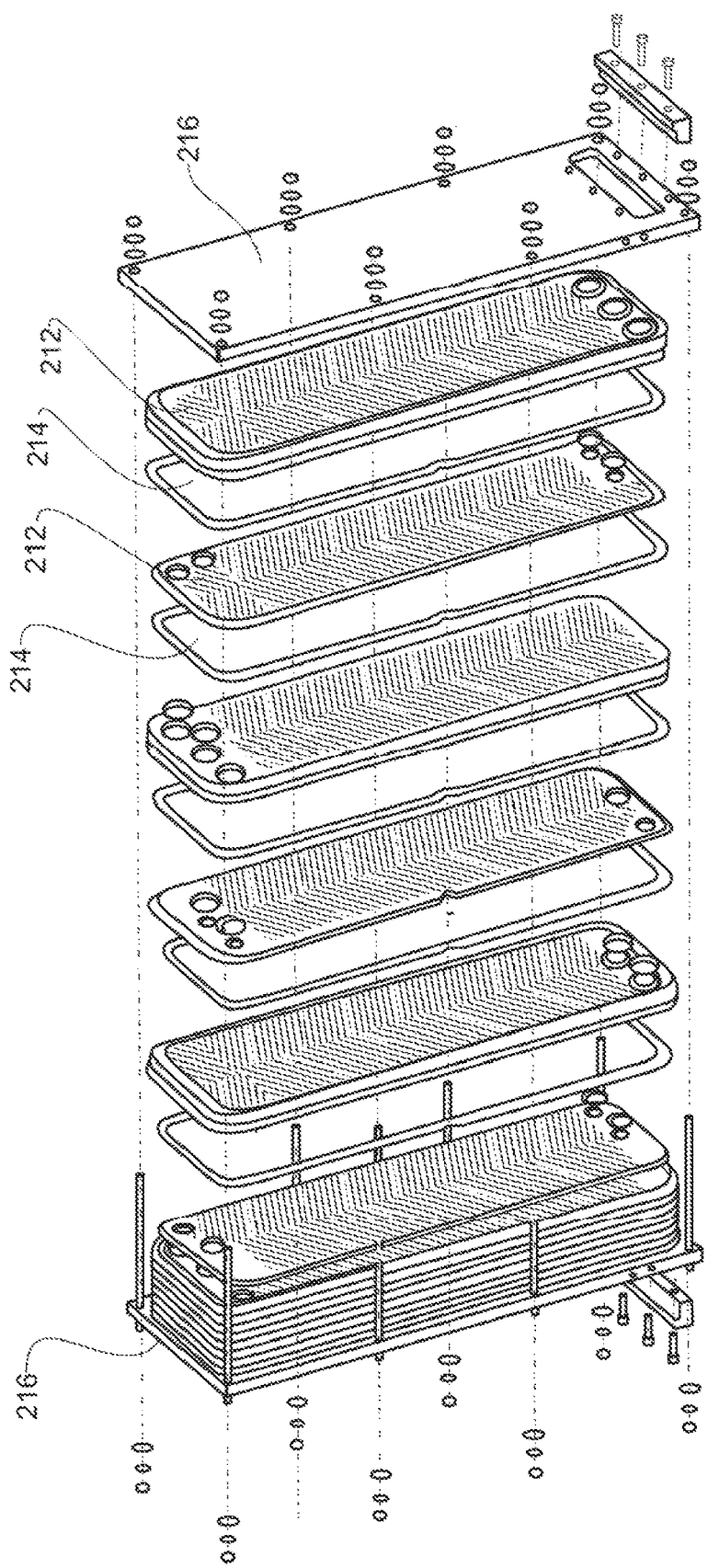
FIG. 2Q is an exploded view of an alternate embodiment of the heat exchanger.
Figure 2R:
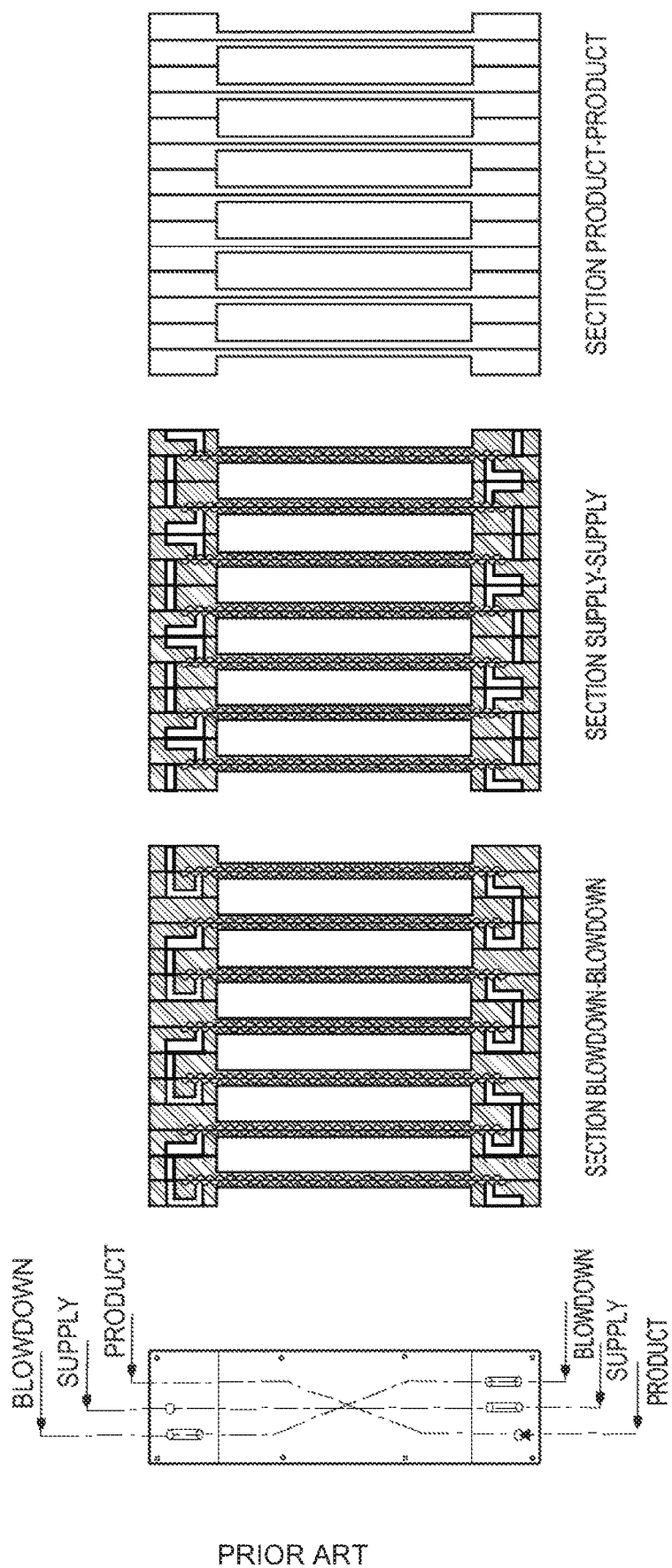
FIG. 2R is a section view of an alternate embodiment of the heat exchanger.

Referring to FIGS. 2P-R, these figures illustrate an alternate embodiment for the heat exchanger 210. In this embodiment, the heat exchanger 210 is a plate heat exchanger having metal plates 212 and plastic plates 214. The metal plates 212 may be manufacture from any metallic materials, such as stainless steel. Other embodiments may include but are not limited to plates manufactured from titanium or metal alloy. The plastic plates 214 are made from any type of plastic capable of performing. In one embodiment, the plate heat exchanger 210 is made from alternately metal and plastic plates. In other embodiments metal plates 212 may be followed by two or more plastic plates 214 as illustrated in FIG. 2R. The plate heat exchanger 210 may begin and/or end with a plate 216 manufacture from the same or different material as the previous plate. In alternate embodiments, plate 216 may be manufactured from a metallic or plastic material. The metal plates 212 consist of two metal plates stacked onto one another creating channels for fluid flow as shown in FIG. 2R.

Referring now to FIG. 3, the exemplary embodiment of the counter flow tube-in-tube heat exchanger 200 may include a fitting assembly 300. The fitting assembly supports installation of the heat exchanger 200 within the water vapor distillation apparatus 100. In addition, the fitting assembly 300 allows the heat exchanger 200 to be easily disconnected from the apparatus for maintenance. The assembly may consist of a first connector 302 (Also identified as connector 206 of FIG. 2) and a second connector 310 shown on FIG. 3. See also, FIGS. 3A-B for cross-section views of the fitting assembly 300.

Still referring to FIG. 3, in the exemplary embodiment of the fitting assembly 300 is manufactured from brass. Other materials may be used to manufacture the fitting assembly 300 including, but are not limited to stainless steel, plastic, copper, copper nickel or titanium. For installation purposes, having the fitting assembly manufactured from similar material as the tubing that attaches to the assembly is preferred. Similar materials allow for the assembly to be installed within the water vapor distillation apparatus using a soldering or welding technique. The fitting assembly 300 is preferably manufactured from materials that are corrosion resistant and heat resistant (250° F.). In addition, the materials preferably allows for a fluid tight connection when the assembly is installed. For applications where the source and blowdown water may be highly concentrated, such as sea water, the fitting assembly 300 may be manufactured from but not limited to copper-nickel or titanium.

Still referring to FIG. 3, the first connector 302 includes a first end 304 and a second end 306. The first end 304 attaches to the heat exchanger 200 as shown in FIGS. 2-2A. The connector may be attached to the heat exchanger 200 by clamping the outer tube 202 using a hose clamp against the outer surface of the first end 304 of the connector 302. The inner tubes 204 of the heat exchanger 200 may also connect to the connector 302 at the first end 304. These tubes may be soldered to the heat exchanger side of the connector 302. Other methods of attachment may include, but are not limited to welding, press fitting, mechanical clamping or insert molding. See also FIGS. 3A-3B for cross-section views of fitting assembly 300.

Figure 3C:
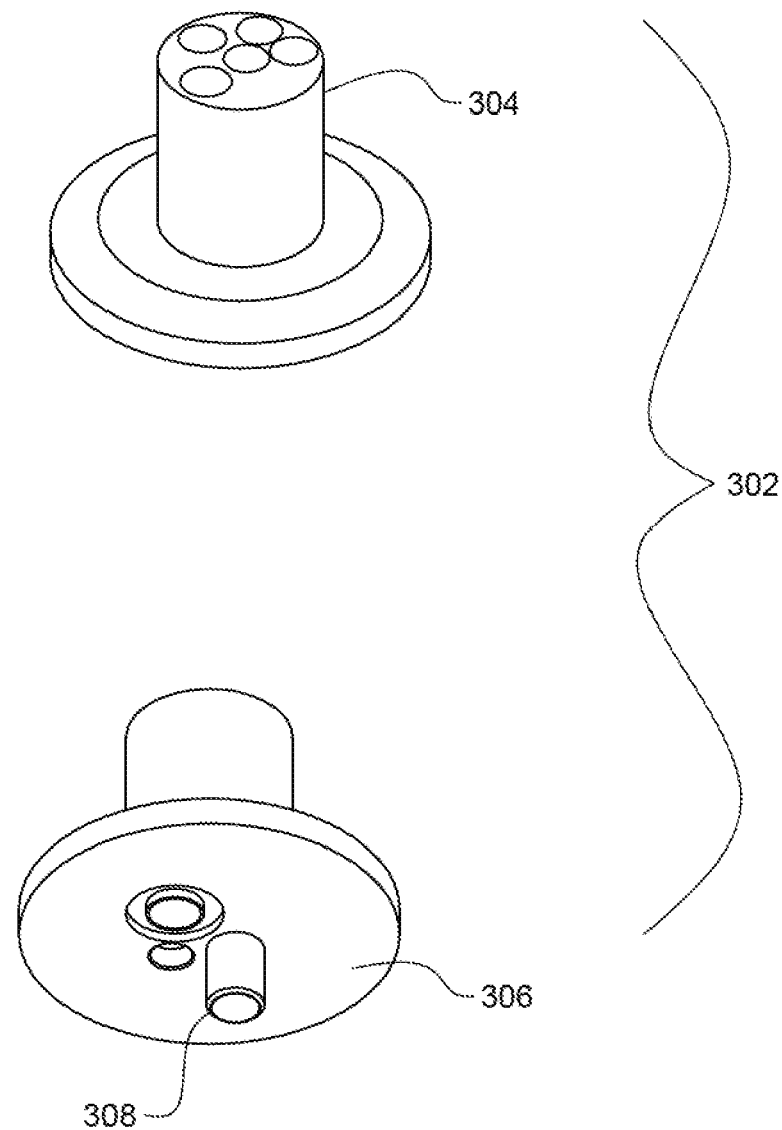
FIG. 3C is an isometric view of the exemplary embodiment for the first connector.
Figure 3D:
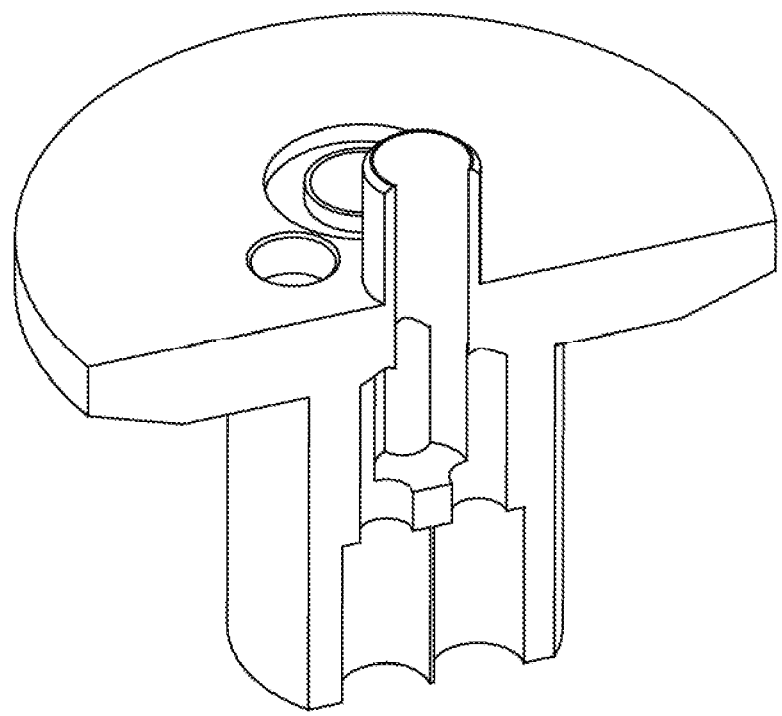
FIG. 3D is a cross-section view of the exemplary embodiment for the first connector.

Now referring to FIG. 3C, in this embodiment the first end 304 of the connector 302 may have five ports. Three ports may be in fluid connection with one another as shown on FIGS. 3D-E. This configuration may combine multiple streams of product water into one stream. Multiple streams of product water increases the amount of heat transfer from the product water to the source water, because there is more product water within the heat exchanger to provide thermal energy to the source water. The remaining ports are separate and provide fluid pathways for blowdown and source water illustrated in FIGS. 3E-F. Alternate embodiments may not have any ports in fluid connection with one another.

Still referring to FIG. 3C, connector 302 has a second end 306 for mating with the second connector 310. This second end 306 may have three ports providing flow paths for product, source and blowdown water. The product flow path may include an extension 308. The extension 308 supports assembling connectors 302 and 310 together because the extension 308 allows for the o-ring groove within the body of the second connector 310 rather than on the mating surface 310. Having the o-ring groove within the body of the second connector 310 allows the flow paths through the connector assembly to be positioned near one another without having overlapping sealing areas.

Figure 3H:
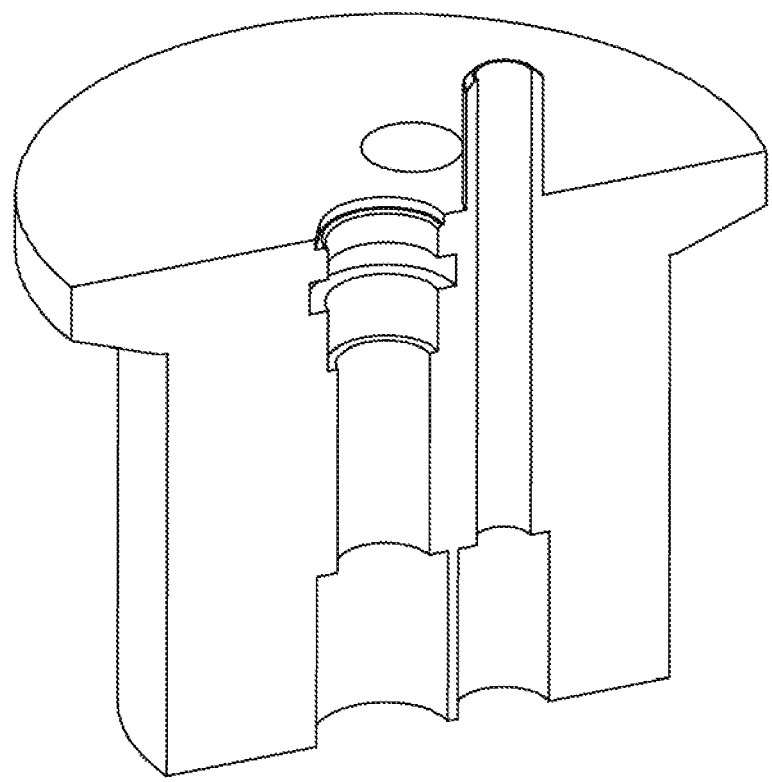
FIG. 3H is a cross-section view of fitting assembly for the tube-in-tube heat exchanger.

Now referring to FIGS. 3G-H, the second connector 310 includes a first end 312 and a second end 314. The first end 312 mates with the first connector 302 as shown on FIG. 3. This end may also include an extension 316 as shown in FIG. 3G. The extension 316 allows for the o-ring groove to be located within the body of the first connector 302 rather than within the surface of end 306 of the first connector 302. In addition, this connector may have a leak path 318 on the first end 312. This path is located around the port for the product water to prevent source or blowdown water from entering the product stream. Blowdown and source water may contain contaminants that affect the quality and safety of the product water. The leak path allows the blowdown and source water to leave the fitting rather than entering the product stream through a drain 320 illustrated on FIGS. 3G-I. In addition to the drain 320, the exemplary embodiment may include three independent fluid paths within the connector 310 illustrated on FIGS. 3I-J.

The first connector 302 may be assembled to the second connector 310 using a Marmon clamp to allow for serviceability of the apparatus. This type of clamp provides an even clamping force and ease of disassembly/reassembly of the connection. Other methods of assembling the connectors together include, but are not limited using a C-clamp or fasteners (i.e. bolts and nuts). In addition, the circumference of the connectors 302 and 310 may be tapered, as shown on FIGS. 3E-F and 3I-J, to receive the clamp during installation of the fitting assembly 300. In other embodiments, the fitting assembly 300 may be permanently joined by welding or soldering the connectors together.

Evaporator Condenser

Figure 4:
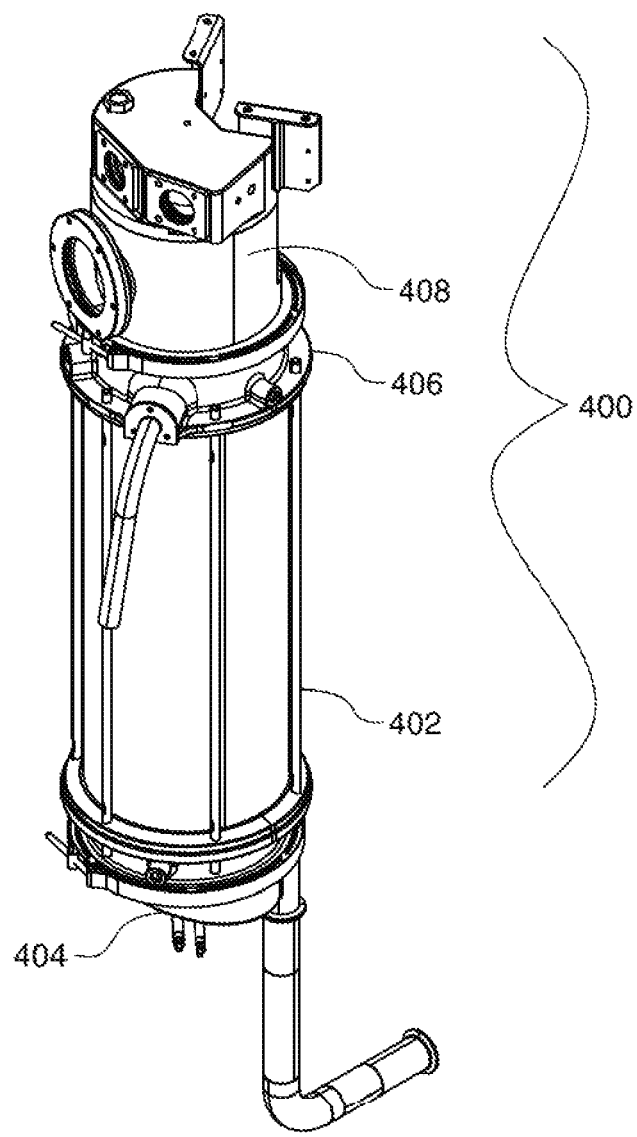
FIG. 4 is an isometric view of the exemplary embodiment of the evaporator/condenser assembly.
Figure 4A:
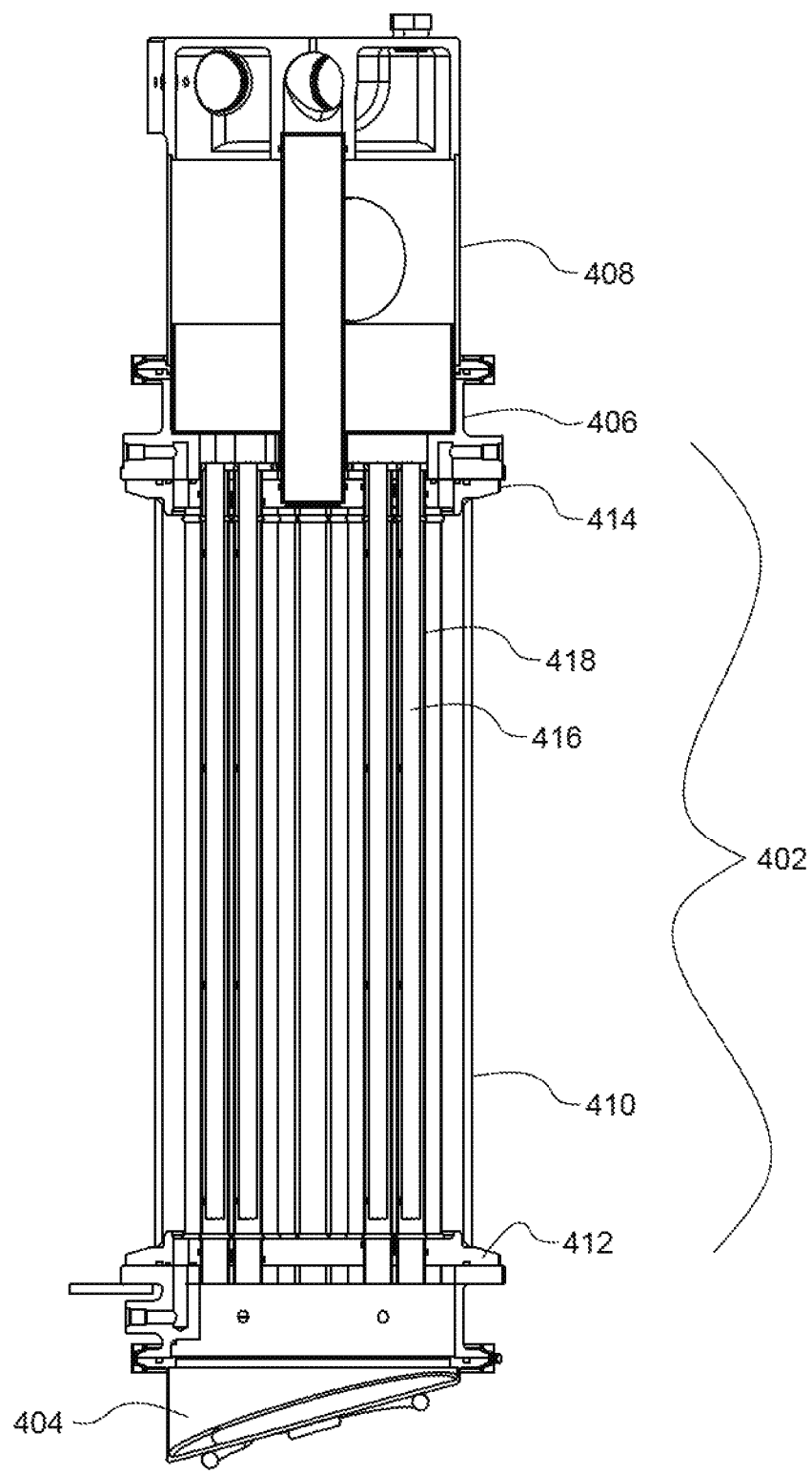
FIG. 4A is a cross-section view of the exemplary embodiment of the evaporator/condenser assembly.
Figure 4B:
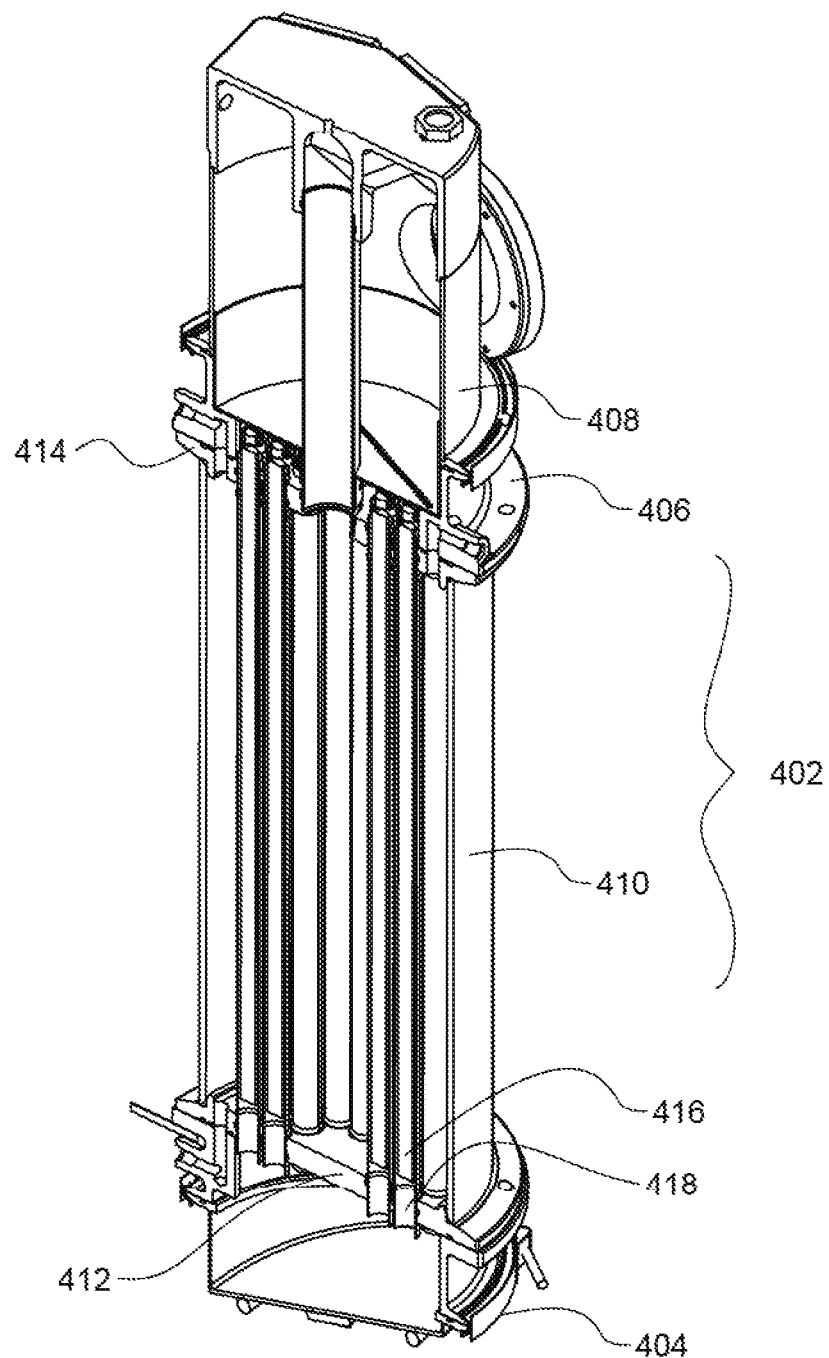
FIG. 4B is an isometric cross-section view of the exemplary embodiment of the evaporator/condenser.
Figure 4C:
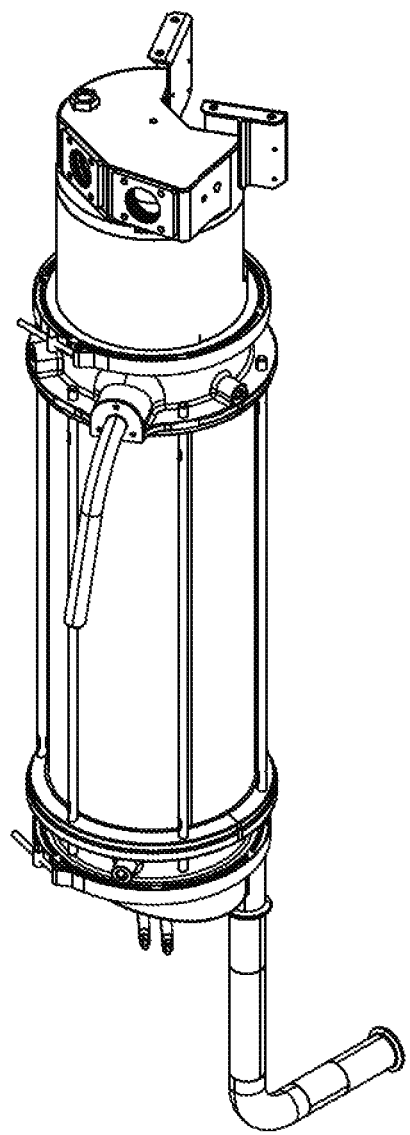
FIG. 4C is an isometric view of an alternate embodiment of the evaporator/condenser assembly.

Now referring to FIGS. 4-4B, the exemplary embodiment of the evaporator condenser (also herein referred to as an "evaporator/condenser") assembly 400 may consist of an evaporator/condenser chamber 402 having a top and bottom. The chamber 402 may include a shell 410, an upper tube sheet 414 and a lower tube sheet 412. Attached to the lower tube sheet 412 is a sump assembly 404 for holding incoming source water. Similarly, attached to the upper tube sheet 414 is an upper flange 406. This flange connects the steam chest 408 to the evaporator/condenser chamber 402. Within the evaporator/condenser chamber 402 are a plurality of rods 416 where each rod is surrounded by a tube 418 as illustrated in FIGS. 4A and 4B. The tubes 418 are in fluid connection with the sump 404 and upper flange 406. See also FIG. 4C illustrating an alternate embodiment of the evaporator/condenser assembly 420.

Figure 5:
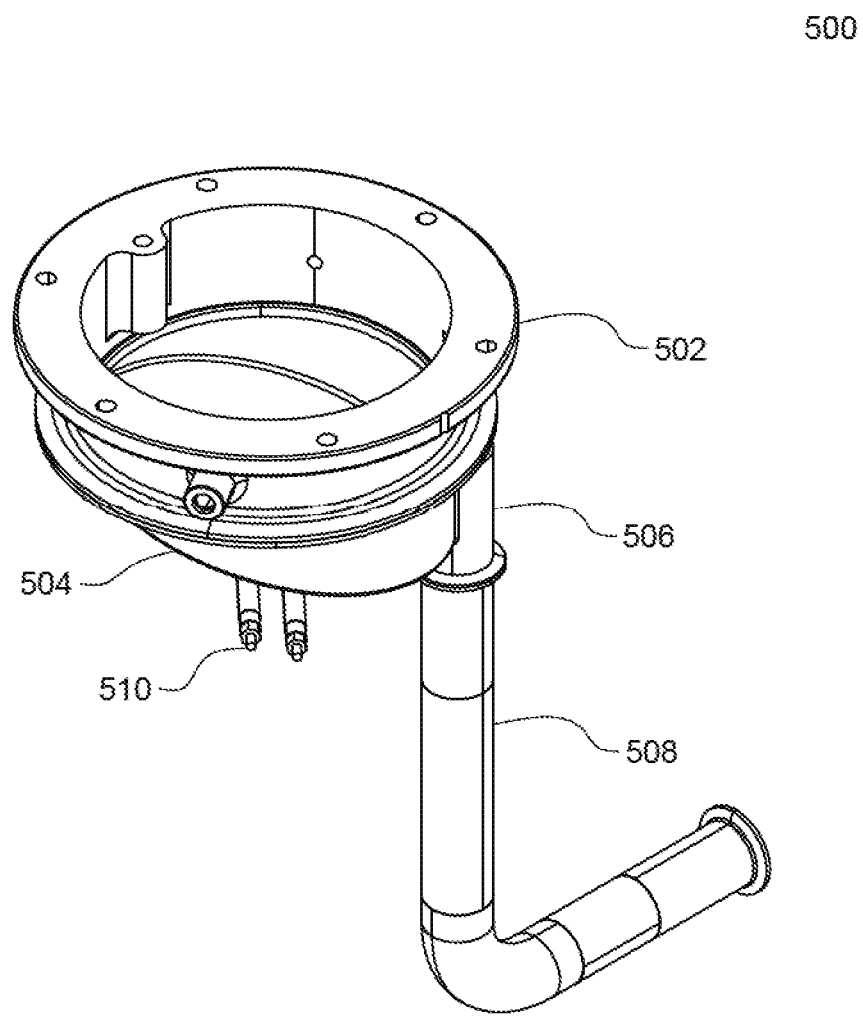
FIG. 5 is an assembly view of the exemplary embodiment of the sump.

Now referring to FIG. 5, the sump assembly 500 (also identified as 404 on FIG. 4) may include an upper housing 502, a lower housing 504, a drain fitting 506, drain pipe 508, and heating element 510. See also FIG. 5A for an exploded view of the sump assembly 500 and FIG. 6 for detailed view of the upper housing 502. The sump assembly 500 contains and heats source water, as well as collects particulate carried by the source water. When the source water changes state from a fluid to a vapor particulate is left behind and is collected in the sump assembly 500.

Figure 5A:
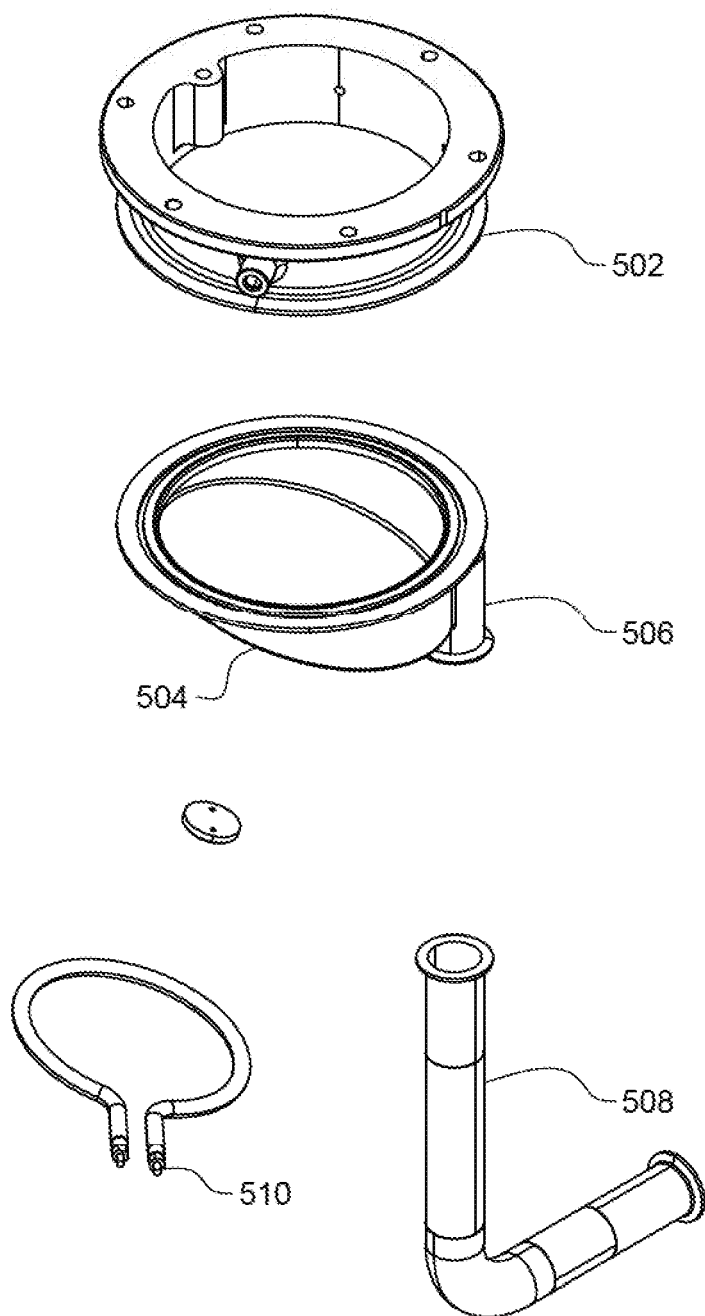
FIG. 5A is an exploded view of the exemplary embodiment of the sump.
Figure 6:
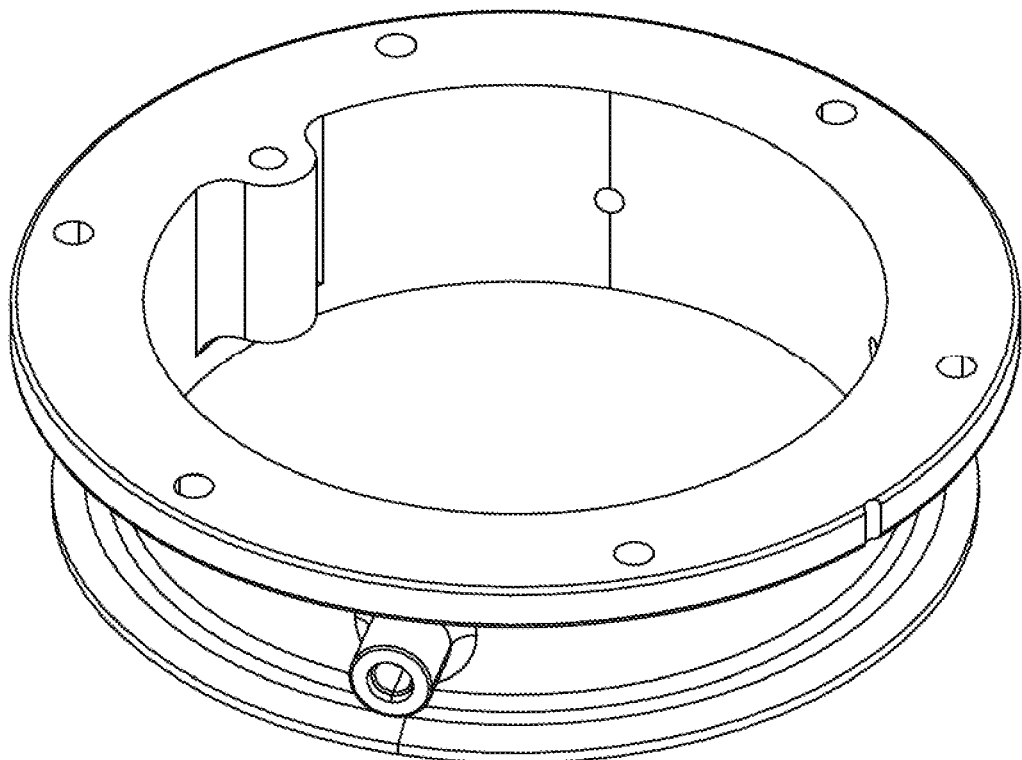
FIG. 6 is an isometric detail view of the flange for the sump assembly.

Still referring to FIGS. 5-5A, the sump assembly 500 may be made from material that is corrosion and high-temperature resistant. A corrosion resistant material is preferred because the sump is exposed to high temperatures, moisture, and corrosive source water. In the exemplary embodiment the sump is manufactured from stainless steel. In an alternate embodiment the sump may be manufactured from RADEL® or other high-temperature plastic in conjunction with an alternate configuration for attaching the heating element 510. For applications where the source water may be highly concentrated, such as sea water, the sump assembly 500 may be manufactured from but not limited to titanium, copper-nickel, naval bronze, or high-temperature plastic.

Still referring to FIGS. 5-5A, the source water may be heated using a heating element 510 of the sump assembly 500. The heat element 510 increases the temperature of the source water during initial start up of the water vapor distillation apparatus 100. This element provides additional thermal energy causing the source water to change from a fluid to a vapor. In the exemplary embodiment, the heat element 510 may be a 120 Volt/1200 Watt resistive element electric heater.

Still referring to FIGS. 5-5A, the sump assembly 500 may include a bottom housing 504 having an angled lower surface in order to assist with the collection of particulate. The bottom housing 504 may have any angle sufficient to collect the particulate in one area of the housing. In the exemplary embodiment the bottom housing 504 has a 17 degree angled-lower surface. In other embodiments, the bottom housing 504 may have a flat bottom.

Still referring to FIGS. 5-5A, the exemplary embodiment may include a drain assembly consisting of a drain fitting 506 and a drain pipe 508. The drain assembly provides access to inside of the evaporator area of the evaporator/condenser to remove particulate buildup without having to disassemble the apparatus. The drain assembly may be located near the bottom of the sump to reduce scaling (buildup of particulates) on the tubes inside the evaporator/condenser. Scaling is prevented by allowing periodic removal of the scale in the sump assembly 500. Having less particulate in the sump assembly 500 reduces the likelihood that particulate will flow into the tubes of the evaporator/condenser. In the exemplary embodiment the drain assembly is positioned to receive particulate from the angled-lower surface of the bottom housing 504. The drain assembly may be made of any material that may be attached to the bottom housing 504 and is corrosion and heat resistant. In the exemplary embodiment, the drain fitting 506 is a flanged sanitary fitting manufactured from stainless steel. Referring now also to FIG. 73, a sump drain 7302 fluid pathway is shown. In some embodiments, sump drain 7302 fluid pathway may be used to facilitate the cleaning or flushing of the apparatus 100. In some embodiments, the sump drain 7302 fluid pathway may be sealed to the outside environment by a valve, for example, but not limited to, a manual ball valve. In some embodiments, the valve may be a non-manual valve, for example, an actuated valve controlled by the control system, and in some of these embodiments, the cleaning and flushing may be at least partially automated.

Still referring to FIGS. 5-5A, attached to the drain fitting 506 may be a drain pipe 508. The drain pipe 508 provides a fluid path way for particulate to travel from the drain fitting 506 out of the evaporator/condenser assembly 400. The drain pipe 508 may be manufactured from any material, with preference that the material is corrosion and heat resistant and is capable of being attached to the drain fitting 506. In the exemplary embodiment, the drain pipe 508 is manufactured from stainless steel. The diameter of the drain pipe 508 is preferably sufficient to allow for removal of particulate from the sump assembly 500. A larger diameter pipe is desirable because there is a less likelihood of the drain pipe 508 becoming clogged with particulate while draining the sump assembly 500.

Figure 7:
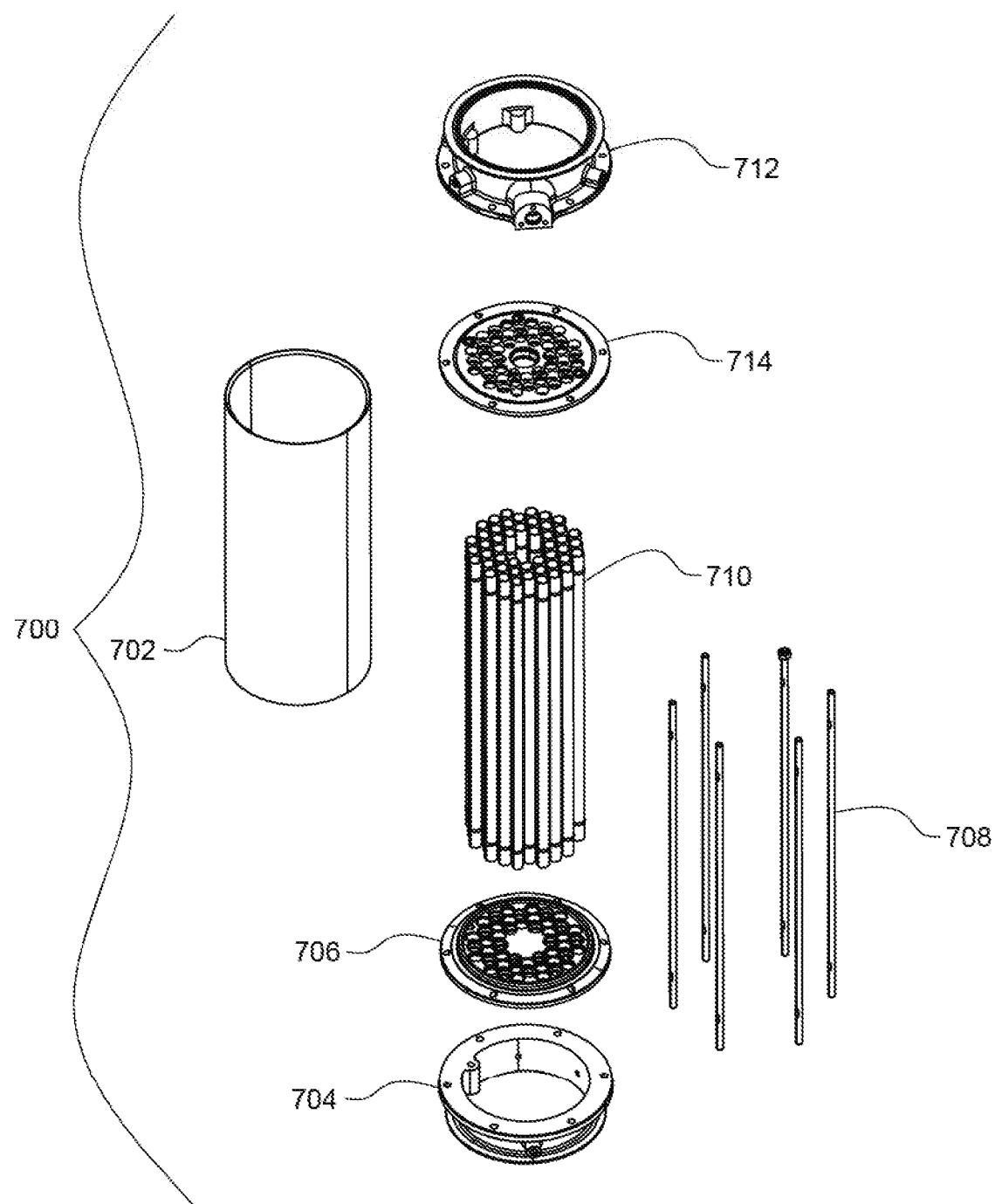
FIG. 7 is an exploded view of the exemplary embodiment of the evaporator/condenser.

Now referring to FIG. 7, the exemplary embodiment of the evaporator/condenser chamber 700 (also identified as 402 of FIG. 4) may include a shell 702 (also identified as 410 of FIGS. 4A-B, a lower flange 704 (also identified as 502 of FIG. 5 and 600 of FIG. 6), a lower-tube sheet 706 (also identified as 412 of FIGS. 4A-B), a plurality of tie rods 708, a plurality of tubes 710 (also identified as 418 of FIGS. 4A-B), an upper flange 712 (also identified as 406 of FIG. 4) and an upper-tube sheet 714 (also identified as 414 of FIGS. 4A-B). See also FIG. 7A for an assembly view evaporator/condenser chamber 700.

Still referring to FIG. 7, the shell 702 defines an internal cavity where thermal energy is transferred from the high-pressure steam to the source water. This heat transfer supports the phase change of the source water from a fluid to a vapor. In addition, the heat transfer also causes the incoming steam to condense into product water. The shell 702 may be manufactured from any material that has sufficient corrosion resistant and strength characteristics. In the exemplary embodiment, the shell 702 is manufactured from fiberglass. It is preferable that the shell has an inner diameter sufficient to contain the desired number of tubes 710. Within the internal cavity of the shell is a plurality of tubes 710 having surface area for transferring thermal energy from the high-pressure steam entering the chamber to source water within the tubes 710.

Still referring to FIG. 7, the evaporator/condenser chamber 700 defines an inner cavity for the condensation of high-pressure steam. Within this cavity is a plurality of tubes 710 that transfer thermal energy from high-pressure steam to source water within the tubes as the steam condensing upon outer surfaces of the tubes. The heat transfer through the tube walls causes the source water to undergo a phase change through a process called thin film evaporation as described in U.S. Patent Application Pub. No. US 2005/0183832 A1 published on Aug. 25, 2005 entitled "Method and Apparatus for Phase Change Enhancement," the contents of which are hereby incorporated by reference herein.

Still referring to FIG. 7, in the tubes 710 of the evaporator/condenser, a Taylor bubble may be developed which has an outer surface including a thin film in contact with an inner surface of the tubes 710. The Taylor bubble is heated as it rises within the tube so that fluid in the thin film transitions into vapor within the bubble.

Figure 7A:
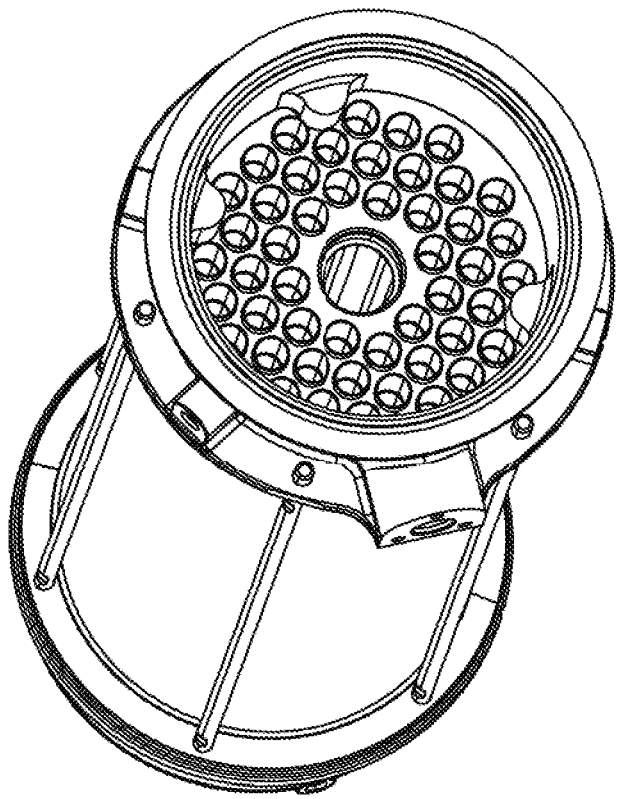
FIG. 7A is an top view of the exemplary embodiment of the evaporator/condenser assembly.
Figure 7B:
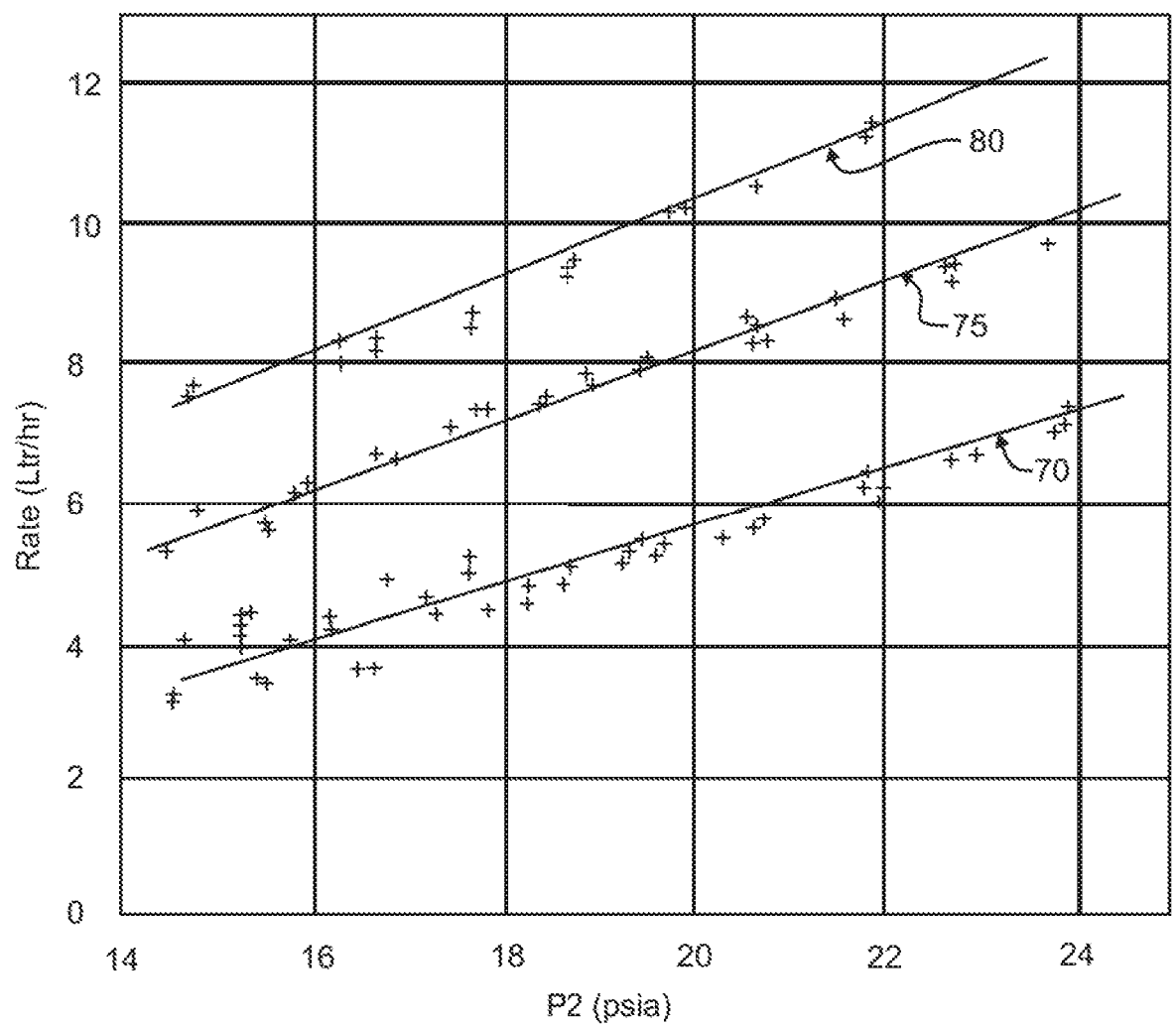
FIG. 7B shows the rate of distillate output for an evaporator as a function of pressure for several liquid boiling modes.

Now referring to FIG. 7B, typically an evaporator may operate in either of two modes: pool boiling mode or thin film mode. In thin film boiling, a thin film of fluid is created on the inner wall of the tubes facilitating heat transfer from the tube wall to the free surface of the fluid. The efficiency of phase change typically increases for thin film mode as compared to pool boiling mode. FIG. 7B shows the difference in the rate of distillate production as a function of condenser pressure for pool boiling and thin film boiling under similar conditions for a representative evaporator. The bottom curve 70 corresponds to pool boiling while the middle curve 75 corresponds to thin film boiling. As will be noted from these two curves, thin film boiling mode offers significantly higher efficiency than pool boiling mode. Thin film boiling is more difficult to maintain than pool boiling, however. Thin film evaporation is typically achieved using apparatus that includes very small openings. This apparatus may easily clog, particularly when the source fluid contains contaminants. Additionally, in thin film mode the water level is typically held just marginally above the tops of the tubes in a vertical tube-type evaporator. For reasons such as this, the apparatus may also be sensitive to movement and positioning of the apparatus.

Referring back to FIG. 7, in the exemplary embodiment the tubes 710 have an outer diameter of 0.75 inches and may be manufactured from copper. In alternate embodiments, the tubes 710 may be manufactured from other materials including but not limited to nickel copper or other composite materials. In various other embodiments, the diameter of the tubes may different, i.e., may be smaller or larger. For possible applications where the source water may be seawater, the tubes 710 may be manufactured from copper-nickel or titanium material. These materials have high corrosion resistant properties to maintain the heat transfer characteristics of the tubes when exposed to highly concentrated source water, such as, salt water. The diameter of the tubes 710 may also vary depending on many variables. The diameter of the tubes 710 may be limited by the inner diameter of the shell 702 and the desired amount of heat transfer efficiency. Another constraint may be serviceability. A smaller diameter is more difficult to remove scale from because the reduced diameter restricts access to the inner surfaces of the tube walls. The length of the tubes 710 may be determined by the length of the inner cavity defined by the shell 702 and the thickness of the tube sheets 706 and 714. In the exemplary embodiment the tubes 710 extend beyond the ends of the tube sheets into the lower flange 704 and upper flange 712.

Figure 8:
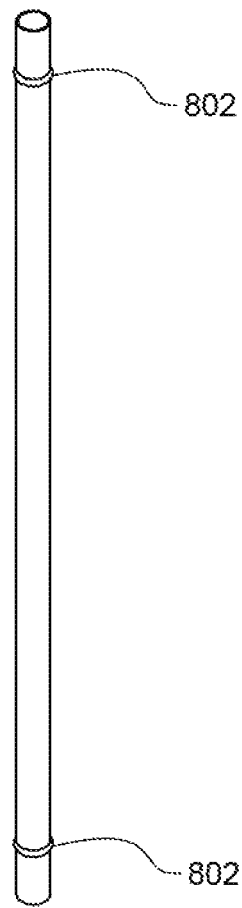
FIG. 8 is an isometric view of the exemplary embodiment of the tube for the evaporator/condenser.

Referring now to FIG. 8, in the exemplary embodiment the tubes 800 (also identified as 710 of FIG. 7A-B) have a bead 802 near each end. The bead 802 prevents the tubes 800 from sliding through the apertures in the lower tube sheet 706 and the upper tube sheet 714.

Figure 9:
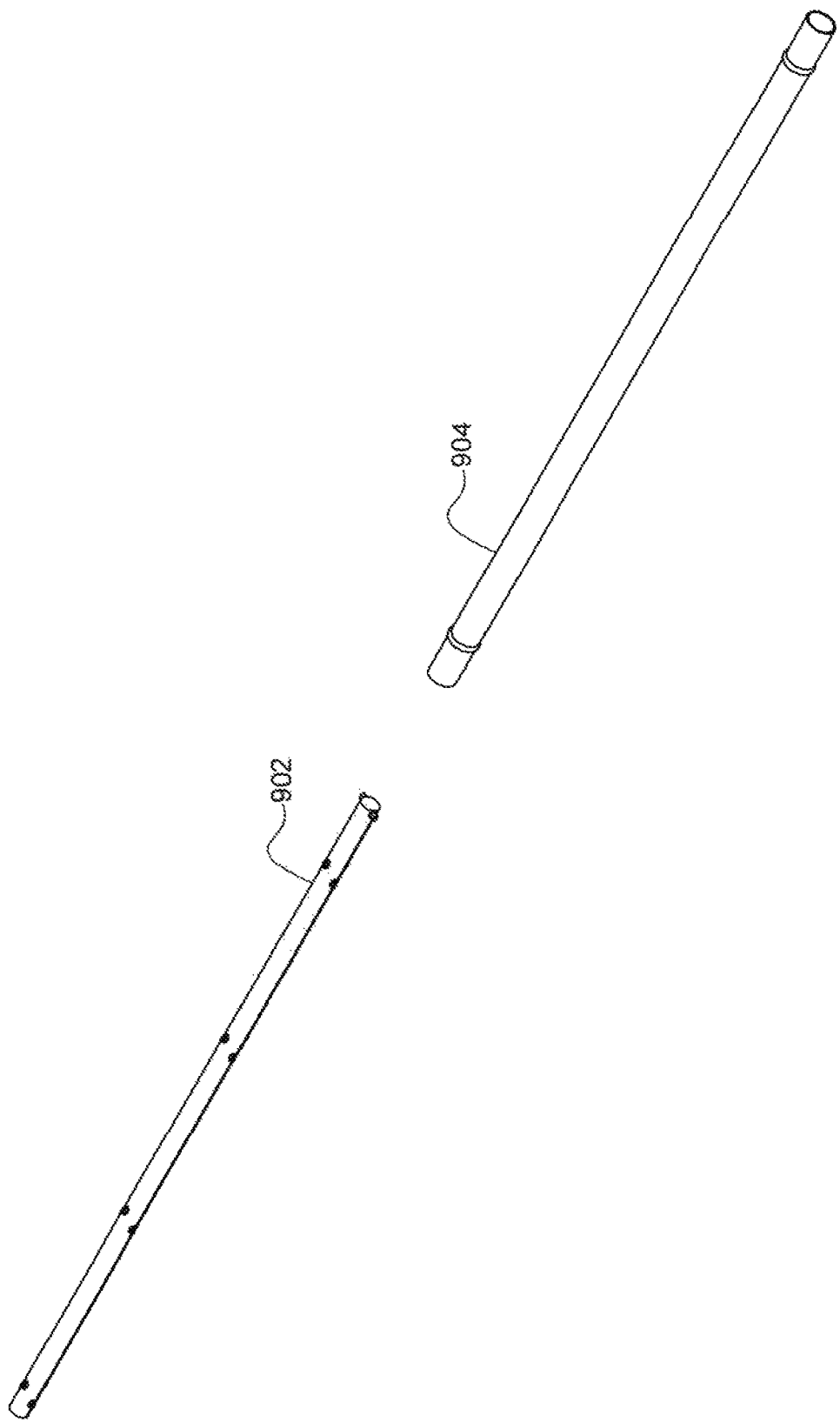
FIG. 9 is an exploded view of the tube and rod configuration for the evaporator/condenser.

Referring now to FIG. 9, improved efficiency of a phase change operation may be achieved by providing packing within the evaporator/condenser tubes 904. The introduction of such packing may allow the evaporator to take on some of the characteristics of thin film mode, due to the interaction between the fluid, the packing and the tube 904. The packing may be any material shaped such that the material preferentially fills the volume of a tube 904 near the tube's longitudinal axis versus the volume near the tube's interior wall. Such packing material serves to concentrate the vapor near the walls of the tube for efficient heat exchange. For example, in the exemplary embodiment the packing may comprise a rod 902. Each rod 902 may be of any cross-sectional shape including a cylindrical or rectangular shape. The cross-sectional area of each packing rod 902 may be any area that will fit within the cross-section of the tube. The cross-sectional area of each rod 902 may vary along the rod's length. A given rod 902 may extend the length of a given evaporator tube 904 or any subset thereof. It is preferable that the rod material be hydrophobic and capable of repeated thermal cycling. In the exemplary embodiment the rods 902 are manufactured from glass fiber filled RYTON® or glass fiber filled polypropylene.

Still referring to FIG. 9, each rod 902 may be positioned anywhere within the tube 904 including preferentially in the upper portion of the tube. In one specific embodiment, each rod is approximately half the length of the associated tube and is positioned approximately in the top half of the tube. The top curve 80 in FIG. 7B shows the increase in boiling efficiency for thin film boiling for a representative evaporator where the evaporator tubes include packing material in approximately the top half of the tubes. With such packing, the phase change efficiency is also, advantageously, much less sensitive to changes in the fluid level above the tubes, the orientation of the tubes with respect to the vertical, the feed pressure for the tubes and other operating parameters for the evaporator. In the exemplary embodiment the rods 902 have approximately the same length as the tubes 904.

Figure 9A:
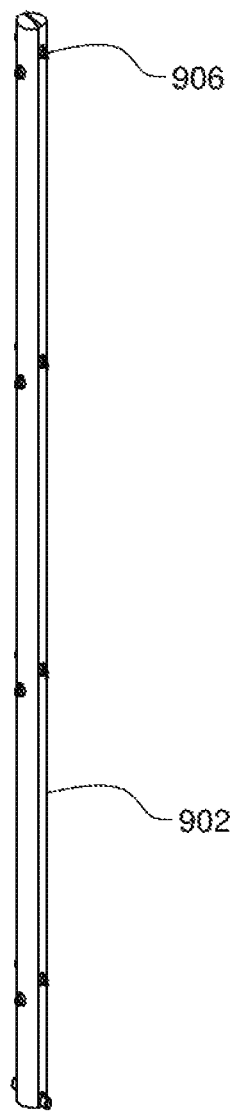
FIG. 9A is an isometric view of the exemplary embodiment of the rod for the evaporator/condenser.

Referring now to FIG. 9A, in the exemplary embodiment, the rods 902 may have a plurality of members 906 extending out from the center and along the longitudinal axis of the rod 902. These members 906 maintain the rod 902 within the center of the tube 904 to produce the most efficient flow path for the source water. Any number of members may be used, however, it is preferential that there is a sufficient number to maintain the rod 902 in the center of the tube 904. In alternate embodiments, the rods 902 may not have members 906. In alternate embodiments the rod 902 may be held in place within the tube 904 by wrapping the rod 902 in a wire or cross drilling holes within the rod 902 to support installation of pins to position the rod 902 within the tube 904.

Figure 10A:
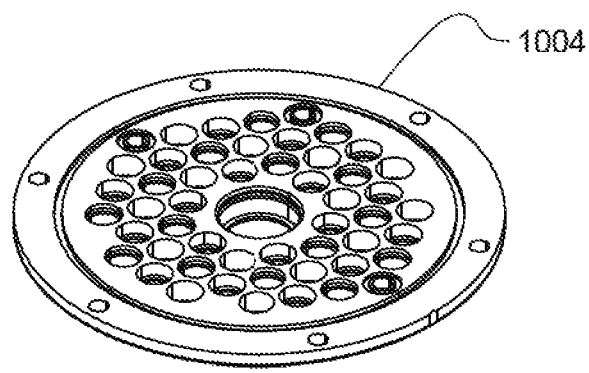
FIG. 10A is an isometric view of the exemplary embodiment of the upper tube sheet.

Referring back to FIG. 7, the tubes 710 (Also identified as 800 of FIG. 8 and 904 of FIG. 9) are secured in place by the pair of tube sheets 706 and 714. These sheets are secured to each end of the shell 702 using the tie rods 708. The tube sheets 706 and 714 have a plurality of apertures that provide a pathway for the source water to enter and exit the tubes 710. When the tubes 710 are installed within the chamber 700, the apertures within the tube sheets 706 and 714 receive the ends of the tubes 710. The lower tube sheet 706 (also identified as 1002 on FIG. 10) is attached to the bottom of the shell 702. See FIG. 10 for a detail view of the lower tube sheet. The upper tube sheet 714 (also identified as 1004 on FIG. 10A) is attached to the top of the shell 702. See FIG. 10 A for a detail view of the upper tube sheet. Both tube sheets have similar dimensions except that the upper tube sheet 714 has an additional aperture located in the center of the sheet. This aperture provides an opening for the high-pressure steam to enter the evaporator/condenser chamber 700.

Still referring to FIG. 7, in the exemplary embodiments the upper-tube sheet 714 and the lower-tube sheet 706 may be manufactured from RADEL®. This material has low creep, hydrolytic stability, thermal stability and low thermal conductivity. Furthermore, tube sheets manufactured from RADEL® may be formed by machining or injection molding. In alternate embodiments, the tube sheets may be manufactured from other materials including but are not limited to G10.

Still referring to FIG. 7, the size of the plurality of apertures within the tube sheets 706 and 714 for receiving the tubes 710 is governed by the outside diameter of the tubes 710. These apertures must be sufficient to receive the end of the tubes 710 and also include a seal. Typically, an o-ring groove is provided within the tube sheets to receive an o-ring. This o-ring provides a water-tight seal between the inner tubes 710 and the tube sheets 706 and 714. In addition, this type of seal simplifies construction, facilitates the use of dissimilar materials within the evaporator/condenser, and allows the tubes 710 to move during repeated thermal cycles. This seal prevents the product water from entering into the sump 500 of FIG. 5 or source water entering the chamber 700. In alternate embodiments, the tubes 710 may be installed within the apertures of the tube sheets 706 and 714 by the using the methods of, but not limited to soldering, welding, press fitting, bonding (i.e. silicone, RTV, epoxy . . . ), brazing or swaging depending on the tube sheet material.

Figure 10:
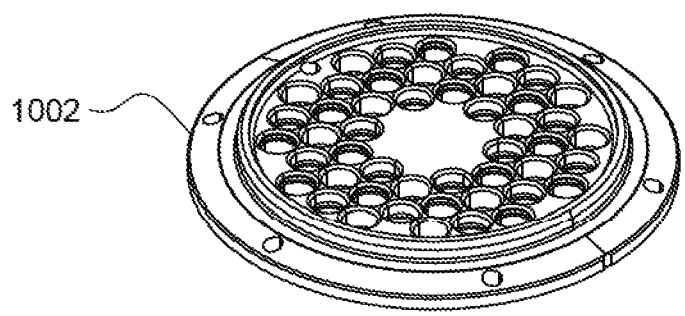
FIG. 10 is an isometric view of the exemplary embodiment of the sump tube sheet.

Now referring to FIG. 10, in the exemplary embodiment the o-ring grooves are located at various depths in the tube sheets 1002 and 1004. The different depths of the o-ring grooves allows the tubes 710 to be positioned more closely together, because the o-ring grooves from adjacent tubes do not overlap one another. Overlapping o-ring grooves do not provide a sufficient seal, thus each o-ring groove must be independent of the other o-ring grooves within the tube sheet. As a result of varying the location of the o-ring grooves at different depths within the tube sheet, adjacent o-ring grooves do not overlap one another allowing the tubes to be positioned closer together. Thus having the tubes 710 located closer to one another allows more tubes to be positioned within the evaporator/condenser chamber 700.

Referring back to FIG. 7, the tube sheets 706 and 714 are also secured to the lower flange 704 and the upper flange 712 using the tie rods 708. The lower flange 704 (also identified as 502 of FIG. 5 and 600 of FIG. 6) connects the sump 500 of FIG. 5 to the evaporator/condenser chamber 700 of FIG. 7. In addition, the lower flange 704 provides a fluid connection for the source water within the sump to the inlet of tubes 710 positioned on the lower tube sheet 706. The lower flange 704 may have any height with preference that the height is sufficient to allow for an even distribution of the source water entering the tubes 710. Typically a flange having a height of one to two inches provides for an even distribution of source water into the tubes 710. In alternate embodiments the height of the flange may be larger to increase the capacity of the sump to collect particulate.

Figure 11:
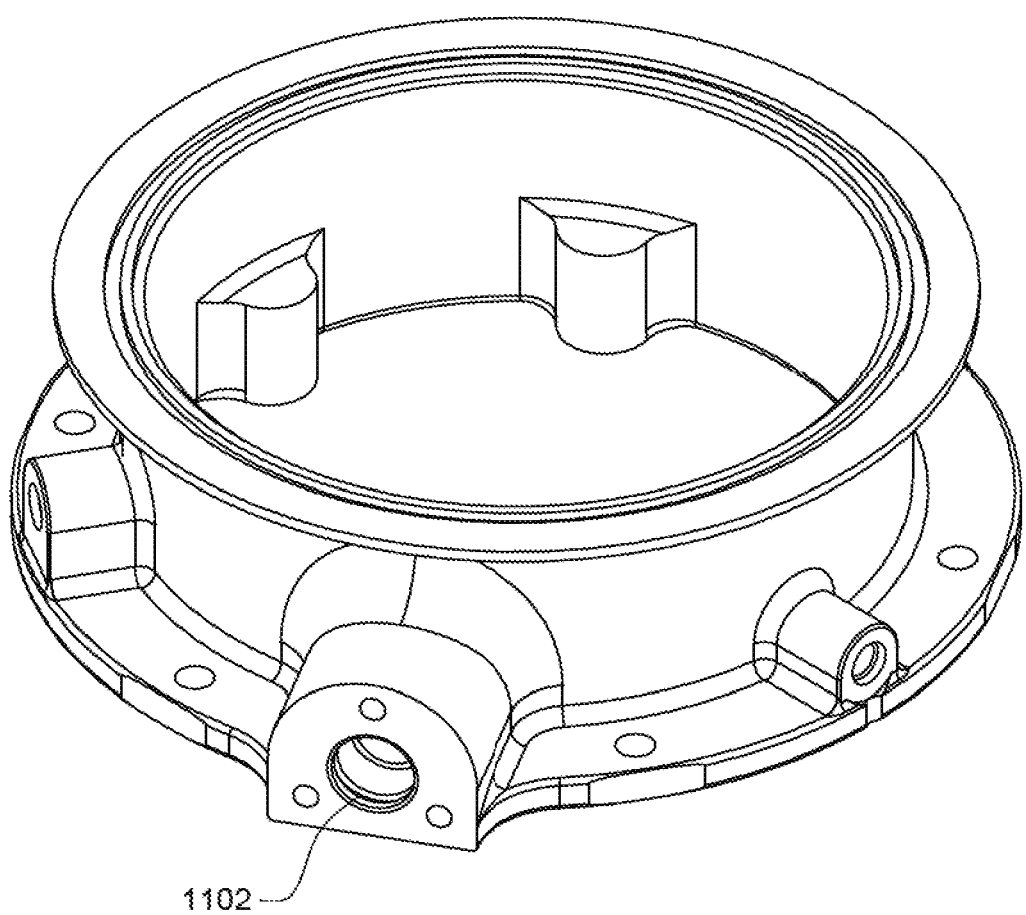
FIG. 11 is a detail view of the top cap for the evaporator/condenser.

Still referring to FIG. 7, the upper flange 712 (also identified as 1100 of FIG. 11) provides a fluid connection between the outlet of the tubes 710 and the steam chest 408 of FIG. 4. In addition, the upper flange 712 collects the source water removed from the low-pressure steam as the steam passes through the steam chest 408. This water is then transferred out of the apparatus through the blowdown port 1102 located within the side of the upper flange 1100 of FIG. 11.

Still referring to FIG. 7, the lower flange 704 and upper flange 712 may be manufactured out of any material having sufficient structural strength and corrosion and temperature resistant properties. In one embodiment, the flanges may be manufactured from RADEL®. In the exemplary embodiment the flanges may be manufactured from nickel-plated aluminum. In other embodiments the lower flange may be manufacture from material including but not limited to stainless steel, titanium and copper-nickel.

Referring to FIG. 7-7A, located near the outer edge of the lower flange 704 and the upper flange 712 is a plurality of apertures to receive the tie rods 708. These rods are axially positioned on a bolt circle concentric to and along the outside perimeter of the shell 702. The length of the tie rods 708 is governed by the length of the shell 702 and the thickness of the lower-tube sheet 706, lower flange 704, upper flange 712 and upper-tube sheet 714. The tie rods 708 may have threaded ends for attaching a threaded fastener onto each end of the rod securing the components of the evaporator/condenser together. In addition, the tie rods 708 may be manufactured from any material that is of sufficient strength for the purpose, such as, stainless steel. Tie rods 708 may be manufactured from other materials including, but not limited to bronze, titanium, fiberglass composite materials, and carbon steel. In the exemplary embodiment, the tie rods 708 may have flats machined near each end to provide a flat surface for receiving a device to hold the rods in place during installation.

Figure 12A:
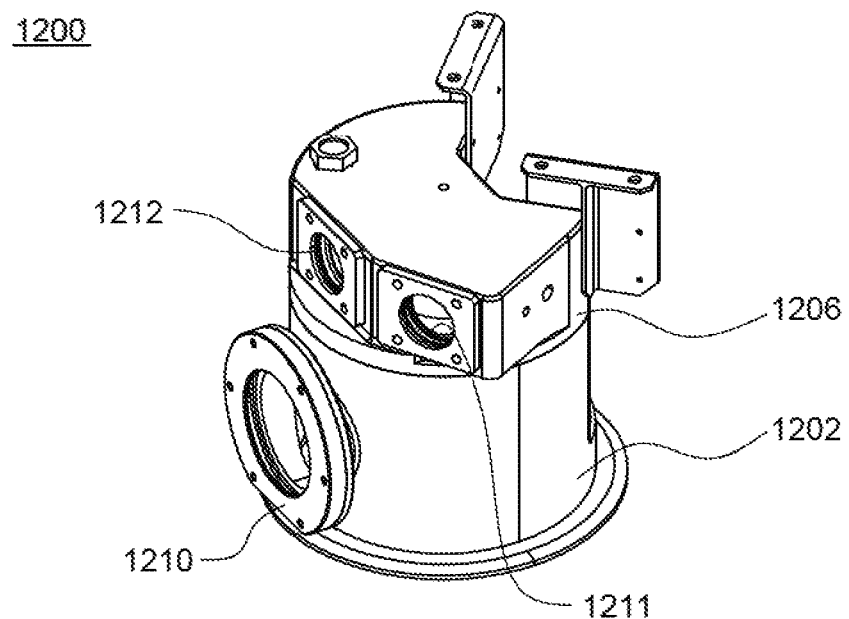
FIG. 12A is an isometric view of the exemplary embodiment of the steam chest.
Figure 12:
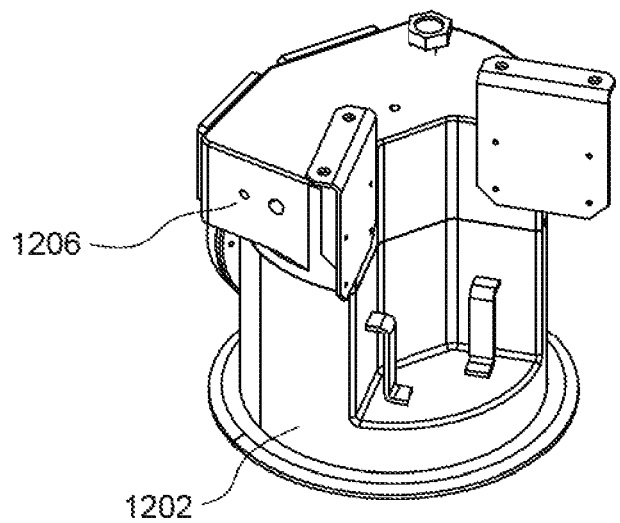
FIG. 12 is an isometric view of the exemplary embodiment of the steam chest.
Figure 12B:
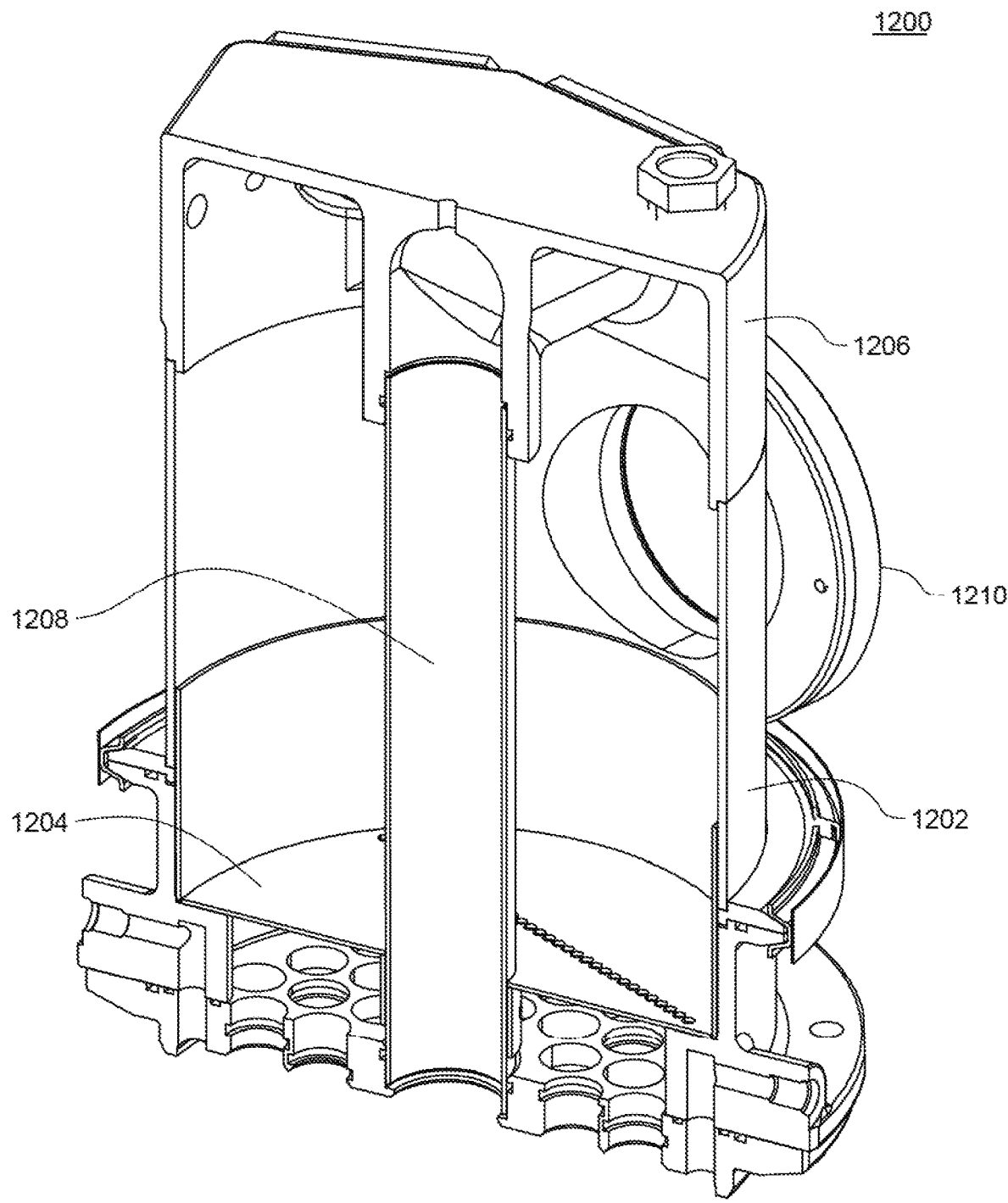
FIG. 12B is a cross-section view of the exemplary embodiment of the steam chest.
Figure 12C:
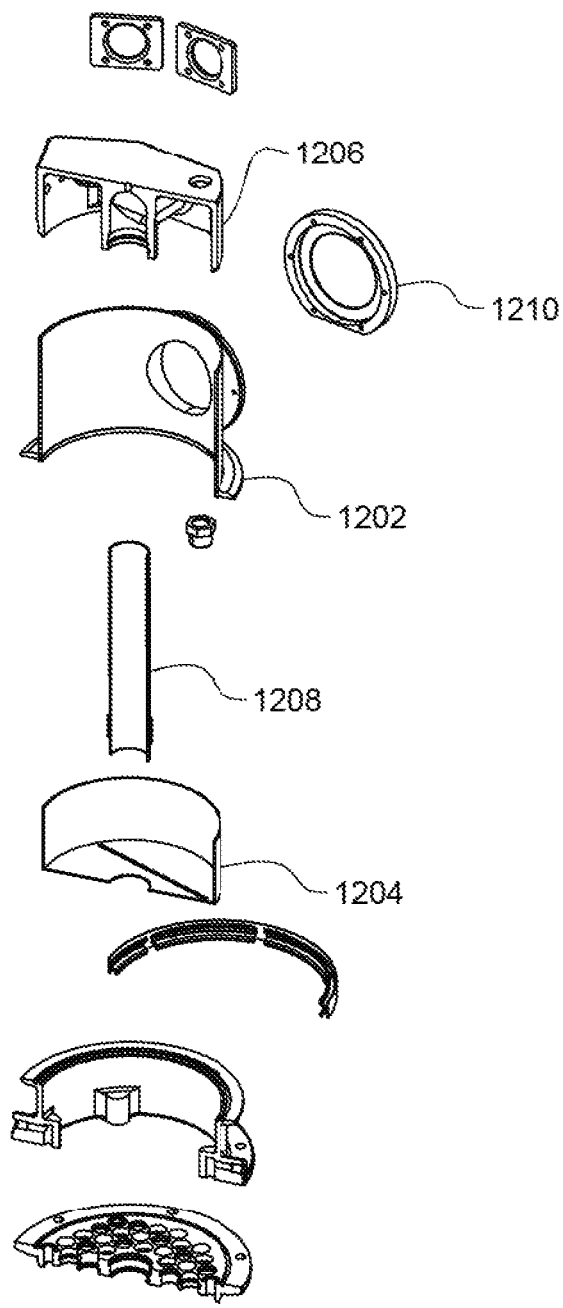
FIG. 12C is an exploded view of the exemplary embodiment of the steam chest.

Referring now to FIGS. 12-12C, connected to the upper flange 1100 (also identified as 712 of FIG. 7) may be a steam chest 1200 (also identified as 408 in FIG. 4). In the exemplary embodiment, the steam chest 1200 may include a base 1202, a steam separator assembly 1204, a cap 1206 and a steam tube 1208. The base 1202 defines an internal cavity for receiving the low-pressure steam created within the tubes 710 of the evaporator area of the evaporator/condenser chamber 700. The base 1202 may have any height such that there is sufficient space to allow water droplets contained within the vapor to be separated. The height of the steam chest allows the water droplets carried by the steam and forcibly ejected from outlets of the tubes 710 from the rapid release of steam bubbles to decelerate and fall back towards the upper flange 712 (also identified as 1100 on FIG. 11).

Still referring to FIGS. 12-12C, within the base 1202 may be a steam separator assembly 1204. This assembly consists of a basket and mesh (not shown in FIGS. 12-12C). The basket contains a quantity of wire mesh. In the exemplary embodiment, the steam separator assembly 1204 removes water droplets from the incoming low-pressure steam by manipulating the steam through a layer of wire mesh. As the steam passes through the mesh the water droplets start to collect on the surfaces of the mesh. These droplets may contain contaminants or particulate. As the droplets increase in size, the water falls onto the bottom of the basket. A plurality of apertures may be located in the bottom of the basket to allow water to collect within the upper flange 712. In addition, these apertures provide a fluid path way for low-pressure steam to enter the steam separator assembly 1204. In addition, the wire mesh provides a barrier from the splashing blowdown water located within the upper flange 712 of the evaporator/condenser.

Still referring to FIGS. 12-12C, in alternate embodiments the steam separator assembly 1204 may contain a series of plates for collecting the water droplets from the low-pressure water vapor as the vapor passes through or around each plate. The plates manipulate the steam to cause water droplets to collect onto the plates. The water is collected in the assembly because the plates are arranged creating sharp bends in the flow path of the steam. These bends reduce the velocity of and change the direction of the steam. The water droplet may continue along their initial trajectory due to momentum. The droplets may then impact the walls or plates of the assembly where the droplets are collected. When enough droplets have collected on the walls or plates of the assembly, the water droplets may fall down towards the upper flange 406 of the evaporator/condenser.

Figure 12D:
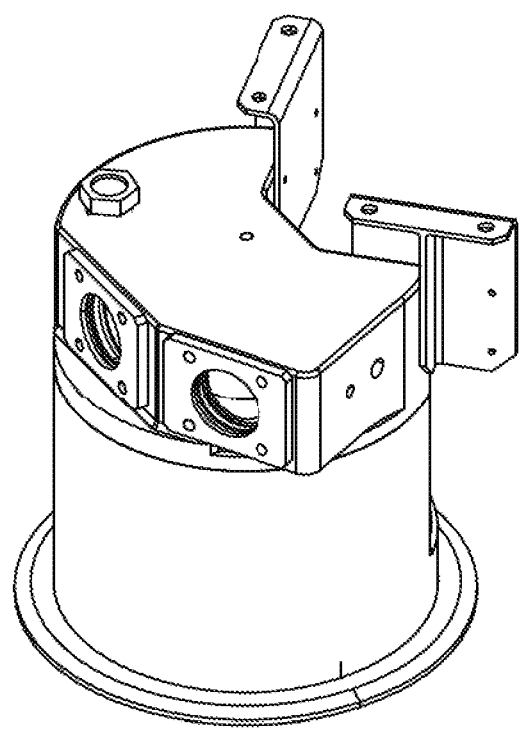
FIG. 12D is an isometric view of an alternate embodiment.

Still referring to FIGS. 12-12C, the base 1202 may also have an observation window 1210. This window allows people operating the apparatus to visually observe the internals of the steam chest to determine if the apparatus is functioning properly. In other embodiments, the steam chest 1200 may not include an observation window 1210. This alternate embodiment is illustrated in FIG. 12D. In still other embodiments, the size and shape of the window may vary. In some embodiments, the steam chest may include multiple windows.

In the exemplary embodiment, the steam separator assembly may be manufactured from stainless steel. Other materials may be used, however, with preference that those materials have corrosion and high temperature resistant properties. Other types of materials may include, but are not limited to RADEL®, titanium, copper-nickel, plated aluminum, fiber composites, and high temperature plastics.

Figure 12E:
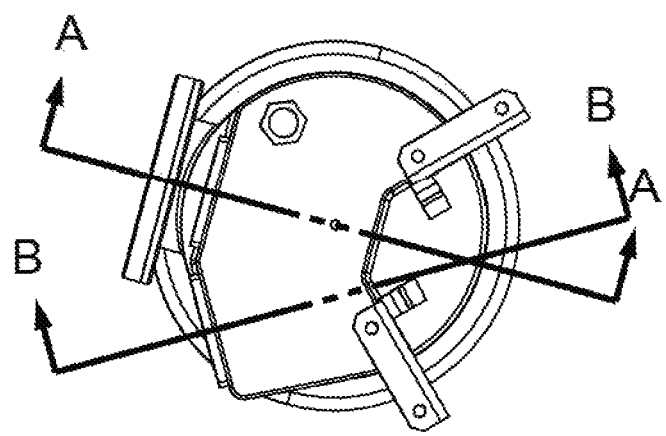
FIG. 12E is a cross-section view of the exemplary embodiment of the steam chest.
Figure 12F:
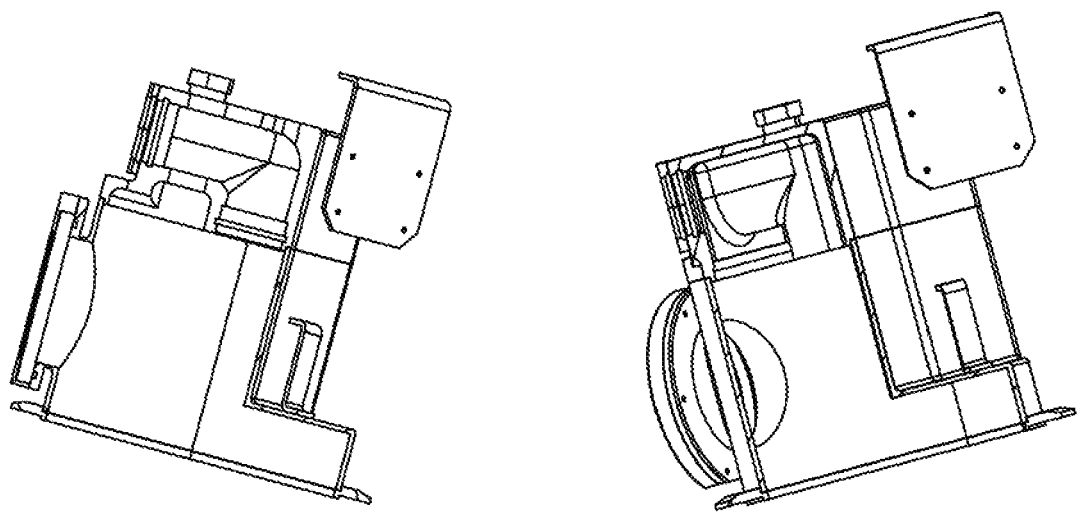
FIG. 12F is a cross-section view of the exemplary embodiment of the steam chest.

Still referring to FIGS. 12-12C, attached to the base 1202 is the cap 1206. The cap and base define the internal cavity for separating the water from the low-pressure steam. In addition, the cap 1206 may have two ports, an outlet port 1211 and inlet port 1212 shown on FIGS. 12B, 12E and 12F. The outlet port provides a fluid path way for the dry low-pressure steam to exit the steam chest 1200. In the exemplary embodiment, the outlet port 1211 is located near the top surface of the cap 1206 because the locating the port away from the outlets of the tubes 710 of the evaporator/condenser promotes dryer steam. In alternate embodiments, however, the outlet port 1211 may have a different location within the cap 1206. Similarly, the inlet port 1212 provides a fluid path way for high-pressure steam to enter the high-pressure steam tube 1208 within the steam chest 1200. In the exemplary embodiment, the inlet port 1212 is located near the top surface of the cap 1206. In alternate embodiments, the inlet port 1212 may have a different location within the cap 1206. In the exemplary embodiment, the cap 1206 is manufactured from plated aluminum. Other types of materials may include, but are not limited to stainless steel, plastics, titanium and copper-nickel. The size of these ports may affect the pressure drop across the compressor.

Still referring to FIGS. 12-12C, connected to the inlet port 1212 within the steam chest 1200 is a steam tube 1208. This tube provides a fluid path way for the high-pressure steam to pass through the steam chest and enter the condenser area of the evaporator/condenser chamber. The inner diameter of the steam tube 1208 may be any size, such that the tube does not adversely affect the flow of high-pressure steam from the regenerative blower to the evaporator/condenser chamber. In the exemplary embodiment the steam tube 1208 may be manufactured from stainless steel. Other materials may be used to manufacture the steam tube 1208, but these materials must have sufficient corrosion resistant and high temperature resistant properties. Such materials may include, but are not limited to plated aluminum, plastics, titanium and copper-nickel. For applications where the source water may be highly concentrated, such as sea water, the steam chest 1200 may be manufactured from but not limited to titanium, nickel, bronze, nickel-copper and copper-nickel.

Figure 13:
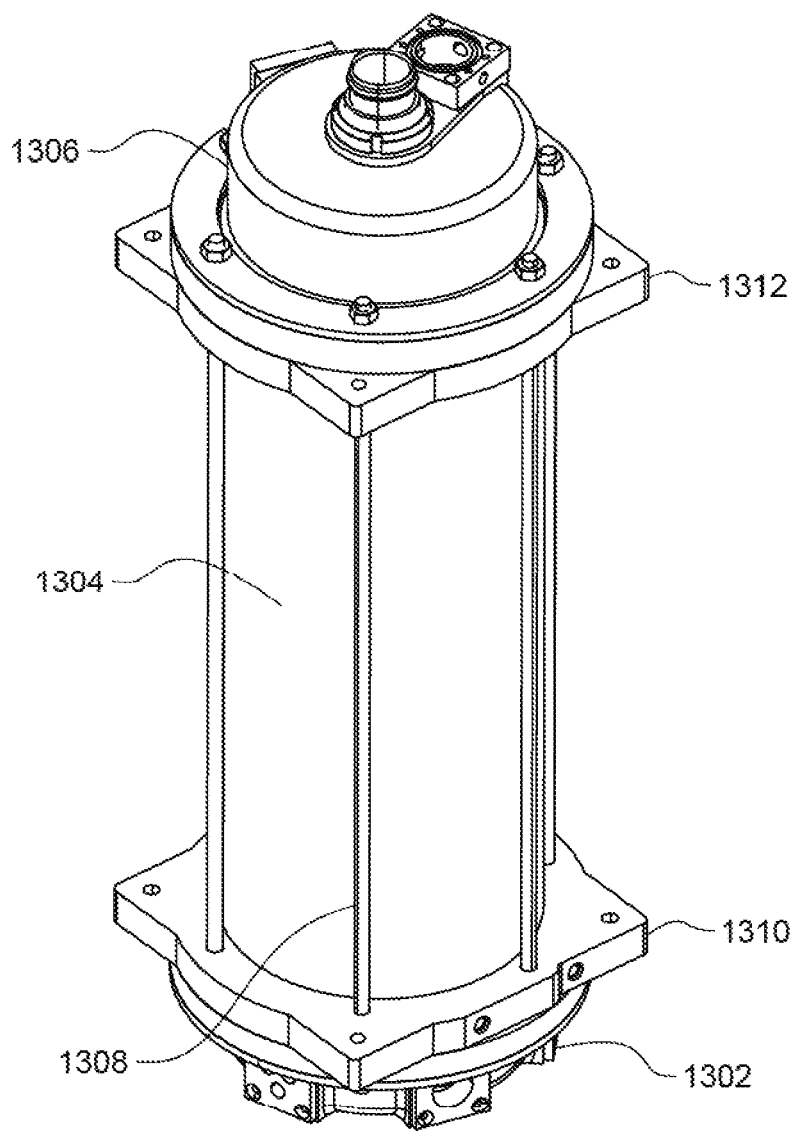
FIG. 13 is an assembly view of an alternate embodiment of the evaporator/condenser.

Referring now to FIGS. 13-13C, an alternate embodiment of the evaporator/condenser assembly 1300 is shown. In this embodiment, the evaporator/condenser assembly 1300 includes a sump 1302, an evaporator/condenser chamber 1304, a mist eliminator assembly 1306, a plurality of tie rids 1308, a lower flange 1310 and an upper flange 1312. See FIG. 13D for a detail view of the evaporator/condenser assembly without the sump 1302.

Figure 13B:
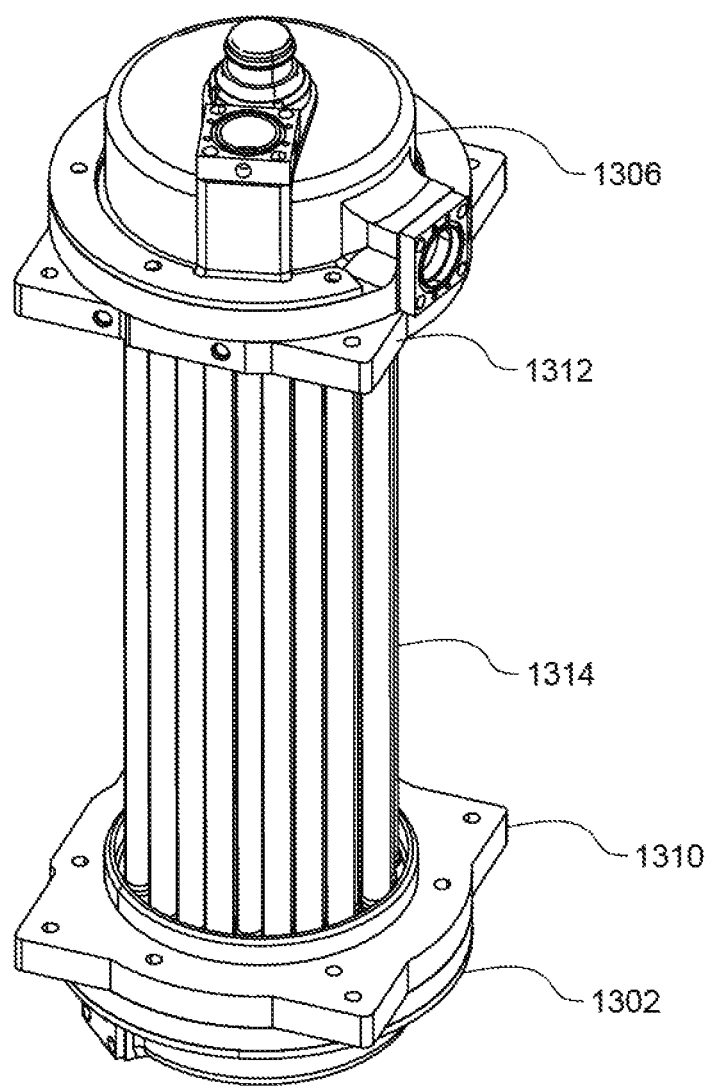
FIG. 13B is an assembly view of an alternate embodiment of the evaporator/condenser illustrating the arrangement of the tubes.
Figure 13D:
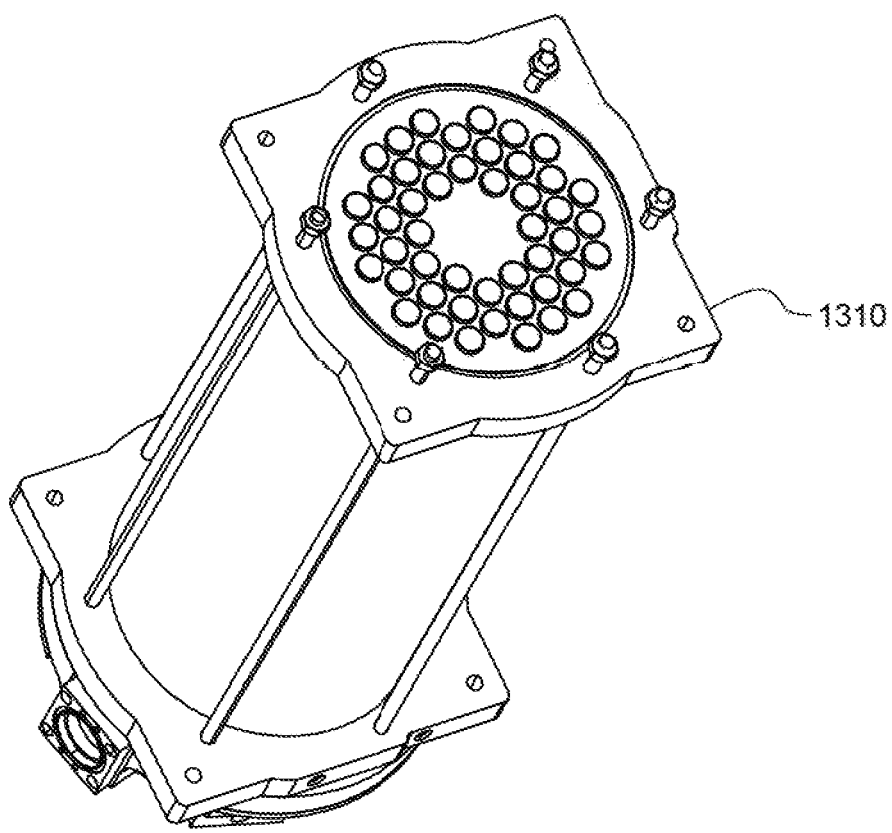
FIG. 13D is an isometric view of the alternate embodiment of the evaporator/condenser without the sump installed.
Figure 13E:
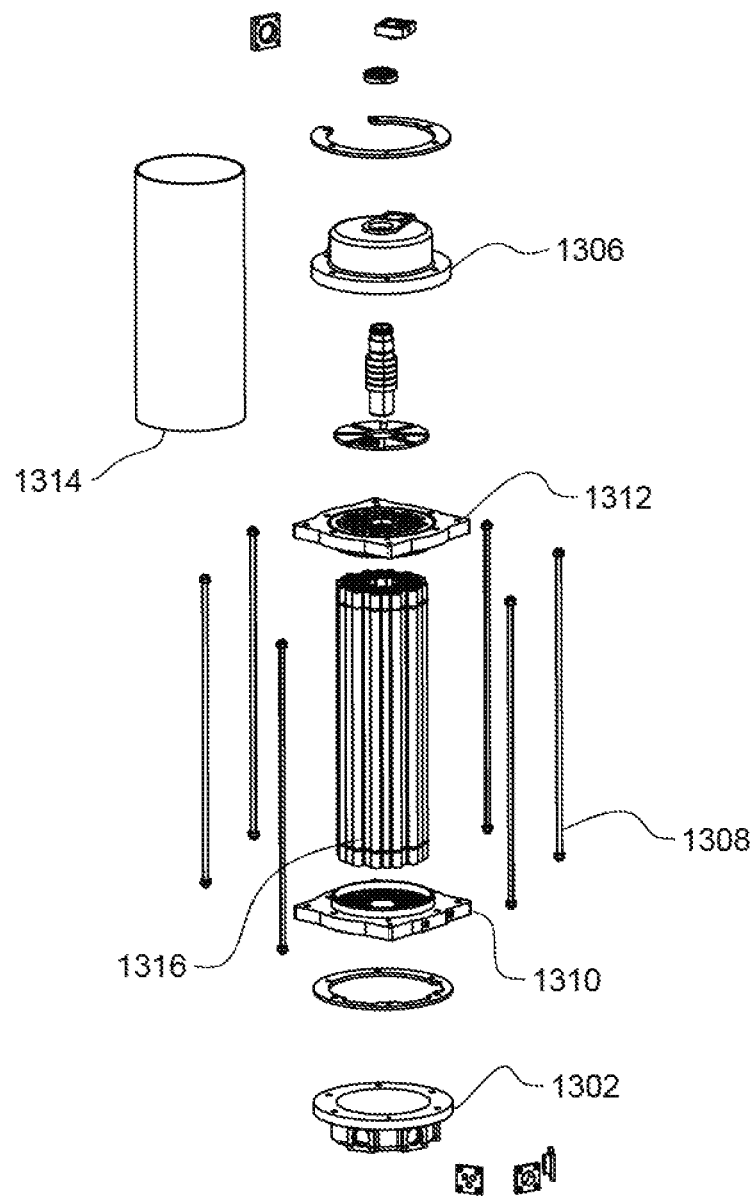
FIG. 13E is an exploded view of the alternate embodiment of the evaporator/condenser.

Now referring to FIG. 13E, the evaporator/condenser chamber may include a shell 1314, a plurality of tubes 1316, a lower flange 1310 and an upper flange 1312. The evaporator/condenser chamber 1304 defines an inner cavity for the condensation of high-pressure steam. Tubes 1316 transfer thermal energy from the high-pressure steam to source water within the tubes when the steam condenses upon the outer surface of the tubes 1316. In this embodiment the tubes 1316 may have an outer diameter of 0.75 inches and manufactured from copper. In alternate embodiments, the tubes 1316 may be manufactured from other materials including but not limited to nickel copper or other composite materials. The diameter of the tubes 1316 may also vary depending on many variables. See previous discussion in the exemplary embodiment concerning the diameter of the tubes. The length of the tubes 1316 may be determined by the length of the inner cavity defined by the shell 1314 and the thickness of the lower flange 1310 and upper flange 1312.

Still referring to FIG. 13E, the tubes 1316 are supported within the inner cavity defined by the shell 1314 by the lower flange 1310 and upper flange 1312, as shown on FIGS. 13B, 13C and 13E. Each flange has a plurality of apertures located axially around the center of the flange. These apertures may contain the ends of the tubes 1316. In addition, the lower flange 1310 and upper flange 1312 also secure the shell 1314 in place and provide pathways to the sump 1302 and the mist eliminator assembly 1306. As the source water fills the sump 1302, some water begins to fill the tubes 1316 located in the inner cavity of the shell 1314. As thermal energy is transferred to the source water in the tubes 1316, the water begins to evaporate. The source water vapor travels through the tubes 1316 and into the mist eliminator assembly 1306. The vapor enters the mist eliminator through the apertures located in the upper flange 1312.

Still referring to FIG. 13E, the shell 1314 is secured to the lower flange 1310 and upper flange 1312 using a plurality of tie rods 1308. These tie rods are positioned outside axially around the perimeter of the shell 1314. In addition, the tie rods 1308 also secure the mist eliminator 1306 to the upper flange 1312 and the sump 1302 to the lower flange 1310. The length of the tie rods is governed by the length of the shell 1314 and the thickness of the lower flange 1310, upper flange 1312, sump 1302 and mist eliminator 1306. The tie rods 1308 may have threaded ends for attaching a threaded fastener onto each end of the rod securing the components of the evaporator/condenser together. In addition, the tie rods 1308 may be manufactured from any material that is of sufficient strength, such as, stainless steel. Tie rods 1308 may be manufactured from other materials including, but not limited to bronze, titanium, fiberglass composite materials, and carbon steel.

Still referring to FIG. 13E, in the exemplary embodiment the shell 1314 is manufactured from fiberglass. Other materials may be used with preference that those materials are corrosion resistant, have low thermal conductivity, and sufficient structural strength to withstand the internal pressures developed during the operation of the evaporator/condenser assembly 1300. See discussion for the exemplary embodiment relating to the size of the inner diameter of the shell.

Still referring to FIG. 13E, the sump 1302 is connected to the lower flange 1310 and is in fluid connection with the tubes 1316 of the evaporator/condenser assembly chamber 1304. The sump 1302 collects the incoming source water from the heat exchanger. The source water enters the sump 1302 through an inlet port locate within the side wall of the sump. In other embodiments the inlet port may be located at a different location (i.e. on the bottom). In this embodiment the sump 1302 is made from a composite material, G10 plastic. In other embodiments the sump 1302 may be manufactured from any other material having sufficient corrosion and high-temperatures resistant properties. Other materials include but are not limited to aluminum RADEL® and stainless steel. The sump 1302 may also include a heating element to provide thermal energy to the source water. This thermal energy assists the source water in changing from a fluid to a vapor.

Figure 14:
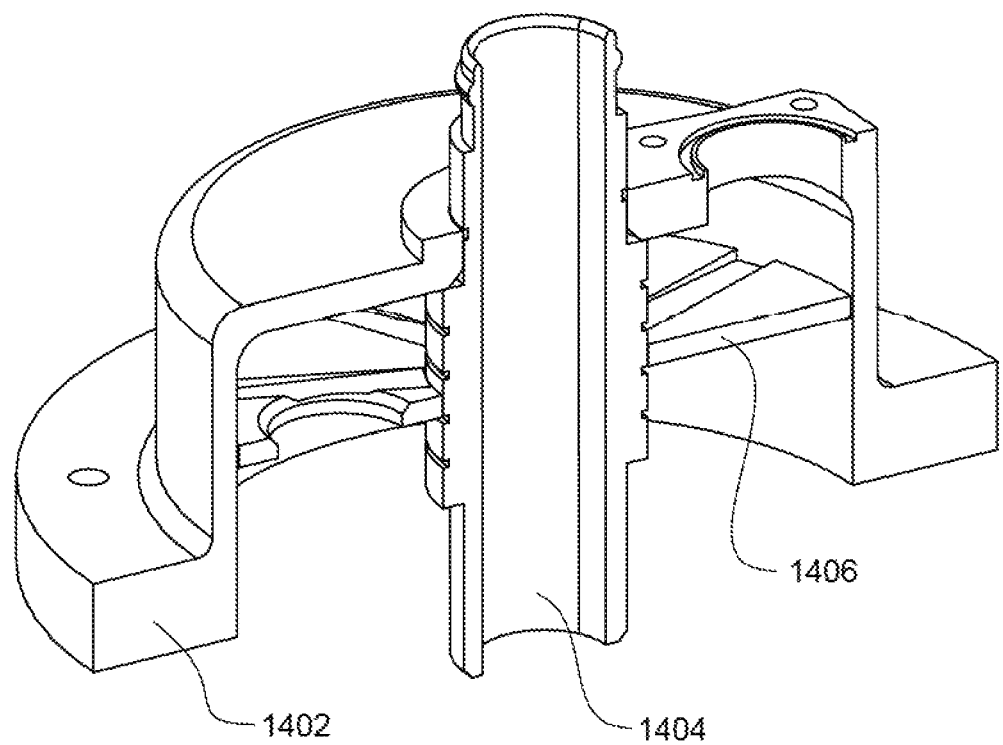
FIG. 14 is an isometric view of the mist eliminator assembly.
Figure 14A:
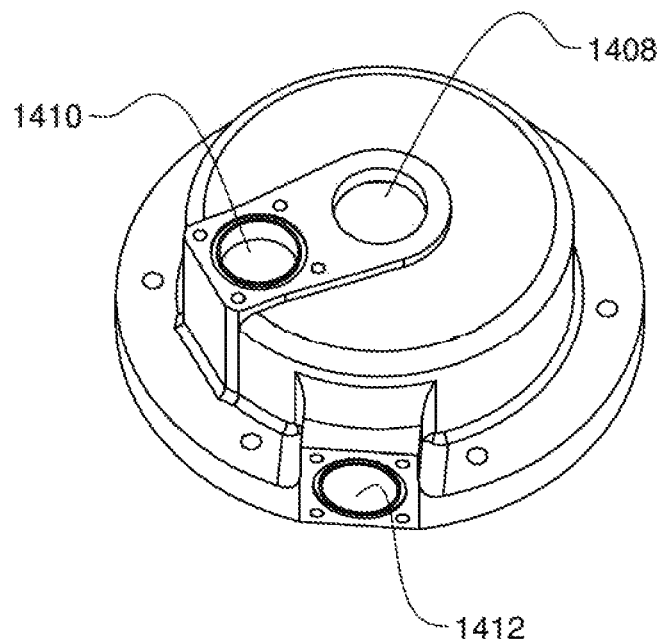
FIG. 14A is an isometric view of the outside of the cap for the mist eliminator.
Figure 14B:
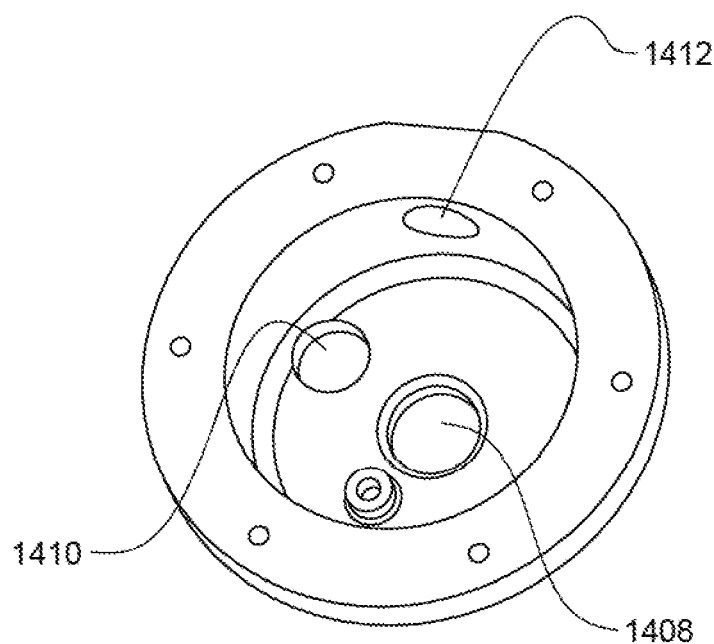
FIG. 14B is an isometric view of the inside of the cap for the mist eliminator.
Figure 14D:
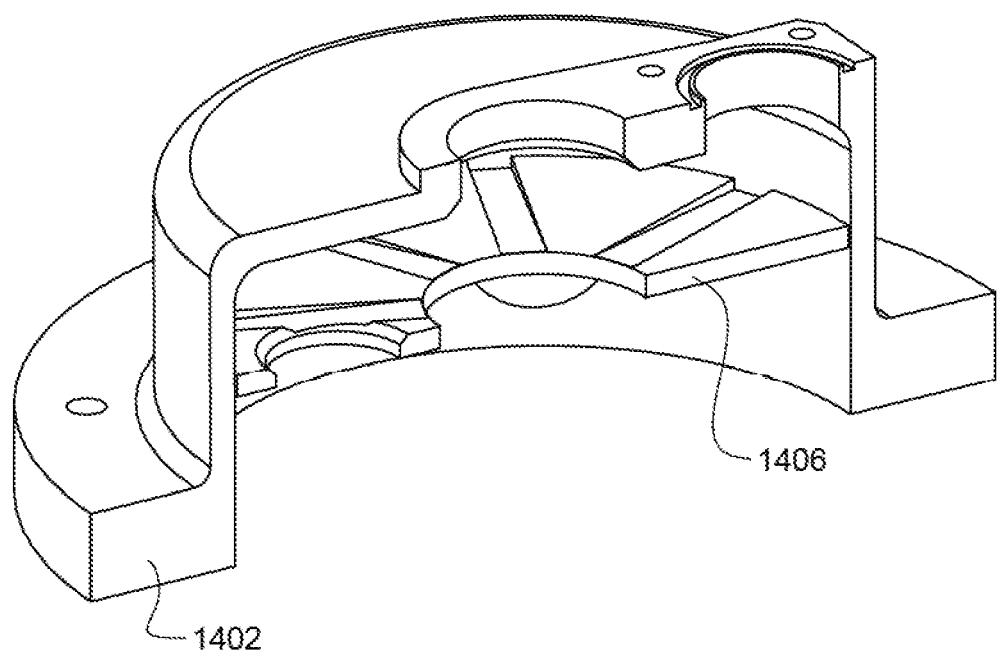
FIG. 14D is a cross-section view of the mist eliminator assembly.

Referring now to FIGS. 14-14C, attached to the upper flange 1312 is the mist eliminator assembly 1400 (also identified as 1306 of FIG. 13). This assembly may consist of a cap 1402, steam pipe 1404, and mist separator 1406 illustrated on FIG. 14. The cap 1402 contains the low-pressure steam that is created from the evaporator side of the evaporator/condenser. The cap 1402 may have three ports 1408, 1410, and 1412 as shown FIGS. 14A-C. See discussion for the steam chest of the exemplary embodiment relating to the height of the volume for removing the water droplets. In addition, the cap 1402 defines a cavity that contains the mist separator 1406 shown on FIGS. 14, 14C and 14D.

Still referring to FIGS. 14-14C, the first port 1408 may be located in the center of the top surface of the cap 1402 and is for receiving the first end of the steam pipe 1404. This port allows the high-pressure steam created by the compressor to re-enter the evaporator/condenser through first end of the steam pipe 1404. The steam pipe 1404 provides a fluid path way for high-pressure steam to enter the evaporator/condenser through the mist eliminator assembly 1400 without mixing with the low-pressure steam entering the mist eliminator assembly 1400. In this embodiment, the steam pipe 1404 is manufactured from stainless steel. In other embodiments the steam pipe may be manufactured from materials including, but not limited to plated aluminum, RADEL®, copper-nickel and titanium. The length of the steam pipe 1404 must be sufficient to allow for connecting with the compressor and passing through the entire mist eliminator assembly 1400. The second end of the steam pipe is received within a port located at the center of the upper flange 1312. The inner diameter of the steam pipe 1404 may affect the pressure drop across the compressor. Another effect on the system is that the steam pipe 1404 reduces the effective volume within the mist eliminator to remove water droplets from the low-pressure steam.

Still referring to FIGS. 14-14C, the steam pipe 1404 also may have a plurality of exterior grooves for receiving the mist separator 1406. The mist separator 1406 is circular plate having an aperture. This aperture allows the low-pressure steam to pass through the plate. In one embodiment a plurality of mist separators are installed within the grooves of the steam pipe 1404. These plates would be oriented such that the aperture is located 180° from the preceding plate. In addition, the plate nearest to the outlet port 1410 would be orientated such that the aperture was 180° from the port. In alternate embodiments the plates may include grooves on the top surface of the plates to collect water droplets. These grooves may be tapered to allow the collected water to flow off the plate and fall down towards the base of the mist eliminator assembly 1400. The mist separator 1406 may be secured to the steam pipe 1404 using a pair of snap rings and a wave washer.

Still referring to FIGS. 14-14C, the second port 1410 may be located also in the top surface of the cap 1402 and allows the dry low-pressure steam to exit the mist eliminator assembly 1400. See previous discussion for the exemplary embodiment concerning the size and location of the outlet port.

Still referring to FIGS. 14-14C, the third port 1412 may be located within the side wall of the cap 1402. This port allows water removed from the low-pressure steam to exit the apparatus. The location of the port is preferably at a height where the blowdown water may exit the mist eliminator assembly 1400 without an excessive buildup of blowdown water within the assembly. In addition, the height of the port preferably is not too low, but rather preferably is sufficient to maintain a level of blowdown water covering the outlets of the tubes. In the exemplary embodiment, a tube may be connected to port 1412 and the blowdown water may pass through a level sensor housing 108 and heat exchanger 102 before exiting the apparatus 100.

Still referring to FIGS. 14-14C, the mist eliminator assembly 1400 may be manufactured from any material having sufficient corrosion and high temperature resistant properties. In this embodiment, the mist eliminator assembly is manufactured from stainless steel. The assembly may be manufactured from other materials including but not limited to RADEL®, stainless steel, titanium, and copper-nickel.

Compressor

The water vapor distillation apparatus 100 may include a compressor 106. In the exemplary embodiment the compressor is a regenerative blower. Other types of compressors may be implemented, but for purposes of this application a regenerative blower is depicted and is described with reference to the exemplary embodiment. The purpose of the regenerative blower is to compress the low-pressure steam exiting the evaporator area of the evaporator/condenser to create high-pressure steam. Increasing the pressure of the steam raises the temperature of the steam. This increase in temperature is desirable because when the high-pressure steam condenses on the tubes of the condenser area of the evaporator/condenser the thermal energy is transferred to the incoming source water. This heat transfer is important because the thermal energy transferred from the high-pressure steam supplies low-pressure steam to the regenerative blower.

The change in pressure between the low-pressure steam and the high-pressure steam is governed by the desired output of product water. The output of the product water is related to the flow rate of the high-pressure steam. If the flow rate of steam for the high-pressure steam from the compressor to the condenser area of the evaporator/condenser is greater than the ability of the condenser to receive the steam then the steam may become superheated. Conversely, if the evaporator side of the evaporator/condenser produces more steam than the compressor is capable of compressing then the condenser side of the evaporator/condenser may not be operating at full capacity because of the limited flow-rate of high-pressure steam from the compressor.

Figure 15:
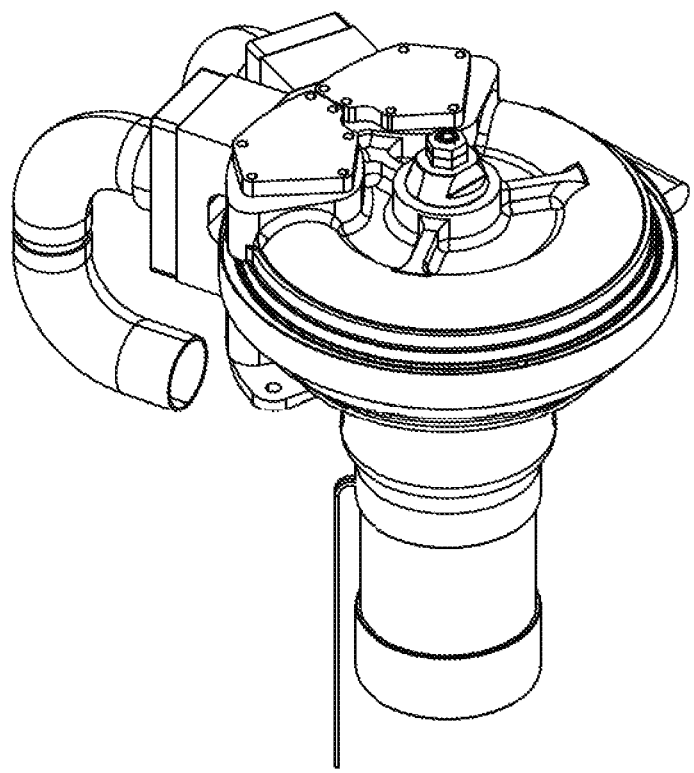
FIG. 15 is assembly view of the exemplary embodiment of a regenerative blower.
Figure 15A:
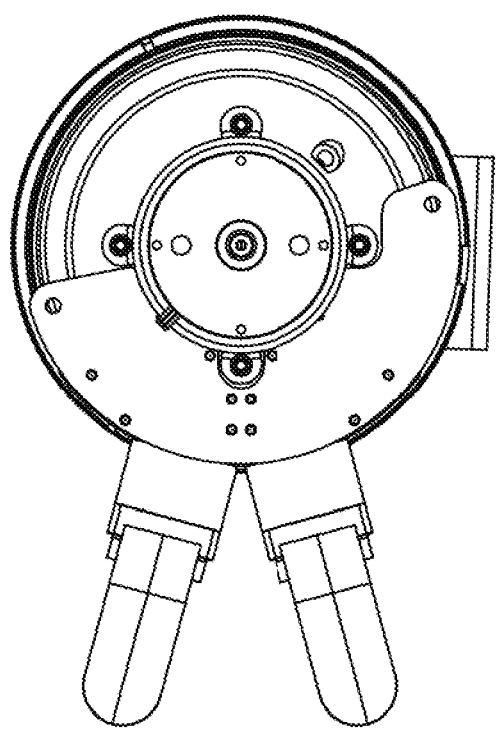
FIG. 15A is bottom view of the exemplary embodiment of the regenerative blower assembly.
Figure 15B:
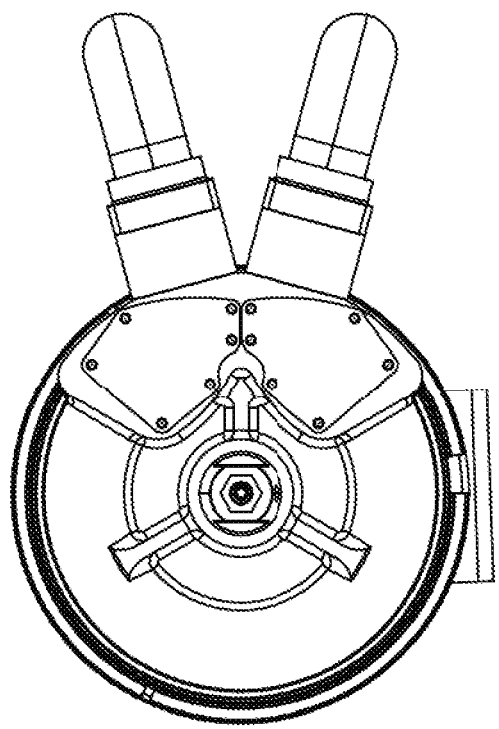
FIG. 15B is a top view of the exemplary embodiment of the regenerative blower assembly.
Figure 15C:
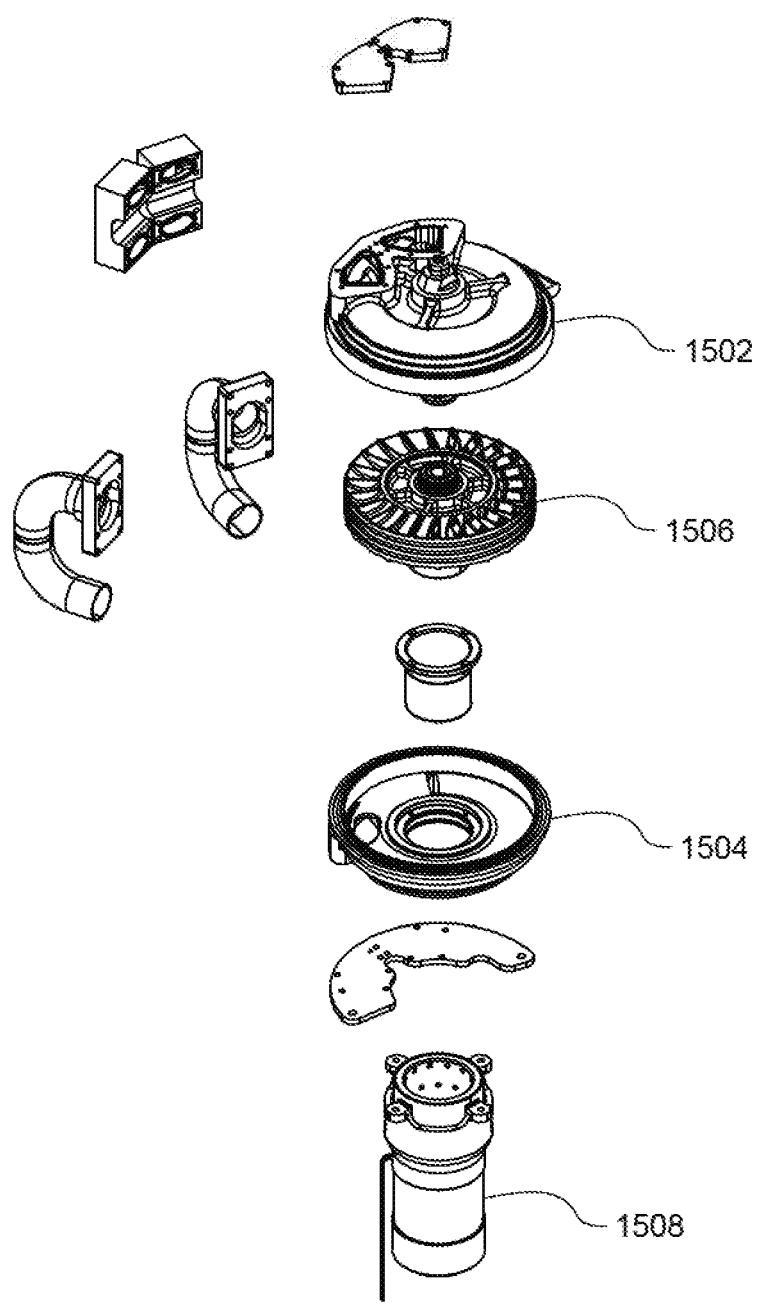
FIG. 15C is an exploded view of the exemplary embodiment of the regenerative blower.
Figure 15D:
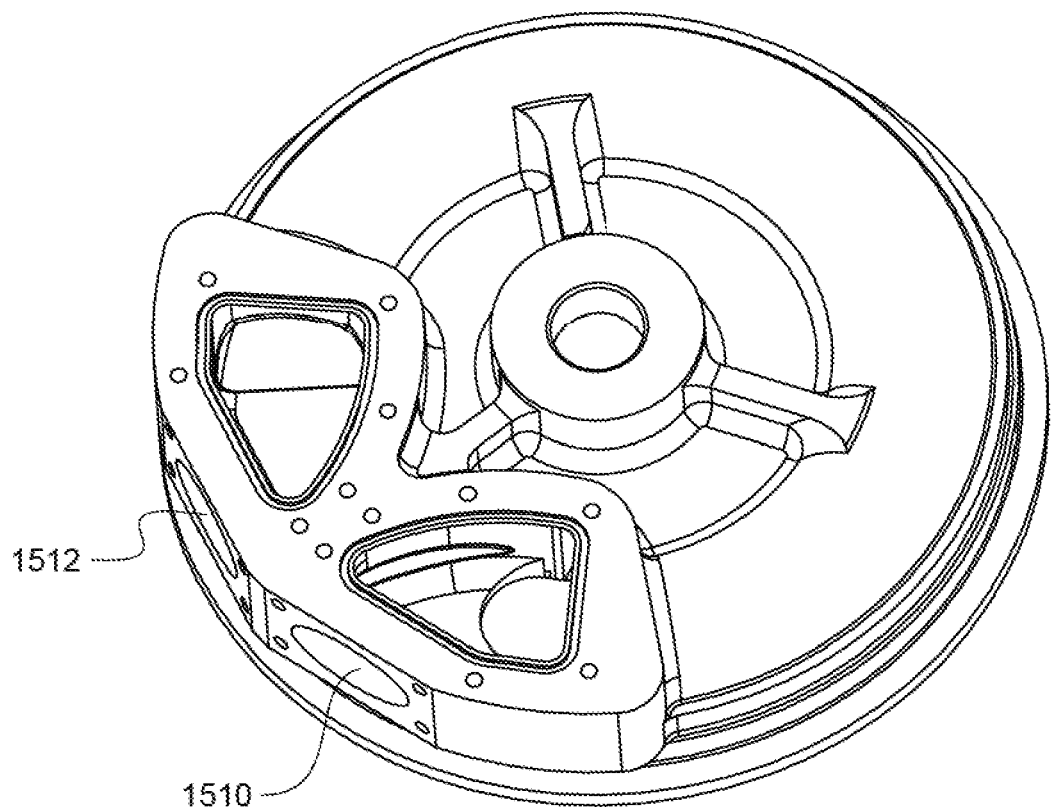
FIG. 15D is a detailed view of the outer surface of the upper section of the housing for the exemplary embodiment of the regenerative blower.
Figure 15E:
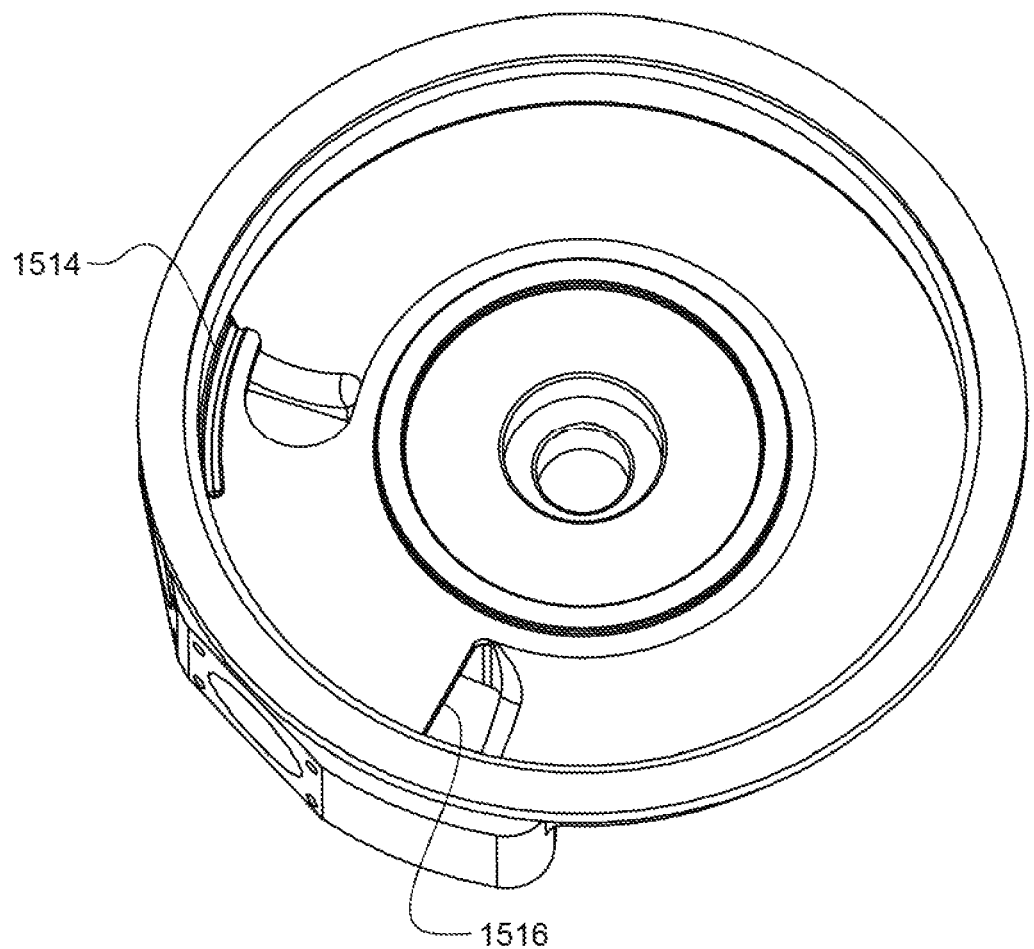
FIG. 15E is a detailed view of the inner surface of the upper section of the housing for the exemplary embodiment of the regenerative blower.
Figure 15F:
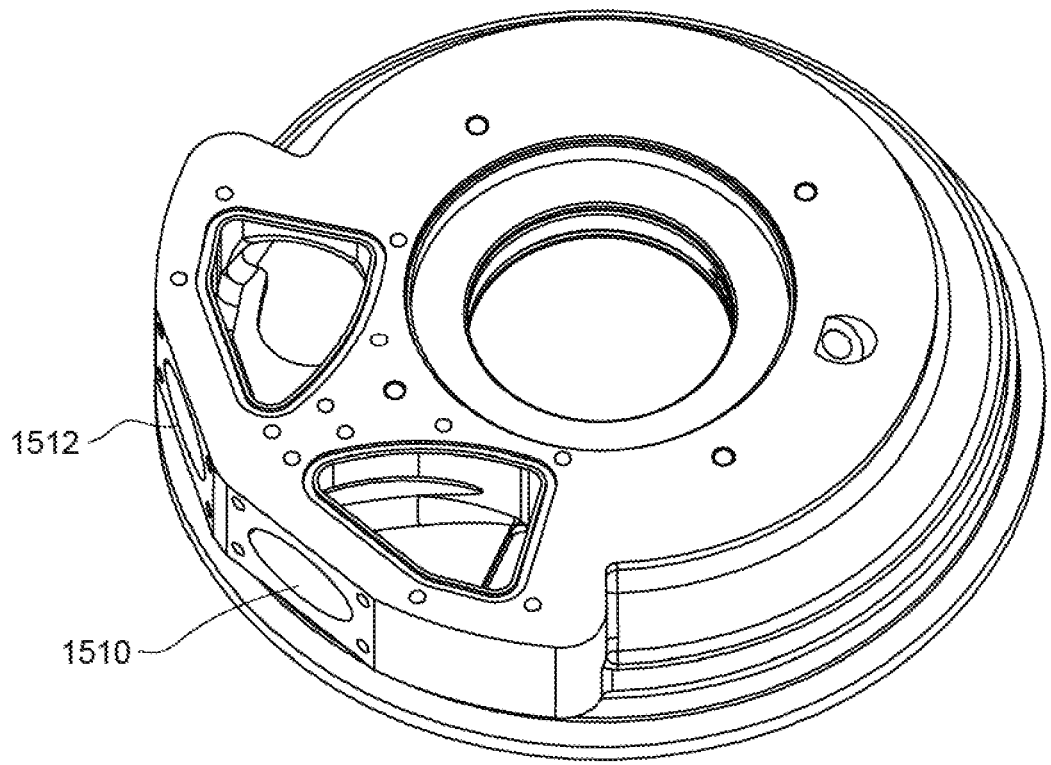
FIG. 15F is a detailed view of the inner surface of the lower section of the housing for the exemplary embodiment of the regenerative blower.
Figure 15G:
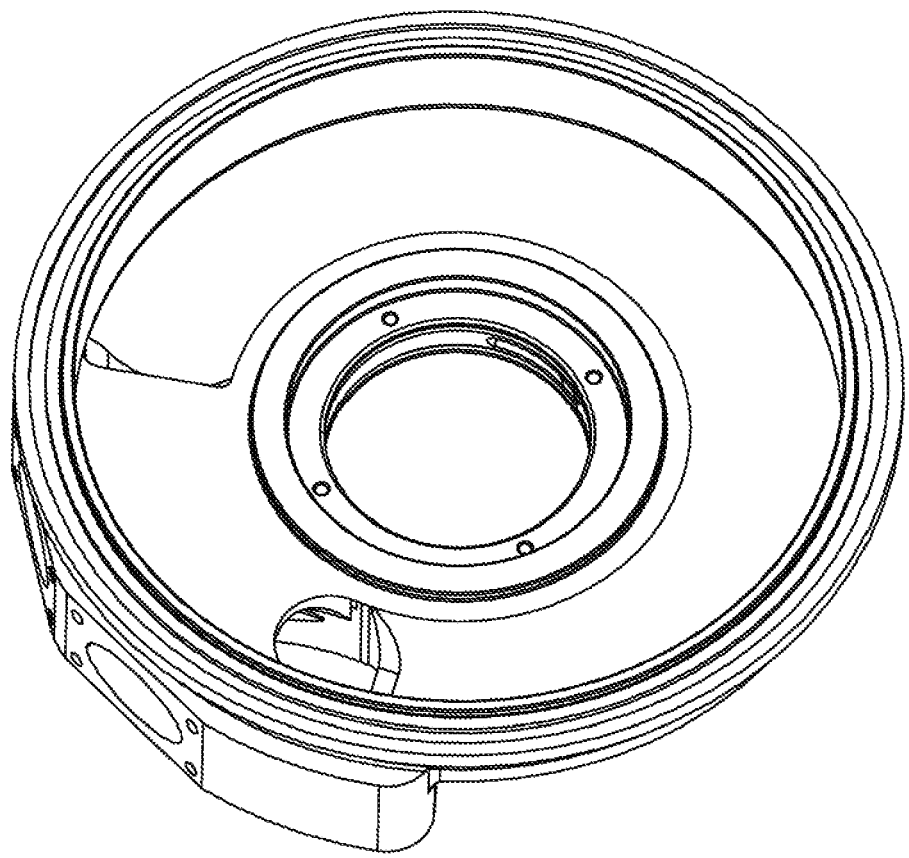
FIG. 15G is a detailed view of the outer surface of the lower section of the housing for the exemplary embodiment of the regenerative blower.
Figure 15H:
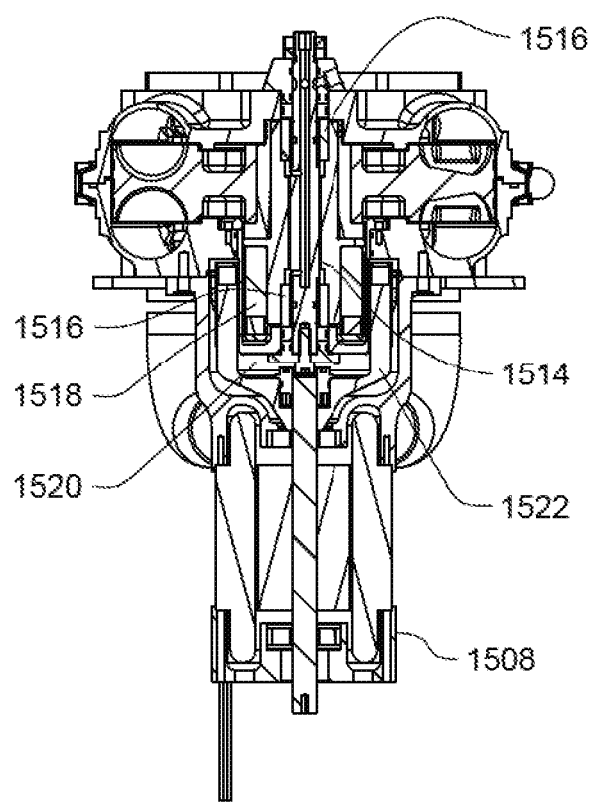
FIG. 15H is a cross-section view of the exemplary embodiment of the regenerative blower.
Figure 15I:
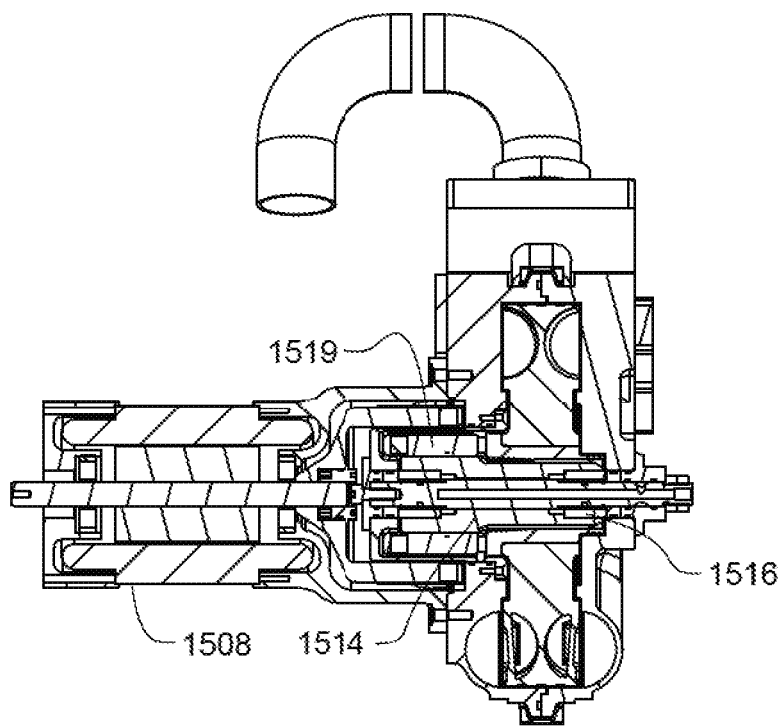
FIG. 15I is a cross-section view of the exemplary embodiment of the regenerative blower.
Figure 15K:
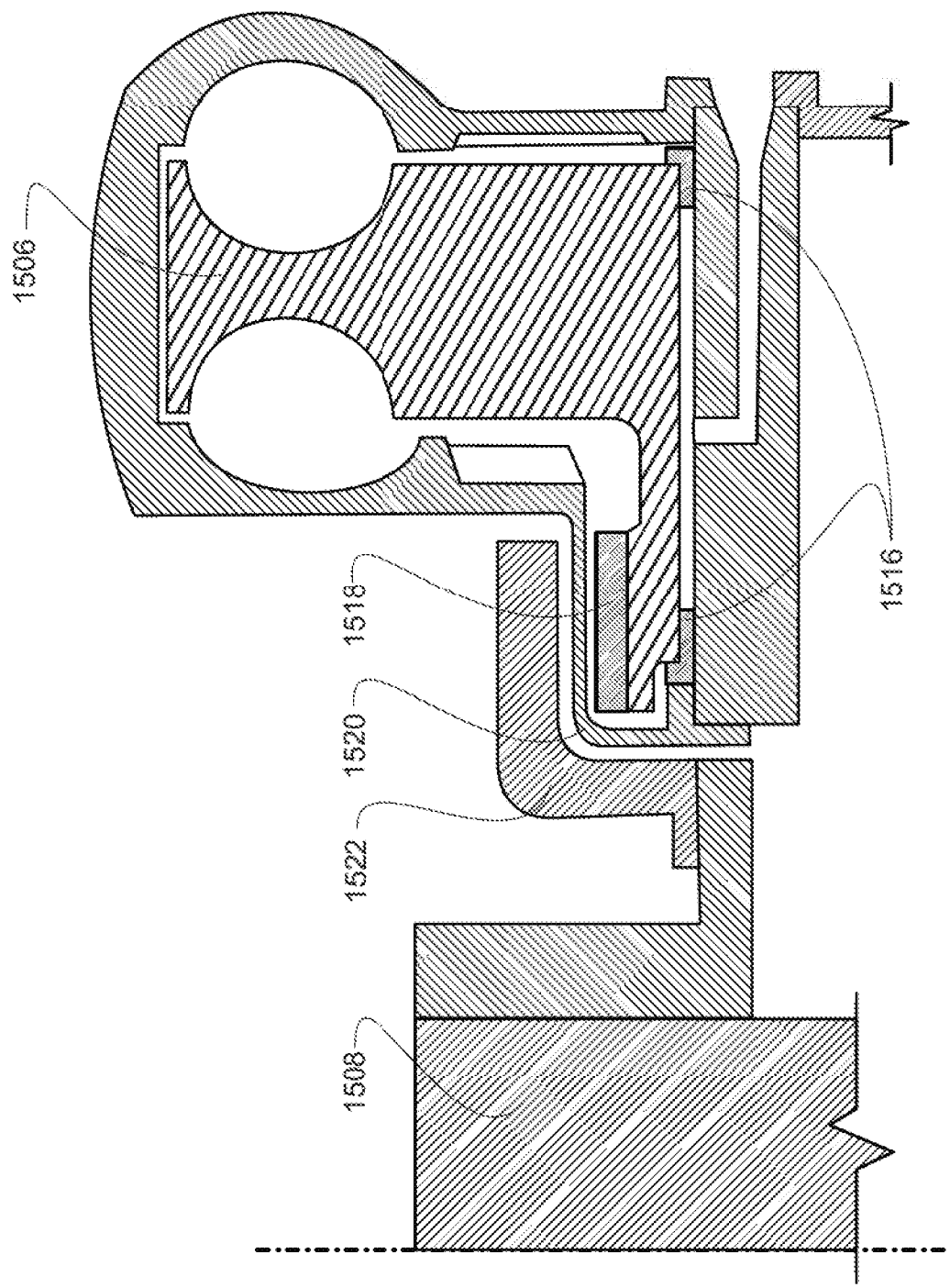
FIG. 15K is a schematic of the exemplary embodiment of the regenerative blower assembly.

Referring now to FIGS. 15-15G, the exemplary embodiment may include a regenerative blower assembly 1500 for compressing the low-pressure steam from the evaporator area of the evaporator/condenser. The regenerative blower assembly 1500 includes an upper housing 1502 and a lower housing 1504 defining an internal cavity as illustrated in FIG. 15C. See FIGS. 15D-G for detail views of the upper housing 1502 and lower housing 1504. Located in the internal cavity defined by the upper housing 1502 and lower housing 1504 is an impeller assembly 1506. The housings may be manufactured from a variety of plastics including but not limited to RYTON®, ULTEM®, or Polysulfone. Alternatively, the housings may be manufactured from materials including but not limited to titanium, copper-nickel, and aluminum-nickel bronze. In the exemplary embodiment the upper housing 1502 and the lower housing 1504 are manufactured from aluminum. In alternate embodiments, other materials may be used with preference that those materials have the properties of high-temperature resistance, corrosion resistance, do not absorb water and have sufficient structural strength. The housings preferably is of sufficient size to accommodate the impeller assembly and the associated internal passageways. Furthermore, the housings preferably provide adequate clearance between the stationary housing and the rotating impeller to avoid sliding contact and prevent leakage from occurring between the two stages of the blower. In addition to the clearances, the upper housing 1502 and the lower 1504 may be mirror images of one another.

Referring now to FIGS. 15D-F, the upper housing 1502 and lower housing 1504 may have an inlet port 1510 and an outlet port 1512. The low-pressure steam from the evaporator/condenser enters the blower assembly 1500 through the inlet port 1510. In the exemplary embodiment, the inlet port is shaped to create a spiral flow around the annular flow channel in the upper housing 1502 and lower housing 1504. After compressing the low-pressure steam, the higher-pressure steam is discharged from the outlet port 1512. Between the inlet ports 1510 and the outlet ports 1512 of the upper housing 1502 and lower housing 1504 the clearances are reduced to prevent the mixing of the high-pressure steam exiting the blower assembly and the low-pressure steam entering the assembly. The exemplary embodiment may include a stripper plate 1516. At this plate the open flow channels provided in the upper housing 1502 and lower housing 1504 allow only the high-pressure steam that is within the impeller blades to pass through to an area near the inlet port 1510, called the inlet region.

Still referring to FIGS. 15D-F, the carryover of the high-pressure steam through the stripper plate 1516 into the inlet region may irreversibly mix with the incoming low-pressure steam entering the blower assembly 1500 from the inlet port 1510. The mixing of the steam may cause an increase in the temperature of the incoming low-pressure steam. The high-pressure steam carryover may also block the incoming flow of low-pressure steam because of the expansion of the high-pressure steam in the inlet region. The decompression duct 1514 in the upper housing 1502 and lower housing 1504 extracts the compressed steam entrapped in the impeller blades and ejects the steam into the inlet region blocking the incoming low-pressure steam.

Still referring to FIGS. 15D-F, the distance between the inlet ports 1510 and outlet ports 1512 is controlled by the size of the stripper plate 1516. In the exemplary embodiment the stripper plate area is optimized for reducing the amount of high-pressure steam carryover into the inlet region and maximizing the working flow channels within the upper housing 1502 and lower housing 1504.

Referring now to FIGS. 15H-K, in the exemplary embodiment the shaft 1514 is supported by pressurized water fed bearings 1516 that are pressed into the impeller assembly 1506 and are supported by the shaft 1514. In this embodiment, the bearings may be manufactured from graphite. In alternate embodiments, the bearings may be manufactured from materials including but not limited to Teflon composites and bronze alloys.

Still referring to FIGS. 15H-K, the water supplied to the pressurized water fed bearings 1516 is preferably clean water as the water may enter the compression chamber of the blower assembly 1500. If the water enters the compression chamber, the water will likely mix with the pure steam. Contaminated water mixing with the pure steam will result in contaminated high-pressure steam. In the exemplary embodiment product water is supplied to the bearings.

Hydrodynamic lubrication is desired for the high-speed blower bearings 1516 of the exemplary embodiment. In hydrodynamic operation, the rotating bearing rides on a film of lubricant, and does not contact the stationary shaft. This mode of lubrication offers the lowest coefficients of friction and wear is essentially non-existent since there is no physical contact of components.

Operating in the other lubrication regimes like Mixed Film Lubrication and Boundary Lubrication results in higher power loss and higher wear rates than hydrodynamic operation. In the exemplary embodiment the blower may operate having hydrodynamic lubrication, film lubrication or a combination of both. The running clearance between the rotating bearing and the stationary shaft; rotating speed of the bearing; and lubricating fluid pressure and flow may affect the bearing lubrication mode.

Referring to FIGS. 15H-K, in a hydrodynamic bearing the limiting load factor may be affected by the thermal dissipation capabilities. When compared to an un-lubricated (or a boundary-lubricated) bearing, a hydrodynamic bearing has an additional mechanism for dissipating heat. The hydrodynamic bearing's most effective way to reject heat is to allow the lubricating fluid to carry away thermal energy. In the exemplary embodiment the bearing-feed water removes thermal energy from the bearings 1516. In this embodiment, the volume of water flowing through the bearing are preferably sufficient to maintain the bearing's temperature within operational limits. In addition, diametrical clearances may be varied to control bearing feed-water flow rate, however, these clearances preferably are not large enough to create a loss of hydrodynamic pressure.

Still referring to FIGS. 15H-K, the amount of bearing-feed water supplied to the bearings 1516 is preferably sufficient to maintain hydrodynamic lubrication. Any excess of bearing-feed water may adversely affect the blower assembly 1500. For example, excess water may quench the high-pressure steam unnecessarily reducing the thermal efficiency of the apparatus. Another adverse affect of excess bearing-feed water may be power loss due to shearing of the fluid water when the excess bearing-feed water is ejected outward from the impeller assembly and forced between the housing wall and the passing impeller blades.

Referring to FIG. 15L, in the exemplary embodiment, a return path 1526 for the bearing-feed water is provided within the blower to prevent excess bearing-feed water from entering the impeller buckets.

Referring back to FIGS. 15H-K, in the exemplary embodiment the bearing feed-water pump maintains a pressure of two to five psi on the input to the pressurized water fed bearings 1516. The bearing-feed-water flow rate may be maintained by having a constant bearing-feed-water pressure. In the exemplary embodiment, the pressure of the bearing-feed water may be controlled to ensure the flow rate of bearing-feed water to bearings 1516.

Still referring to FIGS. 15H-K, in the exemplary embodiment the impeller assembly may be driven by the motor using a magnetic drive coupling rather than a mechanical seal. The lack of mechanical seal results in no frictional losses associated with moving parts contacting one-another. In this embodiment the magnetic drive coupling may include an inner rotor magnet 1518, a containment shell 1520, an outer magnet 1522, and drive motor 1508.

Still referring to FIGS. 15H-K, the inner magnet rotor 1518 may be embedded within a cup. In the exemplary embodiment the magnets are axially positioned. In other embodiments the magnets may be positioned radially. This cup may be manufactured from plastic or metallic materials. In some embodiments the cup material may be but is not limited to RYTON®, ULTEM®, or polysulfone. Similarly, the magnets may be manufactured from materials including but not limited to Ferrite, aluminum-nickel-cobalt, samarium cobalt and neodymium iron boron. In the exemplary embodiment the cup is attached to the impeller assembly 1500. In the exemplary embodiment the cup is press fit onto the shaft 1514. Other methods of attaching the cup may include but are not limited to keyseat and setscrews.

Still referring to FIGS. 15H-K, the magnetic coupling shell 1520 is positioned between inner rotor magnet 1518 and the outer rotor magnet 1522. The magnetic coupling shell 1520 is the pressure vessel or the containment shell for the blower assembly 1500. This shell seals the steam that is being compressed within the blower assembly 1500 preventing the steam from escaping into the surrounding environment.

Still referring to FIGS. 15H-K, Eddy current losses may occur because the shell 1520 is located between the inner rotor magnet 1518 and the outer rotor magnet 1522. If the shell 1520 is electrically conductive then the rotating magnetic field may cause electrical currents to flow through the shell we may cause a loss of power. Conversely, a shell 1520 manufactured from a highly electrically-resistive material is preferred to reduce the amount of Eddy current loss. In the exemplary embodiment titanium may be used for manufacturing the magnetic coupling shell 1520. This material provides a combination of high-electrical resistivity and corrosion resistance. Corrosion resistance is preferred because of the likelihood of contact between the bearing-feed water and the shell 1520. In other embodiments the shell 1520 may be manufactured from plastic materials having a higher electrical resistivity and corrosion resistance properties. In these alternate embodiments the shell 1520 may be manufactured from material including but not limited to RYTON®, ULTEM®, polysulfone, and PEEK.

Still referring to FIGS. 15H-K, the outer rotor magnet 1522 may be connected to a drive motor 1508. This motor rotates the outer rotor magnet 1522 causing the inner rotor magnet to rotate allowing the impeller assembly 1506 to compress the low-pressure steam within the cavity defined by the upper housing 1502 and the lower housing 1504. In the exemplary embodiment the drive motor may be an electric motor. In alternate embodiments the drive may be but is not limited to internal combustion or Stirling engine.

Still referring to FIGS. 15H-K, the blower assembly 1500 may be configured as a two single-stage blower or a two-stage blower. In the operation of a two single-stage blower the incoming low-pressure steam from the evaporator side of the evaporator/condenser is supplied to both the inlet ports of the two separate stages of the blower simultaneously. The first stage may be at the bottom between the lower housing 1504 and the impeller assembly 1506 and the second stage may be at the top between the upper housing 1502 and the impeller assembly 1506. As the impeller assembly 1506 rotates, the incoming low-pressure steam from the inlet port 1510 of both stages is compressed simultaneously and the high-pressure steam exits from the outlet port 1512 of the upper housing 1502 and the outlet port 1512 of the lower housing 1504.

Still referring to FIGS. 15H-K, in contrast the two-stage blower has two distinct compression cycles. During the first compression cycle the low-pressure steam from the evaporator of the evaporator/condenser is supplied to the inlet 1514 of the lower housing. The compressed steam from the first stage exits through the outlet port 1516 in the lower housing and is supplied to the inlet port 1510 of the upper housing 1502. This steam compressed in the first stage is compressed again during the second stage. After the second compression cycle the steam may exit the blower assembly 1500 through the outlet port 1512 of the upper housing 1502 at an increased pressure.

For a given blower design, both the two single-stage blower and the two-stage blower configurations have a unique pressure flow curves. These curves indicate that the two single-stage blower produces a higher flow rate of steam compared to the two-stage blower that produces higher pressure differential. Based on the system operating differential pressure the flow rate and the efficiency of the blower is dependant on the flow characteristics of the blower. Depending on the differential pressure across the blower assembly 1500, one configuration may be preferred over the other. In the exemplary embodiment, the blower assembly 1500 has a two Single-stage blower configuration.

Figure 16:
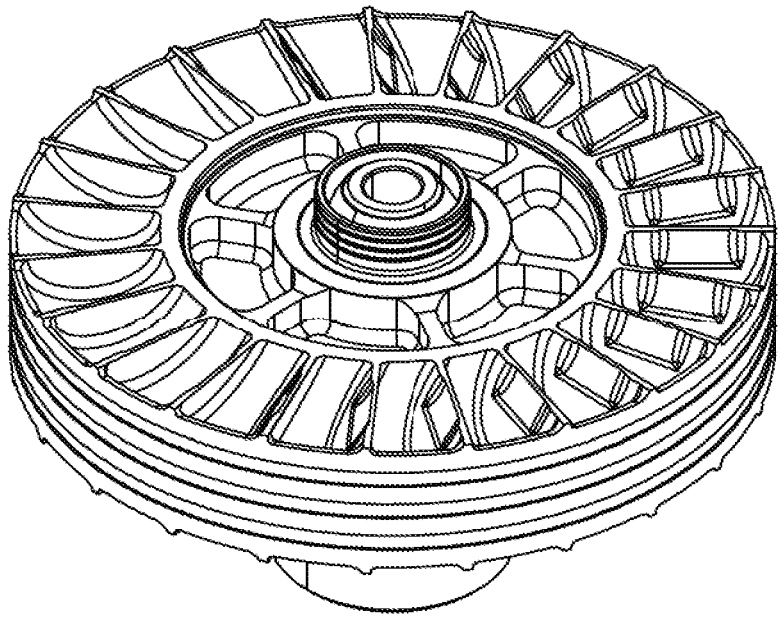
FIG. 16 is a detailed view of the impeller assembly for the exemplary embodiment of the regenerative blower.
Figure 16A:
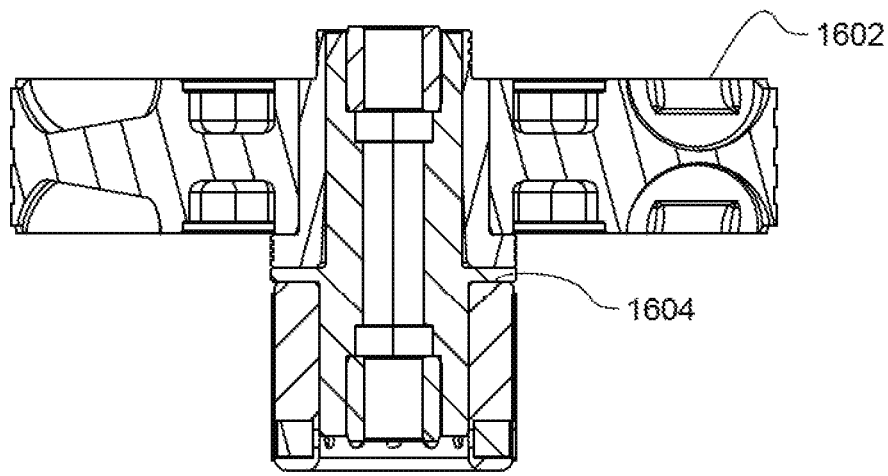
FIG. 16A is a cross-section view of the impeller assembly.

Now referring to FIGS. 16-16A, within the internal cavity defined by the upper housing 1502 and lower housing 1504 is the impeller assembly 1600 (also identified as 1506 of FIG. 15). The impeller assembly 1600 includes a plurality of impeller blades on each side of the impeller 1602 and a spindle 1604. In the exemplary embodiment the impeller 1602 may be manufactured from Radel® and the impeller spindle 1604 may be manufactured from aluminum. In alternate embodiments these parts may be manufactured from materials including but not limited to titanium, PPS, ULTEM®. Other materials may be used to manufacture these parts with preference that these materials have high-temperature resistant properties and do not absorb water. In addition, impeller spindle 1604 may have passages for the return of the bearing-feed water back to the sump. These passages prevent the bearing-feed water from entering the impeller buckets.

Still referring to FIGS. 16-16A, the blades are designed on each side of the impeller 1602 periphery to produce a series of helical flows as the impeller is rotating. This flow causes the steam to repeatedly pass through the blades for additional energy as the steam flows through the open annular channel. The number of blades and the bucket volume may be designed to optimize the desired flow rate and the pressure differential. The number of blades and bucket volume is inversely proportional to each other, thus increasing the number of blades creates higher pressure differential but lower flow rate. The labyrinth grooves on the outer periphery of the impeller 1602 prevents steam leakage across the stages of the blower assembly 1500 thereby increasing the blower efficiency.

Referring back to FIGS. 15H-K, the shaft 1514 is attached to the upper housing 1502 and lower housing 1504 and is stationary. In the exemplary embodiment the shaft 1514 may be manufactured from titanium. In other embodiments the shaft 1514 may be manufactured from materials including but not limited to aluminum oxide, silicon nitride or titanium, and stainless steel having coatings for increasing wear resistance and corrosion resistance properties. In addition the shaft 1514 may have passages channeling the bearing-feed water to the bearings 1516.

Still referring to FIGS. 15H-K, the blower assembly 1500 in a two-stage blower configuration may create a downward axial thrust force. This force is generated because the second stage at the top of the impeller assembly 1506 is at a higher pressure compared to the first stage that is at the bottom of the impeller assembly 1506. In an alternate embodiment, this thrust force may be balanced by an equal and opposite magnetic force created by offsetting the inner rotor magnet 1518 and the outer rotor magnet 1522. This configuration prevents excessive wear of the thrust face of the lower pressurized water fed bearing 1516.

Figure 17:
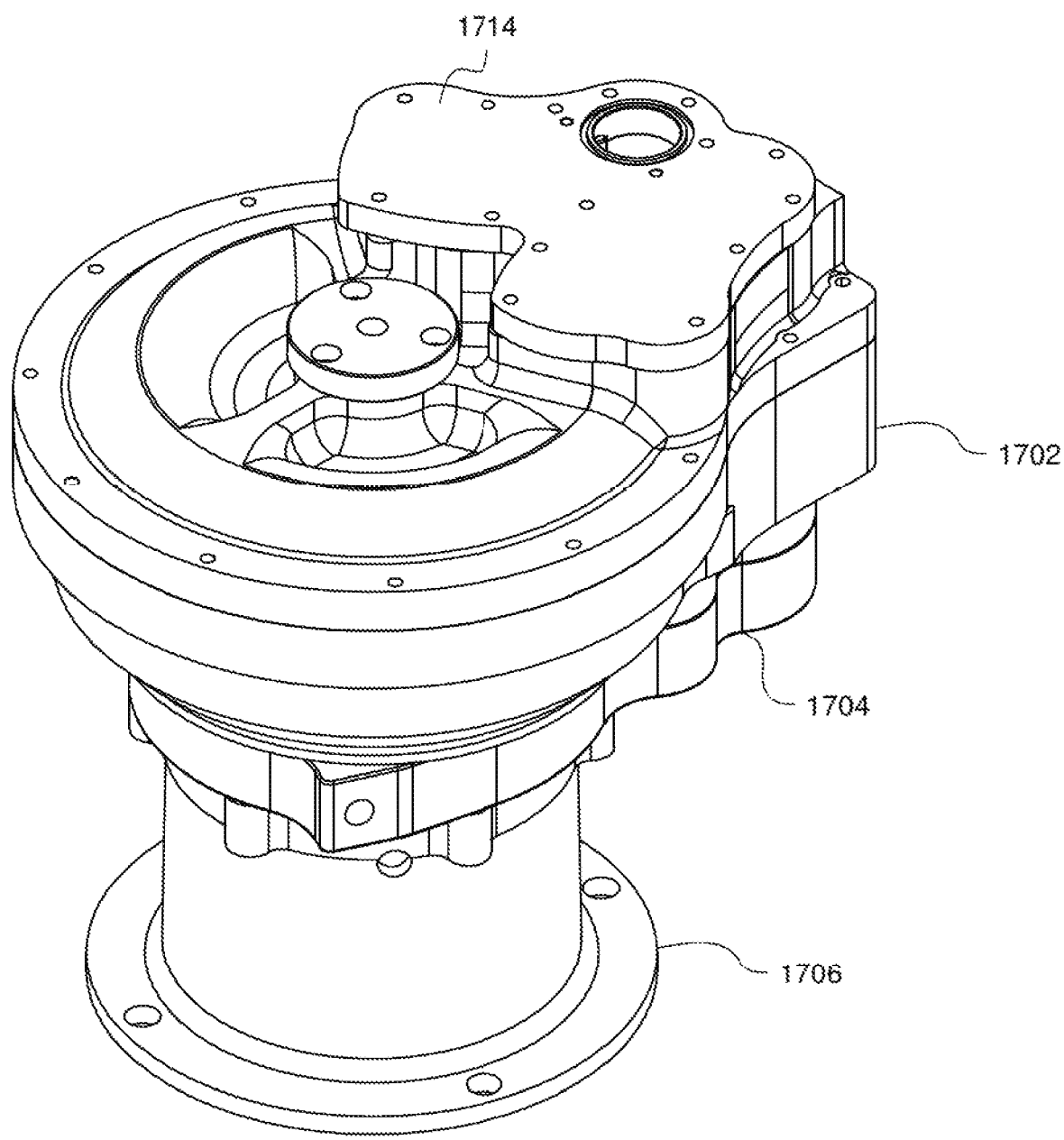
FIG. 17 is an assembly view of the alternate embodiment of a regenerative blower.
Figure 17A:
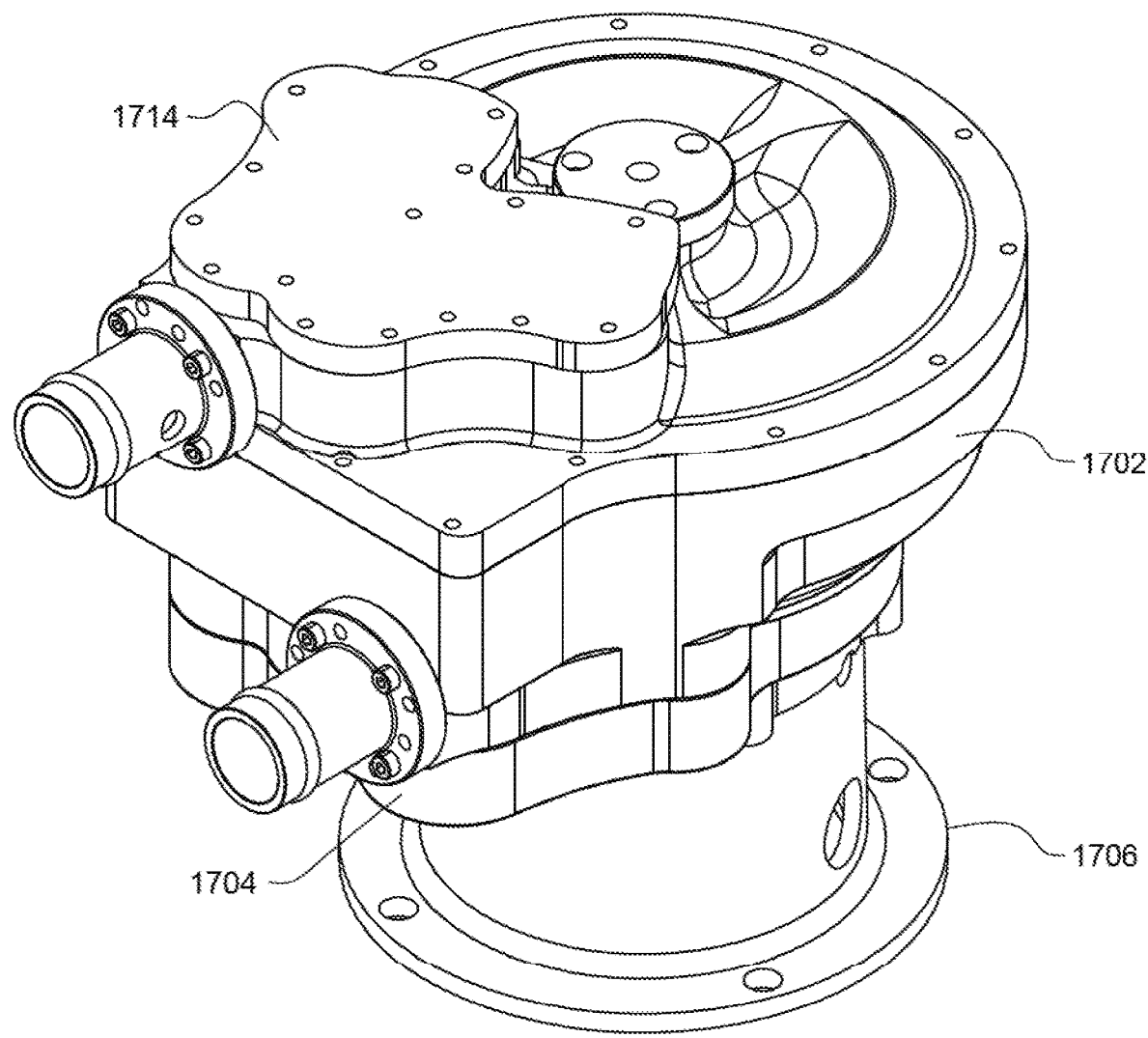
FIG. 17A is an assembly view of the alternate embodiment of a regenerative blower.
Figure 17C:
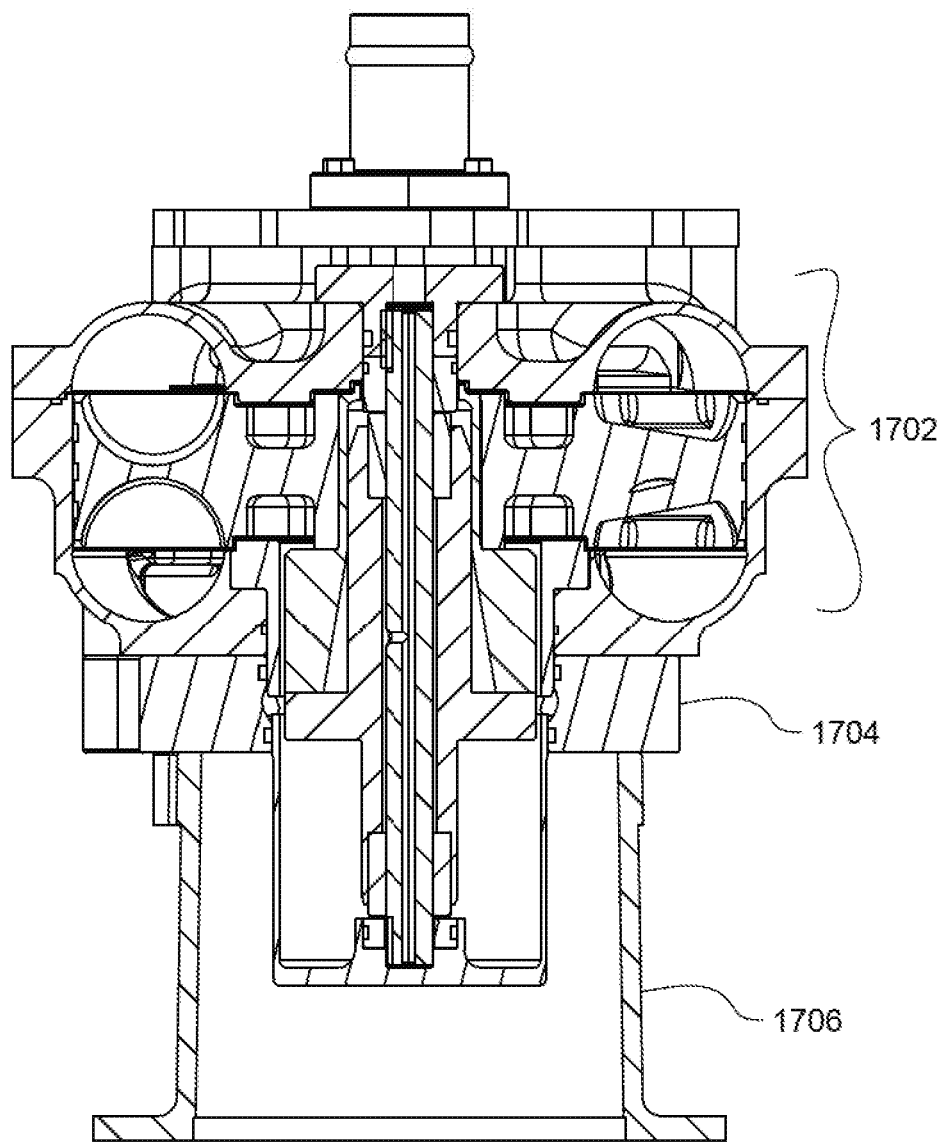
FIG. 17C is a cross-section view of the alternate embodiment of the regenerative blower assembly.
Figure 17D:
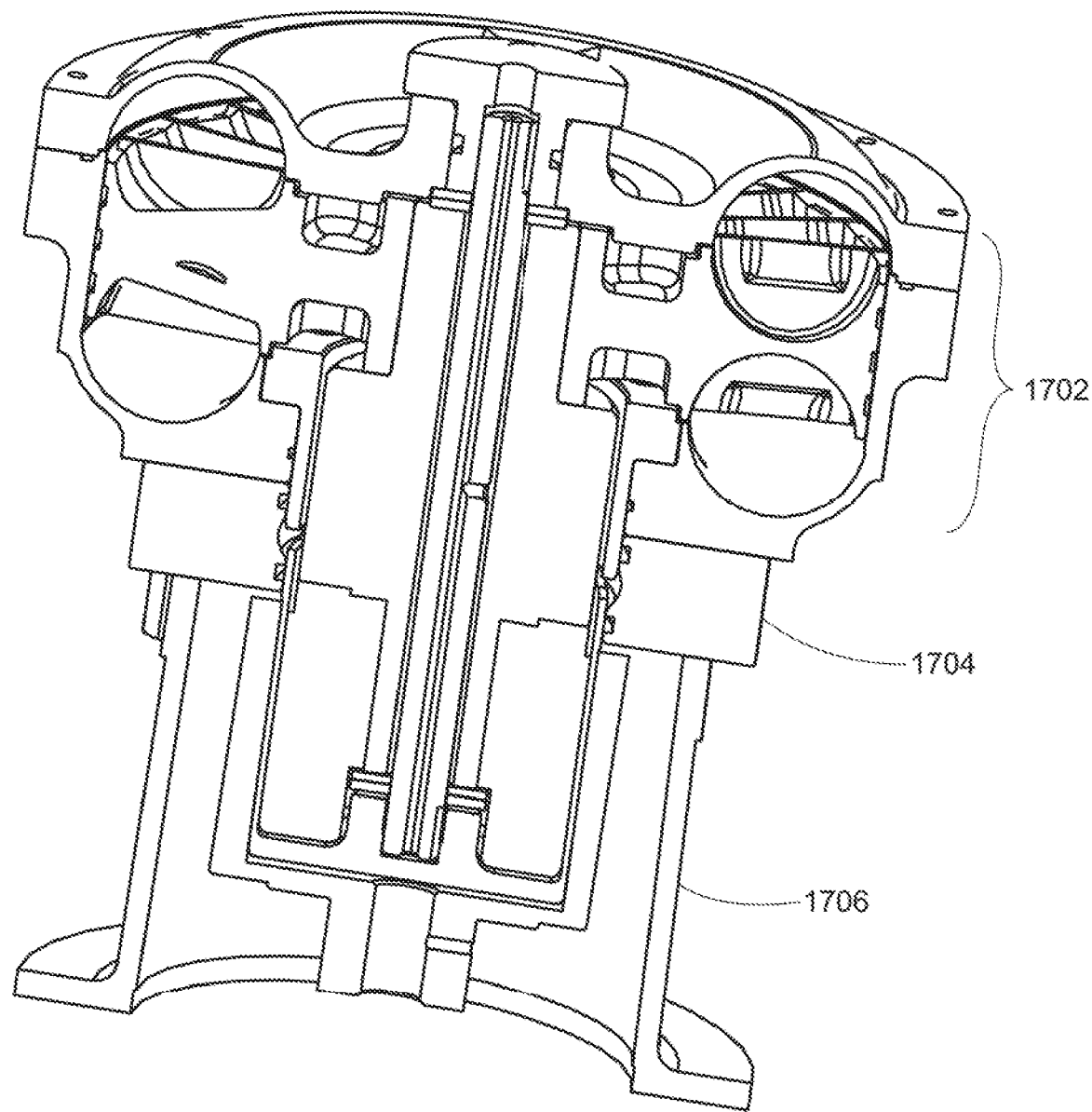
FIG. 17D is a cross-section view of the alternate embodiment of the regenerative blower assembly.
Figure 17E:
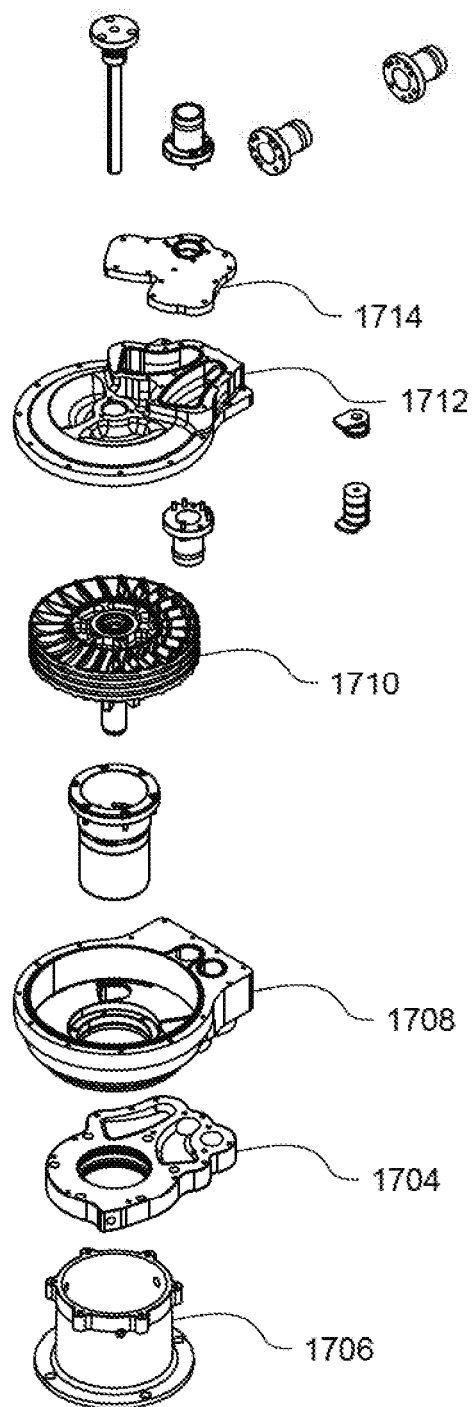
FIG. 17E is an exploded view of the alternate embodiment of the regenerative blower.
Figure 17F:
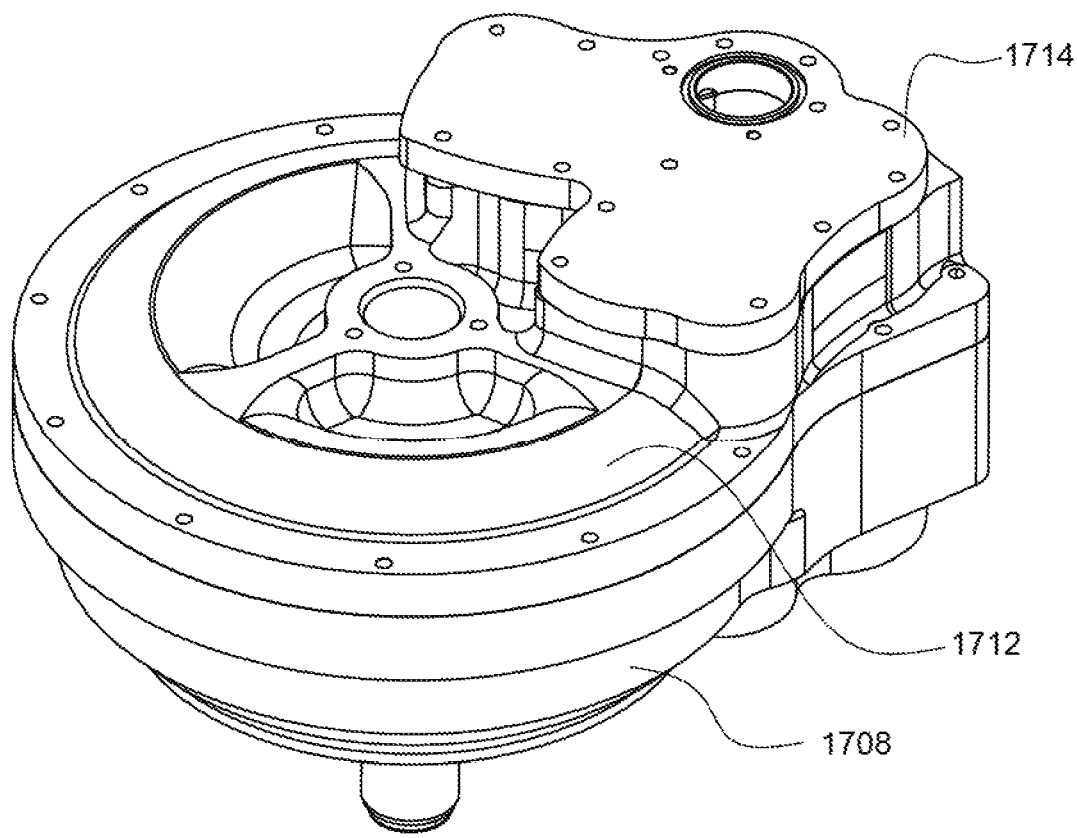
FIG. 17F is an assembly view of the impeller housing.
Figure 17G:
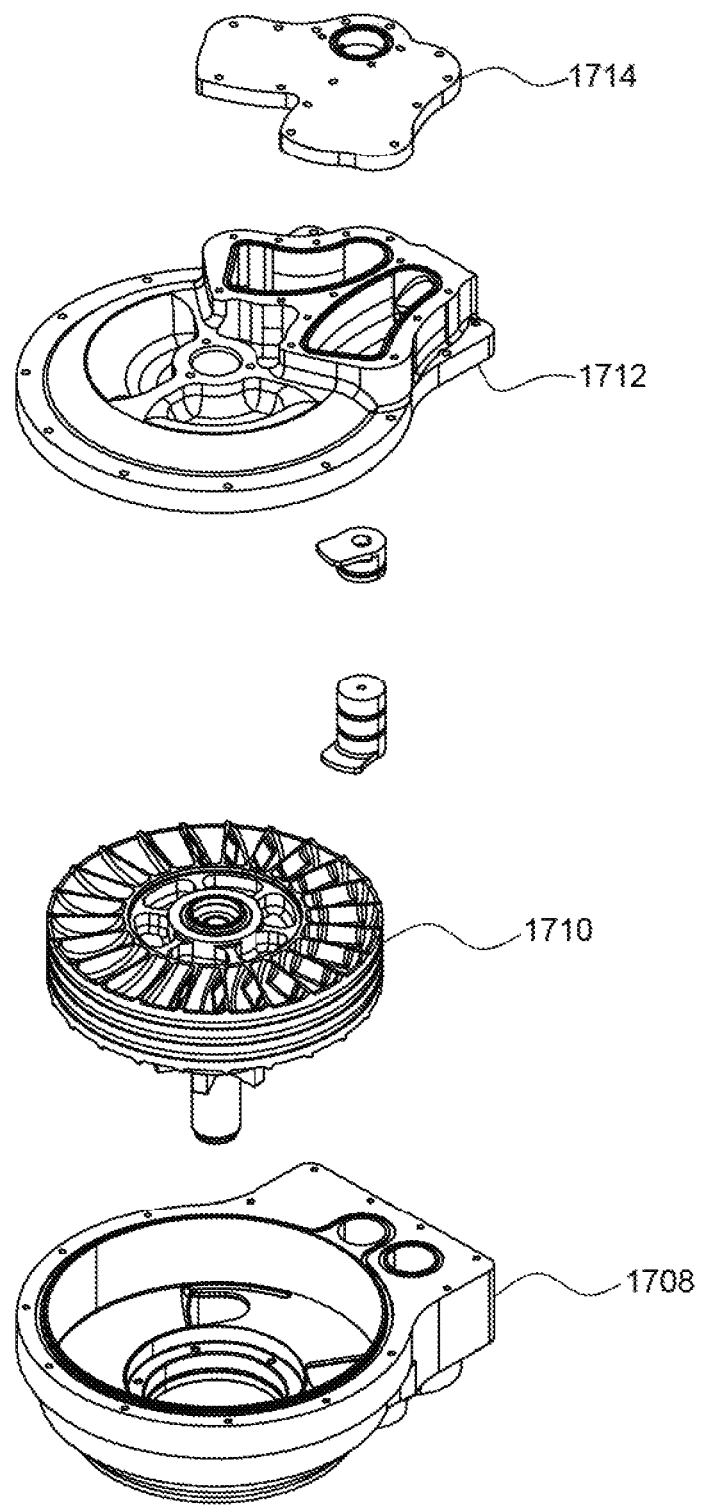
FIG. 17G is an exploded view of the impeller housing.
Figure 17H:
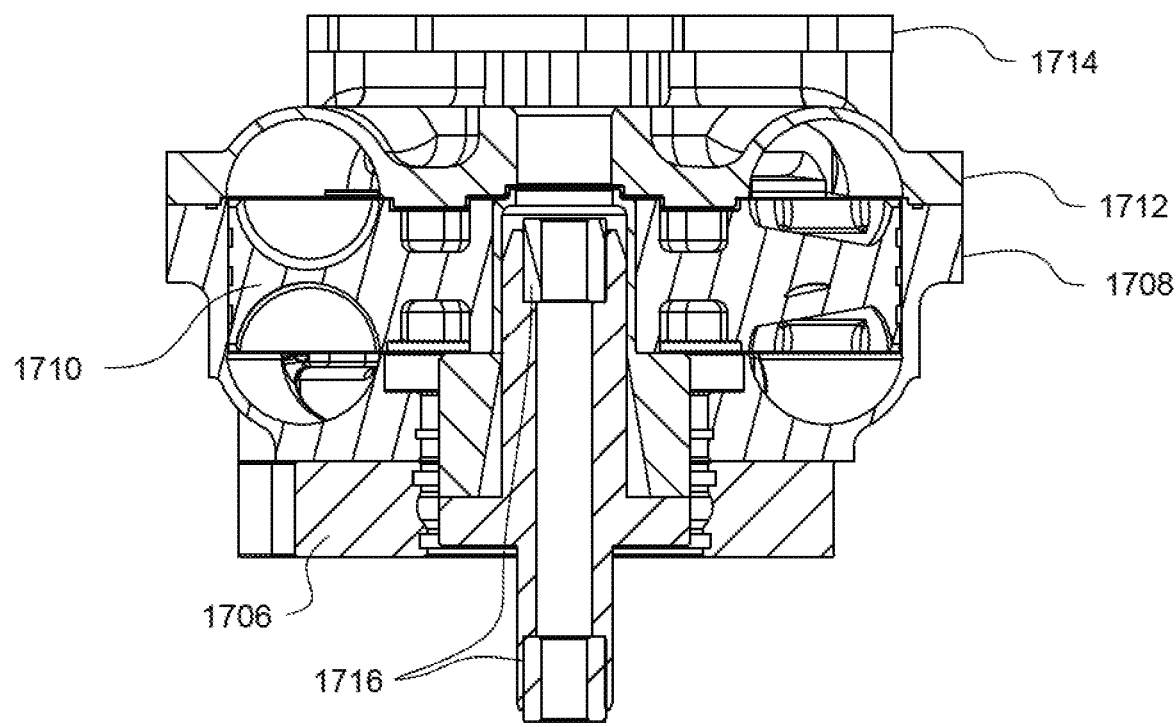
FIG. 17H is a cross-section view of the alternate embodiment for the impeller housing assembly.
Figure 17I:
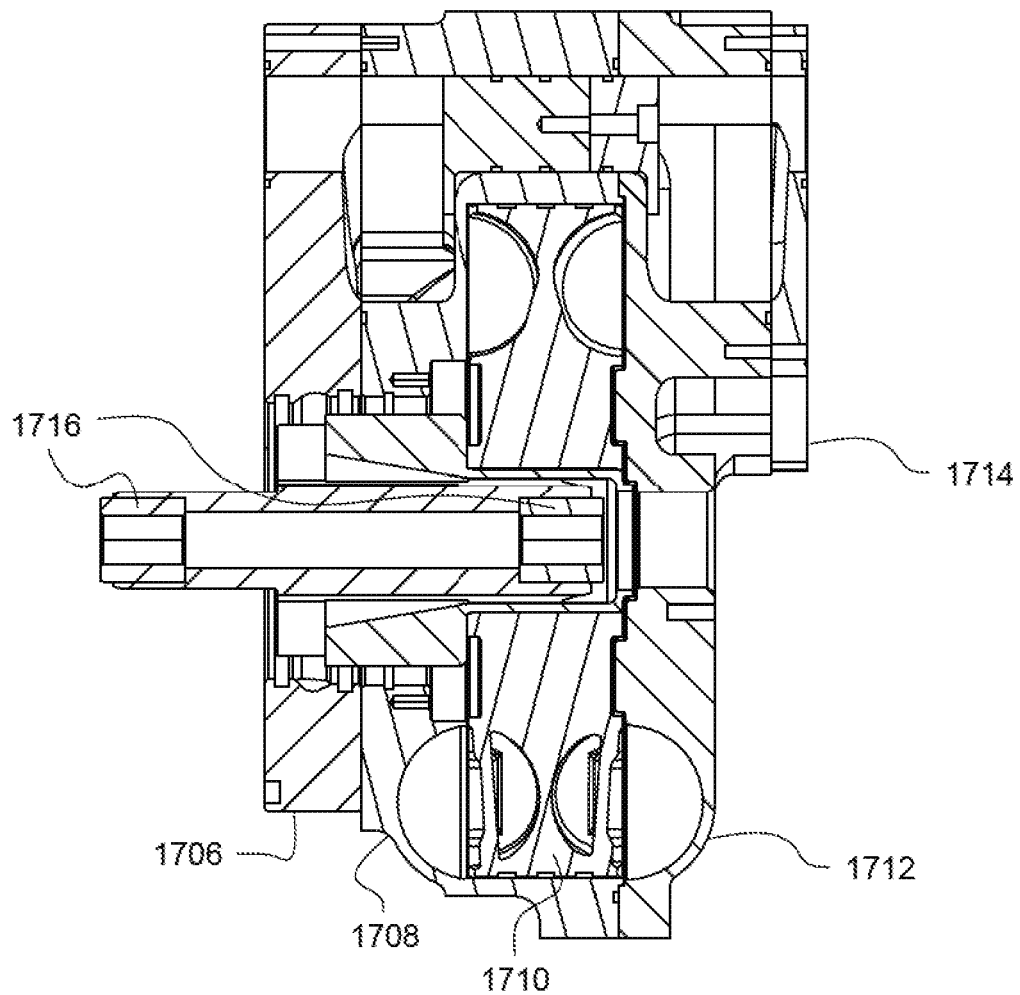
FIG. 17I is a cross-section view of the alternate embodiment for the impeller housing assembly.

Referring now to FIGS. 17-17E, an alternate regenerative blower embodiment 1700 is shown. This embodiment may include an impeller housing assembly 1702, a mounting plate 1704, and a mounting flange 1706. See FIGS. 17B-D for cross-section views of regenerative blower assembly 1700. See also FIG. 17E for an exploded view of the regenerative blower assembly 1700.

Referring now to FIGS. 17-17E, the mounting plate 1704 connects the mounting flange 1706 to the impeller housing assembly 1702. The mounting plate also provides ports that provide fluid pathways into the lower housing 1708 of the impeller housing assembly 1702 as shown on FIG. 17E. In addition, the mounting plate provides passages for the bearing-feed water to exit the blower assembly 1700.

Now referring to FIGS. 17F-I, the impeller housing assembly 1702 may include a lower housing 1708, an impeller assembly 1710, and an upper housing 1712. Also see FIGS. 17H-I for cross-section views of the impeller housing assembly 1702.

Figure 17J:
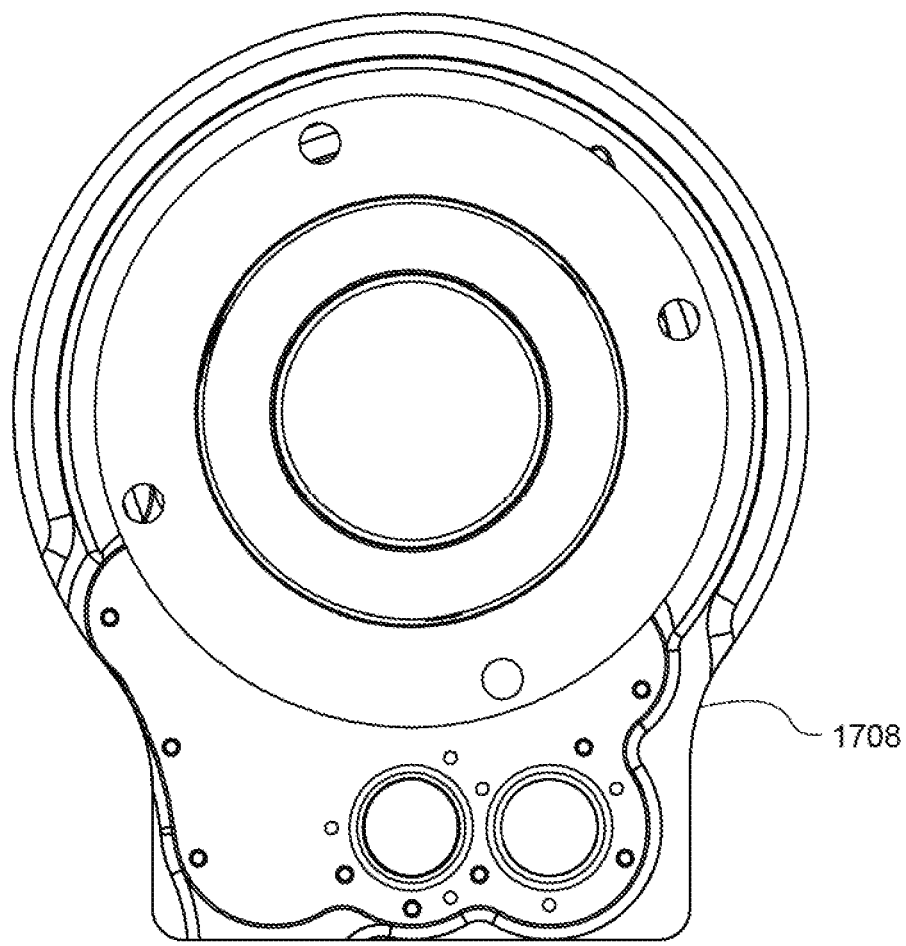
FIG. 17J is a bottom view of the lower section of the impeller housing.
Figure 17K:
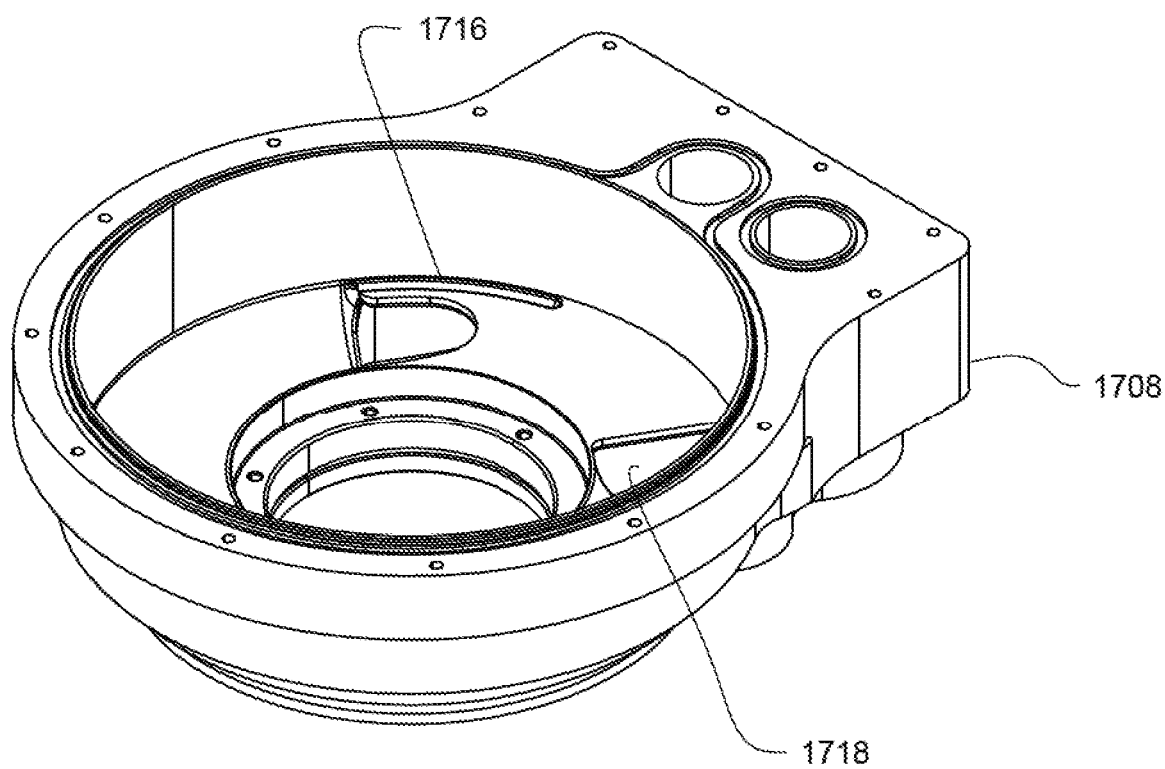
FIG. 17K is a detail view of the inner surface of the lower section of the impeller housing.

Referring now to FIGS. 17F-I, the lower housing 1708 and upper housing 1712 define an interior cavity containing the impeller assembly 1710. This cavity provides a volume for the impeller to compress the incoming low-pressure steam. Steam may enter the impeller housing assembly through inlet ports located within the lower housing 1708 and the upper housing 1712. After the low-pressure steam is compressed by the impeller assembly 1710, the high-pressure steam may exit through outlet ports located in the lower housing 1708 and the upper housing 1712. See FIGS. 17J-K for a detail view of the lower housing 1708. In addition the lower housing 1708 and the upper housing 1712 may be manufactured from but not limited to aluminum, titanium, PPS, and ULTEM®.

Figure 17L:
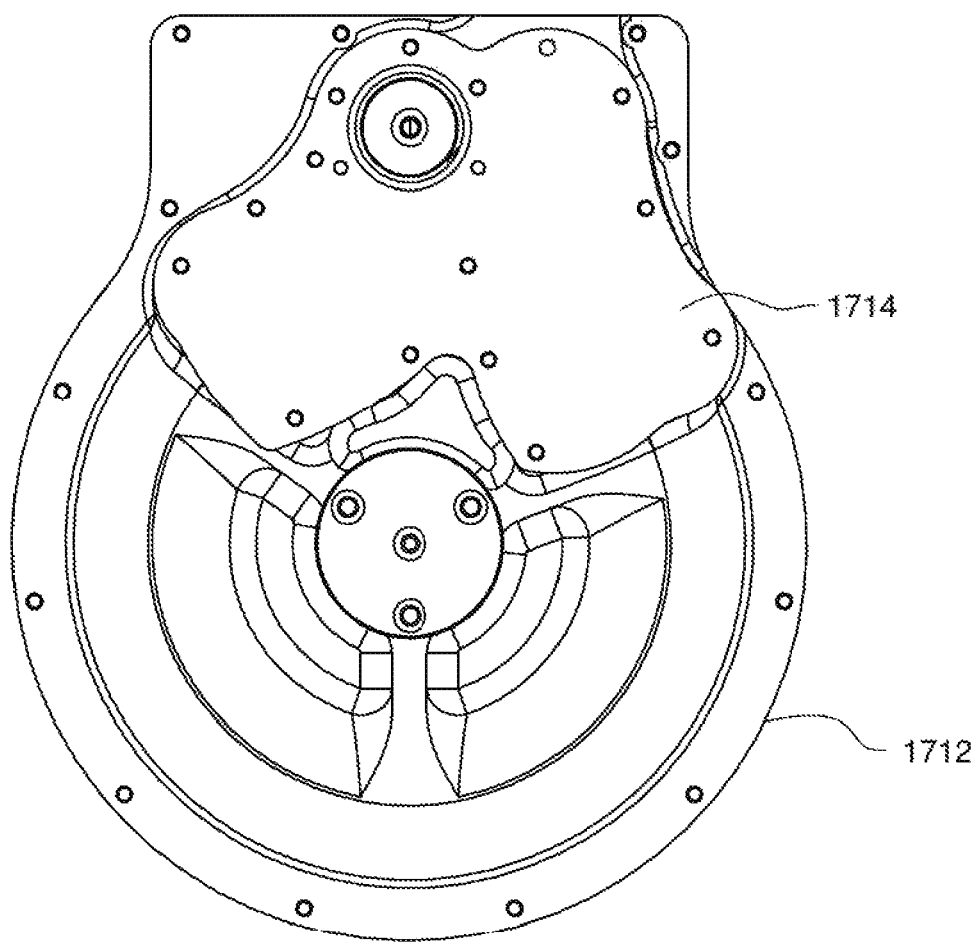
FIG. 17L is a top view of the upper section of the impeller housing assembly.
Figure 17M:
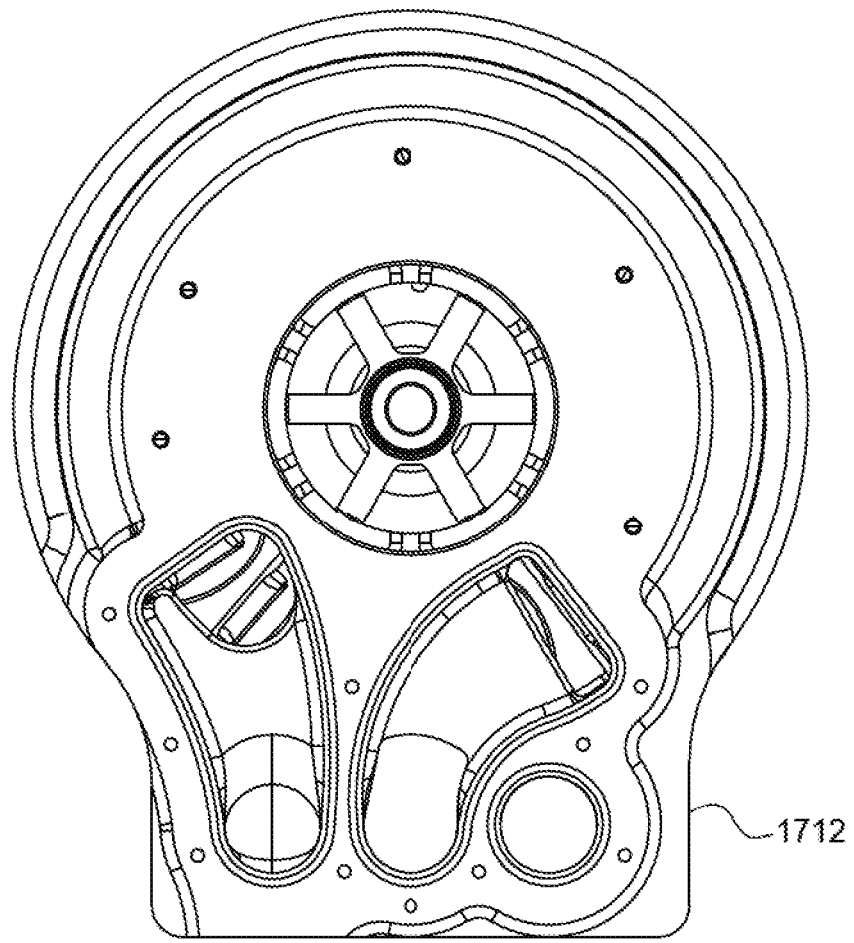
FIG. 17M is a top view of the upper section of the housing for the impeller assembly without the cover installed.

Still referring to FIGS. 17F-I, the upper housing 1712 may include an access cover 1714 attached to the top surface of the housing. See FIG. 17L showing a top view of the upper housing 1712 with the access cover 1714 installed. This cover allows for access to the ports located within the upper housing cover. See FIG. 17M providing a top view of the upper housing 1712 without the access cover 1714 installed. This view illustrates the inlet and outlet ports located within the upper housing 1712.

Figure 17N:
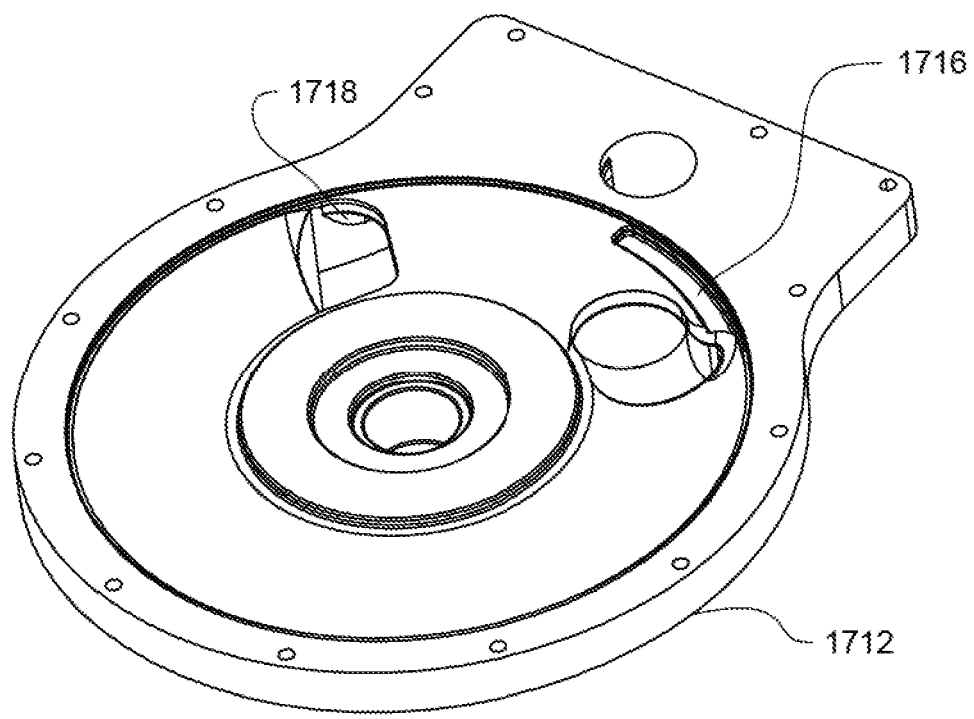
FIG. 17N is a detailed view of the inner surface of the upper section of the housing for the impeller assembly.

Referring now to FIG. 17N, the lower housing 1708 and the upper housing 1712 may include a decompression duct 1716 and a strip plate 1718 on the inner surface of the housings. These features perform similar functions as those described in the exemplary embodiment of the blower assembly 1500.

Figure 18:
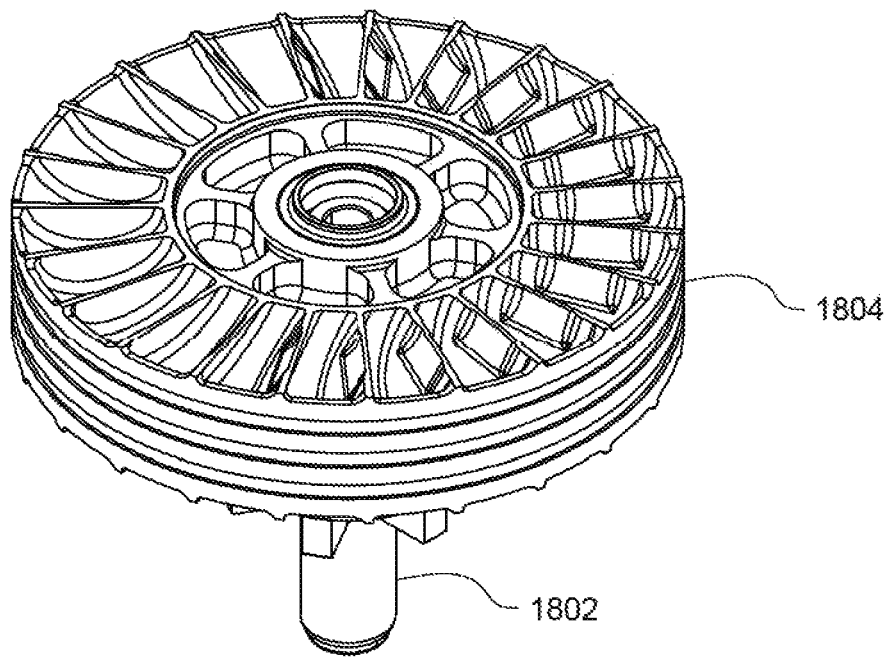
FIG. 18 is a detailed view of the impeller assembly for the alternate embodiment of the regenerative blower.
Figure 18A:
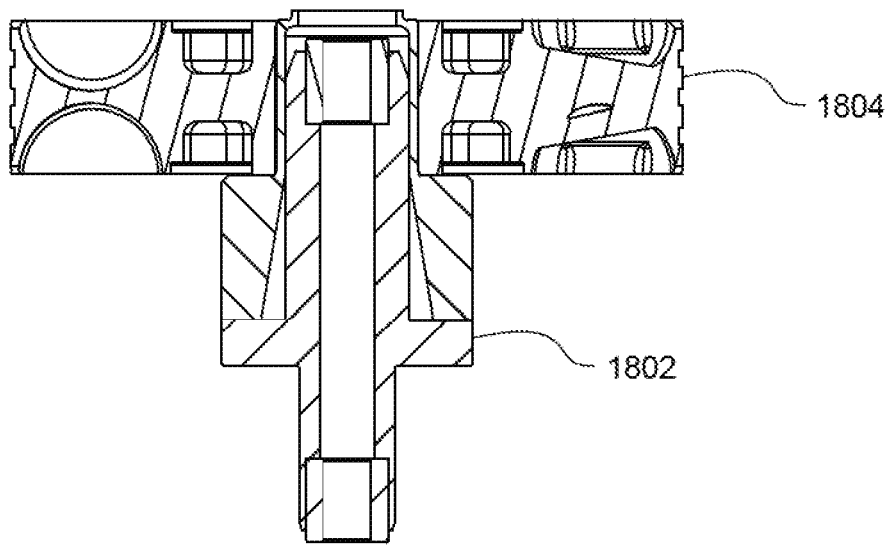
FIG. 18A is a cross-section view of the impeller assembly.

Referring now to FIGS. 18-18A, the inner cavity defined by the lower housing 1708 and upper housing 1712 contains the impeller assembly 1800 (also identified as 1710 of FIG. 17). This assembly may include a spindle 1802 and impeller having blades 1804 as shown on FIGS. 18-18A. As the low-pressure steam enters the inner cavity of the impeller housing 1702, the impeller assembly 1800 compresses the steam as the assembly is rotated.

Still referring to FIGS. 18-18A, the drive motor provides the rotational energy to rotate the impeller 1804 and blades. Located between the inner surface of the spindle and the shaft may be bearings 1716. These bearings support the shaft and allow the impeller 1804 to rotate freely. The bearings 1716 may be located near the ends of the spindle 1802.

In alternate embodiments of the apparatus, low-pressure steam may be compressed using a liquid ring pump as described in U.S. Patent Application Publication No. US 2005/0016828 A1 published on Jan. 27, 2005 and entitled "Pressurized Vapor Cycle Liquid Distillation," the contents of which are hereby incorporated by reference herein.

Level Sensor Assembly

Figure 19:
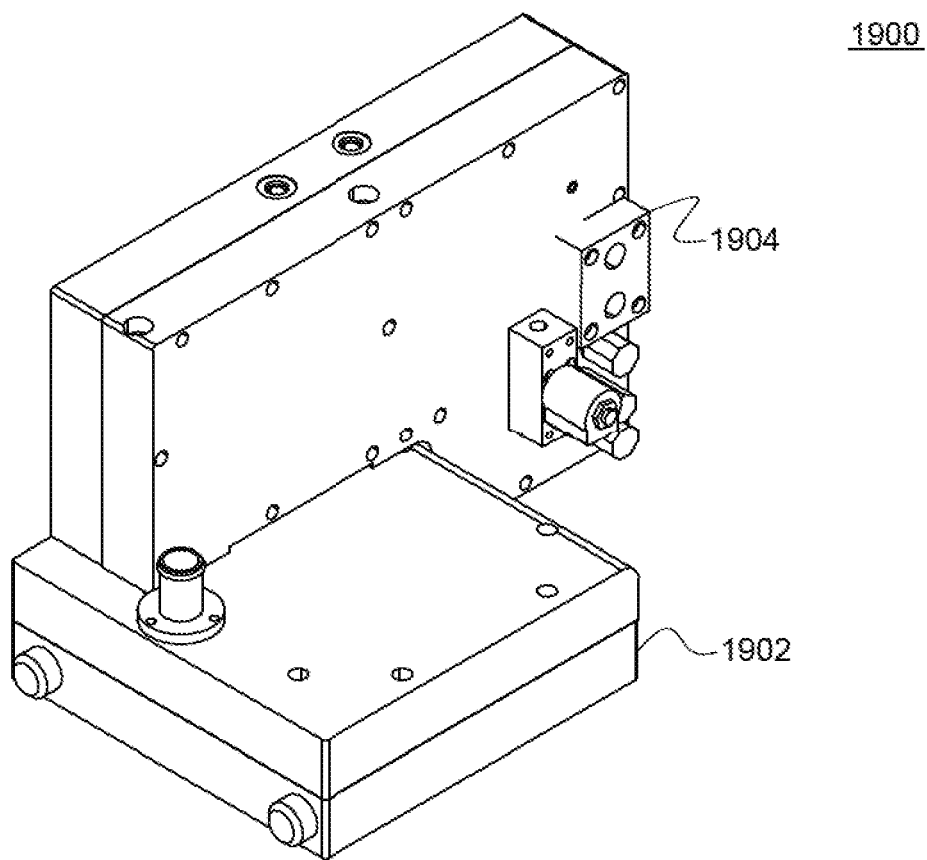
FIG. 19 is an assembly view of the level sensor assembly.

Referring now to FIG. 19, the exemplary embodiment of the water vapor distillation apparatus 100 may also include a level sensor assembly 1900 (also identified as 108 in FIG. 1). This assembly measures the amount of product and/or blowdown water produced by the apparatus 100.

Figure 19A:
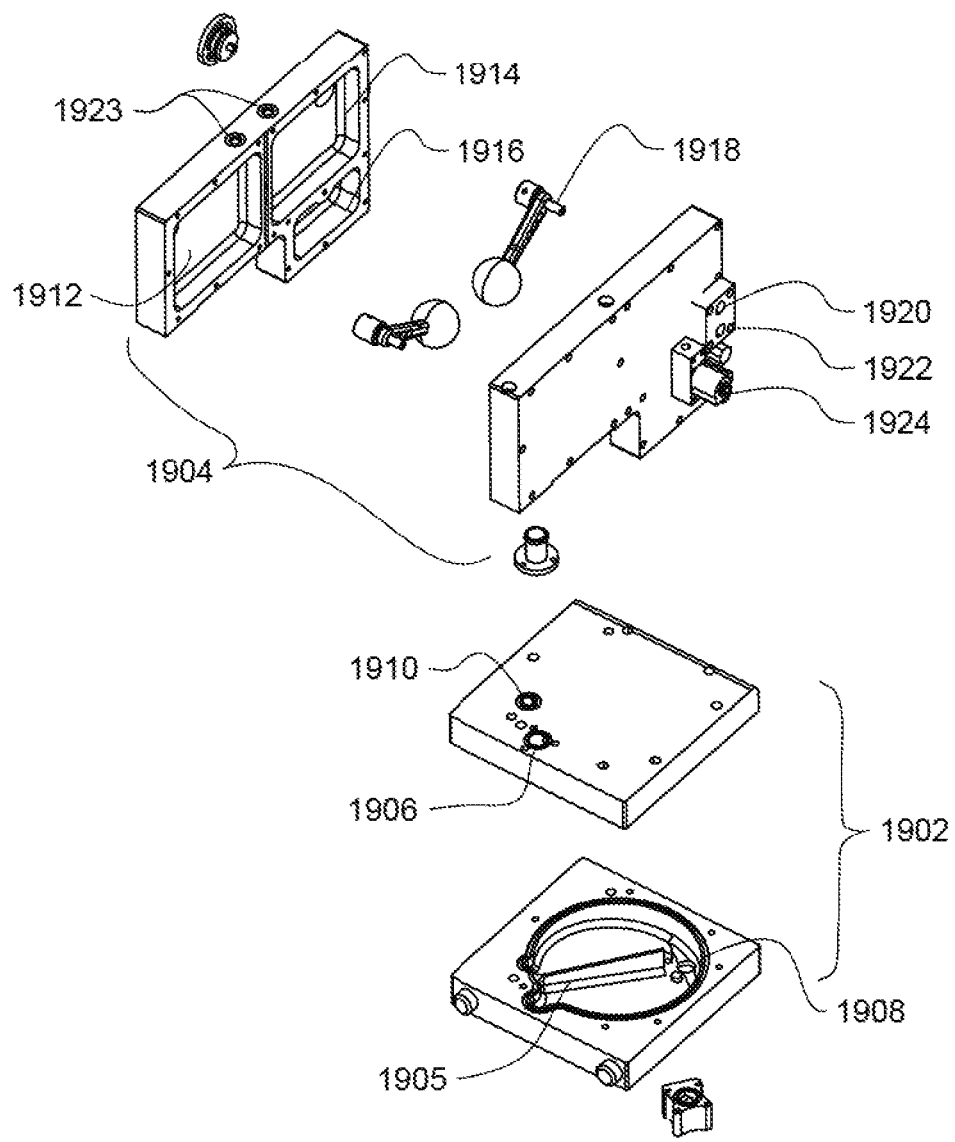
FIG. 19A is an exploded view of the exemplary embodiment of the level sensor assembly.

Referring now to FIGS. 19-19A, the exemplary embodiment of the level sensor assembly 1900 may include a settling tank 1902 and level sensor housing 1904. The settling tank 1902 collects particulate carried within the blowdown water prior to the water entering into the blowdown level sensor tank 1912. The tank removes particulate from the blowdown water by reducing the velocity of the water as it flows through the tank. The settling tank 1902 defines an internal volume. The volume may be divided nearly in half by using a fin 1905 extending from the side wall opposite the drain port 1908 to close proximity of the drain port 1908. This fin 1905 may extend from the bottom to the top of the volume. Blowdown enters through the inlet port 1906 and must flow around the fin 1905 before the water may exit through the level sensing port 1910. As the blowdown enters into the body of the vessel the velocity decreases due to the increase in area. Any particles in the blowdown may fall out of suspension due to the reduction in velocity. The settling tank 1902 may be manufactured out any material having corrosion and heat resistant properties. In the exemplary embodiment the housing is manufactured from RADEL®. In alternate embodiments the settling tank 1902 may be manufactured from other materials including but note limited to titanium, copper-nickel and stainless steel.

Still referring to FIGS. 19-19A, the settling tank 1902 may have three ports an inlet 1906, a drain 1908 and a level sensor port 1910. The inlet port 1906 may be located within the top surface of the settling tank 1902 as shown on FIGS. 19A-B and may be adjacent to the separating fin 1905 and opposite the drain port 1908. This port allows blowdown water to enter the tank. The drain port 1908 may be located in the bottom of the settling tank 1902 as shown on FIGS. 19A-B. The drain port 1908 provides access to the reservoir to facilitate removal of particulate from the tank. In the exemplary embodiment, the bottom of the tank may be sloped towards the drain as illustrated in FIG. 19B. The level sensor port 1910 may be located within the top surface of the tank as illustrated in FIG. 19A and also adjacent to the separating fin 1905 but on the opposite side as the inlet port 1906. This port provides a fluid pathway to the blowdown level sensor reservoir 1912. A fourth port is not shown in FIG. 19A. This port allows blowdown water to exit the level sensor assembly 1900 and enter the heat exchanger. This port may be located within one of the side walls of the upper half of the settling tank 1902 and away from the inlet port 1906.

Still referring to FIGS. 19-19A, in the exemplary embodiment a strainer may be installed within the flow path after the blowdown water exits the blowdown level sensor reservoir 1912 and settling tank 1902. The strainer may collect large particulate while allowing blowdown water to flow to other apparatus components. The strainer may be manufactured from material having corrosion resistant properties. In the exemplary embodiment the strainer is manufactured from stainless steel. In addition, the filter element may be removable to support cleaning of the element. The strainer removes particulate from the blowdown water to limit the amount of particulate that enters the heat exchanger. Excess particulate in the blowdown water may cause the inner tubes of the heat exchanger to clog with scale and sediment reducing the efficiency of the heat exchanger. In addition, particulate may produce blockage preventing the flow of blowdown water through the heat exchanger.

Still referring to FIGS. 19-19A, the settling tank 1902 is in fluid connection with the level sensor housing 1904. This housing may have three interior reservoirs including but not limited to a blowdown level sensor reservoir 1912, a product level sensor reservoir 1914, and a bearing feed-water reservoir 1916. The blowdown level sensor reservoir 1912 is independent of the other reservoirs to prevent contamination from mixing the product water with the blowdown water. The level sensor housing 1904 may be manufactured out any material having corrosion and heat resistant properties. In the exemplary embodiment the housing is manufactured from RADEL®. In other embodiments the housing may be manufactured from other materials including but not limited to titanium, copper-nickel and stainless steel. In other embodiments the housing may be shaped differently with preference that the ball float may have a range of movement of 45 degrees and during this movement there is a constant change in volume of the fluid level.

Still referring to FIGS. 19-19A, within the level sensor housing 1904 there is a blowdown level sensor reservoir 1912. This reservoir is in fluid connection with the settling tank 1902 through measuring port 1910 located within the top surface of the tank 1902. The reservoir provides a location where the rate of blowdown water generated by the apparatus may be measured using a level sensor 1918. As the blowdown water fills the settling tank, some of that water flows through the measuring port 1910 into the blowdown level sensor reservoir 1912. In addition, a vent port 1923 may be located within the top of the reservoir. This port allows air to escape the reservoir allowing blowdown water to fill the cavity. The volume of the reservoir must be sufficient to maintain a level of water. Housings having too small volume may quickly fill and drain adversely affecting the function of the level sensors. In contrast, reservoirs having a large volume may have slower level sensor response times due to the small fluid level height changes for a given increase or decrease in volume. A larger volume may also dampen out the any fluctuations in the water level produced by the operation of the apparatus. Referring now also to FIG. 73, in some embodiments, a blowdown drain 7300 fluid pathway may be included and in fluid connection with the level sensor assembly. In some embodiments, the blowdown drain 7300 fluid pathway may be used to facilitate the cleaning or flushing of the apparatus 100. In some embodiments, the blowdown drain 7300 fluid pathway may be sealed to the outside environment by a valve, for example, but not limited to, a manual ball valve. In some embodiments, the valve may be a non-manual valve, for example, an actuated valve controlled by the control system, and in some of these embodiments, the cleaning and flushing may be at least partially automated.

Still referring to FIGS. 19-19A, the product level sensor reservoir 1914 may be located next to the blowdown level sensor reservoir 1912. The product level reservoir 1914 has an inlet port 1920 and an outlet port 1922. Product water enters the reservoir through the inlet port 1920 and exits the reservoir through the outlet port 1922. The outlet port 1922 may be located below the low end measurement point of the level sensor to improve flow of water out of the reservoir. Similarly, the inlet port 1920 may be located below the low end measurement point of the level sensor to minimize disruption caused by the incoming water. In the exemplary embodiment the inlet port 1920 and outlet port 1922 are located on the side of the level sensor housing 1904 as shown in FIG. 19A. This reservoir provides a space for measuring the rate of product being generated by the apparatus. In addition, a vent port 1923 may be located within the top of the reservoir. This port allows air to escape the reservoir allowing product water to fill the cavity.

Still referring to FIGS. 19-19A, the product level sensor reservoir 1914 is in fluid connection with the bearing feed-water reservoir 1916. An external port 1924 provides a fluid pathway for the product water to flow between the product level sensor reservoir 1914 and the bearing feed-water reservoir 1916 shown on FIG. 19C. Product water enters the bearing feed-water reservoir 1916 through the external port 1924. In addition, the bearing feed-water reservoir 1916 has a supply port 1926 and a return port 1928 shown on FIG. 19C. The supply port 1926 provides a fluid pathway to lubricate the bearings within the regenerative blower assembly. Similarly, a return port 1928 provides a fluid pathway for the product water to return from lubricating the bearings of the regenerative blower assembly. The supply and return ports may be located on the side of the level sensor housing 1904 as shown in FIG. 19C.

Still referring to FIGS. 19-19A, to monitor the amount of product water within the bearing feed-water reservoir 1916 an optical level sensor may be installed. In the exemplary embodiment, the optical level sensor may be located at approximately ⅔ height in the bearing feed-water reservoir 1916. This sensor senses when water is present within the reservoir indicating that there is sufficient water to lubricate the bearings. The sensor may be installed by threading the sensor into the level sensor housing 1904. The sensor may include an o-ring to provide a water-tight seal. In other embodiments the sensor may be but is not limited to conductance sensor, float switches, capacitance sensors, or an ultrasonic sensor.

Figure 19D:
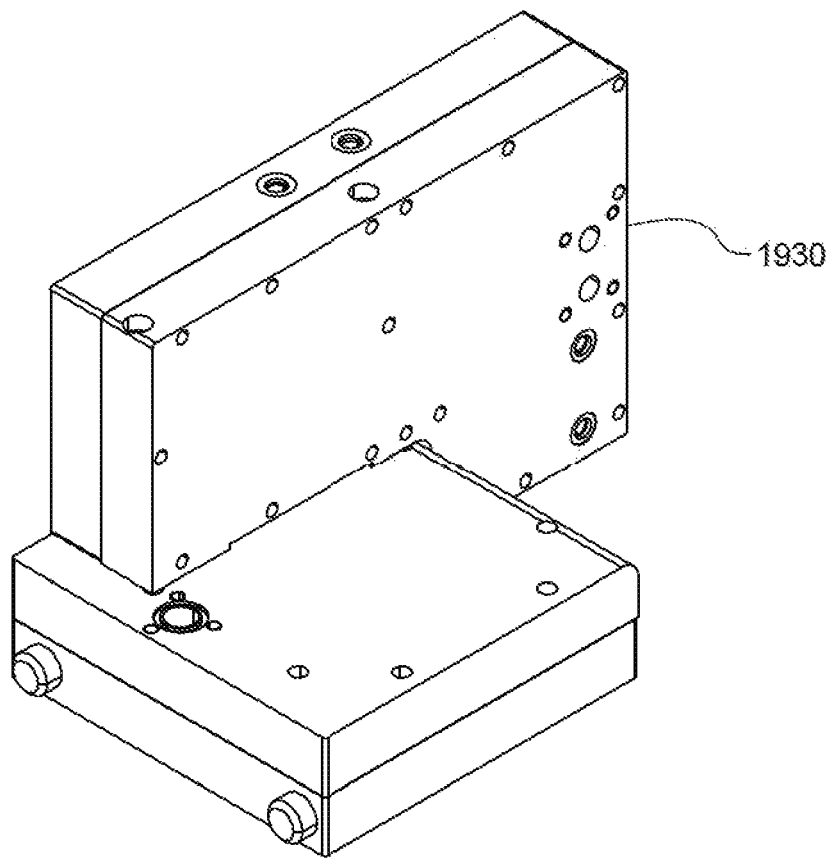
FIG. 19D is an assembly view of an alternate embodiment of the level sensor assembly.
Figure 19E:
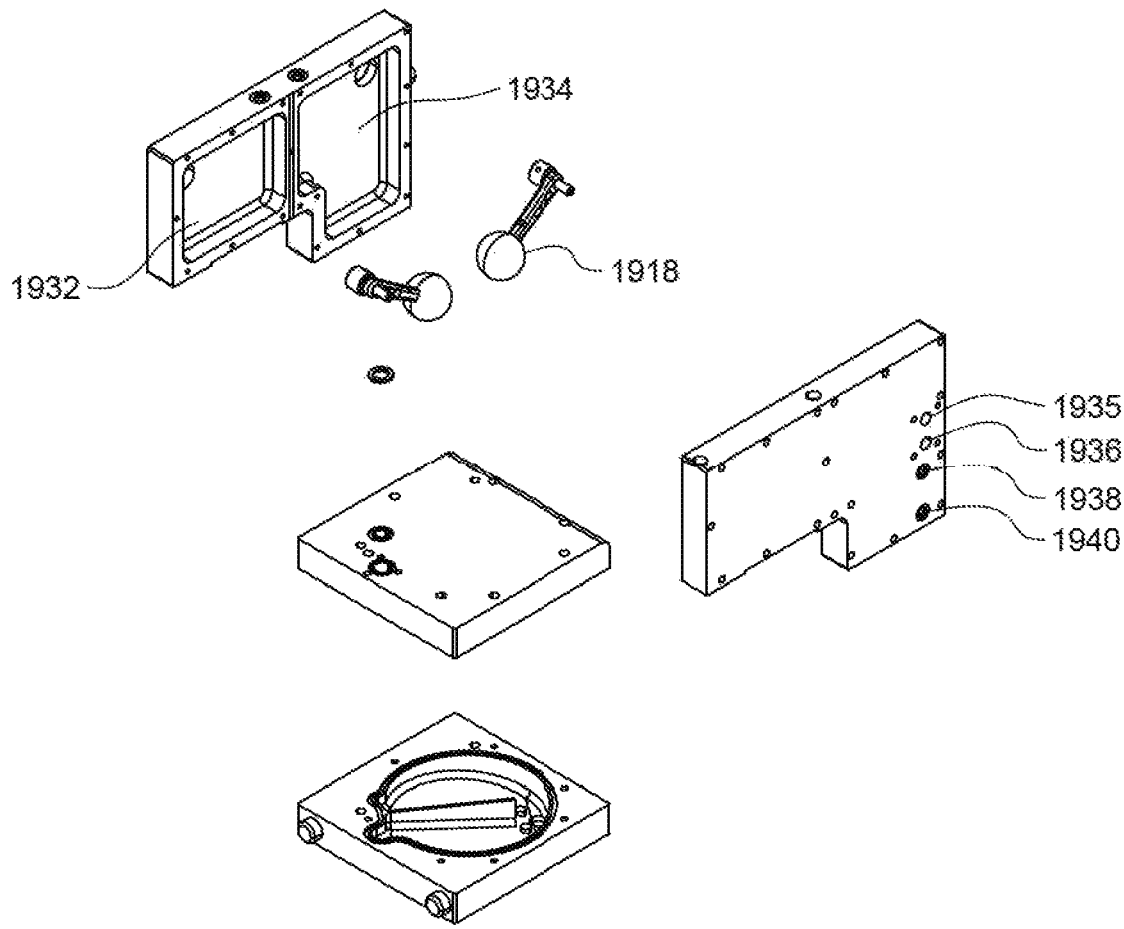
FIG. 19E is an exploded view of an alternate embodiment of the level sensor assembly.

Referring now to FIGS. 19D-F, an alternate level sensor housing 1930 having two reservoirs is shown. Within the level sensor housing 1930 there is a blowdown level sensor reservoir 1932. This reservoir is similar to and performs the same function as the previously described blowdown reservoir 1912 within the level sensor housing 1904. In contrast, the product level sensor reservoir 1934 now contains product water to feed the bearings of the regenerative blower. The bearing feed-water reservoir 1916 of level sensor housing 1904 is eliminated from this configuration. Instead, product water is withdrawn from the product level sensor reservoir to supply water for the regenerative blower.

Still referring to FIGS. 19D-F, the product level sensor reservoir 1934 may have an inlet port 1935, an outlet port 1936, a return port 1938 and a supply port 1940. The inlet port 1935 allows product water to enter the reservoir. Similarly, the outlet port 1936 provides a fluid pathway for product water to leave the housing. Furthermore, the supply port 1940 allows product water to leave the reservoir to lubricate the bearings of the regenerative blower. After passing through the bearings of the regenerative blower, product water may re-enter the product level sensor housing through the return port 1938. These ports may be located any where in the housing, but locating the supply port 1940 and the return port 1938 near the bottom of the housing may limit any adverse effect on the function of the level sensor.

Figure 19G:
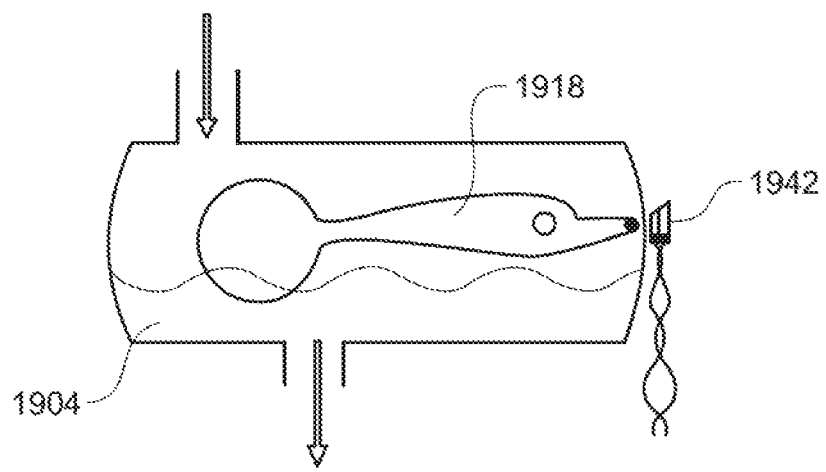
FIG. 19G is a schematic of the operation of the level sensor assembly.
Figure 19H:
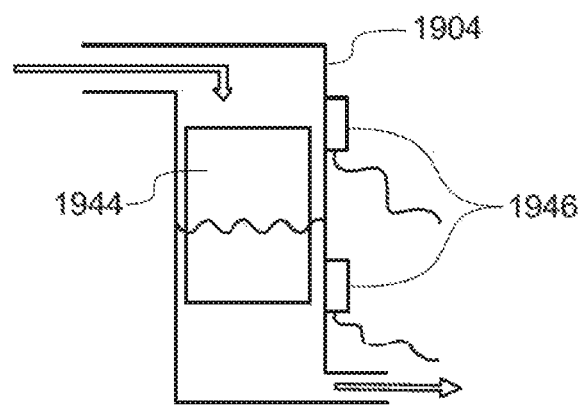
FIG. 19H is an alternate embodiment of the level sensor assembly.

Referring now to FIGS. 19G-H, a sensor 1942 may be positioned on the outside of the level sensor housing 1904 to receive input from the level sensor assembly 1918. Upon receiving input from the level sensor assembly 1918 the sensor 1942 may signal that the water level in the tank is within a particular range or at a particular level. In the exemplary embodiment the sensor may be a continuous analogue sensor. This type of sensor provides continuous feedback as to the position of the level sensor assembly 1918. When the magnets within the level sensors change their position, a change in voltage occurs that is measured and used to determine the location of the sensor. Other embodiments may include but are not limited to a hall sensor or reed switch. FIG. 19H illustrates one possible alternate embodiment for a level sensor assembly including a set of float magnets 1944 and position magnets 1946. The position magnets 1946 are attached to the side of the level sensor housing 1904.

Figure 20:
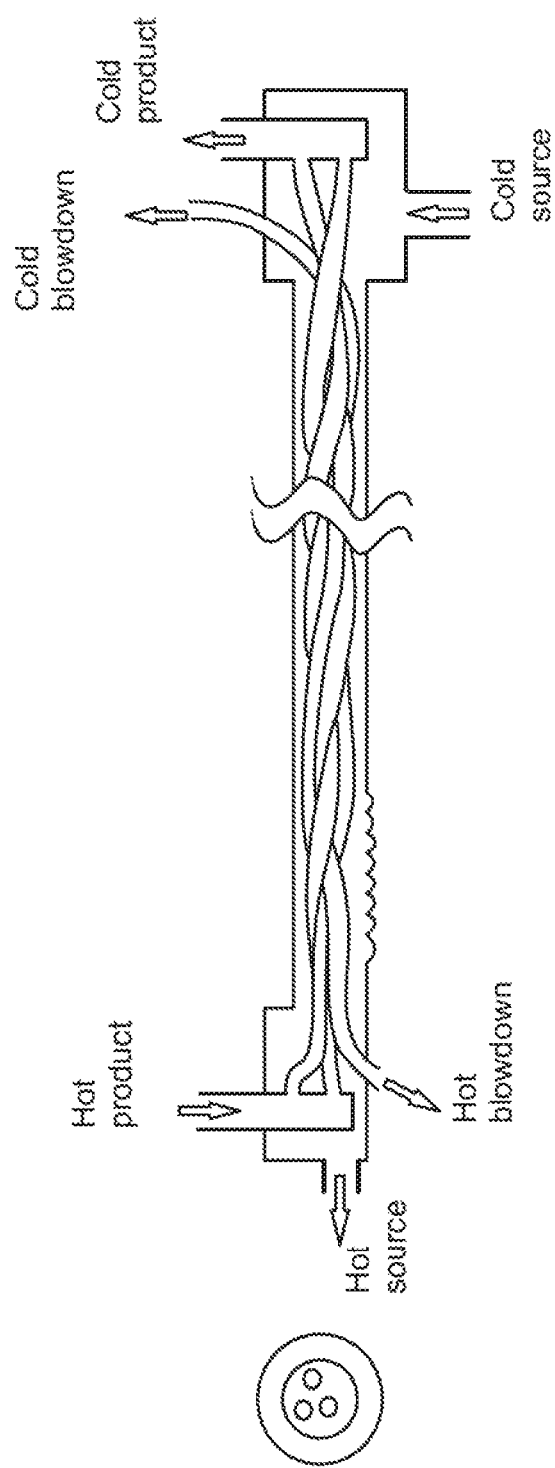
FIG. 20 is an isometric view of level sensor assembly.
Figure 20:
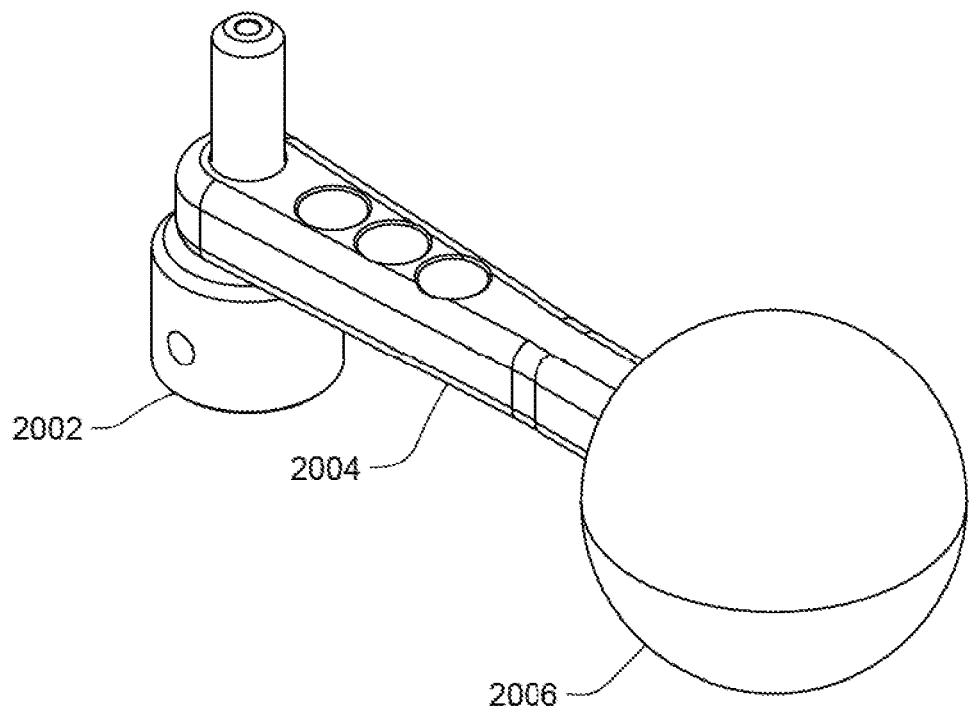
Figure 20A:
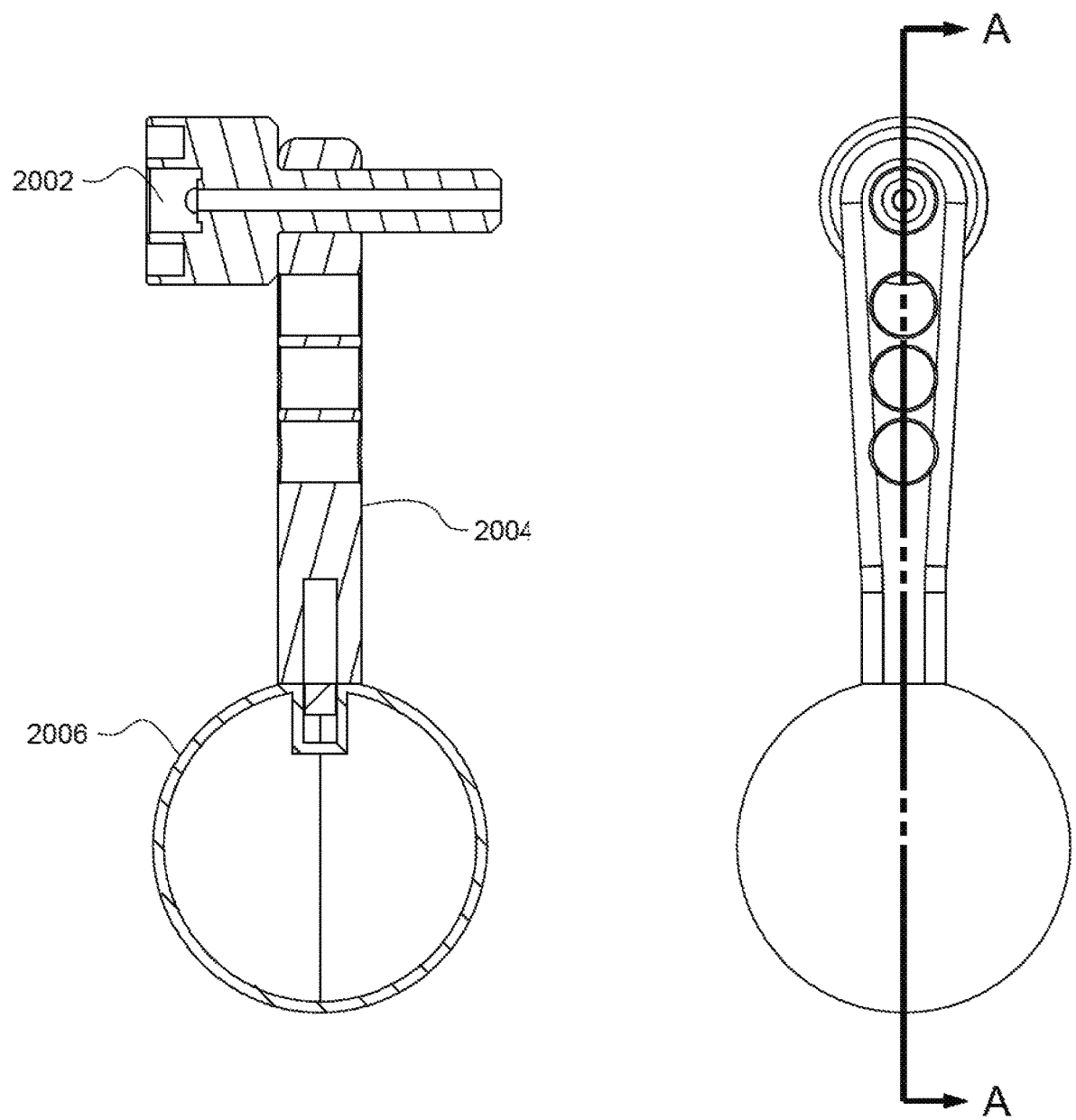
FIG. 20A is cross-section view of the level sensor assembly.

Now referring to FIGS. 20-20A, within the blowdown level sensor reservoir 1912 and the product level sensor reservoir 1914 are level sensors 2000 (also identified as 1918 of FIGS. 19A and 19E). These sensors may include a base 2002, an arm 2004, and a float ball 2006.

Referring still to FIGS. 20-20A, the exemplary embodiment of the level sensors 2000 may include a base 2002 supporting the arm 2004 and the float ball 2006. The assembly also includes two magnets (not shown). The base is connected to the arm and float ball assembly and the assembly pivots on a small diameter axial (not shown). In addition the base 2002 holds two magnets. These magnets are located 180 degrees from one another and are located on face of the base 2002 and parallel to the pivot. In addition, there magnets may be positioned coaxially to the pivot point within the base 2002. In the exemplary embodiment the magnets may be cylinder magnets having an axial magnetization direction.

Referring still to FIGS. 20-20A, the level sensors 2000 measure the rotation of the arm and ball assembly with respect to the pivot. In the exemplary embodiment, the maximum angle of displacement is 45 degrees. In this embodiment the level sensors are installed to prevent the float ball 2006 from being positioned directly below the pivot. In other embodiments the maximum angle of displacement may be as large as 80 degrees. The sensor may monitor the magnets through the wall of the housing. This configuration allows the sensors not to be exposed to corrosive blowdown water and to seal the level sensor housing. The base may be manufactured from any material having corrosion resistant, heat resistant and non-magnetic properties. In the exemplary embodiment the base 2002 is manufactured from G10 plastic. In alternate embodiments the base 2002 may be manufactured from other materials including but not limited to RADEL®, titanium, copper-nickel and fiberglass laminate.

Still referring to FIGS. 20-20A, attached to the base 2002 is an arm 2004. The arm 2004 connects the base 2002 with the float ball 2006. In the exemplary embodiment the arm 2004 is manufactured of G10 plastic material. Other materials may be used to manufacture the arm 2004 with preference that those materials have sufficient high temperature resistant properties. Other materials may include, but are not limited to stainless steel, plastic, RADEL®, titanium, and copper-nickel. The length of the arm is governed by the size of the level sensor reservoirs. In addition, the exemplary embodiment has a plurality of apertures located along and perpendicular to the arm's longitudinal axis. These apertures reduce the weight of the arm and allow the arm to be more sensitive to level changes.

Still referring to FIGS. 20-20A, affixed to the other end of the arm 2004 is a float ball 2006. The float ball 2006 provides surface area for the flow of water to contact. The forces applied to the float ball 2006 by the water cause the level sensor assembly 2000 to pivot about the small diameter shaft. This change in position of the arm will indicate the amount of water in the apparatus. The float ball may be manufactured from any material having corrosion and thermal resistant properties. In addition, the material preferably has a low rate of water absorption. In the exemplary embodiment the float ball is manufactured from hollow stainless steel. For applications where the source water is highly concentrated, such as sea water, the float ball 2006 may be manufactured from any highly corrosion resistant material including but not limited to plastic, titanium and copper-nickel. Furthermore, the float ball 2006 is preferably of the proper size to be positioned within the level sensor housing 1904, such that the float is capable of freely moving. In addition, the size of the float ball 2006 is governed by the size of the level sensor reservoirs.

Figure 21A:
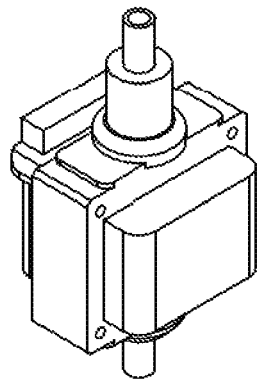
FIG. 21A is an isometric view of the back side of the bearing feed-water pump.
Figure 21:
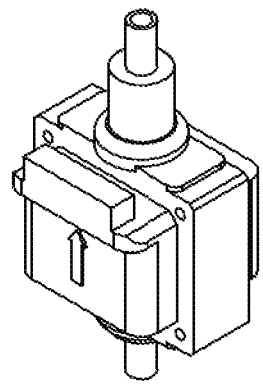
FIG. 21 is an isometric view of the front side of the bearing feed-water pump.

Referring now to FIGS. 21-21A, connected to the supply port 1926 of the bearing feed-water reservoir 1916 may be a bearing feed-water pump 2100 (also identified as 110 on FIGS. 1-1A). The pump 2100 enables the product water to flow from the bearing feed-water reservoir 1916 to the regenerative blower. In the exemplary embodiment, the flow rate is 60 ml/min with a pressure ranging from 2 psi to 2¼ psi. Any type of pump may be used with preference that the pump can supply a sufficient quantity of water to maintain the proper lubricating flow to the bearings within the regenerative blower. In addition, the pump 2100 preferably is heat resistant to withstand the high temperature of the surrounding environment and of the high-temperature product water passing through the pump. In the exemplary embodiment the bearing feed-water pump 110 is a GOTEC linear positive displacement pump, model number ETX-50-VIC. In alternate embodiments, other pump types such as a centrifugal pump may be used with preference that the pump is capable of operating in high temperatures.

Controls

The apparatus may also include a control manifold having a plurality of control valves for the different water flow paths. Typically, this manifold may include a control valve within the inlet piping for the source water to controls the amount of water that enters the apparatus. At excessive pressures the control valve could fail to open or once open may fail to close thus a regulator may be included in inlet piping to regulate the pressure of the source water.

Similarly, the manifold may also include a control valve within the outlet piping carrying blowdown water out of the apparatus. This valve may allow the operator to control the amount of blowdown water leaving the apparatus.

The control manifold may also include a control valve within the outlet piping for the product water. This valve may allow the operator to control the amount of product water leaving the apparatus. In the exemplary embodiment, there is one control valve for each section of outlet piping. Similarly, the apparatus includes a vent valve to release gaseous compounds from the evaporator/condenser. The vent valve maintains operating conditions of the apparatus by venting off small amounts of steam. Releasing steam prevents the apparatus from overheating. Similarly, releasing steam also prevents the buildup of compounds in the condenser space that may prevent the apparatus from functioning.

Typically, the control valves may be same type. In the exemplary embodiment, the controls are solenoid type valves Series 4BKR manufactured from SPARTAN SCIENTIFIC, Boardman, Ohio 44513, model number 9-4BKR-55723-1-002. In alternate embodiments, the controls may be but are not limited to proportional valves. The control valves are electronically operated using an electrical input of zero to five volts.

Moreover, the apparatus may include a backpressure regulator as described in U.S. Patent Application Publication No. US 2005/0194048 A1 published on Sep. 8, 2005 entitled "Backpressure Regulator," the contents of which are hereby incorporated by reference herein.

The water vapor distillation apparatus may include a voltage regulator. Typically, the apparatus may receive single-phase power provided from a traditional wall outlet. In other countries, however, the voltage may differ. To account for this difference in voltage, a voltage regulator may be included in the apparatus to ensure the proper type of voltage is supplied to the electrical components of the apparatus.

In addition, a battery may be included within the system to provide electrical energy to the apparatus. When electrical energy is supplied from a battery the apparatus will preferably include an electrical inverter to change incoming electricity from direct current to alternating current. In other embodiments, the apparatus may receive electrical energy from a Stirling and internal combustion engine. These embodiments may also require an electrical inverter. In other embodiments, the apparatus may include a boost loop to increase the amount of voltage supplied to the apparatus to power the electrical components.

Method of Distilling Water

Also disclosed herein is a method of water vapor distillation including the steps of straining the source water, heating the source water using a heat exchanger, transforming the source water into low-pressure steam, removing water from the source vapor to create dry low-pressure steam, compressing the dry low-pressure steam into high-pressure steam, and condensing the high-pressure steam into product water.

Figure 22:
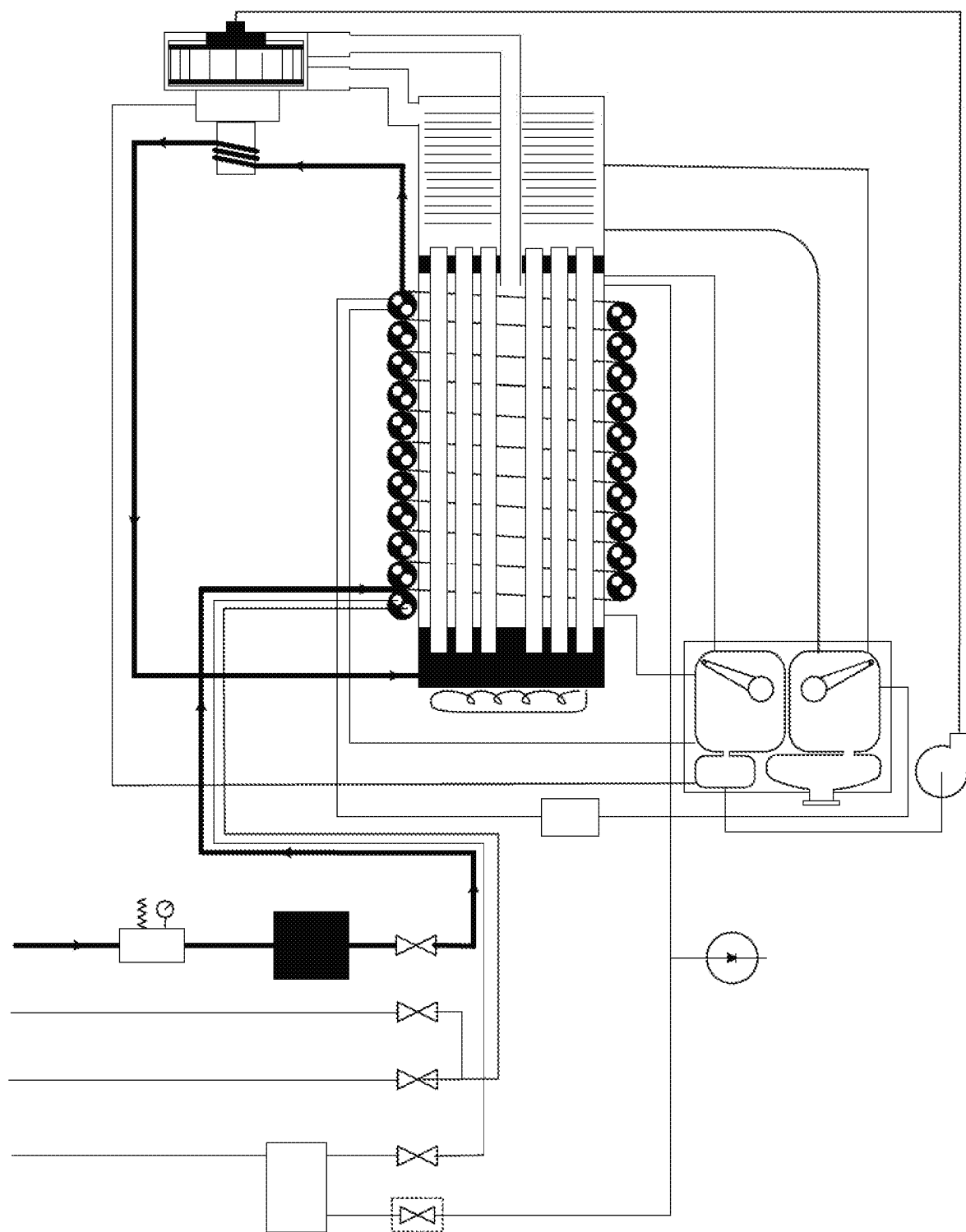
Figure 22A:
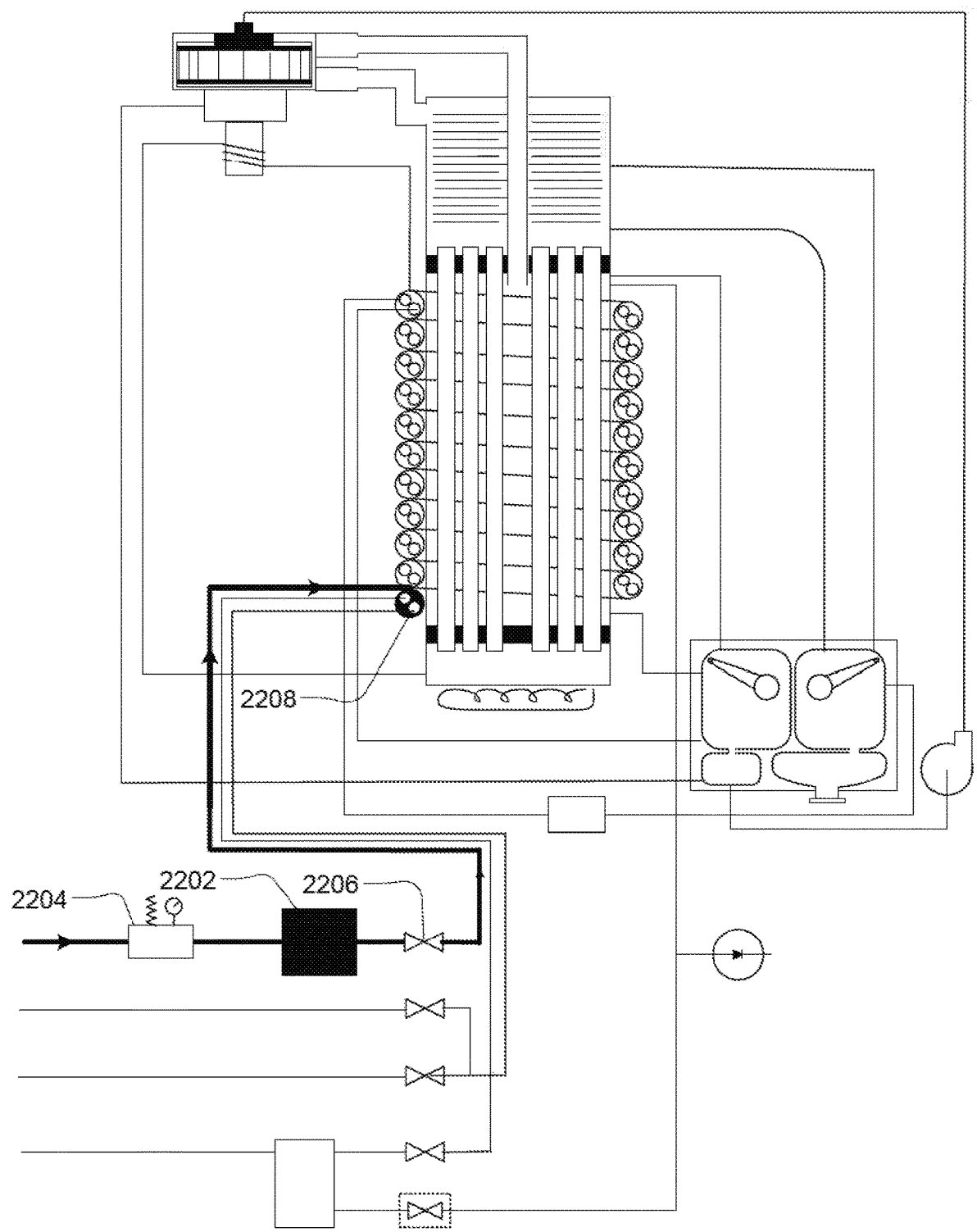

Referring now to FIGS. 22-22A, source water is contaminated water that is transformed into a vapor and later condenses into clean and pure water called, product water. FIG. 22 illustrates the source water fluid paths within the apparatus disclosed previously. The source water enters the apparatus through an inlet tube connected to the heat exchanger as illustrated in FIG. 22A. Typically, a pump may be installed to cause the source water to flow through the inlet tube into the heat exchanger. Within the inlet tube there may be a strainer 2202 installed between where the source water enters the tube and the connection with the heat exchanger, see FIG. 22A. In other embodiments, a regulator 2204 may be positioned within the inlet tube to regulate the flow of the source water into the apparatus. Similarly, in one embodiment, a valve 2206 may be positioned within the inlet tube to isolate the apparatus from the water source.

Referring still to FIGS. 22-22A, in operation, source water passes through a strainer 2202 to remove large particulates. These large particulates may adversely affect the operation of the apparatus, by clogging the inlet and blowdown valves or the inner tubes of the heat exchanger. In addition, particulate may be deposited onto the tubes of the evaporator/condenser reducing the efficiency of the apparatus. In the exemplary embodiment the strainer 2202 is located before the control valves. In other embodiments the strainer may be positioned before the inlet pump (not shown). In the exemplary embodiment the strainer 2202 has a 50 micron user-cleaner unit. In alternate embodiments the apparatus may not include a strainer 2202. After the source water passes through the strainer 2202, the water enters the heat exchanger 2208.

Figure 22B:
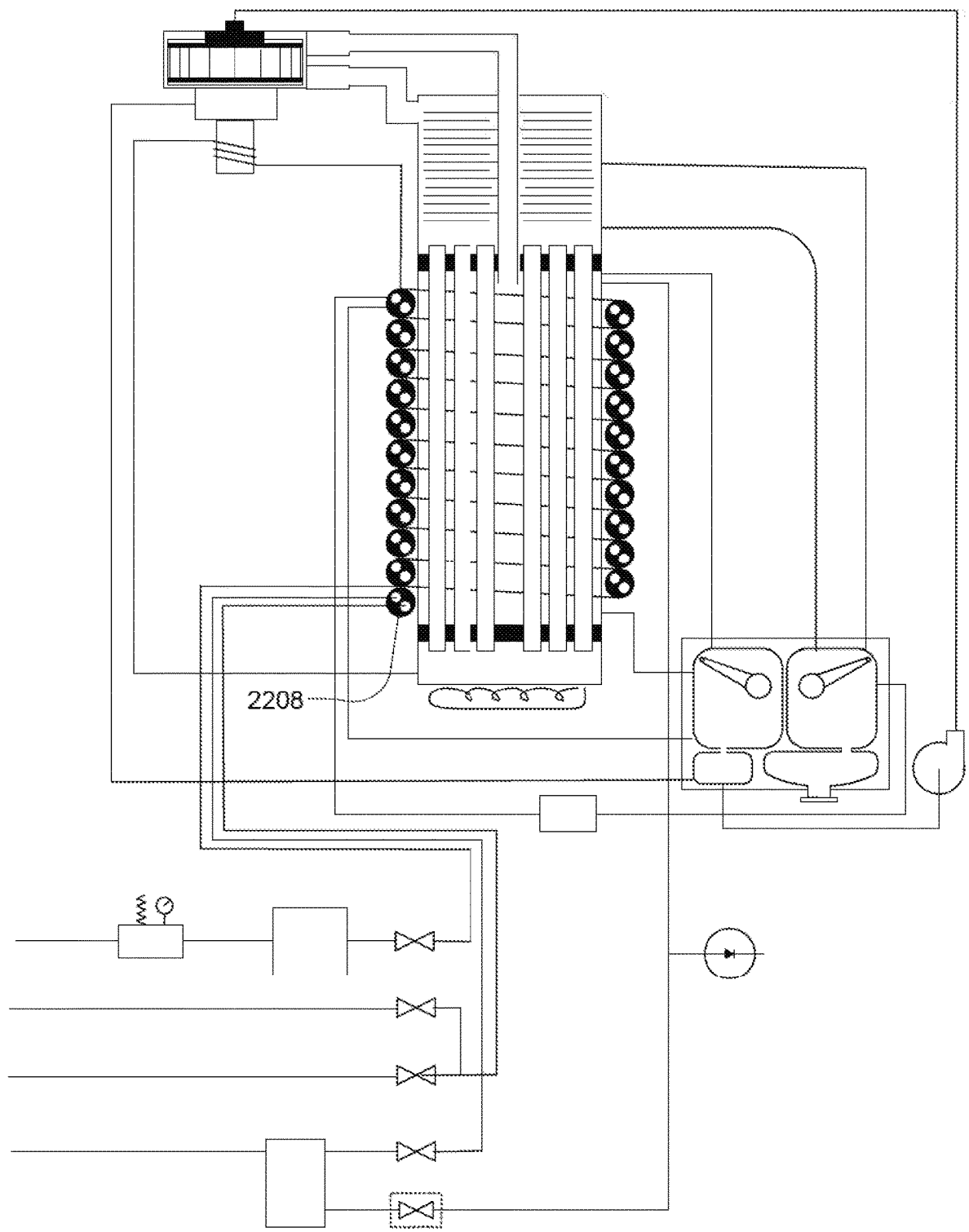

Referring now to FIG. 22B, upon entering the heat exchanger 2208, the source water may fill the outer tube of the heat exchanger 2208. In the exemplary embodiment, the heat exchanger is a counter-flow tube-in-tube heat exchanger. The source water enters the heat exchanger at approximately ambient temperature. Conversely, the product and blowdown water enter the heat exchanger having temperature greater than ambient. The source water enters the heat exchanger at one end and the product and blowdown water enter the heat exchanger at the opposite end. As the source water flows through the heat exchanger the high thermal energy of the product and blowdown water is conducted outwardly from the inner tubes of the heat exchanger to the source water. This increase in the temperature of the source water enables the water to more efficiently change into steam in the evaporator/condenser.

Figure 22C:
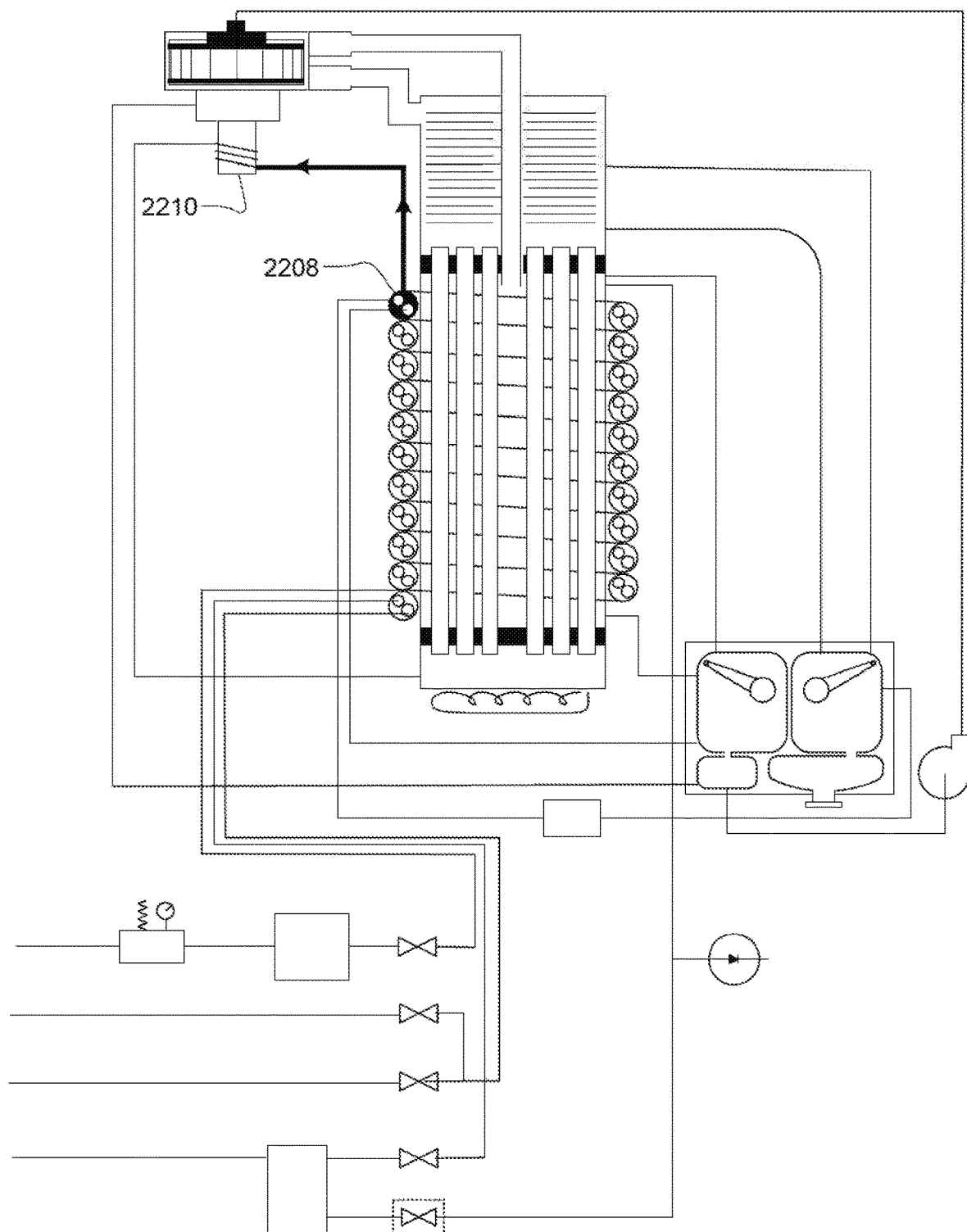
Figure 22D:
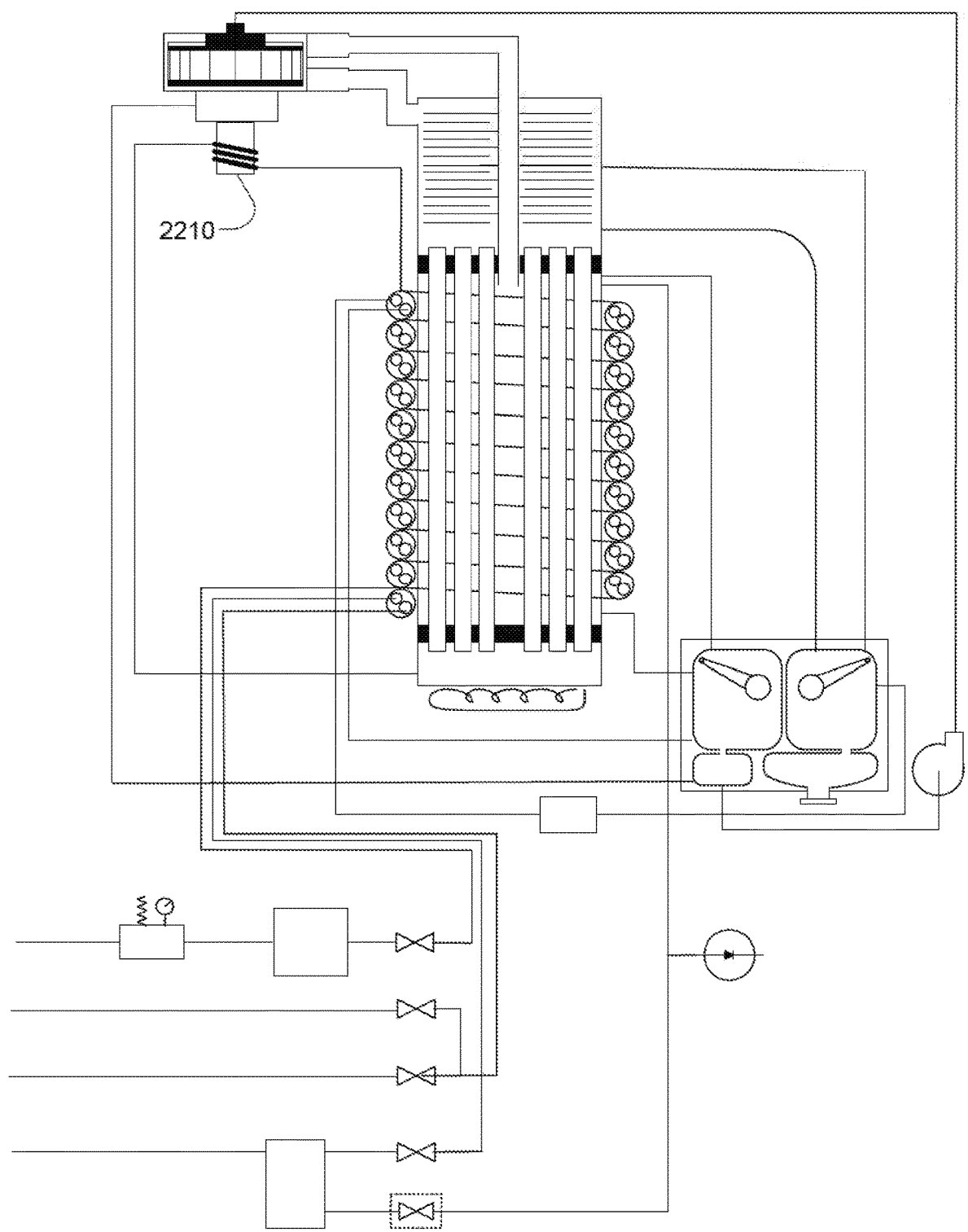

Referring now to FIGS. 22C-D, once the source water passes through the counter-flow tube-in-tube heat exchanger, the water exits the heat exchanger and enters the regenerative blower motor cooling loop. During operation, the regenerative blower motor 2210 creates thermal energy. This thermal energy must be removed from blower motor 2210 for the blower to operate properly. As the source water passes through the blower motor cooling loop the thermal energy created by the blower motor is transferred to the source water. The heat transfer allows the blower motor to maintain a lower operating temperature and raises the temperature of the source water. The higher temperature of the source water increases the efficiency of the apparatus, because less energy is required to produce the phase change of the source water to a vapor. The source water leaves the regenerative blower motor cooling loop enters the evaporator/condenser through the sump 2212, illustrated in FIG. 22E.

Referring now to FIGS. 23-23A, also present in the apparatus is highly concentrated source water, called blowdown water. This water removes particulate from the apparatus to prevent scaling on the tubes of the evaporator/condenser. This fluid may contain any non-volatile contaminants that were present in the source water. These contaminants may include but are not limited to be scale from foulants, heavy metals or organic compounds. Specifically, these foulants may include but not limited to calcium carbonate, magnesium carbonate In addition, blowdown water transfers thermal energy to the source water when passing through the heat exchanger. FIG. 23 shows the blowdown water fluid paths within the apparatus disclosed previously. The blowdown water is collected in the steam chest 2302 as shown in FIG. 23A. As the low-pressure water vapor passes through the steam chest 2302, water droplets are separated from the water vapor. These droplets accumulate in the bottom of the steam chest 2302 and are added to the existing blowdown water. As the level of blowdown water increases, the water exits the steam chest 2302 through a port. Through this port, the blowdown water leaves the steam chest 2302 and enters the level sensor housing 2304, illustrated in FIG. 23A.

Referring now to FIGS. 23B-C, the blowdown water enters the level sensor housing 2304 and fills the settling tank 2306. As the blowdown water passes through the settling tank 2306 particulate within the water settles to the bottom of the tank and thus separating the water from the particulate. Separating the particulate from the water prevents the particulate from entering the heat exchanger. The heat exchanger may be adversely affected by the presence of particulate in the water. Particulate may collect in the inner tubes of the heat exchanger causing the heat exchanger to have a lower efficiency. Particulate may reduce flow of blowdown through the inner tubes reducing the amount of thermal energy capable of being transferred to the source water. In some instances, the collection of particulate may produce a blockage within the inner tubes preventing the flow of blowdown water through the heat exchanger. As blowdown water fills the settling tank 2306, the water may also fill the blowdown level sensor reservoir 2308, illustrated in FIG. 23C.

Referring now to FIGS. 23D-G, upon exiting the level sensor housing 2304, the blowdown water may pass through a strainer 2310 before entering the heat exchanger 2312 shown on FIG. 23E. The strainer 2310 removes particulates within the blowdown water that remain after flowing through the settling tank 2306 of the level sensor housing 2304. Removing particulates from the blowdown water reduces particulate build-up in the heat exchanger and valves within the system. The blow down water enters the heat exchanger 2312 fills one of the inner tubes as shown in FIG. 23E. The water fills the heat exchanger 2312 as shown in FIG. 23F. As the blowdown water passes through the heat exchanger, thermal energy is conducted from the higher temperature blowdown water to the lower temperature source water through the tube containing the blowdown water. The blowdown water exits the heat exchanger illustrated on FIG. 23G. After leaving the heat exchanger, blowdown fluid may pass through a mixing can 2314 to prevent steam being released from the apparatus potentially harming a person or adjacent object. Steam may be periodically vented from the condenser space to maintain the apparatus energy balance. Similarly, gaseous vapors (ex. volatile organic compounds, air) must be purged from the condenser space to maintain proper operation of the apparatus. Both the steam and gaseous vapors are released into the mixing can 2314 having low-temperature blowdown water. By mixing the steam into the blowdown water the steam condenses allowing for steam to be released safely. In other embodiments, there may be a valve positioned in the tubing connecting the heat exchanger 2312 and mixing can 2314 to isolate the mixing can from the apparatus or adjust the flow rate of the blowdown water exiting the apparatus.

Referring now to FIGS. 24-24A, product water is formed when high-pressure steam condenses when contacting the outer surface of the tubes within the evaporator/condenser. FIG. 24 shows the product water fluid paths within the apparatus disclosed previously. The product water is created in the evaporator/condenser 2402 as shown in FIG. 24A. As the high-pressure steam condenses against the outer surface of the tubes of the evaporator/condenser forming water droplets. These droplets accumulate in the bottom of the evaporator/condenser 2402 creating product water. As the level of product water increases, the water exits the evaporator/condenser 2402 through a port and enters the level sensor housing 2404, illustrated in FIG. 24A.

Referring now to FIGS. 24B-24E, the product water may enter the level sensor housing 2404 through a port connected to the product level sensor reservoir 2406 shown on FIG. 24B. This reservoir collects incoming product water and measures the amount of water created by the apparatus. The water exits the product level sensor reservoir 2406 and enters the heat exchanger 2408 illustrated in FIG. 24C. While passing through the heat exchanger 2408, the high-temperature product water transfers thermal energy to the low-temperature source water through the inner tubes of the heat exchanger 2408. FIG. 24D illustrates the product water passing through the heat exchanger 2408. After passing through the heat exchanger 2408, the product water exits the apparatus as illustrated in FIG. 24E. In the exemplary embodiment the apparatus may include a product-divert valve 2410 and product valve 2412. The product valve 2412 allows the operator to adjust the flow rate of product water leaving the apparatus. Typically, the once the reservoir is 50 percent full, then the product valve 2412 is cycled such that the amount of water entering the reservoir is equal to the amount leaving the reservoir. During initial start-up of the system the first several minutes of production the product water produced is rejected as waste by opening the product-divert valve 2410. Once it has been determined that the product is of sufficient quality the product-divert valve 2410 closes and the product valve 2412 begins operation.

Referring now to FIGS. 24F-24H, as product water fills the product level sensor reservoir 2406, water may also enter the bearing feed-water reservoir 2410. The bearing feed-water reservoir 2410 collects incoming product water for lubricating the bearings within the regenerative blower 2412. Product water exits the bearing feed-water tank 2410 and may enter a pump 2414 as shown in FIG. 24G. The pump 2414 moves the product water to the regenerative blower. After leaving the pump 2414, the product water enters the regenerative blower 2412 illustrated on FIG. 24H.

Referring now to FIGS. 24H-24I, upon entering the blower 2412, the product water provides lubrication between the bearings and the shaft of the blower. After exiting the regenerative blower 2412, the product water may re-enter the level sensor housing 2404 through the bearing feed-water reservoir 2410, see FIG. 24I.

Now referring to FIGS. 25-25C, to support the flow of the water throughout the apparatus vent paths may be provided. These paths support the flow of the water through the apparatus by removing air or steam from the apparatus. The vent paths are shown in FIG. 25. FIG. 25A illustrates a vent path from the blowdown level sensor reservoir 2502 to the steam chest 2504 of the evaporator/condenser 2508. This path allows air within the reservoir to exit allowing more blowdown water to enter the reservoir. Similarly, FIG. 25B illustrates a vent path from the product level sensor reservoir 2506 to the evaporator/condenser 2508. This path allows air within the reservoir to exit allowing product water to enter the reservoir. Finally, FIG. 25C shows a vent path from the condenser area of the evaporator/condenser 2508 to allow air within the apparatus to exit the apparatus to the surrounding atmosphere through a mixing can 2510. In addition, this vent path assists with maintaining the apparatus' equilibrium by venting small quantities of steam from the apparatus.

Figure 22E:
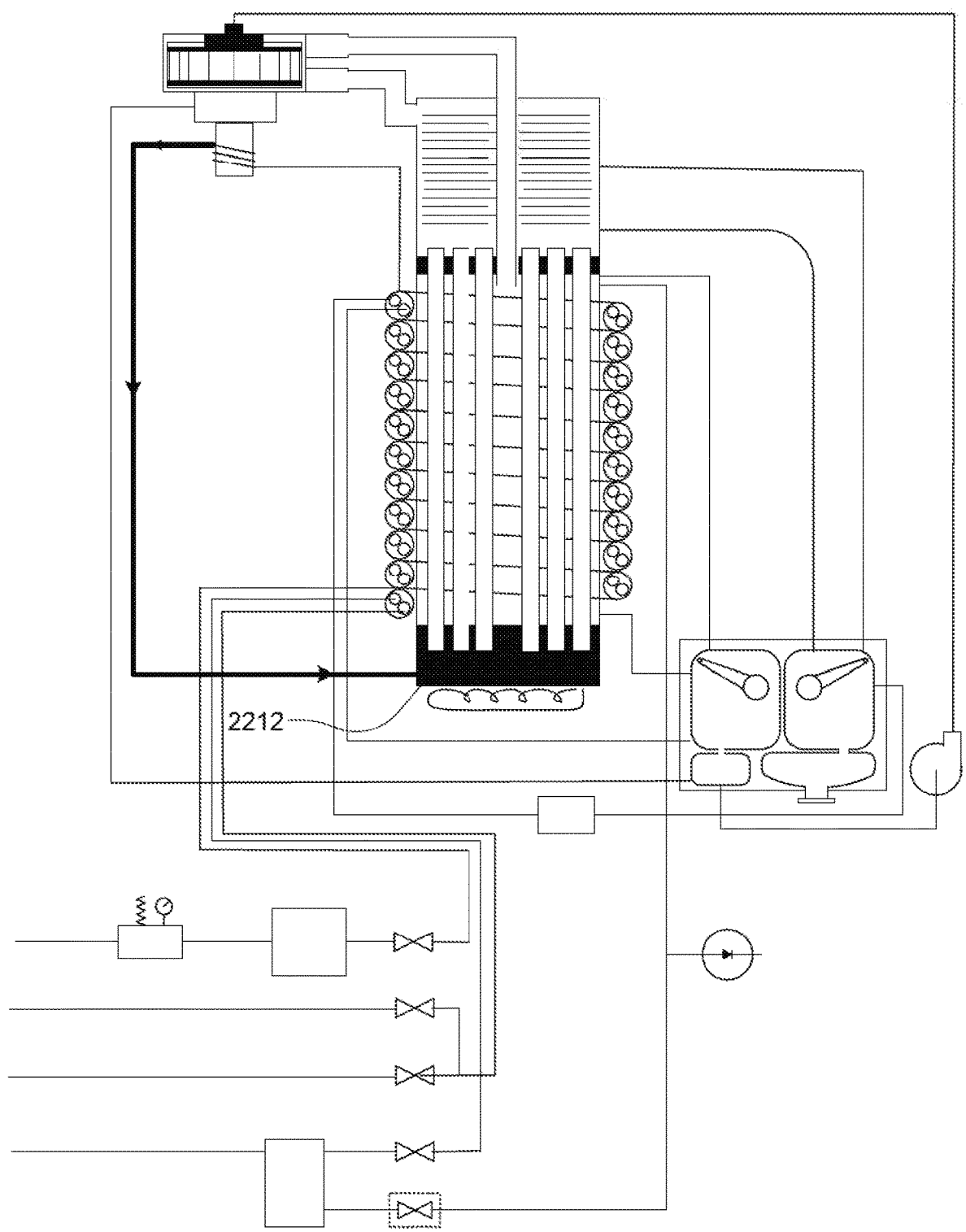

Referring now to FIG. 26, in operation, source water enters the sump 2602 of the evaporator/condenser 2608 in the manner described in FIGS. 22-22E. When source water initially enters the sump 2602, additional thermal energy may be transferred to the water using a heating element. Typically, the heating element may be used during initial start up of the water vapor distillation apparatus. Otherwise the heater will not typically be used. As the amount of source water in the sump increases, the water flows out of the sump and into the tubes 2604 of the evaporator/condenser through ports within a plate 2606 positioned between the sump 2602 and the evaporator/condenser 2608, illustrated in FIG. 26. During initial start-up of the apparatus, the evaporator section of the evaporator/condenser 2608 is flooded with source water until there is sufficient amount of water in the blowdown level sensor reservoir. After initial start-up the tubes 2604 remain full of source water.

Referring now to FIGS. 26A-26E, once in the tubes 2604, the source water is heated from conduction of thermal energy through the tube walls from the high-pressure steam present on the outside of the tubes 2604. FIG. 26A illustrates the wet low-pressure steam flowing through the tubes 2604 of the evaporator/condenser 2608. The wet low-pressure steam travels through the tubes 2604 of the evaporator/condenser 2608 and enters the steam chest 2610 illustrated in FIG. 26B. As steam flows through the interior of the steam chest 2610, the water droplet within the steam are separated from the steam. These droplets collect at the base of the steam chest 2610 and are added to the blowdown water already present in the base, see FIGS. 26C-D. Blowdown water flows out of the apparatus in manner described in FIGS. 23-23G. The dry low-pressure steam exits the steam chest 2610 and enters the regenerative blower 2612 as shown on FIGS. 26E-F.

Now referring to FIGS. 26F-H, once in the regenerative blower 2612, the dry low-pressure steam is compressed creating dry high-pressure steam. After the dry steam is compressed, the high-pressure steam exits the regenerative blower 2612 and enters the steam tube 2614 of the steam chest 2610. See FIGS. 26G-H illustrating the steam exiting the blower 2612 and entering the steam tube 2614 of the steam chest 2610.

Now referring to FIGS. 26H-J, the steam tube 2614 is in fluid connection with the inner cavity of the evaporator/condenser 2608. The steam tube 2614 provides an isolated pathway for the steam to enter the condenser side of the evaporator/condenser 2608 from the blower 2612. The high-pressure steam is isolated to maintain the pressure of the steam and to ensure that the steam has no contaminants. The dry high-pressure steam exits the steam tube 2614 of the steam chest 2610 and enters the inner cavity of the evaporator/condenser 2608. See FIG. 26I showing the inner cavity of the evaporator/condenser 2608 containing high-pressure steam. As the high-pressure steam contacts the outer surfaces tubes 2604 of the evaporator/condenser 2608, the steam transfers thermal energy to the tubes 2604. This energy is conducted through the tube walls to the source water located within the tubes 2604. When the energy is transferred from the steam to the tube walls, the steam condenses from a vapor to a fluid. This fluid is known as product water. As water droplets form on the outside of the tube walls, these droplets flow down to the base of the evaporator/condenser 2608. See FIG. 26J showing the formation of product water within the inner cavity of the evaporator/condenser 2608. When the amount of product water within the cavity is sufficient, product water may flow out of the evaporator/condenser as illustrated in FIGS. 24-24I.

Referring now to FIG. 27, there are several factors that may affect the performance of the apparatus described. One of these factors is pressure difference across the regenerative blower. FIG. 27 is a chart illustrating the relationship between the amount energy required to produce one liter of product water and the change in pressure across the regenerative blower. Ideally, one would want to operate the blower, such that, the most product water is produce using the least amount electricity. From this graph, operating the blower with a pressure differential between 1.5 psi and 2 psi produces a liter of product water using the least amount of energy. Operating the blower at pressures above or below this range increases the amount of energy that is needed to produce one liter of water.

Now referring to FIG. 28, another factor that may affect the performance of the apparatus is the number of heat transfer tubes installed within the inner cavity of the evaporator/condenser assembly. FIG. 28 illustrates the relationship between the number of heat transfer tubes and the rate of production of product water for a given change in pressure across the regenerative blower. From this chart, it is determined that having a greater number of heat transfer tubes increases the production of product water. In this graph, the configuration producing the largest amount of product water per hour is the assembly having 85 tubes. The configuration producing the least amount of water is the assembly having only 43 tubes for pressures below 2 psi.

Referring now to FIG. 29, this figure illustrates the amount of product water created by different heat transfer tube configurations. In this graph, the configuration having 102 heat transfer tubes generated the highest amount of product water. In contrast, the configuration having a shorter tube length and only 48 tubes produced the least amount of product water.

Now referring to FIG. 30, despite having a lower number of tubes than other configurations, the 48 heat transfer tube configuration produces more water per surface area. FIG. 30 illustrates the relationship between the amount of product created and the size of the heat transfer surface area. This chart shows that the 48 heat transfer tube configuration having a tube length of 15 inches is the most efficient design. The least efficient configuration is the 102 heat transfer tube design. Thus, having a large number of tubes within the evaporator/condenser may produce more water, but a design having a lower number of tubes may provide the most efficient use of resources.

Referring now to FIG. 31, this figure illustrates the difference of the performance two 48 heat transfer tube designs. In this chart the difference in the designs is the tube lengths. At various pressure changes across the regenerative blower, this graph contrasts the amount of energy used and rate of production of water for the two configurations. The configuration having the 20 inch long tubes produces slightly more product while consuming slightly less energy at equal pressure differences across the regenerative blower.

Methods of Control

The pressure difference across the compressor directly determines the amount of product water that the apparatus may generate. To ensure a particular amount of product water output from the apparatus, one can adjust the pressure difference across the compressor. Increasing the speed of the compressor will typically result in an increase in pressure differential across the two sides of the evaporator/condenser. Increasing the pressure differential increases rate at which source water is evaporated into clean product water.

One of the limiting factors in controlling the water vapor distillation apparatus 100 is the amount of blowdown water that is required to operate the machine. Without sufficient blowdown water, particulate separated from the source water will remain in the apparatus. This build-up of particulate will adversely affect the operation and efficiency of the apparatus.

To ensure that particulate is removed from the apparatus, there must be a sufficient amount of blowdown water present to carry the particulate out of the apparatus. To determine how much blowdown water is required to operate the apparatus in a particular environment, one must know the quality of the water entering the apparatus (source water). If the source water has a high concentration of particulate then more blowdown water will be needed to absorb and remove the particulate from the apparatus. Conversely, if the source water has a low concentration of particulate then less blowdown water will be required.

To control and observe the amount of product and blowdown water generated by the apparatus a couple of different control methods may be implemented. These schemes may include but are not limited to measuring the level of product and blowdown water within reservoirs located in the apparatus, measuring the flow rate of the product and blowdown water created by the apparatus, measuring the quality of the incoming source water and measuring the output quality of the product water.

The level sensor assembly of the exemplary embodiment may measure both the level of and the flow rate of water. The water level may be measured by the movement of the level sensor assembly. As the water fills the reservoir, the water produces a change in position of the level sensor assembly.

One may determine the flow rate of water by knowing the change in position of the level sensor assembly, the area of the reservoir and the time associated with the change in water level. Using a float sensor to determine flow is advantageous because there is no pressure drop resulting from the use of a float sensor. The flow rate may indicate the performance of the apparatus and whether that performance is consistent with normal operation of the apparatus. This information allows the operator to determine whether the apparatus is functionally properly. For example, if the operator determines the flow rate is below normal operating conditions, then the operator may check the strainer within the inlet piping for impurities or the tubes of the evaporator/condenser for scaling. Similarly, the operator may use the flow rate to make adjustments to the apparatus. These adjustments may include changing the amount of blowdown and product water created. Although a flow rate may indicate performance of the apparatus, this measurement is not required.

The water quality of either the inlet source water or the outlet product water may be used to control the operation of the water vapor distillation apparatus. This control method determines the operation of the machine based on the quality of the water. In one embodiment the conductivity of the product water is monitored. When the conductivity exceeds a specified limit than the sensor sends a signal to shut down the apparatus. In some embodiments the sensors may be, but are not limited to a conductivity sensor. In an alternate embodiment, may include monitoring the conductivity of the blowdown water. When the conductivity of the blowdown water exceeds a specified limit then the sensor sends a signal to increase the amount of source water entering the apparatus. The increase in source water will reduce the conductivity of the blowdown water. In another embodiment, the conductivity of the source water may be monitored. When the conductivity exceeds a specified limit than the sensor sends a signal to adjust the flow rate of the source water. The higher the source water conductivity may result in higher flow rates for the source and blowdown water.

In alternate embodiments, the apparatus may include a control scheme where the apparatus has a steady-state mode. During this mode, the apparatus reduces the amount of power consumed. In other embodiments, the heating elements may remain operating during this mode to maintain a particular temperature or temperature range of the source water in the sump. Maintaining the temperature of the source water in the sump reduces the amount of time for the machine to start generating more product water. In addition, during this mode the regenerative blower is not functioning and the inlet and outlet valves are closed.

Examples of tests that may be performed on a source water sample to analyze the quality of the source water include, but are not limited to, bacterial testing, mineral testing, and chemical testing. Bacterial tests indicate the amount of bacteria that may be present within the sample. The most common type of bacterial test is total coliform.

Mineral testing results may indicate the amount of mineral impurities in the water. Large amounts of minerals and other impurities may pose a health hazard and affect the appearance and usefulness of the water.

Another type of water testing that may be accomplished is chemical testing. Many man-made chemicals may contaminate a water supply and pose health hazards to potential consumers of the water. Unless a specific chemical or type of chemical is suspected to be in the water, this type of test may not be routinely performed as the testing is expensive for unspecified chemical contaminants. However, if a particular chemical is suspected to be present in the source water, a test may be performed. Examples of some specific water quality tests are described below.

pH—measures the relative acidity of the water. A pH level of 7.0 is considered neutral. Pure water has a pH of 7.0. Water with a pH level less than 7.0 is considered to be acidic. The lower the pH, the more acidic the water. Water with a pH greater than 7.0 is considered to be basic or alkaline. The greater the pH, the greater its alkalinity. In the US, the pH of natural water is usually between 6.5 and 8.5. Fresh water sources with a pH below 5 or above 9.5 may not be able to sustain plant or animal species. pH may be determined using any known method in the art for testing.

The pH is preferably measured immediately at the source water test site as changes in temperature affect pH value. Preferably, the water sample is taken at the source at a location away from the "bank", if using a lake, stream, river, puddle, etc, and below the water surface.

Nitrate—Nitrogen is an element required by all living plants and animals to build protein. In aquatic ecosystems, nitrogen is present in many forms. It may combine with oxygen to form a compound called nitrate. Nitrates may come from fertilizers, sewage, and industrial waste. They may cause eutrophication of lakes or ponds. Eutrophication occurs when nutrients (such as nitrates and phosphates) are added to a body of water. These nutrients usually come from runoff from farmlands and lawns, sewage, detergents, animal wastes, and leaking septic systems. The presence of nitrate may be determined using any known method in the art for testing Turpidity—Turbidity refers to how clear or how cloudy the water is. Clear water has a low turbidity level and cloudy or muddy water has a high turbidity level. High levels of turbidity may be caused by suspended particles in the water such as soil, sediments, sewage, and plankton. Soil may enter the water by erosion or runoff from nearby lands. Sediments may be stirred up by too much activity in the water, for example, by fish or humans. Sewage is a result of waste discharge and high levels of plankton may be due to excessive nutrients in the water.

Where the turbidity of the water is high, there will be many suspended particles in it. These solid particles will block sunlight and prevent aquatic plants from getting the sunlight they need for photosynthesis. The plants will produce less oxygen thereby decreasing the DO levels. The plants will die more easily and be decomposed by bacteria in the water, which will reduce the DO levels even further. Turbidity may be determined using any known method in the art for testing Coliform—Where coliform bacteria are present in the water supply it is an indication that the water supply may be contaminated with sewage or other decomposing waste. Usually coliform bacteria are found in greater abundance on the surface film of the water or in the sediments on the bottom.

Fecal coliform, found in the lower intestines of humans and other warm-blooded animals, is one type of coliform bacteria. The presence of fecal coliform in a water supply is a good indication that sewage has polluted the water. Testing may be done for fecal coliform specifically or for total coliform bacteria which includes all coliform bacteria strains and may indicate fecal contamination. The presence of coliform may be determined using any known method in the art for testing.

In operation the water machine may perform conductivity testing of the source water and/or the product water to determine the quality of the water entering and exiting the system. This testing may be accomplished using conductivity sensors installed within the inlet and outlet piping of the system. Water having a high conductivity indicates that the water has greater amount of impurities. Conversely, water having a lower amount of conductivity indicates that water has a lower level of impurities. This type of testing is generic and provides only a general indication of the purity/quality of the water being analyzed.

Other types of testing may be accomplished for analyzing specific levels of the following water impurities/characteristics include but are not limited to pH, hardness, chlorides, color, turbidity, sulfate, chlorine, nitrites nitrates, and coliforms. Typically to analyze the water entering or exiting the machine the operator may first obtain a sample of the water. After obtaining the desired sample the water may then be tested using a water testing kit available from Hach Company, Loveland, Colo. 80539-0389. Other methods of testing the purity of water may include sending the water to laboratory for analysis.

Systems for Distilling Water

Also disclosed herein is where the apparatus for distilling water described previously may be implemented into a distribution system as described in U.S. Publication No. US 2007/0112530 A1 published on May 17, 2007 entitled "Systems and Methods for Distributed Utilities," the contents of which are hereby incorporated by reference herein. Furthermore, a monitoring and/or communications system may also be included within the distribution system as described in U.S. Publication No. US 2007/0112530 A1 published on May 17, 2007 entitled "Systems and Methods for Distributed Utilities," the contents of which are hereby incorporated by reference herein.

Alternate Embodiments

Although the exemplary embodiment of the still/water vapor distillation apparatus has been described, alternate embodiments of still, including alternate embodiments of particular elements of the still (i.e., heat exchanger, evaporator condenser, compressor, etc) are contemplated. Thus, in some alternate embodiments, one of more of the elements are replaced with alternate embodiment elements described herein. In some embodiments, the entire still is replaced by an alternate embodiment, for example, the system as described in one embodiment utilizes the exemplary embodiment as the still while in other embodiments, the system utilizes an alternate embodiment.

Referring to FIGS. 32-32C, alternate embodiments of the water vapor distillation apparatus having a liquid ring pump 3200 disclosed. The ring pump may include a fully rotatable housing that provides maximum reduction in frictional loss yet maintains simplicity of design and cost-effectiveness of production is shown in FIGS. 32 through 32C. As can be seen in FIG. 32, stator 3202 is stationary relative to rotor 3204, and comprises an intake 3206 and exit 3208. Steam is drawn in at pressure $P_1$ and passes into rotor chamber 3210. Rotor 3204 is off-set from a central axis Z upon which the rotating housing and the liquid ring pump are centered. As rotor 3204 turns about central shaft 3212 with rotor bearings 3214, the effective volume of chamber 3210 decreases. Steam is thereby compressed to pressure $P_2$ as it is carried along a rotational path into exit 3208, to be routed to an evaporator/condenser 104 of FIG. 1. Preferably, a rotatable housing (not shown) rotates with the liquid ring in the liquid ring pump, to reduce energy loss due to friction.

Referring to FIGS. 32A-B, the stator 3202 has support structures 3216 in the input and output regions. The individual vanes 3218 of rotor 3204 can be seen below the support structures 3216 in the top view of stator 3202 shown in FIGS. 32A-B, as well as the concentric placement of rotor 3204 about the central axis. This particular embodiment of a liquid ring pump is both axially fed and axially ported and may have a vertical, horizontal, or other orientation during operation. FIG. 32C shows yet another view of this embodiment.

The liquid ring pump 3200 is designed to operate within a fairly narrow range of input and output pressure, such that generally, the apparatus operates in the range of from 5 to 15 psig. Apparatus pressure may be regulated using check valves to release steam from chamber 3210 of FIGS. 32-32C. Improved apparatus performance is preferably achieved by placing exit 3208 of the exhaust port at a specific angle of rotation about the rotor axis, wherein the specific angle corresponds to the pressure rise desired for still operation. One embodiment of a specific port opening angle to regulate apparatus pressure is shown in FIG. 32A. Exit 3208 is placed at approximately 90 degrees of rotation about the rotor access, allowing steam from chamber 3210 to vent. Placing exit 3208 at a high angle of rotation about the stator axis would raise the apparatus pressure and lower pump throughput, while placing exit 3208 at a lower angle of rotation about the stator axis would result in lower apparatus pressure and increased pump throughput. Choosing the placement of exit 3208 to optimize apparatus pressure may yield improved pump efficiency. Further, the placement of exit 3208 to maintain apparatus pressure may minimize apparatus complexity by eliminating check valves at the exhaust ports to chamber 3210, thereby providing a simpler, more cost-effective compressor.

Referring now to FIG. 32D, during operation, it may be desirable to measure the depth of the liquid ring in the compressor, to optimize performance. In the embodiments herein disclosed, liquid ring pump housing 3232 rotates with the liquid ring in the pump, and the temperature of the fluid is typically around 110 degrees C. Methods of measuring ring depth include any one of the usual methods, such as using ultra-sound, radar, floats, fluid conductivity, and optical sensors. Because of the complexities of the rotating housing, use of a capacitive sensor is a preferred embodiment for this measurement, wherein as the depth of the fluid in the capacitor changes, the capacitance of the capacitor also changes.

Still referring to FIG. 32D, a disc-shaped capacitor sensor plate 3234 is mounted to the bottom of rotating housing 3232, equidistant from the bottom surface 3232A of rotating housing 3232, and the bottom surface 3204A of rotor 3204. The capacitor is thus defined by housing 3232, rotor 3204, and capacitor sensor 3234. Leads 3240 connect the capacitor, from capacitor sensor 3234, through a passageway 3236A in rotating housing shaft 3236, to the secondary 3242 of a core transformer, preferably of ferrite (not shown). In one embodiment, the secondary 3242 is rotating at the same speed as the capacitor plate, and is in inductive communication with the primary of the ferrite core transformer. The primary winding 3238 is stationary, and signals to and from the level-measuring capacitor are communicated through the transformer, in this way enabling depth information to be transmitted from a rotating position to a stationary position. Capacitance is measure by determining the LC resonance of the capacitor (C) with the inductance (L) of the transformer secondary. In an exemplary embodiment, an LC oscillator circuit is constructed and the oscillation frequency is used as a measure of the capacitance.

Referring to FIG. 32E, this figure illustrates an alternate design of the pump 3200 to prevent contaminated fluid droplets from being entrained and carried along with vapor to evaporator/condenser 104 of FIG. 1. In such an embodiment, the liquid ring pump 3200 is within the head space of the evaporator/condenser 104, and mist is eliminated as rotating housing 3232 rotates, wherein the rotation creates a cyclone effect, flinging mist and water droplets off by centrifugal force to collide with the still housing and run down to the water in the sump. There may also be fins 3244 extending from the outside of rotating housing 3232 to enhance circulation and rotation of vapor in the annular space between rotating housing 3232 and fixed housing 3228. A steam exit 3242 is provided for passage of steam to evaporator/condenser 104.

Referring now to FIGS. 32F-G, an alternative embodiment for a liquid ring pump 3200 may include a ring pump 3252 with an outer rotatable housing 3254 that encloses a single two-channel stator/body 3256, and a rotor 3258, wherein the seal surface between the rotatable housing 3254 and stationary stator/body 3256 is a cylinder. Two-channel stator/body 3256 is kept stationary in reference to a chamber 3260 of pump 3252 as well as to rotor 3258 and rotatable housing 3254, and comprises an intake 3262 and an exit 3264. Steam is drawn in at pressure $P_1$ and passes through an intake orifice 3266. When the intake orifice 3266 lines up with an intake hole 3268 in rotor 3258 as the rotor spins around stationary stator 3256, the steam passes through intake hole 3268 into a rotor chamber 3270. Rotor 3258 is offset from a central axis Z so that, as rotor 3258 turns, the effective volume of rotor chamber 3270 decreases. In this way, steam is compressed to pressure $P_2$ as it is carried along a rotational path to an exit hole 3272 in rotor 3258. As rotor 3258 turns, exit hole 3272 lines up with an exit orifice 3274 of stationary exit 3264, and the steam at pressure $P_2$ passes through exit orifice 3274 into exit 3264 to be routed to the evaporator/condenser. In such an embodiment, rotatable housing 3254 rotates with water 3276 present in chamber 3260 thereby reducing frictional energy losses due to windage. There may also be a small hole 3278 present in the housing 3254 to permit water 3276 to leave and/or enter chamber 3260, thereby controlling the fluid level in the pump. In addition, rotor 3258 has multiple vanes 3280 that are readily apparent when rotor 3258 is viewed from above, as in FIG. 32G. Individual rotor chamber 3270, and individual intake hole 3268 and exit hole 3272 for each rotor chamber 3270, are also easily seen in this view.

Referring to FIG. 32H, Another alternative embodiment of a liquid ring pump, wherein the interface between rotatable housing 3254 and stator 3256 is conical rather than cylindrical. In this embodiment, a rotor drive shaft 3282 has an end 3286 situated upon a bearing 3284 that allows rotatable rotor housing 3254 to rotate with rotor 3258. Intake 3262 and exit 3264, with corresponding intake orifice 3266 and exit orifice 3274, are kept stationary with respect to rotor 3258 and rotor housing 3254.

Referring now to FIGS. 32F, H and I, other further embodiments may include either a conical or axial seal 3282 present between stationary sections 3264 and 3262 and rotor 3258. In the conical embodiment seen most clearly in FIG. 32I, seal 3282 thereby separates intake orifice 3266 from exit orifice 3274 of rotor 3258 to prevent leaks. The liquid ring pumps shown in FIGS. 32E-I and 7 are both axially fed and radially ported, in contrast with the embodiment of a liquid ring pump, discussed with reference to FIGS. 32-32C (vide supra), which is axially fed and axially ported.

In alternate embodiments, the water vapor distillation apparatus may include a backpressure regulator. Backpressure regulators may assist with maintaining the safe and optimal operation of processes conducted under pressure. In operation the water vapor distillation apparatus may include a backpressure regulator to purify brackish or sea water into drinking water, excess apparatus pressure from start-up volatile components, or created from compressors running off-specification, may constitute a danger to operators if such pressure is not relieved in a safe manner. As well, volatile components present in feed streams at start-up may present contaminants that interfere with proper operation of the apparatus. Backpressure regulators may serve to relieve excess pressure, and to return an operating apparatus to a desired operating pressure.

The water vapor distillation apparatus embodiments described previously generally operate above atmospheric pressure, typically around 10 psig. Such an apparatus advantageously provides higher steam density at the higher pressure, thereby allowing more steam to be pumped through a positive displacement pump than at lower pressure. The resulting higher throughput provides overall improved system efficiency. Further, the higher throughput and higher system pressure reduces the power needed for compressor, and eliminates the need for two additional pumps—one for pumping condensed product and another for pumping blowdown stream. Overall construction is simplified, as many shapes withstand internal pressure better than external pressure. Importantly, operating at super-atmospheric pressure reduces the impact of minor leaks on the overall efficiency and performance. Non-condensable gases such as air inhibit the condensation process, and would be magnified at sub-atmospheric pressure, where minor leaks would serve to suck in air, something which will not occur in a system operating at super-atmospheric pressure.

Referring now to FIGS. 33 and 33A, these figures depict views of a backpressure regulator that may be incorporated into the water vapor distillation apparatus 100 when operating the apparatus above atmospheric pressure. The backpressure regulator 3300 has a vessel 3302 containing an orifice 3304. One side of the orifice is connected to a pressurized conduit of an apparatus (e.g., the outlet of a compressor in a vapor compression distillation apparatus) which may be exposed to the fluctuating elevated pressure. The other side of the orifice terminates in a port 3306. The port 3306 is covered by a movable stop 3308, in the shape of a ball. The stop 3308 is retained to an arm 3310 by means of a retainer 3312 at a fixed distance from a pivot pin 3314. The arm 3310 is attached by a hinge via the pivot pin 3314 to a point with a fixed relation to the orifice port 3306. The arm 3310 includes a counter mass 3316 suspended from the arm that is movable along an axis 3318 such that the distance between the counter mass 3316 and the pivot pin 3314 may be varied. In the embodiment shown in FIG. 33, the axial direction of the orifice 3304 is perpendicular to the direction of the gravitational vector 3320. The backpressure regulator may also include a housing, which prevents foreign matter from entering the regulator and interfering with the function of the internal components.

Still referring to FIGS. 33 and 33A, in operation the arm 3310 maintains a horizontal position with respect to the direction of gravity 3320 when the pressure in the pressurized conduit is below a given set point; this arm position, in this embodiment, is known as the closed position, and corresponds to the stop 3308 covering the port 3306. When the pressure in the conduit exceeds the set point, a force acts on the stop 3308, which results in a torque acting around the pivot pin 3314. The torque acts to rotate the arm 3310 around the pivot pin 3314 in a counter-clockwise direction, causing the arm to move away from its closed position and exposing the port 3306, which allows fluids to escape from the orifice 3304. When the pressure in the conduit is relieved below the set point, the force of gas is no longer sufficient to keep the arm 3310 away from its closed position; thus, the arm 3310 returns to the closed position, and the stop 3308 covers the port 3306.

Still referring to FIGS. 33 and 33A, the arm 3310 acts as a lever in creating adjustable moments and serves to multiply the force applied by the counter mass 3316 through the stop 3308 to the port 3306. This force multiplication reduces the weight needed to close the orifice 3304 as opposed to a design where the stop 3308 alone acts vertically on top of the orifice 3304, as in a pressure cooker. Thus a large port size, to promote expedited venting from a pressurized conduit, may be covered by a relatively lightweight, large-sized stop, the counter mass acting to adjust the desired set point; less design effort may be expended in choosing specific port sizes and stop properties. The addition of an axis 3318 for adjusting the position of the counter mass 3316, in the present embodiment, allows for changes in the multiplier ratio. As the counter mass 3316 is moved to a position closer to the pivot pin 3314, the multiplier ratio is reduced, creating a lower closing force. If the counter mass 3316 is moved farther from the pivot pin 3314, the multiplier ratio is increased, hence increasing the closing force. Therefore, the position of the counter mass 3316 effectively acts to adjust the set point of the backpressure regulator.

Adjustment of the backpressure regulator set point may be useful, when the backpressure regulator is utilized in apparatus at higher altitudes. When the atmospheric pressure is lower, the apparatus operating pressure is commensurately lower. As a result, the temperature of the distillation apparatus is lowered, which may adversely affect apparatus performance. As well, such adjustment allows one to identify set points for the backpressure regulator that are desired by the end user. The use of a counter mass to apply the closing force may also lower cost of the backpressure regulator and reduce component fatigue. In a particular embodiment, the adjustable counter mass is designed to allow a range of set points with a lowest set point substantially less than or equal to 10 psig and a highest set point substantially greater than or equal to 17 psig. Thus various embodiments allow for precise apparatus pressure regulation, unlike devices which act simply as safety relief valves.

Referring now to FIGS. 33B-C, these figures illustrate an alternate embodiment of the back pressure regulator 3300 having an orifice 3326 configured such that the port 3328 is oriented vertically with respect to the direction of gravity 3320. Thus other embodiments may accommodate any orifice orientation while maintaining the use of an adjustable counter mass.

The backpressure regulator may be configured to allow a small leakage rate below the set point in order to purge the build up of volatile gases that act to insulate heat exchange and suppress boiling in a system; the regulator is designed, however, to allow-pressure to build in the pressurized conduit despite this small leakage. In one embodiment release of volatile components from a pressurized conduit, below the set point of the backpressure regulator, may also be achieved through a specifically-designed leak vent while the arm of the backpressure regulator is in the closed position. The leak vent is configured to allow a certain leakage rate from the port or the orifice while the pressure in the conduit is below the set point. Such leak vent may be designed by a variety of means known to those skilled in the art. Non-limiting examples include specific positioning of the stop and port to allow a small opening while the arm is in the closed position; designing the port such that a small opening, not coverable by the stop, is always exposed; specifying a particular rigid, non-compliant seal configuration between the stop and port when the arm is in the closed position; and configuring the orifice leading to the port to have a small opening to allow leakage of fluids.

Referring now FIGS. 33D-G, these figures illustrate alternate embodiments of the back pressure regulator 3300 allowing the leakage of volatiles below the set point. In one alternate embodiment, the port 3332 has a notch 3334 as shown in FIG. 33D and the close-up of region C of FIG. 33D depicted in FIG. 33E. Thus, when a stop is in contact with the port 3332, and the arm of the backpressure regulator is in the closed position, a leak vent is present at the position of the notch 3334 that allows a leakage of fluid. In another alternate embodiment of the backpressure regulator 3300, orifice 3336 has a small opening 3338, as depicted in FIG. 33F and blow up of region E of FIG. 33F depicted in FIG. 33G. The opening 3338 is configured such that a leak vent is created when the stop covers the port 3336 since fluids may leak through the opening 3338.

Various features of a backpressure regulator may be altered or modified. For example, stops to be used with backpressure regulators may have any shape, size, or mass consistent with desired operating conditions, such stops need not be ball-shaped as shown in some embodiments discussed herein. As well, stops of different weight but similar sizes may be utilized with the retainer to alter the set point of the regulator. Similarly, counter masses of different sizes, shapes and masses may be utilized with various embodiments with preference that they are accommodated by the axis and arm configurations (compare 3316 in FIGS. 33 and 33A with 3330 in FIGS. 33B and 33C); such counter masses may be attached and oriented relative to the arm by any of a variety of techniques apparent to those skilled in the art. The pivot pin placement need not be positioned as shown in FIGS. 33-33C, but may be positioned wherever advantageous to provide the mechanical advantage required to achieve a particular pressure set point.

Referring back to FIG. 33, other embodiments of the backpressure regulator 3300 may optionally utilize the drain orifice feature described earlier. Also, embodiments of the backpressure regulator 3300 may not utilize the counter mass force adjustment feature, relying on the specific properties of a stop to provide the set point for the backpressure regulator.

Other embodiments of the water vapor distillation apparatus may not utilize a vessel, but rely on orifices that are intrinsically part of the system. In such instances, the backpressure regulator arm may be directly attached to a portion of the system such that the arm, stop, and counter mass are appropriately oriented for the operation of the regulator.

Now referring to FIG. 34, the vessel 3302 includes a drain orifice 3322. Since the backpressure regulator 3300 may operate within a bounded region 3402 of a large system 3400, the drain orifice 3322 acts as a pathway to release fluids that are purged from the pressurized conduit 3404 through orifice 3304 into the bounded region 3402. The drain orifice 3322 may connect the bounded region 3402 to another area of the larger system, or to the external environment 3406. In addition, the build-up of gases in the bounded region 3402 may result in condensation of such gases. Also, gases purged through the orifice 3304 may be entrained with droplets of fluid that may accumulate in the bounded region 3402. Thus the drain orifice 3322 may also be used to purge any build up of condensables that accumulate in the bounded region 3402; the condensables may also be released from the bounded region using a separate orifice 3408.

Referring now to FIG. 35, in alternate embodiments the apparatus may maintain a constant blowdown water flow to prevent scaling and other accumulation in the apparatus as follows. Water level 3502 in head chamber 3504 is adjusted through a feedback control loop using level sensor L1, valve V1, and source pump 3506, to maintain proper water flow through the blowdown stream 3508. The three-way source pump fill valve 3510 is set to pump water into sump 3512, which causes water level 3502 in head chamber 3504 to rise. As fluid level 3502 rises in head chamber 3504, fluid overflows past a dam-like barrier 3514 into blowdown control chamber 3516 containing blowdown level sensor L1. As required, blowdown valve V1 is controlled to allow water flow from blowdown control chamber 3516 through heat exchanger 3518, to extract heat and cool blowdown stream 3508, and flow out valve V1, through volatile mixer 3520 allowing cooling of hot gases and steam 3522 from the evaporator section 3524, and then completing the blowdown stream, out to waste 3526.

Still referring to FIG. 35, the apparatus may also maintain proper product flow as follows. Product level 3528 builds up in condenser chamber 3530, and enters into product control chamber 3532, where product level sensor L2 is housed. Using a feedback control loop with level sensor L2 and valve V2, product stream 3534 is controlled to flow from product control chamber 3532 through heat exchanger 3518, to extract heat and cool product stream 3534, then through valve V2 and on out to complete the product stream as product water outlet 3536.

The system may preferably be configured to maintain proper liquid ring pump 3538 water level by the use of a fluid recovery system to replenish fluid loss. There are several ways that fluid from the ring pump may be depleted during system operation, including leakage into lower reservoir 3540, expulsion through exhaust port 3542, and evaporation. The leakage and expulsion losses may be large depending on operational parameters, such as the speed of rotation and liquid ring pump 3538 throughput. These leakage and expulsion losses could require total replacement of the fluid in the pump several times per hour. The evaporation loss is typically small.

Referring to FIG. 35, the fluid level in the ring pump 3538 may be maintained by adding additional source water, product water, or preferably by re-circulating liquid water lost from the liquid ring pump for improved system efficiency. In one embodiment the fluid level in the ring pump 3538 is primarily maintained by re-circulation of the fluid accumulated in lower reservoir 3540. Fluid may accumulate in lower reservoir 3540 from leakage from the liquid ring pump 3538 and from fluid expelled in exhaust 3542, captured in mist eliminator 3544 and pumped to lower reservoir 3540. Alternatively, fluid expelled in exhaust 3542 and captured in mist eliminator 3544 may be returned via the liquid ring pump exhaust port. Fluid accumulated in lower reservoir may be re-circulated by one of several pumping mechanisms. One exemplary method is to use a siphon pump.

Still referring to FIG. 35, a minimum depth of water is preferably maintained in the lower reservoir for the siphon pump to perform properly. In one embodiment liquid ring pump control chamber 3546, which houses liquid ring pump level sensor L3 may be used to control the liquid ring pump level and control the level of water in the lower reservoir 3540. Liquid ring pump control chamber 3546 is fluidly connected to liquid ring pump 3538 and lower reservoir 3540. Liquid ring pump 3538 is connected to the three-way source fill valve 3510, which is set to open when the liquid ring pump 3538 requires more water and it is also connected to the liquid ring pump drain valve V3, which opens when it is required to drain water from liquid ring pump 3538 into blowdown stream 3508.

Still referring to FIG. 35, if re-circulated water front lower reservoir 3540 is not primarily used to maintain the fluid level in the liquid ring pump 3538, then either cold source water or product water could to be used. In the event source water were used, the introduction of cold water (which could be approximately 85 degrees C. colder than system temperature) to the liquid ring pump 3538 would decrease system efficiency or alternatively the use of a pre-heater for such cold source water would increase the energy budget of the system. Alternatively, the use of product water, while not adversely affecting system temperature, could decrease production level and, thus, also lead to system inefficiency. At startup, the initial fluid level for the liquid ring pump is preferably supplied from source water.

Now referring to FIG. 35A, in one embodiment the start-up time may be reduced by using an external connecting valve 3550 between source 3548 and blowdown 3508 fluid lines, located adjacent to heat exchanger 3518, on the cold side. To determine the level of fluid in evaporator head 3504 during the initial fill, connecting valve 3550 would be open, blowdown valve BV would be closed, and fluid would be pumped into the system through source line 3548. Connecting blowdown 3508 and source 3548 lines results in equal fluid height in the blowdown level sensor housing 3516 and evaporator head 3504, thereby permitting a determination of fluid level in evaporator head 3504 and enabling the evaporator to be filled to the minimum required level at startup. Using the minimum level required shortens initial warm-up time and prevents spill-over from the evaporator head 3504 through the liquid ring pump 3538 to the condenser 3552 when the liquid ring pump 3538 starts illustrated on FIG. 35.

Still referring to FIG. 35A, the concentration of solids in blowdown stream 3508 may be monitored and controlled to prevent precipitation of materials from solution and thus clogging of the system. Also during start-up, circulating pump 3554 may circulate water through heat exchanger 3518 to pre-heat the heat exchanger to the proper temperature for normal operation. A conductivity sensor (not shown) may be used to determine total dissolved solid (TDS) content by measuring the electrical conductivity of the fluid. In a particular embodiment, the sensor is an inductive sensor, whereby no electrically conductive material is in contact with the fluid stream. If the TDS content in blowdown stream 3508 rises above a prescribed level, for example, during distillation of sea water, the fluid source feed rate is increased. Increasing the fluid source feed rate will increase the rate of blowdown stream 3508, because distilled water production changes only slightly as a function of fluid feed rate, and an increased blowdown stream rate results in reduced concentration of TDS, thereby maintaining overall efficiency and productivity of the system.

Alternate embodiments may also include a fluid control system using level sensors and variable flow valves in a feedback configuration. Optimal operation of the still requires total fluid flow in to closely match total fluid flow out. Maintaining fluid levels in the still at near constant levels accomplishes this requirement. In a particular embodiment, the sensors are capacitive level sensors, a particularly robust sensor for measuring fluid levels. Capacitive level sensors have no moving parts and are insensitive to fouling, and manufacture is simple and inexpensive. Opening of a variable flow valve is controlled by the level of fluid measured by the capacitive level sensor, whereby the fluid level is adjusted at the level sensor location. A rising fluid level causes the valve to open more, increasing flow out of the sensor volume. Conversely, a falling fluid level causes the valve to close more, decreasing flow out of the sensor volume.

Flow rate through the variable flow control valves and from the input pump may be determined using an in-situ calibration technique. The level sensors and associated level sensor volume may be used to determine the fill or empty rate of the sensor volume. By appropriately configuring the control valves, the flow rate calibration of each valve and also of the source pump may be determined.

In one embodiment, a valve block (not shown) may be utilized to consolidate all control valves for the system into a single part, which may be integrated with the fluid flow manifold. A control system comprising a sensor for total dissolved solids and blowdown stream may also be incorporated, as well as a float valve or other device for controlling the height/level of fluid in the head.

Referring back to FIG. 35, there is additionally a steam flow line 3554 from head 3504 to compressor 3538, a steam outlet 3542 for diverting steam to evaporator/condenser, a hot product line 3534 from evaporator/condenser leading through exchanger 3518, which also allows for collection of hot purified condensed product 3528, and a line (not shown) for diverting hot product to compressor 3538 to allow adjustment of water level to keep it constant. There may also be a drain line (not shown), for when the system is shut down.

Referring now to FIGS. 36-36C, alternate embodiments may also include a fluid distribution manifold 3600. FIG. 36 shows one face of the pump side of one particular embodiment of a fluid distribution manifold 3600. Input, in the form of raw source feed, flows through port 3602, and blowdown stream (output) flows through port 3604. Additional output in the form of product flows through port 3606, while port/chamber 3608 provides the vent for volatiles (output) and port 3610 provides the drain (output) for liquid ring pump. FIG. 36A shows the other face of the pump side of the same particular embodiment of fluid distribution manifold 3600. Port/chamber 3608, for output of volatiles, is apparent, as is the drain 3610 for a liquid ring pump. In this view of this particular embodiment, a condenser steam mist eliminator chamber 3612 is visible, as is a mist collector and drain area 3614.

Referring specifically to FIG. 36B, this figure illustrates one face of the evaporator/condenser side of the same particular embodiment of fluid distribution manifold 3600. Raw source feed port 3602, as well as blowdown passage ports 3604 and product passage ports 3606 are readily visible in this view. In addition, evaporator steam passage port 3616 and condenser steam passage port 3618 may be seen.

Referring specifically to FIG. 36B, this figure illustrates the other face of the evaporator/condenser side of the same particular embodiment of fluid distribution manifold 3600. Again blowdown passage port 3604 is visible, as is liquid ring pump drain port 3606, a second condenser steam mist eliminator 3612, evaporator steam mist eliminator 3620, and mist collector and drain area 3614. Also, a sump level control chamber can be seen in this view, along with a product level control chamber 3622 and a liquid ring pump supply feed 3624.

Still referring to FIGS. 36-36C, a fluid distribution manifold 3600 is capable of eliminating most plumbing in a fluid purification system, advantageously incorporating various functionality in one unit, including flow regulation, mist removal, and pressure regulation, thereby simplifying manufacture and significantly reducing overall component parts. The core plates and manifolds may be made of, for example, plastic, metal, or ceramic plates, or any other non-corrosive material capable of withstanding high temperature and pressure. Methods of manufacture for the core plates and manifolds include brazing and over-molding.

Referring now to FIGS. 37-37A, these figures illustrate a fitting assembly that allows fluid interfacing throughout the system in a particular embodiment. For example, there may be a floating fluid interface between the exchanger 3518 (shown on FIG. 35) and the intake/exhaust ports 3220 and 3208 (shown on FIG. 32). FIG. 37A illustrates a connector 3702 that may be welded to the heat exchanger ports (not shown), wherein the connector 3702 connects to the fluid interface 3704 which is in turn in communication with the fluid distribution manifold. FIG. 37A shows a sectional view across line A-A (see FIG. 37). The connector 3702 has the ability to float to compensate for shifts in registration, possibly caused by temperature or manufacturing variations. Sealing is accomplished by the o-ring 3706. As can be seen in the view depicted in FIG. 37, the o-ring seal 3706, upon rotation of line A-A 90 degree about a central axis, the connector 3702 and the fluid interface 3704 lock together to make a fluid interface connection.

Referring now to FIGS. 38-38A, these figures illustrate another embodiment of the evaporator/condenser 3800. As seen in FIG. 38, evaporator/condenser 3800 is a flat evaporator/condenser and contains multiple parallel core layers 3802 and 3804, typically made of copper-nickel alloy or other heat-transferable material, with rib sections 3806 creating channels 3810 and 3812 for directing steam and condensed fluid flow. Steam intake 3814 and product exit 3816 manifolds (as well as dirty intake and volatile exit manifolds, not shown) may connect via a fluid interface to a liquid ring pump/compressor. Bolts 3818 secure core evaporator/condenser 3800 to brackets of external housing of the liquid ring pump/compressor. In operation, every alternating horizontal (as shown in FIGS. 38 and 38A) row 3802 and 3804 comprises evaporator channels 3810 and condenser channels 3812, such that the two functions never overlap on any given layer. FIG. 38A, a detail of FIG. 38, shows more clearly how the combined evaporator/condenser manifolds works. As indicated, rows 3802 do not interact with rows 3804, they are closed off to each other, thereby separating the functions of evaporation and condensation in the horizontal core layers.

Referring now to FIG. 39, this figure illustrates alternate embodiment of the heat exchanger used in the water vapor distillation apparatus, wherein such heat exchangers capitalize on available systemic and heat sources. In one particular embodiment, heat from at least one of a plurality of sources passes through a multi-line heat exchanger 3902 such as depicted in FIG. 39, wherein a series of two-channel heat exchangers such as 3904, 3906, 3908, and 3910 are plumbed to produce a multi-line effect. Note that in the particular multi-line heat exchanger embodiment shown in FIG. 39, the flow of cold intake 3912 passes through all heat exchanger units 3904, 3906, 3908, and 3910; one heat source, for example hot product 3914, flows through heat exchanger units 3904 and 3908; and another heat source, for example hot blowdown stream 3916, flows through heat exchange units 3906 and 3910. In this way, multiple heat sources may be used to exchange with the cold intake flow 3912.

Now referring to FIG. 39A, this figure illustrates an alternate embodiment of the heat exchanger. In this embodiment, the heat exchanger may be a single multi-channel heat exchanger 3918. In this particular embodiment, cold intake 3912, and heat sources such as hot product 3914 and hot blowdown stream 3916, for example, flow through exchanger 3918 simultaneously, but in opposite directions, thereby enabling heat exchange with cold intake 3912 from both heat sources 3914 and 3916 within a single heat exchanger 3912.

Referring now to FIG. 40, one alternate embodiment may include measuring the evaporator and condenser pressures to assess overall system performance and/or provide data to a control system. To avoid the use of expensive sensors that would be required to withstand the elevated temperatures of evaporator/condenser 4002, pressure sensors $P_E$ and $P_C$ are mounted on fluid lines between the cold side of heat exchanger 4004 and corresponding control valves $V_E$ and $V_C$. To avoid measuring a pressure less than the actual pressure of the system, which would occur when fluid is flowing for pressure sensors located at this position, the control valve would be closed momentarily to stop flow. During the "no-flow" period, pressure will be constant from the control valve back to the evaporator or condenser, enabling accurate measurement of the system pressure. No adverse effects on still performance will occur from these short "no-flow" periods.

Referring now to FIGS. 41-41B, this figure illustrates another embodiment of the present disclosure including a filtering mechanism within intake to increase the purity of the final product fluid. A multi unit flip-filter 4100, having a pivot joint 4102 joining at least two filter units 4104 and 4106, is situated within a filter housing 4108 which directs fluid through filter units 4104 and 4106 and facilitates rotation of filter units 4104 and 4106 about central pivot joint 4102. As shown, blowdown stream 4109 passes through flip-filter unit 4104, while intake fluid stream 4110 simultaneously flows from intake through flip-filter unit 4106 en route to purification. After some interval a flip-filter switch (not shown), rotates flip-filter 4100 around its central axis, shown by the dotted line, at flip-filter pivot joint 4102, such that filter unit 4106, now fouled with contaminates filtered from dirty intake fluid, is backwashed by blowdown stream 4109, and filter unit 4104 becomes the filter unit which filters intake fluid stream 4110. In such an embodiment, o-ring gaskets 4112 and 4114 may be utilized as seals between filter units 4104 and 4106 and the fluid flow routes of blowdown stream 4109 and intake fluid stream 4110, respectively.

Referring now to FIGS. 41C-D, the multi-unit flip filter may be a multi-sected circular filter 4112. Multi unit flip-filter 4112, having a pivot point 4114 about which multiple flip-filter units such as 4116 and 4118 pivot, may also be situated within filter housing 4120 that directs fluid flow through individual filter units 4116 and 4118 and facilitates rotation of filter 4112 about pivot point 4114. As shown, blowdown stream 4109 passing through one flip-filter unit 4116, while intake fluid stream 4110 simultaneously flows from intake through flip-filter unit 4118 en route to purification. As in FIG. 41, a flip-filter switch (not shown), rotates flip-filter 4112 around its central axis, shown by the dotted line, at flip-filter pivot point 4114, such that filter unit 4118, now fouled with contaminates filtered from dirty intake fluid, is backwashed by blowdown stream 4109, and filter unit 4116 becomes the filter unit which filters intake fluid stream 4110. A series of seals, as indicated by 4122 and 4124, are utilized between individual filter units 4116 and 4118, to partition blowdown stream 4109 flowing through one filter section, from intake fluid stream 4110 flowing through another filter section.

Now referring to FIGS. 41E-41F, other embodiments may include a manual valve 4122 to change the direction of water flow. Such a valve allows use of, for example, blowdown stream 4109 to continuously clean one unit of each flip-filter, and with a single operation effectively switches which unit is being filtered and which unit is being back-washed, thereby back-washing filter units 4104 or 4106 without the need to actually flip filter 4100 itself. In one particular embodiment when valve 4122 is in position A, filter unit 4104 is filtering intake fluid 4110, and filter unit 4106 is being back-washed with blowdown stream 4109. Upon switching valve 4100 to position B, filter unit 4104 is now being backwashed by blowdown stream 4108, and filter unit 4106 is now filtering input fluid 4110.

Stirling Cycle Engine

The various embodiments of the water vapor distillation apparatus described above may, in some embodiment, may be powered by a Stirling cycle machine (also may be referred to as a Stirling engine). In the exemplary embodiment, the Stirling cycle machine is a Stirling engine described in pending U.S. patent application Ser. No. 12/105,854 filed on Apr. 18, 2008, which is herein incorporated by reference in its entirety. However, in other embodiments, the Stirling cycle machine may be any of the Stirling cycle machines described in the following references, all of which are incorporated by reference in their entirely: U.S. Pat. Nos. 6,381,958; 6,247,310; 6,536,207; 6,705,081; 7,111,460; and 6,694,731.

Stirling cycle machines, including engines and refrigerators, have a long technological heritage, described in detail in Walker, Stirling Engines, Oxford University Press (1980), incorporated herein by reference. The principle underlying the Stirling cycle engine is the mechanical realization of the Stirling thermodynamic cycle: isovolumetric heating of a gas within a cylinder, isothermal expansion of the gas (during which work is performed by driving a piston), isovolumetric cooling, and isothermal compression. Additional background regarding aspects of Stirling cycle machines and improvements thereto is discussed in Hargreaves, The Phillips Stirling Engine (Elsevier, Amsterdam, 1991), which is herein incorporated by reference.

The principle of operation of a Stirling cycle machine is readily described with reference to FIGS. 45A-45E, wherein identical numerals are used to identify the same or similar parts. Many mechanical layouts of Stirling cycle machines are known in the art, and the particular Stirling cycle machine designated generally by numeral 5110 is shown merely for illustrative purposes. In FIGS. 45A to 45D, piston 5112 and a displacer 5114 move in phased reciprocating motion within the cylinders 5116 which, in some embodiments of the Stirling cycle machine, may be a single cylinder, but in other embodiments, may include greater than a single cylinder. A working fluid contained within cylinders 5116 is constrained by seals from escaping around piston 5112 and displacer 5114. The working fluid is chosen for its thermodynamic properties, as discussed in the description below, and is typically helium at a pressure of several atmospheres, however, any gas, including any inert gas, may be used, including, but not limited to, hydrogen, argon, neon, nitrogen, air and any mixtures thereof. The position of the displacer 5114 governs whether the working fluid is in contact with the hot interface 5118 or the cold interface 5120, corresponding, respectively, to the interfaces at which heat is supplied to and extracted from the working fluid. The supply and extraction of heat is discussed in further detail below. The volume of working fluid governed by the position of the piston 5112 is referred to as the compression space 5122.

Figure 45A:
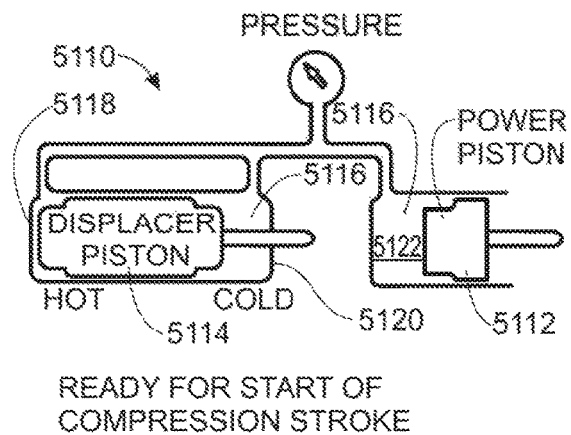
Figure 45B:
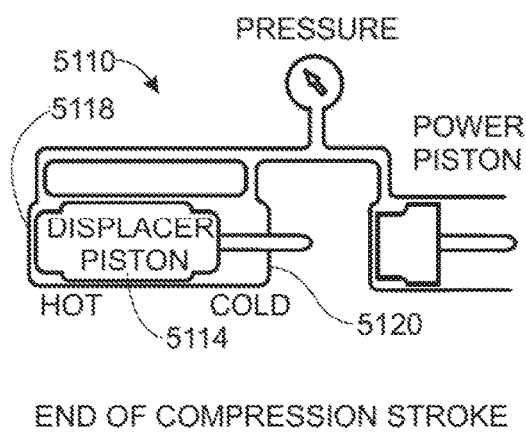
Figure 45C:
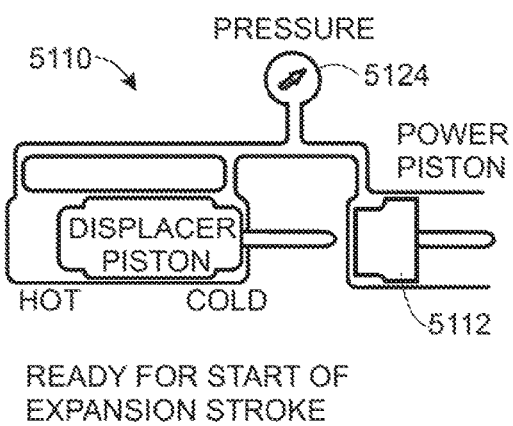

During the first phase of the Stirling cycle, the starting condition of which is depicted in FIG. 45A, the piston 5112 compresses the fluid in the compression space 5122. The compression occurs at a substantially constant temperature because heat is extracted from the fluid to the ambient environment. The condition of the Stirling cycle machine 5110 after compression is depicted in FIG. 45B. During the second phase of the cycle, the displacer 5114 moves in the direction of the cold interface 5120, with the working fluid displaced from the region of the cold interface 5120 to the region of the hot interface 5118. This phase may be referred to as the transfer phase. At the end of the transfer phase, the fluid is at a higher pressure since the working fluid has been heated at constant volume. The increased pressure is depicted symbolically in FIG. 45C by the reading of the pressure gauge 5124.

Figure 45D:
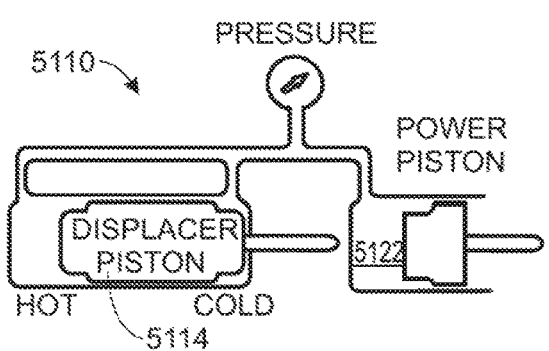
Figure 45E:
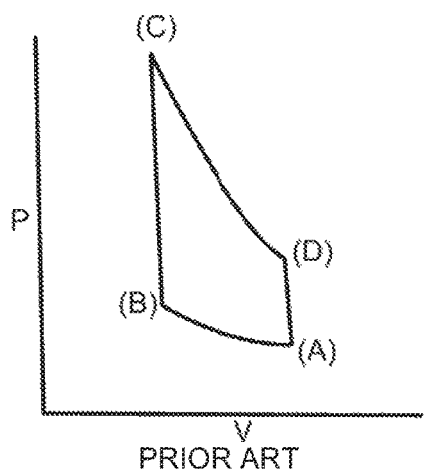

During the third phase (the expansion stroke) of the Stirling cycle machine, the volume of the compression space 5122 increases as heat is drawn in from outside the Stirling cycle machine 5110, thereby converting heat to work. In practice, heat is provided to the fluid by means of a heater head (not shown) which is discussed in greater detail in the description below. At the end of the expansion phase, the compression space 5122 is full of cold fluid, as depicted in FIG. 45D. During the fourth phase of the Stirling cycle machine 5110, fluid is transferred from the region of the hot interface 5118 to the region of the cold interface 5120 by motion of the displacer 5114 in the opposing sense. At the end of this second transfer phase, the fluid fills the compression space 5122 and cold interface 5120, as depicted in FIG. 45A, and is ready for a repetition of the compression phase. The Stirling cycle is depicted in a P-V (pressure-volume) diagram as shown in FIG. 45E.

Additionally, on passing from the region of the hot interface 5118 to the region of the cold interface 5120. In some embodiments, the fluid may pass through a regenerator (shown as 5408 in FIG. 48). A regenerator is a matrix of material having a large ratio of surface area to volume which serves to absorb heat from the fluid when it enters from the region of the hot interface 5118 and to heat the fluid when it passes from the region of the cold interface 5120.

Stirling cycle machines have not generally been used in practical applications due to several daunting challenges to their development. These involve practical considerations such as efficiency and lifetime. Accordingly, there is a need for more Stirling cycle machines with minimal side loads on pistons, increased efficiency and lifetime.

The principle of operation of a Stirling cycle machine or Stirling engine is further discussed in detail in U.S. Pat. No. 6,381,958, issued May 7, 2002, to Kamen et al., which is herein incorporated by reference in its entirety.

Rocking Beam Drive

Referring now to FIGS. 46-48, embodiments of a Stirling cycle machine, according to one embodiment, are shown in cross-section. The engine embodiment is designated generally by numeral 5300. While the Stirling cycle machine will be described generally with reference to the Stirling engine 5300 embodiments shown in FIGS. 46-48, it is to be understood that many types of machines and engines, including but not limited to refrigerators and compressors may similarly benefit from various embodiments and improvements which are described herein, including but not limited to, external combustion engines and internal combustion engines.

FIG. 46 depicts a cross-section of an embodiment of a rocking beam drive mechanism 5200 (the term "rocking beam drive" is used synonymously with the term "rocking beam drive mechanism") for an engine, such as a Stirling engine, having linearly reciprocating pistons 5202 and 5204 housed within cylinders 5206 and 5208, respectively. The cylinders include linear bearings 5220. Rocking beam drive 5200 converts linear motions of pistons 5202 and 5204 into the rotary motion of a crankshaft 5214. Rocking beam drive 5200 has a rocking beam 5216, rocker pivot 5218, a first coupling assembly 5210, and a second coupling assembly 5212. Pistons 5202 and 5204 are coupled to rocking beam drive 5200, respectively, via first coupling assembly 5210 and second coupling assembly 5212. The rocking beam drive is coupled to crankshaft 5214 via a connecting rod 5222.

In some embodiments, the rocking beam and a first portion of the coupling assembly may be located in a crankcase, while the cylinders, pistons and a second portion of the coupling assembly is located in a workspace.

In FIG. 48 a crankcase 5400 most of the rocking beam drive 5200 is positioned below the cylinder housing 5402. Crankcase 5400 is a space to permit operation of rocking beam drive 5200 having a crankshaft 5214, rocking beam 5216, linear bearings 5220, a connecting rod 5222, and coupling assemblies 5210 and 5212. Crankcase 5400 intersects cylinders 5206 and 5208 transverse to the plane of the axes of pistons 5202 and 5204. Pistons 5202 and 5204 reciprocate in respective cylinders 5206 and 5208, as also shown in FIG. 46. Cylinders 5206 and 5208 extend above crankshaft housing 5400. Crankshaft 5214 is mounted in crankcase 5400 below cylinders 5206 and 5208.

FIG. 46 shows one embodiment of rocking beam drive 5200. Coupling assemblies 5210 and 5212 extend from pistons 5202 and 5204, respectively, to connect pistons 5202 and 5204 to rocking beam 5216. Coupling assembly 5212 for piston 5204, in some embodiments, may comprise a piston rod 5224 and a link rod 5226. Coupling assembly 5210 for piston 5202, in some embodiments, may comprise a piston rod 5228 and a link rod 5230. Piston 5204 operates in the cylinder 5208 vertically and is connected by the coupling assembly 5212 to the end pivot 5232 of the rocking beam 5216. The cylinder 5208 provides guidance for the longitudinal motion of piston 5204. The piston rod 5224 of the coupling assembly 5212 attached to the lower portion of piston 5204 is driven axially by its link rod 5226 in a substantially linear reciprocating path along the axis of the cylinder 5208. The distal end of piston rod 5224 and the proximate end of link rod 5226, in some embodiments, may be jointly hinged via a coupling means 5234. The coupling means 5234, may be any coupling means known in the art, including but not limited to, a flexible joint, roller bearing element, hinge, journal bearing joint (shown as 5600 in FIG. 50), and flexure (shown as 5700 in FIGS. 51A and 51B). The distal end of the link rod 5226 may be coupled to one end pivot 5232 of rocking beam 5216, which is positioned vertically and perpendicularly under the proximate end of the link rod 5226. A stationary linear bearing 5220 may be positioned along coupling assembly 5212 to further ensure substantially linear longitudinal motion of the piston rod 5224 and thus ensuring substantially linear longitudinal motion of the piston 5204. In an exemplary embodiment, link rod 5226 does not pass through linear bearing 5220. This ensures, among other things, that piston rod 5224 retains a substantially linear and longitudinal motion.

In the exemplary embodiment, the link rods may be made from aluminum, and the piston rods and connecting rod are made from D2 Tool Steel. Alternatively, the link rods, piston rods, connecting rods, and rocking beam may be made from 4340 steel. Other materials may be used for the components of the rocking beam drive, including, but not limited to, titanium, aluminum, steel or cast iron. In some embodiments, the fatigue strength of the material being used is above the actual load experienced by the components during operation.

Still referring to FIGS. 46-48, piston 5202 operates vertically in the cylinder 5206 and is connected by the coupling assembly 5210 to the end pivot 5236 of the rocking beam 5216. The cylinder 5206 serves, amongst other functions, to provide guidance for longitudinal motion of piston 5202. The piston rod 5228 of the coupling assembly 5210 is attached to the lower portion of piston 5202 and is driven axially by its link rod 5230 in a substantially linear reciprocating path along the axis of the cylinder 5206. The distal end of the piston rod 5228 and the proximate end of the link rod 5230, in some embodiments, is jointly hinged via a coupling means 5238. The coupling means 5238, in various embodiments may include, but are not limited to, a flexure (shown as 5700 in FIGS. 51A and 51B, roller bearing element, hinge, journal bearing (shown as 5600 in FIG. 50), or coupling means as known in the art. The distal end of the link rod 5230, in some embodiments, may be coupled to one end pivot 5236 of rocking beam 5216, which is positioned vertically and perpendicularly under the proximate end of link rod 5230. A stationary linear bearing 5220 may be positioned along coupling assembly 5210 to further ensure linear longitudinal motion of the piston rod 5228 and thus ensuring linear longitudinal motion of the piston 5202. In an exemplary embodiment, link rod 5230 does not pass through linear bearing 5220 to ensure that piston rod 5228 retains a substantially linear and longitudinal motion.

Figure 49A:
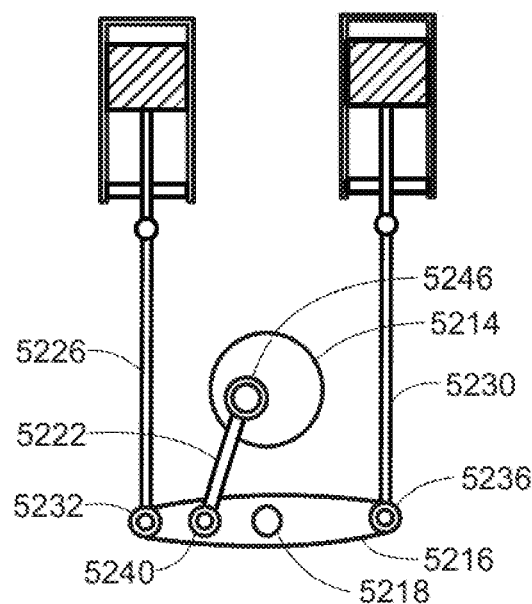
Figure 49B:
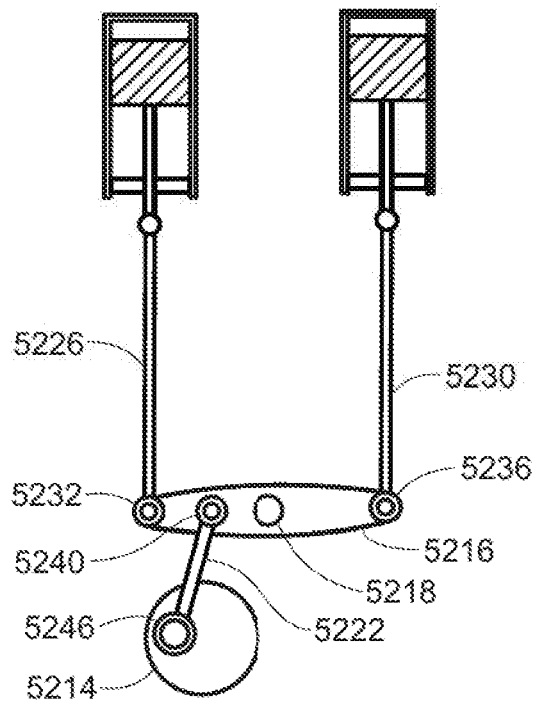

The coupling assemblies 5210 and 5212 change the alternating longitudinal motion of respective pistons 5202 and 5204 to oscillatory motion of the rocking beam 5216. The delivered oscillatory motion is changed to the rotational motion of the crankshaft 5214 by the connecting rod 5222, wherein one end of the connecting rod 5222 is rotatably coupled to a connecting pivot 5240 positioned between an end pivot 5232 and a rocker pivot 5218 in the rocking beam 5216, and another end of the connecting rod 5222 is rotatably coupled to crankpin 5246. The rocker pivot 5218 may be positioned substantially at the midpoint between the end pivots 5232 and 5236 and oscillatorily support the rocking beam 5216 as a fulcrum, thus guiding the respective piston rods 5224 and 5228 to make sufficient linear motion. In the exemplary embodiment, the crankshaft 5214 is located above the rocking beam 5216, but in other embodiments, the crankshaft 5214 may be positioned below the rocking beam 5216 (as shown in FIGS. 49B and 49D) or in some embodiments, the crankshaft 5214 is positioned to the side of the rocking beam 5216, such that it still has a parallel axis to the rocking beam 5216.

Still referring to FIGS. 46-48, the rocking beam oscillates about the rocker pivot 5218, the end pivots 5232 and 5236 follow an arc path. Since the distal ends of the link rods 5226 and 5230 are connected to the rocking beam 5216 at pivots 5232 and 5236, the distal ends of the link rods 5226 and 5230 also follow this arc path, resulting in an angular deviation 5242 and 5244 from the longitudinal axis of motion of their respective pistons 5202 and 5204. The coupling means 5234 and 5238 are configured such that any angular deviation 5244 and 5242 from the link rods 5226 and 5230 experienced by the piston rods 5224 and 5228 is minimized Essentially, the angular deviation 5244 and 5242 is absorbed by the coupling means 5234 and 5238 so that the piston rods 5224 and 5228 maintain substantially linear longitudinal motion to reduce side loads on the pistons 5204 and 5202. A stationary linear bearing 5220 may also be placed inside the cylinder 5208 or 5206, or along coupling assemblies 5212 or 5210, to further absorb any angular deviation 5244 or 5242 thus keeping the piston push rod 5224 or 5228 and the piston 5204 or 5202 in linear motion along the longitudinal axis of the piston 5204 or 5202.

Therefore, in view of reciprocating motion of pistons 5202 and 5204, it is necessary to keep the motion of pistons 5202 and 5204 as close to linear as possible because the deviation 5242 and 5244 from longitudinal axis of reciprocating motion of pistons 5202 and 5204 causes noise, reduction of efficiency, increase of friction to the wall of cylinder, increase of side-load, and low durability of the parts. The alignment of the cylinders 5206 and 5208 and the arrangement of crankshaft 5214, piston rods 5224 and 5228, link rods 5226 and 5230, and connecting rod 5222, hence, may influence on, amongst other things, the efficiency and/or the volume of the device. For the purpose of increasing the linearity of the piston motion as mentioned, the pistons (shown as 5202 and 5204 in FIGS. 46-48) are preferably as close to the side of the respective cylinders 5206 and 5208 as possible.

In another embodiment reducing angular deviation of link rods, link rods 5226 and 5230 substantially linearly reciprocate along longitudinal axis of motion of respective pistons 5204 and 5202 to decrease the angular deviation and thus to decrease the side load applied to each piston 5204 and 5202. The angular deviation defines the deviation of the link rod 5226 or 5230 from the longitudinal axis of the piston 5204 or 5202. Numerals 5244 and 5242 designate the angular deviation of the link rods 5226 and 5230, as shown in FIG. 46. Therefore, the position of coupling assembly 5212 influences the angular displacement of the link rod 5226, based on the length of the distance between the end pivot 5232 and the rocker pivot 5218 of the rocking beam 5216. Thus, the position of the coupling assemblies may be such that the angular displacement of the link rod 5226 is reduced. For the link rod 5230, the length of the coupling assembly 5210 also may be determined and placed to reduce the angular displacement of the link rod 5230, based on the length of the distance between the end pivot 5236 and the rocker pivot 5218 of the rocking beam 5216. Therefore, the length of the link rods 5226 and 5230, the length of coupling assemblies 5212 and 5210, and the length of the rocking beam 5216 are significant parameters that greatly influence and/or determine the angular deviation of the link rods 5226 and 5230 as shown in FIG. 46.

The exemplary embodiment has a straight rocking beam 5216 having the end points 5232 and 5236, the rocker pivot 5218, and the connecting pivot 5240 along the same axis. However, in other embodiments, the rocking beam 5216 may be bent, such that pistons may be placed at angles to each other, as shown in FIGS. 49C and 49D.

Referring now to FIGS. 46-48 and FIGS. 51A-51B, in some embodiments of the coupling assembly, the coupling assemblies 5212 and 5210, may include a flexible link rod that is axially stiff but flexible in the rocking beam 5216 plane of motion between link rods 5226 and 5230, and pistons 5204 and 5202, respectively. In this embodiment, at least one portion, the flexure (shown as 5700 in FIGS. 51A and 51B), of link rods 5226 and 5230 is elastic. The flexure 5700 acts as a coupling means between the piston rod and the link rod. The flexure 5700 may absorb the crank-induced side loads of the pistons more effectively, thus allowing its respective piston to maintain linear longitudinal movement inside the piston's cylinder. This flexure 5700 allows small rotations in the plane of the rocking beam 5216 between the link rods 5226 and 5230 and pistons 5204 or 5202, respectively. Although depicted in this embodiment as flat, which increases the elasticity of the link rods 5226 and 5230, the flexure 5700, in some embodiments, is not flat. The flexure 5700 also may be constructed near to the lower portion of the pistons or near to the distal end of the link rods 5226 and 5230. The flexure 5700, in one embodiment, may be made of #D2 Tool Steel Hardened to 58-62 RC. In some embodiments, there may be more than one flexure (not shown) on the link rod 5226 or 5230 to increase the elasticity of the link rods.

Figure 49C:
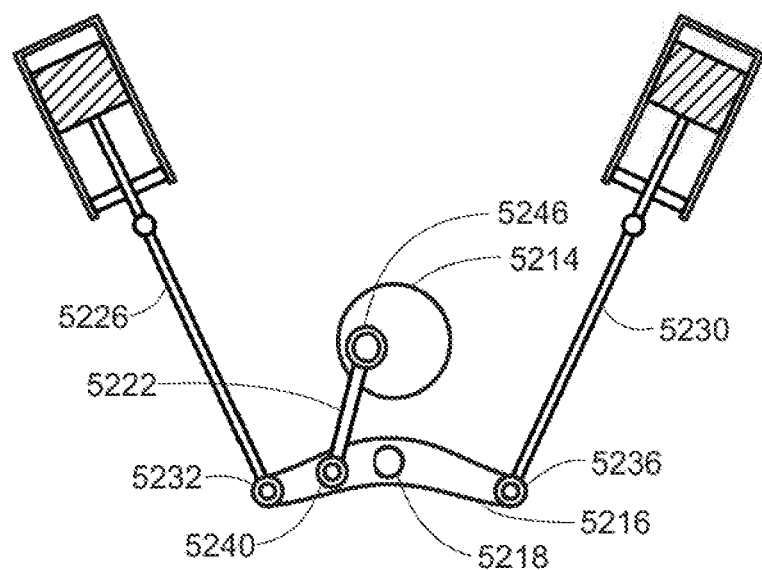
Figure 49D:
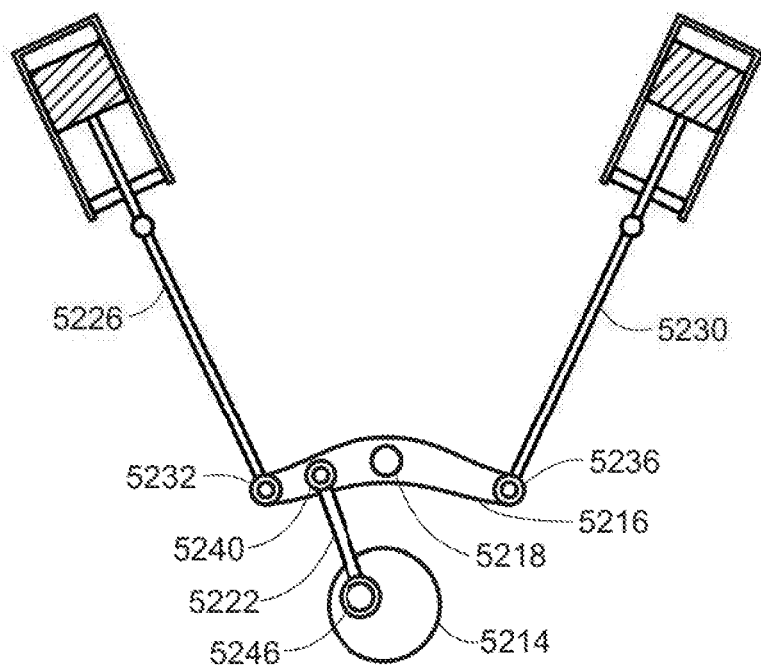

In alternate embodiment, the axes of the pistons in each cylinder housing may extend in different directions, as depicted in FIGS. 49C and 49D. In the exemplary embodiment, the axes of the pistons in each cylinder housing are substantially parallel and preferably substantially vertical, as depicted in FIGS. 46-48, and FIGS. 49A and 49B. FIGS. 49A-49D include various embodiments of the rocking beam drive mechanism including like numbers as those shown and described with respect to FIGS. 2-4. It will be understood by those skilled in that art that changing the relative position of the connecting pivot 5240 along the rocking beam 5216 will change the stroke of the pistons.

Accordingly, a change in the parameters of the relative position of the connecting pivot 5240 in the rocking beam 5216 and the length of the piston rods 5224 and 5228, link rods 5230 and 5226, rocking beam 5216, and the position of rocker pivot 5218 will change the angular deviation of the link rods 5226 and 5230, the phasing of the pistons 5204 and 5202, and the size of the device 5300 in a variety of manner. Therefore, in various embodiments, a wide range of piston phase angles and variable sizes of the engine may be chosen based on the modification of one or more of these parameters. In practice, the link rods 5224 and 5228 of the exemplary embodiment have substantially lateral movement within from −0.5 degree to +0.5 degree from the longitudinal axis of the pistons 5204 and 5202. In various other embodiments, depending on the length of the link rod, the angle may vary anywhere from approaching 0 degrees to 0.75 degrees. However, in other embodiments, the angle may be higher including anywhere from approaching 0 to the approximately 20 degrees. As the link rod length increases, however, the crankcase/overall engine height increases as well as the weight of the engine.

One feature of the exemplary embodiment is that each piston has its link rod extending substantially to the attached piston rod so that it is formed as a coupling assembly. In one embodiment, the coupling assembly 5212 for the piston 5204 includes a piston rod 5224, a link rod 5226, and a coupling means 5234 as shown in FIG. 46. More specifically, one proximal end of piston rod 5224 is attached to the lower portion of piston 5204 and the distal end piston rod 5224 is connected to the proximate end of the link rod 5226 by the coupling means 5234. The distal end of the link rod 5226 extends vertically to the end pivot 5232 of the rocking beam 5216. As described above, the coupling means 5234 may be, but is not limited to, a joint, hinge, coupling, or flexure or other means known in the art. In this embodiment, the ratio of the piston rod 5224 and the link rod 5226 may determine the angular deviation of the link rod 5226 as mentioned above.

In one embodiment of the machine, an engine, such as a Stirling engine, employs more than one rocking beam drive on a crankshaft. Referring now to FIG. 52, an unwrapped "four cylinder" rocking beam drive mechanism 5800 is shown. In this embodiment, the rocking beam drive mechanism has four pistons 5802, 5804, 5806, and 5808 coupled to two rocking beam drives 5810 and 5812. In the exemplary embodiment, rocking beam drive mechanism 5800 is used in a Stirling engine comprising at least four pistons 5802, 5804, 5806, and 5808, positioned in a quadrilateral arrangement coupled to a pair of rocking beam drives 5810 and 5812, wherein each rocking beam drive is connected to crankshaft 5814. However, in other embodiments, the Stirling cycle engine includes anywhere from 1-4 pistons, and in still other embodiments, the Stirling cycle engine includes more than 4 pistons. In some embodiments, rocking beam drives 5810 and 5812 are substantially similar to the rocking beam drives described above with respect to FIGS. 46-48 (shown as 5210 and 5212 in FIGS. 46-48). Although in this embodiment, the pistons are shown outside the cylinders, in practice, the pistons would be inside cylinders.

Still referring to FIG. 52, in some embodiments, the rocking beam drive mechanism 5800 has a single crankshaft 5814 having a pair of longitudinally spaced, radially and oppositely directed crank pins 5816 and 5818 adapted for being journalled in a housing, and a pair of rocking beam drives 5810 and 5812. Each rocking beam 5820 and 5822 is pivotally connected to rocker pivots 5824 and 5826, respectively, and to crankpins 5816 and 5818, respectively. In the exemplary embodiment, rocking beams 5820 and 5822 are coupled to a rocking beam shaft 5828.

In some embodiments, a motor/generator may be connected to the crankshaft in a working relationship. The motor may be located, in one embodiment, between the rocking beam drives. In another embodiment, the motor may be positioned outboard. The term "motor/generator" is used to mean either a motor or a generator.

FIG. 53 shows one embodiment of crankshaft 5814. Positioned on the crankshaft is a motor/generator 5900, such as a Permanent Magnetic ("PM") generator. Motor/generator 5900 may be positioned between, or inboard of the rocking beam drives (not shown, shown in FIG. 52 as 5810 and 5812), or may be positioned outside, or outboard of, rocking beam drives 5810 and 5812 at an end of crankshaft 5814, as depicted by numeral 51000 in FIG. 54A.

When motor/generator 5900 is positioned between the rocking beam drives (not shown, shown in FIG. 52 as 5810 and 5812), the length of motor/generator 5900 is limited to the distance between the rocking beam drives. The diameter squared of motor/generator 5900 is limited by the distance between the crankshaft 5814 and the rocking beam shaft 5828. Because the capacity of motor/generator 5900 is proportional to its diameter squared and length, these dimension limitations result in a limited-capacity "pancake" motor/generator 5900 having relatively short length, and a relatively large diameter squared. The use of a "pancake" motor/generator 5900 may reduce the overall dimension of the engine, however, the dimension limitations imposed by the inboard configuration result in a motor/generator having limited capacity.

Placing motor/generator 5900 between the rocking beam drives exposes motor/generator 5900 to heat generated by the mechanical friction of the rocking beam drives. The inboard location of motor/generator 5900 makes it more difficult to cool motor/generator 5900, thereby increasing the effects of heat produced by motor/generator 5900 as well as heat absorbed by motor/generator 5900 from the rocking beam drives. This may lead to overheating, and ultimately failure of motor/generator 5900.

Referring to both FIGS. 52 and 53, the inboard positioning of motor/generator 5900 may also lead to an unequilateral configuration of pistons 5802, 5804, 5806, and 5808, since pistons 5802, 5804, 5806, and 5808 are coupled to rocking beam drives 5810 and 5812, respectively, and any increase in distance would also result in an increase in distance between pistons 5802, 5804, and pistons 5806 and 5808. An unequilateral arrangement of pistons may lead to inefficiencies in burner and heater head thermodynamic operation, which, in turn, may lead to a decrease in overall engine efficiency. Additionally, an unequilateral arrangement of pistons may lead to larger heater head and combustion chamber dimensions.

The exemplary embodiment of the motor/generator arrangement is shown in FIG. 54A. As shown in FIG. 54A, the motor/generator 51000 is positioned outboard from rocking beam drives 51010 and 51012 (shown as 5810 and 5812 in FIG. 52) and at an end of crankshaft 51006. The outboard position allows for a motor/generator 51000 with a larger length and diameter squared than the "pancake" motor/generator described above (shown as 5900 in FIG. 53). As previously stated, the capacity of motor/generator 51000 is proportional to its length and diameter squared, and since outboard motor/generator 51000 may have a larger length and diameter squared, the outboard motor/generator 51000 configuration shown in FIG. 54A may allow for the use of a higher capacity motor/generator in conjunction with engine.

By placing motor/generator 51000 outboard of drives 51010 and 51012 as shown in the embodiment in FIG. 54A, motor/generator 51000 is not exposed to heat generated by the mechanical friction of drives 51010 and 51012. Also, the outboard position of motor/generator 1000 makes it easier to cool the motor/generator, thereby allowing for more mechanical engine cycles per a given amount of time, which in turn allows for higher overall engine performance.

Also, as motor/generator 51000 is positioned outside and not positioned between drives 51010 and 51012, rocking beam drives 51010 and 51012 may be placed closer together thereby allowing the pistons which are coupled to drives 51010 and 51012 to be placed in an equilateral arrangement. In some embodiments, depending on the burner type used, particularly in the case of a single burner embodiment, equilateral arrangement of pistons allows for higher efficiencies in burner and heater head thermodynamic operation, which in turn allows higher overall engine performance. Equilateral arrangement of pistons also advantageously allows for smaller heater head and combustion chamber dimensions.

Referring again to FIGS. 52 and 53, crankshaft 5814 may have concentric ends 5902 and 5904, which in one embodiment are crank journals, and in various other embodiments, may be, but are not limited to, bearings. Each concentric end 5902, 5904 has a crankpin 5816, 5818 respectively, that may be offset from a crankshaft center axis. At least one counterweight 5906 may be placed at either end of crankshaft 5814 (shown as 51006 in FIG. 54A), to counterbalance any instability the crankshaft 5814 may experience. This crankshaft configuration in combination with the rocking beam drive described above allows the pistons (shown as 5802, 5804, 5806, and 5808 in FIG. 52) to do work with one rotation of the crankshaft 5814. This characteristic will be further explained below. In other embodiments, a flywheel (not shown) may be placed on crankshaft 5814 (shown as 51006 in FIG. 54A) to decrease fluctuations of angular velocity for a more constant speed.

Still referring to FIGS. 52 and 53, in some embodiments, a cooler (not shown) may be also be positioned along the crankshaft 5814 (shown as 51006 in FIG. 54A) and rocking beam drives 5810 and 5812 (shown as 51010 and 51012 in FIG. 54A) to cool the crankshaft 5814 and rocking beam drives 5810 and 5812. In some embodiments, the cooler may be used to cool the working gas in a cold chamber of a cylinder and may also be configured to cool the rocking beam drive. Various embodiments of the cooler are discussed in detail below.

FIGS. 54A-54G depict some embodiments of various parts of the machine. As shown in this embodiment, crankshaft 51006 is coupled to motor/generator 51000 via a motor/generator coupling assembly. Since motor/generator 51000 is mounted to crankcase 51008, pressurization of crankcase with a charge fluid may result in crankcase deformation, which in turn may lead to misalignments between motor/generator 51000 and crankshaft 51006 and cause crankshaft 51006 to deflect. Because rocking beam drives 51010 and 51012 are coupled to crankshaft 51006, deflection of crankshaft 51006 may lead to failure of rocking beam drives 51010 and 51012. Thus, in one embodiment of the machine, a motor/generator coupling assembly is used to couple the motor/generator 51000 to crankshaft 51006. The motor/generator coupling assembly accommodates differences in alignment between motor/generator 51000 and crankshaft 51006 which may contribute to failure of rocking beam drives 51010 and 51012 during operation.

Still referring to FIGS. 54A-54G, in one embodiment, the motor/generator coupling assembly is a spline assembly that includes spline shaft 51004, sleeve rotor 51002 of motor/generator 51000, and crankshaft 51006. Spline shaft 51004 couples one end of crankshaft 51006 to sleeve rotor 51002. Sleeve rotor 51002 is attached to motor/generator 51000 by mechanical means, such as press fitting, welding, threading, or the like. In one embodiment, spline shaft 51004 includes a plurality of splines on both ends of the shaft. In other embodiments, spline shaft 51004 includes a middle splineless portion 51014, which has a diameter smaller than the outer diameter or inner diameter of splined portions 51016 and 51018. In still other embodiments, one end portion of the spline shaft 51016 has splines that extend for a longer distance along the shaft than a second end portion 51018 that also includes splines thereon.

In some embodiments, sleeve rotor 51002 includes an opening 51020 that extends along a longitudinal axis of sleeve rotor 51002. The opening 51020 is capable of receiving spline shaft 51004. In some embodiments, opening 51020 includes a plurality of inner splines 51022 capable of engaging the splines on one end of spline shaft 51004. The outer diameter 51028 of inner splines 51022 may be larger than the outer diameter 51030 of the splines on spline shaft 51004, such that the fit between inner splines 51022 and the splines on spline shaft 51004 is loose (as shown in FIG. 54E). A loose fit between inner splines 51022 and the splines on spline shaft 51004 contributes to maintain spline engagement between spline shaft 51004 and rotor sleeve 51002 during deflection of spline shaft 51004, which may be caused by crankcase pressurization. In other embodiments, longer splined portion 51016 of spline shaft 51004 may engage inner splines 51022 of rotor 51002.

Still referring to FIGS. 54A-54G, in some embodiments, crankshaft 51006 has an opening 51024 on an end thereof, which is capable of receiving one end of spline shaft 51004. Opening 51024 preferably includes a plurality of inner splines 51026 that engage the splines on spline shaft 51004. The outer diameter 51032 of inner splines 51026 may be larger than the outer diameter 51034 of the splines on spline shaft 51004, such that the fit between inner splines 51026 and the splines on spline shaft 51004 is loose (as shown in FIG. 54F). As previously discussed, a loose fit between inner splines 51026 and the splines on spline shaft 51004 contributes to maintain spline engagement between spline shaft 51004 and crankshaft 51006 during deflection of spline shaft 51004, which may be caused by crankcase pressurization. The loose fit between the inner splines 51026 and 51022 on the crankshaft 51006 and the sleeve rotor 51002 and the splines on the spline shaft 51004 may contribute to maintain deflection of spline shaft 51004. This may allow misalignments between crankshaft 51006 and sleeve rotor 51002. In some embodiments, shorter splined portion 51018 of spline shaft 51004 may engage opening 51024 of crankshaft 51006 thus preventing these potential misalignments.

In some embodiments, opening 51020 of sleeve rotor 51002 includes a plurality of inner splines that extend the length of opening 51020. This arrangement contributes to spline shaft 51004 being properly inserted into opening 51020 during assembly. This contributes to proper alignment between the splines on spline shaft 51004 and the inner splines on sleeve rotor 51002 being maintained.

Referring now to FIG. 48, one embodiment of the engine is shown. Here the pistons 5202 and 5204 of engine 5300 operate between a hot chamber 5404 and a cold chamber 5406 of cylinders 5206 and 5208 respectively. Between the two chambers there may be a regenerator 5408. The regenerator 5408 may have variable density, variable area, and, in some embodiments, is made of wire. The varying density and area of the regenerator may be adjusted such that the working gas has substantially uniform flow across the regenerator 5408. Various embodiments of the regenerator 5408 are discussed in detail below, and in U.S. Pat. No. 6,591,609, issued Jul. 17, 2003, to Kamen et al., and U.S. Pat. No. 6,862,883, issued Mar. 8, 2005, to Kamen et al., which are herein incorporated by reference in their entireties. When the working gas passes through the hot chamber 5404, a heater head 5410 may heat the gas causing the gas to expand and push pistons 5202 and 5204 towards the cold chamber 5406, where the gas compresses. As the gas compresses in the cold chamber 5406, pistons 5202 and 5204 may be guided back to the hot chamber to undergo the Stirling cycle again. The heater head 5410 may be a pin head, a fin head, a folded fin head, heater tubes as shown in FIG. 48, or any other heater head embodiment known, including, but not limited to, those described below. Various embodiments of heater head 5410 are discussed in detail below, and in U.S. Pat. No. 6,381,958, issued May 7, 2002, to Kamen et al., U.S. Pat. No. 6,543,215, issued Apr. 8, 2003, to Langenfeld et al., U.S. Pat. No. 6,966,182, issued Nov. 22, 2005, to Kamen et al, and U.S. Pat. No. 7,308,787, issued Dec. 18, 2007, to LaRocque et al., which are herein incorporated by reference in their entireties.

In some embodiments, a cooler 5412 may be positioned alongside cylinders 5206 and 5208 to further cool the gas passing through to the cold chamber 5406. Various embodiments of cooler 5412 are discussed in detail in the proceeding sections, and in U.S. Pat. No. 7,325,399, issued Feb. 5, 2008, to Strimling et al, which is herein incorporated by reference in its entirety.

In some embodiments, at least one piston seal 5414 may be positioned on pistons 5202 and 5204 to seal the hot section 5404 off from the cold section 5406. Additionally, at least one piston guide ring 5416 may be positioned on pistons 5202 and 5204 to help guide the pistons' motion in their respective cylinders. Various embodiments of piston seal 5414 and guide ring 5416 are described in detail below, and in U.S. patent application Ser. No. 10/175,502, filed Jun. 19, 2002, published Feb. 6, 2003 (now abandoned), which is herein incorporated by reference in its entirety.

In some embodiments, at least one piston rod seal 5418 may be placed against piston rods 5224 and 5228 to prevent working gas from escaping into the crankcase 5400, or alternatively into airlock space 5420. The piston rod seal 5418 may be an elastomer seal, or a spring-loaded seal. Various embodiments of the piston rod seal 5418 are discussed in detail below.

In some embodiments, the airlock space may be eliminated, for example, in the rolling diaphragm and/or bellows embodiments described in more detail below. In those cases, the piston rod seals 5224 and 5228 seal the working space from the crankcase.

In some embodiments, at least one rolling diaphragm/ bellows 5422 may be located along piston rods 5224 and 5228 to prevent airlock gas from escaping into the crankcase 5400. Various embodiments of rolling diaphragm 5422 are discussed in more detail below.

Although FIG. 48 shows a cross section of engine 5300 depicting only two pistons and one rocking beam drive, it is to be understood that the principles of operation described herein may apply to a four cylinder, double rocking beam drive engine, as designated generally by numeral 5800 in FIG. 52.

Piston Operation

Referring now to FIGS. 52 and 55, the operation of pistons 5802, 5804, 5806, and 5808 during one revolution of crankshaft 5814 is shown. With a ¼ revolution of crankshaft 5814, piston 5802 is at the top of its cylinder, otherwise known as top dead center, piston 5806 is in upward midstroke, piston 5804 is at the bottom of its cylinder, otherwise known as bottom dead center, and piston 5808 is in downward midstroke. With a ½ revolution of crankshaft 5814, piston 5802 is in downward midstroke, piston 5806 is at top dead center, piston 5804 is in upward midstroke, and piston 5808 is at bottom dead center. With ¾ revolution of crankshaft 5814, piston 5802 is at bottom dead center, piston 5806 is in downward midstroke, piston 5804 is at top dead center, and piston 5808 is in upward midstroke. Finally, with a full revolution of crankshaft 5814, piston 5802 is in upward midstroke, piston 5806 is at bottom dead center, piston 5804 is in downward midstroke, and piston 5808 is at top dead center. During each ¼ revolution, there is a 90 degree phase difference between pistons 5802 and 5806, a 180 degree phase difference between pistons 5802 and 5804, and a 270 degree phase difference between pistons 5802 and 5808. FIG. 56A illustrates the relationship of the pistons being approximately 90 degrees out of phase with the preceding and succeeding piston. Additionally, FIG. 55 shows the exemplary embodiment machine means of transferring work. Thus, work is transferred from piston 5802 to piston 5806 to piston 5804 to piston 5808 so that with a full revolution of crankshaft 5814, all pistons have exerted work by moving from the top to the bottom of their respective cylinders.

Referring now to FIG. 55, together with FIGS. 56A-56C, illustrate the 90 degree phase difference between the pistons in the exemplary embodiment. Referring now to FIG. 56A, although the cylinders are shown in a linear path, this is for illustration purposes only. In the exemplary embodiment of a four cylinder Stirling cycle machine, the flow path of the working gas contained within the cylinder working space follows a figure eight pattern. Thus, the working spaces of cylinders 51200, 51202, 51204, and 51206 are connected in a figure eight pattern, for example, from cylinder 51200 to cylinder 51202 to cylinder 51204 to cylinder 51208, the fluid flow pattern follows a figure eight. Still referring to FIG. 56A, an unwrapped view of cylinders 51200, 51202, 51204, and 51206, taken along the line B-B (shown in FIG. 56C) is illustrated. The 90 degree phase difference between pistons as described above allows for the working gas in the warm section 51212 of cylinder 51204 to be delivered to the cold section 51222 of cylinder 51206. As piston 5802 and 5808 are 90 degrees out of phase, the working gas in the warm section 51214 of cylinder 51206 is delivered to the cold section 51216 of cylinder 51200. As piston 5802 and piston 5806 are also 90 degrees out of phase, the working gas in the warm section 51208 of cylinder 51200 is delivered to the cold section 51218 of cylinder 51202. And as piston 5804 and piston 5806 are also 90 degrees out of phase, so the working gas in the warm section 51210 of cylinder 51202 is delivered to the cold section 51220 of cylinder 51204. Once the working gas of a warm section of a first cylinder enters the cold section of a second cylinder, the working gas begins to compress, and the piston within the second cylinder, in its down stroke, thereafter forces the compressed working gas back through a regenerator 51224 and heater head 51226 (shown in FIG. 56B), and back into the warm section of the first cylinder. Once inside the warm section of the first cylinder, the gas expands and drives the piston within that cylinder downward, thus causing the working gas within the cold section of that first cylinder to be driven through the preceding regenerator and heater head, and into the cylinder. This cyclic transmigration characteristic of working gas between cylinders 51200, 51202, 51204, and 51206 is possible because pistons 5802, 5804, 5806, and 5808 are connected, via drives 5810 and 5812, to a common crankshaft 5814 (shown in FIG. 55), in such a way that the cyclical movement of each piston is approximately 90 degrees in advance of the movement of the proceeding piston, as depicted in FIG. 56A.

Rolling Diaphragm, Metal Bellows, Airlock, and Pressure Regulator

In some embodiments of the Stirling cycle machine, lubricating fluid is used. To prevent the lubricating fluid from escaping the crankcase, a seal is used.

Referring now to FIGS. 57A-59, some embodiments of the Stirling cycle machine include a fluid lubricated rocking beam drive that utilizes a rolling diaphragm 51300 positioned along the piston rod 51302 to prevent lubricating fluid from escaping the crankcase, not shown, but the components that are housed in the crankcase are represented as 51304, and entering areas of the engine that may be damaged by the lubricating fluid. It is beneficial to contain the lubricating fluid for if lubricating fluid enters the working space, not shown, but the components that are housed in the working space are represented as 51306, it would contaminate the working fluid, come into contact with the regenerator 51308, and may clog the regenerator 51308. The rolling diaphragm 51300 may be made of an elastomer material, such as rubber or rubber reinforced with woven fabric or non-woven fabric to provide rigidity. The rolling diaphragm 51300 may alternatively be made of other materials, such as fluorosilicone or nitrile with woven fabric or non-woven fabric. The rolling diaphragm 51300 may also be made of carbon nanotubes or chopped fabric, which is non-woven fabric with fibers of polyester or KEVLAR®, for example, dispersed in an elastomer. In the some embodiments, the rolling diaphragm 51300 is supported by the top seal piston 51328 and the bottom seal piston 51310. In other embodiments, the rolling diaphragm 51300 as shown in FIG. 57A is supported via notches in the top seal piston 51328.

In some embodiments, a pressure differential is placed across the rolling diaphragm 51300 such that the pressure above the seal 51300 is different from the pressure in the crankcase 51304. This pressure differential inflates seal 51300 and allows seal 51300 to act as a dynamic seal as the pressure differential ensures that rolling diaphragm maintains its form throughout operation. FIG. 57A, and FIGS. 57C-57H illustrate how the pressure differential effects the rolling diaphragm. The pressure differential causes the rolling diaphragm 51300 to conform to the shape of the bottom seal piston 51310 as it moves with the piston rod 51302, and prevents separation of the seal 51300 from a surface of the piston 51310 during operation. Such separation may cause seal failure. The pressure differential causes the rolling diaphragm 51300 to maintain constant contact with the bottom seal piston 51310 as it moves with the piston rod 51302. This occurs because one side of the seal 51300 will always have pressure exerted on it thereby inflating the seal 51300 to conform to the surface of the bottom seal piston 51310. In some embodiments, the top seal piston 51328 'rolls over' the corners of the rolling diaphragm 51300 that are in contact with the bottom seal piston 51310, so as to further maintain the seal 51300 in contact with the bottom seal piston 51310. In the exemplary embodiment, the pressure differential is in the range of 10 to 15 PSI. The smaller pressure in the pressure differential is preferably in crankcase 51304, so that the rolling diaphragm 51300 may be inflated into the crankcase 51304. However, in other embodiments, the pressure differential may have a greater or smaller range of value.

The pressure differential may be created by various methods including, but not limited to, the use of the following: a pressurized lubrication system, a pneumatic pump, sensors, an electric pump, by oscillating the rocking beam to create a pressure rise in the crankcase 51304, by creating an electrostatic charge on the rolling diaphragm 51300, or other similar methods. In some embodiments, the pressure differential is created by pressurizing the crankcase 51304 to a pressure that is below the mean pressure of the working space 51306. In some embodiments the crankcase 51304 is pressurized to a pressure in the range of 10 to 15 PSI below the mean pressure of the working space 51306, however, in various other embodiments, the pressure differential may be smaller or greater. Further detail regarding the rolling diaphragm is included below.

Referring now to FIGS. 57C, 57G, and 57H, however, another embodiment of the Stirling machine is shown, wherein airlock space 51312 is located between working space 51306 and crankcase 51304. Airlock space 51312 maintains a constant volume and pressure necessary to create the pressure differential necessary for the function of rolling diaphragm 51300 as described above. In one embodiment, airlock 51312 is not absolutely sealed off from working space 51306, so the pressure of airlock 51312 is equal to the mean pressure of working space 51306. Thus, in some embodiments, the lack of an effective seal between the working space and the crankcase contributes to the need for an airlock space. Thus, the airlock space, in some embodiments, may be eliminated by a more efficient and effective seal.

During operation, the working space 51306 mean pressure may vary so as to cause airlock 51312 mean pressure to vary as well. One reason the pressure may tend to vary is that during operation the working space may get hotter, which in turn may increase the pressure in the working space, and consequently in the airlock as well since the airlock and working space are in fluid communication. In such a case, the pressure differential between airlock 51312 and crankcase 51304 will also vary, thereby causing unnecessary stresses in rolling diaphragms 51300 that may lead to seal failure. Therefore, some embodiments of the machine, the mean pressure within airlock 51312 is regulated so as to maintain a constant desired pressure differential between airlock 51312 and crankcase 51304, and ensuring that rolling diaphragms 51300 stay inflated and maintains their form. In some embodiments, a pressure transducer is used to monitor and manage the pressure differential between the airlock and the crankcase, and regulate the pressure accordingly so as to maintain a constant pressure differential between the airlock and the crankcase. Various embodiments of the pressure regulator that may be used are described in further detail below, and in U.S. Pat. No. 7,310,945, issued Dec. 25, 2007, to Gurski et al., which is herein incorporated by reference in its entirety.

A constant pressure differential between the airlock 51312 and crankcase 51304 may be achieved by adding or removing working fluid from airlock 51312 via a pump or a release valve. Alternatively, a constant pressure differential between airlock 51312 and crankcase 51304 may be achieved by adding or removing working fluid from crankcase 51304 via a pump or a release valve. The pump and release valve may be controlled by the pressure regulator. Working fluid may be added to airlock 51312 (or crankcase 51304) from a separate source, such as a working fluid container, or may be transferred over from crankcase 51304. Should working fluid be transferred from crankcase 51304 to airlock 51312, it may be desirable to filter the working fluid before passing it into airlock 51312 so as to prevent any lubricant from passing from crankcase 51304 into airlock 51312, and ultimately into working space 51306, as this may result in engine failure.

In some embodiments of the machine, crankcase 51304 may be charged with a fluid having different thermal properties than the working fluid. For example, where the working gas is helium or hydrogen, the crankcase may be charged with argon. Thus, the crankcase is pressurized. In some embodiments, helium is used, but in other embodiments, any inert gas, as described herein, may be used. Thus, the crankcase is a wet pressurized crankcase in the exemplary embodiment. In other embodiments where a lubricating fluid is not used, the crankcase is not wet.

In the exemplary embodiments, rolling diaphragms 51300 do not allow gas or liquid to pass through them, which allows working space 51306 to remain dry and crankcase 51304 to be wet sumped with a lubricating fluid. Allowing a wet sump crankcase 51304 increases the efficiency and life of the engine as there is less friction in rocking beam drives 51316. In some embodiments, the use of roller bearings or ball bearings in drives 51316 may also be eliminated with the use of lubricating fluid and rolling diaphragms 51300. This may further reduce engine noise and increase engine life and efficiency.

FIGS. 58A-58E show cross sections of various embodiments of the rolling diaphragm (shown as 51400, 51410, 51412, 51422 and 51424) configured to be mounted between top seal piston and bottom seal piston (shown as 51328 and 51310 in FIGS. 57A and 57H), and between a top mounting surface and a bottom mounting surface (shown as 51320 and 51318 in FIG. 57A). In some embodiments, the top mounting surface may be the surface of an airlock or working space, and the bottom mounting surface may be the surface of a crankcase.

Figure 58A:
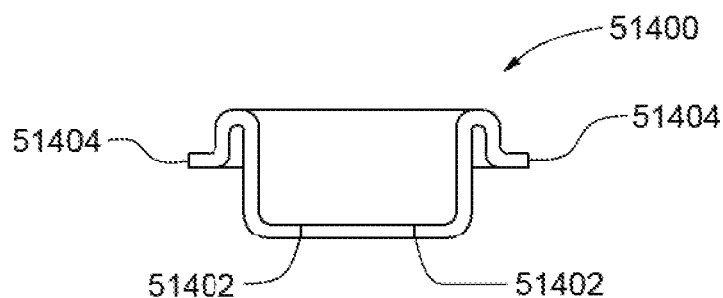
Figure 58B:
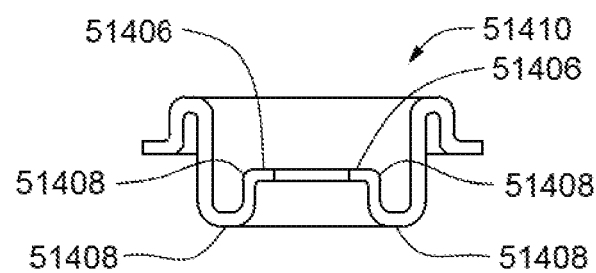
Figure 58C:
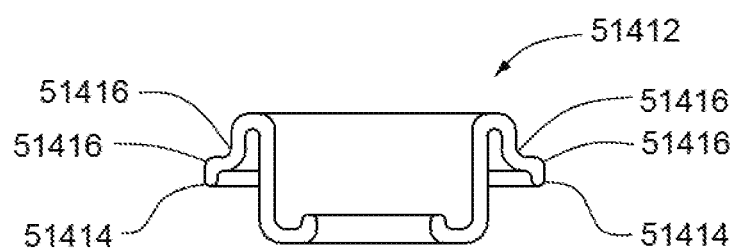

FIG. 58A shows one embodiment of the rolling diaphragm 51400, where the rolling diaphragm 51400 includes a flat inner end 51402 that may be positioned between a top seal piston and a bottom seal piston, so as to form a seal between the top seal piston and the bottom seal piston. The rolling diaphragm 51400 also includes a flat outer end 51404 that may be positioned between a top mounting surface and a bottom mounting surface, so as to form a seal between the top mounting surface and the bottom mounting surface. FIG. 58B shows another embodiment of the rolling diaphragm, wherein rolling diaphragm 51410 may include a plurality of bends 51408 leading up to flat inner end 51406 to provide for additional support and sealing contact between the top seal piston and the bottom seal piston. FIG. 58C shows another embodiment of the rolling diaphragm, wherein rolling diaphragm 51412 includes a plurality of bends 51416 leading up to flat outer end 51414 to provide for additional support and sealing contact between the top mounting surface and the bottom mounting surface.

Figure 58D:
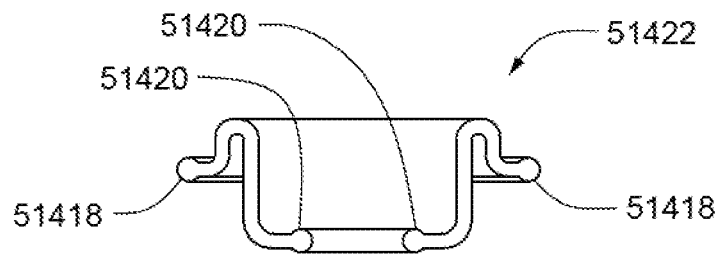
Figure 58E:
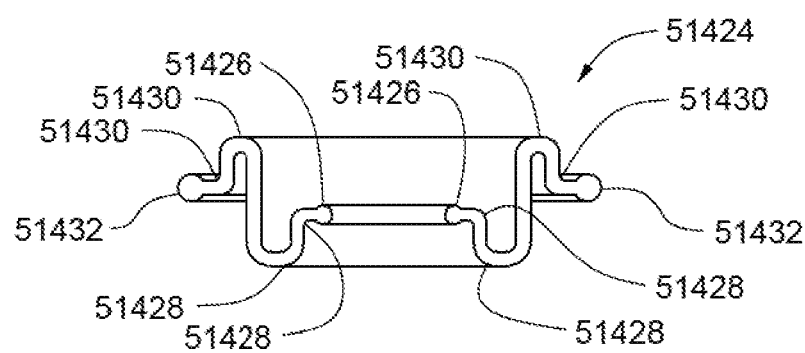

FIG. 58D shows another embodiment of the rolling diaphragm where rolling diaphragm 51422 includes a bead along an inner end 51420 thereof, so as to form an 'o-ring' type seal between a top seal piston and a bottom seal piston, and a bead along an outer end 51418 thereof, so as to form an 'o-ring' type seal between a bottom mounting surface and a top mounting surface. FIG. 58E shows another embodiment of the rolling diaphragm, wherein rolling diaphragm 51424 includes a plurality of bends 51428 leading up to beaded inner end 51426 to provide for additional support and sealing contact between the top seal piston and the bottom seal piston. Rolling diaphragm 51424 may also include a plurality of bends 51430 leading up to beaded outer end 51432 to provide for additional support and sealing contact between the top seal piston and the bottom seal piston.

Although FIGS. 58A through 58E depict various embodiments of the rolling diaphragm, it is to be understood that rolling diaphragms may be held in place by any other mechanical means known in the art.

Referring now to FIG. 59A, a cross section shows one embodiment of the rolling diaphragm embodiment. A metal bellows 51500 is positioned along a piston rod 51502 to seal off a crankcase (shown as 51304 in FIG. 57G) from a working space or airlock (shown as 51306 and 51312 in FIG. 57G). Metal bellows 51500 may be attached to a top seal piston 51504 and a stationary mounting surface 51506. Alternatively, metal bellows 51500 may be attached to a bottom seal piston (not shown), and a top stationary mounting surface. In one embodiment the bottom stationary mounting surface may be a crankcase surface or an inner airlock or working space surface, and the top stationary mounting surface may be an inner crankcase surface, or an outer airlock or working space surface. Metal bellows 51500 may be attached by welding, brazing, or any mechanical means known in the art.

FIGS. 59B-59G depict a perspective cross sectional view of various embodiments of the metal bellows, wherein the metal bellows is a welded metal bellows 51508. In some embodiments of the metal bellows, the metal bellows is preferably a micro-welded metal bellows. In some embodiments, the welded metal bellows 51508 includes a plurality of diaphragms 51510, which are welded to each other at either an inner end 51512 or an outer end 51514, as shown in FIGS. 59C and 59D. In some embodiments, diaphragms 51510 may be crescent shaped 51516, flat 51518, rippled 51520, or any other shape known in the art.

Additionally, the metal bellows may alternatively be formed mechanically by means such as die forming, hydroforming, explosive hydroforming, hydramolding, or any other means known in the art.

The metal bellows may be made of any type of metal, including but not limited to, steel, stainless steel, stainless steel 374, AM-350 stainless steel, Inconel, Hastelloy, Haynes, titanium, or any other high-strength, corrosion-resistant material.

In one embodiment, the metal bellows used are those available from Senior Aerospace Metal Bellows Division, Sharon, Mass., or American BOA, Inc., Cumming, Ga.

Rolling Diaphragm and/or Bellows Embodiments

Various embodiments of the rolling diaphragm and/or bellows, which function to seal, are described above. Further embodiments will be apparent to those of skill in the art based on the description above and the additional description below relating to the parameters of the rolling diaphragm and/or bellows.

In some embodiments, the pressure atop the rolling diaphragm or bellows, in the airlock space or airlock area (both terms are used interchangeably), is the mean-working-gas pressure for the machine, which, in some embodiments is an engine, while the pressure below the rolling diaphragm and/or bellows, in the crankcase area, is ambient/atmospheric pressure. In these embodiments, the rolling diaphragm and/or bellows is required to operate with as much as 3000 psi across it (and in some embodiments, up to 1500 psi or higher). In this case, the rolling diaphragm and/or bellows seal forms the working gas (helium, hydrogen, or otherwise) containment barrier for the machine (engine in the exemplary embodiment). Also, in these embodiments, the need for a heavy, pressure-rated, structural vessel to contain the bottom end of the engine is eliminated, since it is now required to simply contain lubricating fluid (oil is used as a lubricating fluid in the exemplary embodiment) and air at ambient pressure, like a conventional internal combustion ("IC") engine.

The capability to use a rolling diaphragm and/or bellows seal with such an extreme pressure across it depends on the interaction of several parameters. Referring now to FIG. 59H, an illustration of the actual load on the rolling diaphragm or bellows material is shown. As shown, the load is a function of the pressure differential and the annular gap area for the installed rolling diaphragm or bellows seal.

Region 1 represents the portions of the rolling diaphragm and/or bellows that are in contact with the walls formed by the piston and cylinder. The load is essentially a tensile load in the axial direction, due to the pressure differential across the rolling diaphragm and/or bellows. This tensile load due to the pressure across the rolling diaphragm and/or bellows can be expressed as:

$$L_t = P_d * A_a$$

Where
$L_t$=Tensile Load and
$P_d$=Pressure Differential
$A_a$=Annular Area
and $$A_a = p/4 * (D^2 - d^2)$$

Where
D=Cylinder Bore and
d=Piston Diameter

The tensile component of stress in the bellows material can be approximated as:

$$S_t = L_t / (p * (D+d) * t_b)$$

Which reduces to:

$$S_t = P_d / 4 * (D-d)/tb$$

Later, we will show the relationship of radius of convolution, $R_c$, to Cylinder bore (D) and Piston Diameter (d) to be defined as:

$$R_c = (D-d)/4$$

So, this formula for St reduces to its final form:

$$S_t = P_d * R_c / t_b$$

Where
$t_b$=thickness of bellows material

Still referring to FIG. 59H, Region 2 represents the convolution. As the rolling diaphragm and/or bellows material turns the corner, in the convolution, the hoop stress imposed on the rolling diaphragm and/or bellows material may be calculated. For the section of the bellows forming the convolution, the hoop component of stress can be closely approximated as:

$$S_h = P_d * R_c / t_b$$

The annular gap that the rolling diaphragm and/or bellows rolls within is generally referred to as the convolution area. The rolling diaphragm and/or bellows fatigue life is generally limited by the combined stress from both the tensile (and hoop) load, due to pressure differential, as well as the fatigue due to the bending as the fabric rolls through the convolution. The radius that the fabric takes on during this 'rolling' is defined here as the radius of convolution, Rc.

$$R_c = (D-d)/4$$

The bending stress, Sb, in the rolling diaphragm and/or bellows material as it rolls through the radius of convolution, Rc, is a function of that radius, as well as the thickness of the materials in bending. For a fiber-reinforced material, the stress in the fibers themselves (during the prescribed deflection in the exemplary embodiments) is reduced as the fiber diameter decreases. The lower resultant stress for the same level of bending allows for an increased fatigue life limit. As the fiber diameter is further reduced, flexibility to decrease the radius of convolution Rc is achieved, while keeping the bending stress in the fiber under its endurance limit. At the same time, as Rc decreases, the tensile load on the fabric is reduced since there is less unsupported area in the annulus between the piston and cylinder. The smaller the fiber diameter, the smaller the minimum Rc, the smaller the annular area, which results in a higher allowable pressure differential.

For bending around a prescribed radius, the bending moment is approximated by:

$$M = E * I / R$$

Where:
M=Bending Moment
E=Elastic Modulus
I=Moment of Inertia
R=Radius of Bend
Classical bending stress, $S_b$, is calculated as:

$$S_b = M * Y / I$$

Where:
Y=Distance above neutral axis of bending
Substituting yields:

$$S_b = (E * I / R) * Y / I$$

$$S_b = E * Y / R$$

Assuming bending is about a central neutral axis:

$$Y_{max} = t_b / 2$$

$$S_b = E * t_b / (2 * R)$$

In some embodiments, rolling diaphragm and/or bellows designs for high cycle life are based on geometry where the bending stress imposed is kept about one order of magnitude less than the pressure-based loading (hoop and axial stresses). Based on the equation: Sb=E*tb/(2*R), it is clear that minimizing tb in direct proportion to Rc should not increase the bending stress. The minimum thickness for the exemplary embodiments of the rolling diaphragm and/or bellows material or membrane is directly related to the minimum fiber diameter that is used in the reinforcement of the elastomer. The smaller the fibers used, the smaller resultant Rc for a given stress level.

Another limiting component of load on the rolling diaphragm and/or bellows is the hoop stress in the convolution (which is theoretically the same in magnitude as the axial load while supported by the piston or cylinder). The governing equation for that load is as follows:

$$Sh = Pd * Rc / tb$$

Thus, if Rc is decreased in direct proportion to tb, then there is no increase of stress on the membrane in this region. However, if this ratio is reduced in a manner that decreases Rc to a greater ratio than tb then parameters must be balanced. Thus, decreasing tb with respect to Rc requires the rolling diaphragm and/or bellows to carry a heavier stress due to pressure, but makes for a reduced stress level due to bending. The pressure-based load is essentially constant, so this may be favorable—since the bending load is cyclic, therefore it is the bending load component that ultimately limits fatigue life.

For bending stress reduction, tb ideally should be at a minimum, and Rc ideally should be at a maximum. E ideally is also at a minimum. For hoop stress reduction, Rc ideally is small, and tb ideally is large.

Thus, the critical parameters for the rolling diaphragm and/or bellows membrane material are:
 E, Elastic Modulus of the membrane material;
 tb, membrane thickness (and/or fiber diameter);
 Sut, Ultimate tensile strength of the rolling diaphragm and/or bellows; and
 Slcf, The limiting fatigue strength of the rolling diaphragm and/or bellows.

Thus, from E, tb and Sut, the minimum acceptable Rc may be calculated. Next, using Rc, Slcf, and tb, the maximum Pd may be calculates. Rc may be adjusted to shift the bias of load (stress) components between the steady state pressure stress and the cyclic bending stress. Thus, the ideal rolling diaphragm and/or bellows material is extremely thin, extremely strong in tension, and very limber in flexion.

Thus, in some embodiments, the rolling diaphragm and/or bellows material (sometimes referred to as a "membrane"), is made from carbon fiber nanotubes. However, additional small fiber materials may also be used, including, but not limited to nanotube fibers that have been braided, nanotube untwisted yarn fibers, or any other conventional materials, including but not limited to KEVLAR, glass, polyester, synthetic fibers and any other material or fiber having a desirable diameter and/or other desired parameters as described in detail above.

Piston Seals and Piston Rod Seals

Referring now to FIG. 57G, an embodiment of the machine is shown wherein an engine 51326, such as a Stirling cycle engine, includes at least one piston rod seal 51314, a piston seal 51324, and a piston guide ring 51322, (shown as 51616 in FIG. 60). Various embodiments of the piston seal 51324 and the piston guide ring 51322 are further discussed below, and in U.S. Patent Application Publication No. US 2003/0024387 A1 to Langenfeld et al., Feb. 6, 2003 (now abandoned), which, as mentioned before, is incorporated by reference.

FIG. 60 shows a partial cross section of the piston 51600, driven along the central axis 51602 of cylinder, or the cylinder 51604. The piston seal (shown as 51324 in FIG. 57G) may include a seal ring 51606, which provides a seal against the contact surface 51608 of the cylinder 51604. The contact surface 51608 is typically a hardened metal (preferably 58-62 RC) with a surface finish of 12 RMS or smoother. The contact surface 51608 may be metal which has been case hardened, such as 8260 hardened steel, which may be easily case hardened and may be ground and/or honed to achieve a desired finish. The piston seal may also include a backing ring 51610, which is sprung to provide a thrust force against the seal ring 51606 thereby providing sufficient contact pressure to ensure sealing around the entire outward surface of the seal ring 51606. The seal ring 51606 and the backing ring 51610 may together be referred to as a piston seal composite ring. In some embodiments, the at least one piston seal may seal off a warm portion of cylinder 51604 from a cold portion of cylinder 51604.

Referring now to FIG. 61, some embodiments include a piston rod seal (shown as 51314 in FIG. 57G) mounted in the piston rod cylinder wall 51700, which, in some embodiments, may include a seal ring 51706, which provides a seal against the contact surface 51708 of the piston rod 51604 (shown as 51302 in FIG. 57G). The contact surface 51708 in some embodiments is a hardened metal (preferably 58-62 RC) with a surface finish of 12 RMS or smoother. The contact surface 51708 may be metal which has been case hardened, such as 58260 hardened steel, which may be easily case hardened and may be ground and/or honed to achieve a desired finish. The piston seal may also include a backing ring 51710, which is sprung to provide a radial or hoop force against the seal ring 51706 thereby providing sufficient contact hoop stress to ensure sealing around the entire inward surface of seal ring 51706. The seal ring 51706 and the backing ring 51710 may together be referred to as a piston rod seal composite ring.

In some embodiments, the seal ring and the backing ring may be positioned on a piston rod, with the backing exerting an outward pressure on the seal ring, and the seal ring may come into contact with a piston rod cylinder wall 51702. These embodiments require a larger piston rod cylinder length than the previous embodiment. This is because the contact surface on the piston rod cylinder wall 51702 will be longer than in the previous embodiment, where the contact surface 51708 lies on the piston rod itself. In yet another embodiment, piston rod seals may be any functional seal known in the art including, but not limited to, an o-ring, a graphite clearance seal, graphite piston in a glass cylinder, or any air pot, or a spring energized lip seal. In some embodiments, anything having a close clearance may be used, in other embodiments, anything having interference, for example, a seal, is used. In the exemplary embodiment, a spring energized lip seal is used. Any spring energized lip seal may be used, including those made by BAL SEAL Engineering, Inc., Foothill Ranch, Calif. In some embodiments, the seal used is a BAL SEAL Part Number X558604.

The material of the seal rings 51606 and 51706 is chosen by considering a balance between the coefficient of friction of the seal rings 51606 and 51706 against the contact surfaces 51608 and 51708, respectively, and the wear on the seal rings 51606 and 51706 it engenders. In applications in which piston lubrication is not possible, such as at the high operating temperatures of a Stirling cycle engine, the use of engineering plastic rings is used. The embodiments of the composition include a nylon matrix loaded with a lubricating and wear-resistant material. Examples of such lubricating materials include PTFE/silicone, PTFE, graphite, etc. Examples of wear-resistant materials include glass fibers and carbon fibers. Examples of such engineering plastics are manufactured by LNP Engineering Plastics, Inc. of Exton, Pa. Backing rings 51610 and 51710 is preferably metal.

The fit between the seal rings 51606 and 51706 and the seal ring grooves 51612 and 51712, respectively, is preferably a clearance fit (about 0.002"), while the fit of the backing rings 51610 and 51710 is preferably a looser fit, of the order of about 0.005" in some embodiments. The seal rings 51606 and 51706 provide a pressure seal against the contact surfaces 51608 and 51708, respectively, and also one of the surfaces 51614 and 51714 of the seal ring grooves 51612 and 51712, respectively, depending on the direction of the pressure difference across the rings 51606 and 51706 and the direction of the piston 51600 or the piston rod 51704 travel.

FIGS. 62A and 62B show that if the backing ring 51820 is essentially circularly symmetrical, but for the gap 51800, it will assume, upon compression, an oval shape, as shown by the dashed backing ring 51802. The result may be an uneven radial or hoop force (depicted by arrows 51804) exerted on the seal ring (not shown, shown as 51606 and 51706 in FIGS. 60 and 61), and thus an uneven pressure of the seal rings against the contact surfaces (not shown, shown as 51608 and 51708 in FIGS. 60 and 61) respectively, causing uneven wear of the seal rings and in some cases, failure of the seals.

A solution to the problem of uneven radial or hoop force exerted by the piston seal backing ring 51820, in accordance with an embodiment, is a backing ring 51822 having a cross-section varying with circumferential displacement from the gap 51800, as shown in FIGS. 62C and 62D. A tapering of the width of the backing ring 51822 is shown from the position denoted by numeral 51806 to the position denoted by numeral 51808. Also shown in FIGS. 62C and 62D is a lap joint 51810 providing for circumferential closure of the seal ring 51606. As some seals will wear significantly over their lifetime, the backing ring 51822 should provide an even pressure (depicted by numeral 51904 in FIG. 63B) of a range of movement. The tapered backing ring 51822 shown in FIGS. 62C and 62D may provide this advantage.

FIGS. 63A and 63B illustrate another solution to the problem of uneven radial or hoop force of the piston seal ring against the piston cylinder, in accordance with some embodiments. As shown in FIG. 63A, backing ring 51910 is fashioned in an oval shape, so that upon compression within the cylinder, the ring assumes the circular shape shown by dashed backing ring 51902. A constant contact pressure between the seal ring and the cylinder contact surface may thus be provided by an even radial force 51904 of backing ring 51902, as shown in FIG. 63B.

A solution to the problem of uneven radial or hoop force exerted by the piston rod seal backing ring, in accordance with some embodiments, is a backing ring 51824 having a cross-section varying with circumferential displacement from gap 51812, as shown in FIGS. 62E and 62F. A tapering of the width of backing ring 51824 is shown from the position denoted by numeral 51814 to the position denoted by numeral 51816. Also shown in FIGS. 62E and 62F is a lap joint 51818 providing for circumferential closure of seal ring 51706. As some seals will wear significantly over their lifetime, backing ring 51824 should provide an even pressure (depicted by numeral 52004 in FIG. 64B) of a range of movement. The tapered backing ring 51824 shown in FIGS. 62E and 62F may provide this advantage.

FIGS. 64A and 64B illustrate another solution to the problem of uneven radial or hoop force of the piston rod seal ring against the piston rod contact surface, in accordance with some embodiments. As shown in FIG. 64A, backing ring (shown by dashed backing ring 52000) is fashioned as an oval shape, so that upon expansion within the cylinder, the ring assumes the circular shape shown by backing ring 52002. A constant contact pressure between the seal ring 51706 and the cylinder contact surface may thus be provided by an even radial thrust force 52004 of backing ring 52002, as shown in FIG. 64B.

Referring again to FIG. 60, at least one guide ring 51616 may also be provided, in accordance with some embodiments, for bearing any side load on piston 51600 as it moves up and down the cylinder 51604. Guide ring 51616 is also preferably fabricated from an engineering plastic material loaded with a lubricating material. A perspective view of guide ring 51616 is shown in FIG. 65. An overlapping joint 52100 is shown and may be diagonal to the central axis of guide ring 51616.

Lubricating Fluid Pump and Lubricating Fluid Passageways

Referring now to FIG. 66, a representative illustration of one embodiment of the engine 52200 for the machine is shown having a rocking beam drive 52202 and lubricating fluid 52204. In some embodiments, the lubricating fluid is oil. The lubricating fluid is used to lubricate engine parts in the crankcase 52206, such as hydrodynamic pressure fed lubricated bearings. Lubricating the moving parts of the engine 52200 serves to further reduce friction between engine parts and further increase engine efficiency and engine life. In some embodiments, lubricating fluid may be placed at the bottom of the engine, also known as an oil sump, and distributed throughout the crankcase. The lubricating fluid may be distributed to the different parts of the engine 52200 by way of a lubricating fluid pump, wherein the lubricating fluid pump may collect lubricating fluid from the sump via a filtered inlet. In the exemplary embodiment, the lubricating fluid is oil and thus, the lubricating fluid pump is herein referred to as an oil pump. However, the term "oil pump" is used only to describe the exemplary embodiment and other embodiments where oil is used as a lubricating fluid, and the term shall not be construed to limit the lubricating fluid or the lubricating fluid pump.

Referring now to FIGS. 67A and 67B, one embodiment of the engine is shown, wherein lubricating fluid is distributed to different parts of the engine 52200 that are located in the crankcase 52206 by a mechanical oil pump 52208. The oil pump 52208 may include a drive gear 52210 and an idle gear 52212. In some embodiments, the mechanical oil pump 52208 may be driven by a pump drive assembly. The pump drive assembly may include a drive shaft 52214 coupled to a drive gear 52210, wherein the drive shaft 52214 includes an intermediate gear 52216 thereon. The intermediate gear 52216 is preferably driven by a crankshaft gear 52220, wherein the crankshaft gear 52220 is coupled to the primary crankshaft 52218 of the engine 52200, as shown in FIG. 524. In this configuration, the crankshaft 52218 indirectly drives the mechanical oil pump 52208 via the crankshaft gear 52220, which drives the intermediate gear 52216 on the drive shaft 52214, which, in turn, drives the drive gear 52210 of the oil pump 52208.

The crankshaft gear 52220 may be positioned between the crankpins 52222 and 52224 of crankshaft 52218 in some embodiments, as shown in FIG. 68. In other embodiments, the crankshaft gear 52220 may be placed at an end of the crankshaft 52218, as shown in FIGS. 69A-69C.

For ease of manufacturing, the crankshaft 52218 may be composed of a plurality of pieces. In these embodiments, the crankshaft gear 52220 may be to be inserted between the crankshaft pieces during assembly of the crankshaft.

The drive shaft 52214, in some embodiments, may be positioned perpendicularly to the crankshaft 52218, as shown in FIGS. 67A and 69A. However, in some embodiments, the drive shaft 52214 may be positioned parallel to the crankshaft 52218, as shown in FIGS. 69B and 69C.

In some embodiments, the crankshaft gear 52234 and the intermediate gear 52232 may be sprockets, wherein the crankshaft gear 52234 and the intermediate gear 52232 are coupled by a chain 52226, as shown in FIGS. 69C and 70C. In such an embodiments, the chain 52226 is used to drive a chain drive pump (shown as 52600 in FIGS. 70A through 70C).

In some embodiments, the gear ratio between the crankshaft 52218 and the drive shaft 52214 remains constant throughout operation. In such an embodiment, it is important to have an appropriate gear ratio between the crankshaft and the drive shaft, such that the gear ratio balances the pump speed and the speed of the engine. This achieves a specified flow of lubricant required by a particular engine RPM (revolutions per minute) operating range.

In some embodiments, lubricating fluid is distributed to different parts of an engine by an electric pump. The electric pump eliminates the need for a pump drive assembly, which is otherwise required by a mechanical oil pump.

Referring back to FIGS. 67A and 67B, the oil pump 52208 may include an inlet 52228 to collect lubricating fluid from the sump and an outlet 52230 to deliver lubricating fluid to the various parts of the engine. In some embodiments, the rotation of the drive gear 52212 and the idle gear 52210 cause the lubricating fluid from the sump to be drawn into the oil pump through the inlet 52228 and forced out of the pump through the outlet 52230. The inlet 52228 preferably includes a filter to remove particulates that may be found in the lubricating fluid prior to its being drawn into the oil pump. In some embodiments, the inlet 52228 may be connected to the sump via a tube, pipe, or hose. In some embodiments, the inlet 52228 may be in direct fluid communication with the sump.

In some embodiments, the oil pump outlet 52230 is connected to a series of passageways in the various engine parts, through which the lubricating fluid is delivered to the various engine parts. The outlet 52230 may be integrated with the passageways so as to be in direct communication with the passageways, or may be connected to the passageways via a hose or tube, or a plurality of hoses or tubes. The series of passageways are preferably an interconnected network of passageways, so that the outlet 52230 may be connected to a single passageway inlet and still be able to deliver lubricating fluid to the engine's lubricated parts.

FIGS. 71A-71D show one embodiments, wherein the oil pump outlet (shown as 52230 in FIG. 67B) is connected to a passageway 52700 in the rocker shaft 52702 of the rocking beam drive 52704. The rocker shaft passageway 52700 delivers lubricating fluid to the rocker pivot bearings 52706, and is connected to and delivers lubricating fluid to the rocking beam passageways (not shown). The rocking beam passageways deliver lubricating fluid to the connecting wrist pin bearings 52708, the link rod bearings 52710, and the link rod passageways 52712. The link rod passageways 52712 deliver lubricating fluid to the piston rod coupling bearing 52714. The connecting rod passageway (not shown) of the connecting rod 52720 delivers lubricating fluid to a first crank pin 52722 and the crankshaft passageway 52724 of the crankshaft 52726. The crankshaft passageway 52724 delivers lubricating fluid to the crankshaft journal bearings 52728, the second crank pin bearing 52730, and the spline shaft passageway 52732. The spline shaft passageway 52732 delivers lubricating fluid to the spline shaft spline joints 52734 and 52736. The oil pump outlet (not shown, shown in FIG. 67B as 52230) in some embodiments is connected to the main feed 52740. In some embodiments, an oil pump outlet may also be connected to and provide lubricating fluid to the coupling joint linear bearings 52738. In some embodiments, an oil pump outlet may be connected to the linear bearings 52738 via a tube or hose, or plurality of tubes or hoses. Alternatively, the link rod passageways 52712 may deliver lubricating fluid to the linear bearings 52738.

Thus, the main feed 52740 delivers lubricating fluid to the journal bearings surfaces 52728. From the journal bearing surfaces 52728, the lubricating fluid is delivered to the crankshaft main passage. The crankshaft main passage delivers lubricating fluid to both the spline shaft passageway 52732 and the connecting rod bearing on the crank pin 52724.

Lubricating fluid is delivered back to the sump, preferably by flowing out of the aforementioned bearings and into the sump. In the sump, the lubricating fluid will be collected by the oil pump and redistributed throughout the engine.

Distribution

As described above, various embodiments of the system, methods and apparatus may advantageously provide a low-cost, easily maintained, highly efficient, portable, and fail-safe system that can provide a reliable source of drinking water for use in all environments regardless of initial water quality. The system is intended to produce a continuous stream of potable water, for drinking or medical applications, for example, on a personal or limited community scale using a portable power source and moderate power budget. As an example, in some embodiment, the water vapor distillation apparatus may be utilized to produce at least approximately 10 gallons of water per hour on a power budget of approximately 500 watts. This may be achieved through a very efficient heat transfer process and a number of sub-system design optimizations.

The various embodiments of the water vapor distillation apparatus may be powered by a battery, electricity source or by a generator, as described herein. The battery may be a stand alone battery or could be connected to a motor transport apparatus, such as a scooter, any other motor vehicle, which some cases may be a hybrid motor vehicle or a battery powered vehicle.

In one embodiment, the system may be used in the developing world or in a remote village or remote living quarters. The system is especially advantageous in communities with any one or more of the following, for example (but not by limitation): unsafe water of any kind at any time, little to no water technical expertise for installation, unreliable access to replacement supplies, limited access to maintenance and difficult operating environment.

The system acts to purify any input source and transform the input source to high-quality output, i.e., cleaner water. In some applications the water vapor distillation apparatus may be in a community that does not have any municipal infrastructure to provide source water. Thus, in these situations an embodiment of the water vapor distillation apparatus may be capable of accepting source water having varying qualities of purity.

The system is also easy to install and operate. The water vapor distillation apparatus is designed to be an autonomous system. This apparatus may operate independently without having to be monitored by operators. This is important because, in many of the locations where the water vapor distillation apparatus may be installed and or utilized, mechanics may be rare or unreliable.

The system has minimal maintenance requirement. In the exemplary embodiments, the system does not require any consumables and/or disposables, thus, the system itself may be utilized for a period of time absent replacing any elements or parts. This is important because in many applications the water vapor distillation apparatus may be located in a community that lacks people having technical expertise to maintain mechanical devices such as the water vapor distillation apparatus. The system is also inexpensive, making it an option for any community.

In addition, the water vapor distillation apparatus may be used in any community where clean drinking water is not readily or sufficiently available. For example, communities that have both a utility to provide electricity to operate the water vapor distillation device and municipal water to supply the apparatus.

Thus, the water vapor distillation apparatus may be used in communities that may have a utility grid for supply electricity but no clean drinking water. Conversely, the community may have municipal water that is not safe and no utility grid to supply electricity. In these applications, the water vapor distillation apparatus may be powered using devices including, but not limited to a Stirling engine, an internal combustion engine, a generator, batteries or solar panels. Sources of water may include but are not limited to local streams, rivers, lakes, ponds, or wells, as well as, the ocean.

In communities that have no infrastructure the challenge is to locate a water source and be able to supply power to operate the water vapor distillation apparatus. As previously discussed, the water vapor distillation apparatus may be power using several types of devices.

In this type of situation one likely place to install a water vapor distillation apparatus may be in the community clinic or health centers. These places typically have some form of power source and are accessible to the most members of the community.

Again, as described herein, sources of electricity may include a Stirling engine. This type of engine is well suited for application in the water machine because the engine provides a sufficient amount of electrical power to operate the machine without significantly affecting the size of the machine.

The water vapor distillation apparatus may supply approximately between 50 and 250 people per day with water. In the exemplary embodiment, the output is 30 liters per hour. This production rate is suitable for a small village or community's needs. The energy needs include approximately 900 Watts. Thus, the energy requirements are minimal to power the water vapor distillation apparatus. This low power requirement is suitable to a small/remote village or community. Also, in some embodiments, a standard outlet is suitable as the electrical source. The weight of the water vapor distillation apparatus is approximately 90 Kg, in the exemplary embodiment, and the size (H×D×W)—160 cm×50 cm×50 cm.

Knowledge of operating temperatures, TDS, and fluid flows provides information to allow production of potable water under a wide range of ambient temperatures, pressures, and dissolved solid content of the source water. One particular embodiment may utilize a control method whereby such measurements (T, P, TDS, flow rates, etc) are used in conjunction with a simple algorithm and look-up table allowing an operator or computer controller to set operating parameters for optimum performance under existing ambient conditions.

In some embodiments, the apparatus may be incorporated as part of a system for distributing water. Within this system may include a monitoring system. This monitoring system may include, but is not limited to having an input sensor for measuring one or more characteristics of the input to the generation device and an output sensor for measuring consumption or other characteristic of output from the generation device. The monitoring system may have a controller for concatenating measured input and consumption of output on the basis of the input and output sensors.

Where the generation device of a particular utility of a network is a water vapor distillation apparatus, the input sensor may be a flow rate monitor. Moreover, the output sensor may be a water quality sensor including one or more of torpidity, conductivity, and temperature sensors.

The monitoring system may also have a telemetry module for communicating measured input and output parameters to a remote site, either directly or via an intermediary device such as a satellite, and, moreover, the system may include a remote actuator for varying operating parameters of the generator based on remotely received instructions. The monitoring system may also have a self-locating device, such as a GPS receiver, having an output indicative of the location of the monitoring system. In that case, characteristics of the measured input and output may depend upon the location of the monitoring system.

The monitoring system described above may be included within a distributed network of utilities providing sources of purified water. The distributed network has devices for generating water using input sensors for measuring inputs to respective generators, output sensor for measuring consumption of output from respective generators, and a telemetry transmitter for transmitting input and output parameters of a specified generator. Finally, the distributed network may have a remote processor for receiving input and output parameters from a plurality of utility generators.

Referring now to FIG. 42, this figure depicts monitoring generation device 4202. Generation device 4202 may be a water vapor distillation apparatus as disclosed herein. Generation device 4202 may typically be characterized by a set of parameters that describe its current operating status and conditions. Such parameters may include, without limitation, its temperature, its input or output flux, etc., and may be subject to monitoring by means of sensors, as described in detail below.

Still referring to FIG. 42, source water enters the generation device 4202 at inlet 4204 and leaves the generation device at outlet 4206. The amount of source water 4208 entering generation device 4202 and the amount of purified water 4210 leaving generation device 4202 may be monitored through the use of one or more of a variety of sensors commonly used to determine flow rate, such as sensors for determining them temperature and pressure or a rotometer, located at inlet sensor module 4212 and/or at outlet sensor module 4214, either on a per event or cumulative basis. Additionally, the proper functioning of the generation device 4202 may be determined by measuring the turpidity, conductivity, and/or temperature at the outlet sensor module 4214 and/or the inlet sensor module 4212. Other parameters, such as system usage time or power consumption, either per event or cumulatively, may also be determined. A sensor may be coupled to an alarm or shut off switch that may be triggered when the sensor detects a value outside a pre-programmed range.

When the location of the system is known, either through direct input of the system location or by the use of a GPS location detector, additional water quality tests may be run based on location, including checks for known local water contaminates, utilizing a variety of detectors, such as antibody chip detectors or cell-based detectors. The water quality sensors may detect an amount of contaminates in water. The sensors may be programmed to sound an alarm if the water quality value rises above a pre-programmed water quality value. The water quality value is the measured amount of contaminates in the water. Alternatively, a shut off switch may turn off the generation device if the water quality value rises about a pre-programmed water quality value.

Further, scale build-up in the generation device 4202, if any, may be determined by a variety of methods, including monitoring the heat transfer properties of the system or measuring the flow impedance. A variety of other sensors may be used to monitor a variety of other system parameters.

Still referring to FIG. 42, the sensors described above may be used to monitor and/or record the various parameters described above onboard the generation device 4202, or in an alternative embodiment the generation device 4202 may be equipped with a communication system 4214, such as a cellular communication system. The communication system 4214 could be an internal system used solely for communication between the generation device 4202 and the monitoring station 4216. Alternatively, the communication system 4214 could be a cellular communication system that includes a cellular telephone for general communication through a cellular satellite system 4218. The communication system 4214 may also employ wireless technology such as the Bluetooth open specification. The communication system 4214 may additionally include a GPS (Global Positioning System) locator.

Still referring to FIG. 42, the communication system 4214 enables a variety of improvements to the generation device 4202, by enabling communication with a monitoring station 4216. For example, the monitoring station 4216 may monitor the location of the generation device 4202 to ensure that use in an intended location by an intended user. Additionally, the monitoring station 4216 may monitor the amount of water and/or electricity produced, which may allow the calculation of usage charges. Additionally, the determination of the amount of water and/or electricity produced during a certain period or the cumulative hours of usage during a certain period, allows for the calculation of a preventative maintenance schedule. If it is determined that a maintenance call is required, either by the calculation of usage or by the output of any of the sensors used to determine water quality, the monitoring station 4216 may arrange for a maintenance visit. In the case that a GPS (Global Positioning System) locator is in use, monitoring station 4216 may determine the precise location of the generation device 4202 to better facilitate a maintenance visit. The monitoring station 4216 may also determine which water quality or other tests are most appropriate for the present location of the generation device 4202. The communication system 4214 may also be used to turn the generation device 4202 on or off, to pre-heat the device prior to use, or to deactivate the system in the event the system is relocated without advance warning, such as in the event of theft.

Now referring to FIG. 43, the use of the monitoring and communication system described above facilitates the use of a variety of utility distribution systems. An organization 43, such as a Government agency, non-governmental agency (NGO), or privately funded relief organization, a corporation, or a combination of these, could provide distributed utilities, such as safe drinking water or electricity, to a geographical or political area, such as an entire country. The organization 43 may then establish local distributors 44A, 44B, and 44C. These local distributors could preferably be a monitoring station 4216 (See FIG. 42) previously described. In one possible arrangement, organization 43 could provide some number of generation devices 4202 (See FIG. 42) to the local distributor 44, etc. In another possible arrangement, the organization 43 could sell, loan, or make other financial arrangements for the distribution of the generation devices 4202 (See FIG. 42). The local distributor 44, etc. could then either give these generation devices to operators 45, etc., or provide the generation devices 4202 (See FIG. 42) to the operators though some type of financial arrangement, such as a sale or micro-loan.

Still referring to FIG. 43, the operator 45 could then provide distributed utilities to a village center, school, hospital, or other group at or near the point of water access. In one exemplary embodiment, when the generation device 4202 (See FIG. 42) is provided to the operator 45 by means of a micro-loan, the operator 45 could charge the end users on a per-unit bases, such as per watt hour in the case of electricity or per liter in the case of purified water. Either the local distributor 44 or the organization 43 may monitor usage and other parameters using one of the communication systems described above. The distributor 44 or the organization 43 could then recoup some of the cost of the generation device 45 (See FIG. 42) or effect repayment of the micro-loan by charging the operator 4312 for some portion of the per-unit charges, such as 50%. The communication systems described additionally may be used to deactivate the generation device 4202 (See FIG. 42) if the generation device is relocated outside of a pre-set area or if payments are not made in a timely manner. This type of a distribution system may allow the distribution of needed utilities across a significant area quickly, while then allowing for at least the partial recoupment of funds, which, for example, could then be used to develop a similar system in another area.

Now referring to FIG. 44, this figure illustrates a conceptual flow diagram of one possible way to incorporate an alternate embodiment of the water vapor distillation apparatus into a system. In an embodiment of this type, fluid flows through the system from an intake 4404 into an exchanger 4406 wherein exchanger 4406 receives heat from at least one of a plurality of sources including a condenser 4402, a head 4408, and exhaust (not shown) from a power source such as an internal or external combustion engine. Fluid continues flowing past heat exchanger 4406 into a sump 4410 and into a core 4412 in thermal contact with condenser 4402. In the core 4412, the fluid is partially vaporized. From core 4412, the vapor path proceeds into head 4408 in communication with a compressor 4414, and from there into condenser 4402. After the vapor has condensed, fluid proceeds from condenser 4402 through heat exchanger 4406, and finally into an exhaust region 4416 and then out as final distilled product.

Referring to FIGS. 44 and 44A, a power source 4418 may be used to power the overall system. Power source 4418 may be coupled to a motor (not shown) that is used to drive compressor 4414, particularly when compressor 4414 is a steam pump, such as a liquid ring pump or a regenerative blower. The power source 4418 may also be used to provide electrical energy to the other elements of the apparatus shown in FIG. 44. Power source 4418 may be, for example, an electrical outlet, a standard internal combustion (IC) generator or an external combustion generator. In one exemplary embodiment, the power source is a Stirling cycle engine. An IC generator and an external combustion generator advantageously produce both power and thermal energy as shown in FIG. 44A, where engine 4420 produces both mechanical and thermal energy. Engine 4420 may be either an internal combustion engine or an external combustion engine. A generator 4422, such as a permanent magnet brushless motor, is coupled to a crankshaft of the engine 4420 and converts the mechanical energy produced by the engine 4420 to electrical energy, such as power 4424. Engine 4420 also produces exhaust gases 4426 and heat 4428. The thermal energy produced by the engine 4420 in the form of exhaust gas 4426 and heat 4428 may be advantageously used to provide heat to the system.

Referring to FIG. 44, heat from a power source 4418 may be recaptured by channeling the exhaust into the insulated cavity that surrounds the apparatus, which may lie between external housing and the individual apparatus components. In one embodiment, exhaust may blow across a finned heat exchanger that heats source fluid prior to entering the evaporator/condenser 4402. In other embodiments, the source fluid flows past a tube-in-tube heat exchanger as described above with reference to the exemplary embodiment.

Referring now to FIG. 72A, one embodiment of the system is shown. The system includes two basic functional components that may be combined within a single integral unit or may be capable of separate operation and coupled as described herein for the purpose of local water purification. FIG. 72A depicts an of the system in which a power unit 528010 is coupled electrically, via cable 528014, to provide electrical power to a water vapor distillation apparatus 528012, with exhaust gas from the power unit 528010 coupled to convey heat to the water distillation unit 528012 via an exhaust duct 528016.

In the exemplary embodiment, the power unit 528010 is a Stirling cycle engine. The Stirling cycle engine may be any of the embodiments described herein. Thermal cycle engines are limited, by second law of thermodynamics, to a fractional efficiency, i.e., a Carnot efficiency of (TH−TC)/TH, where TH and TC are the temperatures of the available heat source and ambient thermal background, respectively. During the compression phase of a heat engine cycle, heat must be exhausted from the system in a manner not entirely reversible, thus there will always be a surfeit of exhaust heat. More significantly, moreover, not all the heat provided during the expansion phase of the heat engine cycle is coupled into the working fluid. Here, too, exhaust heat is generated that may be used advantageously for other purposes. The total heat thermodynamically available (i.e., in gas hotter than the ambient environment) in the burner exhaust is typically on the order of 10% of the total input power. For a power unit delivering on the order of a kilowatt of electrical power, as much as 700 W of heat may be available in an exhaust stream of gas at temperatures in the vicinity of 200° C. In accordance with embodiments of the present apparatus, system and methods, the exhaust heat, as well as the electrical power generated by an engine-powered generator, are used in the purification of water for human consumption, thereby advantageously providing an integrated system to which only raw water and a fuel need be provided.

Moreover, external combustion engines, such as Stirling cycle engines, are capable of providing high thermal efficiency and low emission of pollutants, when such methods are employed as efficient pumping of oxidant (typically, air, and, referred to herein and in any appended claims, without limitation, as "air") through the burner to provide combustion, and the recovery of hot exhaust leaving the heater head. In many applications, air is pre-heated, prior to combustion, nearly to the temperature of the heater head, so as to achieve the stated objectives of thermal efficiency. However, the high temperature of preheated air, desirable for achieving high thermal efficiency, complicates achieving low-emission goals by making it difficult to premix the fuel and air and by requiring large amounts of excess air in order to limit the flame temperature. Technology directed toward overcoming these difficulties in order to achieve efficient and low-emission operation of thermal engines is described, for example, in U.S. Pat. No. 6,062,023 (Kerwin, et al.) issued May 16, 2000, and incorporated herein by reference.

External combustion engines are, additionally, conducive to the use of a wide variety of fuels, including those most available under particular local circumstances; however the teachings of the present description are not limited to such engines, and internal combustion engines are also within the scope of the current disclosure. Internal combustion engines, however, impose difficulties due to the typically polluted nature of the exhausted gases, and external combustion engines are preferably employed.

Still referring to FIG. 72A, an embodiment of a power unit 528010 is shown schematically in FIG. 72B. Power unit 528010 includes an external combustion engine 528101 coupled to a generator 528102. In an exemplary embodiment, the external combustion engine 528101 is a Stirling cycle engine. The outputs of the Stirling cycle engine 528101 during operation include both mechanical energy and residual heat energy. Heat produced in the combustion of a fuel in a burner 528104 is applied as an input to the Stirling cycle engine 528101, and partially converted to mechanical energy. The unconverted heat or thermal energy accounts for approximately 65 to 85% of the energy released in the burner 528104. The ranges given herein are approximations and the ranges may vary depending on the embodiment of water vapor distillation apparatus used in the system and the embodiment of the Stirling engine (or other generator) used in the system.

This heat is available to provide heating to the local environment around the power unit 528110 in two forms: a smaller flow of exhaust gas from the burner 528104 and a much larger flow of heat rejected at the cooler 528103 of the Stirling engine. Power unit 528110 may also be referred to as an auxiliary power unit (APU). The exhaust gases are relatively hot, typically 100 to 300° C., and represent 10 to 20% of the thermal energy produced by the Stirling engine 528101. The cooler rejects 80 to 90% of the thermal energy at 10 to 20° C. above the ambient temperature. The heat is rejected to either a flow of water or, more typically, to the air via a radiator 528107. Stirling cycle engine 528101 is preferably of a size such that power unit 528010 is transportable.

As shown in FIG. 72B, Stirling engine 528101 is powered directly by a heat source such as burner 528104. Burner 528104 combusts a fuel to produce hot exhaust gases which are used to drive the Stirling engine 528101. A burner control unit 528109 is coupled to the burner 528104 and a fuel canister 528110. Burner control unit 528109 delivers a fuel from the fuel canister 528110 to the burner 528104. The burner controller 528109 also delivers a measured amount of air to the burner 528104 to advantageously ensure substantially complete combustion. The fuel combusted by burner 528104 is preferably a clean burning and commercially available fuel such as propane. A clean burning fuel is a fuel that does not contain large amounts of contaminants, the most important being sulfur. Natural gas, ethane, propane, butane, ethanol, methanol and liquefied petroleum gas ("LPG") are all clean burning fuels when the contaminants are limited to a few percent. One example of a commercially available propane fuel is HD-5, an industry grade defined by the Society of Automotive Engineers and available from Bernzomatic. In accordance with an embodiment of the system, and as discussed in more detail below, the Stirling engine 528101 and burner 528104 provide substantially complete combustion in order to provide high thermal efficiency as well as low emissions. The characteristics of high efficiency and low emissions may advantageously allow use of power unit 528010 indoors.

Generator 528102 is coupled to a crankshaft (not shown) of Stirling engine 528101. It should be understood to one of ordinary skill in the art that the term generator encompasses the class of electric machines such as generators wherein mechanical energy is converted to electrical energy or motors wherein electrical energy is converted to mechanical energy. The generator 528102 is preferably a permanent magnet brushless motor. A rechargeable battery 528113 provides starting power for the power unit 528010 as well as direct current ("DC") power to a DC power output 528112. In a further embodiment, APU 528010 also advantageously provides alternating current ("AC") power to an AC power output 528114. An inverter 528116 is coupled to the battery 528113 in order to convert the DC power produced by battery 528113 to AC power. In the embodiment shown in FIG. 72B, the battery 528113, inverter 528116 and AC power output 528114 are disposed within an enclosure 528120.

Utilization of the exhaust gas generated in the operation of power unit 528010 is now described with reference to the schematic depiction of an embodiment of the system shown in FIG. 72C. Burner exhaust is directed through a heat conduit 528016 into enclosure 528504 of the water vapor distillation apparatus unit designated generally by numeral 528012. Heat conduit 528016 is preferably a hose that may be plastic or corrugated metal surrounded by insulation, however all means of conveying exhaust heat from power unit 528010 to water purification unit 528012 are within the scope of the system. The exhaust gas, designated by arrow 528502, blows across a heat exchanger 528506 (in the exemplary embodiment, a hose-in-hose heat exchanger is used, in other embodiments, a finned heat exchanger is used), thereby heating the source water stream 528508 as it travels to the water vapor distillation (which is also referred to herein as a "still") evaporator 528510. The hot gas 528512 that fills the volume surrounded by insulated enclosure 528504 essentially removes all thermal loss from the still system since the gas temperature within the insulated cavity is hotter than surface 528514 of the still itself. Thus, there is substantially no heat flow from the still to the ambient environment, and losses on the order of 75 W for a still of 10 gallon/hour capacity are thereby recovered. A microswitch 528518 senses the connection of hose 528016 coupling hot exhaust to purification unit 528012 so that operation of the unit may account for the influx of hot gas.

In accordance with alternate embodiments adding heat to exhaust stream 528502 is within the scope of the system, whether through addition of a post-burner (not shown) or using electrical power for ohmic heating.

During initial startup of the system, power unit 528010 is activated, providing both electrical power and hot exhaust. Warm-up of the still 528012 is significantly accelerated since the heat exchanger 528506 is initially below the dew point of the moisture content of the exhaust, since the exhaust contains water as a primary combustion product. The heat of vaporization of this water content is available to heat source water as the water condenses on the fins of the heat exchanger. The heat of vaporization supplements heating of the heat exchanger by convection of hot gas within the still cavity. For example, in the fin heat exchanger embodiment, heating of the fins by convection continues even after the fins reach the dew point of the exhaust.

In accordance with other embodiments of the system, power unit 528010 and still 528012 may be further integrated by streaming water from the still through the power unit for cooling purposes. The use of source water for cooling presents problems due to the untreated nature of the water. Whereas using the product water requires an added complexity of the system to allow for cooling of the power unit before the still has warmed up to full operating conditions.

Referring again to FIG. 44, other embodiments may include the use of additives in solid form, wherein such additives could be embedded in a time-release matrix inserted into the flow-through channel of intake 4404. In one particular embodiment, replacement additive would need to be inserted periodically by the user. In yet another embodiment, a powder form of an additive could be added in a batch system wherein the powder is added, for example in tablet form, to an external reservoir containing water to be purified wherein the additive is uniformly mixed, similar to the batch system for adding liquid additives described above.

Still referring to FIG. 44, pre-treatment of the source water may occur prior to or within intake 4404. Pre-treatment operations may include, but is not limited to gross-filtering; treatment with chemical additives such as polyphosphates, polyacetates, organic acids, or polyaspartates; and electrochemical treatment such as an oscillating magnetic field or an electrical current; degassing; and UV treatment. Additives may be added in liquid form to the incoming liquid stream using a continuous pumping mechanism such as a roller pump or pulsatile pump, including a standard diaphragm pump or piezoelectric diaphragm pump. Alternatively, the additives may be added by a semi-continuous mechanism using, for example, a syringe pump, which would require a re-load cycle, or a batch pumping system, wherein a small volume of the additive would be pumped into a holding volume or reservoir external to the system that uniformly mixes the additive with the liquid before the liquid flows into the system. It is also envisioned that the user could simply drop a prescribed volume of the additive into, for example, a bucket containing the liquid to be purified. Liquid additive may be loaded as either a lifetime quantity (i.e., no consumables for the life of the machine), or as a disposable amount requiring re-loading after consumption.

Still referring to FIG. 44, similarly post-treatment of the product water may occur preferably within an external output region (not shown). Post-treatment operations may include, but is not limit to taste additives such as sugar-based additives for sweetening, acids for tartness, and minerals. Other additives, including nutrients, vitamins, stabilized proteins such as creatinine, and fats, and sugars may also be added. Such additives may be added either in liquid or solid form, whether as a time-release tablet through which the output liquid flows or a powder added to an external reservoir such as through a batch system. Alternatively, the additive may be added to the output liquid via an internal coating of a separate collection reservoir or container, for example, by leaching or dissolution on contact. In such embodiments, the ability to detect purified liquid with and without the additive may be preferred. Detection systems in accordance with various embodiments include pH analysis, conductivity and hardness analysis, or other standard electrical-based assays. Such detection systems allow for replacement of additives, as needed, by triggering a signal mechanism when the additive level/quantity is below a pre-set level, or is undetectable.

In another embodiment, liquid characteristics, such as for example water hardness, is monitored in the output and may be coupled with an indicator mechanism which signals that it is preferable to add appropriate additives.

In yet another embodiment, ozone is systemically generated using, for example, electric current or discharge methods, and added to the output product for improved taste. Alternatively, air may be pumped through a HEPA filter bubbling through the product water to improve palatability of the water.

Similarly, it is envisioned that other embodiments may include means for detecting nucleic acids, antigens and bio-organisms such as bacteria. Examples of such detection means include nanoscale chemistry and biochemistry microarrays known in the field and currently commercially available. Such arrays may also be used to monitor the presence and/or absence of nutrients and other additives in the purified product, as discussed above.

In another embodiment, UV treatment may be used post-purification, for example in a storage barrel or other container, to aid in maintenance of the purified product.

Referring again to FIG. 73, in various embodiments, the apparatus 100 may include at least one product conductivity cell 7304. In various embodiments, the product conductivity cell 7304 may be located in the product line downstream of the liquid heat exchanger and prior to the valve manifold. As described in more detail above, the conductivity of the product may be used in one or more control systems of the apparatus. The resulting readings and/or signals of the product conductivity cell 7304 may, in some embodiments, be communicated to at least one conductivity meter (not shown) and the meter may determine the conductivity and display one or more indications on the outside of the apparatus, i.e., such that user's of the system may monitor and/or determine same. In various other embodiments, the signals from the product conductivity cell 7304 are sent to the controller to be used for one or more control systems and/or methods for the apparatus. In some embodiments, the signals from the product conductivity cell 7304 may be sent both to the conductivity meter and to the controller. In some embodiments, in addition, the signals may be sent to one or more additional receiving devices including, but not limited to, a remote device and/or remote user interface and/or remote computer. In some embodiments, the conductivity and/or information related thereto may be both displayed on the outside of the apparatus as well as used by the controller. In some embodiments, the outside display may include, but is not limited to, one or more of the following displays: numbers (e.g., values), words, one or more colored light indicators and/or one or more symbols that may indicate one or more conditions to a user/viewer, wherein condition may include, but are not limited to, one or more of the following: condition of the apparatus and/or condition of the product.

In some embodiments, the signals from the product conductivity cell 7304 are correlated to determine the quality of product. Depending on the determined quality of the product, the product may either be diverted or will be actual product. For example, where the product does not meet a minimum threshold for quality, the product will be diverted and/or dumped and not progress to actual product. In some embodiments, the threshold may be 20 microsiemens and, for example, where the product exceeds 20 microsiemens per centimeter squared, the product is diverted. However, in various embodiments, the threshold may be higher or lower than 20 microsiemens.

In some embodiments, the conductivity meter is any conductivity meter known in the art including, but not limited to, a CDTX-90-1P made by Omega, Delaware, U.S.A. In some embodiments, the product conductivity cell 7304 may be any product conductivity cell known in the art including, but not limited to, a CDCE-90-001 made by Omega, Delaware, U.S.A. In various embodiments, the probe of the product conductivity cell 7304 is located such that it is in contact with the product in the fluid line, i.e., within the fluid pathway.

In various embodiments, the apparatus may include at least one control board wherein the various components, as described herein, are electrically connected such that a processor may control the system In various embodiments, the apparatus may include at least one current transducer. In some embodiments, at least one current transducer may be connected to the control board and at the inlet/main power of the apparatus. The at least one current transducer may measure the current usage of the total system. Using the current usage, the system may determine the relative condition of the system, for example, but not limited to, calculating changes in power usage and/or, whether the power usage exceeded a maximum threshold or is below a minimum threshold. However, in various embodiments, the system may determine the relative condition of the system using the at least one current transducer signals in one or more various calculations and/or in some embodiments a user may determine the relative condition of the system using the at least one current transducer system log. In some embodiments, the system may, to run a system test, actuate all of the components of the system and determine the power consumption. In some embodiments, any current transducer known in the art may be used, for example, the CR4110-15 made by CR Magnetics, St. Louis, Mo., U.S.A.

Controls

In some embodiments, the system includes at least two processors, a motor control engine processor ("MCE") and an ARM control processor. In various embodiments, the control system controls the production of product in the apparatus 100. The source fills the sump and the source is heated to produce steam. The steam temperature is maintained through the controls system controlling the heater and the vent valve. In some embodiments, both the product and blowdown flow to holding tanks. The product level is controlled by changing the duty cycle on the product and product divert valve duty cycles. The blowdown level is maintained, in some embodiments, by two controllers. The blowdown controller maintains its target level through adjusting the blowdown valve. The source controller also works to maintain the blowdown level. The source controller set point/target is higher, in some embodiments, than the blowdown controller set point/target. The source controller adjusts the source valve duty cycle. Maintaining the source controller set point/target higher than the blowdown set point provides continuous feeding of at least a volume of source water into the apparatus 100.

Referring also to FIG. 75, an overview of the states 7500 of the water vapor distillation apparatus is shown. The main control system of the device controls each state. Although various other embodiments may be used, for illustration purposes, one example of an embodiment of the various states 7500 of the main control system is described below. However, in various other embodiments, additional states may be used and/or the order of states may be different as well as the targets/thresholds, etc., that are given for illustration purposes. Additionally, the names given for each states are for illustration purposes and other names may be used in various embodiments.

Process

When the water system starts 7502, the apparatus 100 is in the idle 7504 state. In the idle 7504 state, all controllers are turned to "off" and the apparatus is not heating. When the user presses the button to start the system it goes into the fill 7506 state. The fill 7506 state opens the source valve allowing source water to fill the sump and overflow into the blow down tank and product tank if needed. Thus, the fill 7506 state ensures that the sump is full before the system begins to heat. Once the desired level is reached in the blow down and product tanks the system enters the heat 7508 state. In the heat 7508 state, the heater in the sump is maximized to its highest state and the controller waits until the temperature rises to an appropriate/predetermined/desired value, which, in some embodiments, may be about 100° C., and in some embodiments, may be 105° C. However, in various other embodiments, may be higher or lower than 105° C. Once the low pressure steam temperature, high pressure steam temperature and sump temperatures, reach the appropriate/predetermined/desired temperatures which, in some embodiments may be 105° C., 105° C., and 103° C., respectively, the system goes into the heat exchanger prime 7510 state.

The heat exchanger prime 7510 state controls the levels on the product and the blow down level sensors and waits for the temperature to rise to a higher degree. In some embodiments, in the heat exchanger prime 7510 state, the source valve is opened to a predetermine/fixed duty cycle, e.g., 5%, which, in various embodiments, may be higher or lower than 5%. In some embodiments, the blow down is controlled to, e.g., 50%. Thus, in various embodiments, source water moving into the system/machine becomes steam by opening the source valve and some water becomes blow down. In various embodiments, the blow down level is maintained, e.g., at 50%, by controlling the duty cycle of the valve. In the heat exchanger prime 7510 state, the heater is maintained on and is maximized, in some embodiments, to its highest state. Also, in heat exchanger prime 7510 state, source water moves into the system/machine and the blow down and product controllers are actuated/initiated/activated.

The low pressure steam temperature, high pressure steam temperature, sump temperature and motor temperature are monitored. Once the low pressure steam temperature, high pressure steam temperature, sump temperature and motor temperature reach the appropriate/predetermined/desired temperatures, which, in some embodiments, may be greater than or equal to 112° C., greater than or equal to 112° C., greater than or equal to 110° C. and greater than or equal to 90° C., respectively, and the product level is greater than or equal to the minimum start level, which serves to ensure that there is some product water being generated/producing, the system goes into the start pump 7512 state.

In start pump 7512 state the bearing feed pump is commanded to run at a designated/predetermined speed. Also, in the start pump 7512 state, the blower motor is started, which starts the impeller spinning. Also, during the start pump 7512 state, in some embodiments, the vent valve is actuated at a predetermined value, for example, for example, a predetermined value, in some embodiments, is anywhere between 50-100%. This acts to vent any contained gasses that have accumulated in the condenser, of the evaporator/condenser, space. In some embodiments, it is beneficial to remove these from the system. Thus, during start pump 7512 state, the vent valve is held anywhere between 50-100%, in various embodiments, for the duration of the start pump 7512 state.

Once the impeller reaches speed (predetermined speed) and once the blow down tank level reaches the correct level and the reported motor speed is within a "MotorErrorSpeed" (e.g., a predetermined speed that may vary in various embodiments) rpm of the commanded speed the system enters the run 7514 state. During the run 7514 state, the apparatus is producing product water.

During the run 7514 state the source valve and the blow down valve controllers maintain the system/machine with a threshold amount of source water entering, blow down and product water exiting. This ensures that the system/machine does not flood or dry out. The controllers maintain this level by actuating the source valve and the blow down valve.

Also, during run 7514 state, the low pressure steam temperature is monitored and held at a predetermined temperature, which, in some embodiments may be about 111.5° C. The low steam pressure temperature is maintained, in some embodiments, at the predetermined temperature by actuating the sump heater if the temperature falls below the predetermined. If the temperature is above the predetermined temperature, e.g. in some embodiments, 111.5° C., the vent valve may be actuated/opened. A heater controller and a vent valve controller controls the vent valve duty cycle and both the heater controller and a vent valve controller monitor the low pressure steam temperature. Thus, they the heater controller and a vent valve controller are controlled by the low pressure steam temperature.

In various embodiments, a minimum vent valve duty cycle is maintained. In some embodiments, if the temperature increases above a predetermined threshold, the vent duty cycle is increased to above the minimum vent valve duty cycle. This maintains a vent of gasses out of the condenser of the evaporator/condenser.

The product valve duty cycle controls the product level by receiving the product sensor readings. In various embodiments, the product valve duty cycle works to maintain the product level at a predetermined level, which, in some embodiments, may be 50% of the product level sensor. The product level is controlled by actuating the product valve, i.e., by opening or closing the product valve more or less to increase or decrease the product level.

From the run 7514 state the system will go into the flow measurement 7518 state every "FlowCheckTime" seconds (e.g., a predetermined amount of time, i.e., seconds, that may vary in various embodiments) which may be referred to as the count to flowcheck time 7516. During this state, the control system determines both the product flow rate and the blow down rate. Once the count to flowcheck time 7516 has been met, the flow measurement 7518 is taken.

With respect to the product flow rate, the flow measurement 7518 state includes emptying a product collection container to a certain level and then proceed to a product fill state which closes the empty process and determines the amount of time it takes to fill the contained back to a preset value (e.g., to measure the amount of product the apparatus is producing in a given amount of time). In some embodiments, if the production rate/flow rate drops below a preset/predetermined/threshold value, or if the production rate/flow rate exceeds a preset/predetermined/threshold value, the system may alert the user. In some embodiments, if the product flow rate is less than 350 ml/min, a low production system warning may register to the controller. This low production system warning may be cleared, in some embodiments, once the product flow rate is greater than 350 ml/. In some embodiments, a warning does not necessarily stop the system, but in other embodiments, a warning may stop the system. After the flow measurement 7518 is taken the system reverts to the run 7414 state.

With respect to the blow down flow rate, the flow measurement 7518 state includes emptying a blow down collection container to a certain level and then proceed to a blow down fill state which closes the empty process and determines the amount of time it takes to fill the contained back to a preset value (e.g., to measure the amount of product the apparatus is producing in a given amount of time). In some embodiments, if the production rate/flow rate drops below a preset/predetermined/threshold value, or if the production rate/flow rate exceeds a preset/predetermined/threshold value, the system may alert the user. In some embodiments, if the blow down flow rate is less than 35%, the system will transition to blow down full state and if using external tanks/container/holding tanks, transition to idle 7504 state. If the blow down flow rate is greater than 50%, the system will calculate blow down flow and calculate the average flow and if using external tanks/container/holding tanks, transition to idle 7504 state. After the flow measurement 7518 is taken the system reverts to the run 7414 state. The blowdown flow rate may be adjusted The system will stay in the run 7514 state until the user button is pressed 7520. The system will then go into the standby 7522 state. In the standby 7522 state the motor is turned off but the heater maintains predetermined low pressure steam temperature of, in some embodiments, about 112.5° C., however, in other embodiments, the heater may maintain a low pressure steam temperature of less than 112.5° C. or greater than 112.5° C. In the standby 7522 state, the system maintains the system in a warm state and controls the source water flow but the blower is not running. In some embodiments, the system, in the standby 7522 state actuates the source valve at a low duty cycle and maintains the blow down flow. Maintaining the temperature at about 112.5° C. (or the predetermined temperature, which may be greater or less than 112.5° C.) maintains the system in a boiling then condensing cycle. Where the apparatus is attached to a product water holding tank, which in some embodiments may include a product level sensor, when the level sensor signals indicate to the processor that the tank is full, the controller puts the system into standby 7522 state.

From the standby 7522 state a short (e.g., less than 3 second) button press will revert the system to idle 7504 state. A button press longer than e.g., 3 seconds, will revert the system to the heat exchanger prime 7510 state. Pressing the user button for less than e.g., 3 seconds in any state but standby 7522 will take the system back to the idle 7504 state. Any system fault detected will take the system to the idle 7504 state. Recoverable system faults will attempt to restart the process once the fault state is cleared. However, as stated above, the order of steps, the times given, the button presses, etc., may vary in various embodiments are given here as examples.

The control system includes various tasks running on the processor. The various tasks communicate one to another through a shared memory block, i.e., registers that get written and read by the various tasks.

Events

In various embodiments, one or more events or conditions of the apparatus/system may cause action by the control system. The following are various events; one or more may cause action by the control system in various embodiments. In various embodiments, the event may vary and the values given may vary through various embodiments. The examples below are given as exemplary embodiments; however, the values may vary in various embodiments.

Button presses. While the UI button is being pressed a loop counter is being incremented. On button release the counter is checked. If the button is held more than 4 counts (0.2 Sec.) a short button press is signaled. If the button is held more than 40 counts (2 Sec.) a long button press is signaled.

Error Signal. If a system error has been set and the water state machine is not in the idle state an error is signaled.

RESTART Signal. In some embodiments, this is a Signal to restart the system after an error.

FRAME_TICK sig. Sent on each 50 mSec. timer tick. Used for timing and checking for events.

In some embodiments, various events may not be signaled to the state machine, however, they may be checked by a handler and handled there.

SPILL event. Once the system/machine is activated, but before the system/machine begins to run, the controller first determines whether there is sufficient water in the system to enter the heat state. Thus, in the full state, this is a confirmation to ensure there is sufficient water to start the heater. In some embodiments, for example, if the blow down tank level is greater than the fill set point and the product level is greater than 30%, then the SPILL event is handled. The default fill set point is 90% in some embodiments. The spill event is only checked in some embodiments in the Fill 7506 state HOT event. The HOT event is the transition from the heat state to the heat exchanger prime state. In some embodiments, if the low pressure steam temperature is greater than the heat exit temperature and the high pressure steam temperature is greater than the heat exit temperature and the sump temperature is greater than the heat exit temp minus a predetermine amount, e.g. 2° C., then the HOT event is signaled. In some embodiments, the hot event is only checked for in the Heat 7508 state. In some embodiments, the default heat exit temp is 105° C. However, in various other embodiments, these temperatures may vary.

PRIMED event. If the low pressure temperature is greater than the Heat Exchanger Prime 7510 exit temperature and the high pressure temperature is greater than the Heat Exchanger Prime 7510 exit temp and the sump temperature is greater than the Heat Exchanger Prime 7510 exit temperature minus 2° C. and the product level is greater than the minimum product level start and the motor temp is greater than the motor run OK temperature then, in some embodiments, the PRIMED event is signaled.

In various embodiments, the default the Heat Exchanger Prime 7510 exit temp is 112° C. The minimum product level start default value is 20%. The motor run OK temp default is 90° C. In some embodiments, the primed event is only checked for in the Heat Exchanger Prime 7510 state.

STARTED event. If the blow down tank level is less than the blow down run level set point plus the source level offset and the motor speed is within 200 rpm of the commanded value the STARTED event, in some embodiments, is signaled. In some embodiments, the blow down run level set point default value is 40%. The source level offset default value is 10%. In some embodiments, the started event is only checked for in the start pump state.

BDHigh timer event. If the blow down level has been greater than a predetermined percentage, e.g. 90%, for a predetermined time, e.g. 4 minutes, or more the BDHigh timer event is signaled. In some embodiments, the BDHigh timer event is only checked for in the run state.

BDLow timer event. If the blow down valve duty cycle has been less than or equal to a predetermined percentage, e.g., 2%, for a predetermined time, e.g., 4 minutes, or more, the BDLow timer event is signaled. The BDLow timer event is checked for in the Heat Exchanger Prime 7510, Run 7514 and Standby 7522 states.

ProdHigh timer event. If the product level has been greater than a predetermined percentage, e.g. 90%, for a predetermined time, e.g. 5 minutes, or more, the ProdHigh timer event is signaled. In some embodiments, the ProdHigh timer event is only checked for in the Run 7514 state.

ProdLow timer event. If the product valve and the product divert valve have both had a duty cycle of less than or equal to a predetermined percentage, e.g. 2%, for a predetermine time, e.g. 5 minutes, or more, the ProdLow timer event is signaled. In some embodiments, the ProdLow timer event is only checked for in the Run state 7514.

State timer event. If the system has been in the current state longer than the state max timer value the State timer event is signaled. In some embodiments, the State timer event is checked for in all states except Idle 7504, Run 7514 and Standby 7522.

LPUnderTemp event. In some embodiments, if the low pressure temperature is less than a predetermined temperature, e.g. 104° C., the LPUnderTemp event is signaled. The LPUnderTemp event, in some embodiments, is only checked for in the Run 7514 state.

Conductivity high event. In some embodiments, if the conductivity is greater than CondoLimitQ10 for more than CondoErrTime seconds the conductivity high event is signaled. In some embodiments, the default CondoLimitQ10 is 10.0 uS/cm. In some embodiments, the default CondoErrTime is 1800 seconds. In some embodiments, the conductivity high event is only checked for in the Run 7514 state.

Slipped Coupling event. If the LP temp is less then 1.5° less than the high pressure temperature and the product and divert valve duty cycles are less than a predetermined percentage, e.g. 10%, the slipped coupling event is signaled. In some embodiments, the slipped coupling event is only checked for in the Run 7514 state.

Controllers

In various embodiments, one or more controllers of the apparatus/system are used by the control system to control the system. The following are various controllers; one or more may be included in various embodiments of the control system.

Blow down level control. In some embodiments, the blow down level controller in various embodiments controls the blow down valve duty cycle. This controller uses the blow down tank level for feedback. During Heat Exchanger Prime 7510 state it is run as a PI controller. During the Start Pump 7512 and Run 7514 states it is run as a P only controller. In some embodiments, the blow down level controller may be disabled in all other states. This controller uses a different P value for Heat Exchanger Prime 7510 state than Start Pump 7512 and Run 7514 states.

Heater control. The heater control controller controls the heater duty cycle. It defaults to using the low-pressure temperature for feedback. If the HeaterUseSumpTemp register is set, this controller may use the sump temperature for feedback. During the Heat 7508, Heat Exchanger Prime 7510, Start Pump 7512 and Run 7514 states it is run as a PI controller. In some embodiments, this controller may be disabled during other states.

Product level control. This controller controls the product level based on product level sensor and adjusts the product valve duty cycle and product diver duty cycle. During the Heat Exchanger Prime 7510, Start Pump 7512 and Run 7514 states this controller runs as a PI controller. During other states, in some embodiments, this controller is disabled.

Source flow controller. This controller controls the source flow based on the blow down level sensor by activating or varying the source valve duty cycle. In various embodiments, this controller is run as a PID controller during the Fill 7506, Heat 7508, Start Pump 7512 and Run 7514. This controller may start when entering the Heat Exchanger Prime 7510 state. In some embodiments, during the Heat Exchanger Prime 7510 state this controller may be disabled if the blow down level is too high. In some embodiments, during the Heat Exchanger Prime 7510 state this controller may and enabled if the blow down level is too low.

Thus, the source flow controller and the blow down controller receive information from the blow down level sensor and regulate the source valve and the blow down valve, respectively, based on the blow down level sensor information, e.g., level. The gains and the controls for the source flow controller and the blow down controller ensure that the system/machine takes in a greater volume of source water compared with the volume of water boiling off as product water, such that excessive water is input into the system/machine that comes out as blow down water, wherein the system/machine does not run dry, i.e., this method prevents the system from running dry. Also, this method ensures that the system/machine does not over utilize source water and create excess blow down. Thus, the system/machine maintains a balance between the amount of source water that enters the system/machine, the amount of blow down, and the amount of product water produced by the system/machine. This balance is maintained by a single sensor, the blow down level sensor, together with two controllers, the source flow controller and the blow down controller.

In some embodiments, for example, the blow down controller may be preprogrammed to maintain the blow down level at a lower level than the source flow controller. For example, in some embodiments, the blow down controller may be preprogrammed to maintain the blow down level at 50%, and the source flow controller may be preprogrammed to maintain the blow down level at 60%. Thus, the two controllers counteract one another. However, because in various embodiments the source flow controller is a PID controller, while the blow down controller is a PI controller, overtime, the PID source flow controller ultimately may maintain the 60%, while the blow down controller will continue to attempt to maintain 50%, but will not reach the 50%. Thus, the source flow controller will open the source valve until the blow down level sensor indicates the preprogrammed level, e.g., 60%. This control system may be beneficial for many reasons, including, but not limited to, that the blow down controller will maintain a level lower than the source controller, which, in many embodiments, prevents flooding.

Vent control—In some embodiments, the vent control controls the low pressure temperature based on the low pressure temperature sensor and the vent valve duty cycle. The vent controller may be broken up into four segments. The first segment may be for temperatures below "ventLowTempQ10", which, in some embodiments, may be 100° C. The vent valve may behave according to state, which, in some embodiments may be heat/run at 100/0% respectively. The second segment may be for between "ventLowTempQ10", which, in some embodiments, may be 100° C. and "ventMidTempQ10", 112° C. In some embodiments, in this segment, the vent valve command is generated by the equation LPSteamTemp−ventLowTempQ10*ventLowGainQ10. In the next segment "ventMidTempQ10 to" ventHighTempQ10" the command is generated by command+(LPSteamTemp−vent-MidTempQ10) ventHighGainQ10. In some embodiments, if the temperature is above "ventHighTempQ10", which, in some embodiments, may be 118° C., the command is set to "highTempVentValvePct", which, in some embodiments, may be 100%. During the Run 7514 state the vent valve, in the exemplary embodiments, is not fully closed, thus allowing gas venting in the system.

Motor Control Engine. In some embodiments, the system includes a motor control engine controller ("MCE") and a MCE processor. The MCE is a dedicated processor for controlling the motors. The MCE controls both the motors and the heater. MCE includes a message task which takes the information from the MCE processor and puts it into shared memory and then the safety task reads it out of shared memory and acts on it appropriately.

Data Logging

In various embodiments, the apparatus includes a USB port or other, for communication with external machines, e.g., computers, smart-phones and other devices having an ability to receive and/or send messages to the apparatus, and/or software or other applications (collectively referred to herein as "external applications"). The system, in some embodiments, also may include a cell modem for communication. In various embodiments, data from the control system and processors is logged and may be transferred to external applications. This may allow for external monitoring of the apparatus/system. In some embodiments, the apparatus may be preprogrammed to upload logging data at a predetermined time/intervals, e.g., every 12 hours. Below is an exemplary embodiments, however, in various embodiments, the task may vary. The terminology and names given to commands may vary in various embodiments.

In the exemplary embodiments, a data logging task handles the communications with the external applications. In various embodiments, the task first checks whether the USB port is initialized. If it is not, the task initializes the port. If the port is initialized the task checks for and reads the message from the serial port. On a peek command the task parses the location to peek and returns the value. On a poke command the task parses the location to poke and the value to poke. The task then sets the poked value to be used in shared memory and returns the status of the poke command. On an unpoke command the task first checks to see if this is an "unpoke all" or "unpoke one" value command Where the command is an "unpoke all" the task restores all the original values to the shared memory used values. For "unpoke one" value, the task parses the unpoke location and restores the original value to the shared memory used value and returns the OK status. On a "display poked" command the system buffers the location and value of all the poked values and returns the buffer. On a "data" command the system buffers and sends all the constant data buffers and sends all the computed values and then sends the done string. On a flash command the system saves the constants to the flash memory and returns an "OK" flag.

Secure Digital Memory Card ("SD") Logging

In various embodiments, the system includes an SD card and the data is logged onto the SD card. The SD card also may handles communication with the cell modem. An exemplary embodiments, of the SD task is described below.

The SD task, in some embodiments, handles the reading and writing of data on the SD card and the interface to the cell modem. All SD card access must be done through the SD logging task. On startup it initializes the file system, creates directories if needed, reads the last state and motor time files and logs an entry into the data log file. Data will be logged to the log file every SDLogTime seconds (default is 300 seconds). The log file name has the date and device ID embedded. The disk has a current directory where log data is written. There are also monthly backup directories to save old data. When the file is sent to the modem it is then moved into that months backup directory. Before writing to the log file the system checks the free space on the disk. If there is less than 1 MB of space left it will start purging old data by deleting the files in the oldest months directory. It will continue to delete files until there is more than 1 MB of free space.

Shared Memory

In various embodiments, the system software uses a shared memory class to exchange data between the tasks. In some embodiments, there are two sections of shared memory: the constants section and the computed section. In the exemplary embodiment, all data in the shared memory is stored and retrieved as 32 bit integers. Any data filtering or scaling is done in the "putValue" function based on the index of the value being saved.

The constants section contains gains and other machine constants. These values are stored in flash memory ("flash"). When the system starts up the constant values are read from flash. If the cyclical redundancy check ("CRC") on the flash copy is correct the flash values are loaded into the random access memory ("RAM") image. If the CRC is not correct the hard coded default values are loaded in to the RAM. When the value of a constant is needed by the software it is read using the shared memory "getGain" method. It is passed in the index of the constant and the constant value is returned. In some embodiments, the only method for the software to write a constant value is to use the poke functionality. The shared memory method "copyGainToPoked" would need to be used, which received (or is "passed") the index of the constant to change and the value to change it to. The gainFlag constant may be a predetermined/preprogrammed constant set by the user. Thus, in some embodiments, the user is responsible for setting the "gainFlag" for that constant to indicate that the value in the table is a poked value. To restore the poked value to its original value the shared memory "copyPokedToGain" method is called. In some embodiments, calling this method will restore all poked constants to their original values.

In some embodiments, the computed section contains values that are read from the input/output ("IO") or calculated during normal operation. These values are periodically overwritten as new values are read or calculated. When other software tasks need to read a computed value they use the shared memory method "getValue". This method is passed the index of the value to read and returns the value at that index. In some embodiments, the software writes values into the computed section using the "putValue" method of the shared memory class. The method is passed the index of the location to write and the value to be written. Initially the written values are stored in a holding array. In some embodiments, at least once in each control loop of the water task the function is called to copy all data from the holding array into the used array. If the poked flag for that value is set the data for that value is not copied. The values for the computed section can be poked, in some embodiments, only through the "External App" interface. The "handlePoke" method of the "DataLog" class will change the value in the computed table at the specified index and set the poked flag to keep this data from being overwritten by the update loop. In some embodiments, the value may be unpoked by calling the "clearPokedComputed" method of the shared memory class. This will unpoke all poked computed values. The poked flag will be cleared and the next data update loop will overwrite with the latest computed value.

IO Points

The system includes various input and output points ("IO") where the controls receive an input and/or sends an output. In various embodiments, one or more of the following may be included as IO Points. In other embodiments, additional IO Points may be included and in some embodiments, all of the following may be included. The description below separates the Analog Input Points from the Digital IO Points. Additionally, the description below describes an exemplary embodiment and in various other embodiments, the various inputs and outputs may include additional functionality and/or meaning. The terminology may also vary in various embodiments.

Analog Inputs

Low Pressure Steam Temperature. This input reports the temperature of the steam on the low pressure side. It is read in as AD counts and converted to temperature using a look up table.

High Pressure Steam Temperature. This input reports the temperature of the steam on the high pressure side. It is read in as AD counts and converted to temperature using a look up table.

Sump Temperature. This input reports the temperature of the sump. It is read in as AD counts and converted to temperature using a look up table.

Motor Temperature. This input reports the temperature of the motor stator. It is read in as AD counts and converted to temperature using a look up table.

Product Level. This input reports the water level in the product holding tank. The AD counts read are converted to a percent full value using a slope/intercept function.

Blow Down Level. This input reports the water level in the blow down holding tank. The AD counts read are converted to a percent full value using a slope/intercept function.

Current Sensor. This input reports the system current. The AD counts read are converted to amps using a slope/intercept function.

Conductivity. This input reports the product water conductivity. The AD counts read and converted to uS/cm using a slope/intercept function.

Digital Inputs

MCE Awake. Signal from the MCE processor that it is running and able to process requests and commands.

UI SW. User interface switch. A 0.2 second to 2 second press is interpreted by the system as a short button press and press greater than 2 seconds is interpreted as a long button press.

Source Tank Full. An optional input to be used when the UseExternalTanks register is set. This input is attached to the source tank float. It reads a one if the tank is full and a zero if the tank is empty.

Product Tank Full. An optional input to be used when the UseExternalTanks register is set. This input is attached to the product tank float (level sensor). It reads a one if the tank is full and a zero if the tank is empty.

Digital Outputs

MCE Enable. Output to the MCE processor to enable it to take commands and requests. This line is connected to the MCE processors reset line. It should give a method for the ARM processor to reset the MCE processor if needed.

MUX Line. This output switches the analog input mux. When it is low: AD channel 3 is reading the Product level AD and channel 4 is reading the Blow Down level AD. When it is high: AD channel 3 is reading the conductivity sensor and channel 4 is reading the current sensor.

Source Valve. The source valve controls water into the system. It is controlled based on the desired level in the blow down tank. In some embodiments, the desired level is set a little higher that the desired blow down controllers blow down level to assure water is always coming into the system.

Blowdown Valve. This valve controls the water flow out of the blow down tank. This valve is controlled to maintain the level of the blow down tank. The valve, in the exemplary embodiment, is always set a little lower than the source valves desired tank level to maintain water flow into the system.

Product Valve. This valve controls the product flow out of the product holding tank. This valve is controlled to maintain the desired level in the product tank.

Vent Valve. This valve controls venting the system. The vent valve is used to control the Low pressure steam temperature.

Product Divert Valve. This valve is used to control the product tank level. When diverting the product is desired the product divert valve may be used instead of the product valve.

Red UI LED. In some embodiments, there is a red LED on the UI panel which is on 100% of the time when there is an active fault. If there is an active warning the red user LED will flash at a 50% duty cycle. If there is no fault it is off. However, in various other embodiments, the color of the indicator may vary.

Yellow UI LED. In some embodiments, there is a yellow LED on the UI panel. It blinks with the duty cycle of the heater. However, in various other embodiments, the color of the indicator may vary.

Green UI LED. In some embodiments, there is a green LED on the UI panel. It blinks at a 50% duty cycle if the system is not producing good/acceptable, within a predetermined threshold, water. It is on steady if the system is producing good water. However, in various other embodiments, the color of the indicator may vary.

Red Status LED. In some embodiments, there is a red LED on the PC board. In some embodiments, it remains "off" in the Heat Exchanger Prime 7510 state and all the flow measurement states. It blinks at a 50% duty cycle in the Idle 7504, Start Pump 7512 and Standby 7522 states. It is on steady in the Fill 7506, Heat 7508 and Run 7514 states. However, in various other embodiments, the color of the indicator may vary.

Green Status LED. In some embodiments, there is a green LED on the PC board. It remains "off" in the Fill 7506 state. It blinks at a 50% duty cycle in the Idle 7504 and Run 7514 states. It is on steady in the Heat 7508, Heat Exchanger Prime 7510, Start Pump 7512 flow measurement and standby states.

Counter. This output turns on the motor time counter. In some embodiments, it is turned "on" when the commanded motor speed is greater than 50 rpm. In some embodiments, it is turned "off" when the commanded motor speed is less than 50 rpm.

Bearing feed pump. This output turns the bearing feed pump "on" and "off". It is turned "on" when the motor is commanded to run. It is turned "off" when the motor is turned off.

System Integrity Tasks

The control system as described herein uses a variety of processors, and IOs to complete events, as discussed above. Using memory the control systems logs the performance information of the apparatus and may determine system errors, inefficiencies, etc., and diagnose the causes. Additionally, the control system may either allow recovery from a system error or not. In some embodiments, the system may attempt to restart following an error if the error did not occur in the Idle 7504 state. In some embodiments, for over temperature faults the system may wait until the temperatures drop within acceptable ranges before restarting. In some embodiments, the software may retry starting the system at least three times. In some embodiments, after the third restart attempt, the system may stay in the Idle 7504 state. In some embodiments, if the system stays in the Run 7514 state for a predetermined amount of time, e.g., 20 minutes, or is manually turned off by the operator/user, the retry counter may be reset to zero. In some embodiments, all of the sensor faults must persist for a predetermined amount of time, e.g., 2 seconds, before the system may consider it a true fault. In some embodiments, the system integrity tasks run in the same thread as the water and the hardware tasks. Below is Table 1 including a list of error types that may be determined using the control system. An example of the condition which triggers the error is also given, as well as whether recovery is permitted. The conditions given are for illustration purposes and although in some embodiments, these may be used, in other embodiments, the values, etc., may differ.

The system, in the exemplary embodiment, uses the ARM processor watchdog timer. The timeout may be set for 10 seconds. Each time a task goes through its main processing loop it calls the watchdog update method passing in its task id bit. When the water, hardware and system integrity bits are all set, the software tickles the watchdog and clears the watchdog bits. This may be beneficial in some embodiments as it assures that all critical tasks are running.

TABLE 1

| Error Description | Condition | Recovery |
| --- | --- | --- |
| Low Pressure Thermistor Open | AD reading >1005 counts | No |
| High Pressure Themistor Open | AD reading >1005 counts | No |
| Sump Thermistor Open | AD reading >1005 counts | No |
| Motor Thermistor Open | AD reading >1005 counts | No |
| Low Pressure Thermistor Short | AD reading <30 counts | No |
| High Pressure Themistor Short | AD reading <30 counts | No |
| Sump Thermistor Short | AD reading <30 counts | No |
| Motor Thermistor Short | AD reading <30 counts | No |
| Product Level Open | AD reading >900 counts | No |
| Blow Down Level Open | AD reading >900 counts | No |
| Product Level Short | AD reading <250 counts | No |
| Blow Down Level Short | AD reading <250 counts | No |
| Low Pressure Over Temp | Low Pressure temp >125° C. | Retry After Clear |
| High Pressure Over Temp | High Pressure temp >149° C. | Retry After Clear |
| Sump Over Temp | Sump temp >125° C. | Retry After Clear |
| Motor Over Temp | Motor temp >180° C. | Retry After Clear |
| IRAM Over Temp | Motor temp >100° C. | Retry After Clear |
| BD Level High | During Run state Blow Down level is >90% for more than 4 min. | Retry After Clear |
| BD Level Low | During Run, Prime and Standby states Blow Down valve duty cycle <=2% for more than 4 min. | Retry After Clear |

TABLE 1-continued

| Error Description | Condition | Recovery |
| --- | --- | --- |
| Product Level High | During Run state Product level is >90% for more than 5 min. | Retry After Clear |
| Product Level Low | During Run state Product and divert valves duty cycle <=2% for more than 5 min. | Retry After Clear |
| System too Cold | During Run state Low Pressure temp <104° C. | Retry After Clear |
| Too long in State | In fill state >12 min or In heat state >4 hours or In hx prime state >2.5 hours or In start pump state >8 min | No |
| Lack of water in sump | Sump temp >115° C. and Sump temp-LP temp >25° C. | Retry After Clear |
| Error Reading from Flash | CRC or data length error reading flash memory | No |
| Error Writing to Flash | Error writing constant values to flash memory | No |
| Motor Error | Commanded motor speed >50 and actual to commanded motor speed difference is > MotorErrorSpeed rpm for > MotorErrorTime seconds | Retry After Clear |
| Magnetic coupling slipping | HPTemp-LPTemp <1.5° C. and Prod and Divert duty <10% | Retry After Clear |
| Heater Fault | Not Implemented | Retry After Clear |
| Over Current | System current >13A | Retry After fault |
| Conductivity Sensor Open | Not Implemented | No |
| Conductivity Sensor Short | AD reading <150 counts | No |
| Conductivity Too High | In Run state Conductivity > CondoLimitQ10 for > CondoErrTime Seconds | No |
| MCE Communications Fault | No response from MCE after 5 retries at 10 sec per retry | No |
| MCE Fault | No MCE awake signal after reasserting MCE Enable for 20 consecutive tries | No |

MCE

The MCE message task handles the communications between the ARM control processor and the MCE processor. In some embodiments, there are 2 discrete digital signals between the ARM and the MCE processors: the MCEEnable line and the MCEAwake line. The MCEEnable line is an output from the ARM processor and an input to the MCE processor. This line is set to "0" to enable the MCE. While MCEEnable is a "1" the MCE processor is held in the reset state.

The MCEAwake line is an output from the MCE processor and an input to the ARM processor. In some embodiments, the MCE_msg task will only process messages if the MCEAWAKE line is active. If the MCEAwake line is not active the MCEEnable line is reset to the enable state. If after a predetermined amount of time, e.g., 60 seconds, of asserting the MCEEnable line the MCEAwake line does not become active an MCE Fault may be issued.

The MceMsg process function creates the processing signals as events occur. It will then distribute them to a heater command state machine. If the heater command state machine does not handle the signal it is then passed to the motor command state machine. If the MCE state machine does not handle the event, e.g., if the event is a response that was not expected, an error message is sent to the MCE. However, if the MCE state machine does handle the event, a status request is sent to the MCE. If a response to the command is not received within a predetermined time, e.g. 10 seconds, the command is reissued. If no response is received after a predetermined number of attempts, e.g. 5 retries, the MCE Communications Fault is signaled. MCE status is returned in the command response packets.

Therefore, the control system described above may be used to determine the integrity of the apparatus/system and also, with information relating to the rate of water product production, the control system may signal when the system should undergo maintenance, including, but not limited to, cleaning/de-scaling. In some embodiments, the system may signal that the maintenance is needed, e.g., post a message to the external application and/or indicate same on a User Interface on the machine, including, but not limited to, one or more of: LEDs, text message, symbol/icon, etc. In some embodiments, the system may automatically undergo a maintenance procedure, e.g., cleaning/de-scaling, however, in other embodiments, the maintenance procedure may be performed manually and then confirmed through, e.g., a user interface, that the maintenance was completed.

Communication with an external application also presents many methods for controlling the apparatus remotely. For example, with regular logs and software communication, a user may determine which apparatus needs maintenance and may schedule same remotely. This may be desirable/beneficial for many reasons, including, but not limited to, running one or more water vapor distillation apparatus/machines remotely in various countries/regions including, but not limited to, areas that are very remote or scarcely populated.

In various embodiments, the one or more water vapor distillation apparatus/machines may include communications with a remote device or server, e.g., a web site or a remote computer. The communication may be established using one or more, but not limited to, the following: cell modem, internet, Ethernet, and/or land line/telephone line. In various embodiments, bi-directional communications may be established between a remote device or server and the one or more water vapor distillation apparatus/machines.

Referring now also to FIG. 76, in some embodiments, the at least one water vapor distillation apparatus/machine/system may include a system for communications which may, in some embodiments, include a "backend" and an external manager. In some embodiments, the backend may be a HTTP server and SMS Dispatcher with interfaces for connecting the at least one water vapor distillation apparatus/machine/system as well as External Manager(s). The Backend acts as a bridge between the External Manager and the at least one water vapor distillation apparatus/machine/system. In some embodiments, the Backend may be configured by the External Manager to provide automated interactions with the device. In some embodiments, the Backend may act as a go-between entity to provide interactivity between the at least one water vapor distillation apparatus/machine/system and the External Manager.

In various embodiments, the External Manager may be a process that configures the server to indirectly configure and interact with at least one water vapor distillation apparatus/machine/system.

The at least one water vapor distillation apparatus/machine/system, in some embodiments, is an HTTP client. These embodiments may be used in many situations, including, but not limited to, when the at least one water vapor distillation apparatus/machine/system is remotely located and connected via cell modem. In this embodiment, the at least one water vapor distillation apparatus/machine/system may not, in some embodiments, always be connected to lower costs, and also, where the cell model infrastructure may not be 100% reliable. In these embodiments, the server is always be running Therefore, in these embodiments, the at least one water vapor distillation apparatus/machine/system is the client and the backend is the server.

In some embodiments, the backend may wake the at least one water vapor distillation apparatus/machine/system by issuing an SMS "shoulder tap" message. In various embodiments, this message contains no data, but may indicate that the device may connect to the server to receive instructions, updated, communications, etc.

In various embodiments, the External Manager directly interacts solely with the Backend via its HTTP server interface through a special "External Manager" interface. In some embodiments, the external interface to the at least one water vapor distillation apparatus/machine/system is an HTTP interface implemented over an SSL security layer using TCP/IP sockets. In some embodiments, the API may be compatible with the AJAX "web services" pattern used in many web based technologies.

In various embodiments, connections to the at least one water vapor distillation apparatus/machine/system are stateless. Correspondingly, in these embodiments, all commands are synchronous. Any changes in state on the at least one water vapor distillation apparatus/machine/system are realized by the calling client making multiple synchronous requests and computing the difference between those calls.

In various embodiments, each request comes into the at least one water vapor distillation apparatus/machine/system in the form of an XML message. A request is processed and its response is sent back to the caller in the form of an XML message.

In some embodiments, a manual cleaning/de-scaling may be performed by using pressurized clean water and flushing to system. In some embodiments, the apparatus may be connected to an acid cleaning solution for flushing/cleaning. In some embodiments, a pump is used to pump the water and/or cleaning solution through the apparatus/machine.

A system for providing product water may include a source tank, containing a volume of source water, and a product tank, containing a volume of product water. Both the source tank and the product tank may include level sensors to determine the level of water. In these embodiments, the control system enters the water task Fill 7506, etc., states only when there is a sufficient volume of water in the source tank and if the product tank is not full. The water task will then run until either the product tank is full or the source tank is below a predetermined volume. The machine then enters into the Idle 7504 state. In some embodiments, the source tank may be fluidly connected to a pressurizing pump which pumps the water into the apparatus.

Referring now also to FIG. 77, in some embodiments, the water vapor distillation apparatus may be housed within a shell/case 7700 (which may also be referred to as a housing). In some embodiments, the shell/case may be as shown in FIG. 77. Referring now also to FIG. 78, in some embodiments, a filter/strainer assembly 7704 may be located in a compartment area that, in some embodiments, may be easily accessible by users. In some embodiments, the filter/strainer assembly 7704 may be used to strain debris from the source water prior to the water entering the water vapor distillation apparatus. In various embodiments, the source water enters the filter/strainer assembly 7704 through an input nozzle assembly 7732. In some embodiments, it may be desirable that users have access to the filter/strainer assembly 7704 to remove, empty/clean the filter/strainer, then replace. However, in some embodiments, the filter/strainer assembly 7704 may be located within the case/shell 7700 and behind a door, or other. In some embodiments of these embodiments, the filter/strainer assembly 7704 may be accessible, but may require the opening of a door or latch. In other embodiments of this embodiment, the filter/strainer assembly 7704 may be accessible by removal of one or more sections of the case/shell 7700 (discussed in further detail below). In various embodiments of the system, however, a filter and/or a strainer may be located outside of the system and/or outside of the case/shell, but positioned such that a source water fluid passes through the filter and/or strainer before entering the apparatus.

Referring now also to FIG. 78, in some embodiments, the case/shell 7700 may include a user interface 7702, which, in some embodiments may include, but is not limited to, one or more of the following: one or more LEDs, one or more buttons, one or more screens, including, but not limited to, a touch screen which may include, but is not limited to, a 3D, or 3-dimensional, touch screen. In some embodiments, the user interface 7702 may also include an overlay or other to protect the one or more features of the user interface. In some embodiments, the overlay or other may provide protection from water and/or temperatures, e.g., hot or cold.

Referring now also to FIGS. 79A-79E, various views of one embodiments of the case/shell 7700 are shown. In various embodiments, including the embodiments shown in these FIGS., the case/shell 7700 includes one or more sections, which, in some embodiments, may include two sections, but in other embodiments, may include two or more sections. In some embodiments, the case/shell 7700 may include a cold section 7706 and at least one hot section 7708. As shown in the embodiment shown in FIGS. 79A-79E, the hot section 7708 may include two sections 7710, 7712. In some embodiments this may be desirable for a user and/or technician to gain entry to one side of the hot section without having to remove the other side of the hot section. In some embodiments, this may be desirable/beneficial for many reasons, including, but not limited to, the efficiency and/or reduced cost to manufacture. In various embodiments, the various embodiments of the case/shell 7700 may be made from any materials, including, but not limited to, one or more of the following: fiberglass, plastic, metal.

In various embodiments, the cold section 7706 may be the section covering the electronics assembly, the hydraulic manifold, including, but not limited to, the valve manifold and the conductivity cell. These embodiments include one or more sections of the case/shell 7700 may be desirable for many reasons, including, but not limited to, ease and safety of a user and/or service technician gaining entrance to the cold section to service the electronic assemblies, valves, etc., without being exposed to the very hot section 7708.

As shown in FIGS. 79A-79E, in various embodiments, the case/shell 7700 includes a drain 1 port 7716 and a drain 2 port 7718 for draining the blow down and the product water. In various embodiments, the case/shell 7700 includes at least one electrical cord input 7714, allowing for an electrical cord to plug into the input 7714 and provide electricity to the electronics assembly, etc.

Referring now to FIG. 80, in various embodiments, the shape of the case/shell 7720 may be as shown. In some embodiments of these embodiments of the case/shell 7722, as shown, for example, in FIG. 81, the case/shell 7720 may include a filter/strainer assembly 7724 that may be located in a compartment area that, in some embodiments, may be easily accessible by users. In some embodiments, the filter/strainer assembly 7724 may be used to strain debris from the source water prior to the water entering the water vapor distillation apparatus. In some embodiments, it may be desirable that users have access to the filter/strainer assembly 7724 to remove, empty/clean the strainer/filter, then replace. In some embodiments, however, the filter/strainer assembly 7724 may be located within the case/shell 7722 and behind a door, or other. In some embodiments of these embodiments, the filter/strainer assembly 7724 may be accessible, but may require the opening of a door or latch. In other embodiments of this embodiment, the filter/strainer assembly 7724 may be accessible by removal of one or more sections of the case/shell (discussed in further detail below). In various embodiments of the system, however, a filter and/or a strainer may be located outside of the system and/or outside of the case/shell, but positioned such that a source water fluid passes through the filter and/or strainer before entering the apparatus.

Referring now also to FIGS. 81 and 82, in some embodiments, the case/shell 7722 may include a user interface 7726, which, in some embodiments may include, but is not limited to, one or more of the following: one or more LEDs, one or more buttons, one or more screens, including, but not limited to, a touch screen which may include, but is not limited to, a 3D, or 3-dimensional, touch screen. In some embodiments, the user interface 7726 may also include an overlay or other to protect the one or more features of the user interface. In some embodiments, the overlay or other may provide protection from water and/or temperatures, e.g., hot or cold.

In some embodiments, the case/shell 7722 includes one or more sections, which, in some embodiments, may include two sections, but in other embodiments, may include two or more sections. In some embodiments, the case/shell 7722 may include a cold section 7728 and at least one hot section 7730. In some embodiments, the hot section 7730 may include two sections. In some embodiments this may be desirable for a user and/or technician to gain entry to one side of the hot section 7730 without having to remove the other side of the hot section. In some embodiments, this may be desirable/beneficial for many reasons, including, but not limited to, the efficiency and/or reduced cost to manufacture. In various embodiments, the various embodiments of the case/shell 7722 may be made from any materials, including, but not limited to, one or more of the following: fiberglass, plastic, metal.

In various embodiments, the cold section 7728 of the case/shell 7722 may be the section covering the electronics assembly, the hydraulic manifold, including, but not limited to, the valve manifold and the conductivity cell. The embodiments include one or more sections of the case/shell 7722 may be desirable for many reasons, including, but not limited to, ease and safety of a user and/or service technician gaining entrance to the cold section 7728 of the case/shell 7722 to service the electronic assemblies, valves, etc., without being exposed to the hot section 7730 of the water vapor distillation apparatus. In some embodiments, access to one or more sections may require at least one tool.

In various embodiments, the case/shell 7722 includes a drain 1 port and a drain 2 port for draining the blow down and the product water. In various embodiments, the case/shell includes at least one electrical cord input 7714, allowing for an electrical cord to plug into the input 7714 and provide electivity to the electronics assembly, etc.

Referring now also to FIG. 83, one embodiment of the water vapor distillation apparatus 8300 is partially shown. In some embodiments, the water vapor distillation apparatus may be housed inside one or more of the embodiments of the case/shell shown herein, or may be housed inside another embodiments of a case/shell. In various embodiments, the water vapor distillation apparatus may include various components, including, but not limited to, an embodiment of a steam chest 8302, an evaporator/condenser 8304, a heat exchanger 8306, a compressor 8308 and a cap 8310 on the compressor.

Referring now also to FIGS. 84A-84F and FIGS. 85A-85B, various partial views of a water vapor distillation apparatus configuration are shown. In various embodiments, one or more brackets 8400, 8402 may be used to stabilize the various elements of the water vapor distillation apparatus such that, during transportation, for example, the various elements of the water vapor distillation apparatus maintain their location and connections within the case/shell. Some embodiments of the brackets 8400, 8402 are shown in FIGS. 84A-84F and FIGS. 85A-85B. In some embodiments of these embodiments of the brackets 8400, 8402, the brackets 8400, 8402 may be made from plastic. However, in other embodiments, the brackets 8400, 8402 may be made from metal or another material.

As shown in the FIGS., some embodiments include a hot/cold divider 8406 to divide the hot section of the water vapor distillation apparatus from the cold section of the water vapor distillation apparatus. This divider 8406, in some embodiments, contributes to the maintenance of the temperature in the hot section, i.e., the hot/cold divider 8406 may, in some embodiments, be a thermal insulator. In some embodiments, the various bracket systems employed within the water vapor distillation apparatus may attach to the hot/cold divider 8406.

In various embodiments of the water vapor distillation apparatus, the apparatus includes a blow down level sensor 8408 and a product level sensor 8410. In some embodiments, the sensors may be identical, but each may be in fluid communication with a different fluid path in the system. In some embodiments, the product level sensor 8410 is located lower in the system as the product is gravity fed from the evaporative/condenser.

In various embodiments of the water vapor distillation apparatus, the apparatus includes a valve manifold 8412. In some embodiments, this may be a hydraulic valve manifold. In some embodiments, the hydraulic valve manifold may be connected to the conductivity cell 8414 (sometimes referred to as a condo cell). Additional views of the manifold 8412 and the valves are shown in FIGS. 85A and 85B.

Referring also to FIGS. 85A and 85B, in some embodiments, the water vapor distillation apparatus includes a base/basin 8416, and a foam bottom base 8418 that sits within the base/basin 8416. The base/basin 8416, in some embodiments, may serve as a central connection point for the various elements/components of the water vapor distillation apparatus. In various embodiments, the water vapor distillation apparatus is a modular system, e.g., one element or component may be removed from the system without dismantling the entire system. For example, the hydraulic manifold 8420 is designed to be easily disconnected from the system, removed, and replaced, without removing other elements/components of the system. The basin 8416 therefore serves as the base for the apparatus/system to connect.

In various embodiments, the foam bottom base 8418 may serve as an insulator and/or thermal insulation element/component. FIG. 85B shows a detail view of section A shown in FIG. 85A.

Referring now also to FIG. 86, another embodiment of the water vapor distillation apparatus, shown in exploded view, is shown together with the case/shell assembly. Together, the water vapor distillation apparatus and the case/shell form a system 8600.

As shown, the cold case cover assembly 8602 separates from the hot case/cover assembly 8604. The cold/case cover assembly 8602 covers the cold components of the water vapor distillation apparatus, including, but not limited to, the electronics assembly 8606, the scale mitigation assembly 8608, the condo cell 8610 and the hydraulic manifold as well as the electronics plug-ins (not shown, see FIG. 87D as 8612). The hot case/cover assembly 8604 covers the hot components of the water vapor distillation apparatus, including, but not limited to, the sump (with heater), the evaporator/condenser 8614, the steam chest 8616, the compressor/regenerative blower 8618 and the tube-in-tube heat exchanger 8620. In some embodiments, a tool, e.g., a Phillips head screwdriver, may be used to remove the hot section 8604 of the case/cover assembly. In some embodiments, no tool may be required. In some embodiments, a tool may be required to remove the hot section 8604 of the case/cover assembly, but not the cold section 8602 of the case/cover assembly. Referring now also to FIG. 87A, an embodiment of the bracket assembly 8622 is shown. These embodiments of the bracket assembly include an E/C bracket 8624 which is a ring bracket that clamps around the outside of the evaporator/condenser 8614 and attaches to the bracket assembly 8622. Together, the bracket assembly 8622 and E/C bracket 8624 maintain the stability of the position of the components within the case/shell.

As discussed above, the water vapor distillation apparatus, in various embodiments, is a modular apparatus. The various components may each be easily removed without disassembling the entire apparatus. For example, the heat exchanger 8620 may be unclamped and lifted out of the apparatus, to then easily remove the other components of the system. FIG. 87C shows the apparatus with the heat exchanger having been removed. Referring also to FIG. 88, the hydraulic manifold 8626 includes a steam/water mixing chamber 8628, and a condo (or conductivity) cell which includes a conductivity probe 8630 a condo cell casing 8632 a condensate tubing assembly 8634, o-rings/seals 8636, 8638, 8642, 8644, a hydraulic valve manifold mounting plate 8640, a hydraulic valve manifold 8646, which includes valves 8648, including check valves 8650. The hydraulic manifold, in various embodiments, also may include a mixing chamber 8628 support ring 8652.

Referring also to FIG. 87A, some embodiments of the water vapor distillation apparatus include a scale mitigator 8654. Various embodiments of the scale mitigator 8654 may be used, which includes, but are not limited to, the SCALESTICK manufactured by Southeastern Filtration & Equipment Solutions of Canton, Ga., U.S.A. However, in various other embodiments, various methods, processes, systems and/or apparatus for scale mitigation may be used.

Referring also to FIG. 87B, in various embodiments, the basin 8656 may include a drain 1 port 8658 and drain 2 port 8660 (or a first drain port 8658 and a second drain port 8660) for the product drain and the blow down drain. An electrical cord input 8662 may also be included. In various embodiments, the system may include an electrical cord with various connectors for use in various areas of the world.

Referring now also to FIG. 87D, the water vapor distillation apparatus electronics assembly 8606, in some embodiments, may be a closed assembly, i.e., may be designed such that a user or service technician may not easily gain entry. However, the water vapor distillation apparatus may include electronics plug-ins such that devices may be easily plugged into the water vapor distillation apparatus and be in communication with the electronics assembly without having to open the electronics assembly. For example, the water vapor distillation apparatus may include electronics plug-ins for one or more device, including, but not limited to, an external product level sensor and/or an external pump. Additionally, in various embodiments, the water vapor distillation apparatus system may include a port/button cover 8664, which, in some embodiments, may be located in the filter/strainer compartment, which includes a cover 8664, which, in some embodiments, may be a protective cover, covering one or more of, but not limited to, the following: a reset button, a state change button, an Ethernet port and/or an Secure Digital Memory Card ("SD card") port. In some embodiments, where the water vapor distillation apparatus may not be connected to the Internet and/or have wireless service, e.g., in locations in the world where Internet/wireless service is not available and/or reliably available, updates to the software of the system may be performed using an SD card. In various embodiments, the water vapor distillation apparatus may include a filter/strainer assembly 8666, which, in some embodiments, may include an input nozzle assembly 8668.

In various embodiments, the water vapor distillation system may include a divider 8670 which divides the cold portion from the hot portion of the apparatus and system. Various embodiments of the water vapor distillation system may include a user interface 8672, which may include one or more of the features described with respect to various embodiments of the water vapor distillation system, and may include an overlay 8674.

In various embodiments, the mist eliminator may include one or more of the embodiments shown in FIGS. 90A-98B.

Referring now also to FIGS. 90A-90E, various views of one embodiment of a mist eliminator 9000 are shown. In this embodiment, the mist eliminator 9000 may include three sections, a top section 9002, a middle section 9004, and a bottom section 9006. In some embodiments, legs 9008, 9010, 9012 are attached to the bottom section 9006. In various embodiments, the top section 9002, a middle section 9004, and a bottom section 9006 are connected with a connecting mechanism, which may include, but is not limited to, screws. In some embodiments, the mist eliminator 9000 is made stainless steel, aluminum and/or plastic, and in various embodiments, may be made from any material including any type of metal and/or any type of plastic.

The mist eliminator 9000 in various embodiments may be sized to fit within the steam chest (described above) and the legs 9008, 9010, 9012 may attach to holes in the evaporator condenser (described above) wherein the evaporator condenser in various embodiments may include holes to accommodate receipt of the legs 9008, 9010, 9012.

In various embodiments, the bottom section 9006 may be sized such that the edge of the bottom section 9006 rests against the inside wall of the steam chest. In various embodiments, the bottom section 9006 may include one or more cut openings 9014, 9016, 9018, 9020, 9022. Steam from the evaporator condenser may travel past the bottom section 9006 and water may travel past the bottom section 9006.

The middle section 9004 includes an edge that may rest against the inside wall of the steam chest. In various embodiments, the middle section 9004 includes edge openings 9024, 9026, 9028, 9030, 9032, 9034 about the circumference of the middle section 9004. The middle section 9004 also includes an opening 9036.

The top section 9002 in various embodiments is generally cone-shaped and provides a cap to the mist eliminator assembly 9000.

Steam may pass through the opening 9036 and also through the edge openings 9024, 9026, 9028, 9030, 9032, 9034 and cut openings 9014, 9016, 9018, 9020, 9022, as well as around the outside circumferential edge of the bottom section 9006, middle section 9004 and the top section 9002. The shape of the top section 9002 forces the steam to change direction. Water vapor that travels through the opening 9036 will hit the underside of the top section 9002 and drip down and eventually, to the sump. Thus, to the extent water passes through from the evaporator condenser with the steam, when the steam, which changes direction when it reaches the top section 9002, changes direction, the water is incapable of following the same path because the water cannot change direction as it has a higher mass. This results in the water being separated from the steam. The water may reach the underside of the top section 9002 and then, as there is no opening in the top section 9002, falls to the middle section 9004, and may travel through the edge openings 9024, 9026, 9028, 9030, 9032, 9034 and cut openings 9014, 9016, 9018, 9020, 9022 and back to the sump.

In various embodiments, the three sections 9002, 9004, 9006 are generally cone-shaped and therefore, to the extent water reaches a surface of one or more of the three sections 9002, 9004, 9006, the water will tend to drip downwards towards the sump.

Referring now also to FIGS. 91A and 91B, another embodiment of a mist eliminator 9100 is shown. In this embodiment, the mist eliminator 9100 may include two sections, a top section 9102 and a bottom section 9004. In some embodiments, legs 9106, 9108, 9110 are attached to the bottom section 9104. In various embodiments, the top section 9102 and a bottom section 9104 are connected with a connecting mechanism, which may include, but is not limited to, screws. In some embodiments, the mist eliminator 9100 is made stainless steel, aluminum and/or plastic, and in various embodiments, may be made from any material including any type of metal and/or any type of plastic.

The mist eliminator 9100 in various embodiments may be sized to fit within the steam chest (described above) and the legs 9106, 9108, 9110 may attach to holes in the evaporator condenser (described above) wherein the evaporator condenser in various embodiments may include holes to accommodate receipt of the legs 9106, 9108, 9110.

In various embodiments, the bottom section 9104 may be sized such that the edge of the bottom section 9104 rests against the inside wall of the steam chest. In various embodiments, the bottom section 9104 may include one or more edge openings 9114, 9116, 9118, 9120, 9122. Steam from the evaporator condenser may travel past the bottom section 9104 to the top section 9102. The bottom section 9104, in various embodiments, includes an opening 9036.

The top section 9102 in various embodiments is generally cone-shaped and provides a cap to the mist eliminator assembly 9100.

Steam may pass through the opening 9112 and also through the edge openings 9024, 9026, 9028, 9030, 9032, 9034 and edge openings 9114, 9116, 9118, 9120, 9122, as well as around the outside circumferential edge of the bottom section 9104 and the top section 9102. The shape of the top section 9102 forces the steam to change direction. Water vapor that travels through the opening 9112 will hit the underside of the top section 9102 and drip down and eventually, to the sump. Thus, to the extent water passes through from the evaporator condenser with the steam, when the steam, which changes direction when it reaches the top section 9102, changes direction, the water is incapable of following the same path because the water cannot change direction as it has a higher mass. This results in the water being separated from the steam. The water may reach the underside of the top section 9102 and then, as there is no opening in the top section 9102, falls to the bottom section 9104, and may travel through the edge openings 9114, 9116, 9118, 9120, 9122 and opening 9112 and back to the sump.

In various embodiments, the top section 9102 and bottom section 9104 are generally cone-shaped and therefore, to the extent water reaches a surface of one of the sections 9102, 9104 the water will tend to drip downwards towards the sump.

Referring now to FIGS. 92A-92B, another embodiment of a mist eliminator 9200 assembly 9200 is shown. In this embodiment, a plurality of mist eliminator caps 9202 are attached to a bottom section 9204. In various embodiments, the bottom section 9202 includes a plurality of openings 9212 that may be configured to line up with the openings in the upper tube sheet 1004 (shown in FIG. 10A) of the evaporator condenser.

In some embodiments, legs 9206, 9208, 9210 are attached to the bottom section 9204. In some embodiments, the mist eliminator 9200 is made stainless steel, aluminum and/or plastic, and in various embodiments, may be made from any material including any type of metal and/or any type of plastic.

The mist eliminator 9200 in various embodiments may be sized to fit within the steam chest (described above) and the legs 9206, 9208, 9210 may attach to holes in the evaporator condenser (described above) wherein the evaporator condenser in various embodiments may include holes to accommodate receipt of the legs 9206, 9208, 9210.

In various embodiments, the bottom section 9204 may be sized such that the edge of the bottom section 9204 rests against the inside wall of the steam chest.

Steam may pass through the plurality of openings 9212 and also through the a lower sections 9226 of the plurality of mist eliminator caps 9202, which are open to the upper section 9228 of the plurality of mist eliminator caps 9202, as well as around the outside circumferential edge of the bottom section 9204. The shape of the upper section 9228 forces the steam to change direction. Water vapor that travels through the plurality of openings 9212 will hit the underside of the upper section 9228 and drip down and eventually, to the sump. Thus, to the extent water passes through from the evaporator condenser with the steam, when the steam, which changes direction when it reaches the upper section 9228, changes direction, the water is incapable of following the same path because the water cannot change direction as it has a higher mass. This results in the water being separated from the steam. The water may reach the underside of the upper section 9228 and then, as there is no opening in the upper section 9228, falls to the bottom section 9204, and may travel through the edge openings 9214, 9216, 9218, 9220, 9222, 9224 and plurality of openings 9212 and back to the sump.

In various embodiments, the upper sections 9228, and in some embodiments, the bottom section 9204 are generally cone-shaped and therefore, to the extent water reaches a surface of the upper sections 9228 or the bottom section 9204, the water will tend to drip downwards towards the sump.

Referring now also to FIGS. 93A and 93B, another embodiment of a mist eliminator assembly 9300 is shown. In this embodiment, a mist eliminator assembly 9300 is a cap that attaches to each of the plurality of rods (not shown, shown in FIG. 9A as 902) within the tubes in the evaporator condenser assembly. Steam flows past the bottom section 9304, as indicated by the arrow, and then past the top section 9302. The shape of the top section 9302 forces the steam to change direction. Water vapor thus travels past the bottom section 9304 and then hits the underside of the top section 9302 and drips down, back to the sump. Thus, to the extent water passes through from the evaporator condenser with the steam, when the steam, which changes direction when it reaches the top section 9302, changes direction, the water is incapable of following the same path because the water cannot change direction as it has a higher mass. This results in the water being separated from the steam. The water may reach the underside of the top section 9302 and then, as there is no opening in the top section 9302, falls back to the sump.

Referring now also to FIG. 94, in some embodiments, a chevron shaped mist eliminator 9400 may be used. In this embodiment, the steam is subjected to a plurality of tortuous pathways including tortuous pathways 9404, 9406, 9408. The steam changes directions many times. As such, any water that may have entered the mist eliminator will be separated from the steam as the water is unable to change directions with the steam. The water may then drip back to the sump.

In some embodiments, the mist eliminator 9400 is made of stainless steel, aluminum and/or plastic, and in various embodiments, may be made from any material including any type of metal and/or any type of plastic.

The mist eliminator 9400 in various embodiments may be sized to fit within the steam chest (described above) and the leg 9408 may attach to a hole in the evaporator condenser (described above) wherein the evaporator condenser in various embodiments may include holes to accommodate receipt of the leg 9408.

Referring now also to FIGS. 95A and 95B, an embodiment of a baffle port is shown. In various embodiments, the baffle port may be inserted into the steam chest, as shown in FIGS. 96 and 97. FIGS. 96 and 97 show various embodiments of the mist eliminator (9400, 9200 respectively) inside the steam chest. A partial view of the evaporative condenser is shown.

Referring now to FIGS. 98A and 98B, another embodiment of a mist eliminator 9800 is shown. In this embodiment, three layers of mesh 9802, which, in some embodiments, may be made from stainless steel or steel, are stacked with spacers in between. One or more legs 9804 may be attached to the layers of mesh 9802. The mist eliminator 9800 in various embodiments may be sized to fit within the steam chest (described above) and the one or more legs 9804 may attach to a hole in the evaporator condenser (described above) wherein the evaporator condenser in various embodiments may include holes to accommodate receipt of the leg 9404 (or one or more legs).

In some embodiments, the mist eliminator 9400 is made of stainless steel, aluminum, PTFE and/or plastic, and in various embodiments, may be made from any material including any type of metal and/or any type of plastic.

In various embodiments, each layer of the mesh may include edge openings 9806, 9808, 9810, 9812, 9814, 9816. In some embodiments, the layers of mesh 9802 may be sized such that the edge touches the inside wall of the steam chest. Water may drip through the openings 9806, 9808, 9810, 9812, 9814, 9816 and to the sump.

In various embodiments, the three layers of mesh are staggered with respect to one another. This creates a tortuous path for the steam and therefore, the steam changes directions when flowing through the mesh. Thus, the location of the mesh openings with respect to each layer of the three layers of mesh 9802 forces the steam to change direction. To the extent water passes through from the evaporator condenser with the steam, when the steam changes direction, the water is incapable of following the same path because the water cannot change direction as it has a higher mass. This results in the water being separated from the steam. The water may falls back to the sump.

In various embodiments, the water vapor distillation apparatus and/or the various embodiments of the mist eliminator assembly may include a splash guard above the mist eliminator. In various embodiments, the splash guard may be constructed of a hydrophobic material.

In some embodiments, the splash guard may be constructed of one or more layers of mesh. In some embodiments, where two or more layers of mesh are used, the two or more layers of mesh may be rotated ninety-degrees from each other.

In various embodiments, the splash guard may be made of stainless steel, aluminum, PTFE and/or plastic, and in various embodiments, may be made from any material including any type of metal and/or any type of plastic.

Referring now also to FIGS. 99A-99C, various views of one embodiment of a mist eliminator 10000 are shown. In this embodiment, the mist eliminator 10000 may include six sections, a ring frame 10002, a screen section 10004, a cone frame section 10006, a top section 10008, a middle section 10010, and a bottom section 10012. In some embodiments, legs 10014, 10016, 10018 are attached to the bottom section 10012. In various embodiments, the various sections may be molded and heat staked together. In various embodiments, the cone frame section 10006 receives the screen section 10004, which, in various embodiments, may be cone shaped. In various embodiments, the screen section 10004 may be made from a mesh filter, which, in some embodiments, may be made of PTFE, or polytetrafluorethylene. In some embodiments, the PTFE mesh section 10004 may include mesh openings of 0.025 inches and maybe 0.010 inches thick. In some embodiments, the ring frame 10002, cone frame section 10006, top section 10008, middle section 10010, bottom section 10012 are made from RYTON® thermoplastic, however, in various other embodiments, these sections may be made from stainless steel, aluminum and/or plastic, and in various embodiments, may be made from any material including any type of metal and/or any type of plastic.

The mist eliminator 10000 in various embodiments may be sized to fit within the steam chest (various embodiments of which are described above and below) and the legs 10014, 10016 may attach to holes in the evaporator condenser (various embodiments of which are described above and below) wherein the evaporator condenser in various embodiments may include holes to accommodate receipt of the legs 10014, 10016.

In various embodiments, the bottom section 10012 may be sized such that the edge of the bottom section 10012 rests against the inside wall of the steam chest. In various embodiments, the bottom section 10016 may include one or more cut openings 10020, 10022, 10024, 10026, 10028. Steam from the evaporator condenser may travel past the bottom section 10012 and water may travel past the bottom section 10012.

The middle section 10010 includes an edge that may rest against the inside wall of the steam chest. In various embodiments, the middle section 10010 includes edge openings 10030, 10032, 10034, 10036, 10038 about the circumference of the middle section 10010. The middle section 10010 also includes an opening 10040.

The top section 10008 in various embodiments is generally cone-shaped. Steam may pass through the opening 10040 and also through the edge openings 10030, 10032, 10034, 10036, 10038 and cut openings 10020, 10022, 10024, 10026, 10028, as well as around the outside circumferential edge of the bottom section 10012, middle section 10010 and the top section 10008. The shape of the top section 10008 forces the steam to change direction. Water vapor that travels through the opening 10040 will hit the underside of the top section 10008 and drip down and eventually, to the sump. Thus, to the extent water passes through from the evaporator condenser with the steam, when the steam, which changes direction when it reaches the top section 10008, changes direction, the water is incapable of following the same path because the water cannot change direction as it has a higher mass. This results in the water being separated from the steam. The water may reach the underside of the top section 10008 and then, as there is no opening in the top section 10008, falls to the middle section 10010, and may travel through the edge openings 10030, 10032, 10034, 10036, 10038 and cut openings 10020, 10022, 10024, 10026, 10028 and back to the sump.

In various embodiments, the sections 10004, 10006, 10008, 10010, 10012, are generally cone-shaped and therefore, to the extent water reaches a surface of one or more of the three sections 1004, 1006, 1008, 10010, 10012, the water will tend to drip downwards towards the sump.

In various embodiments, the top section 10008 may include a tab portion 10042. This section of the mist eliminator 10000 is configured to be located underneath the low pressure steam outlet port. Thus, the tab portion 10042 may be beneficial for many reasons, including, but not limited to, preventing/minimizing/reducing water droplets from being pulled to the compressor/regenerative blower, which, in some instances, may contaminate the compressor/regenerative blower.

In various embodiments, the water vapor distillation apparatus and/or the various embodiments of the mist eliminator assembly may include a splash guard above the mist eliminator. In various embodiments, the splash guard may be constructed of a hydrophobic material.

In some embodiments, the splash guard may be constructed of one or more layers of mesh. In some embodiments, where two or more layers of mesh are used, the two or more layers of mesh may be rotated ninety-degrees from each other.

In various embodiments, the splash guard may be made of stainless steel, aluminum, PTFE and/or plastic, and in various embodiments, may be made from any material including any type of metal and/or any type of plastic.

Referring now also to FIGS. 100A-100C, another embodiment of the case/shell 10100 is shown. In various embodiments, the case/shell 10100 may include one or more of the following a level switch plug in 10102 and an IEC power plug 10104. In various other embodiments, other power plugs may be used, in some embodiments, these may be regulatory compliant power plugs, but in other embodiment, may not be regulatory compliant power plugs. Below these plugs, in various embodiments, outlet ports may be located for product water 10106, divert water 10108, and blowdown water 10110. At the bottom of the various ports, a source water inlet 10112 may be located. In various embodiments, locating the ports and inlets in this configuration may be beneficial/desirable for many reasons, including, but not limited to, the product water port 10106 is located on the top, therefore, if there's any leakage from the connection, the product water does not get contaminated. However, if there is any leakage from the divert water 10108, blowdown water 10110, or source water 10112 ports, they will not contaminate the product water outlet 10106. Additionally, if there is any mud or dirt that is splashed onto the case/shell 10100, the product water port 10106, being located at a higher location from the bottom, will be less likely to be contaminated.

In various embodiments, the case/shell 10100 may be water tight and in some embodiments, may include an IPX3 leak seal rating. In some embodiments, the case/shell 10100 may be sprayed with water without any ingress inside.

Referring now also to FIG. 101, in various embodiments, the case/shell 10100 may include at least two covers, a hot cover 10114 and a cold cover 10116, which are separated by a divider 10118. The hot cover 10114 covers the "hot" components of the water vapor distillation apparatus, and the cold cover 10116 covers the "cold" components of the water vapor distillation apparatus. In various embodiments, the case/shell 10100 may include hand-holds 10124, 10126 for ease of removal of the hot cover 10114. In various embodiments, the cold cover 10116 may be locked with a mechanism requiring tools to unlock. Once the cold cover door is open, in various embodiments, the hot cover 10114 may only be removed by first undoing another mechanism that attached the hot cover 10114 to the divider 10118. In some embodiments, the hot cover 10114 is attached to the divider 10118 using screws. However, in various other embodiments, any attachment mechanism may be used. Thus, in various embodiments, cold cover 10116 must be unlocked before the hot cover 10114 may be opened. This is beneficial for many reasons, including, but not limited to, preventing access to the hot area, which may be dangerous, to anyone except someone with the tools to open the cold cover 10116 and open the hot cover 10114, which may be, e.g., a service technician.

Referring also to FIG. 104, in various embodiments, the case/shell 10100 may include one or more hand holds. In some embodiments, there may be two hand holds located each in the front 10126, 10128 and back 10130, 10132 of the case/shell 10100.

Referring now also to FIG. 105, a first drain port 10134 and a second drain port 10136 may be, in some embodiments, located in the front of the case/shell 10100 within a hand hold 10128. The first drain port 10134 may be for draining the sump and the second drain port 10136 may be for draining blowdown water. The first drain port 10134 and the second drain port 10136 may include drain valves, which, in various embodiments, may be as shown in as 10138. In various embodiments, the drain valve 10138 may be a manual ball valve. In various embodiments, the drain ports 10134, 10136 may be located in the front of the case/shell, and therefore accessible through opening the cold cover 10116. This may be beneficial/desirable for many reasons, including, but not limited to, accessing the drain ports without having to access the hot components of the water vapor distillation apparatus.

Referring now also to FIG. 106, in various embodiments, mechanisms for securing the system during shipments, for example, and or for securing the system to lifting straps for transporting the system may be located on the chassis 10144. In some embodiments, the mechanisms may be "D-rings 10140, 10142, and in various embodiments, one or more D-rings may be located on each side of the chassis 10144. In various embodiments, other mechanisms may be used and/or the mechanisms may be located in various locations and in various quantities on the chassis 10144 or elsewhere on the case/shell 10100. In various embodiments, the D-rings 10140, 10142, or other mechanisms, may be attached to the molded chassis 10144 at manufacture.

In various embodiments, the case/shell 10100 may include one or more drain ports on the bottom of the chassis 10144. In various embodiments, there may be a drain port for draining the cold side and the hot side. In some embodiments, there may be more than one drain port on the hot side and/or on the cold side. In some embodiments, the various drain ports may include a screen or other feature to allow moisture/fluid to drain out of the system but to protect the inside of the system from any foreign matter access, for example, prevention of insects and other foreign matter from entering the system.

In various embodiments, the case/shell 10100 may include at least one user interface feature 10146 which in some embodiments may include, but is not limited to, one or more of the following: one or more LEDs, one or more buttons, one or more screens, including, but not limited to, a touch screen which may include, but is not limited to, a 3D, or 3-dimensional, touch screen. In some embodiments, the user interface 10146 may also include an overlay or other to protect the one or more features of the user interface. In some embodiments, the overlay or other may provide protection from water and/or temperatures, e.g., hot or cold. The user interface in this embodiment may have one or more of the characteristics and/or features described herein with respect to the user interface. In various embodiments, the user interface may include one or more LEDs (light-emitting diodes) and a 7-segment display. In various embodiments, the LEDs may indicate one or more of the following: power is connected to the system; error; apparatus in start-up state; apparatus in production state; and/or wireless cell connectivity and connection.

In some embodiments, the LEDs may be solid. In some embodiments, one or more LEDs may flash. For example, in some embodiments, the wireless connectivity and connection LED may remain solid to indicate that the apparatus is connected and flash to indicate that the apparatus is receiving and sending data.

In various embodiments, the at least one seven-segment displays may display error codes, system status and/or service status. The at least one seven-segment display displays text. In some embodiments, the system may include at least one button which, in some embodiments, may be a run/idle button to allow the user/service technician to clear errors and toggle the apparatus in and out of the run state. In some embodiments, the system may include a maintenance button that may allow a user/service technician to select safety override, descale, and disinfect.

Referring now also to FIG. 107, an embodiment of a fluid diagram is shown.

In various embodiments, the cold side includes an electronics control module 10146. In various embodiments, the electronics control module 10146 is cooled by source water. Therefore, raw source water coming into the water vapor distillation apparatus is flushed passed the electronics control module 10146 to keep the electronics control module 10146 cooled. In various embodiments, the electronics control module 10146 may be configured to receive 85-265 volts of AC power.

In various embodiments, the system may receive source water from anything, including, but not limited to, a municipal water supply, which is pressurized, or a non-municipal water supply, which is non-pressurized. Therefore, in some embodiments, the system includes a regulator 10150 and a source pump 10152. The regulator 10150 is used when the system is connected to a municipal water supply and the source pump 10152 is used when the system is not. In various embodiments, a level switch may be used (not shown) in the non-municipal source water supply. In various embodiments, when the level switch is plugged into the system, the system recognizes this and therefore recognizes that the source pump 10152 will be used. In some embodiments, when the source pump 10152 is plugged in, the system looks for the level switch to be plugged in as well. In various embodiments, if the regulator is plugged in, then the system does not look for a level switch to be plugged into the system. In various embodiments, the level switch may be a 5 volt level switch.

Referring now also to FIG. 108, in various embodiments, a valve manifold 10154 is included in the water vapor distillation apparatus. In various embodiments, the valve manifold 10154 includes a steam/water mixing chamber 10156 (which may also be referred to as a mixing can), which is permanently mounted onto the base and chassis of the case/shell, a manifold interconnect cold side 10158 and a manifold interconnect hot side 10160. The manifold interconnect cold side 10158 and a manifold interconnect hot side 10160 are welded together, in some embodiments, using vibration welding, and then connected to the steam/water mixing chamber 10156. In some embodiments, the manifold interconnect cold side 10158 may be molded onto the steam/water mixing chamber 10156, and then the manifold interconnect hot side 10160 is welded to the manifold interconnect cold side 10158, which, in this embodiment, is actually part of the steam/water mixing chamber 10156.

In various embodiments, the steam/water mixing chamber 10156 includes a cover 10162 that attached to the steam/water mixing chamber 10156 to seal the chamber. In various embodiments, the valve manifold 10154 includes valves 10164 controlling the source water, blowdown in and steam vent fluid paths. In various embodiments, the valve manifold may control more or less fluid lines and in some embodiments, may control one or more of the above-mentioned, but may control others as well or instead place of the fluid lines.

A clip 10168 attaches over the valves 10164. The valves 10164 are each a separate unit and are together clamped onto the steam/water mixing chamber 10156 using a lock clamp 10166. The lock clamp 10166, in some embodiments, is rotatable mounted to the steam/water mixing chamber 10156 and rotation in a first direction allows the valves 10164 to be unlocked and removed, and rotation in a second direction allows the valves 10164 to be locked onto the steam/water mixing chamber 10156. This configuration may be beneficial/desirable for many reasons, including, but not limited to, the ability to remove individual valves from the valve manifold 10154 and replace individual valves when desired. Thus, each valve is individually serviceable.

In various embodiments, the manifold interconnect cold side 10158 and the manifold interconnect hot side 10160 may be plastic, welded pieces, and in some embodiments, may be vibration welded together. The manifold interconnect cold side 10158 and the manifold interconnect hot side 10160 includes molded fluid paths 10170 that accommodate fluid from the hot side, which are connected via hot side fluid inlets 10172, such that fluid from the hot side may flow through the hot side fluid inlets 10172 and then into the fluid lines formed by the manifold interconnect cold side 10158 and the manifold interconnect hot side 10160. This configuration may be beneficial for many reasons, including, but not limited to, not having tubing connecting from the hot side to the cold side, which may reduce the incidence of occlusions and or steam egress. Rather, the tubing connects directly to the hot side fluid inlets 10172, which allow for the fluid to flow to the cold side.

In various embodiments, the valve manifold 10164 is made from molded plastic. However, in other embodiment, the valve manifold 10164 may be made from other materials, including, but not limited to, metal.

In some embodiments, the manifold interconnect hot side 10160 may be located such that it is partially on the hot side of the system. In some embodiments, an opening in the divider 10118 to accommodate a portion of the manifold interconnect hot side 10160. In various embodiments, the mixing can or steam/water mixing chamber 10156 may include a copper tube for steam to flow through. This may be beneficial/desirable for many reasons, including, but not limited to, that the system is quieter with the use of the copper tube for the steam.

In various embodiments, the valve manifold 10154 may also include at least one check valve 10172. In various embodiments, the check valve 10172 acts as a vacuum relief valve. In various embodiments, to overcome a vacuum that may be formed due to cooling within the system, e.g., cooling forming pressure excess of 0.5 PSI, the check valve 10172 allows that vacuum to be equalized.

Referring now also to FIG. 109, in various embodiments, a conductivity manifold 10174 may be included. The conductivity manifold 10174 is located adjacent to the valve manifold 10154, and serves as the product water manifold. In this way, the two valve manifolds 10154, 10174 are completely separate, fluidicly, therefore, the product water and source water, blowdown, etc., are not intermingled in the same manifold, maintaining the integrity of the product water. This may be beneficial for many reasons, including, but not limited to, prevention of contamination of the product water in the event of a leak. In some embodiments, the two manifolds 10154, 10174 may be made from the same parts but there may be an air gap maintained between them. In various embodiments, the two manifolds 10154, 10174 do not have shared fluid lines.

Similar to the valve manifold 10154, the conductivity manifold 10174 includes condo valves 10176 that are held onto the fluid line manifold 10178 using a mechanism, which, in the embodiment shown, is a condo clip 10180. The conductivity probes 10182, 10184 are located, in this embodiment, on opposite sides of the fluid line manifold 10178. As discussed above, the condo valves 10176 are separately removable and replaceable. By removing the condo clip 10180, the condo valves 10176 may be removed and replacement. In various embodiments, the condo clip 10180 may be replaced by another mechanism that allows for the removal and replacement of the valves. In some embodiments, the valves may not be replaceable.

Referring now also to FIGS. 110-113, another embodiment of the level sensor assembly 10186 is shown. In various embodiments of the water vapor distillation apparatus, the apparatus includes at least two level sensor assemblies, 10186, 10188, as shown in FIG. 102, one for each the blowdown water and product water.

In various embodiments, the level sensor assembly 10186 includes a top cover 10190 mated to a bottom cover 10192. In various embodiments, the top cover 10190 includes a vent 10194 which, in various embodiments, allows for air displacement by the incoming water/fluid. The level sensor 10196 is pivotably connected to a sensor stand 10198 which is located between the top cover 10190 and the bottom cover 10192. The level sensor 10196 includes at least one magnet 10200. The level sensor 10196 is molded of plastic in various embodiments, however, in other embodiments; the level sensor 10196 may be made of another material, for example, metal.

The level sensor assembly 10186 includes a printed circuit board 10202 which in some embodiments is heat staked onto the top cover 10190. Hall Sensors determine the position of the magnets 10200.

The level sensor assembly 10186 is attached to a liquid manifold, and in the embodiments shown herein, the water vapor distillation apparatus and system includes two manifolds, a product water manifold 10204 and a blowdown water manifold 10206. The liquid manifolds 10204, 10206 are mounted onto the chassis 10144. Fluid from the manifold 10204, 10206 enters the level sensor assembly 10186 through a bottom cover opening 10208. The fluid rising in the housing causes the level sensor 10196 to rise and pivot, and in doing so, the distance the level sensor 10196 moves is detected by the Hall Sensors using the magnets 10200 in the level sensor 10196. The fluid leaving through the bottom cover opening 10208 causes the level sensor 10196 to fall and pivot, and in doing so, the distance the level sensor 10196 moves is detected by the Hall Sensors using the magnets 10200 in the level sensor 10196.

In various embodiments, the magnets 10200 are K&J Magnetics part no. D44SH, made by K&J Magnetics, Inc., Plumsteadville, Pa., U.S.A.

The level sensor assembly 10186 is attached to the manifolds 10204, 10206 using posts on the manifolds 10204, 10206 that connect through the post holes 10210, 10212 on the bottom cover opening 10208 of the level sensor assembly 10186, and are spring clipped. In some embodiments, the spring clips are McMaster-Carr part no. 86795T28, made by McMaster-Carr of Robbinsville, N.J., U.S.A. However, in various other embodiments, different clips may be used. Thus, the level sensor assembly 10186 is easily removable and replaceable by unclipping the level sensor assembly 10186 from the respective manifold 10204, 10206.

Referring now also to FIGS. 114-115B, an embodiment of the heat exchanger 10214 is shown. The heat exchanger 10214 may include many of the features described above with respect to the various embodiments of the heat exchanger. In the embodiment shown, the heat exchanger 10214 includes another embodiment of the terminations. The terminations include a source water termination 10218 and a tube termination 10216. The source water termination 20218 seals the source water from the ends of the tubes within the heat exchanger 10214. The tube termination 10216 slides over the tubes in the heat exchanger 10214 and seals each tube from each other. One exit includes the two tubes carrying clean water, the other exit includes the two tubes carrying dirty water. In various embodiments, the source water termination 10218 and the tube termination 10216 are made from overmolded EPTM RYTON®.

The tube termination 10216 attaches to the source water termination 10218 and is held together by a wire bale 10220. In various embodiments, the wire bale 10220 is made from steel wire and is in tension to hold. In various embodiments, the wire bale 10220 may be made from other materials, including, but not limited to, plastic and other types of metals.

The tube termination 10216 includes barbs 10222, 10224 which attach to silicone hoses in the water vapor distillation apparatus.

Referring now also to FIGS. 116-121, another embodiment of the regenerative blower/compressor 10300. In this embodiment, the shaft 10302 includes a cavity 10304 that allows the water to flow to lubricate the bearings 10306, 10308. The water flows through the cavity 10304 and then enters the space where the bearings 10306, 10308 are located through a bearing feed opening 10310. Thus, the bearings 10306, 10308 are hydrodynamic bearings. In various embodiments, the bearings 10306, 10308 may be graphite bearings. In various embodiments, the shaft 10302 includes ceramic sleeves 10312, 10314, which are ceramic coated metal. The ceramic sleeves 10312, 10314 contact the bearings 10306, 10308.

The compressor 10300 includes a top compressor housing 13316 and a bottom compressor housing 10318. The top compressor housing 10316 and the bottom compressor housing 10318 are, in various embodiments, made from RYTON® plastic, however, in various other embodiments, may be made from any type of metal or plastic or a hybrid of metal and plastic. The impeller 10320 is located between the top compressor housing 10316 and the bottom compressor housing 10318. In various embodiments, the impeller 10320 is made from RYTON® plastic, however, in various other embodiments, may be made from any type of metal or plastic or a hybrid of metal and plastic. The bearing feed water provides the lubrication for the bearings 10306, 10308 which provides a liquid disc for the impeller 10320 to rotate upon.

The compressor 10300 includes a can motor including a stator assembly 10328 and a magnet rotor 10324. The magnet rotor 10324 is integrated into the shaft of the impeller 10320. The compressor 10300 includes an impeller magnet seal assembly 10326 that encapsulates the magnet rotor 10324. Thus, the stator assembly 10328 drives the magnetic shaft or magnetic rotor 10324 of the impeller 10320. In various embodiments, the bearing water may cool the stator assembly 10328.

In various embodiments, at least one Hall Effect Sensor is used as an encoder to determine the speed of the can motor based on the variability of the magnetic field. In some embodiments, there are three Hall Effect Sensors used. In various other embodiments, one or more Hall Effect Sensors may be used. Still also referring to FIG. 121, the stator assembly 10328 is shown with two Hall Effect Sensors 10330, 10332 which are located on stator printed circuit board assemblies 10334, 10336. The stator assembly 10328 also includes a stator pack 10338 which terminates with three wires 10340, a positive, a negative and a ground. The three wires 10324 are connected to the electronics control module 10148. In some embodiments, the connection to the electronics control module 10148 may be via an IP54 rated connector.

Referring now also to FIGS. 122-127B, an embodiment of the evaporator/condenser assembly 10350 is shown. The evaporator/condenser assembly 10350 includes a sump assembly 10352. The sump assembly 10352 includes a sump nozzle 10358. This sump nozzle 10358 connects to the valve for the sump first drain port 10134. This configuration allows for a user/technician to drain the sediment and other buildup out of the sump assembly 10352. The sump assembly 10352, in some embodiments, includes press concealed heat studs 10360 to hold a thermal switch and thermistor (not shown) to the sump. The thermistor may be used to determine the temperature within the sump 10352 and the thermal switch may turn the heating element 10356 off if the temperature within the sump assembly 10352 exceeds a pre-determined threshold. In some embodiments, the heating element 10356 may be a 1200 Watt heating elements. In some embodiments, the thermistor may be an OMEGA IN 04004, made by OMEGA Engineering, Inc., of Stamford, Conn., U.S.A. In some embodiments, the sump housing 10352 is made from 316 Stainless Steel, which may be beneficial/desirable for many reasons, including, but not limited to, its resistance to corrosion from in the source water. However, in various embodiments, the sump housing 10354 may be made from other metals and/or from plastic.

The sump assembly 10352 is connected to the bottom tubesheet assembly 10362. In various embodiments, the bottom tubesheet assembly 10362 includes a lower over molded sealing element 10364 which in some embodiments, is over molded with EPDM rubber. The over molded sealing element 10364 provides individual sealing for each of the tube assemblies. Thus, the tube assemblies 10366 fit individually through the openings 10368 in the over molded plastic sealing element 10364. The bottom tubesheet assembly housing 10370, which in various embodiments is made from plastic, includes, in some embodiments, mounting feet 10372, 10374, 10376, for mounting the evaporator/condenser assembly 10350 onto the chassis 10144 using, in some embodiments, wire bales (not shown). The wire bales fit over receiver channels 10378, 10380, 10382 on the upper portion of the mounting feet 10372, 10374, 10376.

In various embodiments, the bottom tubesheet assembly 10362 includes a pin locating feature (not shown) that accommodates pins that are located on the chassis 10144. Once one of the pins is located, then the evaporator/condenser assembly 10350 is in the correct location and may be clamped to the chassis 10144. In various embodiments, marman clamps may be used to secure the evaporator/condenser assembly 10350 onto the chassis 10144 and within the water vapor distillation apparatus.

In various embodiments, a top tubesheet assembly 10384 includes a housing 10386, which, in various embodiments, may be made from plastic or any other material. The top tubesheet assembly 10384 may include an upper over molded sealing element 10388 which in some embodiments, is over molded with EPDM rubber. The upper over molded sealing element 10388 provides individual sealing for each of the tube assemblies. Thus, the tube assemblies 10366 fit individually through the openings 10390 in the upper over molded plastic sealing element 10388. In various embodiments, the wall height of the housing 10386 of the top tubesheet assembly 10384 is higher than that of the bottom tubesheet assembly 10362. This may be beneficial for many reasons, including, but not limited to, prevention/reduction of water carryover and therefore, water contamination.

In various embodiments, the top tubesheet assembly 10384 may include a weir 10392 which, in various embodiments, is angled such that the weir 10392 assists the water in going down the weir port 10394. The weir 10392 is configured to allow for sufficiently fast draining of water at boiling temperature. The weir 10392, in various embodiments, includes a weir cap 10396, which, in various embodiments, may include rib features or other features to increase the strength of the weir cap 10396. The weir port 10394 is connected to the blowdown water fluid path.

In various embodiments, the upper tubesheet assembly 10384 includes a condenser vent port 10398 that is connected to the condenser space of the evaporator/condenser assembly 10350, and a tube connecting to the condenser vent port 10398 connects also to the product water manifold 10204. In various embodiments, the upper tubesheet assembly 10384 includes a condenser vent port 10400 that is connected to the condenser space of the evaporator/condenser assembly 10350, and a tube connecting to the condenser vent port 10398 connects also to the steam vent that goes to the steam valve.

In various embodiments, the evaporator/condenser assembly 10350 may include an evaporator/condenser 10402 which, in various embodiments, may contain one or more of the elements and/or characteristics as described above with respect to various embodiments of the evaporator/condenser. However, in the embodiments shown, the evaporator/condenser 10402 includes a tube retainer 10404 which, in various embodiments, may be made of RYTON, however, in various embodiments, may be made of metal, which may include, but is not limited to, Stainless Steel. However, in various embodiments, the tube retainer 10404 holds the tubes 10366, which in various embodiments may be made from metal or plastic, but in some embodiments, may be made from copper or stainless steel, or any other material, including any metal or plastic. In various embodiments, the tube retainer 10404 retains the tubes in the evaporator/condenser 10402 when servicing the filler rods 10406, e.g., when removing the filler rods 10406.

In various embodiments, the evaporator side of the evaporator/condenser 10402 includes a temperature sensor.

Some embodiments of the filler rods 10406, which may also be called packing rods, may include nubs 10408 distributed about the outer surface of the filler rod 10406. In various embodiments, the nubs 10408 near the top of the filler rods 10406 may be larger than those at the bottom. In various embodiments, the nubs 10408 near the ends of the filler rods 10406 may be larger than those in the middle. In various embodiments, the filler rods 10406 may be made from RYTON®, but in other embodiments, may be made from any material, including, but not limited to, metal or plastic. In various embodiments, the filler rods 10406 may be sized such that they have a diameter that is about 0.25 inches smaller than the tubes 10366. In some embodiments, the ends of the filler rods 10406 may include a hollowed out portion 10410. This may be desirable/beneficial for many reasons, including, but not limited to, the filler rods 10406 require less plastic to manufacture, therefore may be less expensive, and/or the filler rods 10406 may weigh less.

In various embodiments, the steam chest 10412 may be clamped onto the evaporator/condenser assembly 10350 using marman clamps. However, in various embodiments, the steam chest 10412 may be attached using bolts or other mechanisms of attachment.

In various embodiments, the shell of the evaporator/condenser 10402 is made from RYTON® or another plastic, however, in various embodiments, the evaporator/condenser 10402 shell may be made from Stainless Steel or another metal, or may be made from a different plastic. In various embodiments, the evaporator/condenser 10402 may include one or more wings 10414 for attaching the evaporator/condenser assembly 10350 to the chassis 10144. In some embodiments, the wings 10414 attach to struts in the chassis 10144 for stability.

Referring now also to FIGS. 129-133, in various embodiments, a first conductivity sensor 10500 may be used to determine quantify the quality of the product water before the product water leaves the system. In various embodiments, the product water enters the conductivity cell, where the conductivity probe or sensor is housed, various embodiments of which have been described herein, and if the first conductivity sensor 10500 returns a value to the controller that is outside a pre-determined threshold value or a range of value, then a divert valve 10504 is opened and the product water is disposed of and not released through the product water path, rather, the water flows to the divert output 10512. However, if the first conductivity sensor 10500 returns a value to the controller that is within a pre-determined threshold value or a range of value, then a first product valve 10502 is opened and the product water is released from the system through the product water output port 10510.

In some embodiments, a second conductivity sensor 10506 and a second conductivity cell may be included in the system. In these embodiments, once the first product valve 10502 is opened, the product water flows through a second product valve 10508 and then into the second conductivity sensor 10506. If the second conductivity sensor 10506 returns a value to the controller that is outside a pre-determined threshold value or a range of value, then the second product valve 10508 is closed and the system is placed into a fault condition. However, if the second conductivity sensor 10506 returns a value to the controller that is within a pre-determined threshold value or a range of value, then the system may continue to product water.

In some embodiments, the second conductivity sensor 10506 and second product valve 10508 may be located within the water vapor distillation apparatus, as shown in FIGS. 107 and 131, for example. However, in some embodiments, the second conductivity sensor 10506 and second product valve 10508 may be located outside the water vapor distillation apparatus as a modular system that may be connected to the product output, for example, as shown in FIG. 130.

In various embodiments, the first conductivity sensor 10500 and the second conductivity sensor 10506 may be any conductivity sensor, which may include one from made by OMEGA Engineering, Inc., of Stamford, Conn., U.S.A. However, in various embodiments, the first conductivity sensor 10500 and the second conductivity sensor 10506 may be one as shown in FIG. 132. Referring now also to FIG. 132, in some embodiments, another embodiment of a conductivity sensor 10514 may be used. In this embodiment, the conductivity sensor 10514 includes three probes 10516, 10518, 10520 that are connected by cable. The impedance between the three probes 10516, 10518, 10520 is measured. If any one of the resistances is below a threshold, this indicates that the conductivity is too high and registers a fault condition. As described above, in various embodiments, the fault condition in the first conductivity sensor 10500 would open the divert valve 10504. The fault condition in the second conductivity sensor 10506 would register as a system fault condition, in some embodiments, and shut-down the production of product water in the system.

In various embodiments of this embodiment of the conductivity sensor 10514, the resistance between the probes 10516, 10518, 10520 is fixed at 500 k Ohms. Thus, in various embodiments, the conductivity sensor 10514 includes three Stainless Steel conductivity probes 10516, 10518, 10520 (which, in various other embodiments, may be made from another material), at least one probe thermistor, and in some embodiments, a probe thermistor for each probe 10516, 10518, 10520, and 500 k Ohm resistors between each probe 10516, 10518, 10520 (external to the water). The resistance between the probes 10516, 10518, 10520 is measured by an impedance measurement circuit, which, in some embodiments, may be an Analog Devices AD5934, however in other embodiments; another impedance measurement circuit may be used. Analog switches are used to multiplex between pairs of probes 10516, 10518, 10520. The at least one thermistor is embedded in at least one probe to measure the temperature of the water. In some embodiments, each probe 10516, 10518, 10520 includes an embedded thermistor.

Conductivity (in uS/cm normalized to 25 deg Celsius temperature)=cell calibration constant (eg 400000 uS/cm per Ohm)/resistance (in Ohms)/(1+0.02*(temperature (in deg C.)−25)), where "temperature" is measured by the at least one thermistor, the cell calibration constant is related to the probe 10516, 10518, 10520 geometry and spacing and "0.02" is the percent change (i.e., 2%) per degree Celsius in conductivity, where 2% per degree Celsius is an approximation that varies depending on the specific dissolved solids within the water.

Thus, in various embodiments, under regular operations of the system, if the product water is acceptable, or if there's air in the product line, 500 k Ohms resistance will be measured between the probes 10516, 10518, 10520. However, if a cable/lead brakes or fails, the measured impendance jumps drastically to a mega impedance and the cable failure will be detected by the system immediately. Thus, there is a clear and certain delineation between a broken probe and any other condition. If the conductivity sensor 10514 encounters air, the impedance is infinite between the probes 10516, 10518, 10520. With the 500 k Ohms resistance between the probes 10516, 10518, 10520, the conductivity sensor 10514 distinguishes between air and a broken probe.

The 500 k Ohm resistors, in various embodiments, are used to provide an upper bound on the observed resistance. Without these resistors, the measured resistance may be >>1 MegaOhm when ultrapure water with conductivity <<1 uS/cm is present. With high resistances, it may be difficult to accurately measure resistances over many orders of magnitude and such high resistances would be indistinguishable from open-circuit cables. In the system, cable/lead faults are easily detected.

In various embodiments of this embodiments of the conductivity sensor 10514, the probes 10516, 10518, 10520 may include temperature sensors/thermistors. In various embodiments, during disinfection using steam (discussed below), the temperature sensors may feed temperature information to the controller to confirm that the temperature in the product output fluid lines reached the appropriate temperature to successfully disinfect. In various embodiments, because these are redundant temperature sensors in each of the probes 10516, 10518, 10520, if one fails for any reasons, it is likely one of the other two will provide temperature readings. Additionally, using these redundant temperature sensors, in various embodiments, the controls may perform an integrity check on the temperature sensors by comparing the readings and determining if any one appears to be outside a threshold range from the other temperature sensor's readings.

In some embodiments, a dedicated processor may be included in the system that communicates with both conductivity sensors 10500, 10506. In some embodiments, the various valves may be configured to fail safe, e.g., if the valve brakes or malfunctions, the valve closes. In various embodiments, when the system registers a fault condition, the system shuts down.

The conductivity control system described herein may be used to detect various conditions of the system and also serves to be a redundant system. Therefore, if a valve malfunctions, for example, if the first product water valve 10502 malfunctions and is left open, then the second product valve 10508 serves to maintain the product water in the system.

In various embodiments of the system, a flow meter may be installed in the product water line between the first product valve 10502 and the second product valve 10508. The flow meter would communicate with the controller and indicate whether there is flow between the two valves 10502, 10508. If there is flow and the control system indicates that both the valves 10502, 10508 are closed, this would indicate a fault condition of one or both of the valves.

In some embodiments, the control system may run periodic tests at pre-programmed times or at regular intervals or on demand that compares the readings of the first conductivity sensor 10500 with the second conductivity sensor 10506. In some embodiments, if the readings differ greater than a pre-determined threshold amount, then the system indicates a fault condition.

In some embodiments, during the course of the system running and producing product water, when the conductivity determined by the first the first conductivity sensor 10500 and the second conductivity sensor 10506 differ greater than a pre-determined threshold amount, then the system indicates a fault condition.

Referring now also to FIG. 133, in various embodiments, a method and system for determining conductivity of water includes using a first conductivity sensor and the system receiving a first conductivity sensor reading 10524. Next, the system determines whether the reading from the first conductivity sensor is within an acceptable range 10526. If it is, then the first product valve is opened 10530 and the second product valve is opened 10532 and then, using a second conductivity sensor, the system receives a second conductivity sensor reading 10534. Next, the system determines whether the reading from the second conductivity sensor is within an acceptable range 10526. If it is, then the system may, in some embodiments, determine whether the first conductivity sensor reading differs more than a threshold amount from the second conductivity reading 10538. However, in some embodiments, step 10538 may not be included each time the method is used, but in some embodiments, may be included every other time, and/or at an interval, and/or on demand, and/or at pre-determined and/or pre-programmed times. If the system determines that the first conductivity sensor reading differs more than a threshold amount from the second conductivity reading 10538, then a fault condition is indicated 10528. If not, then the product water goes to the output and no fault is indicated.

If it is determined that either the first conductivity sensor reading 10526 or the second conductivity sensor reading 10536 is not within the acceptable range, or threshold range for acceptability, then a fault condition is indicated 10528.

In various embodiments, when the divert valve 10504 is open, the second conductivity sensor 10506 may be shut down or the control system does not expect to receive a reading. Thus, if the control system receives a reading from the second conductivity sensor 10506, then the system indicates a fault condition as this indicates a leak or a valve malfunction.

In various embodiments, the system may include an override button 10522. This override button may be used by a user/technician to clear a fault condition. In various embodiments, the override button may be behind a mechanical guard or within a locked area or door and therefore, the system may only be overridden by a user/technician with a key. In various embodiments, to override a fault condition, the system may require the button be held down for a pre-determined time. In some embodiments, overriding includes the system/water vapor distillation apparatus purges product water from the system.

In some embodiments, if the conductivity readings for either the first conductivity sensor 10500 or the second conductivity sensor 10506, or both, are not within a pre-determined/pre-programmed acceptable range, then, in some embodiments, the system may continue running and making product water, but the second product valve 10508 and/or the first product valve 10502 are closed. The system may then determine an occlusion condition and then the system will automatically go to a fault condition.

In some embodiments, the threshold amount may be different for the first conductivity sensor 10500 and the second conductivity sensor 10506. In some embodiments, for example, the threshold for the first conductivity sensor 10500 may be about 10 microsiemens per centimeter at 25 degrees Celsius. In some embodiments, for example, the threshold for the second conductivity sensor 10506 may be about 40 microsiemens per centimeter at 25 degrees Celsius. Thus, in some embodiments, the first conductivity sensor 10500 may be more robust and divert product water that may have met the threshold of the second conductivity sensor 10506. This configuration may be beneficial for many reasons, including, but not limited to, ensuring that the criteria for allowing product water to proceed to the output is more robust where diverting the product water is still an option. Once the product water passes the first product valve 10502, divert is not available.

In various embodiments, the user interface LEDs may indicate different colors and/or flashing or steady, depending on the state the system/water vapor distillation apparatus is in. In some embodiments, the LEDs may indicate, using color, or lighting one or another LED, whether the product water is being run (which may mean dispensed or past the first product valve 10502) or diverted. In some embodiments, the 7-segment display may indicate the state. IN some embodiments, either the LEDs or the 7-segment display, or both, may indicate the state, including, but not limited to, if the system is in a fault condition.

In some embodiments, the system may use the following method to determine whether the system/water vapor distillation apparatus has water flowing through using the product Level Sensor Assembly (as described above), the first product valve 10502 and the second product valve 10508. The system closes both the first product valve 10502 and the second product valve 10508, and then the system watches the readings from the product Level Sensor Assembly. If the level in the product Level Sensor Assembly changes, then this indicates that at least one of the first product valve 10502 or the second product valve 10508 is working. This may be beneficial for many reasons, including, but not limited to, ensuring that at least one of the first product valve 10502 or the second product valve 10508 is functioning to prevent unintentional output of product water.

In some embodiments, the system includes a method for disinfection. In some embodiments, the water vapor distillation apparatus, using the evaporator/condenser assembly, introduces steam in excess of 100 degrees Celsius through the product water 10544 and divert 10542 fluid lines. In various embodiments, this method disinfects the various components and fluid lines in the system. In various embodiments, this method may begin by a user/technician connecting a particular hose to the outputs which may be diverted to a bucket of water to quench the steam. In some embodiments, the system may be placed into the disinfect state by toggling using either the button 10522 and or using another component of the user interface, and/or being connected to a computer and the computer instructing the system to enter into the disinfect state. Once in the disinfect state, in various embodiments, the sump heater 10356 is turned on and the system runs to bring the water to a higher temperature than during regular distillation for a pre-programmed or pre-determined period of time. In some embodiments, the disinfect may be a pre-set program in the system and using the user interface, the user/technician may toggle through various programs until placing the system into the disinfect state.

In various embodiments, the disinfection method may include closing the first and/or the second product valves 10502, 10508. Heat transfer may raise the temperature in the fluid lines and valves beyond the first product valve 10502 to an appropriate temperature to successfully disinfect, without actually applying the steam to those areas. In this way, steam would be prevented from leaving the product outlet 10510 which may be beneficial for many reasons, including, but not limited to, preventing the possibility of steam emerging from the system which may be hazardous. In this embodiment, any user may run the disinfection state, rather than limiting the running of the disinfection state to a technician. This embodiment also would not require a hose be applied to the product outlet 10510 for the disinfection, or water to quench the steam.

In various embodiments, the product water fluid lines and specific components keep the product water at a higher pressure than the blowdown water/specific components for the blowdown water. In this way, blowdown water is less likely and/or unlikely to flow to and comingle with the product water.

In various embodiments, the system may include multiple printed circuit boards (PCB). In some embodiments, the system may include a first PCB, a machine control processor, which includes the controls for producing water and controlling the system for producing water, a second PCB, a host control processor, which communicates with the machine control processor, and includes the user interface controls and controls for the remote agent subsystem (described in more detail below), including the logging system, amongst other controls. A third PCB, the power PCB, may also be included which includes all of the controls for the power for the system. The power PCB also communicates with the machine control board. A forth PCB, a personal computer PCB, includes the controls for the personal computer and also communicates with the machine control board and the host control board. This electronics configuration may be beneficial/desirable for many reasons, including, but not limited to, where changes in the memory are desired because of, e.g., software for the user interface, only the host control board is affected and therefore, only one board, the host control board, need be modified and/or replaced. Additionally, this configuration creates a modularized electronics system where systems may be custom fitted to particular locations. For example, various locations may require a more robust user interface, and/or various modes of connectivity, and various locations may require a very simple user interface. For example, some locations may require Wi-Fi, while others do not. Thus, the components for Wi-Fi may be customized onto some host controls boards and not others, to lower the expense where the function is not desired. Various versions of the host control board may be used depending on the systems ultimate location and therefore, the other three PCBs would be identical and only the host control board would differ. Switching out one PCB to customize a system provides versatility and modularity to the system. Additionally, the microprocessor on the machine control board may be smaller than the one used on the host control board. Thus, by separating the two boards, the expense for the machine control board may be less than the host control board because the machine control board may not require a large microprocessor. Additionally, all of the heat dissipating devices may be placed on the power PCB. Thus, this makes the system more efficient for managing heat in the PCBs. In some embodiments, the power PCB may be mounted to a heat sink 10546, which in some embodiments, may be an aluminum plate (or other heat dissipating metal) pressed onto the back of the electronics assembly, which, in some embodiments, together with the electronics assembly, sandwich the copper tube that feeds source water to the electronics control assembly to provide cooling to the electronics. This cooling fluid line also provides cooling to the power PCB. In some embodiments, a heat sink 10546 temperature controller may be included in the system.

In various embodiments, the system includes a heat sink valve 10548. Thus, as source water comes into the system, the source water flows by the heat sink 10546 and in some instances, when the mixing can valve 10550 is open, and the heat sink valve 10548 is closed, will flow to the mixing can 10156. This provides a cooling loop for the system even when product water is not being made (i.e., the water vapor distillation apparatus is not heating or running) However, when the water vapor distillation apparatus is heating or running, the source water comes into the system, the source water flows by the heat sink 10546 and in some instances, when the mixing can valve 10550 is closed, and the heat sink valve 10548 is open, will flow to the sump 10354. Thus, whether or not the system is in run or heat mode, the electronics control module and the heat sink 10546 will be cooled by incoming source water.

In some embodiments, the user interface may be a smart phone, for example, a QUALCOM-based phone. In some embodiments, the user interface may be a SAMSUNG Galaxy S4, however, in various embodiments; the smart phone may be any smart phone. The smart phone may be customizably programmed and attached to the system.

In various embodiments, the system may include a tilt sensor, which in some embodiments, may be a 3-axis accelerometer. In some embodiments, the tilt sensor may be positioned on the machine control processor. In some embodiments, the system controls may not allow the water vapor distillation apparatus to run if the system does not meet a threshold level, which the controls system receives from the tilt sensor.

Some embodiments of the system may include a GPS, which, in some embodiments, may be located on the host control processor. This may be desirable for many reasons, including, but not limited to, remotely tracking the location of the system and therefore, in some embodiments, changing thresholds and other controls based on the location of the system thereby responding to potentially different needs in response to different water and/or climate conditions.

Referring now also to FIG. 134, in various embodiments, the can motor may be controlled based on the motor temperature. In various embodiments, a controller receives the motor temperature 10552 and the output is the desired motor speed 10554 and then this runs through a controller limiter/saturation max and min speed 10556, which yields the commanded motor speed 10558. This is fed into the motor controller 10560, which drives the motor 10562, and then heat comes off the motor which is plugged onto the motor temperature 10564. In various embodiments, the controller may target 160 degrees Celsius as the motor temperature.

In some embodiments, the temperature may remain constant but over time, the motor speed may decrease due to decreased efficiency which may be present from time to time due to various conditions, for example, scaling. This controls method is beneficial/desirable for many reasons, including, but not limited to, if the motor speed were constant, than the temperature would rise. This could create negative conditions for the system. Thus, by maintaining a constant temperature, the temperature does not reach a negative level but the motor speed decreases.

Referring now also to FIG. 135, in various embodiments, the system includes controls for the low pressure ("LP") water temperature, which refers to the water under low pressure, i.e., the source water, which is in the evaporator side of the evaporator/condenser 10402. The LP desired temperature 10566 is fed into the heater controller 10568. Also, an enable signal if fed into the heater controller 10568. The output of the heater controller 10568 is heater duty cycle/heater drive signal (0 to 100) 10570 and then this is limited (heater limit 10572), which then controls the actual heater electronics 10574. The LP temperature is reduced 10576 and it this is fed into the vent controller 10578. The vent controller 10578 is enabled and a desired temperature is output as a vent valve command 10580. The command is fed to the vent electronics 10582 which is fed back to the LP temperature desired temperature 10566. The control of the heater and the vent is mutually exclusive. When the system is heating, the vent is open to control the pressure within the system.

Referring now also to FIG. 136, in various embodiments, the system includes a product controller. The desired product water level 10584 is fed into the product level controller 10586. The output is the product valve duty cycle 10588. The product valve duty cycle 10588 is then fed into the valve electronics 10590. The fluid flows to the desired level (determined using the product level sensor assembly 10592)

Referring now also to FIGS. 137-140 in various embodiments, the system, and in some embodiments, there may be multiple systems/devices 10594 included in a network (this disclosure is not limited to single or multiple devices, rather, this method/system/network may be used with at least one system/device), communicates 10596 by way of a cell phone network, Wi-Fi, Ethernet, Modem, 4G, Iridium Satellite Modem or other satellite model, and/or any other mechanism to connect to the internet, for example, with at least one external manager 10600 through a cloud 10598. However, in some embodiments, a single system/device 10602 may communicate 10604, for example, using a USB-based communications link/connection, with one external manager 10606. The at least one external managers 10600 may connect to the cloud 10598 using any communication mechanism, including, but not limited to, web pages, web-based API and/or SQL. In various embodiments, the at least one external manager 10600 may include server pages, analytic devices and or WaterView. In various embodiments, the cloud 10598 may include at least one database and at least one cloud server.

As the data in the system/device (whether a single system 10602 or multiple systems/devices 10594 on a network) changes, the data is written to a persistent file or log. In embodiments where the device/systems are communicating through the internet, at a pre-determined time, for example, at 11:59 p.m., or at pre-determined/pre-programmed intervals, the communications 10596 connect to the internet and the system connects to the cloud 10598. The data is uploaded/moved to the cloud. The one or more external managers 10600 may download the data to a server and/or a computer device, and the data is therefore backed up both by the cloud 10598 and the one or more external managers 10600.

Each time the data is updated, the most up-to-date data and/or state is uploaded into the live/most recent state and the old state is moved to a history. At the end of an interval, for example, 24 hours, of device/system run, the at least one external manager 10600 may review the data and determine if changes are needed, etc. In various embodiments, only changes in state/data are logged. However, in some embodiments, for sensors, valves, etc., that may be constantly changing; the system may log the data at a pre-determined/pre-programmed interval, e.g., every 5 minutes. Logging only the changes or logging data in intervals may be beneficial for many reasons, including, but not limited to, transferring and/or logging less data overall which is more efficient.

In various embodiments, the at least one external manager, either 10606 or 10600, may set the state for the systems/devices.

In various embodiments, for example, the embodiment shown in FIG. 137, the at least one systems/devices 10594 may connect/communicate 10596 with the cloud 10598 at pre-programmed intervals, e.g., every 2 hours. This is beneficial for many reasons, including, but not limited to, the systems/devices 10594 at all times which may decrease the opportunity for hacking into the systems/devices 10594, and/or compromising the systems/devices 10594. If one or more of the at least one external managers 10600 desires to connect to one or more systems/device 10594 at a given time that is outside when the at least one systems/device 10594 are connected to the cloud 10598, the at least one external manager 10600 may shoulder tap the cloud 10598 and communicate to the cloud 10598 that the at least one external manager 10600 wants to communicate with one or more systems/devices 10594. The cloud 10598 may send a text message to the at least one or more systems/device 10594 that tells the at least one or more systems/devices 10594 to connect to the cloud 10598. This configuration may be beneficial for many reasons, including, but not limited to, conserving bandwidth as the at least one external managers 10600 do not have of stay connected to the cloud 10598 or the at least one systems/devices 10594 all the time, rather, only when it is necessary.

This network communications configuration may be used for remotely controlling and/or remotely monitoring the one or more systems/devices 10594. Additionally, This network communications configuration may be used for downloading, remotely, software updates and/or reconfiguring one or more systems/devices 10594.

In addition, the following is incorporated herein by reference in its entirety: U.S. patent application Ser. No. 10/713,617 filed Nov. 13, 2003, Publication No. US-2005-0016828 published Jan. 27, 2005, now U.S. Pat. No. 7,597,784 issued Oct. 6, 2009 and entitled Pressurized Vapor Cycle Liquid Distillation.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A method for determining the quality of a distilled product water at a distilled product water output comprising:
   providing a controller;
   providing a first conductivity sensor in a distilled product fluid path for the distilled product water in communication with the controller;
   providing a first product valve downstream from the first conductivity sensor and in communication with the controller;
   providing a second product valve downstream from the first product valve and in communication with the controller;
   providing a second conductivity sensor in the distilled product fluid path downstream from the second product valve and in communication with the controller;
   providing a divert valve downstream from the first conductivity sensor and upstream from the first product valve and in communication with the controller;
   the controller comparing a first conductivity value from the first conductivity sensor to a first threshold, opening the first valve when the first conductivity value is less than the first threshold, then opening the second valve and then comparing a second conductivity value from the second conductivity sensor to a second threshold and indicating a fault condition when the second conductivity value is more than the second threshold.

2. The method of claim 1, further comprising the controller opening the divert valve and maintaining the first product valve and second product valve in a closed position when the first conductivity value is greater than the first threshold.

3. The method of claim 1, further comprising wherein the first threshold is lower than the second threshold.

4. The method of claim 1, further comprising comparing the first conductivity value to the second conductivity value and indicating a fault condition when the first conductivity value differs from the second conductivity value by more than a predetermined value.

5. The method of claim 1, further comprising:
   determining that either the first conductivity value or the second conductivity value is not within an acceptable range, or a threshold range for acceptability; and
   indicating a fault condition.

6. The method of claim 1, further comprising wherein the first conductivity sensor and the second conductivity sensor comprising:
   three probes connected by a cable, at least one of the three probes comprising a temperature sensor and wherein the resistance between each of the three probes is 500 k Ohms.

7. A method for determining the quality of a distilled product water at a distilled product water output comprising:
   providing a controller;
   providing a first conductivity sensor in a distilled product fluid path for the distilled product water, in communication with the controller;
   providing a first product valve downstream from the first conductivity sensor and in communication with the controller;
   providing a second product valve downstream from the first product valve and in communication with the controller;
   providing a second conductivity sensor in the distilled product fluid path, downstream from the first product valve and in communication with the controller; and
   the controller receiving a first conductivity value from the first conductivity sensor and opening the first valve if the first conductivity value is within a first acceptable range, opening the second valve, then receiving a second conductivity value from the second conductivity sensor and indicating a fault if the second conductivity value is outside a second acceptable range, the second acceptable range being larger than the first acceptable range.

8. The method of claim 7, further comprising providing a divert valve downstream from the first conductivity sensor and upstream from the first product valve and in communication with the controller.

9. The method of claim 8, further comprising the controller determining that the first conductivity value is not within a first acceptable range and opening the divert valve and maintaining the first product valve and second product valve in a closed position.

10. The method of claim 7, further comprising the controller indicating a fault condition when the second conductivity value differs from the first conductivity value by more than a predetermined value.

11. The method of claim 7, further comprising wherein the first conductivity sensor and the second conductivity sensor comprising:
   three probes connected by a cable, at least one of the three probes comprising a temperature sensor and wherein the resistance between each of the three probes is 500 k Ohms.

12. The method of claim 1 where in the first threshold is 10 microsiemens per centermeter at 25 degrees Celsius and the second threshold is 40 microsiemens per centermeter at 25 degrees Celsius.

13. The method of claim 1 where in the second threshold is four times higher than the first threshold.

14. The method of claim 1 further comprising a first interface LED that lights up when the distilled product flows though the divert valve.

15. The method of claim 1 further comprising a multi-segment display that communicates a fault condition.

16. The method of claim 14 further comprising a second interface LED that lights up when the distilled product flows though the first product valve.

* * * * *